US005851824A

United States Patent [19]

Harpold et al.

[11] Patent Number: 5,851,824

[45] Date of Patent: Dec. 22, 1998

[54] HUMAN CALCIUM CHANNEL α-1C/α-1D, α-2, β-1, AND γSUBUNITS AND CELLS EXPRESSING THE DNA

[75] Inventors: Michael M. Harpold; Steven B. Ellis, both of San Diego; Mark E. Williams, Carlsbad; Daniel H. Feldman, San Diego; Ann F. McCue, La Mesa, all of Calif.; Robert Brenner, Austin, Tex.

[73] Assignee: Sibia Neurosciences, Inc., La Jolla, Calif.

[21] Appl. No.: 223,305

[22] Filed: Apr. 4, 1994

Related U.S. Application Data

[63] Continuation of Ser. No. 868,354, Apr. 10, 1992, abandoned, which is a continuation-in-part of Ser. No. 745,206, Aug. 15, 1991, Pat. No. 5,429,921, which is a continuation-in-part of Ser. No. 620,250, Nov. 30, 1990, abandoned, which is a continuation-in-part of Ser. No. 176,899, Apr. 4, 1988, abandoned, and a continuation-in-part of Ser. No. 482,384, Feb. 20, 1990, Pat. No. 5,386,025, and Ser. No. 603,751, filed as PCT/US89/01480, Apr. 4, 1988, abandoned, which is a continuation-in-part of Ser. No. 176,899, Apr. 4, 1988, abandoned.

[51] Int. Cl.$^{6}$ ........................ C12N 15/12; C07K 14/435; C07K 14/705

[52] U.S. Cl. ........................ 435/325; 435/69.1; 435/356; 435/358; 435/364; 435/365; 435/370; 435/254.11; 435/320.1; 536/23.5; 536/24.31

[58] Field of Search ............................ 536/23.5, 24.31; 435/240.2, 254.11, 320.1, 69.1, 325, 356, 358, 364, 370, 365

[56] References Cited

U.S. PATENT DOCUMENTS

| | | | |
|---|---|---|---|
| 4,788,135 | 11/1988 | Davis et al. | 435/6 |
| 4,912,202 | 3/1990 | Campbell et al. | 530/388.22 |
| 4,954,436 | 9/1990 | Froehner et al. | 424/1.49 |
| 5,024,939 | 6/1991 | Gorman | 435/69.1 |
| 5,051,403 | 9/1991 | Mijanich et al. | 514/12 |
| 5,189,020 | 2/1993 | Mijanich et al. | 514/12 |
| 5,264,371 | 11/1993 | Miljanich et al. | 436/503 |
| 5,424,218 | 6/1995 | Miljanich et al. | 436/503 |

FOREIGN PATENT DOCUMENTS

| | | |
|---|---|---|
| 2085502 | of 0000 | Canada . |
| 0507170 | 3/1992 | European Pat. Off. . |
| 0556651 | 4/1993 | European Pat. Off. . |
| 8907608 | 8/1989 | WIPO . |
| 8909834 | 10/1989 | WIPO . |
| 9113077 | 9/1991 | WIPO . |
| 9308469 | 4/1993 | WIPO . |
| 9504144 | 2/1995 | WIPO . |

OTHER PUBLICATIONS

Pragnell, et al., "Cloning and tissue–specific expression of the brain calcium channel β–subunit," *FEBS Letters*, 291: 253 (1991).

DeJongh, et al., "Subunits of purified calcium channels," *J.Biol.Chem.*, 265(25): 14738–14741 (1990). (Best available copy, sufficiently legible for applicant to read).

Carbone, et al., "Ca currents in human neuroblastoma IMR32 cells: kinetics, permeability and pharmacology," *Pfluegers Arch.* 416:170–179 (1990).(Best available copy, sufficiently legible for applicant to read).

Snutch, T. P., et al. (1990) Proc. Natl. Acad. Sci. USA 87: 3391–95.

Young, R. A., et al. (1993) *ibid.* 80: 1194–98.

Sharp, A. H., et al. (1989) J. Biol. Chem. 264: 2816–25.

Sambrook, J., et al. (1987) Molecular Cloning: a Laboratory Manual, 2nd Ed. Cold Spring Harbor (NY) Press. Chapter 11 (Selected Pages).

Powers et al, (1991) Assignment of the Human Gene for the $\alpha_1$ Subunit of the Cardiac DHP–Sensitive $Ca^{2+}$ Channel (CCHL1A1) to Chromosome 12p 12–pter *Genomics 10*:835–839.

Bosse et al., "The cDNA and deduced amino acid sequence of the γ subunit of the L–type calcium channel from rabbit skeletal mauscle," *FEBS*, 267(1):153–156 (1990).

Burns, et al., "Calcium channel activity of purified human synexin and structure of the human synexin gene," *P.N.A.S.* 86:3798–3802 (1989).

Campbell et al., "32,000–Dalton subunit ofthe 1, 4–dihydropyridine receptor," *Ann. N.Y. Acad. Sci.*, 560:251–257 (1989).

Dascal, N., "The use of *Xenopus* oocytes for the study of ion channels," *CRC Critical Rev. Biochem.*, 22(4):317–387 (1987).

Jay et al., "Primary Structure of the γ subunit of the DHP–sensitive calcium cahnnel from skeletal muscle," *Science*, 248:490–492 (1990).

Jay et al., "Structural characterization of the dihydropyridine–sensitive calcium channel $\alpha_2$–subunit and the associated δ peptides," *J. Biol. Chem.*, 266(5): 3287–3293 (1991).

Starr et al., "Primary structure of a calcium channel that is highly expressed in the rat cerebellum," *P.N.A.S.*, 88:5621–5625 (1991).

Ahlijanian et al., "Subunit structure and localization of dihydropyridine–sensitive calcium channels in mammalian brain, spinal cord, and retina," *Neuron*, 4:819–832 (1990).

Blount et al., "Assembly Intermediates of the Mouse Muscle Nicotinic Acetylcholine Receptor in Stably Transfected Fibroblasts," *J. Cell. Biol.*, 111:2601 (1990).

Dascal et al., "Expression of modulation of voltage–gated calcium channels after RNA injection in *Xenopus* oocytes," *Science*, 231:1147–1150 (1986).

(List continued on next page.)

*Primary Examiner*—David L. Fitzgerald

*Attorney, Agent, or Firm*—Stephanie L. Seidman; Brown Martin Haller and McClain

[57] ABSTRACT

Isolated DNA encoding each of human calcium channel $\alpha_1$-, $\alpha_2$-, β- and γ-subunits, including subunits that arise as splice variants of primary transcripts, is provided. Cells and vectors containing the DNA and methods for identifying compounds that modulate the activity of human calcium channels are also provided.

64 Claims, 4 Drawing Sheets

OTHER PUBLICATIONS

Hess et al., "Calcium channels in vertebrate cells," *Ann. Rev. Neurosci.*, 13:337–356 (1990).

Stanley et al., "Characterization of a Calcium Current in a Vertebrate Cholinergic Presynaptic Nerve Terminal," *J. Neurosci.*, 11:985 (1991).

Wei, et al., "Heterologous regulation of the cardiac $Ca^{2+}$ channel $\alpha_1$ subunit by skeletal muscle β and γ subunits," *J. Biol. Chem.* 266:21943–21947 (1991).

Ahlijanian et al., "Phosphorylation of an α1–like subunit of an ω–conotoxin–sensitive brain clacium channel by cAMP–dependent protein kinase and protein kinase C," *J. Biol. Chem.*, 266:20192 (1991).

Hullin et al., "Calcium channel β subunit heterogeneity: functional expression of cloned cDNA from heart, aorta and brain," *EMBO J.*, 11:885 (1992).

Kim et al., "Rat brain expresses an alternatively spliced form of the dihydropyridine–sensitive L–type calcium channel α2 subunit," *P.N.A.S.*, 89:3251 (1992).

Sakamoto et al., "A Monoclonal Antibody to the β Subunit of the Skeletal Muscle Dihydropyridine Receptor Immunoprecipitates the Brain ω–Conotoxin GVIA Receptor," *J. Biol. Chem.*, 266:18914 (1991).

Tsien et al., "Molecular diversity of voltage–dependent $ca^{2+}$ channels,"*Trends in Pharmacol. Sci.*, 12:349 (1991).

Cruz, L. J. et al. (1987) Biochem 26 : 820–24.

Breitbart, R. E, et al. (1987) Ann. Rev. Biochem. 56 : 467–95.

Claudio, T. (1987) Proc. Natl. Acad. Sci. USA 84: 5967–71.

Seager, M.J., et al. (1988) Ann. NY Acad. Sci. 522: 162–75.

Vaghy, P. L., et al. (1988) ibid., 176–86.

Leung, A. T., et al. (1988) ibid., 43–46.

Kim et al., "IgG from patients with Lambert–Eaton syndrome blocks voltage–dependent calcium channels," *Science*, 239:405–408 (1988).

Claudio et al., "Genetic reconstitution of functional acetylcholine receptor channels in mouse fibroblasts,"*Science*, 238:1688–1694 (1987).

Tanabe et al., "Primary structure of the receptor for calcium channel blockers from skeletal muscle," *Nature* 328:313–318 (1987).

Nakayama et al., "Purification of a putative $ca^{2+}$ channel protein from rabbit skeletal muscle," *J. Biol. Chem.*, 262:6572–6576 (1987).

Vaghy et al., "Identification of a novel 1,4–dihydropyridine–and phenylalkylamine–binding polypeptide in calcium channel preparations," *J. Biol. Chem.*, 262(29):14337–14342 (1987).

Leung et al., "Structural characterization of the 1,4–dihydropyridine receptor of the voltage–dependent $Ca^{2+}$ channel from rabbit skeletal muscle," *J. Biol. Chem.*, 262(17):7943–7946 (1987).

Takahashi et al., "Subunit structure of dihydropyridine–sensitive calcium channels from skeletal muscle," *Proc. Natl. Acad. Sci (USA)*, 84:5478–5482 (1987).

Takahashi and Catterall, "Dihydropyridine–sensitive calcium channels in cardiac and skeletal muscle membranes: studies with antibodies against the α–subunits," *Biochemistry*, 26(17):5518–5526 (1987).

Morton and Froehner, "Monoclonal antibody identifies a 200–kDA subunit of the dihydropyridine–sensitive calcium channel," *J.Biol. Chem.*, 262(25):11904–11907 (1987).

Barhanin et al., "The calcium channel antagonists receptor from rabbit skeletal muscle: reconstitution after purification and subunit characterization," *Eur. J. Biochem.*, 164:525–531 (1987).

Sieber et al., "The 165–kDA peptide of the purified skeletal muscle dihydropyridine receptor contains the known regulatory sites of the calcium channel," *Eur. J. Biochem.*, 167:117–122 (1987).

Lang et al., "The effect of myasthenic syndrome antibody on presynaptic calcium channels in the mouse," *J. Physiol.*, 390:257–270 (1987).

Curran and Morgan, "Barium modules c–fos expression and post–translational modification," *Proc. Natl. Acad. Sci.*, 83:3521–8524 (1986).

Fisch et al., "c–fos sequences necessary for basal expression and induction by epidermal growth factor, 12–0–tetradecanoyl phorbol–13–acetate, and the calcium ionophore," *Mol. Cell. Biol.*, 7(10):3490–3502 (1987).

Noda et al., "Existence of distinct sodium channel messenger RNAs in rat brain," *Nature*, 320:188–192 (1986).

Noda et al., "Expression of functional sodium channels from cloned cDNA," *Nature*, 322:826–828 (1986).

Mierendorf et al., "Gene isolation by screening κgtll libraries with antiboides," *Methods in Enz.*, 152:458–469 (1986).

Gustin et al., "Ion channels in yeast," *Science*, 233:1195–1197 (1986).

Striessnig et al., "Photoaffinity labelling of the phenylalkylamine receptor of the skeletal muscle transverse–tubule calcium channel," *FEBS Letters*, 212:(2)247–253 (1987).

Froehner, New insights into the molecular structure of the dihydropyridine–sensitive calcium channel,: *TINS*, 11(3):90–92 (1968).

Catterall et al., "Molecular properties of dihydropyridine–sensitive calcium channels in skeletal muscle," *J. Bio. Chem.*, 263(8):3535–3538 (1988).

Curtis et al., "Purification of the calcium anatagonist receptor of the voltage–sensitive calcium channel from skeletal muscle transverse tubules," *Biochemistry*, 23(10):211–2118 (1984).

Borsotto et al., "The 1,4–dihydropyridine receptor associated with the skeletal muscle voltage–dependent $ca^{2+}$ channel," *J. Biol. Chem.*, 260(26):14255–14263 (1985).

Cooper et al., "Purification and characterization of the dihydropyridine–sensitive voltage–dependent calcium channel from cardiac tissue," *J. Biol. Chem.*, 262(2):509–512 (1987).

Wood, "Gene cloning based on long oligonucleotide probes," *Methods in Enzymology*, 152:443–447 (1987).

Schmidt et al., "Immunochemical analysis of subunit structure of 1,5–dihydropyridine receptors associated with voltage–dependent $Ca^{2+}$ channels in skeletal, cardiac, and smooth muscles," *Biochemistry*, 25:3492–3495 (1986).

Mishina et al., "Location of functional regions of acetylcholine receptor α–subunit by site–directed mutagenesis," *Nature*, 313:364–369 (1985).

Hamill et al., "Improved patch–clamp techniques for high–resolution current recording from cells and cell–free membrane patches," *Pfluger Archiv. European Journal of Physiology*, 391:85–100 (1981).

Hess et al., "Different modes of Ca channel gating behvior favored by dihydropyridine Ca agoinst and antagonists," *Nature*, 311:538–544 (1984).

Leung et al., "Biochemical and ultrastructural characterization of the 1,4–dihydropyridine receptor from rabbit skeletal muscle," *J. of Biol. Chem.*, 263(2):994–1001 (1988).

Imagawa et al., "Phosphorylation of the 1,4–dihydroyridine receptor of the voltage–dependent $Ca^{2+}$ channel by an intrinsic protein kinase in isolated triads from rabbit skeletal muscle," *J. of Biol. Chem.*, 262(17):8333–8339 (1987).

Miller, Multiple calcium channels and neuronal function, *Science*, 235:46–52 (1987).

Kozak, "An analysis of 4'–noncoding sequences from 699 vertebrate messenger RNAs," *Nucleic Acids Research*, 15(20):8125–8148 (1987).

von Heijne, "Signal sequences: the limits of variation," *Jour. of Mol. Biol.*, 184:99–105 (1985).

Hubbard et al., "Synthesis and processing of asparagine–linked oligosaccharides[1,2]," *Ann. Rev. Biochem.*, 50:555–583 (1981).

Feramisco et al., "Optimal spatial requirements for the location of basic residues in peptide substrates for the cyclic AMP–dependent protein kinase," *Journal of Biological Chemistry*, 255(9):4240–4235 (1980).

Takahashi et al., "Identification of an α subunit of dihydropyridine–sensitive brain calcium channels," *Science*, 236:88–91 (1987).

Hofmann et al., "Regulation of the L–type calcium channel," *TIPS*, 8:393–398 (1987).

Curtis et al., "Reconstitution of the voltage–sensitive calcium channel purified from skeletal muscle transverse tubules," *Biochemistry*, 25:3077–3083 (1986).

Smith et al., "Calcium channel activity in a purified dihydropyridine–receptor preparation of skeletal muscle," *Biochemistry*, 26:7182–7188 (1987).

Meshi et al., "Nucleotide sequence of the 30K protein cistron of cowpea strain of tobacco mosaic virus," *Nucleic Acids Research*, 10(19):6111–6117 (1982).

Nikaido et al., "Molecular cloning of cDNA encoding human interleukin–2 receptor," *Nature*, 311:631–636 (1984).

Roberts et al., "Paraneoplastic myasthenic syndrome IgG inhibits $^{45}Ca^{2+}$ flux in a human small cell carcinoma line," *Nature*, 317:737–739 (1995).

Starr et al., "Primary structure of a calcium channel that is highly expressed in rat cerebellum," *Proc. Natl. Acad. Sci. USA* 88:5621–5625 (1991).

Snutch et al., "Distinct calcium channels are generated by alternative splicing and are differentially expressed in the mammaliam CNS," *Neuron*, 7:45–57 (1991).

Hui et al., "Molecular cloning of multiple sybtypes of a novel rat brain isoform of the $a_1$ subunit of the voltage–dependent calcium channel," *Neuron*, 7:35–44 (1991).

Bean et al., "Classes of calcium channels in vertebrate cells," *Ann. Rev. Physiol.*, 51:367–384 (1989).

Swandulla et al., "Docalcium channel classifications account for neuronal calcium channel diversity?" *TINS*, 14(2):46–51 (1991).

Ruth et al.., "Primary structure of the β subunit of the DHP–sensitive calcium channel from skeletal muscle," *Science*, 245:1115–1118 (1989).

Mikami et al., "Primary structure and functional expression of the cardiac dihydropyridine–sensitive calcium channel," *Nature*, 340:230–233 (1989).

Biel et al., "Primary stucture and functional expression of a high voltage activated calcium channel from rabbit lung," *FEBS Letters*, 269(2):409–412 (1990).

Mori et al., "Primary structure and functional expression from complementary DNA of a brain calcium channel," *Nature*, 350:398–402 (1991).

Snutch et al., "Rat brain expresses a heterogeneous family of calcium channels," *Proc. Natl. Acad. Sci. USA*, 87:3391–3395 (1990).

Perez–Reyes et al., "Molecular diversity of L–type calcium channels," *J. of Biol. Chem.*, 265(33):20430–20436 (1990).

Perez–Reyes, et al., "Induction of calcium currents by the expression of the $\alpha_1$–subunit of the dihydropyridine receptor from skeletal muscle," *Nature*, 340:233–236 (1989).

Koch et al., "Characterization of cDNA clones encoding two putative isoforms of the $\alpha_1$–subunit of the dihydropyridine–sensitive voltage–dependent calcium channel isolated from rat brain and rat aorta," *FEBS Letters*, 250(2):386–388 (1989).

Slish et al., "Evidence for the existence of a cardiac specific isoform of the $\alpha_1$–subunit of the voltage dependent calcium channel," *FEBS Letters*, 250(2):509–514 (1989).

Varadi et al., "Developmental regulation of expression of the $\alpha_1$ and $\alpha_2$ subunits mRNAs of the voltage–dependent calcium channel in a differentiating myogenic cell line," *FEBS Letters*, 250 (2)CE:515–518 (1989).

Ruth et al., "Primary structure of the α–subunit of the DHP–sensitive calcium channel from skeletal muscle," *Science*, 245:1115–1118 (1989).

Jongh et al., "Subunits of purified calcium channels: a 212–kDa form of $\alpha_1$ and partial amino acid sequence of a phosphorylation site of an independent β–subunit," *Proc. Natl. Acad. Sci. USA*, 86:8585–8589 (1989).

Hamilton et al., "Subunit composition of the purified dihydropyridine binding protein from skeletal muscle," *Biochemistry*, 28:7820–7828 (1989).

Nunoki et al., "Activation of purified calcium channels by stoichiometric protein phosphorylation," *proc. Natl. Acad. Sci. USA*, 86:6816–6820 (1989).

Ichida et al., "Photoaffinity labeling with dihydropyridine derivatives of crude membranes from rat skeletal, cardiac, ileal, and uterine muscles and whole brain," *J. Biochem.*, 105:767–774 (1989).

Sharp and Campbell, "Characterization of the 1.4–dihydropyridine receptor using subunit–specific polyclonal antibodies," *J. Bio. Chem.*, 264(5):2816–2825 (1989).

Campbell et al., "The biochemistry and molecular biology of the dihydropyridine–sensitive calcium channel," *TINS*, 11(10):425–430 (1988).

Pelzer et al., "Properties and regulation of calcium channels in muscle cells," *Rev. Physiol. Biochem. Pharmacol.*, 114:107–207 (1990).

Kim et al., "Studies on the structural requirements for the activity of the skeletal muscle dihydropyridine receptor/ slow $CA^{2+}$ channel," *J. Biol. Chem.*, 265(20):11858–11863 (1990).

Lotan et al., "Specific block of calcium channel expression by a fragment of dihydropyridine receptor cDNA," *Science*, 243:666–669 (1989).

Rampe et al., "[$^3$H]Pn200–110 binding in a fibroblast cell line transformed with the $\alpha_1$ subunit of the skeletal muscle L–type $Ca^{2+}$ channel," *Biochem. and Biophys. Research Communications*, 169(3):825–831 (1990).

Adams et al., "Intramembrane charge movement restored in dysgenic skeletal muscle by injection of dihydropyridine receptor cDNAs," *Nature*, 346:569–572 (1990).

Tanabe et al., "Cardiac–type excitation–contraction coupling in dysgenic skeletal muscle injected with cardiac dihydropyridine receptor cDNA," *Nature*, 344:451–453 (1990).

Tanabe et al., "Regions of the skeletal muscle dihydropyridine receptor critical for excitation–contraction coupling," *Nature*, 346:567–569 (1991).

Regulla et al., "Identification of the site of interaction of the dihydropyridine channel blockers nitrendipine and azidopine with the calcium–channel $\alpha_1$ subunit," *EMBO Journal*, 10(1):45–49 (1991).

Williams et al., "Structure and funtional expression of $\alpha_1$, $\alpha_2$, and β subunits of a novel human neuronal calcium channel subtype," *Neuron*, 8:71–84 (1992).

Olivera et al., "Conotoxins," *J. of Biol. Chem.*, 266(33):22067–22070 (1991).

Seino et al., "Cloning of $\alpha_1$ subunit of a voltage–dependent calcium channel expresed in pancreatic β cells," *Proc. Natl. Acad. Sci. USA*, 89:584–588 (1992).

Perez–Reyes et al., "Cloning and Expression of a Cardiac/Brain β subunit of the L–type calcium channel," *J. of Biol. Chem.*, 267(3):1792–1797 (1992).

Miller, R., "Voltage–sensitive $Ca^{2+}$ channels," *J. of Biol. Chem.*, 267(3):1403–1406 (1992).

Artalejo et al., "ω–Conotoxin GVIA blocks a $Ca^{2+}$ current in bovine chromaffin cells that is not of the 'classic' N type," *Neuron*, 8:85–95 (1992).

Kasai, H., "Tonic inhibition and rebound facilitation of a neuronal calcium channel by a GTP–binding protein," *Proc. Natl. Acad. Sci. USA*, 88:8855–8859 (1991).

Sher et al., "Voltage–operated calcium channels in small cell lung carcinoma cell lines: pharamacological, functional, and immunological properties," *Cancer Research*, 5:3892–3896 (1990).

Sher et al., "ω–Conotoxin binding and effects on calcium channel function in human neuroblastoma and rat pheochromocytoma cell lines," *FEBS Letters*, 235:(1,2):178–182 (1988).

Koch et al., "cDNA cloning of a dihydropyridine–sensitive calcium channel from rat aorta," *J. of Biol. Chem.*, 265(29):17786–17791 (1990).

Cohen et al., "Distribution of $Ca^{2+}$ channels on frog motor nerve terminals revealed by fluorescent ω–conotoxin," *J. of Neuroscience*, 11(4):1032–1039 (1991).

Brust, et al., "Human neuronal voltage–dependent calcium channels: studies on subunit structure and role in channel assembly," *Neuropharmacology* 32(11):1089–1102 (1993).

Williams, et al., "Structure and functional characterization of neuronal $\alpha_{1E}$ calcium channel subtypes," *J. Biol. Chem. 269 (35)* :22347–22357 (1994).

HUMAN CALCIUM CHANNEL α-1C/α-1D, α-2, β-1, AND γ SUBUNITS AND CELLS EXPRESSING THE DNA

This is a continuation of application Ser. No. 07/868,345, filed Apr. 10, 1992, now abandoned which is a continuation-in-part of U.S. Ser. No. 745,206, filed Aug. 15, 1991, now U.S. Pat. No. 5,429,921 which is a continuation-in-part of U.S. Ser. No. 620,250, filed Nov. 30, 1990, now abandoned, which is a continuation-in-part of U.S. Ser. No. 176,899, filed Apr. 4, 1988, now abandoned, and is also a continuation-in-part of U.S. Ser. No. 482,384, filed Feb. 20, 1990, now U.S. Pat. No. 5,386,025 and is also a continuation-in-part of U.S. Ser. No. 603,751, filed under 35 U.S.C. §371 on Nov. 8, 1990 now abandoned, which was based on International Application PCT/US89/01408, filed Apr. 4, 1988, now abandoned, which is a continuation-in-part of U.S. Ser. No. 176,899, filed Apr. 4, 1988, now abandoned.

TECHNICAL FIELD

The present invention relates to molecular biology and pharmacology. More particularly, the invention relates to calcium channel compositions and methods of making and using same.

BACKGROUND OF THE INVENTION

Calcium channels are membrane-spanning, multi-subunit proteins that allow controlled entry of $Ca^{2+}$ ions into cells from the extracellular fluid. Cells throughout the animal kingdom, and at least some bacterial, fungal and plant cells, possess one or more types of calcium channels.

The most common type of calcium channel is voltage dependent. All "excitable" cells in animals, such as neurons of the central nervous system, peripheral nerve cells, and muscle cells, including those of skeletal muscles, cardiac muscles, and venous and arterial smooth muscles, have voltage-dependent calcium channels.

In a voltage-dependent channel, the "opening" to allow an influx of $Ca^{2+}$ ions into the cells requires a depolarization to a certain level of the potential difference between the inside of the cell bearing the channel and the extracellular medium bathing the cell. The rate of influx of $Ca^{2+}$ into the cell depends on this potential difference.

Multiple types of calcium channels have been identified in mammalian cells from various tissues, including skeletal muscle, cardiac muscle, lung, smooth muscle and brain, [see, e.g., Bean, B. P. (1989) *Ann. Rev. Physiol.* 51:367–384 and Hess, P. (1990) *Ann. Rev. Neurosci.* 56:337]. The different types of calcium channels have been broadly categorized into four classes, L-, T-, N-, and P-type, distinguished by current kinetics, holding potential sensitivity and sensitivity to calcium channel agonists and antagonists. Four subtypes of neuronal voltage-dependent calcium channels have been proposed [Swandulla, D. et al. (1991) *Trends Neurosci.* 14:46].

At the present time, the rabbit skeletal muscle calcium channel is the most well-characterized of the calcium channels. It contains two large subunits, designated $\alpha_1$ and $\alpha_2$, which have molecular weights between about 130 and about 200 kilodaltons ("kD"), and a number, one to three, of different smaller subunits, of less than about 60 kD in molecular weight. At least one of the larger subunits and possibly some of the smaller subunits are glycosylated. Some of the subunits are capable of being phosphorylated.

The $\alpha_1$ subunit has a molecular weight of about 150 to about 170 kD when analyzed by sodium dodecylsulfate ("SDS")-polyacrylamide gel electrophoresis ("PAGE") after isolation from mammalian muscle tissue and has specific binding sites for various 1,4-dihydropyridines ("DHPs") and phenylalkylamines. Under non-reducing conditions (in the presence of N-ethylmaleimide), the $\alpha_2$ subunit migrates in SDS-PAGE as a band corresponding to a molecular weight of about 160–190 kD. Upon reduction, a large fragment, molecular weight about 130–150 kD, and smaller fragments are released. There is evidence that the $\alpha_2$ subunit and the large fragment produced under reducing conditions are glycosylated with at least N-linked sugars and do not specifically bind the 1,4-dihydropyridines and phenylalkylamines that specifically bind to the $\alpha_1$ subunit.

The β subunit of the rabbit skeletal muscle calcium channel has an apparent molecular mass of 52–65 kD (as determined by SDS-PAGE analysis). It contains consensus phosphorylation sites and has been shown by biochemical methods to be phosphorylated. This subunit is insensitive to reducing conditions. The γ subunit of the calcium channel is not observed in all purified preparations. It appears to be a glycoprotein with an apparent molecular mass of 30–33 kD, as determined by SDS-PAGE analysis.

Characterization of a particular type of calcium channel by analysis of whole cells is severely restricted by the presence of mixed populations of different types of calcium channels in the majority of cells. Although single-channel recording methods can be used to examine individual calcium channels, such analysis reveals nothing about the molecular structure or biochemical composition of the channel. Furthermore, in this type of analysis, the channel is isolated from other cellular constituents that might be important for natural functions and pharmacological interactions.

In order to study calcium channel structure and function, large amounts of pure channel protein are needed. Because of the complex nature of these multisubunit proteins, the varying concentrations of calcium channels in tissue sources of the protein, the presence of mixed populations of calcium channels in tissues, and the modifications of the native protein that can occur during the isolation procedure, it is extremely difficult to obtain large amounts of highly purified, completely intact calcium channel protein.

Characterization of the gene or genes encoding calcium channels provides another means of characterization of different types of calcium channels. The amino acid sequence determined based on the complete nucleotide sequence of the coding region of a gene encoding a calcium channel protein represents the actual primary structure of the protein. Furthermore, secondary structure of the calcium channel protein and the relationship of the protein to the membrane may be predicted based on analysis of the primary structure. For instance, hydropathy plots of the $\alpha_1$ subunit protein of the rabbit skeletal muscle calcium channel indicate that it contains four internal repeats, each containing six putative transmembrane regions [Tanabe, T. et al. (1987) *Nature* 328:313].

The cDNA and corresponding amino acid sequences of the $\alpha_1$, $a_2$, β and γ subunits of the rabbit skeletal muscle calcium channel have been determined [see, Tanabe et al. (1987) *Nature* 328:313–318; International Application No. WO 89/09834, filed in the national stage as U.S. application Ser. No. 07/603,751, now abandoned which is a continuation-in-part of U.S. application Ser. No. 07/176, 899; now abandoned Ruth et al. (1989) *Science* 245:1115–1118; and U.S. patent application Ser. No. 482, 384, filed Feb. 20, 1990 now U.S. Pat. No. 5386,025]. In addition, the cDNA and corresponding amino acid sequences of $\alpha_1$ subunits of rabbit cardiac muscle [Mikami, A. et al. (1989) *Nature* 340:230–233] and lung [Biel, M. (1990) *FEBS Letters* 269:409–412] calcium channels have been determined. In addition, cDNA clones encoding a rabbit brain calcium channel (designated the BI channel) have been isolated [Mori, Y. et al. (1991) *Nature* 350:398–402].

Partial cDNA clones encoding portions of several different subtypes, referred to as rat brain class A, B, C and D, of the calcium channel $\alpha_1$ subunit have been isolated from rat brain cDNA libraries [Snutch, T. et al. (1990) *Proc. Natl. Acad. Sci. USA* 87:3391–3395]. More recently full-length rat brain class A [Starr, T. et al. (1991) *Proc. Natl. Acad. Sci. USA* 88:5621–5625] and class C [Snutch, T. et al. (1991) *Neuron* 7:45–57] cDNA clones have been isolated. Although the amino acid sequence encoded by the rat brain class C DNA is approximately 95% identical to that encoded by the rabbit cardiac muscle calcium channel $\alpha_1$ subunit-encoding DNA, the amino acid sequence encoded by the rat brain class A DNA shares only 33% sequence identity with the amino acid sequence encoded by the rabbit skeletal or cardiac muscle $\alpha_1$ subunit-encoding DNA. A cDNA clone encoding another rat brain calcium channel $\alpha_1$ subunit has also been obtained [Hui, A. et al. (1991) *Neuron* 7:35–44]. The amino acid sequence encoded by this clone is ~70% homologous to the proteins encoded by the rabbit skeletal and cardiac muscle calcium channel DNA. A cDNA clone closely related to the rat brain class C $\alpha_1$ subunit-encoding cDNA and sequences of partial cDNA clones closely related to other partial cDNA clones encoding apparently different calcium channel $\alpha_1$ subunits have also been isolated [see Snutch, T. et al. (1991) *Neuron* 7:45–57; Perez-Reyes, E. et al. (1990) *J. Biol. Chem.* 265:20430; and Hui, A. et al. (1991) *Neuron* 7:35–44].

Successful expression of cDNA encoding calcium channel subunits has only been achieved with three of the six or seven different rabbit or rat $\alpha_1$ subunit cDNA clones discussed above. Voltage-dependent calcium currents have been detected in murine L cells transfected with DNA encoding the rabbit skeletal muscle calcium channel $\alpha_1$ subunit [Perez-Reyes et al. (1989) *Nature* 340:233–236 (1989)]. These currents were enhanced in the presence of the calcium channel agonist Bay K 8644. Bay K 8644-sensitive $Ba^{2+}$ currents have been detected in oöcytes injected with in vitro transcripts of the rabbit cardiac muscle calcium channel $\alpha_1$ subunit cDNA [Mikami, A. et al. (1989) *Nature* 340:230–233]. These currents were substantially reduced in the presence of the calcium channel antagonist nifedipine. Barium currents of an oöcyte co-injected with RNA encoding the rabbit cardiac muscle calcium channel $\alpha_1$ subunit and the RNA encoding the rabbit skeletal muscle calcium channel $\alpha_2$ subunit were more than 2-fold larger than those of oöcytes injected with transcripts of the rabbit cardiac calcium channel $\alpha_1$ subunit-encoding cDNA. Similar results were obtained when oöcytes were co-injected with RNA encoding the rabbit lung calcium channel $\alpha_1$ subunit and the rabbit skeletal muscle calcium channel $\alpha_2$ subunit. The barium current was greater than that detected in oöcytes injected only with RNA encoding the rabbit lung calcium channel $\alpha_1$ subunit [Biel, M. et al. (1990) *FEBS Letters* 269:409–412]. Inward barium currents have been detected in oöcytes injected with in vitro RNA transcripts encoding the rabbit brain BI channel [Mori et al. (1991) *Nature* 350:398–402]. These currents were increased by two orders of magnitude when in vitro transcripts of the rabbit skeletal muscle calcium channel $\alpha_2$, $\beta$, or $\alpha_2$, $\beta$ and $\gamma$ subunits were co-injected with transcripts of the BI-encoding cDNA. Barium currents in oöcytes co-injected with transcripts encoding the BI channel and the rabbit skeletal muscle calcium channel $\alpha_2$ and $\beta$ were unaffected by the calcium channel antagonists nifedipine or ω-CgTx and inhibited by Bay K 8644 and crude venom from *Agelenopsis aperta.*

The results of studies of recombinant expression of rabbit calcium channel $\alpha_1$ subunit-encoding cDNA clones and transcripts of the cDNA clones indicate that the $\alpha_1$ subunit forms the pore through which calcium enters cells. The relevance of the barium currents generated in these recombinant cells to the actual current generated by calcium channels containing as one component the respective $\alpha_1$ subunits in vivo is unclear. Because addition of in vitro transcripts of rabbit skeletal muscle calcium channel $\alpha_2$ and/or $\beta$ and $\gamma$-encoding cDNA significantly enhances the barium currents in the recombinant cells, it appears that in order to completely and accurately characterize and evaluate different calcium channel types, it is essential to examine the functional properties of recombinant channels containing all of the subunits as found in vivo.

Because calcium channels are present in various tissues and have a central role in regulating intracellular calcium ion concentrations, they are implicated in a number of vital processes in animals, including neurotransmitter release, muscle contraction, pacemaker activity, and secretion of hormones and other substances. These processes appear to be involved in numerous human disorders, such as central nervous system and cardiovascular diseases. Calcium channels, thus, are also implicated in numerous disorders.

Although there has been limited success in expressing DNA encoding rabbit and rat calcium channel subunits, far less has been achieved with respect to human calcium channels. Little is known about human calcium channel structure and function and gene expression. An understanding of the structure and function of calcium channels would permit identification of substances that, in some manner, modulate the activity of calcium channels and that have potential for use in treating such disorders.

A number of compounds useful for treating various cardiovascular diseases in animals, including humans, are thought to exert their beneficial effects by modulating functions of voltage-dependent calcium channels present in cardiac and/or vascular smooth muscle. Many of these compounds bind to calcium channels and block, or reduce the rate of, rate of influx of $Ca^{2+}$ into the cells in response to depolarization of the cell membrane.

An understanding of the pharmacology of compounds that interact with calcium channels in other organ systems, such as the central nervous system ("CNS"), will aid in the rational design of compounds that specifically interact with the specific subtypes of human calcium channels to have desired therapeutic effects, such as in the treatment of neurodegenerative and cardiovascular disorders. Such understanding and the ability to rationally design therapeutically effective compounds have been hampered by an inability to independently determine the types of human calcium channels and the molecular nature of individual subtypes, particularly in the CNS, and by the unavailability of pure preparations of specific channel subtypes to use for evaluation of the specificity of calcium channel-effecting compounds. Thus, identification of DNA encoding human calcium channel subunits and the use of such DNA for expression of calcium channel subunits and functional calcium channels would aid in screening and designing therapeutically effective compounds.

Therefore, it is an object herein, to provide DNA encoding tissue specific calcium channel subunits and to provide eukaryotic cells bearing recombinant human calcium channels. It is also an object to provide assays for identification of potentially therapeutic compounds that act as calcium channel antagonists and agonists.

SUMMARY OF THE INVENTION

Eukaryotic cells containing DNA encoding one or more human calcium channel subunits or containing RNA transcripts of cDNA clones encoding one or more of the subunits are provided. In preferred embodiments, the cells contain DNA or RNA encoding an $\alpha_1$ subunit, preferably at least an $\alpha_{1D}$ or $\alpha_{1B}$ subunit. In more preferred embodiments, the cells containing DNA or RNA encoding additional heterologous subunits, including at least one human β, $\alpha_2$ or γ subunits. In such embodiments, eukaryotic cells stably or transiently transfected with any combination of one, two, three or four of the subunit-encoding cDNA clones, such as $\alpha_1$, $\alpha_1$+β, $\alpha_1$+β+α, etc., are provided.

In preferred embodiments, the cells express such heterologous calcium channel subunits and include one or more of the subunits in membrane spanning heterologous calcium channels. In more preferred embodiments, the eukaryotic cells express functional, heterologous calcium channels which are capable of gating the passage of calcium channel selective ions and/or binding a compound, which at a physiological concentration modulates the activity of the heterologous calcium channel. The heterologous calcium channels of such cells are distinguishable from endogenous calcium channels of the host cell. In certain embodiments, the eukaryotic cells express that include at least one heterologous calcium channel subunit.

In most preferred embodiments, the calcium channels that are expressed on the surface of the eukaryotic cells are composed substantially or entirely of subunits encoded by the heterologous DNA or RNA.

In certain embodiments the recombinant eukaryotic cells are produced by transfection with DNA encoding one or more of the subunits or are injected with RNA transcripts of cDNA encoding human calcium channel subunits. The DNA may be introduced as a linear DNA fragment or may be included in an expression vector for stable or transient expression of the subunit-encoding DNA. Vectors containing DNA encoding human calcium channel subunits are also provided.

The eukaryotic cells that express heterologous receptors may be used in assays for calcium channel function or, in the case of cells transformed with fewer subunit-encoding nucleic acids than necessary to constitute a functional recombinant human calcium channel, such cells may be used to assess the effects of additional subunits on calcium channel activity. The additional subunits can be provided by subsequently transfecting such a cell with one or more DNA clones or RNA transcripts encoding human calcium channel subunits.

In preferred embodiments, the recombinant eukaryotic cells may be used in methods for identifying compounds that modulate calcium channel activity. In particular, the cells are used in assays that identify agonists and antagonists of calcium channel activity in humans and/or assessing the contribution of the various calcium channel subunits to the transport and regulation of transport of calcium ions.

Assays using the eukaryotic cells for identifying compounds that modulate calcium channel activity are provided.

Isolated and purified DNA fragments that encode human calcium channel subunits are provided. DNA encoding $\alpha_1$ subunits of a human calcium channel, and RNA, encoding such subunits, made upon transcription of such DNA are provided. In particular, DNA fragments encoding $\alpha_1$ subunits of voltage-dependent human calcium channels type B (also referred to as voltage-dependent calcium channel (hereinafter VDCC) IV), type C (also referred to as VDCC II) and type D (also referred to as VDCC III) are provided.

In particular, DNA encoding an $\alpha_{1D}$ subunit that includes the amino acids substantially as set forth as residues 10–2161 of sequence ID No. 1 is provided. DNA encoding an $\alpha_{1D}$ subunit that includes substantially the amino acids set forth as Sequence ID No. 23 is also provided. DNA encoding an $\alpha_{1C}$ subunit that includes the amino acids substantially as set forth in sequence ID No. 3 or sequence ID No. 6 and DNA encoding an $\alpha_{1B}$ subunit that includes an amino acid sequence substantially as set forth in sequence ID No. 8 or in sequence ID No. 7 are also provided.

DNA encoding $\alpha_2$ subunits of a human calcium channel, and RNA, encoding such subunits, made upon transcription of such a DNA are provided. DNA encoding splice variants of the $\alpha_2$ subunit, including tissue specific splice variants are also provided. In particular, DNA encoding the $\alpha_{2a}$–$\alpha_{2e}$ subunit subtypes is provided. In particularly preferred embodiments, the DNA encoding the $\alpha_2$ subunit is produced by alternative processing of a primary transcript that includes DNA encoding the amino acids set forth in sequence ID Sequence ID No. 20.

Isolated and purified DNA fragments encoding human calcium channel β subunits, including DNA encoding β subunit splice variants are provided. In particular, DNA encoding the subunit splice variants $\beta_1$–$\beta_5$ (alternatively devoted $\beta_{1-1}$ through $\beta_{1-5}$, respectively) is provided. RNA, encoding β subunits, made upon transcription of the DNA is also provided.

In particular, DNA encoding a β subunit that is produced by alternative processing of a primary transcript that includes DNA encoding the amino acids set forth in sequence ID No. 19 is provided. DNA encoding a β subunit that is encoded by a transcript that lacks one or more of the following sequences of nucleotides: nucleotides 14–34 of Sequence ID No. 12, nucleotides 13–34 of Sequence ID No. 12, nucleotides 35–55 of Sequence ID No 12, nucleotides 56–190 of Sequence ID No. 12 or nucleotides 191–271 of Sequence ID No. 12 is also provided.

DNA encoding γ subunits of human calcium channels is also provided. RNA, encoding γ subunits, made upon transcription of the DNA are also provided. In particular, DNA containing the sequence of nucleotides set forth in Sequence ID No. 14 is provided.

Full-length DNA clones and corresponding RNA transcripts, encoding the $\alpha_{1d}$, $\alpha_{1B}$, $\alpha_2$ and β subunits of human calcium channels are provided. Also provided are DNA clones encoding substantial and significant portions of $\alpha_{1C}$ and γ subunits of voltage-dependent human calcium channels for the preparation of full-length DNA clones encoding $\alpha_{1C}$ and γ subunits.

Nucleic acid probes containing at least about 14 contiguous nucleotides of an $\alpha_{1D}$, $\alpha_{1C}$, $\alpha_{1B}$, $\alpha_2$, β or γ subunit DNA are provided. Methods using the probes for the isolation and cloning of calcium channel subunit-encoding cDNA, including splice variants within tissues and inter-tissue variants are also provided.

In other embodiments, purified human calcium channel subunits and purified human calcium channels are provided. The subunits and receptors can be isolated from a eukaryotic cell transfected with DNA that encodes the subunit.

In another embodiment, immunoglobulins or antibodies obtained from the serum of an animal immunized with a substantially pure preparation of a human calcium channel, human calcium channel subunit or epitope-containing fragment of a human calcium subunit are provided. Monoclonal antibodies produced using a human calcium channel, human calcium channel subunit or epitope-containing fragment thereof as an immunogen are also provided. *Escherichia coli* fusion proteins including a fragment of a human calcium channel subunit may also be used as immunogen. Such fusion proteins may contain a bacterial protein or portion thereof, such as the *E. coli* TrpE protein, fused to a calcium channel subunit peptide. The immunoglobulins that are produced using the calcium channel subunits or purified calcium channels as immunogens have, among other properties, the ability to specifically and preferentially bind to and/or cause the immunoprecipitation of a human calcium channel or a subunit thereof which may be present in a biological sample or a solution derived from such a biological sample.

A diagnostic method for determining the presence of Lambert Eaton Syndrome (LES) in a human, based on immunological reactivity of LES immunoglobulin G (IgG) with a human calcium channel subunit or a eukaryotic cell which expresses a recombinant human calcium channel subunit, is also provided. In particular, an immunoassay method for diagnosing Lambert-Eaton Syndrome in a person by combining serum from the person (test serum) with $\alpha_1$ subunit of a human calcium channel and $\alpha_2$ subunit of a human calcium channel and ascertaining whether antibodies in the test serum react with one or both of the subunits, or a recombinant cell which expresses one or both of the subunits to a greater extent than antibodies in control serum (e.g., from a person or group of persons known to be free of the Syndrome) is provided. Any immunoassay procedure known in the art for detecting antibodies against a given antigen in serum can be employed in the method.

DETAILED DESCRIPTION OF THE INVENTION

Definitions

Figure 1:
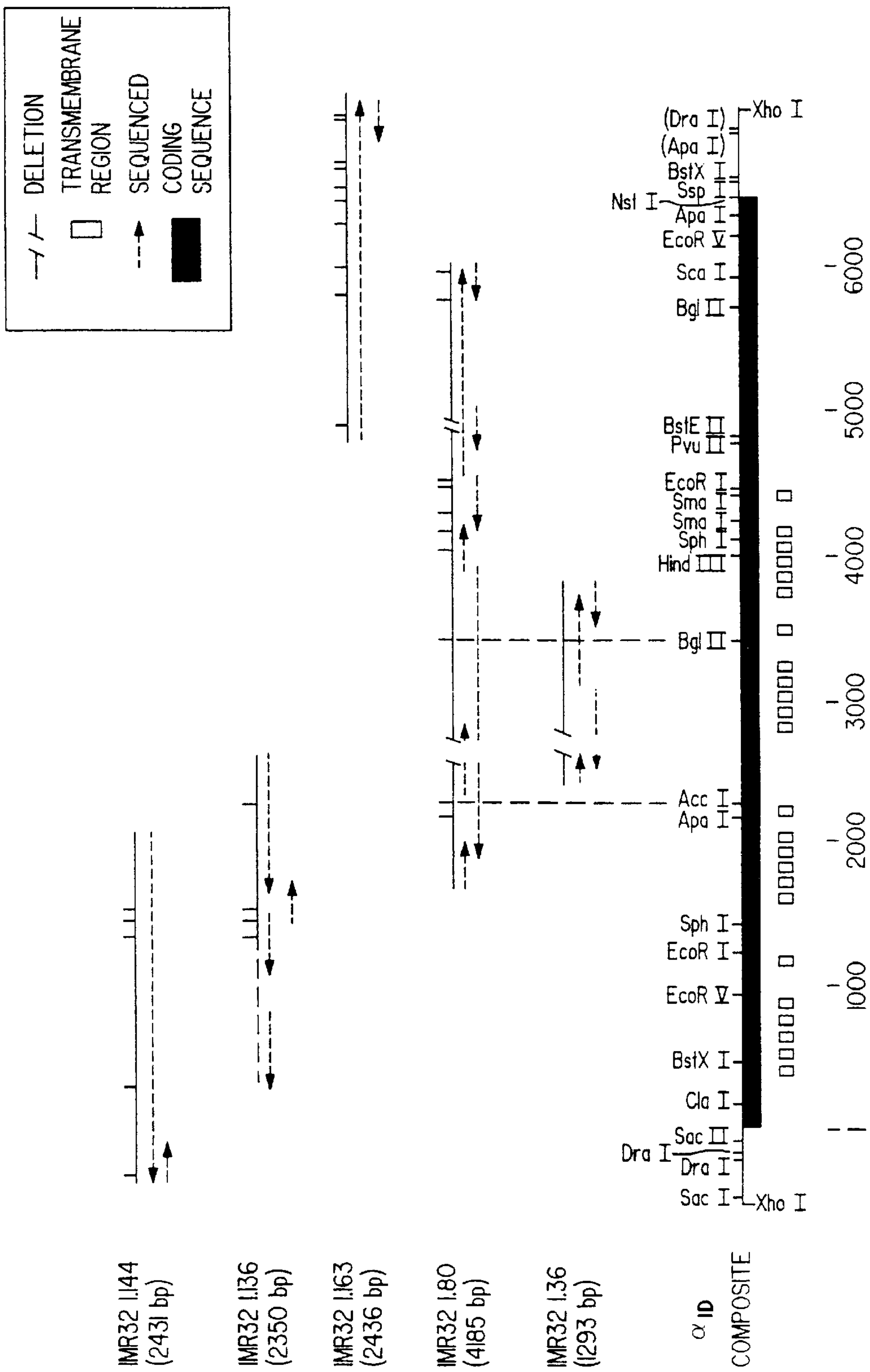
FIG. 1 represents a restriction map of a nucleic acid sequence encoding a human neuronal calcium channel $\alpha_{1D}$ subunit and the sequencing strategy used to derive the complete coding sequence from various partial cDNA clones.

Unless defined otherwise, all technical and scientific terms used herein have the same meaning as is commonly understood by one of skill in the art to which this invention belongs. All patents and publications referred to herein are incorporated by reference herein.

As used herein, the $\alpha_1$ subunit types are designated as type $\alpha_{1B}$, $\alpha_{1C}$, and $\alpha_{1D}$. These subtypes may also be also referred to as VDCC IV, VDCC II and VDCC III, respectively. Subunit subtypes, which are splice variants, are referred to, for example as $\alpha_{1B-1}$, $\alpha_{1B-2}$. Subtypes of the $\beta$ subunit that arise as splice variants are designated with a numerical subscript, such as $\beta_1$. Subtypes of the $\alpha_2$ subunit that arise as splice variants are designated by lower case letter, such as $\alpha_{2a}$, . . . $\alpha_{2c}$.

As used herein, a splice variant refers to a variant produced by differential processing of a primary transcript of genomic DNA that results in more than one type of mRNA. Splice variants may occur within a single tissue type or among tissues (tissue-specific variants). Thus, cDNA clones that encode calcium channel subunit subtypes that have different amino acid sequences are referred to herein as "splice variants".

As used herein, a "calcium channel selective ion" is an ion that is capable of flowing through, or being blocked from flowing through, a calcium channel which spans a cellular membrane under conditions which would substantially similarly permit or block the flow of $Ca^{2+}$. $Ba^{2+}$ is an example of an ion which is a calcium channel selective ion.

As used herein, a compound that modulates calcium channel activity is one that affects the ability of the calcium channel to pass calcium channel selective ions. Such compounds include calcium channel antagonists and agonists and compounds that exert their effect on the activity of the calcium channel directly or indirectly.

As used herein, a "substantially pure" subunit or protein is a subunit or protein that is sufficiently free of other polypeptide contaminants to appear homogeneous by SDS-PAGE or to be unambiguously sequenced.

As used herein, heterologous or foreign DNA and RNA are used interchangeably and refer to DNA or RNA that does not occur naturally as part of the genome in which it is present or which is found in a location or locations in the genome that differ from that in which it occurs in nature. It is DNA or RNA that is not endogenous to the cell and has been artificially introduced into the cell. Examples of heterologous DNA include, but are not limited to, DNA that encodes a calcium channel subunit and DNA that encodes RNA or proteins that mediate or alter expression of endogenous DNA by affecting transcription, translation, or other regulatable biochemical processes. The cell that expresses the heterologous DNA, such as DNA encoding the calcium channel subunit, may contain DNA encoding the same or different calcium channel subunits. The heterologous DNA need not be expressed and may be introduced in a manner such that it is integrated into the host cell genome or is maintained episomally.

As used herein, operative linkage of heterologous DNA to regulatory and effector sequences of nucleotides, such as promoters, enhancers, transcriptional and translational stop sites, and other signal sequences, refers to the functional relationship between such DNA and such sequences of nucleotides. For example, operative linkage of heterologous DNA to a promoter refers to the physical and functional relationship between the DNA and the promoter such that the transcription of such DNA is initiated from the promoter by an RNA polymerase that specifically recognizes, binds to and transcribes the DNA in reading frame.

As used herein, isolated, substantially pure DNA refers to DNA fragments purified according to standard techniques employed by those skilled in the art [see, e.g., Maniatis et al. (1982) *Molecular Cloning: A Laboratory Manual*, Cold Spring Harbor Laboratory Press, Cold Spring Harbor, N.Y.].

As used herein, expression refers to the process by which nucleic acid is transcribed into mRNA and translated into peptides, polypeptides, or proteins. If the nucleic acid is derived from genomic DNA, expression may, if an appropriate eukaryotic host cell or organism is selected, include splicing of the mRNA.

As used herein, vector or plasmid refers to discrete elements that are used to introduce heterologous DNA into cells for either expression of the heterologous DNA or for replication of the cloned heterologous DNA. Selection and use of such vectors and plasmids are well within the level of skill of the art.

As used herein, expression vector includes vectors capable of expressing DNA fragments that are in operative linkage with regulatory sequences, such as promoter regions, that are capable of effecting expression of such DNA fragments. Thus, an expression vector refers to a recombinant DNA or RNA construct, such as a plasmid, a phage, recombinant virus or other vector that, upon introduction into an appropriate host cell, results in expression of the cloned DNA. Appropriate expression vectors are well known to those of skill in the art and include those that are replicable in eukaryotic cells and/or prokaryotic cells and those that remain episomal or may integrate into the host cell genome.

As used herein, a promoter region refers to the portion of DNA of a gene that controls transcription of DNA to which it is operatively linked. The promoter region includes specific sequences of DNA that are sufficient for RNA polymerase recognition, binding and transcription initiation. This portion of the promoter region is referred to as the promoter. In addition, the promoter region includes sequences that modulate this recognition, binding and transcription initiation activity of the RNA polymerase. These sequences may be cis acting or may be responsive to trans acting factors. Promoters, depending upon the nature of the regulation, may be constitutive or regulated.

As used herein, a recombinant eukaryotic cell is a eukaryotic cell that contains heterologous DNA or RNA.

As used herein, a recombinant or heterologous calcium channel refers to a calcium channel that contains one or more subunits that are encoded by heterologous DNA that has been introduced into and expressed in a eukaryotic cells that expresses the recombinant calcium channel. A recombinant calcium channel may also include subunits that are produced by DNA endogenous to the cell. In certain embodiments, the recombinant or heterologous calcium channel may contain only subunits that are encoded by heterologous DNA.

As used herein, "functional" with respect to a recombinant or heterologous calcium channel means that the channel is able to provide for and regulate entry of calcium channel selective ions (e.g., $Ca^{2+}$ or $Ba^{2+}$) in response to a stimulus and/or bind ligands with affinity for the channel, and that such calcium channel activity is distinguishable (e.g., electrophysiologically, pharmacologically, etc.) from any identified endogenous calcium channel activity that might be present in the host cell.

As used herein, a peptide having an amino acid sequence substantially as set forth in a particular Sequence ID No. includes peptides that have the same function but may include minor variations in sequence, such as conservative amino acid changes or minor deletions or insertions that do not alter the activity of the peptide. The activity of a calcium channel receptor subunit peptide refers to its ability to form functional calcium channels with other such subunits.

As used herein, a physiological concentration of a compound is that which is necessary and sufficient for a biological process to occur. For example, a physiological concentration of a calcium channel selective ion is a concentration of the calcium channel selective ion necessary and sufficient to provide an inward current when the channels open.

As used herein, activity of a calcium channel refers to the movement of a calcium selective ion through a calcium channel. Such activity may be measured as the amount of current which flows through the recombinant channel in response to a stimulus.

As used herein, a "functional assay" refers to an assay that identifies functional calcium channels. A functional assay, thus, is an assay to assess function.

As understood by those skilled in the art, assay methods for identifying compounds, such as antagonists and agonists, that modulate calcium channel activity, generally requires comparison to a control. One type of a "control" cell or "control" culture is a cell or culture that is treated substantially the same as the cell or culture exposed to the test compound except that the control culture is not exposed to the test compound. Another type of a "control" cell or "control" culture may be a cell or a culture of cells which are identical to the transfected cells except the cells employed for the control culture do not express functional calcium channels. In this situation, the response of test cell to the test compound compared to the response (or lack of response) of the receptor-negative cell to the test compound, when cells or cultures of each type of cell are exposed to substantially the same reaction conditions in the presence of the compound being assayed. For example, in methods that use patch clamp electrophysiological procedures, the same cell can be tested in the presence and absence of the test compound, by changing the external solution bathing the cell as known in the art.

Assays for identifying compounds that modulate calcium channel activity and assays for diagnosing Lambert-Eaton Syndrome Assays for identifying compounds that modulate calcium channel activity In vitro methods for identifying compounds, such as calcium channel agonist and antagonists, that modulate the activity of calcium channels using eukaryotic cells that express heterologous human calcium channels are provided.

In particular, the assays use eukaryotic cells that express heterologous human calcium channel subunits encoded by heterologous DNA provided herein, for screening potential calcium channel agonists and antagonists which are specific for human calcium channels and particularly for screening for compounds that are specific for particular human calcium channel subtypes. Such assays may be used in conjunction with methods of rational drug design to select among agonists and antagonists, which differ slightly in structure, those particularly useful for modulating the activity of human calcium channels, and to design or select compounds that exhibit tissue specific calcium channel antagonist and agonist activities.

These assays should accurately predict the relative therapeutic efficacy of a compound for the treatment of certain disorders in humans. In addition, since tissue specific calcium channel subunits are provided, cells with tissue specific recombinant calcium channels may be prepared and used in assays for identification of human calcium channel subtype-specific drugs.

The assays involve contacting the cell membrane of a recombinant eukaryotic cell which expresses at least one subunit of a human calcium channel, preferably at least an $\alpha_1$ subunit of a human calcium channel, with a test compound and measuring the ability of the test compound to specifically bind to the membrane or alter or modulate the activity of a heterologous calcium channel on the membrane.

In preferred embodiments, the assay uses a recombinant cell which has a calcium channel containing an $\alpha_1$ subunit of a human calcium channel in combination with a β-subunit of a human calcium channel and/or an $\alpha_2$ subunit of a human calcium channel. Recombinant cell expressing heterologous calcium channels containing each of the $\alpha_1$, β and $\alpha_2$ human subunits, and, optionally, a γ subunit of a human calcium channel are especially preferred for use in such assays.

In certain embodiments, the assays for identifying compounds that modulate calcium channel activity are practiced by measuring the calcium channel activity of a eukaryotic cell having a heterologous, functional calcium channel when such cell is exposed to a solution containing the compound being tested and a calcium channel selective ion and comparing the measured calcium channel activity to the calcium channel activity of the same cell or a substantially identical control cell in a solution not containing the test compound. The cell is maintained in a solution having a concentration of calcium channel selective ions sufficient to provide an inward current when the channels open. Especially preferred for use, is a recombinant cell expressing calcium channels that include each of the $\alpha_1$, β and $\alpha_2$ human subunits, and, optionally, a γ subunit of a human calcium channel. Methods for practicing such assays are known to those of skill in the art. For example, for similar methods applied with *Xenopus laevis* oöcytes and acetylcholine receptors, see e.g., Mishina et al. [(1985) *Nature* 313:364] and, with such oöcytes and sodium channels [see, e.g., Noda et al. (1986) *Nature* 322:826–828]. For similar studies which have been carried out with the acetylcholine receptor, see, e.g., Claudio et al. [(1987) *Science* 238:1688–1694].

The assays provided herein, thus use cells, provided herein, that express heterologous functional calcium channels and measure functionally, such as electrophysiologically, the ability of a test compound to potentiate, antagonize or otherwise modulate the magnitude and duration of the flow of calcium channel selective ions, such as $Ca^{++}$ or $Ba^{++}$, through the heterologous functional channel. The amount of current which flows through the recombinant calcium channels of a cell may be determined directly, such as electrophysiologically, or by monitoring an independent reaction which occurs intracellularly and which is directly influenced in a calcium (or other) ion dependent manner.

Any method for assessing the activity of a calcium channel may be used in conjunction with the cells and assays provided herein. For example, in one embodiment of the method for testing a compound for its ability to modulate calcium channel activity, the amount of current is measured by its modulation of a reaction which is sensitive to calcium channel selective ions and uses a eukaryotic cell which expresses a heterologous calcium channel and also contains a transcriptional control element operatively linked for expression to a structural gene that encodes an indicator protein. The transcriptional control element used for transcription of the indicator gene is responsive in the cell to a calcium channel selective ion, such as $Ca^{2+}$ and $Ba^{+}$. The details of such transcriptional based assays are described in commonly owned PCT International Patent Application No. PCT/US91/5625, filed Aug. 7, 1991, which claims priority to copending commonly owned U.S. application Ser. No. 07/563,751, filed Aug. 7, 1990, now U.S. Pat. No. 5,401,629 the contents of which applications are herein incorporated by reference thereto.

Assays for diagnosis of LES

LES is an autoimmune disease characterized by an insufficient release of acetylcholine from motor nerve terminals which normally are responsive to nerve impulses. Immunoglobulins (IgG) from LES patients block individual voltage-dependent calcium channels and thus inhibit calcium channel activity [Kim and Neher, *Science* 239:405–408 (1988)]. A diagnostic assay for Lambert Eaton Syndrome (LES) is provided herein. The diagnostic assay for LES relies on the immunological reactivity of LES IgG with the human calcium channel $\alpha_1$ subunit alone or in combination with human calcium β subunit. For example, such an assay may be based on immunoprecipitation of LES IgG by the human calcium channel subunits provided herein.

Identification and isolation of DNA encoding human calcium channel subunits

Methods for identifying and isolating DNA encoding $\alpha_1$, $\alpha_2$, β and γ subunits of human calcium channels are provided.

Identification and isolation of such DNA may be accomplished by hybridizing, under appropriate conditions, generally high stringency, restriction enzyme-digested human DNA with a labeled probe having at least 14 nucleotides and derived from any contiguous portion of DNA having a sequence of nucleotides set forth herein by sequence identification number. Once a hybridizing fragment is identified in the hybridization reaction, it can be cloned employing standard cloning techniques known to those of skill in the art. This method can be used to identify genomic DNA encoding the subunit or cDNA encoding splice variants of human calcium channel subunits generated by alternative splicing of the primary transcript of genomic subunit DNA. For instance, DNA, cDNA or genomic DNA, encoding a calcium channel subunit may be identified by hybridization to a DNA probe and characterized by methods known to those of skill in the art, such as restriction mapping and DNA sequencing, and compared to the DNA provided herein in order to identify heterogeneity or divergence in the sequences the DNA. Such sequence differences may indicate that the transcripts from which the cDNA was produced result from alternative splicing of a primary transcript.

Oligonucleotides corresponding to regions of sequence differences have been used to isolate, by hybridization, DNA encoding the full-length splice variant and can be used to isolate genomic clones. A probe, based on a nucleotide sequence disclosed herein, which encodes at least a portion of a subunit of a human calcium channel, such as a tissue-specific exon, may be used as a probe to clone related DNA, to clone a full-length cDNA clone or genomic clone encoding the human calcium channel subunit.

Labeled (e.g., radioactively or enzymatically labeled) RNA or single-stranded DNA of at least 14 substantially contiguous bases, preferably at least 30 contiguous bases of a nucleic acid which encodes at least a portion of a human calcium channel subunit, the sequence of which nucleic acid corresponds to a segment of a nucleic acid sequence disclosed herein by reference to a Sequence ID No. are provided. Such nucleic acid segments may be used as probes in the methods provided herein for cloning DNA encoding calcium channel subunits. See, generally, Sambrook et al. (1989) *Molecular Cloning: A Laboratory Manual,* 2nd Edition, Cold Spring Harbor Laboratory Press.

In addition, nucleic acid amplification techniques, which are well known in the art, can be used to locate splice variants of calcium channel subunits by employing oligonucleotides based on DNA sequences surrounding the divergent sequence primers for amplifying human RNA or genomic DNA. Size and sequence determinations of the amplification products can reveal splice variants. Furthermore, isolation of human genomic DNA sequences by hybridization can yield DNA containing multiple exons, separated by introns, that correspond to different splice variants of transcripts encoding human calcium channel subunits.

DNA encoding types and subtypes of each of the $\alpha_1$, $\alpha_2$, $\beta$ and $\gamma$ subunit of voltage-dependent human calcium channels has been cloned herein by screening human cDNA libraries prepared from isolated poly A+ mRNA from cell lines or tissue of human origin having such calcium channels. Among the sources of such cells or tissue for obtaining mRNA are human brain tissue or a human cell line of neural origin, such as a neuroblastoma cell line, human skeletal muscle or smooth muscle cells, and the like. Methods of preparing cDNA libraries are well known in the art [see generally Ausubel et al. (1987) *Current Protocols in Molecular Biology,* Wiley-Interscience, New York; and Davis et al. (1986) *Basic Methods in Molecular Biology,* Elsevier Science Publishing Co., New York].

With respect to each of the respective subunits of a human calcium channel ($\alpha_1$, $\alpha_2$, $\beta$ or $\gamma$), once the DNA encoding the channel subunit was identified by a nucleic acid screening method, the isolated clone was used for further screening to identify overlapping clones. Some of the cloned DNA fragments can and have been subcloned into an appropriate vector such as pIBI24/25 (IBI, New Haven, Conn.), M13mp18/19, pGEM4, pGEM3, pGEM7Z, pSP72 and other such vectors known to those of skill in this art, and characterized by DNA sequencing and restriction enzyme mapping. A sequential series of overlapping clones may thus be generated for each of the subunits until a full-length clone can be prepared by methods, known to those of skill in the art, that include identification of translation initiation (start) and translation termination (stop) codons. For expression of the cloned DNA, the 5' noncoding region and other transcriptional and translational control regions of such a clone may be replaced with an efficient ribosome binding site and other regulatory regions as known in the art. Examples II–VI, below, describe in detail the cloning of each of the various subunits of a human calcium channel as well as subtypes and splice variants, including tissue-specific variants thereof. In the instances in which partial sequences of a subunit are disclosed, it is well within the skill of the art, in view of the teaching herein, to obtain the corresponding full-length nucleotide sequence encoding the subunit, subtype or splice variant thereof.

Identification and isolation of DNA encoding $\alpha_1$ subunits

At least three voltage-dependent calcium channel $\alpha_1$ subunit genes, which are expressed in the human central nervous system, have been identified and have been designated as $\alpha_{1B}$ (or VDCC IV), $\alpha_{1C}$ (or VDCC II) and $\alpha_{1D}$ (or VDCC III). DNA, isolated from a human neuronal cDNA library, that encodes each of the three VDCC subunit types has been isolated. DNA encoding subtypes of each of the types, which arise as splice variants are also provided. Subtypes are herein designated, for example, as $\alpha_{1B-1}$, $\alpha_{1B-2}$.

The $\alpha_1$ subunits types B, C, and D of voltage-dependent calcium channels, and subtypes thereof, differ with respect to sensitivity to known classes of calcium channel agonists and antagonists, such as dihydropyridines (DHPs), phenylalkylamines, omega conotoxin ($\omega$-CgTx) and pyrazonoylguanidines.

DNA that encodes an $\alpha_1$-subunit that binds to at least one compound selected from among dihydropyridines, phenylalkylamines, $\omega$-CgTx and pyrazonoylguanidines is provided. For example, the $\alpha_{1B}$ subunit provided herein appears to specifically interact with $\omega$-CgTx in N-type channels, and the $\alpha_{1D}$ subunit provided herein specifically interacts with DHPs in L-type channels.

Identification and Isolation of DNA Encoding the $\alpha_{1D}$ Human Calcium Channel Subunit The $\alpha_{1D}$ subunit cDNA has been isolated using fragments of the rabbit skeletal muscle calcium channel $\alpha_1$ subunit cDNA as a probe to screen a cDNA library of a human neuroblastoma cell line, IMR32, to obtain clone $\alpha$1.36. This clone was used as a probe to screen additional IMR32 cell cDNA libraries to obtain overlapping clones, which were then employed for screening until a sufficient series of clones to span the length of the nucleotide sequence encoding the human $\alpha_{1D}$ subunit were obtained. Full-length clones encoding $\alpha_{1D}$ were constructed by ligating portions of partial $\alpha_1$1D clones as described in Example II. The various cDNA clones from which the coding sequence for the $\alpha_{1D}$ subunit was derived are set forth in FIG. 1. In the Figure, the heavy line represents the $\alpha_{1D}$ coding sequence. Overlapping clones from which the complete sequence was derived are shown above the composite restriction map. Sequence ID No. 1 shows the 7,635 nucleotide sequence of the cDNA encoding the $\alpha_{1D}$ subunit. There is a 6,483 nucleotide sequence reading frame which encodes a sequence of 2,161 amino acids (as set forth in Sequence ID No. 1).

Sequence ID No. 2 provides the sequence of an alternative exon encoding the IS6 transmembrane domain [see Tanabe, T., et al. (1987) *Nature* 328:313–318 for a description of transmembrane domain terminology] of the $\alpha_{1D}$ subunit.

Sequence ID No. 1 also shows the 2,161 amino acid sequence deduced from the human neuronal calcium channel $\alpha_{1D}$ subunit DNA. Based on the amino acid sequence, the $\alpha_{1D}$ protein has a calculated Mr of 245,163. The amino acid sequence determined and reported here is about 70% identical to that described by Tanabe et al. (1987) *Nature* 328:313–318). The $\alpha_{1D}$ subunit of the calcium channel contains four putative internal repeated sequence regions. Four internally repeated regions represent 24 putative transmembrane segments, and the amino- and carboxyl-termini extend intracellularly. The sequence of another $\alpha_{1D}$ splice variant is set forth in Sequence ID No. 23 (see, e.g., Example II A.2.d)

The $\alpha_{1D}$ subunit has been shown to mediate DHP-sensitive, high-voltage-activated, long-lasting calcium channel activity. This calcium channel activity was detected when oöcytes were co-injected with RNA transcripts encoding an $\alpha_{1D}$ and $\beta$ or $\alpha_{1D}$, $\alpha_2$ and $\beta$ subunits. This activity was distinguished from $Ba^{2+}$ currents detected when oöcytes were injected with RNA transcripts encoding the $\beta\pm\alpha_2$ subunits. These currents pharmacologically and biophysically resembled $Ca^{2+}$ currents reported for uninjected o öcytes.

Identification and Isolation of DNA Encoding the $\alpha_{1B}$ Human Calcium Channel Subunit DNA encoding the $\alpha_{1B}$ subunit was isolated by screening a human basal ganglia cDNA library with fragments of the rabbit skeletal muscle calcium channel $\alpha_1$ subunit-encoding cDNA. A portion of one of the positive clones was used to screen an IMR32 cell cDNA library. Clones that hybridized to the basal ganglia DNA probe were used to further screen an IMR32 cell cDNA library to identify overlapping clones that in turn were used to screen a human hippocampus cDNA library. In this way, a sufficient series of clones to span nearly the entire length of the nucleotide sequence encoding the human $\alpha_{1B}$ subunit was obtained. PCR amplification of specific regions of the IMR32 cell $\alpha_{1B}$ mRNA yeilded additional segments of the $\alpha_{1B}$ coding sequence.

A full-length $\alpha_{1B}$ DNA clone was constructed by ligating portions of the partial cDNA clones as described in Example II.C. Sequence ID Nos. 7 and 8 show the nucleotide sequences of DNA clones encoding the $\alpha_{1B}$ subunit as well as the deduced amino acid sequences. The $\alpha_{1B}$ subunit to by Sequence ID No. 7 is referred to as the $\alpha_{1B-1}$ subunit to distinguish it from another $\alpha_{1B}$ subunit, $\alpha_{1B-2}$, encoded by the nucleotide sequence shown as Sequence ID No. 8, which is derived from alternative splicing of the $\alpha_{1B}$ subunit transcript.

Additional splice variants of the $\alpha_{1B}$ transcript have been identified by PCR amplification of IMR32 cell mRNA using oligonucleotide primers designed according to nucleotide sequences within the $\alpha_{1B-1}$-encoding DNA. These divergent coding sequences corresponding to $\alpha_{1B}$ subunits with variable amino acid sequences in the IS6 transmembrane domain.

Identification and Isolation of DNA Encoding the $\alpha_{1C}$ Human Calcium Channel Subunit Numerous $\alpha_{1C}$-specific DNA clones were isolated. Characterization of the sequence revealed the $\alpha_{1C}$ coding sequence, the $\alpha_{1C}$ initiation of translation sequence, and an alternatively spliced region of $\alpha_{1C}$. Alternatively spliced variants of the $\alpha_{1C}$ subunit have been identified. Sequence ID No. 3 sets forth DNA encoding an $\alpha_{1C}$ subunit. The DNA sequence set forth in Sequence ID No. 4 and No. 5 encode two possible amino terminal ends of the $\alpha_{1C}$ protein. Sequence ID No. 6 encodes an alternative exon for the IV S3 transmembrane domain.

The isolation and identification of DNA clones encoding portions of the $\alpha_{1C}$ subunit is described in detail in Example II.

Identification and isolation DNA encoding the β human calcium channel subunit

To isolate DNA encoding the β subunit, a human hippocampus cDNA library was screened by hybridization to a DNA fragment encoding a rabbit skeletal muscle calcium channel β subunit. A hybridizing clone was selected and was in turn used to isolate overlapping clones until the overlapping clones encompassing DNA encoding the entire the human calcium channel β subunit were isolated and sequenced.

Five alternatively spliced forms of the human calcium channel β subunit have been identified. These forms are designated $\beta_1$, expressed in skeletal muscle, $\beta_2$, expressed CNS, $\beta_3$, also expressed CNS, $\beta_4$, expressed in aorta tissue and HEK 293 cells, and $\beta_5$, expressed in HEK 293 cells. A full-length DNA clone encoding the $\beta_2$ subunit has been constructed. The subunits $\beta_1$, $\beta_2$, $\beta_4$ and $\beta_5$ have been identified by PCR analysis as alternatively spliced forms of the β subunit.

The alternatively spliced variants were identified by comparison of amino acid sequences encoded by the human neuronal and rabbit skeletal muscle calcium channel β subunit-encoding DNA. This comparison revealed a 45-amino acid deletion in the human β subunit compared to the rabbit subunit. Using DNA from the region as a probe for DNA cloning, as well as PCR analysis and DNA sequencing of this area of sequence divergence, alternatively spliced forms of the human calcium channel β subunit transcript were identified. For example, the sequence of DNA encoding one splice variant $\beta_2$ is set forth in Sequence ID No. 9. Sequence ID No. 10 sets forth the sequence of the $\beta_3$ subunit (nt 1–1851, including 3' untranslated sequence nt 1795–1851), which is another splice variant of the β subunit primary transcript. $\beta_2$ and $\beta_3$ are human neuronal β subunits. DNA distinctive for a portion of a β subunit ($\beta_4$) of a human aortic calcium channel and also human embryonic kidney (HEK) cells is set forth in Sequence ID No. 12 (nt 1–13 and 191–271). The sequence of DNA encoding a portion of a human calcium channel β subunit expressed in skeletal muscle ($\beta_1$) is shown in Sequence ID No. 12 except that nt 4–34 are absent.

Identification and isolation DNA encoding the $\alpha_2$ human calcium channel subunit DNA encoding a human neuronal calcium channel $\alpha_2$ subunit was isolated in a manner substantially similar to that used for isolating DNA encoding the $\alpha_1$ subunit, except that a human genomic DNA library was probed under low and high stringency conditions with a fragment of DNA encoding the rabbit skeletal muscle calcium channel $\alpha_2$ subunit. The fragment included nucleotides having a sequence corresponding to the nucleotide sequence between nucleotides 43 and 272 inclusive of rabbit back skeletal muscle calcium channel $\alpha_2$ subunit cDNA as disclosed in PCT International Patent Application Publication No. WO 89/09834, which corresponds to U.S. application Ser. No. 07/620,520, which is a continuation-in-part of U.S. Ser. No. 176,899, filed Apr. 4, 1988, which applications have been incorporated herein by reference.

Example IV describes the isolation of DNA clones encoding $\alpha_2$ subunits of a human calcium channel from a human DNA library using genomic DNA and cDNA clones, identified by hybridization to the genomic DNA, as probes.

Sequence ID No. 11 shows the sequence of DNA encoding an $\alpha_2$ subunit. As described in Example V, PCR analysis of RNA from human skeletal muscle, brain tissue and aorta using oligonucleotide primers specific for a region of the human neuronal $\alpha_2$ subunit cDNA that diverges from the rabbit skeletal muscle calcium channel $\alpha_2$ subunit cDNA identified splice variants of the human calcium channel $\alpha_2$ subunit transcript.

Identification and isolation of DNA encoding the γ human calcium channel subunit DNA encoding a human neuronal calcium channel γ subunit has been isolated as described in detail in Example VI. Sequence ID No. 14 shows the nucleotide sequence at the 3'-end of this DNA which includes a reading frame encoding a sequence of 43 amino acid residues.

Preparation of recombinant eukaryotic cells containing DNA encoding heterologous calcium channel subunits DNA encoding one or more of the calcium channel subunits or a portion of a calcium channel subunit may be introduced into a host cell for expression or replication of the DNA. Such DNA may be introduced using methods described in the following examples or using other procedures well known to those skilled in the art. Incorporation of cloned DNA into a suitable expression vector, transfection of eukaryotic cells with a plasmid vector or a combination of plasmid vectors, each encoding one or more distinct genes or with linear DNA, and selection of transfected cells are also well known in the art [see, e.g., Sambrook et al. (1989) *Molecular Cloning: A Laboratory Manual,* Second Edition, Cold Spring Harbor Laboratory Press].

Cloned full-length DNA encoding any of the subunits of a human calcium channel may be introduced into a plasmid vector for expression in a eukaryotic cell. Such DNA may be genomic DNA or cDNA. Host cells may be transfected with one or a combination of said plasmids, each of which encodes at least one calcium channel subunit. Alternatively, host cells may be transfected with linear DNA using methods well known to those of skill in the art.

While the DNA provided herein may be expressed in any eukaryotic cell, including yeast cells such as *P. pastoris* (see, e.g., Cregg et al. (1987) *Bio/Technology* 5:479], mammalian expression systems for expression of the DNA encoding the human calcium channel subunits provided herein are preferred.

The heterologous DNA may be introduced by any method known to those of skill in the art, such as transfection with a vector encoding the heterologous DNA. Particularly preferred vectors for transfection of mammalian cells are the pSV2dhfr expression vectors, which contain the SV40 early promoter, mouse dhfr gene, SV40 polyadenylation and splice sites and sequences necessary for maintaining the vector in bacteria, cytomegalovirus (CMV) promoter-based vectors such as pCMV or pCDNA1, and MMTV promoter-based vectors. DNA encoding the human calcium channel subunits has been inserted in the vector pCDNA1 at a position immediately following the CMV promoter.

Stably or transiently transfected mammalian cells may be prepared by methods known in the art by transfecting cells with an expression vector having a selectable marker gene such as the gene for thymidine kinase, dihydrofolate reductase, neomycin resistance or the like, and growing the transfected cells under conditions selective for cells expressing the marker gene. Functional voltage-dependent calcium channels have been produced in HEK 293 cells transfected with a derivative of the vector pCDNA1 that contains DNA encoding a human calcium channel subunit.

The heterologous DNA may be maintained in the cell as an episomal element or may be integrated into chromosomal DNA of the cell. The resulting recombinant cells may then be cultured or subcultured (or passaged, in the case of mammalian cells) from such a culture or a subculture thereof. Methods for tranfection, injection and culturing recombinant cells are known to the skilled artisan. Eukaryotic cells in which DNA or RNA may be introduced, include any cells that are transfectable by such DNA or RNA or into which such DNA may be injected. Virtually any eukaryotic cell can serve as a vehicle for heterologous DNA. Preferred cells are those that can also express the DNA and RNA and most preferred cells are those that can form recombinant or heterologous calcium channels that include one or more subunits encoded by the heterologous DNA. Such cells may be identified empirically or selected from among those known to be readily transfected or injected. Preferred cells for introducing DNA include those that can be transiently or stably transfected and include, but are not limited to cells of mammalian origin, such as COS cells, mouse L cells, CHO cells, human embryonic kidney cells, African green monkey cells and other such cells known to those of skill in the art, amphibian cells, such as *Xenopus laevis* oöcytes, or those of yeast such as *Saccharomyces cerevisiae* or *Pichia pastoris.* Preferred cells for expressing injected RNA transcripts include *Xenopus laevis* oöcytes. Cells that are preferred for transfection of DNA are those that readily and efficiently transfected. Such cells are known to those of skill in the art or may be empirically identified. Preferred cells include DG44 cells and HEK 293 cells, particularly HEK 293 cells that have been adapted for growth in suspension and that can be frozen in liquid nitrogen and then thawed and regrown. Such HEK 293 cells are described, for example in U.S. Pat. No. 5,024,939 to Gorman [see, also Stillman et al. (1985) *Mol. Cell. Biol.* 5:2051–2060].

The cells may be used as vehicles for replicating heterologous DNA introduced therein or for expressing the heterologous DNA introduced therein. In certain embodiments, the cells are used as vehicles for expressing the heterologous DNA as a means to produce substantially pure human calcium channel subunits or heterologous calcium channels. Host cells containing the heterologous DNA may be cultured under conditions whereby the calcium channels are expressed. The calcium channel subunits may be purified using protein purification methods known to those of skill in the art. For example, antibodies, such as those provided herein, that specifically bind to one or more of the subunits may be used for affinity purification of the subunit or receptors containing the subunits.

A substantially pure $\alpha_2$ subunit of a human calcium channel, an $\alpha_2$ subunit of a human calcium channel, a $\beta$ subunit of a human calcium channel and a $\gamma$ subunit of a human calcium channel are provided. Substantially pure isolated calcium channels that contain at least one of the human calcium channel subunits are also provided.

In other embodiments, a eukaryotic cell that contains heterologous DNA encoding at least one of an $\alpha_1$ subunit of a human calcium channel, an $\alpha_2$ subunit of a human calcium channel, a $\beta$ subunit of a human calcium channel and a $\gamma$ subunit of a human calcium channel are provided. In accordance with one preferred embodiment, the heterologous DNA is expressed in the eukaryotic cell and preferably encodes a human calcium channel $\alpha_1$ subunit.

In particularly preferred aspects, the eukaryotic cell which contains the heterologous DNA expresses it and forms a recombinant functional calcium channel activity. In more preferred aspects, the recombinant calcium channel activity is readily detectable because it is a type that is absent from the untransfected host cell or is of a magnitude not exhibited in the untransfected cell.

Preferred among such cells is a recombinant eukaryotic cell with a functional heterologous calcium channel. The recombinant cell can be produced by introduction of and expression of heterologous DNA or RNA transcripts encoding an $\alpha_1$ subunit of a human calcium channel, more preferably also expressing, a heterologous DNA encoding a $\beta$ subunit of a human calcium channel and/or heterologous DNA encoding an $\alpha_2$ subunit of a human calcium channel. Especially preferred is the expression in such a recombinant cell of each of the $\alpha_1$, $\beta$ and $\alpha_2$ subunits encoded by such heterologous DNA or RNA transcripts, and optionally expression of heterologous DNA or an RNA transcript encoding a $\gamma$ subunit of a human calcium channel.

In certain embodiments, the eukaryotic cell with a heterologous calcium channel is produced by introducing into the cell a first composition, which contains at least one RNA transcript that is translated in the cell into a subunit of a human calcium channel. In preferred embodiments, the subunits that are translated include an $\alpha_1$ subunit of a human calcium channel. More preferably, the composition that is introduced contains an RNA transcript which encodes an $\alpha_1$ subunit of a human calcium channel and also contains (1) an RNA transcript which encodes a $\beta$ subunit of a human calcium channel and/or (2) an RNA transcript which encodes an $\alpha_2$ subunit of a human calcium channel. Especially preferred is the introduction of RNA encoding an $\alpha_1$, a $\beta$ and an $\alpha_2$ human calcium channel subunit, and, optionally, a $\gamma$ subunit of a human calcium channel.

Methods for in vitro transcription of a cloned DNA and injection of the resulting RNA into eukaryotic cells are well known in the art. Transcripts of any of the full-length DNA encoding any of the subunits of a human calcium channel may be injected alone or in combination with other transcripts into eukaryotic cells for expression in the cells. Amphibian oöcytes are particularly preferred for expression of in vitro transcripts of the human calcium channel subunit cDNA clones provided herein.

The functional calcium channels may preferably include at least an $\alpha_1$ subunit and a $\beta$ subunit of a human calcium channel. Eukaryotic cells expressing these two subunits and also cells expressing additional subunits, have been prepared by transfection of DNA and by injection RNA transcripts.

Such cells have exhibited voltage-dependent calcium channel activity attributable to calcium channels that contain one or more of the heterologous human calcium channel subunits. For example, eukaryotic cells expressing heterologous calcium channels containing an $\alpha_2$ subunit in addition to the $\alpha_1$ subunit and a β subunit have been shown to exhibit increased calcium selective ion flow across the cellular membrane in response to depolarization, indicating that the, the $\alpha_2$ subunit may potentiate calcium channel function.

Eukaryotic cells which express heterologous calcium channels containing at least a human $\alpha_1$ subunit, a human β subunit and a human $\alpha_2$ subunit are preferred. Eukaryotic cells transformed with a composition containing cDNA or an RNA of transcript that encodes an $\alpha_1$ subunit alone or in combination with a β and/or an $\alpha_2$ subunit may be used to produce cells that express functional calcium channels. Since recombinant cells expressing human calcium channels containing all of the of the human subunits encoded by the injected heterologous cDNA or RNA are especially preferred, it is desirable to inject or transfect such host cells with a sufficient concentration of the subunit-encoding nucleic acids to form calcium channels that contain the human subunits encoded by heterologous DNA or RNA. The precise amounts and ratios of DNA or RNA encoding the subunits may be empirically determined and optimized for a particular combination of subunits, cells and assay conditions.

With respect to measurement of the activity of functional heterologous calcium channels, preferably, endogenous ion channel activity and, if desired, and heterologous channel activity of channels that do not contain the desired subunits, of a host cell can be inhibited to a significant extent by chemical, such as pharmacological and electrophysiological, means, such as use of differential holding potential, to increase the S/N ratio of the measured heterologous calcium channel activity.

Among the uses for eukaryotic cells which recombinantly express one or more subunits are assays for determining whether a test compound has calcium channel agonist or antagonist activity. Desirably, a host cell for the expression of calcium channel subunits does not produce endogenous calcium channel subunits of the type or in an amount that substantially interferes with the detection of heterologous calcium channel subunits in ligand binding assays or detection of heterologous calcium channel function, such as generation of calcium current, in functional assays.

With respect to ligand binding assays, the host cells preferably should not produce endogenous calcium channels which interact with compounds having, at physiological concentrations (e.g., nanomolar or picomolar amounts), affinity for one or a combination of the heterologous or recombinant calcium channel subunits that contain one or all of the human calcium channel subunits provided herein.

With respect to ligand binding assays for identifying a compound which has affinity for calcium channels, cells are employed which express, preferably, at least a heterologous $\alpha_1$ subunit. Transfected eukaryotic cells which express at least an $\alpha_1$ subunit may be used to determine the ability of a test compound to specifically alter the activity of a calcium channel. Such ligand binding assays may be performed on intact transfected cells or membranes prepared therefrom.

The capacity of a test compound to bind to or otherwise interact with membranes that contain heterologous calcium channels or subunits thereof may be determined by using any appropriate method, such as competitive binding analysis, such as Scatchard plots, in which the binding capacity of such membranes is determined in the presence and absence of one or more concentrations of a compound having known affinity for the calcium channel. Where necessary, the results may be compared to a control experiment designed in accordance with methods known to those of skill in the art. For example, as a negative control, the results may be compared to those of assays of an identically treated membrane preparation from host cells which have not been transfected with one or more subunit-encoding nucleic acids.

Stably or transiently transfected cells or injected cells which express voltage-dependent human calcium channels containing one or more of the subunits of a human calcium channel desirably may be used in assays to identify agents, such as calcium channel agonists and antagonists, that modulate calcium channel activity. Functionally testing the activity of test compounds, including compounds having unknown activity, for calcium channel agonist or antagonist activity to determine if the test compound potentiates, inhibits or otherwise alters the flow of calcium through a human calcium channel can be accomplished by (a) maintaining a eukaryotic cell which is transfected or injected to express a heterologous functional calcium channel capable of regulating the flow of calcium channel selective ions into the cell in a medium containing calcium channel selective ions (i) in the presence of and (ii) in the absence of a test compound; (b) maintaining the cell under conditions such that the heterologous calcium channels are substantially closed and endogenous calcium channels of the cell are substantially inhibited (c) depolarizing the membrane of the cell maintained in step (b) to an extent and for an amount of time sufficient to cause (preferably, substantially only) the heterologous calcium channels to become permeable to the calcium channel selective ions; and (d) comparing the amount and duration of current flow into the cell in the presence of the test compound to that of the current flow into the cell, or a substantially similar cell, in the absence of the test compound.

Functional recombinant or heterologous calcium channels may be identified by any method known to those of skill in the art. For example, electrophysiological procedures for measuring the current across an ion-selective membrane of a cell, which are well known, may be used. The amount and duration of the flow of calcium selective ions through heterologous calcium channels of a recombinant cell containing DNA encoding one or more of the subunits provided herein has been measured using electrophysiological recordings using a voltage clamp, such as the whole-cell patch clamp technique. In order to improve the sensitivity of the assays, known methods can be used to eliminate or reduce non-calcium currents and calcium currents resulting from endogenous calcium channels, when measuring calcium currents through recombinant channels. For example, the dihydropyridine Bay K 8644 specifically enhances L-type calcium channel function by increasing the duration of the open state of the channels (see, e.g., Hess, J. B., et al. (1984) *Nature* 311:538–544]). Prolonged opening of the channels results in calcium currents of increased magnitude and duration. Tail currents can be observed upon repolarization of the cell membrane after activation of ion channels by a depolarizing voltage command. The opened channels require a finite time to close or "deactivate" upon repolarization, and the current that flows through the channels during this period is referred to as a tail current. Because Bay K 8644 prolongs opening events in calcium channels, it tends to prolong these tail currents and make them more pronounced.

EXAMPLES

The following examples are included for illustrative purposes only and are not intended to limit the scope of the invention.

Example I

PREPARATION OF LIBRARIES USED FOR ISOLATION OF DNA ENCODING HUMAN NEURONAL VOLTAGE-DEPENDENT CALCIUM CHANNEL SUBUNITS

A. RNA Isolation

1. IMR32 Cells

IMR32 cells were obtained from the American Type Culture Collection (ATCC Accession No. CCL127, Rockville, Md.) and grown in DMEM, 10% fetal bovine serum, 1% penicillin/streptomycin (GIBCO, Grand Island, N.Y.) plus 1.0 mM dibutyryl cAMP (dbcAMP) for ten days. Total RNA was isolated from the cells according to the procedure described by H. C. Birnboim [(1988) *Nucleic Acids Research* 16:1487–1497]. Poly($A^+$) RNA was selected according to standard procedures (see, e.g., Sambrook et al. (1989) *Molecular Cloning, A Laboratory Manual*, Cold Spring Harbor Laboratory Press; pg. 7.26–7.29).

2. Human Thalamus Tissue

Human thalamus tissue (2.34 g), obtained from the National Neurological Research Bank, Los Angeles, Calif., that had been stored frozen at −70° C. was pulverized using a mortar and pestle in the presence of liquid nitrogen and the cells were lysed in 12 ml of lysis buffer (5M guanidinium isothiocyanate, 50 mM TRIS, pH 7.4, 10 mM EDTA, 5% β-mercaptoethanol). Lysis buffer was added to the lysate to yield a final volume of 17 ml. N-laurylsarcosine and CsCl were added to the mixture to yield final concentrations of 4% and 0.01 g/ml, respectively, in a final volume of 18 ml.

The sample was centrifuged at 9,000 rpm in a Sorvall SS34 rotor for 10 min at room temperature to remove the insoluble material as a pellet. The supernatant was divided into two equal portions and each was layered onto a 2-ml cushion of a solution of 5.7M CsCl, 0.1M EDTA contained in separate centrifuge tubes to yield approximately 9 ml per tube. The samples were centrifuged in an SW41 rotor at 37,000 rpm for 24 h at 20° C.

After centrifugation, each RNA pellet was resuspended in 3 ml ETS (10 mM TRIS, pH 7.4, 10 mM EDTA, 0.2% SDS) and combined into a single tube. The RNA was precipitated with 0.25M NaCl and two volumes of 95% ethanol.

The precipitate was collected by centrifugation and resuspended in 4 ml PK buffer (0.05M TRIS, pH 8.4, 0.14M NaCl, 0.01M EDTA, 1% SDS). Proteinase K was added to the sample to a final concentration of 200 μg/ml. The sample was incubated at 22° C. for 1 h, followed by extraction with an equal volume of phenol:chloroform:isoamylalcohol (50:48:2) two times, followed by one extraction with an equal volume of chloroform: isoamylalcohol (24:1). The RNA was precipitated with ethanol and NaCl. The precipitate was resuspended in 400 μl of ETS buffer. The yield of total RNA was approximately 1.0 mg. Poly $A^+$ RNA (30 μg) was isolated from the total RNA according to standard methods as stated in Example I.A.1.

B. Library Construction

Double-stranded cDNA was synthesized according to standard methods (see, e.g., Sambrook et al. (1989) IN: *Molecular Cloning, A Laboratory Manual,* Cold Spring Harbor Laboratory Press, Chapter 8). Each library was prepared in substantially the same manner except for differences in: 1) the oligonucleotide used to prime the first strand cDNA synthesis, 2) the adapters that were attached to the double-stranded cDNA, 3) the method used to remove the free or unused adapters, and 4) the size of the fractionated cDNA ligated into the λ phage vector.

1. IMR32 cDNA library #1

Single-stranded cDNA was synthesized using IMR32 poly($A^+$) RNA (Example I.A.1.) as a template and was primed using oligo $(dT)_{12-18}$ (Collaborative Research Inc., Bedford, Mass.). The single-stranded cDNA was converted to double-stranded cDNA and the yield was approximately 2 μg. EcoI adapters:

5'-AATTCGGTACGTACACTCGAGC-3' = 22-mer (SEQ ID No. 15)
3'-        GCCATGCATGTGAGCTCG-5' = 18-mer, (SEQ ID No. 16)

also containing SnaBI and XhoI restriction sites were then added to the double-stranded cDNA according to the following procedure.

a. Phosphorylation of 18-mer

The 18-mer was phosphorylated using standard methods (see, e.g., Sambrook et al. (1989) IN: *Molecular Cloning, A Laboratory Manual,* Cold Spring Harbor Laboratory Press, Chapter 8) by combining in a 10 μl total volume the 18 mer (225 pmoles) with $[^{32}P]\gamma$-ATP (7000 Ci/mmole; 1.0 μl) kinase (2 U) and incubating at 37° C. for 15 minutes. After incubation 1 μL 10 mM ATP and an addition 2 U of kinase were added and incubated at 37° C. for 15 minutes. Kinase was then inactivated by boiling for 10 minutes.

b. Hybridization of 22-mer

The 22-mer was hybridized to the phosphorylated 18-mer by addition of 225 pmoles of the 22-mer (plus water to bring volume to 15 μl), and incubation at 65° C. for 5 minutes. The reaction was then allowed to slowly cool to room temperature.

The adapters were thus present at a concentration of 15 pmoles/μl, and were ready for cDNA-adapter ligation.

c. Ligation of Adapters to cDNA

After the EcoRI, SnaBI, XhoI adapters were ligated to the double-stranded cDNA using a standard protocol (see, e.g., Sambrook et al. (1989) IN: *Molecular Cloning, A Laboratory Manual,* Cold Spring Harbor Laboratory Press, Chapter 8), the ligase was inactivated by heating the mixture to 72° C. for 15 minutes. The following reagents were added to the cDNA ligation reaction and heated at 37° C. for 30 minutes:

| | |
|---|---|
| cDNA ligation reaction | 20 μl |
| water | 24 μl |
| 10x kinase buffer | 3 μl |
| 10 mM ATP | 1 μl |
| kinase (2 U/μl) | 2 μl |
| | 50 μl |

The reaction was stopped by the addition of 2 μl 0.5M EDTA, followed by one phenol/chloroform extraction and one chloroform extraction.

d. Size Selection and Packaging of cDNA

The double-stranded cDNA with the EcoRI, SnaBI, XhoI adapters ligated was purified away from the free or unligated adapters using a 5 ml Sepharose CL-4B column (Sigma, St. Louis, Mo.). 100 μl fractions were collected and those containing the cDNA, determined by monitoring the radioactivity, were pooled, ethanol precipitated, resuspended in TE buffer and loaded onto a 1% agarose gel. After the electrophoresis, the gel was stained with ethidium bromide and the 1 to 3 kb fraction was cut from the gel. The cDNA embedded in the agarose was eluted using the "Geneluter Electroelution System" (Invitrogen, San Diego, Calif.). The eluted cDNA was collected by ethanol precipitation and resuspended in TE buffer at 0.10 pmol/μl. The cDNA was ligated to 1 μg of EcoRI digested, dephosphorylated λgt11 in a 5 μl reaction volume at a 2- to 4- fold molar excess ratio of cDNA over the λgt11 vector. The ligated λgt11 containing the cDNA insert was packaged into λ phage virions in vitro using the Gigapack (Stratagene, La Jolla, Calif.) kit. The packaged phage were plated on an *E. coli* Y1088 bacterial lawn in preparation for screening.

2. IMR32 cDNA Library #2

This library was prepared as described (Example I.B.1.) with the exception that 3 to 9 kb cDNA fragments were ligated into the λgt11 phage vector rather than the 1 to 3 kb fragments.

3. IMR32 cDNA Library #3

IMR32 cell poly($A^+$) RNA (Example I.A.1.) was used as a template to synthesize single-stranded cDNA. The primers for the first strand cDNA synthesis were random primers (hexadeoxy-nucleotides [pd$(N)_6$] Cat #5020-1, Clontech, Palo Alto, Calif.). The double-stranded cDNA was synthesized (Example I.B.1.), EcoRI, SnaBI, XhoI adapters were added to the cDNA (Example I.B.1.), the unligated adapters were removed (Example I.B.1.), and the double-stranded cDNA with the ligated adapters was fractionated on an agarose gel (Example I.B.1.). The cDNA fraction greater than 1.8 kb was eluted from the agarose (Example I.B.1.), ligated into λgt11, packaged, and plated into a bacterial lawn of Y1088 (Example I.B.1.).

4. IMR32 cDNA Library #4

IMR32 cell poly($A^+$) RNA (Example I.A.1.) was used as a template to synthesize single-stranded cDNA. The primers for the first strand cDNA synthesis were oligonucleotides 89–365a specific for the $\alpha_{1D}$ (VDCC III) type $\alpha_1$-subunit (see Example II.A.) coding sequence (the complementary sequence of nt 2417 to 2446, Sequence ID No. 1), 89–495 specific for the $\alpha_{1C}$ (VDCC II) type $\alpha_1$-subunit (see Example II.B.) coding sequence (the complementary sequence of nt 852 to 873, Sequence ID No. 6), and 90–12 specific for the VDCC II type $\alpha_1$-subunit coding sequence (the complementary sequence of nt 2496 to 2520, Sequence ID No. 6). The cDNA library was then constructed as described (Example I.B.3), except that the cDNA size-fraction greater than 1.5 kb was eluted from the agarose rather than the greater than 1.8 kb fraction.

5. IMR32 cDNA Library #5

The cDNA library was constructed as described (Example I.B.3.) with the exception that the size-fraction greater than 1.2 kb was eluted from the agarose rather than the greater than 1.8 kb fraction.

6. Human Thalamus cDNA Library #6

Human thalamus poly($A^+$) RNA (Example I.A.2.) was used as a template to synthesize single-stranded cDNA. Oligo (dT) was used to prime the first strand synthesis (Example I.B.1.). The double-stranded cDNA was synthesized (Example I.B.1.) and EcoRI, KpnI, NcoI adapters of the following sequence:

5' CCATGGTACCTTCGTTGACG 3' = 20 mer (SEQ. ID NO. 17)
3' GGTACCATGGAAGCAACTGCTTAA 5' = 24 mer (SEQ. ID NO. 18)

were ligated to the double-stranded cDNA as described (Example I.B.1.) with the 20-mer replacing the 18-mer and the 24-mer replacing the 22-mer. The unligated adapters were removed by passing the cDNA-adapter mixture through a 1 ml Bio Gel A-50 (Bio-Rad Laboratories, Richmond, Calif.) column. Fractions (30 μl) were collected and 1 μl of each fraction in the first peak of radioactivity was electrophoresed on a 1% agarose gel. After electrophoresis, the gel was dried on a vacuum gel drier and exposed to x-ray film. The fractions containing cDNA fragments greater than 600 bp were pooled, ethanol precipitated, and ligated into λgt11 (Example I.B.1.). The construction of the cDNA library was completed as described (Example I.B.1.).

C. Hybridization and washing Conditions

Hybridization of radiolabelled nucleic acids to immobilized DNA for the purpose of screening cDNA libraries, DNA Southern transfers, or northern transfers was routinely performed in standard hybridization conditions [5×SSPE, 5× Denhardt's, 50% deionized formamide, 200 μg/ml sonicated herring sperm DNA (Cat #223646, Boehringer Mannheim Biochemicals, Indianapolis, Ind.)]. The recipes for SSPE and Denhardt's and the preparation of deionized formamide are described, for example, in Sambrook et al. (1989) *Molecular Cloning, A Laboratory Manual*, Cold Spring Harbor Laboratory Press, Chapter 8). In some hybridizations, lower stringency conditions were used in that 10% deionized formamide replaced 50% deionized formamide described for the standard hybridization conditions.

The washing conditions for removing the non-specific probe from the filters was either high, medium, or low stringency as described below:

1) high stringency: 0.1×SSPE, 0.1% SDS, 65° C.
2) medium stringency: 0.2×SSPE, 0.1% SDS, 50° C.
3) low stringency: 1.0×SSPE, 0.1% SDS, 50° C.

Example II

ISOLATION OF DNA ENCODING THE HUMAN NEURONAL CALCIUM CHANNEL $\alpha_1$ SUBUNIT

The isolation and characterization of DNA encoding the three human neuronal VDCC $\alpha_1$ subunit genes are described in detail in this example.

A. Isolation of DNA encoding the $a_{1D}$ subunit

1. Reference List of Partial $\alpha_{1D}$ cDNA Clones

Numerous $\alpha_{1D}$-specific cDNA clones were isolated in order to characterize the complete $\alpha_{1D}$ coding sequence plus portions of the 5' and 3' untranslated sequences. Sequence ID No. 1 shows the complete $\alpha_{1D}$ DNA coding sequence, plus 510 nucleotides of $\alpha_{1D}$ 5' untranslated sequence ending in the guanidine nucleotide adjacent to the adenine nucleotide of the proposed initiation of translation as well as 642 nucleotides of 3' untranslated sequence. Also shown in Sequence ID No. 1 is the deduced amino acid sequence. Shown below is a list of partial cDNA clones used to characterize the $\alpha_{1D}$ sequence and the nucleotide position of each clone relative to the full-length $\alpha_{1D}$ cDNA sequence (i.e., Sequence ID No. 1). Restriction maps of the partial $\alpha_{1D}$ cDNA clones are shown in FIG. 1. The isolation and characterization of these clones are described below (Example II.A.2.).

| | | |
|---|---|---|
| IMR32 | 1.144 | nt. 1 to 510 of Sequence ID No. 1 5' untranslated sequence, nt. 511 to 2431, Sequence ID No. 1 |
| IMR32* | 1.136 | nt. 1627 to 2988, Sequence ID No. 1 nt. 1 to 104 of Sequence ID No. 2 additional exon, |
| IMR32@ | 1.80 | nt. 2083 to 6468, Sequence ID No. 1 |
| IMR32# | 1.36 | nt. 2857 to 4281, Sequence ID No. 1 |
| IMR32 | 1.163 | nt. 5470 to 7635, Sequence ID No. 1 |

* 5' of nt 1627, IMR32 1.136 encodes an intron and an additional exon described in Example II.A.2.d.
@ IMR32 1.80 contains two deletions, nt 2984 to 3131 and nt 5303 to 5349 (Sequence ID No. 1). The 148 nt deletion (nt. 2984 to 3131) was corrected by performing a polymerase chain reaction described in Example II.A.3.b.
\# IMR32 1.36 contains a 132 nt deletion (nt. 3081 to 3212).

2. Isolation and Characterization of Individual clones listed in Example II.A.1.

a. IMR32 1.36

Two million recombinants of the IMR32 cDNA library #1 (Example I.B.1.) were screened in duplicate at a density of approximately 200,000 plaques per 150 mm plate using a mixture of radiolabelled fragments of the coding region of the rabbit skeletal muscle calcium channel $\alpha_1$ cDNA[for the sequence of the rabbit skeletal muscle calcium channel $\alpha_1$ subunit cDNA, see, Tanabe et al. (1987). *Nature* 328:313–318]:

| Fragment | Nucleotides |
|---|---|
| KpnI-EcoRI | −78 to 1006 |
| EcoRI-XhoI | 1006 to 2653 |
| ApaI-ApaI | 3093 to 4182 |
| BglII-SacI | 4487 to 5310 |

The hybridization was performed using low stringency hybridization conditions (Example I.C.) and the filters were washed under low stringency (Example I.C.). Only one $\alpha_{1D}$-specific recombinant (IMR32 1.36) of the $2\times10^6$ screened was identified. IMR32 1.36 was plaque purified by standard methods (J. Sambrook et al. (1989) *Molecular Cloning, A Laboratory Manual,* Cold Spring Harbor Laboratory Press, Chapter 8) subcloned into pGEM3 (Promega, Madison, Wis.) and characterized by DNA sequencing.

b. IMR32 1.80

Approximately $1\times10^6$ recombinants of the IMR32 cDNA library #2 (Example I.B.2.) were screened in duplicate at a density of approximately 100,000 plaques per 150 mm plate using the IMR32 1.36 cDNA fragment (Example II.A.1) as a probe. Standard hybridization conditions were used (Example I.C), and the filters were washed under high stringency (Example I.C.). Three positive plaques were identified one of which was IMR32 1.80. IMR32 1.80 was plaque purified by standard methods, restriction mapped, subcloned, and characterized by DNA sequencing.

c. IMR32 1.144

Approximately $1\times10^6$ recombinants of the IMR32 cDNA library #3 (Example I.B.3) were screened with the EcoRI-PvuII fragment (nt 2083 to 2518, Sequence ID No. 1) of IMR32 1.80. The hybridization was performed using standard hybridization conditions (Example I.C.) and the filters were washed under high stringency (Example I.C.). Three positive plaques were identified one of which was IMR32 1.144. IMR32 1.144 was plaque purified, restriction mapped, and the cDNA insert was subcloned into pGEM7Z (Promega, Madison, Wis.) and characterized by DNA sequencing. This characterization revealed that IMR32 1.144 has a series of ATG codons encoding seven possible initiating methionines (nt 511 to 531, Sequence ID No. 1). PCR analysis, and DNA sequencing of cloned PCR products encoding these seven ATG codons confirmed that this sequence is present in the $\alpha_{1D}$ transcript expressed in dbcAMP-induced IMR32 cells.

d. IMR32 1.136

Approximately $1\times10^6$ recombinants of the IMR32 cDNA library #4 (Example I.B.4) were screened with the EcoRI-PvuII fragment (nt 2083 to 2518, Sequence ID No. 1) of IMR32 1.80 (Example II.A.1.). The hybridization was performed using standard hybridization conditions (Example I.C.) and the filters were washed under high stringency (Example I.C.). Six positive plaques were identified one of which was IMR32 1.136. IMR32 1.136 was plaque purified, restriction mapped, and the cDNA insert was subcloned into a standard plasmid vector, e.g., pSP72 (Promega, Madison, Wis.), and characterized by DNA sequencing. This characterization revealed that IMR32 1.136 encodes an incompletely spliced $\alpha_{1D}$ transcript. The clone contains nucleotides 1627 to 2988 of Sequence ID No. 1 preceded by an approximate 640 bp intron. This intron is then preceded by a 104 nt exon (Sequence ID No. 2) which is an alternative exon encoding the IS6 transmembrane domain [see, e.g., Tanabe et al. (1987) *Nature* 328:313–318 for a description of the IS1 to IVS6 transmembrane terminology] of the $\alpha_{1D}$ subunit and can replace nt 1627 to 1730, Sequence ID No. 1, to produce a completely spliced $\alpha_{1D}$ transcript (Sequence ID No. 23).

e. IMR32 1.163

Approximately $1\times10^6$ recombinants of the IMR32 cDNA library #3 (I.B.3.) were screened with the NcoI-XhoI fragment of IMR32 1.80 (Example II.A.1.) containing nt 5811 to 6468 (Sequence ID No. 1). The hybridization was performed using standard hybridization conditions (Example I.C.) and the filters were washed under high stringency (Example I.C.). Three positive plaques were identified one of which was IMR32 1.163. IMR32 1.163 was plaque purified, restriction mapped, and the cDNA insert was subcloned into a standard plasmid vector, e.g., pSP72 (Promega, Madison, Wis.), and characterized by DNA sequencing. This characterization revealed that IMR32 1.163 contains the $\alpha_{1D}$ termination codon, nt 6994 to 6996 (Sequence ID No. 1).

3. Construction of a Full-length $\alpha_{1D}$ cDNA [pVDCCIII(A)]

$\alpha_{1D}$ cDNA clones IMR32 1.144, IMR32 1.136, IMR32 1.80, and IMR32 1.163 (Example II.A.2.) overlap and include the entire $\alpha_{1D}$ coding sequence, nt 511 to 6993 (Sequence ID No. 1), with the exception of a 148 bp deletion, nt 2984 to 3131 (Sequence ID No. 1). Portions of these partial cDNA clones were ligated to generate a full-length $\alpha_{1D}$ cDNA in a eukaryotic expression vector. The resulting vector was called pVDCCIII(A). The construction of PVDCCIII(A) was performed in four steps described in detail below: (1) the construction of pVDCCIII/5' using portions of IMR32 1.144, IMR32 1.136, and IMR32 1.80, (2) the construction of pVDCCIII/5'.3 that corrects the 148 nt deletion in the IMR32 1.80 portion of pVDCCIII/5', (3) the construction of pVDCCIII/3'.1 using portions of IMR32

1.80 and IMR32 1.163, and (4) the ligation of a portion of the pVDCCIII/5'.3 insert, the insert of pVDCCIII/3'.1, and pcDNA1 (Invitrogen, San Diego, Calif.) to form pVDCCIII (A). The vector pcDNA1 is a eukaryotic expression vector containing a cytomegalovirus (CMV) promoter which is a constitutive promoter recognized by mammalian host cell RNA polymerase II.

Each of the DNA fragments used in preparing the full-length construct was purified by electrophoresis through an agarose gel onto DE81 filter paper (Whatman, Clifton, N.J.) and elution from the filter paper using 1.0M NaCl, 10 mM TRIS, pH 8.0, 1 mM EDTA. The ligations typically were performed in a 10 $\mu$l reaction volume with an equal molar ratio of insert fragment and a two-fold molar excess of the total insert relative to the vector. The amount of DNA used was normally about 50 ng to 100 ng.

a. pVDCCIII/5'

To construct pVDCCIII/5', IMR32 1.144 (Example II.A.2.c.) was digested with XhoI and EcoRI and the fragment containing the vector (pGEM7Z), $\alpha_{1D}$ nt 1 to 510 (Sequence ID No. 1), and $\alpha_{1D}$ nt 511 to 1732 (Sequence ID No. 1) was isolated by gel electrophoresis. The EcoRI-ApaI fragment of IMR32 1.136 (Example II.A.2.d.) nucleotides 1732 to 2667 (Sequence ID No. 1) was isolated, and the ApaI-HindIII fragment of IMR32 1.80 (Example II.A.2.b.), nucleotides 2667 to 4492 (Sequence ID No. 1) was isolated. The three DNA clones were ligated to form pVDCCIII/5' containing nt 1 to 510 (5' untranslated sequence; Sequence ID No. 1) and nt 511 to 4492 (Sequence ID No. 1).

b. pVDCCIII/5'.3

Comparison of the IMR32 1.36 and IMR32 1.80 DNA sequences revealed that these two cDNA clones differ through the $\alpha_{1D}$ coding sequence, nucleotides 2984 to 3212. PCR analysis of IMR32 1.80 and dbcAMP-induced (1.0 mM, 10 days) IMR32 cytoplasmic RNA (isolated according to Ausubel, F. M. et al. (Eds) (1988) *Current Protocols in Molecular Biology,* John Wiley and Sons, New York) revealed that IMR32 1.80 had a 148 nt deletion, nt 2984 to 3131 (Sequence ID No. 1), and that IMR32 1.36 had a 132 nt deletion, nt 3081 to 3212. To perform the PCR analysis, amplification was primed with $\alpha_{1D}$-specific oligonucleotides 112 (nt 2548 to 2572, Sequence ID No. 1) and 311 (the complementary sequence of nt 3928 to 3957, Sequence ID No. 1). These products were then reamplified using $\alpha_{1D}$-specific oligonucleotides 310 (nt 2583 to 2608 Sequence ID No. 1) and 312 (the complementary sequence of nt 3883 to 3909). This reamplified product contains AccI and BglII restriction sites (FIG. 1). The reamplified PCR product was digested with AccI and BglII and the AccI-BglII fragment, nt 2764 to 3890 (Sequence ID No. 1) was cloned into AccI-BglII digested pVDCCIII/5' to replace the AccI-BglII pVDCCIII/5' fragment that had the deletion. This new construct was named pVDCCIII/5'.3. DNA sequence determination of pVDCCIII/5'.3 through the amplified region confirmed the 148 nt deletion in IMR32 1.80.

c. pVDCCIII/3'.1

To construct pVDCCIII/3'.1, the cDNA insert of IMR32 1.163 (Example II.A.2.e.) was subcloned into pBluescript II (Stratagene, La Jolla, Calif.) as an XhoI fragment. The XhoI sites on the cDNA fragment were furnished by the adapters used to construct the cDNA library (I.B.3.). The insert was oriented such that the translational orientation of the insert of IMR32 1.163 was opposite to that of the lacZ gene present in the plasmid, as confirmed by analysis of restriction enzyme digests of the resulting plasmid. This was done to preclude the possibility of expression of $\alpha_{1D}$ sequences in DH5$\alpha$ cells transformed with this plasmid due to fusion with the lacZ gene. This plasmid was then digested with HindIII and BglII and the HindIII-BGlII fragment (the HindIII site comes from the vector and the BglII site is at nt 6220, Sequence ID No. 1) was eliminated, thus deleting nt 5200 to 6220 (Sequence ID No. 1) of the IMR32 1.163 clone and removing this sequence from the remainder of the plasmid which contained the 3' BglII-XhoI fragment, nt 6220 to 7635 (Sequence ID No. 1). pVDCCIII/3'.1 was then made by splicing together the HindIII-PvuII fragment from IMR32 1.80 (nucleotides 4492–5294, Sequence ID No. 1), the PvuII-BglII fragment of IMR32 1.163 (nucleotides 5294 to 6220, Sequence ID No. 1) and the HindIII-BglII-digested pBluescript plasmid containing the 3' BglII/XhoI IMR32 1.163 fragment (nt 6220 to 7635, Sequence ID No. 1).

d. pVDCCIII(A): the Full-length $\alpha_{1D}$ construct

To construct PVDCCIII (A), the DraI-HindIII fragment (5' untranslated sequence nt 327 to 510, Sequence ID No. 1 and coding sequence nt 511 to 4492, Sequence ID No. 1) of pVDCCIII/5'.3 (Example II.A.3.b.) was isolated; the HindIII-XhoI fragment of pVDCCIII/3'.1 (containing nt 4492 to 7635, Sequence ID No. 1, plus the XhoI site of the adapter) (Example II.A.3.c.) was isolated; and the plasmid vector, pcDNA1, was digested with EcoRV and XhoI and isolated on an agarose gel. These three DNA clones were ligated and MC1061-P3 (Invitrogen, San Diego, Calif.) was transformed. Isolated clones were analyzed by restriction mapping and DNA sequencing and pVDCCIII(A) was identified which had the fragments correctly ligated together: DraI-HindIII, HindIII-XhoI, XhoI-EcoRV with the blunt-end DraI and EcoRV site ligating together to form the circular plasmid.

The amino-terminus of the $\alpha_{1D}$ subunit is encoded by the seven consecutive 5' methionine codons (nt 511 to 531, Sequence ID No. 1). This 5' portion plus nt 532 to 537, encoding two lysine residues, were deleted from pVDCCIII (A) and replaced with an efficient ribosomal binding site (5'-ACCACC-3') to form pVDCCIII.RBS(A). Expression experiments in which transcripts of this construct were injected into Xenopus laevis oöcytes did not result in an enhancement in the recombinant voltage-dependent calcium channel expression level relative to the level of expression in oöcytes injected with transcripts of pVDCCIII(A).

B. Isolation of DNA encoding the $\alpha_{1C}$ subunit

1. Reference List of Partial $\alpha_{1C}$ cDNA Clones

Figure 2:
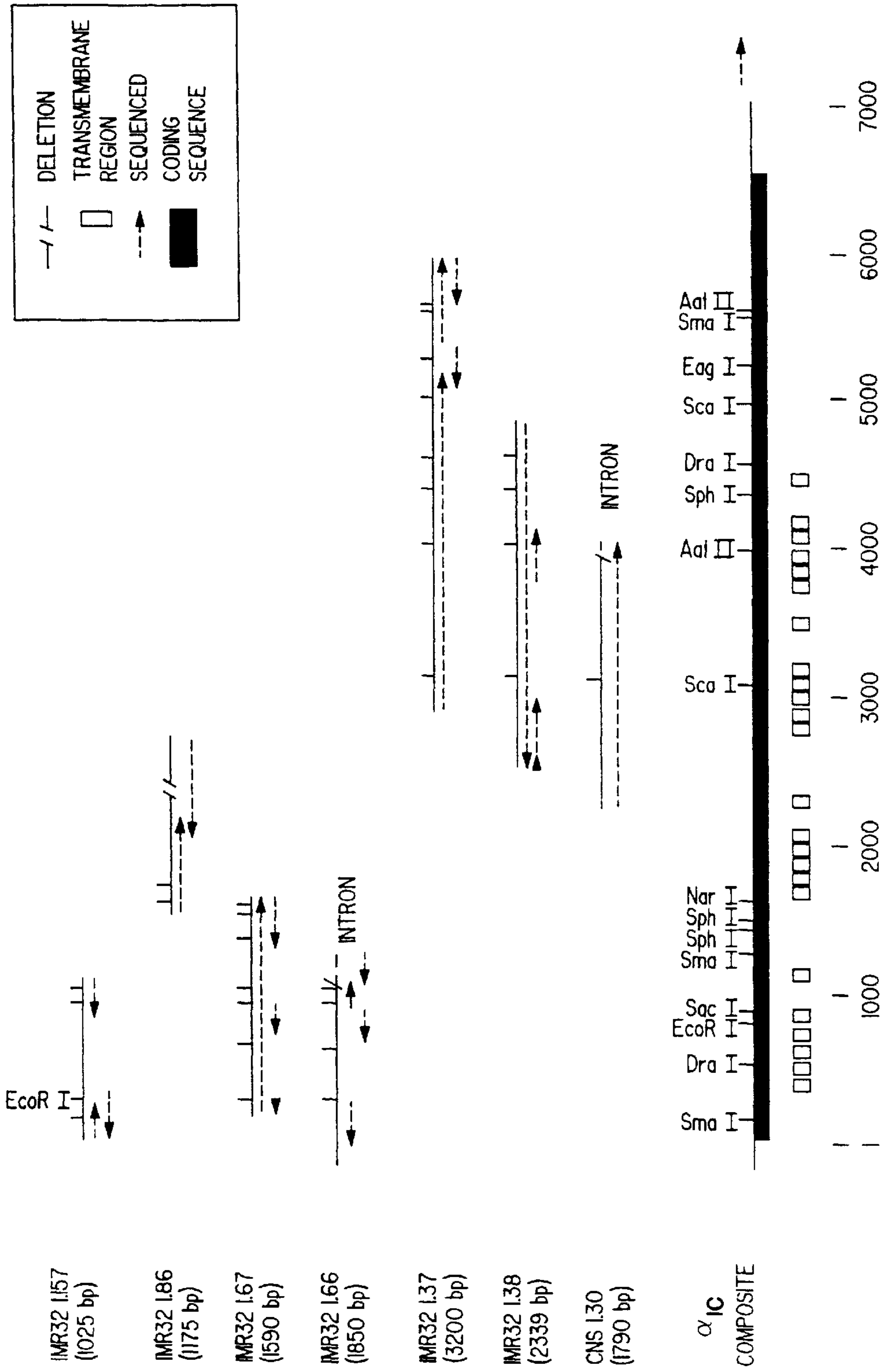
FIG. 2 represents a restriction map of a nucleic acid sequence encoding most of a human neuronal calcium channel $\alpha_{1C}$ subunit and the sequencing strategy used to derive the coding sequence from various cDNA clones.

Numerous $\alpha_{1C}$-specific cDNA clones were isolated in order to characterize the $\alpha_{1C}$ coding sequence, the $\alpha_{1C}$ initiation of translation, and an alternatively spliced region of $\alpha_{1C}$. Sequence ID No. 3 sets forth the characterized $\alpha_{1C}$ coding sequence (nt 1 to 5904) and deduced amino acid sequence. Sequence ID No. 4 and No. 5 encode two possible amino terminal ends of the $\alpha_{1C}$ protein. Sequence ID No. 6 encodes an alternative exon for the IV S3 transmembrane domain. Shown below is a list of clones used to characterize the $\alpha_{1C}$ sequence and the nucleotide position of each clone relative to the characterized $\alpha_{1C}$ sequence (Sequence ID No. 3). Restriction maps of the partial $\alpha_{1C}$ cDNA clones are shown in FIG. 2. The isolation and characterization of these cDNA clones are described below (Example II.B.2).

| | | |
|---|---|---|
| IMR32 | 1.66 (Sequence ID No. 50) | nt 1 to 916, Sequence ID No. 3 nt 1 to 132, Sequence ID No. 4 |
| IMR32 | 1.157 (Sequence ID No. 24) | nt 1 to 873, Sequence ID No. 3 nt 1 to 89, Sequence ID No. 5 |
| IMR32 | 1.67 | nt 50 to 1717, Sequence ID No. 3 |
| *1MR32 | 1.86 | nt 1366 to 2583, Sequence ID No. 3 |
| @1.16G | | nt 758 to 867, Sequence ID No. 3 |
| IMR32 | 1.37 | nt 2804 to 5904, Sequence ID No. 3 |
| CNS | 1.30 (Sequence ID No. 29, nt. 87–1875) | nt 2199 to 3903, Sequence ID No. 3 nt 1 to 84 of alternative exon, Sequence ID No. 6 |
| IMR32 | 1.38 | nt 2448 to 4702, Sequence ID No. 3 nt 1 to 84 of alternative exon, Sequence ID No. 6 |

* IMR32 1.86 has a 73 nt deletion compared to the rabbit cardiac muscle calcium channel $\alpha_1$ subunit cDNA sequence.
@1.16G is an $\alpha_{1c}$ genomic clone.

2. Isolation and Characterization of Clones Described Example II.B.1.

a. CNS 1.30

Approximately $1\times10^6$ recombinants of the human thalamus cDNA library No. 6 (Example I.B.6.) were screened with fragments of the rabbit skeletal muscle calcium channel $\alpha_1$ cDNA described in Example II.A.2.a. The hybridization was performed using standard hybridization conditions (Example I.C.) and the filters were washed under low stringency (Example I.C.). Six positive plaques were identified, one of which was CNS 1.30. CNS 1.30 was plaque purified, restriction mapped, subcloned, and characterized by DNA sequencing. CNS 1.30 (set forth in Sequence ID No. 28, at 87–1815) encodes $\alpha_{1C}$-specific sequence nt 2199 to 3903 (Sequence ID No. 3) followed by nt 1 to 84 of one of two identified alternative $\alpha_{1C}$ exons (Sequence ID No. 6). 3' of Sequence ID No. 6, CNS 1.30 contains an intron and, thus, CNS 1.30 encodes a partially spliced $\alpha_{1C}$ transcript.

b. 1.16G

Approximately $\times10^6$ recombinants of a λEMPL3-based human genomic DNA library (Cat # HL1006d Clontech Corp., Palo Alto, Calif.) were screened using a rabbit skeletal muscle cDNA fragment (nt−78 to 1006, Example II.A.2.a.). The hybridization was performed using standard hybridization conditions (Example I.C.) and the filters were washed under low stringency (Example I.C.). Fourteen positive plaques were identified, one of which was 1.16G. Clone 1.16G was plaque purified, restriction mapped, subcloned, and portions were characterized by DNA sequencing. DNA sequencing revealed that 1.16G encodes $\alpha_{1C}$ -specific sequence as described in Example II.A.1.

c. IMR32 1.66 and IMR32 1.67

Approximately $1\times10^6$ recombinants of IMR32 cDNA library #5 (Example I.B.5.) were screened with a 151 bp KpnI-SacI fragment of 1.16G (Example II.B.2.b.) encoding $\alpha_{1C}$ sequence (nt 758 to 867, Sequence ID No. 3). The hybridization was performed using standard hybridization conditions (Example I.C.). The filters were then washed in 0.5×SSPE at 65° C. Of the positive plaques, IMR32 1.66 and IMR32 1.67 were identified. The hybridizing plaques were purified, restriction mapped, subcloned, and characterized by DNA sequencing. Two of these cDNA clones, IMR32 1.66 and 1.67, encode $\alpha_{1C}$ subunits as described (Example II.B.1.). In addition, IMR32 1.66 encodes a partially spliced $\alpha_{1C}$ transcript marked by a GT splice donor dinucleotide beginning at the nucleotide 3' of nt 916 (Sequence ID No. 3). The intron sequence within 1.66 is 101 nt long. IMR32 1.66 encodes the $\alpha_{1C}$ initiation of translation, nt 1 to 3 (Sequence ID No. 3) and 132 nt of 5' untranslated sequence (Sequence ID No. 4) precede the start codon in IMR32 1.66 (set forth in Sequence ID. No. 30).

d. IMR32 1.37 and IMR32 1.38

Approximately $2\times10^6$recombinants of IMR32 cDNA library #1 (Example I.B.1.) were screened with the CNS 1.30 cDNA fragment (Example II.B.2.a.). The hybridization was performed using low stringency hybridization conditions (Example I.C.) and the filters were washed under low stringency (Example I.C.). Four positive plaques were identified, plaque purified, restriction mapped, subcloned, and characterized by DNA sequencing. Two of the clones, IMR32 1.37 and IMR32 1.38 encode $\alpha_{1C}$-specific sequences as described in Example II.B.1.

Figure 3:
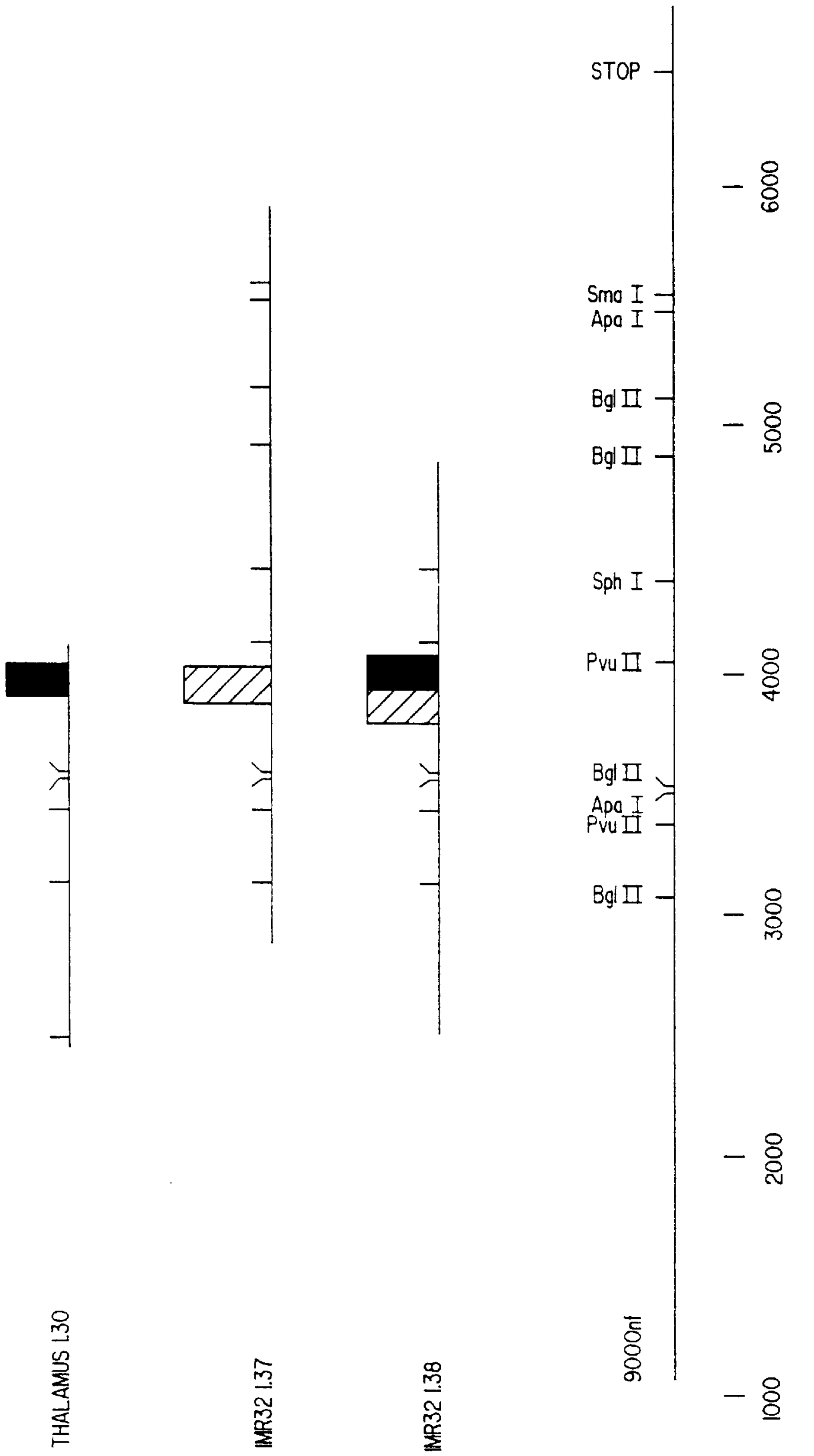
FIG. 3 depicts an alternative splicing pattern of a nucleic acid sequence encoding a human neuronal calcium channel $\alpha_{1C}$ subunit.

DNA sequence comparison of IMR32 1.37 and IMR32 1.38 revealed that the $\alpha_{1C}$ transcript includes two exons that encode the IVS3 transmembrane domain. IMR32 1.37 has a single exon, nt 3904 to 3987 (Sequence ID No. 3) and IMR32 1.38 (set forth in Sequence ID. No. 31) appears to be anomalously spliced to contain both exons juxtaposed, nt 3904 to 3987 (Sequence ID No. 3) followed by nt 1 to 84 (Sequence ID No. 6). The alternative splice of the $\alpha_{1C}$ transcript to contain either of the two exons encoding the IVS3 region was confirmed by comparing the CNS 1.30 sequence to the IMR32 1.37 sequence. CNS 1.30 (set forth in Sequence ID. No. 29, nt 87–1875) contains nt 1 to 84 (Sequence ID No. 6) preceded by the identical sequence contained in IMR32 1.37 for nt 2199 to 3903 (Sequence ID No. 3). As described in Example II.B.2.a., an intron follows nt 1 to 84 (Sequence ID No. 6). Two alternative exons have been spliced adjacent to nt 3903 (Sequence ID No. 3) represented by CNS 1.30 and IMR32 1.37. The alternative splicing of this region is schematically depicted in FIG. 3 (see, also, Sequence ID. Nos. 24, 29, 30 and 31). The solid box represents nt 1 to 84 (Sequence ID No. 6) and the striped box represents nt 3904 to 3987 (Sequence ID No. 3).

e. IMR32 1.86

IMR32 cDNA library #1 (Example I.B.1.) was screened in duplicate using oligonucleotide probes 90-9 (nt 1462 to 1491, Sequence ID No. 3) and 90-12 (nt 2496 to 2520, Sequence ID No. 3). These oligonucleotide probes were chosen in order to isolate a clone that encodes the $\alpha_{1C}$ subunit between the 3' end of IMR32 1.67 (nt 1717, Sequence ID No. 3) and the 5' end of CNS 1.30 (nt 2199, Sequence ID No. 3). The hybridization conditions were standard hybridization conditions (Example I.C.) with the exception that the 50% deionized formamide was reduced to 20%. The filters were washed under low stringency (Example I.C.). Three positive plaques were identified one of which was IMR32 1.86. IMR32 1.86 was plaque purified, subcloned, and characterized by restriction mapping and DNA sequencing. IMR32 1.86 encodes $\alpha_{1C}$ sequences as described in Example II.B.1. Characterization by DNA sequencing revealed that IMR32 1.86 contains a 73 nt deletion compared to the DNA encoding rabbit cardiac muscle calcium channel $\alpha_1$ subunit [Mikami et al. (1989) *Nature* 340:230], nt 2191 to 2263. These missing nucleotides correspond to nt 2176–2248 of Sequence ID No. 3. Because the 5'-end of CNS 1.30 overlaps the 3'-end of IMR32 1.86, some of these missing nucleotides, i.e., nt 2205–2248 of Sequence ID No. 3, are accounted for by CNS 1.30. The remaining missing nucleotides of the 73 nucleotide deletion in IMR32 1.86 (i.e., nt 2176–2204 Sequence ID No. 3) were determined by PCR analysis of dbcAMP-induced IMR32 cell RNA. The 73 nt deletion is a frame-shift mutation and, thus, needs to be corrected. The exact human sequence through this region, (which has been determined by the DNA sequence of CNS 1.30 and PCR analysis of IMR32 cell RNA) can be inserted into IMR32 1.86 by standard methods, e.g., replacement of a restriction fragment or site-directed mutagenesis.

f. IMR32 1.157

One million recombinants of IMR32 cDNA library #4 (Example I.B.4.) were screened with an XhoI-EcoRI fragment of IMR32 1.67 encoding $\alpha_{1C}$ nt 50 to 774 (Sequence ID No. 3). The hybridization was performed using standard hybridization conditions (Example I.C.). The filters were washed under high stringency (Example I.C.). One of the positive plaques identified was IMR32 1.157 (set forth in Sequence ID. No. 24). This plaque was purified, the insert was restriction mapped and subcloned to a standard plasmid vector (e.g., pGEM7Z, Promesa, Madison, Wis.). The cDNA was characterized by DNA sequencing. IMR32 1.157 possibly encodes an alternative 5' portion of the $\alpha_{1C}$ sequence beginning with nt 1 to 89 (Sequence ID No. 5) which is then followed by nt 1 to 873 (Sequence ID No. 3). Analysis of the 1.66 and 1.157 5' sequence is described below (Example II.B.3.).

3. Characterization of the $\alpha_{1C}$ Initiation of Translation Site

The human sequences represent possible alternative 5' ends of the $\alpha_{1C}$ transcript encoding the region of initiation of translation. IMR32 1.66 closely matches the CaCB receptor cDNA sequence and diverges from the CaCB receptor cDNA sequence in the 5' direction beginning at nt 122 (Sequence ID No. 4). The start codon identified in the CaCB receptor cDNA sequence is enclosed in a box and is the same start codon used to describe the $\alpha_{1C}$ coding sequence, nt 1 to 3 (Sequence ID No. 3). The functional significance of the IMR32 1.157 sequence, nt 1 to 89 (Sequence ID No. 5), is unknown, however, chimeric sequence between 1.157 and the $\alpha_{1C}$ coding sequence can be constructed and functional differences can be tested. IMR32 1.157 does not contain an initiation codon, however, one can be cloned by screening IMR32 cell cDNA libraries using probes corresponding to Sequence ID No. 5.

C. Isolation of partial cDNA clones encoding the $\alpha_{1B}$ subunit and construction of a full-length clone A human basal ganglia cDNA library was screened with the rabbit skeletal muscle $\alpha_1$ subunit cDNA fragments (see Example II.A.2.a for description of fragments) under low stringency conditions. One of the hybridizing clones was used to screen an IMR32 cell cDNA library to obtain additional partial $\alpha_{1B}$ cDNA clones, which were in turn used to further screen an IMR32 cell cDNA library for additional partial cDNA clones. One of the partial IMR32 $\alpha_{1B}$ clones was used to screen a human hippocampus library to obtain a partial $\alpha_{1B}$ clone encoding the 3' end of the $\alpha_{1B}$ coding sequence. The sequence of some of the regions of the partial cDNA clones was compared to the sequence of products of PCR analysis of IMR32 cell RNA to determine the accuracy of the cDNA sequences.

PCR analysis of IMR32 cell RNA and genomic DNA using oligonucleotide primers corresponding to sequences located 5' and 3' of the STOP codon of the DNA encoding the $\alpha_{1B}$ subunit revealed an alternatively spliced $\alpha_{1B}$-encoding mRNA in IMR32 cells. This second mRNA product is the result of differential splicing of the $\alpha_{1D}$ subunit transcript to include another exon that is not present in the mRNA corresponding to the other 3' $\alpha_{1B}$ cDNA sequence that was initially isolated. To distinguish these splice variants of the $\alpha_{1B}$ subunit, the subunit encoded by a DNA sequence corresponding to the form containing the additional exon is referred to as $\alpha_{1B-1}$ (Sequence ID No. 7), whereas the subunit encoded by a DNA sequence corresponding to the form lacking the additional exon is referred to as $\alpha_{1B-2}$ (Sequence ID No. 8). The sequence of $\alpha_{1B-1}$ diverges from that of $\alpha_{1B-2}$ beginning at nt 6633 (Sequence ID No. 7). Following the sequence of the additional exon in $\alpha_{1B-1}$ (nt 6633–6819; Sequence ID No. 7), the $\alpha_{1B-1}$ and $\alpha_{1B-2}$ sequences are identical (i.e., nt 6820–7362 in Sequence ID No. 7 and nt 6633–7175 in Sequence ID No. 8). Sequence ID No. 7 and No. 8 set forth 143 nt of 5' untranslated sequence (nt 1–143) as well as 202 nt of 3' untranslated sequence (nt 7161–7362, Sequence ID No. 7) of the DNA encoding $\alpha_{1B-1}$ and 321 nt of 3' untranslated sequence (nt 6855–7175, Sequence ID No. 8) of the DNA encoding $\alpha_{1B-2}$.

PCR analysis of the IS6 region of the $\alpha_{1B}$ transcript revealed additional splice variants based on multiple fragment sizes seen on an ethidium bromide-stained agarose gel containing the products of the PCR reaction.

A full-length $\alpha_{1B-1}$ cDNA clone designated pcDNA-$\alpha_{1B-1}$ was prepared in an eight-step process as follows.

STEP 1

The SacI restriction site of pGEM3 (Promega, Madison, Wis.) was destroyed by digestion at the SacI site, producing blunt ends by treatment with T4 DNA polymerase, and religation. The new vector was designated pGEMΔSac.

STEP 2

Fragment 1 (HindIII/KpnI; nt 2337 to 4303 of Sequence ID No. 7) was ligated into HindIII/KpnI digested pGEM3ΔSac to produce p$\alpha$1.177HK.

STEP 3

Fragment 1 has a 2 nucleotide deletion (nt 3852 and 3853 of Sequence ID No. 7). The deletion was repaired by inserting a PCR fragment (fragment 2) of IMR32 RNA into p$\alpha$1.177HK. Thus, fragment 2 (NarI/KpnI; nt 3828 to 4303 of Sequence ID No. 7) was inserted into NarI/KpnI digested pal.177HK replacing the NarI/KpnI portion of fragment 1 and producing p$\alpha$1.177HK/PCR.

STEP 4

Fragment 3 (KpnI/KpnI; nt 4303 to 5663 of Sequence ID No. 7) was ligated into KpnI digested p$\alpha$1.177HK/PCR to produce p$\alpha$1B5'K.

STEP 5

Fragment 4 (EcoRI/HindIII; EcoRI adaptor plus nt 1 to 2337 of Sequence ID No. 7) and fragment 5 (HindIII/XhoI fragment of p$\alpha$1B5'K; nt 2337 to 5446 of Sequence ID No. 7) were ligated together into EcoRI/IXhoI digested pcDNA1 (Invitrogen, San Diego, Calif.) to produce p$\alpha$1B5'.

STEP 6

Fragment 6 (EcoRI/EcoRI; EcoRI adapters on both ends plus nt 5749 to 7362 of Sequence ID No. 7) was ligated into EcoRI digested pBluescript II KS (Stratagene, La Jolla, Calif.) with the 5' end of the fragment proximal to the KpnI site in the polylinker to produce p$\alpha$1.230.

STEP 7

Fragment 7 (KpnI/XhoI; nt 4303 to 5446 of Sequence ID No. 7), and fragment 8 (XhoI/CspI; nt 5446 to 6259 of Sequence ID No. 7) were ligated into KpnI/CspI digested p$\alpha$1.230 (removes nt 5749 to 6259 of Sequence ID No. 7 that was encoded in p$\alpha$1.230 and maintains nt 6259 to 7362 of Sequence ID No. 7) to produce p$\alpha$1B3'.

STEP 8

Fragment 9 (SphI/XhoI; nt 4993 to 5446 of Sequence ID No. 7) and fragment 10 (XhoI/XbaI; nt 5446 to 7319 of Sequence ID No. 7) were ligated into SphI/XbaI digested pcDNA1 (removes nt 4993 to 5446 of Sequence ID No. 7 that were encoded in p$\alpha$1B5' and maintains nt 1 to 4850 of Sequence ID No. 7) to produce pcDNA$\alpha_{1B-1}$.

The resulting construct, pcDNA$\alpha_{1B-1}$, contains, in pcDNA1, a full-length coding region encoding $\alpha_{1B-1}$ (nt 144–7362, Sequence ID No. 7), plus 5' untranslated sequence (nt 1–143, Sequence ID No. 7) and 3' untranslated sequence (nt 7161–7362, Sequence ID No. 7) under the transcriptional control of the CMV promoter.

Example III

ISOLATION OF cDNA CLONES ENCODING THE HUMAN NEURONAL CALCIUM CHANNEL $\beta$ subunit A. Isolation of partial cDNA clones encoding the $\beta$ subunit and construction of a full-length clone encoding the $\beta$ subunit A human hippocampus cDNA library was screened with the rabbit skeletal muscle calcium channel $\beta$ subunit cDNA fragment (nt 441 to 1379) [for isolation and sequence of the rabbit skeletal muscle calcium channel $\beta$ subunit cDNA, see U.S. patent application Ser. No. 482,384 or Ruth et al. (1989) *Science* 245:1115] using standard hybridization conditions (Example I.C.). A portion of one of the hybridizing clones was used to rescreen the hippocampus library to obtain additional cDNA clones. The cDNA inserts of hybridizing clones were characterized by restriction mapping and DNA sequencing and compared to the rabbit skeletal muscle calcium channel $\beta$ subunit cDNA sequence.

Portions of the partial $\beta$ subunit cDNA clones were ligated to generate a full-length clone encoding the entire $\beta$ subunit. Sequence ID No. 9 shows the $\beta$ subunit coding sequence (nt 1–1434) as well as a portion of the 3' untranslated sequence (nt 1435–1546). The deduced amino acid sequence is also provided in Sequence ID No. 9. In order to perform expression experiments, full-length $\beta$ subunit cDNA clones were constructed as follows.

Step 1: DNA fragment 1 (~800 bp of 5' untranslated sequence plus nt 1–277 of Sequence ID No. 9) was ligated to DNA fragment 2 (nt 277–1546 of Sequence ID No. 9 plus 448 bp of intron sequence) and cloned into pGEM7Z. The resulting plasmid, p$\beta$1–1.18, contained a full-length $\beta$ subunit clone that included a 448-bp intron.

Step 2: To replace the 5' untranslated sequence of p$\beta$1–1.18 with a ribosome binding site, a double-stranded adapter was synthesized that contains an EcoRI site, sequence encoding a ribosome binding site (5'-ACCACC-3') and nt 1–25 of Sequence ID No. 9. The adapter was ligated to SmaI-digested p$\beta$1–1.18, and the products of the ligation reaction were digested with EcoRI.

Step 3: The EcoRI fragment from step 2 containing the EcoRI adapter, efficient ribosome binding site and nt 1–1546 of Sequence ID No. 9 plus intron sequence was cloned into a plasmid vector and designated p$\beta$1–1.18RBS.

Step 4: To generate a full-length clone encoding the $\beta$ subunit lacking intron sequence, DNA fragment 3 (nt 69–1146 of Sequence ID No. 9 plus 448 bp of intron sequence followed by nt 1147–1546 of Sequence ID No. 9), was subjected to site-directed mutagenesis to delete the intron sequence, thereby yielding p$\beta$1(−). The EcoRI-XhoI fragment of p$\beta$1-1.18RBS (containing of the ribosome binding site and nt 1–277 of Sequence ID No. 9) was ligated to the XhoI-EcoRI EcoRI fragment of p$\beta$1(−) (containing of nt 277–1546 of Sequence ID No. 9) and cloned into pcDNA1 with the initiation of translation proximal to the CMV promoter. The resulting expression plasmid was designated pHBCaCH$\beta$1bA.

B. Splice Variant $\beta_3$

DNA sequence analysis of the DNA clones encoding the $\beta$ subunit indicated that in the CNS at least two alternatively spliced forms of the same human $\beta$ subunit primary transcript are expressed. One form is represented by the sequence shown in Sequence ID No. 9 and is referred to as $\beta_2$. The sequences of $\beta_2$ and the alternative form, $\beta_3$, diverge at nt 1334 (Sequence ID No. 9). The complete $\beta_3$ sequence (nt 1–1851), including 3' untranslated sequence (nt 1795–1851), is set forth in Sequence ID No. 10.

Example IV

Figure 4:
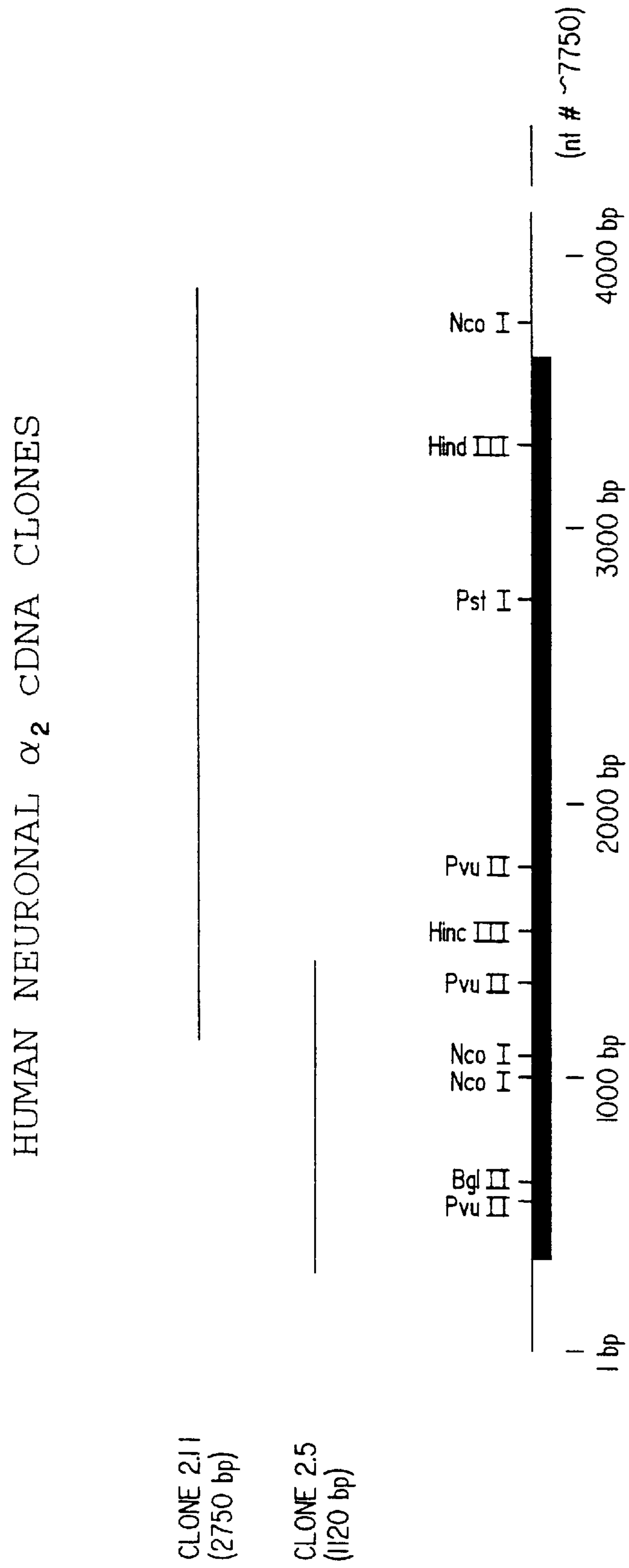
FIG. 4 is a restriction map of a nucleic acid sequence encoding a human neuronal calcium channel $\alpha_2$ subunit, and the various cDNA clones from which the complete coding sequence was derived.

ISOLATION OF cDNA CLONES ENCODING THE HUMAN NEURONAL CALCIUM CHANNEL $\alpha_2$-subunit A. Isolation of cDNA clones A schematic of human neuronal calcium channel $\alpha_2$ subunit cDNA clones that overlap to encode the complete coding sequence is shown in FIG. 4. The complete human neuronal $\alpha_2$ coding sequence (nt 35–3307) plus a portion of the 5' untranslated sequence (nt 1 to 34) as well as a portion of the 3' untranslated sequence (nt 3308–3600) is set forth in Sequence ID No. 11.

To isolate DNA encoding the human neuronal $\alpha_2$ subunit, human $\alpha_2$ genomic clones first were isolated by probing human genomic Southern blots using a rabbit skeletal muscle calcium channel $\alpha_2$ subunit cDNA fragment [nt 43 to 272, Ellis et al. (1988) *Science* 240:1661]. Human genomic DNA was digested with EcoRI, electrophoresed, blotted, and probed with the rabbit skeletal muscle probe using standard hybridization conditions (Example I.C.) and low stringency washing conditions (Example I.C.). Two restriction fragments were identified, 3.5 kb and 3.0 kb. These EcoRI restriction fragments were cloned by preparing a $\lambda$gt11 library containing human genomic EcoRI fragments ranging from 2.2 kb to 4.3 kb. The library was screened as described above using the rabbit $\alpha_2$ probe, hybridizing clones were isolated and characterized by DNA sequencing. HGCaCH$\alpha$2.20 contained the 3.5 kb fragment and HGCaCH$\alpha$2.9 contained the 3.0 kb fragment.

Restriction mapping and DNA sequencing revealed that HGCaCH$\alpha$2.20 contains an 82 bp exon (nt 130 to 211 of the human $\alpha_2$ coding sequence, Sequence ID No. 11) on a 650 bp PstI-XbaI restriction fragment and that HGCaCH$\alpha$2.9 contains 105 bp of an exon (nt 212 to 316 of the coding sequence, Sequence ID No. 11) on a 750 bp XbaI-BglII restriction fragment. These restriction fragments were used to screen the human basal ganglia cDNA library (Example II.C.2.a.). HBCaCH$\alpha$2.1 was isolated (nt 29 to 1163, Sequence ID No. 11) and used to screen a human brain stem cDNA library (ATCC Accession No. 37432) obtained from the American Type Culture Collection, Parklawn Drive, Rockville, Md. 20852. Two clones were isolated, HBCaCH$\alpha$2.5 (nt 1 to 1162, Sequence ID No. 11) and HBCaCH$\alpha$2.8 (nt 714 to 1562, Sequence ID No. 11, followed by 1600 nt of intervening sequence). A 2400 bp fragment of HBCaCH$\alpha$2.8 (beginning at nt 759 of Sequence ID No. 11 and ending at a SmaI site in the intron) was used to rescreen the brain stem library and to isolate HBCaCH$\alpha$2.11 (nt 879 to 3600, Sequence ID No. 11). Clones HBCaCH$\alpha$2.5 and HBCaCH$\alpha$2.11 overlap to encode an entire human brain $\alpha_2$ protein.

B. Construction of pHBCaCH$\alpha_2$A

To construct pHBCaCH$\alpha_2$A containing DNA encoding a full-length human calcium channel $\alpha_2$ subunit, an (EcoRI)-PvuII fragment of HBCaCH$\alpha$2.5 (nt 1 to 1061, Sequence ID No. 11, EcoRI adapter, PvuII partial digest) and a PvuII-PstI fragment of HBCaCH$\alpha$2.11 (nt 1061 to 2424 Sequence ID No. 11; PvuII partial digest) were ligated into EcoRI-PstI-digested pIBI24 (Stratagene, La Jolla, Calif.). Subsequently, an (EcoRI)-PstI fragment (nt 1 to 2424 Sequence ID No. 11) was isolated and ligated to a PstI-(EcoRI) fragment (nt 2424 to 3600 Sequence ID No. 11) of HBCaCH$\alpha$2.11 in EcoRI-digested pIBI24 to produce DNA, HBCaCH$\alpha$2, encoding a full-length human brain $\alpha_2$ subunit. The 3600 bp EcoRI insert of HBCaCH$\alpha$2 (nt 1 to 3600, Sequence ID No. 11) was subcloned into pcDNA1 (pHBCaCH$\alpha$2A) with the methionine initiating codon proximal to the CMV promoter. The 3600 bp EcoRI insert of HBCaCH$\alpha$2 was also subcloned into pSV2dHFR [Subramani et al. (1981). *Mol. Cell. Biol.* 1:854–864] which contains the SV40 early promoter, mouse dihydrofolate reductase (dhfr) gene, SV40 polyadenylation and splice sites and sequences required for maintenance of the vector in bacteria.

Example V

DIFFERENTIAL PROCESSING OF THE HUMAN $\beta$ TRANSCRIPT AND THE HUMAN $\alpha_2$ TRANSCRIPT A. Differential processing of the $\beta$ transcript PCR analysis of the human $\beta$ transcript present in skeletal muscle, aorta, hippocampus and basal ganglia, and HEK 293 cells revealed differential processing of the region corresponding to nt 615–781 of Sequence ID No. 9 in each of the tissues (see Sequence ID. No. 19). Four different sequences that result in five different processed $\beta$ transcripts through this region were identified. The $\beta$ transcripts from the different tissues contained different combinations of the four sequences, except for one of the $\beta$ transcripts, expressed in HEK 293 cells ($\beta_5$), which lacked all four.

None of the $\beta$ transcripts contained each of the four sequences; however, for ease of reference, all four sequences are set forth end-to-end as a single long sequence in Sequence ID No. 12 (nt. 1 to 323) and Sequence ID No. 19(nt 615 to 937). The four sequences that are differentially processed are sequence 1 (nt 14–34 in Sequence ID No. 12 nt. 628 to 648 in SEQ ID NO. 19), sequence 2 (nt 35–55 in Sequence ID No. 12 nt. 649 to 699 in Sequence ID No. 19), sequence 3 (nt 56–190 in Sequence ID No. 12 nt. 649 to 669 in Sequence ID No. 19) and sequence 4 (nt 191–271 in Sequence ID No. 12. The sequences of these splice variants, designated $\beta_1$–$\beta_5$ are forth in sequence ID Nos. 37, 9, 10, 38 and 39, respectively. The forms of the $\beta$ transcript that have been identified include: (1) a form that lacks sequence 1 called $\beta_1$ (expressed in skeletal muscle Sequence ID No. 19 in which nt. 628 to 648 are not present), (2) a form that lacks sequences 2 and 3 called $\beta_2$ (expressed in CNS Sequence ID No. 19 in which nt. 649 to 804 are not present), (3) a form that lack sequences 1, 2 and 3 called $\beta_4$ (expressed in aorta and HEK cells Sequence ID No. 19 in which nt. 627 to 804 are not present) and (4) a form that lacks sequences 1–4 called $\beta_5$ (expressed in HEK cells Sequence ID No. 19 in which nt. 627 to 885 are not present). Additionally, the $\beta_4$ and $\beta_5$ forms contain the guanine nucleotide (nt 13 in Sequence ID No. 12 nt. 627 in Sequence ID No. 19) which is absent in the $\beta_1$ and $\beta_2$ forms. The sequences of these splice variants, designated $\beta_1$–$\beta_5$ are forth in sequence ID Nos. 37 , 9, 10, 38 and 39, respectively.

B. Differential processing of transcripts encoding the $\alpha_2$ subunit.

The complete human neuronal $\alpha_2$ coding sequence (nt 35–3307) plus a portion of the 5' untranslated sequence (nt 1 to 34) as well as a portion of the 3' untranslated sequence (nt 3308–3600) is set forth as Sequence ID No. 11.

PCR analysis of the human $\alpha_1$ transcript present in skeletal muscle, aorta, and CNS revealed differential processing of the region corresponding to nt 1595–1942 of Sequence ID #11 in each of the tissues.

The analysis indicated that the primary transcript of the genomic DNA that includes the nucleotides corresponding to nt. 1595–1942 also includes an additional sequence, Sequence ID No. 13: 5'CCTATTGGTGTAGGTATACCAA-CAATTAATTTAA GAAAAAGGAGACCCAATATCCAG 3' inserted between nt. 1624 and 1625 of Sequence ID No. 11 the resulting molecule is set for in Sequence ID No. 20. Five alternatively spliced variant transcripts that differ in the presence or absence of one to three different portions of the region of the primary transcript (i.e., Sequence ID No. 20) that includes the region of nt. 1595–1942 of Sequence ID No. 11 plus Sequence ID No. 13 inserted between nt. 1624 and 1625 have been identified. The five $\alpha_2$-encoding transcripts from the different tissues include different combinations of the three sequences, except for one of the $\alpha_2$ transcripts expressed in aorta which lacks all three sequences. None of the $\alpha_2$ transcripts contained each of the three sequences. The sequences of the three regions that are differentially processed are sequence 1 (Sequence ID #13), sequence 2 (Sequence ID No. 21), and sequence 3 Sequence ID #22). The five $\alpha_2$ forms identified are (1) a form that lacks sequence 3 called $\alpha_{2a}$ (expressed in skeletal muscle Sequence ID No. 20 in which nt. 1965 to 1985 are not present), (2) a form that lacks sequence 1 called $\alpha_{2b}$ (expressed in CNS Sequence ID No. 11), (3) a form that lacks sequences 1 and 2 called $\alpha_{2c}$ expressed in aorta Sequence ID No. 11 in which nt. 1682 to 1696 are not present), (4) a form that lacks sequences 1, 2 and 3 called $\alpha_{2d}$ (expressed in aorta Sequence ID No. 11 in which n. 1625 to 1639 and nucleotides 1908 to 1928 are not present) and (5) a form that lacks sequences 1 and 3 called $\alpha_{2e}$ (expressed in aorta). The sequences of subunits $\alpha_{2a}$–$\alpha_{2e}$ are set forth in SEQ ID NOs. 33, 11, 34, 35 and 36 respectively.

Example VI

ISOLATION OF DNA ENCODING A CALCIUM CHANNEL $\gamma$ SUBUNIT FROM A HUMAN BRAIN cDNA LIBRARY DNA encoding a human calcium channel $\gamma$ subunit was isolated from a human hippocampus cDNA library.

A. Isolation of cDNA clones

Approximately $1\times10^6$ recombinants from a $\lambda$gt11 -based human hippocampus cDNA library (Clontech catalog #HL1088b, Palo Alto, Calif.) were screened by hybridization to a 484 bp sequence of the rabbit skeletal muscle calcium channel $\gamma$ subunit cDNA (nucleotides 621–626 of the coding sequence plus 438 nucleotides of 3'-untranslated sequence) contained in vector $\gamma$J10 [Jay, S. et al. (1990). *Science* 248:490–492]. Hybridization was performed using moderate stringency conditions (20% deionized formamide, 5× Denhardt's, 6×SSPE, 0.2% SDS, 20 $\mu$g/ml herring sperm DNA, 42° C.) and the filters were washed under low stringency (see Example I.C.). A plaque that hybridized to this probe was purified and insert DNA was subcloned into pGEM7Z. This cDNA insert was designated $\gamma$1.4.

B. Characterization of $\gamma$1.4

$\gamma$1.4 was confirmed by DNA hybridization and characterized by DNA sequencing. The 1500 bp SstI fragment of $\gamma$1.4 hybridized to the rabbit skeletal muscle calcium channel $\gamma$ subunit cDNA $\gamma$J10 on a Southern blot. Sequence analysis of this fragment revealed that it contains of approximately 500 nt of human DNA sequence and ~1000 nt of $\lambda$gt11 sequence (included due to apparent destruction of one of the EcoRI cloning sites in $\lambda$gt11 ). The human DNA sequence contains of 129 nt of coding sequence followed immediately by a translational STOP codon and 3' untranslated sequence (Sequence ID No. 14).

To isolate the remaining 5' sequence of the human γ subunit cDNA, human CNS cDNA libraries and/or preparations of mRNA from human CNS tissues can first be assayed by PCR methods using oligonucleotide primers based on the γ cDNA-specific sequence of γ1.4. Additional human neuronal γ subunit-encoding DNA can isolated from cDNA libraries that, based on the results of the PCR assay, contain γ-specific amplifiable cDNA. Alternatively, cDNA libraries can be constructed from mRNA preparations that, based on the results of PCR assays, contain γ-specific amplifiable transcripts. Such libraries are constructed by standard methods using oligo dT to prime first-strand cDNA synthesis from poly $A^+$ RNA (see Example I.B.). Alternatively, first-strand cDNA can be specified by priming first-strand cDNA synthesis with a γ cDNA-specific oligonucleotide based on the human DNA sequence in γ1.4. A cDNA library can then be constructed based on this first-strand synthesis and screened with the γ-specific portion of γ1.4.

Example VII

RECOMBINANT EXPRESSION OF HUMAN NEURONAL CALCIUM CHANNEL SUBUNIT-ENCODING cDNA AND RNA TRANSCRIPTS IN MAMMALIAN CELLS

A. Recombinant Expression of the Human Neuronal Calcium Channel $\alpha_2$ subunit cDNA in DG44 Cells 1. Stable Transfection of DG44 Cells DG44 cells [$dhfr^-$ Chinese hamster ovary cells; see, e.g., Urlaub, G. et al. (1986) *Som. Cell Molec. Genet.* 12:555–566] obtained from Lawrence Chasin at Columbia University were stably transfected by $CaPO_4$ precipitation methods [Wigler et al. (1979) *Proc. Natl. Acad. Sci. USA* 76:1373–1376] with pSV2dhfr vector containing the human neuronal calcium channel $\alpha_2$-subunit cDNA (see Example IV) for polycistronic expression/selection in transfected cells. Transfectants were grown on 10% DMEM medium without hypoxanthine or thymidine in order to select cells that had incorporated the expression vector. Twelve transfectant cell lines were established as indicated by their ability to survive on this medium.

2. Analysis of $\alpha_2$ Subunit cDNA Expression in Transfected DG44 Cells

Total RNA was extracted according to the method of Birnboim [(1988) *Nuc. Acids Res.* 16:1487–1497] from four of the DG44 cell lines that had been stably transfected with pSV2dhfr containing the human neuronal calcium channel $\alpha_2$ subunit cDNA. RNA (~15 μg per lane) was separated on a 1% agarose formaldehyde gel, transferred to nitrocellulose and hybridized to the random-primed human neuronal calcium channel $\alpha_2$ cDNA (hybridization: 50% formamide, 5×SSPE, 5× Denhardt's, 42° C.; wash :0.2×SSPE, 0.1% SDS, 65° C.). Northern blot analysis of total RNA from four of the DG44 cell lines that had been stably transfected with pSV2dhfr containing the human neuronal calcium channel $\alpha_2$ subunit cDNA revealed that one of the four cell lines contained hybridizing MRNA the size expected for the transcript of the $\alpha_2$ subunit cDNA (5000 nt based on the size of the cDNA) when grown in the presence of 10 mM sodium butyrate for two days. Butyrate nonspecifically induces transcription and is often used for inducing the SV40 early promoter [Gorman, C. and Howard, B. (1983) *Nucleic Acids Res.* 11:1631]. This cell line, 44$\alpha_2$-9, also produced mRNA species smaller (several species) and larger (6800 nt) than the size expected for the transcript of the $\alpha_2$ cDNA (5000 nt) that hybridized to the $\alpha_2$ cDNA-based probe. The 5000- and 6800-nt transcripts produced by this transfectant should contain the entire $\alpha_2$ subunit coding sequence and therefore should yield a full-length $\alpha_2$ subunit protein. A weakly hybridizing 8000-nucleotide transcript was present in untransfected and transfected DG44 cells. Apparently, DG44 cells transcribe a calcium channel $\alpha_2$ subunit or similar gene at low levels. The level of expression of this endogenous $\alpha_2$ subunit transcript did not appear to be affected by exposing the cells to butyrate before isolation of RNA for northern analysis.

Total protein was extracted from three of the DG44 cell lines that had been stably transfected with pSV2dhfr containing the human neuronal calcium channel $\alpha_2$ subunit cDNA. Approximately $10^7$ cells were sonicated in 300 μl of a solution containing 50 mM HEPES, 1 mM EDTA, 1 mM PMSF. An equal volume of 2× loading dye [Laemmli, U.K. (1970). *Nature* 227:680] was added to the samples and the protein was subjected to electrophoresis on an 8% polyacrylamide gel and then electrotransferred to nitrocellulose. The nitrocellulose was incubated with polyclonal guinea pig antisera (1:200 dilution) directed against the rabbit skeletal muscle calcium channel $\alpha_2$ subunit (obtained from K. Campbell, University of Iowa) followed by incubation with [$^{125}$I]-protein A. The blot was exposed to X-ray film at −70° C. Reduced samples of protein from the transfected cells as well as from untransfected DG44 cells contained immunoreactive protein of the size expected for the $\alpha_2$ subunit of the human neuronal calcium channel (130–150 kDa). The level of this immunoreactive protein was higher in 44$\alpha_2$-9 cells that had been grown in the presence of 10 mM sodium butyrate than in 44$\alpha_2$-9 cells that were grown in the absence of sodium butyrate. These data correlate well with those obtained in northern analyses of total RNA from 44$\alpha_2$-9 and untransfected DG44 cells. Cell line 44$\alpha_2$-9 also produced a 110-kDa immunoreactive protein which may be either a product of proteolytic degradation of the full-length $\alpha_2$ subunit or a product of translation of one of the shorter (<5000 nt) mRNAs produced in this cell line that hybridized to the $\alpha_2$ subunit cDNA probe.

B. Expression of DNA encoding human neuronal calcium channel $\alpha_1$, $\alpha_2$ and β subunits in HEK cells Human embryonic kidney cells (HEK 293 cells) were transiently and stably transfected with human neuronal DNA encoding calcium channel subunits. Individual transfectants were analyzed electrophysiologically for the presence of voltage-activated barium currents and functional recombinant voltage-dependent calcium channels were.

1. Transfection of HEK 293 Cells

Separate expression vectors containing DNA encoding human neuronal calcium channel $\alpha_{1D}$, $\alpha_2$ and β subunits, plasmids PVDCCIII(A), pHBCaCH$\alpha_2$A, and pB1–1.18, respectively, were constructed as described in Examples II.A.3, IV.B. and III.B.3., respectively. These three vectors were used to transiently co-transfect HEK 293 cells. For stable transfection of HEK 293 cells, vector pHBCaCH$\beta_1$bA (Example III.B.3.) was used in place of pB1–1.18 to introduce the DNA encoding the β subunit into the cells along with pVDCCIII(A) and pHBCaCH$\alpha_2$A.

a. Transient Transfection

Expression vectors PVDCCIII (A), pHBCaCH$\alpha_2$A and pB1–1.18 were used in two sets of transient transfections of HEK 293 cells (ATCC Accession No. CRL1573). In one transfection procedure, HEK 293 cells were transiently cotransfected with the $\alpha_1$ subunit cDNA expression plasmid, the $\alpha_2$ subunit cDNA expression plasmid, the β subunit cDNA expression plasmid and plasmid pCMVβgal (Clontech Laboratories, Palo Alto, Calif.). Plasmid pCMVβgal contains the lacZ gene (encoding *E. coli* β-galactosidase) fused to the cytomegalovirus (CMV) promoter and was included in this transfection as a marker gene for monitoring the efficiency of transfection. In the other transfection procedure, HEK 293 cells were transiently co-transfected with the $\alpha_1$ subunit cDNA expression plasmid PVDCCIII(A) and pCMVβgal. In both transfections, 2–4×$10^6$ HEK 293 cells contained in a 10-cm tissue culture plate were transiently co-transfected with 5 μg of each of the plasmids included in the experiment according to standard $CaPO_4$ precipitation transfection procedures (Wigler et al. (1979) *Proc. Natl. Acad. Sci. USA* 76:1373–1376). The transfectants were analyzed for β-galactosidase expression by direct staining of the product of a reaction involving β-galactosidase and the X-gal substrate [Jones, J. R. (1986) *EMBO* 5:3133–3142] and by measurement of β-galactosidase activity [Miller, J. H. (1972) Experiments in Molecular Genetics, pp. 352–355, Cold Spring Harbor Press]. To evaluate subunit cDNA expression in these transfectants, the cells were analyzed for subunit transcript production (northern analysis), subunit protein production (immunoblot analysis of cell lysates) and functional calcium channel expression (electrophysiological analysis).

b. Stable Transfection

HEK 293 cells were transfected using the calcium phosphate transfection procedure [*Current Protocols in Molecular Biology*, Vol. 1, Wiley Inter-Science, Supplement 14, Unit 9.1.1–9.1.9 (1990)]. Ten-cm plates, each containing one-to-two million HEK 293 cells, were transfected with 1 ml of DNA/calcium phosphate precipitate containing 5 μg pVDCCIII(A), 5 μg pHBCaCH$\alpha_2$A, 5 μg pHBCaCH$\beta_1$bA, 5 μg pCMVBgal and 1 μg pSV2neo (as a selectable marker). After 10–20 days of growth in media containing 500 μg G418, colonies had formed and were isolated using cloning cylinders.

2. Analysis of HEK 293 Cells Transiently Transfected with DNA Encoding Human Neuronal Calcium Channel Subunits a. Analysis of β-galactosidase Expression Transient transfectants were assayed for β-galactosidase expression by β-galactosidase activity assays (Miller, J. H., (1972) Experiments in Molecular Genetics, pp. 352–355, Cold Spring Harbor Press) of cell lysates (prepared as described in Example VII.A.2) and staining of fixed cells (Jones, J. R. (1986) *EMBO* 5:3133–3142). The results of these assays indicated that approximately 30% of the HEK 293 cells had been transfected.

b. Northern Analysis

Poly $A^+$ RNA was isolated using the Invitrogen Fast Trak Kit (InVitrogen, San Diego, Calif.) from HEK 293 cells transiently transfected with DNA encoding each of the $\alpha_1$, $\alpha_2$ and β subunits and the lacZ gene or the $\alpha_1$ subunit and the lacZ gene. The RNA was subjected to electrophoresis on an agarose gel and transferred to nitrocellulose. The nitrocellulose was then hybridized with one or more of the following radiolabeled probes: the lacZ gene, human neuronal calcium channel $\alpha_{1D}$ subunit-encoding cDNA, human neuronal calcium channel $\alpha_2$ subunit-encoding cDNA or human neuronal calcium channel β subunit-encoding cDNA. Two transcripts that hybridized with the $\alpha_1$ subunit-encoding cDNA were detected in HEK 293 cells transfected with the DNA encoding the $\alpha_1$, $\alpha_2$, and β subunits and the lacZ gene as well as in HEK 293 cells transfected with the $\alpha_1$ subunit cDNA and the lacZ gene. One mRNA species was the size expected for the transcript of the $\alpha_1$ subunit cDNA (8000 nucleotides). The second RNA species was smaller (4000 nucleotides) than the size expected for this transcript. RNA of the size expected for the transcript of the lacZ gene was detected in cells transfected with the $\alpha_1$, $\alpha_2$ and β subunit-encoding cDNA and the lacZ gene and in cells transfected with the $\alpha_1$ subunit cDNA and the lacZ gene by hybridization to the lacZ gene sequence.

RNA from cells transfected with the $\alpha_1$, $\alpha_2$ and β subunit-encoding cDNA and the lacZ gene was also hybridized with the $\alpha_2$ and β subunit cDNA probes. Two mRNA species hybridized to the $\alpha_2$ subunit cDNA probe. One species was the size expected for the transcript of the $\alpha_2$ subunit cDNA (4000 nucleotides). The other species was larger (6000 nucleotides) than the expected size of this transcript. Multiple RNA species in the cells co-transfected with $\alpha_1$, $\alpha_2$ and β subunit-encoding cDNA and the lacZ gene hybridized to the β subunit cDNA probe. Multiple β-subunit transcripts of varying sizes were not unexpected since the β subunit cDNA expression vector contains two potential poly$A^+$ addition sites.

C. Electrophysiological Analysis

Individual transiently transfected HEK 293 cells were assayed for the presence of voltage-dependent barium currents using the whole-cell variant of the patch clamp technique [Hamill et al. (1981). *Pflugers Arch.* 391:85–100]. HEK 293 cells transiently transfected with pCMVβgal only were assayed for barium currents as a negative control in these experiments. The cells were placed in a bathing solution that contained barium ions to serve as the current carrier. Choline chloride, instead of NaCl or KCl, was used as the major salt component of the bath solution to eliminate currents through sodium and potassium channels. The bathing solution contained 1 mM $MgCl_2$ and was buffered at pH 7.3 with 10 mM HEPES (pH adjusted with sodium or tetraethylammonium hydroxide). Patch pipettes were filled with a solution containing 135 mM CsCl, 1 mM $MgCl_2$, 10 mM glucose, 10 mM EGTA, 4mM ATP and 10 mM HEPES (pH adjusted to 7.3 with tetraethylammonium hydroxide). Cesium and tetraethylammonium ions block most types of potassium channels. Pipettes were coated with Sylgard (Dow-Corning, Midland, Mich.) and had resistances of 1–4 megohm. Currents were measured through a 500 megohm headstage resistor with the Axopatch IC (Axon Instruments, Foster City, Calif.) amplifier, interfaced with a Labmaster (Scientific Solutions, Solon, Ohio) data acquisition board in an IBM-compatible PC. PClamp (Axon Instruments) was used to generate voltage commands and acquire data. Data were analyzed with pClamp or Quattro Professional (Borland International, Scotts Valley, Calif.) programs.

To apply drugs, "puffer" pipettes positioned within several micrometers of the cell under study were used to apply solutions by pressure application. The drugs used for pharmacological characterization were dissolved in a solution identical to the bathing solution. Samples of a 10 mM stock solution of Bay K 8644 (RBI, Natick, Mass.), which was prepared in DMSO, were diluted to a final concentration of 1 μM in 15 mM $Ba^{2+}$-containing bath solution before they were applied.

Twenty-one negative control HEK 293 cells (transiently transfected with the lacZ gene expression vector pCMVβgal only) were analyzed by the whole-cell variant of the patch clamp method for recording currents. Only one cell displayed a discernable inward barium current; this current was not affected by the presence of 1 μM Bay K 8644. In addition, application of Bay K 8644 to four cells that did not display $Ba^{2+}$ currents did not result in the appearance of any currents.

Two days after transient transfection of HEK 293 cells with $\alpha_1$, $\beta_2$ and β subunit-encoding cDNA and the lacZ gene, individual transfectants were assayed for voltage-dependent barium currents. The currents in nine transfectants were recorded. Because the efficiency of transfection of one cell can vary from the efficiency of transfection of another cell, the degree of expression of heterologous proteins in individual transfectants varies and some cells do not incorporate or express the foreign DNA. Inward barium currents were detected in two of these nine transfectants. In these assays, the holding potential of the membrane was −90 mV. The membrane was depolarized in a series of voltage steps to different test potentials and the current in the presence and absence of 1 μM Bay K 8644 was recorded. The inward barium current was significantly enhanced in magnitude by the addition of Bay K 8644. The largest inward barium current (~160 pA) was recorded when the membrane was depolarized to 0 mV in the presence of 1 AM Bay K 8644. A comparison of the I–V curves, generated by plotting the largest current recorded after each depolarization versus the depolarization voltage, corresponding to recordings conducted in the absence and presence of Bay K 8644 illustrated the enhancement of the voltage-activated current in the presence of Bay K 8644.

Pronounced tail currents were detected in the tracings of currents generated in the presence of Bay K 8644 in HEK 293 cells transfected with $\alpha_1$, $\alpha_2$ and β subunit-encoding cDNA and the lacZ gene, indicating that the recombinant calcium channels responsible for the voltage-activated barium currents recorded in this transfected appear to be DHP sensitive.

The second of the two transfected cells that displayed inward barium currents expressed a ~50 pA current when the membrane was depolarized from −90 mV. This current was nearly completely blocked by 200 μM cadmium, an established calcium channel blocker.

Ten cells that were transiently transfected with the DNA encoding the $\alpha_1$ subunit and the lacZ gene were analyzed by whole-cell patch clamp methods two days after transfection. One of these cells displayed a 30 pA inward barium current. This current amplified 2-fold in the presence of 1 μM Bay K 8644. Furthermore, small tail currents were detected in the presence of Bay K 8644. These data indicate that expression of the human neuronal calcium channel $\alpha_{1D}$ subunit-encoding cDNA in HEK 293 yields a functional DHP-sensitive calcium channel.

3. Analysis of HEK 293 Cells Stably Transfected with DNA Encoding Human Neuronal Calcium Channel Subunits Individual stably transfected HEK 293 cells were assayed electrophysiologically for the presence of voltage-dependent barium currents as described for electrophysiological analysis of transiently transfected HEK 293 cells (see Example VII.B.2.c). In an effort to maximize calcium channel activity via cyclic-AMP-dependent kinase-mediated phosphorylation [Pelzer, et al. (1990) *Rev. Physiol. Biochem. Pharmacol.* 114:107–207], cAMP (Na salt, 250 μM) was added to the pipet solution and forskolin (10 μM) was added to the bath solution in some of the recordings. Qualitatively similar results were obtained whether these compounds were present or not.

Barium currents were recorded from stably transfected cells in the absence and presence of Bay K 8644 (1 μM). When the cell was depolarized to −10 mV from a holding potential of −90 mV in the absence of Bay K 8644, a current of approximately 35pA with a rapidly deactivating tail current was recorded. During application of Bay K 8644, an identical depolarizing protocol elicited a current of approximately 75 pA, accompanied by an augmented and prolonged tail current. The peak magnitude of currents recorded from this same cell as a function of a series of depolarizing voltages were assessed. The responses in the presence of Bay K 8644 not only increased, but the entire current-voltage relation shifted about −10 mV. Thus, three typical hallmarks of Bay K 8644 action, namely increased current magnitude, prolonged tail currents, and negatively shifted activation voltage, were observed, clearly indicating the expression of a DHP-sensitive calcium channel in these stably transfected cells. No such effects of Bay K 8644 were observed in untransfected HEK 293 cells, either with or without cAMP or forskolin.

C. Use of pCMV-based vectors and pcDNA1-based vectors for expression of DNA encoding human neuronal calcium channel subunits 1. Preparation of Constructs To determine if the levels of recombinant expression of human calcium channel subunit cDNAs in host cells could be enhanced by using pCMV-based instead of pcDNA1-based expression vectors, additional expression vectors were constructed. The full-length $\alpha_{1D}$ cDNA from PVDCCIII(A) (see Example II.A.3.d), the full-length $\alpha_2$ cDNA, contained on a 3600 bp EcoRI fragment from HBCaCH$\alpha_2$ (see Example IV.B) and a full-length β subunit cDNA from pHBCaCH$\beta_1$bA (see Example III.B.3) were separately subcloned into plasmid pCMVβgal. Plasmid pCMVβgal was digested with NotI to remove the lacZ gene. The remaining vector portion of the plasmid, referred to as pCMV, was blunt-ended at the NotI sites. The full-length $\alpha_2$ and β cDNAs, contained on separate EcoRI fragments, were isolated, blunt-ended and separately ligated to the blunt-ended vector fragment of pCMV locating the cDNAs between the CMV promoter and SV40 polyadenylation sites in pCMV. To ligate the $\alpha_{1D}$ -encoding cDNA with PCMV, the restriction sites in the polylinkers immediately 5' of the CMV promoter and immediately 3' of the SV40 polyadenylation site were removed from pCMV. A polylinker was added at the NotI site. The polylinker had the following sequence (Sequence Nos. 27 and 28):

| | | | | | | | |
|---|---|---|---|---|---|---|---|
| GGCCGC | *Eco*RI | *Sal*I | *Pst*I | *Eco*RV | *Hin*dIII | *Xba*II | GT |
| CG | site | site | site | site | site | site | CACCGG |
| *Not*I | | | | | | | ↑ Destroys *Not.* |

The $\alpha_{1D}$ cDNA, isolated as a BamHI/XhoI fragment from pVDCCIII(A), was then ligated to XbaII/SaII-digested pCMV to place it between the CMV promoter and SV40 polyadenylation site.

Plasmid pCMV contains the CMV promoter as does pcDNA1, but differs from pcDNA1 in the location of splice donor/splice acceptor sites relative to the inserted subunit-encoding DNA. After inserting the subunit-encoding DNA into pCMV, the splice donor/splice acceptor sites are located 3' of the CMV promoter and 5' of the subunit-encoding DNA start codon. After inserting the subunit-encoding DNA into pcDNA1, the splice donor/splice acceptor sites are located 3' of the subunit cDNA stop codon.

2. Transfection of HEK 293 Cells

HEK 293 cells were transiently co-transfected with the $\alpha_{1D}$, $\alpha_2$ and β subunit-encoding DNA in pCMV or with the $\alpha_{1D}$, $\alpha_2$ and β subunit-encoding DNA in pcDNA1, (vectors pVDCCIII(A), pHBCaCH$\alpha_2$A and pHBCaCH$\beta_1$bA) as described in Example VII.B.1.a. Plasmid pCMVβgal was included in each transfection to as a measure of transfection efficiency. The results of β-galactosidase assays of the transfectants (see Example VII.B.2.), indicated that HEK 293 cells were transfected equally efficiently with pCMV- and pcDNA1-based plasmids.

3. Northern Analysis

Total and polyA$^+$ RNA were isolated from the transiently transfected cells as described in Examples VII.A.2 and II.B.2.b. Northern blots of the RNA were hybridized with he following radiolabeled probes: $\beta_{1D}$ cDNA, human neuronal calcium channel $\alpha_2$ subunit cDNA and DNA encoding the human neuronal calcium channel β subunit. Messenger RNA of sizes expected for $\alpha_{1D}$, $\alpha_2$ and β subunit transcripts were detected in all transfectants. A greater amount of the $\alpha_{1D}$ transcript was present in cells that were co-transfected with pCMV-based plasmids then in cells that were co-transfected with pcDNA1-based plasmids. Equivalent amounts of $\alpha_2$ and β subunit transcripts were detected in all transfectants.

D. Expression in xenopus laevis oöcytes of RNA encoding human neuronal calcium channel subunits Various combinations of the transcripts of DNA encoding the human neuronal $\alpha_{1D}$, $\alpha_2$ and β subunits prepared in vitro were injected into Xenopus laevis oöcytes. Those injected with combinations that included $\alpha_{1D}$ exhibited voltage-activated barium currents.

1. Preparation of Transcripts

Transcripts encoding the human neuronal calcium channel $\alpha_{1D}$, $\alpha_2$ and β subunits were synthesized according to the instructions of the mCAP mRNA CAPPING KIT (Strategene, La Jolla, Calif. catalog #200350). Plasmids pVDCC III.RBS(A), containing of pcDNA1 and the $\alpha_{1D}$ cDNA that begins with a ribosome binding site and the eighth ATG codon of the coding sequence (see Example III.A.3.d), plasmid pHBCaCH$\alpha_1$A containing of pcDNAl and an $\alpha_2$ subunit cDNA (see Example IV), and plasmid pHBCaCH$\beta_1$bA containing of pcDNAl and the β cDNA lacking intron sequence and containing a ribosome binding site (see Example III), were linearized by restriction digestion. The $\alpha_{1D}$ cDNA- and $\alpha_2$ subunit-encoding plasmids were digested with XhoI, and the β subunit-encoding plasmid was digested with EcoRV. The DNA insert was transcribed with T7 RNA polymerase.

2. Injection of oöcytes

Xenopus laevis oöcytes were isolated and defolliculated by collagenase treatment and maintained in 100 mM NaCl, 2 mM KCl, 1.8 mM $CaCl_2$, 1 mM $MgCl_2$, 5 mM HEPES, pH 7.6, 20 μg/ml ampicillin and 25 μg/ml streptomycin at 19°–25° C. for 2 to 5 days after injection and prior to recording. For each transcript that was injected into the o öcyte, 6 ng of the specific mRNA was injected per cell in a total volume of 50 nl.

3. Intracellular Voltage Recordings

Injected oöcytes were examined for voltage-dependent barium currents using two-electrode voltage clamp methods [Dascal, N. (1987) *CRC Crit. Rev. Biochem.* 22:317]. The pClamp (Axon Instruments) software package was used in conjunction with a Labmaster 125 kHz data acquisition interface to generate voltage commands and to acquire and analyze data. Quattro Professional was also used in this analysis. Current signals were digitized at 1–5 kHz, and filtered appropriately. The bath solution contained of the following: 40 mM $BaCl_2$, 36 mM tetraethylammonium chloride (TEA-Cl), 2 mM KCl, 5 mM 4-aminopyridine, 0.15 mM niflumic acid, 5 mM HEPES, pH 7.6.

a. Electrophysiological Analysis of oöCytes Injected with Transcripts Encoding the Human Neuronal Calcium Channel $\alpha_1$, $\alpha_2$ and β-subunits Uninjected oöcytes were examined by two-electrode voltage clamp methods and a very small (25 nA) endogenous inward $Ba^{2+}$ current was detected in only one of seven analyzed cells.

Oöcytes coinjected with $\alpha_{1D}$, $\alpha_2$ and β subunit transcripts expressed sustained inward barium currents upon depolarization of the membrane from a holding potential of −90 mV or −50 mV (154±129 nA, n=21). These currents typically showed little inactivation when test pulses ranging from 140 to 700 msec. were administered. Depolarization to a series of voltages revealed currents hat first appeared at approximately −30 mV and peaked at approximately 0 mV.

Application of the dihydropyridine Bay K 8644 increased the magnitude of the currents, prolonged the tail currents present upon repolarization of the cell and induced a hyperpolarizing shift in current activation. Bay K 8644 was prepared fresh from a stock solution in DMSO and introduced as a 10×concentrate directly into the 60 μl bath while the perfusion pump was turned off. The DMSO concentration of the final diluted drug solutions in contact with the cell never exceeded 0.1%. Control experiments showed that 0.1% DMSO had no effect on membrane currents.

Application of the dihydropyridine antagonist nifedipine (stock solution prepared in DMSO and applied to the cell as described for application of Bay K 8644) blocked a substantial fraction (91±6%, n=7) of the inward barium current in oöcytes coinjected with transcripts of the $\alpha_{1D}$, $\alpha_2$ and β subunits. A residual inactivating component of the inward barium current typically remained after nifedipine application. The inward barium current was blocked completely by 50 μM $Cd^{2+}$, but only approximately 15% by 100 μM $Ni^{2+}$.

The effect of ωCgTX on the inward barium currents in oöcytes co-injected with transcripts of the $\alpha_{1D}$, $\alpha_2$, and β subunits was investigated. ωCgTX (Bachem, Inc., Torrance Calif.) was prepared in the 15 mM $BaCl_2$ bath solution plus 0.1% cytochrome C (Sigma) to serve as a carrier protein. Control experiments showed that cytochrome C had no effect on currents. A series of voltage pulses from a −90 mV holding potential to 0 mV were recorded at 20 msec. intervals. To reduce the inhibition of ωCgTX binding by divalent cations, recordings were made in 15 mM $BaCl_2$, 73.5 mM tetraethylammonium chloride, and the remaining ingredients identical to the 40 mM $Ba^{2+}$ recording solution.

Bay K 8644 was applied to the cell prior to addition to ωCgTX in order to determine the effect of ωCgTX on the DHP-sensitive current component that was distinguished by the prolonged tail currents. The inward barium current was blocked weakly (54±29%, n=7) and reversibly by relatively high concentrations (10–15 μM) of ωCgTX. Both the test currents and the accompanying tail currents were blocked progressively within two to three minutes after application of ωCgTX, but both recovered partially as the ωCgTX was flushed from the bath.

b. Analysis of Oöcytes Injected with only a Transcripts Encoding the Human Neuronal Calcium Channel $\alpha_{1D}$ or Transcripts Encoding an $\alpha_{1D}$ and other Subunits The contribution of the $\alpha_2$ and β subunits to the inward barium current in oöcytes injected with transcripts encoding the $\alpha_{1D}$, $\alpha_2$ and β subunits was assessed by expression of the $\alpha_{1D}$ subunit alone or in combination with either the β subunit or the $\alpha_2$ subunit. In oöcytes injected with only the transcript of a $\alpha_{1D}$ cDNA, no $Ba^{2+}$ currents were detected (n=3). In oöcytes injected with transcripts of $\alpha_{1D}$ and β cDNAs, small (108±39 nA) $Ba^{2+}$ currents were detected upon depolarization of the membrane from a holding potential of −90 mV that resembled the currents observed in cells injected with transcripts of $\alpha_{1D}$, $\alpha_2$ and β cDNAs, although the magnitude of the current was less. In two of the four o ocytes injected with transcripts of the $\alpha_{1D}$ and β cDNAs, the $Ba^{2+}$ currents exhibited a sensitivity to Bay K 8644 that was similar to the Bay K 8644 sensitivity of $Ba^{2+}$ currents expressed in oöcytes injected with transcripts encoding the $\alpha_{1D}$ $\alpha_1$−, $\alpha_2$ and β subunits.

Three of five oöcytes injected with transcripts encoding the $\alpha_{1D}$ and $\alpha_2$ subunits exhibited very small $Ba^{2+}$ currents (15–30 nA) upon depolarization of the membrane from a holding potential of −90 mV. These barium currents showed little or no response to Bay K 8644.

c. Analysis of Oöcytes Injected with Transcripts Encoding the Human Neuronal Calcium Channel $\alpha_2$ and/or β Subunit To evaluate the contribution of the $\alpha_{1D}$ $\alpha_1$-subunit to the inward barium currents detected in oöcytes co-injected with transcripts encoding the $\alpha_{1D}$, $\alpha_2$ and β subunits, oöcytes injected with transcripts encoding the human neuronal calcium channel $\alpha_2$ and/or β subunits were assayed for barium currents. Oöcytes injected with transcripts encoding the $\alpha_2$ subunit displayed no detectable inward barium currents (n=5). Oöcytes injected with transcripts encoding a β subunit displayed measurable (54±23 nA, n=5) inward barium currents upon depolarization and oöcytes injected with transcripts encoding the $\alpha_2$ and β subunits displayed inward barium currents that were approximately 50% larger (80±61 nA, n=18) than those detected in oöcytes injected with transcripts of the β cDNA only.

The inward barium currents in oöcytes injected with transcripts encoding the β subunit or $\alpha_2$ and β subunits typically were first observed when the membrane was depolarized to −30 mV from a holding potential of −90 mV and peaked when the membrane was depolarized to 10 to 20 mV. Macroscopically, the currents in oöcytes injected with transcripts encoding the $\alpha_2$ and β subunits or with transcripts encoding the β subunit were indistinguishable. In contrast to the currents in oöcytes co-injected with transcripts of $\alpha_{1D}$, $\alpha_2$ and β subunit cDNAs, these currents showed a significant inactivation during the test pulse and a strong sensitivity to the holding potential. The inward barium currents in o ocytes co-injected with transcripts encoding the $\alpha_2$ and β subunits usually inactivated to 10–60% of the peak magnitude during a 140-msec pulse and were significantly more sensitive to holding potential than those in oöcytes co-injected with transcripts encoding the $\alpha_{1D}$, $\alpha_2$ and β subunits. Changing the holding potential of the membranes of oöcytes co-injected with transcripts encoding the 2 and β subunits from −90 to −50 mV resulted in an approximately 81% (n=11) reduction in the magnitude of the inward barium current of these cells. In contrast, the inward barium current measured in oöcytes co-injected with transcripts encoding the $\alpha_{1D}$, $\alpha_2$ and β subunits were reduced approximately 24% (n=11) when the holding potential was changed from −90 to −50 mV.

The inward barium currents detected in oöcytes injected with transcripts encoding the $\alpha_2$ and β subunits were pharmacologically distinct from those observed in oöcytes co-injected with transcripts encoding the $\alpha_{1D}$, $\alpha_2$ and β subunits. oöcytes injected with transcripts encoding the $\alpha_2$ and β subunits displayed inward barium currents that were insensitive to Bay K 8644 (n=11). Nifedipine sensitivity was difficult to measure because of the holding potential sensitivity of nifedipine and the current observed in oöcytes injected with transcripts encoding the $\alpha_2$ and β subunits. Nevertheless, two oöcytes that were co-injected with transcripts encoding the $\alpha_2$ and β subunits displayed measurable (25 to 45 nA) inward barium currents when depolarized from a holding potential of −50 mV. These currents were insensitive to nifedipine (5 to 10 μM). The inward barium currents in oöcytes injected with transcripts encoding the $\alpha_2$ and β subunits showed the same sensitivity to heavy metals as the currents detected in oöcytes injected with transcripts encoding the $\alpha_{1D}$, $\alpha_2$ and β subunits.

The inward barium current detected in oöcytes injected with transcripts encoding the human neuronal $\alpha_2$ and β subunits has pharmacological and biophysical properties that resemble calcium currents in uninjected Xenopus oöcytes. Because the amino acids of this human neuronal calcium channel β subunit lack hydrophobic segments capable of forming transmembrane domains, it is unlikely that recombinant β subunits alone can form an ion channel. It is more probable that a homologous endogenous $\alpha_1$, subunit exists in oöcytes and that the activity mediated by such an $\alpha_1$, subunit is enhanced by expression of a human neuronal β subunit.

While the invention has been described with some specificity, modifications apparent to those with ordinary skill in the art may be made without departing from the scope of the invention. Since such modifications will be apparent to those of skill in the art, it is intended that this invention be limited only by the scope of the appended claims.

What is claimed is:

1. An isolated DNA molecule, comprising a sequence of nucleotides that encodes an $\alpha_1$-subunit of a human calcium channel selected from the group consisting of:

an $\alpha_{1C}$ subunit comprising the sequence of amino acids set forth in SEQ ID NO. 45;

an $\alpha_{1D}$ subunit comprising the sequence of amino acids of the $\alpha_1$-subunit set forth in SEQ ID NO. 49; or comprising the sequence of amino acids of the $\alpha_1$-subunit set forth in SEQ ID NO. 151; and a human calcium channel $\alpha_1$-subunit that is encoded by DNA capable of hybridizing under conditions of high stringency with DNA that is fully complementary to an mRNA transcript native to a human cell that encodes one of the aforesaid human calcium channel $\alpha_1$-subunits, wherein: the $\alpha_1$-subunit is an $\alpha_{1C}$- or $\alpha_{1D}$-subunit; such that any probe that contains at least 14 contiguous bases from the coding portion of the $\alpha_1$-encoding DNA is capable of hybridizing under conditions of high stringency to the DNA that if fully complementary to the mRNA transcript.

2. The DNA molecule of claim 1, wherein the $\alpha_1$-subunit is a human neural calcium $\alpha_1$ subunit.

3. The DNA molecule of claim 1, wherein the $\alpha_1$ subunit is an $\alpha_{1D}$-subunit.

4. The DNA molecule of claim 1, wherein the $\alpha_1$ subunit is an $\alpha_{1C}$-subunit.

5. A cultured eukaryotic cell, comprising heterologous DNA that encodes a human calcium channel $\alpha_1$-subunit and has the nucleotide sequence of the DNA molecule of claim 1 and heterologous DNA that encodes a human calcium channel $\alpha_{2b}$-subunit, wherein:

the $\alpha_{2b}$ subunit is a human calcium channel $\alpha_{2b}$-subunit comprising the amino acid sequence set forth in SEQ ID NO: 52 or a human calcium channel $\alpha_{2b}$ subunit encoded by DNA capable of hybridizing under conditions of high stringency with DNA that is fully complementary to the mRNA transcript native to a human cell that encodes the aforesaid human calcium channel $\alpha_{2b}$ subunit such that any probe that contains at least 14 contiguous bases from the coding portion of the DNA that encodes the $\alpha_{2b}$-subunit hybridizes under conditions of high stringency to the DNA that is fully complementary to the mRNA transcript; and the cell is a mammalian cell or yeast cell.

6. The DNA molecule of claim 1, comprising the sequence of nucleotides set forth in SEQ ID No. 1, 3 or 23.

7. An isolated DNA molecule of claim 1 that encodes an $\alpha_1$-subunit of a human calcium channel, comprising the sequence of nucleotides set forth in SEQ ID NO. 3.

8. An isolated DNA molecule of claim 1 that encodes an $\alpha_1$-subunit of a human calcium channel, comprising sequence of nucleotides set forth in SEQ ID NO. 6.

9. An isolated DNA molecule of claim 1 that encodes an $\alpha_1$-subunit of a human calcium channel, comprising the sequence set forth in SEQ ID NO. 1.

10. An isolated DNA molecule of claim 1 that encodes an $\alpha_1$-subunit of a human calcium channel, comprising the sequence of nucleotides set forth in SEQ ID NO. 23.

11. An isolated and purified mRNA molecule degenerate with the DNA molecule of claim 1.

12. A cultured eukaryotic cell, comprising heterologous DNA having the sequence of the DNA molecule of claim 1, wherein the cell is a mammalian cell or a yeast cell.

13. The eukaryotic cell of claim 12, further comprising additional DNA encoding at least one subunit selected from the group consisting of a human calcium channel β-subunit, a human calcium channel $\alpha_2$-subunit, and a human calcium channel γ-subunit, wherein:

the $\alpha_2$-subunit is selected from the group consisting of:

an $\alpha_2$-subunit comprising the sequence set forth in SEQ ID NO: 53, an $\alpha_2$-subunit comprising the sequence set forth in SEQ ID NO: 54, an $\alpha_2$-subunit comprising the sequence set forth in SEQ ID NO: 55, an $\alpha_2$-subunit comprising the sequence set forth in SEQ ID NO: 56, and an $\alpha_2$-subunit comprising the amino acid sequence of an $\alpha_{2a}$, $\alpha_{2c}$, $\alpha_{2d}$, or $\alpha_{2e}$ subunit polypeptide, wherein the additional DNA encoding the α2-subunit is capable of hybridizing under conditions of high stringency with DNA that is fully complementary to an mRNA transcript native to a human cell that encodes the amino acid sequence set forth in SEQ ID NO: 53, 54, 55, or 56, such that any probe that contains at least 14 contiguous bases from the coding portion of the DNA encoding the α2-subunit hybridizes under conditions of high stringency to the DNA that is fully complementary to the mRNA transcript that encodes an $\alpha_2$-subunit;

the β-subunit is selected from the group consisting of:

a β-subunit comprising the sequence of amino acids set forth in SEQ ID NO: 40, a β-subunit comprising the sequence of amino acids set forth in SEQ ID NO: 41, a β-subunit comprising the sequence of amino acids set forth in SEQ ID NO: 42, a β-subunit comprising the sequence of amino acids set forth in SEQ ID NO: 43, a β-subunit comprising the sequence of amino acids set forth in SEQ ID NO: 44, and a human calcium channel β-subunit encoded by DNA capable of hybridizing under conditions of high stringency with DNA that is fully complementary to an mRNA transcript native to a human cell that encodes one of the aforesaid β subunits, such that any probe that contains at least 14 contiguous bases from the coding portion of the DNA that encodes the β-subunit hybridizes under conditions of high stringency to the DNA that is fully complementary to the mRNA transcript that encodes a β-subunit;

the γ-subunit is selected from the group consisting of:

a γ-subunit native to a human cell which comprises the sequence of amino acids set forth in SEQ ID NO: 57, and a human calcium channel γ-subunit encoded by DNA capable of hybridizing under conditions of high stringency with DNA that is fully complementary to an mRNA transcript native to a human cell that encodes the aforesaid γ-subunit, such that any probe that contains at least 14 contiguous bases from the coding portion of the DNA that encodes the γ-subunit hybridizes under conditions of high stringency to the DNA that is fully complementary to the mRNA transcript that encodes a γ-subunit.

14. The eukaryotic cell of claim 13, wherein the additional DNA comprises DNA encoding an $\alpha_2$-subunit of a human calcium channel selected from an $\alpha_{2a}$, $\alpha_{2c}$, $\alpha_{2d}$ and $\alpha_{2e}$ subunit.

15. The eukaryotic cell of claim 14, wherein the calcium channel is a human skeletal muscle calcium channel or human aortic calcium channel.

16. The eukaryotic cell of claim 13, wherein the additional DNA comprises DNA encoding a β-subunit of a human calcium channel.

17. The eukaryotic cell of claim 13, wherein the additional DNA comprises DNA encoding a γ-subunit of a human calcium channel.

18. The eukaryotic cell of claim 13, that has a functional heterologous voltage dependent calcium channel that contains at least one subunit encoded by the heterologous DNA, wherein the at least one subunit is an $\alpha_1$-subunit of a human calcium channel.

19. The eukaryotic cell of claim 18, wherein the functional heterologous voltage dependent calcium channel contains at least two subunits encoded by the heterologous DNA and the subunits encoded by the heterologous DNA, in addition to the $\alpha_1$-subunit, are a β-subunit or an $\alpha_2$-subunit.

20. The eukaryotic cell of claim 19, wherein the calcium channel contains at least three subunits that are encoded by the heterologous DNA.

21. The eukaryotic cell of claim 20, wherein the calcium channel contains four subunits encoded by the heterologous DNA.

22. The eukaryotic ell of claim 12 that has a functional heterologous voltage dependent calcium channel that contains a subunit encoded by the heterologous DNA, wherein the only heterologous ion channels that are expressed by the cell are calcium channels.

23. The eukaryotic cell of claim 22 selected from the group consisting of an HEK 293 cell, a Chinese hamster ovary cell, an African green monkey cell, and a mouse L cell.

24. The eukaryotic cell of claim 12 selected from the group consisting of HEK 293 cell, a Chinese hamster ovary cell, an African green monkey cell, and a mouse L cell.

25. An isolated eukaryotic cell with a functional, heterologous calcium channel, produced by a process comprising introducing into the cell at least one RNA transcript selected from the group consisting of a first RNA which is translatable in said cell into an $\alpha_1$-subunit of a human calcium channel, a second RNA which is translatable in said cell into a β-subunit of a human calcium channel, a third RNA which is translatable in said cell into an $\alpha_2$-subunit of a human calcium channel, and a fourth RNA which is translatable in said cell into a γ-subunit of a human calcium channel, wherein the cell is a mammalian cell, yeast cell, or amphibian oöcyte, and wherein:

the $\alpha_1$-subunit is selected from the group consisting of:

an $\alpha_{1C}$-subunit comprising the sequence of amino acids set forth in SEQ ID NO: 45, an $\alpha_{1D}$-subunit comprising the sequence of amino acids set forth in SEQ ID NO: 49 or SEQ ID NO: 51, an $\alpha_{1D}$-subunit having the sequence of an $\alpha_{1D}$-subunit native to a human cell that comprises the sequence of amino acids set forth in SEQ ID NO: 50, and a human calcium channel $\alpha_1$-subunit, wherein the $\alpha_1$-subunit is an $\alpha_{1C}$- or $\alpha_{1D}$-subunit encoded by DNA capable of hybridizing under conditions of high stringency with DNA that is fully complementary to an mRNA transcript native to a human cell that encodes one of the aforesaid human calcium channel $\alpha_1$-subunits, such that any probe that contains at least 14 contiguous bases from the coding portion of the DNA that encodes the $\alpha_1$-subunit hybridizes under conditions of high stringency to the DNA that is fully complementary to the mRNA transcript that encodes an $\alpha_1$-subunit;

the $\alpha_2$-subunit is selected from the group consisting of:

an $\alpha_2$-subunit comprising the sequence set forth in SEQ ID NO: 53, an $\alpha_2$-subunit comprising the sequence set forth in SEQ ID NO: 54, an $\alpha_2$-subunit comprising the sequence set forth in SEQ ID NO: 55, an $\alpha_2$-subunit comprising the sequence set forth in SEQ ID NO: 56, and an $\alpha_2$-subunit comprising the amino acid sequence of an $\alpha_{2a}$, $\alpha_{2c}$, $\alpha_{2d}$, or $\alpha_{2e}$ subunit polypeptide, wherein DNA encoding the α2-subunit is capable of hybridizing under conditions of high stringency with DNA that is fully complementary to an mRNA transcript native to a human cell that encodes the amino acid sequence set forth in SEQ ID NO: 53, 54, 55, or 56, such that any probe that contains at least 14 contiguous bases from the coding portion of the DNA that encodes the α2-subunit hybridizes under conditions of high stringency to the DNA that is fully complementary to the mRNA transcript that encodes an $\alpha_2$-subunit;

the β-subunit is selected from the group consisting of:

a β-subunit comprising the sequence of amino acids set forth in SEQ ID NO: 40, a β-subunit comprising the sequence of amino acids set forth in SEQ ID NO: 41, a β-subunit comprising the sequence of amino acids set forth in SEQ ID NO: 42, a β-subunit comprising the sequence of amino acids set forth in SEQ ID NO: 43, a β-subunit comprising the sequence of amino acids set forth in SEQ ID NO: 44, and a human calcium channel β-subunit encoded by DNA capable of hybridizing under conditions of high stringency with DNA that is fully complementary to an mRNA transcript native to a human cell that encodes one of the aforesaid β subunits, such that any probe that contains at least 14 contiguous bases from the coding portion of the DNA that encodes the β-subunit hybridizes under conditions of high stringency to the DNA that is fully complementary to the mRNA transcript that encodes a β-subunit;

the γ-subunit is selected from the group consisting of:

a γ-subunit native to a human cell which comprises the sequence of amino acids set forth in SEQ ID NO: 57, and a human calcium channel γ-subunit encoded by DNA capale of hybridizing under conditions of high stringency with DNA that is fully complementary to an mRNA transcript native to a human cell that comprises the sequence of nucleotides set forth in SEQ ID NO: 14, wherein T residues are replaced by U, such that any probe that contains at least 14 contiguous bases from the coding portion of the DNA that encodes the γ-subunit hybridizes under conditions of high stringency to the DNA that is fully complementary to the mRNA transcript that encodes a γ-subunit; and the only heterologous ion channels that are expressed by the cell are calcium channels.

26. The eukaryotic cell of claim 25 which is an amphibian oöcyte.

27. An isolated eukaryotic cell with a functional heterologous calcium channel, produced by a process comprising introducing into the cell at least one RNA transcript that is translatable in the cell into an $\alpha_2$-subunit of a human calcium channel, and optionally introducing into the cell one or more RNA transcripts selected from the group consisting of an RNA that is translatable in the cell into an $\alpha_1$-subunit of a human calcium channel, an RNA that is translatable in the cell into a β-subunit of a human calcium channel, and an RNA that is translatable in the cell into a γ-subunit of a human calcium channel, wherein:

the cell is a mammalian cell, yeast cell, or amphibian oöcyte;

the only heterologous ion channels that are expressed by the cells are calcium channels; and the $\alpha_2$ subunit is a human calcium channel $\alpha_{2b}$-subunit comprising the amino acid sequence set forth in SEQ ID NO: 52 or a human calcium channel $\alpha_{2b}$ subunit encoded by DNA capable of hybridizing under conditions of high stringency with DNA that is fully complementary to an mRNA transcript native to a human cell that encodes the aforesaid human calcium channel $\alpha_{2b}$ subunit such that any probe that contains at least 14 contiguous bases from the coding portion of the DNA that encodes the $\alpha_{2b}$-subunit hybridizes under conditions of high stringency to the DNA that is fully complementary to the mRNA transcript.

28. The isolated eukaryotic cell of claim 27, wherein:

the $\alpha_1$-subunit is selected from the group consisting of:

an $\alpha_{1C}$-subunit comprising the sequence of amino acids set forth in ID NO: 45, an $\alpha_{1D}$-subunit comprising the sequence of amino acids set forth in ID NO: 49 or SEQ ID NO: 51, an $\alpha_{1D}$-subunit having the sequence of an $\alpha_{1D}$-subunit native to the human cell that comprises the sequence of amino acids set forth in SEQ ID NO: 50, and a human calcium channel $\alpha_1$-subunit, wherein the $\alpha_1$-subunit is an $\alpha_{1C}$- or $\alpha_{1D}$-subunit encoded by DNA capable of hybridizing under conditions of high stringency with DNA that is fully complementary to an mRNA transcript native to a human cell that encodes one of the aforesaid human calcium channel $\alpha_1$-subunits, such that any probe that contains at least 14 contiguous bases from the coding portion of the DNA that encodes the $\alpha_1$-subunit hybridizes under conditions of high stringency to the DNA that is fully complementary to the mRNA transcript that encodes an $\alpha_1$-subunit;

the β-subunit is selected from the group consisting of:

a β-subunit comprising the sequence of amino acids set forth in SEQ ID NO: 40, a β-subunit comprising the sequence of amino acids set forth in SEQ ID NO: 41, a β-subunit comprising the sequence of amino acids set forth in SEQ ID NO: 42, a β-subunit comprising the sequence of amino acids set forth in SEQ ID NO: 43, a β-subunit comprising the sequence of amino acids set forth in SEQ ID NO: 44, and a human calcium channel β-subunit encoded by DNA capable of hybridizing under conditions of high stringency with DNA that is fully complementary to an mRNA transcript native to a human cell that encodes one of the aforesaid human calcium channel β-subunits, such that any probe that contains at least 14 contiguous bases from the coding portion of the DNA that encodes the β-subunit hybridizes under conditions of high stringency to the DNA that is fully complementary to the mRNA transcript that encodes a β-subunit;

the γ-subunit is selected from the group consisting of:

a γ-subunit native to a human cell which comprises the sequence of amino acids set forth in SEQ ID NO: 57, and a human calcium channel γ-subunit encoded by DNA capable of hybridizing under conditions of high stringency with DNA that is fully complementary to an mRNA transcript native to a human cell that comprises the sequence of nucleotides set forth in SEQ ID NO: 14, wherein T residues are replaced by U, such that any probe that contains at least 14 contiguous bases from the coding portion of the DNA that encodes the γ-subunit hybridizes under conditions of high stringency to the DNA that is fully complementary to the mRNA transcript that encodes a γ-subunit; and the only heterologous ion channels that are expressed by the cell are calcium channels.

29. An isolated DNA molecule, comprising a sequence of nucleotides that encodes an $\alpha_1$-subunit of a human calcium channel native to a human cell selected from the group consisting of:

an $\alpha_{1C}$ subunit comprising the sequence of nucleic acids set forth in SEQ ID NO: 45 or 46, an $\alpha_{1D}$ subunit comprising the sequence of amino acids set forth in SEQ ID NO: 49, 50, or 51, and a human calcium channel $\alpha_1$-subunit that is encoded by DNA capable of hybridizing under conditions of high stringency with DNA that is fully complementary to an mRNA transcript native to a human cell that encodes one of the aforesaid human calcium channel $\alpha_1$-subunits;

wherein the $\alpha_1$-subunit binds to at least one compound selected from the group consisting of a dihydropyridine, a phenylalkylamine, ω-CgTx, and a pyrazonoylguanidine.

30. An isolated DNA molecule, comprising a sequence of nucleotides that encodes an $\alpha_1$-subunit of a human calcium channel selected from the group consisting of:

an $\alpha_{1C}$ subunit comprising the sequence of nucleic acids set forth in SEQ ID NO: 45 or 46, an $\alpha_{1D}$ subunit comprising the sequence of amino acids set forth in SEQ ID NO: 49, 50, or 51, and a human calcium channel $\alpha_1$-subunit that is encoded by DNA capable of hybridizing under conditions of high stringency with DNA that is fully complementary to an mRNA transcript native to a human cell that encodes one of the aforesaid human calcium channel $\alpha_1$-subunits;

wherein the $\alpha_1$-subunit is a naturally occurring $\alpha_{1C}$ or $\alpha_{1D}$-subunit.

31. An isolated DNA molecule, comprising a sequence of nucleotides encoding the sequence of amino acids set forth in SEQ ID NO: 45.

32. An isolated DNA molecule, comprising a sequence of nucleotides encoding a human calcium channel $\alpha_{1C}$ subunit native to a human cell that comprises the sequence of amino acids set forth in SEQ ID NO: 46.

33. An isolated DNA probe, comprising the sequence of nucleotides set forth in SEQ ID NO: 2.

34. An isolated DNA probe, comprising a sequence of nucleotides that encodes the sequence of amino acids set forth in SEQ ID NO: 50.

35. An isolated DNA molecule, comprising a sequence of nucleotides encoding a human calcium channel $\alpha_{1D}$ subunit native to a human cell that comprises the sequence of amino acids set forth in SEQ ID NO: 50.

36. An isolated DNA molecule, comprising a sequence of nucleotides encoding the sequence of amino acids set forth in SEQ ID NO: 49.

37. An isolated DNA molecule, comprising a sequence of nucleotides encoding the sequence of amino acids set forth in SEQ ID NO: 51.

38. An isolated DNA molecule, comprising a sequence of nucleotides that encodes an $\alpha_2$-subunit of a human calcium channel selected from the group consisting of:

an $\alpha_2$-subunit comprising the sequence set forth in SEQ ID NO: 53, an $\alpha_2$-subunit comprising the sequence set forth in SEQ ID NO: 54, an $\alpha_2$-subunit comprising the sequence set forth in SEQ ID NO: 55, an $\alpha_2$-subunit comprising the sequence set forth in SEQ ID NO: 56, and an $\alpha_2$-subunit comprising the amino acid sequence of an $\alpha_{2a}$, $\alpha_{2c}$, $\alpha_{2d}$, or $\alpha_{2e}$ subunit polypeptide, wherein the DNA molecule is capable of hybridizing under conditions of high stringency with DNA that is fully complementary to an mRNA transcript native to a human cell that encodes the amino acid sequence set forth in SEQ ID NO: 53, 54, 55, or 56, such that any probe that contains at least 14 contiguous bases from the coding portion of the DNA molecule hybridizes under conditions of high stringency to the DNA that is fully complementary to the mRNA transcript.

39. A DNA molecule of claim 38, comprising a sequence of nucleotides that encodes an $\alpha_{2d}$-subunit.

40. An isolated DNA molecule of claim 38 that encodes an $\alpha_2$-subunit of a human calcium channel, comprising the sequence of nucleotides set forth in SEQ ID NO. 33.

41. An isolated DNA molecule of claim 38 that encodes an $\alpha_2$-subunit of a human calcium channel, comprising the sequence of nucleotides set forth in SEQ ID NO: 34.

42. An isolated DNA molecule of claim 38 that encodes an $\alpha_2$-subunit of a human calcium channel, comprising the sequence of nucleotides set forth in SEQ ID NO: 35.

43. An isolated DNA molecule of claim 38 that encodes an $\alpha_2$-subunit of a human calcium channel, comprising the sequence of nucleotides set forth in SEQ ID NO: 36.

44. An isolated and purified mRNA molecule degenerate with the DNA molecule of claim 38.

45. An isolated DNA molecule, comprising a sequence of nucleotides that encodes an $\alpha_{2b}$-subunit of a human calcium channel comprising the amino acid sequence set forth in SEQ ID NO: 52 or is a human calcium channel $\alpha_{2b}$ subunit encoded by DNA capable of hybridizing under conditions of high stringency with DNA that is fully complementary to an mRNA transcript native to a human cell that encodes the aforesaid human calcium channel $\alpha_{2b}$ subunit such that any probe that contains at least 14 contiguous bases from the coding portion of the DNA that encodes the $\alpha_{2b}$-subunit hybridizes under conditions of high stringency to the DNA that is fully complementary to the mRNA transcript.

46. An isolated DNA molecule of claim 45 that encodes an $\alpha_{2b}$-subunit of a human calcium channel, comprising the sequence of nucleotides set forth in SEQ ID NO. 11.

47. An isolated DNA molecule, comprising a sequence of nucleotides that encodes:

an $\alpha_2$-subunit of a human calcium channel comprising the amino acid sequence set forth in SEQ ID NO: 53, 54, 55, 56, or a naturally occurring human calcium channel $\alpha_2$ subunit, wherein the $\alpha_2$-subunit is an $\alpha_{2a}$, $\alpha_{2c}$, $\alpha_{2d}$, or $\alpha_{2e}$ subtype and is encoded by DNA capable of hybridizing under conditions of high stringency with DNA that is fully complementary to an mRNA transcript native to a human cell that encodes one of the aforesaid human calcium channel $\alpha_2$-subunits.

48. An isolated DNA molecule, comprising the sequence of nucleotides set forth in SEQ ID No. 11.

49. An isolated DNA molecule, comprising the sequence of nucleotides set forth in SEQ ID Nos. 53, 54, 55 or 56.

50. An isolated DNA molecule, comprising a sequence of nucleotides that encodes a β-subunit of a human calcium channel selected from the group consisting of:

a β-subunit comprising the sequence of amino acids set forth in SEQ ID NO: 40, a β-subunit comprising the sequence of amino acids set forth in SEQ ID NO: 41, a β-subunit comprising the sequence of amino acids set forth in SEQ ID NO: 42, a β-subunit comprising the sequence of amino acids set forth in SEQ ID NO: 43, a β-subunit comprising the sequence of amino acids set forth in SEQ ID NO: 44, and a human calcium channel β-subunit that is encoded by DNA capable of hybridizing under conditions of high stringency with DNA that is fully complementary to an mRNA transcript native to a human cell that encodes one of the aforesaid β subunits, such that any probe containing 14 contiguous bases from the coding portion of the DNA molecule hybridizes under conditions of high stringency to the DNA that is fully complementary to the mRNA transcript.

51. The DNA molecule of claim 50, wherein the β subunit is a $\beta_{1-1}$, $\beta_{1-2}$, $\beta_{1-3}$, $\beta_{1-4}$, or $\beta_{1-5}$ subunit.

52. An isolated DNA molecule of claim 50 that encodes a β-subunit of a human calcium channel, comprising the sequence of nucleotides set forth in SEQ ID NO: 9.

53. An isolated DNA molecule of claim 50 that encodes a β-subunit of a human calcium channel, comprising the sequence of nucleotides set forth in SEQ ID NO: 10.

54. An isolated DNA molecule of claim 50 that encodes a β-subunit of a human calcium channel, comprising the sequence of nucleotides set forth in SEQ ID NO: 37.

55. An isolated DNA molecule of claim 50 that encodes a β-subunit of a human calcium channel, comprising the sequence of nucleotides set forth in SEQ ID NO: 38.

56. An isolated DNA molecule of claim 50 that encodes a β-subunit of a human calcium channel, comprising the sequence of nucleotides set forth in SEQ ID NO: 39.

57. An isolated and purified mRNA molecule degenerate with the DNA molecule of claim 50.

58. An isolated DNA molecule, comprising a sequence of nucleotides that encodes a naturally occurring β-subunit of a human calcium channel selected from the group consisting of:

a β-subunit comprising the sequence of amino acids set forth in SEQ ID NO: 40, a β-subunit comprising the sequence of amino acids set forth in SEQ ID NO: 41, a β-subunit comprising the sequence of amino acids set forth in SEQ ID NO: 42, a β-subunit comprising the sequence of amino acids set forth in SEQ ID NO: 43, a β-subunit comprising the sequence of amino acids set forth in SEQ ID NO: 44, and a human calcium channel β-subunit that is encoded by DNA capable of hybridizing under conditions of high stringency with DNA that is fully complementary to an mRNA transcript native to a human cell that encodes one of the aforesaid β subunits.

59. An isolated DNA molecule, comprising a sequence of nucleotides that encodes the sequence of amino acids set forth in SEQ ID NO: 40.

60. An isolated DNA molecule, comprising a sequence of nucleotides that encodes the sequence of amino acids set forth in SEQ ID NO: 41.

61. An isolated DNA molecule, comprising a sequence of nucleotides that encodes the sequence of amino acids set forth in SEQ ID NO. 42.

62. The DNA molecule of claim 58, comprising a sequence of nucleotides that encodes the amino acids set forth in SEQ ID NO. 43.

63. An isolated DNA molecule, comprising a sequence of nucleotides that encodes the sequence of amino acids set forth in SEQ ID NO: 44.

64. An isolated DNA molecule, comprising the sequence of nucleotides set forth in SEQ ID Nos: 9, 10, 37, 38 or 39.

* * * * *

UNITED STATES PATENT AND TRADEMARK OFFICE

CERTIFICATE OF CORRECTION

PATENT NO. : 5,851,824
DATED : December 22, 1998
INVENTOR(S) : Michael M. Harpold et al.

It is certified that error appears in the above-identified patent and that said Letters Patent is hereby corrected as shown below:

Title page,
Item [75], the residence of inventor Daniel H. Feldman should be -- Gainesville, Fla. -- rather than "San Diego [, Calif.]".

Item [56], the following additional citation should appear:

-- Sharp *et al.*, "Identification and characterization of the dihydropyridine-binding subunit of the skeletal muscle dihydropyridine receptor," *J. Biol. Chem.* 62(25): 12309-12315 (1987). --

Column 311, claim 1,
Line 65, the SEQ ID NO. should be -- 51 --, not "151".

Column 315, claim 25,
Line 59, "$\alpha 2$" should be printed as -- $\alpha_2$ --.

Signed and Sealed this

First Day of January, 2002

Attest:

JAMES E. ROGAN

Attesting Officer

*Director of the United States Patent and Trademark Office*

SEQUENCE LISTING ( 1 ) GENERAL INFORMATION:

( iii ) NUMBER OF SEQUENCES: 57

( 2 ) INFORMATION FOR SEQ ID NO:1:

( i ) SEQUENCE CHARACTERISTICS:
( A ) LENGTH: 7635 base pairs
( B ) TYPE: nucleic acid
( C ) STRANDEDNESS: double
( D ) TOPOLOGY: linear ( ii ) MOLECULE TYPE: DNA (genomic)

( ix ) FEATURE:
( A ) NAME/KEY: CDS
( B ) LOCATION: 511..6996

( ix ) FEATURE:
( A ) NAME/KEY: 5'UTR
( B ) LOCATION: 1..510

( ix ) FEATURE:
( A ) NAME/KEY: 3'UTR
( B ) LOCATION: 6994..7635

( xi ) SEQUENCE DESCRIPTION: SEQ ID NO:1:

```
GGGCGAGCGC CTCCGTCCCC GGATGTGAGC TCCGGCTGCC CGCGGTCCCG AGCCAGCGGC     60

GCGCGGGCGG CGGCGGCGGG CACCGGGCAC CGCGGCGGGC GGGCAGACGG GCGGGCATGG    120

GGGGAGCGCC GAGCGGCCCC GGCGGCCGGG CCGGCATCAC CGCGGCGTCT CTCCGCTAGA    180

GGAGGGGACA AGCCAGTTCT CCTTTGCAGC AAAAAATTAC ATGTATATAT TATTAAGATA    240

ATATATACAT TGGATTTTAT TTTTTTAAAA AGTTTATTTT GCTCCATTTT TGAAAAAGAG    300

AGAGCTTGGG TGGCGAGCGG TTTTTTTTTA AAATCAATTA TCCTTATTTT CTGTTATTTG    360

TCCCCGTCCC TCCCCACCCC CCTGCTGAAG CGAGAATAAG GGCAGGGACC GCGGCTCCTA    420

CCTCTTGGTG ATCCCCTTCC CCATTCCGCC CCCGCCCCAA CGCCCAGCAC AGTGCCCTGC    480

ACACAGTAGT CGCTCAATAA ATGTTCGTGG ATG ATG ATG ATG ATG ATG ATG AAA    534
                                Met Met Met Met Met Met Met Lys
                                  1                   5

AAA ATG CAG CAT CAA CGG CAG CAG CAA GCG GAC CAC GCG AAC GAG GCA    582
Lys Met Gln His Gln Arg Gln Gln Gln Ala Asp His Ala Asn Glu Ala
     10                  15                  20

AAC TAT GCA AGA GGC ACC AGA CTT CCT CTT TCT GGT GAA GGA CCA ACT    630
Asn Tyr Ala Arg Gly Thr Arg Leu Pro Leu Ser Gly Glu Gly Pro Thr
 25                  30                  35                  40

TCT CAG CCG AAT AGC TCC AAG CAA ACT GTC CTG TCT TGG CAA GCT GCA    678
Ser Gln Pro Asn Ser Ser Lys Gln Thr Val Leu Ser Trp Gln Ala Ala
                 45                  50                  55

ATC GAT GCT GCT AGA CAG GCC AAG GCT GCC CAA ACT ATG AGC ACC TCT    726
Ile Asp Ala Ala Arg Gln Ala Lys Ala Ala Gln Thr Met Ser Thr Ser
             60                  65                  70

GCA CCC CCA CCT GTA GGA TCT CTC TCC CAA AGA AAA CGT CAG CAA TAC    774
Ala Pro Pro Pro Val Gly Ser Leu Ser Gln Arg Lys Arg Gln Gln Tyr
         75                  80                  85

GCC AAG AGC AAA AAA CAG GGT AAC TCG TCC AAC AGC CGA CCT GCC CGC    822
Ala Lys Ser Lys Lys Gln Gly Asn Ser Ser Asn Ser Arg Pro Ala Arg
     90                  95                 100

GCC CTT TTC TGT TTA TCA CTC AAT AAC CCC ATC CGA AGA GCC TGC ATT    870
Ala Leu Phe Cys Leu Ser Leu Asn Asn Pro Ile Arg Arg Ala Cys Ile
105                 110                 115                 120
```

-continued

```
AGT ATA GTG GAA TGG AAA CCA TTT GAC ATA TTT ATA TTA TTG GCT ATT      918
Ser Ile Val Glu Trp Lys Pro Phe Asp Ile Phe Ile Leu Leu Ala Ile
                125                 130                 135

TTT GCC AAT TGT GTG GCC TTA GCT ATT TAC ATC CCA TTC CCT GAA GAT      966
Phe Ala Asn Cys Val Ala Leu Ala Ile Tyr Ile Pro Phe Pro Glu Asp
            140                 145                 150

GAT TCT AAT TCA ACA AAT CAT AAC TTG GAA AAA GTA GAA TAT GCC TTC     1014
Asp Ser Asn Ser Thr Asn His Asn Leu Glu Lys Val Glu Tyr Ala Phe
        155                 160                 165

CTG ATT ATT TTT ACA GTC GAG ACA TTT TTG AAG ATT ATA GCG TAT GGA     1062
Leu Ile Ile Phe Thr Val Glu Thr Phe Leu Lys Ile Ile Ala Tyr Gly
    170                 175                 180

TTA TTG CTA CAT CCT AAT GCT TAT GTT AGG AAT GGA TGG AAT TTA CTG     1110
Leu Leu Leu His Pro Asn Ala Tyr Val Arg Asn Gly Trp Asn Leu Leu
185                 190                 195                 200

GAT TTT GTT ATA GTA ATA GTA GGA TTG TTT AGT GTA ATT TTG GAA CAA     1158
Asp Phe Val Ile Val Ile Val Gly Leu Phe Ser Val Ile Leu Glu Gln
                205                 210                 215

TTA ACC AAA GAA ACA GAA GGC GGG AAC CAC TCA AGC GGC AAA TCT GGA     1206
Leu Thr Lys Glu Thr Glu Gly Gly Asn His Ser Ser Gly Lys Ser Gly
            220                 225                 230

GGC TTT GAT GTC AAA GCC CTC CGT GCC TTT CGA GTG TTG CGA CCA CTT     1254
Gly Phe Asp Val Lys Ala Leu Arg Ala Phe Arg Val Leu Arg Pro Leu
        235                 240                 245

CGA CTA GTG TCA GGA GTG CCC AGT TTA CAA GTT GTC CTG AAC TCC ATT     1302
Arg Leu Val Ser Gly Val Pro Ser Leu Gln Val Val Leu Asn Ser Ile
    250                 255                 260

ATA AAA GCC ATG GTT CCC CTC CTT CAC ATA GCC CTT TTG GTA TTA TTT     1350
Ile Lys Ala Met Val Pro Leu Leu His Ile Ala Leu Leu Val Leu Phe
265                 270                 275                 280

GTA ATC ATA ATC TAT GCT ATT ATA GGA TTG GAA CTT TTT ATT GGA AAA     1398
Val Ile Ile Ile Tyr Ala Ile Ile Gly Leu Glu Leu Phe Ile Gly Lys
                285                 290                 295

ATG CAC AAA ACA TGT TTT TTT GCT GAC TCA GAT ATC GTA GCT GAA GAG     1446
Met His Lys Thr Cys Phe Phe Ala Asp Ser Asp Ile Val Ala Glu Glu
            300                 305                 310

GAC CCA GCT CCA TGT GCG TTC TCA GGG AAT GGA CGC CAG TGT ACT GCC     1494
Asp Pro Ala Pro Cys Ala Phe Ser Gly Asn Gly Arg Gln Cys Thr Ala
        315                 320                 325

AAT GGC ACG GAA TGT AGG AGT GGC TGG GTT GGC CCG AAC GGA GGC ATC     1542
Asn Gly Thr Glu Cys Arg Ser Gly Trp Val Gly Pro Asn Gly Gly Ile
    330                 335                 340

ACC AAC TTT GAT AAC TTT GCC TTT GCC ATG CTT ACT GTG TTT CAG TGC     1590
Thr Asn Phe Asp Asn Phe Ala Phe Ala Met Leu Thr Val Phe Gln Cys
345                 350                 355                 360

ATC ACC ATG GAG GGC TGG ACA GAC GTG CTC TAC TGG ATG AAT GAT GCT     1638
Ile Thr Met Glu Gly Trp Thr Asp Val Leu Tyr Trp Met Asn Asp Ala
                365                 370                 375

ATG GGA TTT GAA TTG CCC TGG GTG TAT TTT GTC AGT CTC GTC ATC TTT     1686
Met Gly Phe Glu Leu Pro Trp Val Tyr Phe Val Ser Leu Val Ile Phe
            380                 385                 390

GGG TCA TTT TTC GTA CTA AAT CTT GTA CTT GGT GTA TTG AGC GGA GAA     1734
Gly Ser Phe Phe Val Leu Asn Leu Val Leu Gly Val Leu Ser Gly Glu
        395                 400                 405

TTC TCA AAG GAA AGA GAG AAG GCA AAA GCA CGG GGA GAT TTC CAG AAG     1782
Phe Ser Lys Glu Arg Glu Lys Ala Lys Ala Arg Gly Asp Phe Gln Lys
    410                 415                 420

CTC CGG GAG AAG CAG CAG CTG GAG GAG GAT CTA AAG GGC TAC TTG GAT     1830
Leu Arg Glu Lys Gln Gln Leu Glu Glu Asp Leu Lys Gly Tyr Leu Asp
425                 430                 435                 440
```

-continued

```
TGG   ATC   ACC   CAA   GCT   GAG   GAC   ATC   GAT   CCG   GAG   AAT   GAG   GAA   GAA   GGA      1878
Trp   Ile   Thr   Gln   Ala   Glu   Asp   Ile   Asp   Pro   Glu   Asn   Glu   Glu   Glu   Gly
                        445                           450                           455

GGA   GAG   GAA   GGC   AAA   CGA   AAT   ACT   AGC   ATG   CCC   ACC   AGC   GAG   ACT   GAG      1926
Gly   Glu   Glu   Gly   Lys   Arg   Asn   Thr   Ser   Met   Pro   Thr   Ser   Glu   Thr   Glu
                  460                           465                           470

TCT   GTG   AAC   ACA   GAG   AAC   GTC   AGC   GGT   GAA   GGC   GAG   AAC   CGA   GGC   TGC      1974
Ser   Val   Asn   Thr   Glu   Asn   Val   Ser   Gly   Glu   Gly   Glu   Asn   Arg   Gly   Cys
            475                           480                           485

TGT   GGA   AGT   CTC   TGT   CAA   GCC   ATC   TCA   AAA   TCC   AAA   CTC   AGC   CGA   CGC      2022
Cys   Gly   Ser   Leu   Cys   Gln   Ala   Ile   Ser   Lys   Ser   Lys   Leu   Ser   Arg   Arg
      490                           495                           500

TGG   CGT   CGC   TGG   AAC   CGA   TTC   AAT   CGC   AGA   AGA   TGT   AGG   GCC   GCC   GTG      2070
Trp   Arg   Arg   Trp   Asn   Arg   Phe   Asn   Arg   Arg   Arg   Cys   Arg   Ala   Ala   Val
505                           510                           515                           520

AAG   TCT   GTC   ACG   TTT   TAC   TGG   CTG   GTT   ATC   GTC   CTG   GTG   TTT   CTG   AAC      2118
Lys   Ser   Val   Thr   Phe   Tyr   Trp   Leu   Val   Ile   Val   Leu   Val   Phe   Leu   Asn
                        525                           530                           535

ACC   TTA   ACC   ATT   TCC   TCT   GAG   CAC   TAC   AAT   CAG   CCA   GAT   TGG   TTG   ACA      2166
Thr   Leu   Thr   Ile   Ser   Ser   Glu   His   Tyr   Asn   Gln   Pro   Asp   Trp   Leu   Thr
                  540                           545                           550

CAG   ATT   CAA   GAT   ATT   GCC   AAC   AAA   GTC   CTC   TTG   GCT   CTG   TTC   ACC   TGC      2214
Gln   Ile   Gln   Asp   Ile   Ala   Asn   Lys   Val   Leu   Leu   Ala   Leu   Phe   Thr   Cys
            555                           560                           565

GAG   ATG   CTG   GTA   AAA   ATG   TAC   AGC   TTG   GGC   CTC   CAA   GCA   TAT   TTC   GTC      2262
Glu   Met   Leu   Val   Lys   Met   Tyr   Ser   Leu   Gly   Leu   Gln   Ala   Tyr   Phe   Val
      570                           575                           580

TCT   CTT   TTC   AAC   CGG   TTT   GAT   TGC   TTC   GTG   GTG   TGT   GGT   GGA   ATC   ACT      2310
Ser   Leu   Phe   Asn   Arg   Phe   Asp   Cys   Phe   Val   Val   Cys   Gly   Gly   Ile   Thr
585                           590                           595                           600

GAG   ACG   ATC   TTG   GTG   GAA   CTG   GAA   ATC   ATG   TCT   CCC   CTG   GGG   ATC   TCT      2358
Glu   Thr   Ile   Leu   Val   Glu   Leu   Glu   Ile   Met   Ser   Pro   Leu   Gly   Ile   Ser
                        605                           610                           615

GTG   TTT   CGG   TGT   GTG   CGC   CTC   TTA   AGA   ATC   TTC   AAA   GTG   ACC   AGG   CAC      2406
Val   Phe   Arg   Cys   Val   Arg   Leu   Leu   Arg   Ile   Phe   Lys   Val   Thr   Arg   His
                  620                           625                           630

TGG   ACT   TCC   CTG   AGC   AAC   TTA   GTG   GCA   TCC   TTA   TTA   AAC   TCC   ATG   AAG      2454
Trp   Thr   Ser   Leu   Ser   Asn   Leu   Val   Ala   Ser   Leu   Leu   Asn   Ser   Met   Lys
            635                           640                           645

TCC   ATC   GCT   TCG   CTG   TTG   CTT   CTG   CTT   TTT   CTC   TTC   ATT   ATC   ATC   TTT      2502
Ser   Ile   Ala   Ser   Leu   Leu   Leu   Leu   Leu   Phe   Leu   Phe   Ile   Ile   Ile   Phe
      650                           655                           660

TCC   TTG   CTT   GGG   ATG   CAG   CTG   TTT   GGC   GGC   AAG   TTT   AAT   TTT   GAT   GAA      2550
Ser   Leu   Leu   Gly   Met   Gln   Leu   Phe   Gly   Gly   Lys   Phe   Asn   Phe   Asp   Glu
665                           670                           675                           680

ACG   CAA   ACC   AAG   CGG   AGC   ACC   TTT   GAC   AAT   TTC   CCT   CAA   GCA   CTT   CTC      2598
Thr   Gln   Thr   Lys   Arg   Ser   Thr   Phe   Asp   Asn   Phe   Pro   Gln   Ala   Leu   Leu
                        685                           690                           695

ACA   GTG   TTC   CAG   ATC   CTG   ACA   GGC   GAA   GAC   TGG   AAT   GCT   GTG   ATG   TAC      2646
Thr   Val   Phe   Gln   Ile   Leu   Thr   Gly   Glu   Asp   Trp   Asn   Ala   Val   Met   Tyr
                  700                           705                           710

GAT   GGC   ATC   ATG   GCT   TAC   GGG   GGC   CCA   TCC   TCT   TCA   GGA   ATG   ATC   GTC      2694
Asp   Gly   Ile   Met   Ala   Tyr   Gly   Gly   Pro   Ser   Ser   Ser   Gly   Met   Ile   Val
            715                           720                           725

TGC   ATC   TAC   TTC   ATC   ATC   CTC   TTC   ATT   TGT   GGT   AAC   TAT   ATT   CTA   CTG      2742
Cys   Ile   Tyr   Phe   Ile   Ile   Leu   Phe   Ile   Cys   Gly   Asn   Tyr   Ile   Leu   Leu
      730                           735                           740

AAT   GTC   TTC   TTG   GCC   ATC   GCT   GTA   GAC   AAT   TTG   GCT   GAT   GCT   GAA   AGT      2790
Asn   Val   Phe   Leu   Ala   Ile   Ala   Val   Asp   Asn   Leu   Ala   Asp   Ala   Glu   Ser
745                           750                           755                           760
```

-continued

```
CTG AAC ACT GCT CAG AAA GAA GAA GCG GAA GAA AAG GAG AGG AAA AAG     2838
Leu Asn Thr Ala Gln Lys Glu Glu Ala Glu Glu Lys Glu Arg Lys Lys
                765                 770                 775

ATT GCC AGA AAA GAG AGC CTA GAA AAT AAA AAG AAC AAC AAA CCA GAA     2886
Ile Ala Arg Lys Glu Ser Leu Glu Asn Lys Lys Asn Asn Lys Pro Glu
            780                 785                 790

GTC AAC CAG ATA GCC AAC AGT GAC AAC AAG GTT ACA ATT GAT GAC TAT     2934
Val Asn Gln Ile Ala Asn Ser Asp Asn Lys Val Thr Ile Asp Asp Tyr
        795                 800                 805

AGA GAA GAG GAT GAA GAC AAG GAC CCC TAT CCG CCT TGC GAT GTG CCA     2982
Arg Glu Glu Asp Glu Asp Lys Asp Pro Tyr Pro Pro Cys Asp Val Pro
    810                 815                 820

GTA GGG GAA GAG GAA GAG GAA GAG GAG GAG GAT GAA CCT GAG GTT CCT     3030
Val Gly Glu Glu Glu Glu Glu Glu Glu Glu Asp Glu Pro Glu Val Pro
825                 830                 835                 840

GCC GGA CCC CGT CCT CGA AGG ATC TCG GAG TTG AAC ATG AAG GAA AAA     3078
Ala Gly Pro Arg Pro Arg Arg Ile Ser Glu Leu Asn Met Lys Glu Lys
                845                 850                 855

ATT GCC CCC ATC CCT GAA GGG AGC GCT TTC TTC ATT CTT AGC AAG ACC     3126
Ile Ala Pro Ile Pro Glu Gly Ser Ala Phe Phe Ile Leu Ser Lys Thr
            860                 865                 870

AAC CCG ATC CGC GTA GGC TGC CAC AAG CTC ATC AAC CAC CAC ATC TTC     3174
Asn Pro Ile Arg Val Gly Cys His Lys Leu Ile Asn His His Ile Phe
        875                 880                 885

ACC AAC CTC ATC CTT GTC TTC ATC ATG CTG AGC AGT GCT GCC CTG GCC     3222
Thr Asn Leu Ile Leu Val Phe Ile Met Leu Ser Ser Ala Ala Leu Ala
    890                 895                 900

GCA GAG GAC CCC ATC CGC AGC CAC TCC TTC CGG AAC ACG ATA CTG GGT     3270
Ala Glu Asp Pro Ile Arg Ser His Ser Phe Arg Asn Thr Ile Leu Gly
905                 910                 915                 920

TAC TTT GAC TAT GCC TTC ACA GCC ATC TTT ACT GTT GAG ATC CTG TTG     3318
Tyr Phe Asp Tyr Ala Phe Thr Ala Ile Phe Thr Val Glu Ile Leu Leu
                925                 930                 935

AAG ATG ACA ACT TTT GGA GCT TTC CTC CAC AAA GGG GCC TTC TGC AGG     3366
Lys Met Thr Thr Phe Gly Ala Phe Leu His Lys Gly Ala Phe Cys Arg
            940                 945                 950

AAC TAC TTC AAT TTG CTG GAT ATG CTG GTG GTT GGG GTG TCT CTG GTG     3414
Asn Tyr Phe Asn Leu Leu Asp Met Leu Val Val Gly Val Ser Leu Val
        955                 960                 965

TCA TTT GGG ATT CAA TCC AGT GCC ATC TCC GTT GTG AAG ATT CTG AGG     3462
Ser Phe Gly Ile Gln Ser Ser Ala Ile Ser Val Val Lys Ile Leu Arg
    970                 975                 980

GTC TTA AGG GTC CTG CGT CCC CTC AGG GCC ATC AAC AGA GCA AAA GGA     3510
Val Leu Arg Val Leu Arg Pro Leu Arg Ala Ile Asn Arg Ala Lys Gly
985                 990                 995                 1000

CTT AAG CAC GTG GTC CAG TGC GTC TTC GTG GCC ATC CGG ACC ATC GGC     3558
Leu Lys His Val Val Gln Cys Val Phe Val Ala Ile Arg Thr Ile Gly
                1005                1010                1015

AAC ATC ATG ATC GTC ACC ACC CTC CTG CAG TTC ATG TTT GCC TGT ATC     3606
Asn Ile Met Ile Val Thr Thr Leu Leu Gln Phe Met Phe Ala Cys Ile
            1020                1025                1030

GGG GTC CAG TTG TTC AAG GGG AAG TTC TAT CGC TGT ACG GAT GAA GCC     3654
Gly Val Gln Leu Phe Lys Gly Lys Phe Tyr Arg Cys Thr Asp Glu Ala
        1035                1040                1045

AAA AGT AAC CCT GAA GAA TGC AGG GGA CTT TTC ATC CTC TAC AAG GAT     3702
Lys Ser Asn Pro Glu Glu Cys Arg Gly Leu Phe Ile Leu Tyr Lys Asp
    1050                1055                1060

GGG GAT GTT GAC AGT CCT GTG GTC CGT GAA CGG ATC TGG CAA AAC AGT     3750
Gly Asp Val Asp Ser Pro Val Val Arg Glu Arg Ile Trp Gln Asn Ser
1065                1070                1075                1080
```

-continued

```
GAT TTC AAC TTC GAC AAC GTC CTC TCT GCT ATG ATG GCG CTC TTC ACA      3798
Asp Phe Asn Phe Asp Asn Val Leu Ser Ala Met Met Ala Leu Phe Thr
                1085                1090                1095

GTC TCC ACG TTT GAG GGC TGG CCT GCG TTG CTG TAT AAA GCC ATC GAC      3846
Val Ser Thr Phe Glu Gly Trp Pro Ala Leu Leu Tyr Lys Ala Ile Asp
            1100                1105                1110

TCG AAT GGA GAG AAC ATC GGC CCA ATC TAC AAC CAC CGC GTG GAG ATC      3894
Ser Asn Gly Glu Asn Ile Gly Pro Ile Tyr Asn His Arg Val Glu Ile
        1115                1120                1125

TCC ATC TTC TTC ATC ATC TAC ATC ATC ATT GTA GCT TTC TTC ATG ATG      3942
Ser Ile Phe Phe Ile Ile Tyr Ile Ile Ile Val Ala Phe Phe Met Met
    1130                1135                1140

AAC ATC TTT GTG GGC TTT GTC ATC GTT ACA TTT CAG GAA CAA GGA GAA      3990
Asn Ile Phe Val Gly Phe Val Ile Val Thr Phe Gln Glu Gln Gly Glu
1145                1150                1155                1160

AAA GAG TAT AAG AAC TGT GAG CTG GAC AAA AAT CAG CGT CAG TGT GTT      4038
Lys Glu Tyr Lys Asn Cys Glu Leu Asp Lys Asn Gln Arg Gln Cys Val
                1165                1170                1175

GAA TAC GCC TTG AAA GCA CGT CCC TTG CGG AGA TAC ATC CCC AAA AAC      4086
Glu Tyr Ala Leu Lys Ala Arg Pro Leu Arg Arg Tyr Ile Pro Lys Asn
            1180                1185                1190

CCC TAC CAG TAC AAG TTC TGG TAC GTG GTG AAC TCT TCG CCT TTC GAA      4134
Pro Tyr Gln Tyr Lys Phe Trp Tyr Val Val Asn Ser Ser Pro Phe Glu
        1195                1200                1205

TAC ATG ATG TTT GTC CTC ATC ATG CTC AAC ACA CTC TGC TTG GCC ATG      4182
Tyr Met Met Phe Val Leu Ile Met Leu Asn Thr Leu Cys Leu Ala Met
    1210                1215                1220

CAG CAC TAC GAG CAG TCC AAG ATG TTC AAT GAT GCC ATG GAC ATT CTG      4230
Gln His Tyr Glu Gln Ser Lys Met Phe Asn Asp Ala Met Asp Ile Leu
1225                1230                1235                1240

AAC ATG GTC TTC ACC GGG GTG TTC ACC GTC GAG ATG GTT TTG AAA GTC      4278
Asn Met Val Phe Thr Gly Val Phe Thr Val Glu Met Val Leu Lys Val
                1245                1250                1255

ATC GCA TTT AAG CCT AAG GGG TAT TTT AGT GAC GCC TGG AAC ACG TTT      4326
Ile Ala Phe Lys Pro Lys Gly Tyr Phe Ser Asp Ala Trp Asn Thr Phe
            1260                1265                1270

GAC TCC CTC ATC GTA ATC GGC AGC ATT ATA GAC GTG GCC CTC AGC GAA      4374
Asp Ser Leu Ile Val Ile Gly Ser Ile Ile Asp Val Ala Leu Ser Glu
        1275                1280                1285

GCA GAC CCA ACT GAA AGT GAA AAT GTC CCT GTC CCA ACT GCT ACA CCT      4422
Ala Asp Pro Thr Glu Ser Glu Asn Val Pro Val Pro Thr Ala Thr Pro
    1290                1295                1300

GGG AAC TCT GAA GAG AGC AAT AGA ATC TCC ATC ACC TTT TTC CGT CTT      4470
Gly Asn Ser Glu Glu Ser Asn Arg Ile Ser Ile Thr Phe Phe Arg Leu
1305                1310                1315                1320

TTC CGA GTG ATG CGA TTG GTG AAG CTT CTC AGC AGG GGG GAA GGC ATC      4518
Phe Arg Val Met Arg Leu Val Lys Leu Leu Ser Arg Gly Glu Gly Ile
                1325                1330                1335

CGG ACA TTG CTG TGG ACT TTT ATT AAG TTC TTT CAG GCG CTC CCG TAT      4566
Arg Thr Leu Leu Trp Thr Phe Ile Lys Phe Phe Gln Ala Leu Pro Tyr
            1340                1345                1350

GTG GCC CTC CTC ATA GCC ATG CTG TTC TTC ATC TAT GCG GTC ATT GGC      4614
Val Ala Leu Leu Ile Ala Met Leu Phe Phe Ile Tyr Ala Val Ile Gly
        1355                1360                1365

ATG CAG ATG TTT GGG AAA GTT GCC ATG AGA GAT AAC AAC CAG ATC AAT      4662
Met Gln Met Phe Gly Lys Val Ala Met Arg Asp Asn Asn Gln Ile Asn
    1370                1375                1380

AGG AAC AAT AAC TTC CAG ACG TTT CCC CAG GCG GTG CTG CTG CTC TTC      4710
Arg Asn Asn Asn Phe Gln Thr Phe Pro Gln Ala Val Leu Leu Leu Phe
1385                1390                1395                1400
```

-continued

AGG TGT GCA ACA GGT GAG GCC TGG CAG GAG ATC ATG CTG GCC TGT CTC 4758
Arg Cys Ala Thr Gly Glu Ala Trp Gln Glu Ile Met Leu Ala Cys Leu
1405 1410 1415

CCA GGG AAG CTC TGT GAC CCT GAG TCA GAT TAC AAC CCC GGG GAG GAG 4806
Pro Gly Lys Leu Cys Asp Pro Glu Ser Asp Tyr Asn Pro Gly Glu Glu
1420 1425 1430

CAT ACA TGT GGG AGC AAC TTT GCC ATT GTC TAT TTC ATC AGT TTT TAC 4854
His Thr Cys Gly Ser Asn Phe Ala Ile Val Tyr Phe Ile Ser Phe Tyr
1435 1440 1445

ATG CTC TGT GCA TTT CTG ATC ATC AAT CTG TTT GTG GCT GTC ATC ATG 4902
Met Leu Cys Ala Phe Leu Ile Ile Asn Leu Phe Val Ala Val Ile Met
1450 1455 1460

GAT AAT TTC GAC TAT CTG ACC CGG GAC TGG TCT ATT TTG GGG CCT CAC 4950
Asp Asn Phe Asp Tyr Leu Thr Arg Asp Trp Ser Ile Leu Gly Pro His
1465 1470 1475 1480

CAT TTA GAT GAA TTC AAA AGA ATA TGG TCA GAA TAT GAC CCT GAG GCA 4998
His Leu Asp Glu Phe Lys Arg Ile Trp Ser Glu Tyr Asp Pro Glu Ala
1485 1490 1495

AAG GGA AGG ATA AAA CAC CTT GAT GTG GTC ACT CTG CTT CGA CGC ATC 5046
Lys Gly Arg Ile Lys His Leu Asp Val Val Thr Leu Leu Arg Arg Ile
1500 1505 1510

CAG CCT CCC CTG GGG TTT GGG AAG TTA TGT CCA CAC AGG GTA GCG TGC 5094
Gln Pro Pro Leu Gly Phe Gly Lys Leu Cys Pro His Arg Val Ala Cys
1515 1520 1525

AAG AGA TTA GTT GCC ATG AAC ATG CCT CTC AAC AGT GAC GGG ACA GTC 5142
Lys Arg Leu Val Ala Met Asn Met Pro Leu Asn Ser Asp Gly Thr Val
1530 1535 1540

ATG TTT AAT GCA ACC CTG TTT GCT TTG GTT CGA ACG GCT CTT AAG ATC 5190
Met Phe Asn Ala Thr Leu Phe Ala Leu Val Arg Thr Ala Leu Lys Ile
1545 1550 1555 1560

AAG ACC GAA GGG AAC CTG GAG CAA GCT AAT GAA GAA CTT CGG GCT GTG 5238
Lys Thr Glu Gly Asn Leu Glu Gln Ala Asn Glu Glu Leu Arg Ala Val
1565 1570 1575

ATA AAG AAA ATT TGG AAG AAA ACC AGC ATG AAA TTA CTT GAC CAA GTT 5286
Ile Lys Lys Ile Trp Lys Lys Thr Ser Met Lys Leu Leu Asp Gln Val
1580 1585 1590

GTC CCT CCA GCT GGT GAT GAT GAG GTA ACC GTG GGG AAG TTC TAT GCC 5334
Val Pro Pro Ala Gly Asp Asp Glu Val Thr Val Gly Lys Phe Tyr Ala
1595 1600 1605

ACT TTC CTG ATA CAG GAC TAC TTT AGG AAA TTC AAG AAA CGG AAA GAA 5382
Thr Phe Leu Ile Gln Asp Tyr Phe Arg Lys Phe Lys Lys Arg Lys Glu
1610 1615 1620

CAA GGA CTG GTG GGA AAG TAC CCT GCG AAG AAC ACC ACA ATT GCC CTA 5430
Gln Gly Leu Val Gly Lys Tyr Pro Ala Lys Asn Thr Thr Ile Ala Leu
1625 1630 1635 1640

CAG GCG GGA TTA AGG ACA CTG CAT GAC ATT GGG CCA GAA ATC CGG CGT 5478
Gln Ala Gly Leu Arg Thr Leu His Asp Ile Gly Pro Glu Ile Arg Arg
1645 1650 1655

GCT ATA TCG TGT GAT TTG CAA GAT GAC GAG CCT GAG GAA ACA AAA CGA 5526
Ala Ile Ser Cys Asp Leu Gln Asp Asp Glu Pro Glu Glu Thr Lys Arg
1660 1665 1670

GAA GAA GAA GAT GAT GTG TTC AAA AGA AAT GGT GCC CTG CTT GGA AAC 5574
Glu Glu Glu Asp Asp Val Phe Lys Arg Asn Gly Ala Leu Leu Gly Asn
1675 1680 1685

CAT GTC AAT CAT GTT AAT AGT GAT AGG AGA GAT TCC CTT CAG CAG ACC 5622
His Val Asn His Val Asn Ser Asp Arg Arg Asp Ser Leu Gln Gln Thr
1690 1695 1700

AAT ACC ACC CAC CGT CCC CTG CAT GTC CAA AGG CCT TCA ATT CCA CCT 5670
Asn Thr Thr His Arg Pro Leu His Val Gln Arg Pro Ser Ile Pro Pro
1705 1710 1715 1720

-continued

```
GCA AGT GAT ACT GAG AAA CCG CTG TTT CCT CCA GCA GGA AAT TCG GTG     5718
Ala Ser Asp Thr Glu Lys Pro Leu Phe Pro Pro Ala Gly Asn Ser Val
                1725                1730                1735

TGT CAT AAC CAT CAT AAC CAT AAT TCC ATA GGA AAG CAA GTT CCC ACC     5766
Cys His Asn His His Asn His Asn Ser Ile Gly Lys Gln Val Pro Thr
            1740                1745                1750

TCA ACA AAT GCC AAT CTC AAT AAT GCC AAT ATG TCC AAA GCT GCC CAT     5814
Ser Thr Asn Ala Asn Leu Asn Asn Ala Asn Met Ser Lys Ala Ala His
        1755                1760                1765

GGA AAG CGG CCC AGC ATT GGG AAC CTT GAG CAT GTG TCT GAA AAT GGG     5862
Gly Lys Arg Pro Ser Ile Gly Asn Leu Glu His Val Ser Glu Asn Gly
    1770                1775                1780

CAT CAT TCT TCC CAC AAG CAT GAC CGG GAG CCT CAG AGA AGG TCC AGT     5910
His His Ser Ser His Lys His Asp Arg Glu Pro Gln Arg Arg Ser Ser
1785                1790                1795                1800

GTG AAA AGA ACC CGC TAT TAT GAA ACT TAC ATT AGG TCC GAC TCA GGA     5958
Val Lys Arg Thr Arg Tyr Tyr Glu Thr Tyr Ile Arg Ser Asp Ser Gly
                1805                1810                1815

GAT GAA CAG CTC CCA ACT ATT TGC CGG GAA GAC CCA GAG ATA CAT GGC     6006
Asp Glu Gln Leu Pro Thr Ile Cys Arg Glu Asp Pro Glu Ile His Gly
            1820                1825                1830

TAT TTC AGG GAC CCC CAC TGC TTG GGG GAG CAG GAG TAT TTC AGT AGT     6054
Tyr Phe Arg Asp Pro His Cys Leu Gly Glu Gln Glu Tyr Phe Ser Ser
        1835                1840                1845

GAG GAA TGC TAC GAG GAT GAC AGC TCG CCC ACC TGG AGC AGG CAA AAC     6102
Glu Glu Cys Tyr Glu Asp Asp Ser Ser Pro Thr Trp Ser Arg Gln Asn
    1850                1855                1860

TAT GGC TAC TAC AGC AGA TAC CCA GGC AGA AAC ATC GAC TCT GAG AGG     6150
Tyr Gly Tyr Tyr Ser Arg Tyr Pro Gly Arg Asn Ile Asp Ser Glu Arg
1865                1870                1875                1880

CCC CGA GGC TAC CAT CAT CCC CAA GGA TTC TTG GAG GAC GAT GAC TCG     6198
Pro Arg Gly Tyr His His Pro Gln Gly Phe Leu Glu Asp Asp Asp Ser
                1885                1890                1895

CCC GTT TGC TAT GAT TCA CGG AGA TCT CCA AGG AGA CGC CTA CTA CCT     6246
Pro Val Cys Tyr Asp Ser Arg Arg Ser Pro Arg Arg Arg Leu Leu Pro
            1900                1905                1910

CCC ACC CCA GCA TCC CAC CGG AGA TCC TCC TTC AAC TTT GAG TGC CTG     6294
Pro Thr Pro Ala Ser His Arg Arg Ser Ser Phe Asn Phe Glu Cys Leu
        1915                1920                1925

CGC CGG CAG AGC AGC CAG GAA GAG GTC CCG TCG TCT CCC ATC TTC CCC     6342
Arg Arg Gln Ser Ser Gln Glu Glu Val Pro Ser Ser Pro Ile Phe Pro
    1930                1935                1940

CAT CGC ACG GCC CTG CCT CTG CAT CTA ATG CAG CAA CAG ATC ATG GCA     6390
His Arg Thr Ala Leu Pro Leu His Leu Met Gln Gln Gln Ile Met Ala
1945                1950                1955                1960

GTT GCC GGC CTA GAT TCA AGT AAA GCC CAG AAG TAC TCA CCG AGT CAC     6438
Val Ala Gly Leu Asp Ser Ser Lys Ala Gln Lys Tyr Ser Pro Ser His
                1965                1970                1975

TCG ACC CGG TCG TGG GCC ACC CCT CCA GCA ACC CCT CCC TAC CGG GAC     6486
Ser Thr Arg Ser Trp Ala Thr Pro Pro Ala Thr Pro Pro Tyr Arg Asp
            1980                1985                1990

TGG ACA CCG TGC TAC ACC CCC CTG ATC CAA GTG GAG CAG TCA GAG GCC     6534
Trp Thr Pro Cys Tyr Thr Pro Leu Ile Gln Val Glu Gln Ser Glu Ala
        1995                2000                2005

CTG GAC CAG GTG AAC GGC AGC CTG CCG TCC CTG CAC CGC AGC TCC TGG     6582
Leu Asp Gln Val Asn Gly Ser Leu Pro Ser Leu His Arg Ser Ser Trp
    2010                2015                2020

TAC ACA GAC GAG CCC GAC ATC TCC TAC CGG ACT TTC ACA CCA GCC AGC     6630
Tyr Thr Asp Glu Pro Asp Ile Ser Tyr Arg Thr Phe Thr Pro Ala Ser
2025                2030                2035                2040
```

```
CTG ACT GTC CCC AGC AGC TTC CGG AAC AAA AAC AGC GAC AAG CAG AGG      6678
Leu Thr Val Pro Ser Ser Phe Arg Asn Lys Asn Ser Asp Lys Gln Arg
                2045                2050                2055

AGT GCG GAC AGC TTG GTG GAG GCA GTC CTG ATA TCC GAA GGC TTG GGA      6726
Ser Ala Asp Ser Leu Val Glu Ala Val Leu Ile Ser Glu Gly Leu Gly
            2060                2065                2070

CGC TAT GCA AGG GAC CCA AAA TTT GTG TCA GCA ACA AAA CAC GAA ATC      6774
Arg Tyr Ala Arg Asp Pro Lys Phe Val Ser Ala Thr Lys His Glu Ile
        2075                2080                2085

GCT GAT GCC TGT GAC CTC ACC ATC GAC GAG ATG GAG AGT GCA GCC AGC      6822
Ala Asp Ala Cys Asp Leu Thr Ile Asp Glu Met Glu Ser Ala Ala Ser
    2090                2095                2100

ACC CTG CTT AAT GGG AAC GTG CGT CCC CGA GCC AAC GGG GAT GTG GGC      6870
Thr Leu Leu Asn Gly Asn Val Arg Pro Arg Ala Asn Gly Asp Val Gly
2105                2110                2115                2120

CCC CTC TCA CAC CGG CAG GAC TAT GAG CTA CAG GAC TTT GGT CCT GGC      6918
Pro Leu Ser His Arg Gln Asp Tyr Glu Leu Gln Asp Phe Gly Pro Gly
                2125                2130                2135

TAC AGC GAC GAA GAG CCA GAC CCT GGG AGG GAT GAG GAG GAC CTG GCG      6966
Tyr Ser Asp Glu Glu Pro Asp Pro Gly Arg Asp Glu Glu Asp Leu Ala
            2140                2145                2150

GAT GAA ATG ATA TGC ATC ACC ACC TTG TAGCCCCCAG CGAGGGGCAG            7013
Asp Glu Met Ile Cys Ile Thr Thr Leu
        2155                2160

ACTGGCTCTG GCCTCAGGTG GGGCGCAGGA GAGCCAGGGG AAAAGTGCCT CATAGTTAGG    7073

AAAGTTTAGG CACTAGTTGG GAGTAATATT CAATTAATTA GACTTTTGTA TAAGAGATGT    7133

CATGCCTCAA GAAAGCCATA AACCTGGTAG GAACAGGTCC CAAGCGGTTG AGCCTGGCAG    7193

AGTACCATGC GCTCGGCCCC AGCTGCAGGA AACAGCAGGC CCCGCCCTCT CACAGAGGAT    7253

GGGTGAGGAG GCCAGACCTG CCCTGCCCCA TTGTCCAGAT GGGCACTGCT GTGGAGTCTG    7313

CTTCTCCCAT GTACCAGGGC ACCAGGCCCA CCCAACTGAA GGCATGGCGG CGGGGTGCAG    7373

GGGAAAGTTA AAGGTGATGA CGATCATCAC ACCTGTGTCG TTACCTCAGC CATCGGTCTA    7433

GCATATCAGT CACTGGGCCC AACATATCCA TTTTTAAACC CTTTCCCCCA AATACACTGC    7493

GTCCTGGTTC CTGTTTAGCT GTTCTGAAAT ACGGTGTGTA AGTAAGTCAG AACCCAGCTA    7553

CCAGTGATTA TTGCGAGGGC AATGGGACCT CATAAATAAG GTTTTCTGTG ATGTGACGCC    7613

AGTTTACATA AGAGAATATC AC                                             7635
```

( 2 ) INFORMATION FOR SEQ ID NO:2:

( i ) SEQUENCE CHARACTERISTICS:
( A ) LENGTH: 104 base pairs
( B ) TYPE: nucleic acid
( C ) STRANDEDNESS: double
( D ) TOPOLOGY: linear ( i i ) MOLECULE TYPE: DNA (genomic)

( i x ) FEATURE:
( A ) NAME/KEY: CDS
( B ) LOCATION: 1..102

( i x ) FEATURE:
( A ) NAME/KEY: misc_feature
( B ) LOCATION: 1..104
( D ) OTHER INFORMATION: /note= "A 104-nucleotide alternative exon of alpha-1D."

( x i ) SEQUENCE DESCRIPTION: SEQ ID NO:2:

```
GTA AAT GAT GCG ATA GGA TGG GAA TGG CCA TGG GTG TAT TTT GTT AGT        48
Val Asn Asp Ala Ile Gly Trp Glu Trp Pro Trp Val Tyr Phe Val Ser
  1               5                  10                  15
```

-continued

CTG ATC ATC CTT GGC TCA TTT TTC GTC CTT AAC CTG GTT CTT GGT GTC 96
Leu Ile Ile Leu Gly Ser Phe Phe Val Leu Asn Leu Val Leu Gly Val
20 25 30

CTT AGT GG 104
Leu Ser ( 2 ) INFORMATION FOR SEQ ID NO:3:

( i ) SEQUENCE CHARACTERISTICS:
( A ) LENGTH: 5904 base pairs
( B ) TYPE: nucleic acid
( C ) STRANDEDNESS: single
( D ) TOPOLOGY: linear ( i i ) MOLECULE TYPE: DNA (genomic)

( i x ) FEATURE:
( A ) NAME/KEY: CDS
( B ) LOCATION: 1..5904

( x i ) SEQUENCE DESCRIPTION: SEQ ID NO:3:

ATG GTC AAT GAG AAT ACG AGG ATG TAC ATT CCA GAG GAA AAC CAC CAA 48
Met Val Asn Glu Asn Thr Arg Met Tyr Ile Pro Glu Glu Asn His Gln
1 5 10 15

GGT TCC AAC TAT GGG AGC CCA CGC CCC GCC CAT GCC AAC ATG AAT GCC 96
Gly Ser Asn Tyr Gly Ser Pro Arg Pro Ala His Ala Asn Met Asn Ala
20 25 30

AAT GCG GCA GCG GGG CTG GCC CCT GAG CAC ATC CCC ACC CCG GGG GCT 144
Asn Ala Ala Ala Gly Leu Ala Pro Glu His Ile Pro Thr Pro Gly Ala
35 40 45

GCC CTG TCG TGG CAG GCG GCC ATC GAC GCA GCC CGG CAG GCT AAG CTG 192
Ala Leu Ser Trp Gln Ala Ala Ile Asp Ala Ala Arg Gln Ala Lys Leu
50 55 60

ATG GGC AGC GCT GGC AAT GCG ACC ATC TCC ACA GTC AGC TCC ACG CAG 240
Met Gly Ser Ala Gly Asn Ala Thr Ile Ser Thr Val Ser Ser Thr Gln
65 70 75 80

CGG AAG CGC CAG CAA TAT GGG AAA CCC AAG AAG CAG GGC AGC ACC ACG 288
Arg Lys Arg Gln Gln Tyr Gly Lys Pro Lys Lys Gln Gly Ser Thr Thr
85 90 95

GCC ACA CGC CCG CCC CGA GCC CTG CTC TGC CTG ACC CTG AAG AAC CCC 336
Ala Thr Arg Pro Pro Arg Ala Leu Leu Cys Leu Thr Leu Lys Asn Pro
100 105 110

ATC CGG AGG GCC TGC ATC AGC ATT GTC GAA TGG AAA CCA TTT GAA ATA 384
Ile Arg Arg Ala Cys Ile Ser Ile Val Glu Trp Lys Pro Phe Glu Ile
115 120 125

ATT ATT TTA CTG ACT ATT TTT GCC AAT TGT GTG GCC TTA GCG ATC TAT 432
Ile Ile Leu Leu Thr Ile Phe Ala Asn Cys Val Ala Leu Ala Ile Tyr
130 135 140

ATT CCC TTT CCA GAA GAT GAT TCC AAC GCC ACC AAT TCC AAC CTG GAA 480
Ile Pro Phe Pro Glu Asp Asp Ser Asn Ala Thr Asn Ser Asn Leu Glu
145 150 155 160

CGA GTG GAA TAT CTC TTT CTC ATA ATT TTT ACG GTG GAA GCG TTT TTA 528
Arg Val Glu Tyr Leu Phe Leu Ile Ile Phe Thr Val Glu Ala Phe Leu
165 170 175

AAA GTA ATC GCC TAT GGA CTC CTC TTT CAC CCC AAT GCC TAC CTC CGC 576
Lys Val Ile Ala Tyr Gly Leu Leu Phe His Pro Asn Ala Tyr Leu Arg
180 185 190

AAC GGC TGG AAC CTA CTA GAT TTT ATA ATT GTG GTT GTG GGG CTT TTT 624
Asn Gly Trp Asn Leu Leu Asp Phe Ile Ile Val Val Val Gly Leu Phe
195 200 205

AGT GCA ATT TTA GAA CAA GCA ACC AAA GCA GAT GGG GCA AAC GCT CTC 672
Ser Ala Ile Leu Glu Gln Ala Thr Lys Ala Asp Gly Ala Asn Ala Leu
210 215 220

-continued

```
GGA GGG AAA GGG GCC GGA TTT GAT GTG AAG GCG CTG AGG GCC TTC CGC      720
Gly Gly Lys Gly Ala Gly Phe Asp Val Lys Ala Leu Arg Ala Phe Arg
225                 230                 235                 240

GTG CTG CGC CCC CTG CGG CTG GTG TCC GGA GTC CCA AGT CTC CAG GTG      768
Val Leu Arg Pro Leu Arg Leu Val Ser Gly Val Pro Ser Leu Gln Val
                245                 250                 255

GTC CTG AAT TCC ATC ATC AAG GCC ATG GTC CCC CTG CTG CAC ATC GCC      816
Val Leu Asn Ser Ile Ile Lys Ala Met Val Pro Leu Leu His Ile Ala
            260                 265                 270

CTG CTT GTG CTG TTT GTC ATC ATC ATC TAC GCC ATC ATC GGC TTG GAG      864
Leu Leu Val Leu Phe Val Ile Ile Ile Tyr Ala Ile Ile Gly Leu Glu
        275                 280                 285

CTC TTC ATG GGG AAG ATG CAC AAG ACC TGC TAC AAC CAG GAG GGC ATA      912
Leu Phe Met Gly Lys Met His Lys Thr Cys Tyr Asn Gln Glu Gly Ile
    290                 295                 300

GCA GAT GTT CCA GCA GAA GAT GAC CCT TCC CCT TGT GCG CTG GAA ACG      960
Ala Asp Val Pro Ala Glu Asp Asp Pro Ser Pro Cys Ala Leu Glu Thr
305                 310                 315                 320

GGC CAC GGG CGG CAG TGC CAG AAC GGC ACG GTG TGC AAG CCC GGC TGG     1008
Gly His Gly Arg Gln Cys Gln Asn Gly Thr Val Cys Lys Pro Gly Trp
                325                 330                 335

GAT GGT CCC AAG CAC GGC ATC ACC AAC TTT GAC AAC TTT GCC TTC GCC     1056
Asp Gly Pro Lys His Gly Ile Thr Asn Phe Asp Asn Phe Ala Phe Ala
            340                 345                 350

ATG CTC ACG GTG TTC CAG TGC ATC ACC ATG GAG GGC TGG ACG GAC GTG     1104
Met Leu Thr Val Phe Gln Cys Ile Thr Met Glu Gly Trp Thr Asp Val
        355                 360                 365

CTG TAC TGG GTC AAT GAT GCC GTA GGA AGG GAC TGG CCC TGG ATC TAT     1152
Leu Tyr Trp Val Asn Asp Ala Val Gly Arg Asp Trp Pro Trp Ile Tyr
    370                 375                 380

TTT GTT ACA CTA ATC ATC ATA GGG TCA TTT TTT GTA CTT AAC TTG GTT     1200
Phe Val Thr Leu Ile Ile Ile Gly Ser Phe Phe Val Leu Asn Leu Val
385                 390                 395                 400

CTC GGT GTG CTT AGC GGA GAG TTT TCC AAA GAG AGG GAG AAG GCC AAG     1248
Leu Gly Val Leu Ser Gly Glu Phe Ser Lys Glu Arg Glu Lys Ala Lys
                405                 410                 415

GCC CGG GGA GAT TTC CAG AAG CTG CGG GAG AAG CAG CAG CTA GAA GAG     1296
Ala Arg Gly Asp Phe Gln Lys Leu Arg Glu Lys Gln Gln Leu Glu Glu
            420                 425                 430

GAT CTC AAA GGC TAC CTG GAT TGG ATC ACT CAG GCC GAA GAC ATC GNT     1344
Asp Leu Lys Gly Tyr Leu Asp Trp Ile Thr Gln Ala Glu Asp Ile Xaa
        435                 440                 445

CCT GAG AAT GAG GAC GAA GGC ATG GAT GAG GAG AAG CCC CGA AAC AGA     1392
Pro Glu Asn Glu Asp Glu Gly Met Asp Glu Glu Lys Pro Arg Asn Arg
    450                 455                 460

GGC ACT CCG GCG GGC ATG CTT GAT CAG AAG AAA GGG AAG TTT GCT TGG     1440
Gly Thr Pro Ala Gly Met Leu Asp Gln Lys Lys Gly Lys Phe Ala Trp
465                 470                 475                 480

TTT AGT CAC TCC ACA GAA ACC CAT GTG AGC ATG CCC ACC AGT GAG ACC     1488
Phe Ser His Ser Thr Glu Thr His Val Ser Met Pro Thr Ser Glu Thr
                485                 490                 495

GAG TCC GTC AAC ACC GAA AAC GTG GCT GGA GGT GAC ATC GAG GGA GAA     1536
Glu Ser Val Asn Thr Glu Asn Val Ala Gly Gly Asp Ile Glu Gly Glu
            500                 505                 510

AAC TGC GGG GCC AGG CTG GCC CAC CGG ATC TCC AAG TCA AAG TTC AGC     1584
Asn Cys Gly Ala Arg Leu Ala His Arg Ile Ser Lys Ser Lys Phe Ser
        515                 520                 525

CGC TAC TGG CGC CGG TGG AAT CGG TTC TGC AGA AGG AAG TGC CGC GCC     1632
Arg Tyr Trp Arg Arg Trp Asn Arg Phe Cys Arg Arg Lys Cys Arg Ala
    530                 535                 540
```

-continued

| | | | | | | | | | | | | | | | | |
|---|---|---|---|---|---|---|---|---|---|---|---|---|---|---|---|---|
| GCA | GTC | AAG | TCT | AAT | GTC | TTC | TAC | TGG | CTG | GTG | ATT | TTC | CTG | GTG | TTC | 1680 |
| Ala | Val | Lys | Ser | Asn | Val | Phe | Tyr | Trp | Leu | Val | Ile | Phe | Leu | Val | Phe | |
| 545 | | | | | 550 | | | | | 555 | | | | | 560 | |
| CTC | AAC | ACG | CTC | ACC | ATT | GCC | TCT | GAG | CAC | TAC | AAC | CAG | CCC | AAC | TGG | 1728 |
| Leu | Asn | Thr | Leu | Thr | Ile | Ala | Ser | Glu | His | Tyr | Asn | Gln | Pro | Asn | Trp | |
| | | | | 565 | | | | | 570 | | | | | 575 | | |
| CTC | ACA | GAA | GTC | CAA | GAC | ACG | GCA | AAC | AAG | GCC | CTG | CTG | GCC | CTG | TTC | 1776 |
| Leu | Thr | Glu | Val | Gln | Asp | Thr | Ala | Asn | Lys | Ala | Leu | Leu | Ala | Leu | Phe | |
| | | | 580 | | | | | 585 | | | | | 590 | | | |
| ACG | GCA | GAG | ATG | CTC | CTG | AAG | ATG | TAC | AGC | CTG | GGC | CTG | CAG | GCC | TAC | 1824 |
| Thr | Ala | Glu | Met | Leu | Leu | Lys | Met | Tyr | Ser | Leu | Gly | Leu | Gln | Ala | Tyr | |
| | | 595 | | | | | 600 | | | | | 605 | | | | |
| TTC | GTG | TCC | CTC | TTC | AAC | CGC | TTT | GAC | TGC | TTC | GTC | GTG | TGT | GGC | GGC | 1872 |
| Phe | Val | Ser | Leu | Phe | Asn | Arg | Phe | Asp | Cys | Phe | Val | Val | Cys | Gly | Gly | |
| | 610 | | | | | 615 | | | | | 620 | | | | | |
| ATC | CTG | GAG | ACC | ATC | CTG | GTG | GAG | ACC | AAG | ATC | ATG | TCC | CCA | CTG | GGC | 1920 |
| Ile | Leu | Glu | Thr | Ile | Leu | Val | Glu | Thr | Lys | Ile | Met | Ser | Pro | Leu | Gly | |
| 625 | | | | | 630 | | | | | 635 | | | | | 640 | |
| ATC | TCC | GTG | CTC | AGA | TGC | GTC | CGG | CTG | CTG | AGG | ATT | TTC | AAG | ATC | ACG | 1968 |
| Ile | Ser | Val | Leu | Arg | Cys | Val | Arg | Leu | Leu | Arg | Ile | Phe | Lys | Ile | Thr | |
| | | | | 645 | | | | | 650 | | | | | 655 | | |
| AGG | TAC | TGG | AAC | TCC | TTG | AGC | AAC | CTG | GTG | GCA | TCC | TTG | CTG | AAC | TCT | 2016 |
| Arg | Tyr | Trp | Asn | Ser | Leu | Ser | Asn | Leu | Val | Ala | Ser | Leu | Leu | Asn | Ser | |
| | | | 660 | | | | | 665 | | | | | 670 | | | |
| GTG | CGC | TCC | ATC | GCC | TCC | CTG | CTC | CTT | CTC | CTC | TTC | CTC | TTC | ATC | ATC | 2064 |
| Val | Arg | Ser | Ile | Ala | Ser | Leu | Leu | Leu | Leu | Leu | Phe | Leu | Phe | Ile | Ile | |
| | | 675 | | | | | 680 | | | | | 685 | | | | |
| ATC | TTC | TCC | CTC | CTG | GGG | ATG | CAG | CTC | TTT | GGA | GGA | AAG | TTC | AAC | TTT | 2112 |
| Ile | Phe | Ser | Leu | Leu | Gly | Met | Gln | Leu | Phe | Gly | Gly | Lys | Phe | Asn | Phe | |
| | 690 | | | | | 695 | | | | | 700 | | | | | |
| GAT | GAG | ATG | CAG | ACC | CGG | AGG | AGC | ACA | TTC | GAT | AAC | TTC | CCC | CAG | TCC | 2160 |
| Asp | Glu | Met | Gln | Thr | Arg | Arg | Ser | Thr | Phe | Asp | Asn | Phe | Pro | Gln | Ser | |
| 705 | | | | | 710 | | | | | 715 | | | | | 720 | |
| CTC | CTC | ACT | GTG | TTT | CAG | ATC | CTG | ACC | GGG | GAG | GAC | TGG | AAT | TCG | GTG | 2208 |
| Leu | Leu | Thr | Val | Phe | Gln | Ile | Leu | Thr | Gly | Glu | Asp | Trp | Asn | Ser | Val | |
| | | | | 725 | | | | | 730 | | | | | 735 | | |
| ATG | TAT | GAT | GGG | ATC | ATG | GCT | TAT | GGG | GGC | CCC | TCT | TTT | CCA | GGG | ATG | 2256 |
| Met | Tyr | Asp | Gly | Ile | Met | Ala | Tyr | Gly | Gly | Pro | Ser | Phe | Pro | Gly | Met | |
| | | | 740 | | | | | 745 | | | | | 750 | | | |
| TTA | GTC | TGT | ATT | TAC | TTC | ATC | ATC | CTC | TTC | ATC | TCT | GGA | AAC | TAT | ATC | 2304 |
| Leu | Val | Cys | Ile | Tyr | Phe | Ile | Ile | Leu | Phe | Ile | Ser | Gly | Asn | Tyr | Ile | |
| | | 755 | | | | | 760 | | | | | 765 | | | | |
| CTA | CTG | AAT | GTG | TTC | TTG | GCC | ATT | GCT | GTG | GAC | AAC | CTG | GCT | GAT | GCT | 2352 |
| Leu | Leu | Asn | Val | Phe | Leu | Ala | Ile | Ala | Val | Asp | Asn | Leu | Ala | Asp | Ala | |
| | 770 | | | | | 775 | | | | | 780 | | | | | |
| GAG | AGC | CTC | ACA | TCT | GCC | CTA | AAG | GAG | GAG | GAA | GAG | GAG | AAG | GAG | AGA | 2400 |
| Glu | Ser | Leu | Thr | Ser | Ala | Leu | Lys | Glu | Glu | Glu | Glu | Glu | Lys | Glu | Arg | |
| 785 | | | | | 790 | | | | | 795 | | | | | 800 | |
| AAG | AAG | CTG | GCC | AGG | ACT | GCC | AGC | CCA | GAG | AAG | AAA | CAA | GAG | TTG | GTG | 2448 |
| Lys | Lys | Leu | Ala | Arg | Thr | Ala | Ser | Pro | Glu | Lys | Lys | Gln | Glu | Leu | Val | |
| | | | | 805 | | | | | 810 | | | | | 815 | | |
| GAG | AAG | CCG | GCA | GTG | GGG | GAA | TCC | AAG | GAG | GAG | AAG | ATT | GAG | CTG | AAA | 2496 |
| Glu | Lys | Pro | Ala | Val | Gly | Glu | Ser | Lys | Glu | Glu | Lys | Ile | Glu | Leu | Lys | |
| | | | 820 | | | | | 825 | | | | | 830 | | | |
| TCC | ATC | ACG | GCT | GAC | GGA | GAG | TCT | CCA | CCC | GCC | ACC | AAG | ATC | AAC | ATG | 2544 |
| Ser | Ile | Thr | Ala | Asp | Gly | Glu | Ser | Pro | Pro | Ala | Thr | Lys | Ile | Asn | Met | |
| | | 835 | | | | | 840 | | | | | 845 | | | | |
| GAT | GAC | CTC | CAG | CCC | AAT | GAA | AAT | GAG | GAT | AAG | AGC | CCC | TAC | CCC | AAC | 2592 |
| Asp | Asp | Leu | Gln | Pro | Asn | Glu | Asn | Glu | Asp | Lys | Ser | Pro | Tyr | Pro | Asn | |
| | 850 | | | | | 855 | | | | | 860 | | | | | |

-continued

```
CCA GAA ACT ACA GGA GAA GAG GAT GAG GAG GAG CCA GAG ATG CCT GTC   2640
Pro Glu Thr Thr Gly Glu Glu Asp Glu Glu Glu Pro Glu Met Pro Val
865                 870                 875                 880

GGC CCT CGC CCA CGA CCA CTC TCT GAG CTT CAC CTT AAG GAA AAG GCA   2688
Gly Pro Arg Pro Arg Pro Leu Ser Glu Leu His Leu Lys Glu Lys Ala
                885                 890                 895

GTG CCC ATG CCA GAA GCC AGC GCG TTT TTC ATC TTC AGC TCT AAC AAC   2736
Val Pro Met Pro Glu Ala Ser Ala Phe Phe Ile Phe Ser Ser Asn Asn
            900                 905                 910

AGG TTT CGC CTC CAG TGC CAC CGC ATT GTC AAT GAC ACG ATC TTC ACC   2784
Arg Phe Arg Leu Gln Cys His Arg Ile Val Asn Asp Thr Ile Phe Thr
        915                 920                 925

AAC CTG ATC CTC TTC TTC ATT CTG CTC AGC AGC ATT TCC CTG GCT GCT   2832
Asn Leu Ile Leu Phe Phe Ile Leu Leu Ser Ser Ile Ser Leu Ala Ala
    930                 935                 940

GAG GAC CCG GTC CAG CAC ACC TCC TTC AGG AAC CAT ATT CTG TTT TAT   2880
Glu Asp Pro Val Gln His Thr Ser Phe Arg Asn His Ile Leu Phe Tyr
945                 950                 955                 960

TTT GAT ATT GTT TTT ACC ACC ATT TTC ACC ATT GAA ATT GCT CTG AAG   2928
Phe Asp Ile Val Phe Thr Thr Ile Phe Thr Ile Glu Ile Ala Leu Lys
                965                 970                 975

ATG ACT GCT TAT GGG GCT TTC TTG CAC AAG GGT TCT TTC TGC CGG AAC   2976
Met Thr Ala Tyr Gly Ala Phe Leu His Lys Gly Ser Phe Cys Arg Asn
            980                 985                 990

TAC TTC AAC ATC CTG GAC CTG CTG GTG GTC AGC GTG TCC CTC ATC TCC   3024
Tyr Phe Asn Ile Leu Asp Leu Leu Val Val Ser Val Ser Leu Ile Ser
        995                 1000                1005

TTT GGC ATC CAG TCC AGT GCA ATC AAT GTC GTG AAG ATC TTG CGA GTC   3072
Phe Gly Ile Gln Ser Ser Ala Ile Asn Val Val Lys Ile Leu Arg Val
    1010                1015                1020

CTG CGA GTA CTC AGG CCC CTG AGG GCC ATC AAC AGG GCC AAG GGG CTA   3120
Leu Arg Val Leu Arg Pro Leu Arg Ala Ile Asn Arg Ala Lys Gly Leu
1025                1030                1035                1040

AAG CAT GTG GTT CAG TGT GTG TTT GTC GCC ATC CGG ACC ATC GGG AAC   3168
Lys His Val Val Gln Cys Val Phe Val Ala Ile Arg Thr Ile Gly Asn
                1045                1050                1055

ATC GTG ATT GTC ACC ACC CTG CTG CAG TTC ATG TTT GCC TGC ATC GGG   3216
Ile Val Ile Val Thr Thr Leu Leu Gln Phe Met Phe Ala Cys Ile Gly
            1060                1065                1070

GTC CAG CTC TTC AAG GGA AAG CTG TAC ACC TGT TCA GAC AGT TCC AAG   3264
Val Gln Leu Phe Lys Gly Lys Leu Tyr Thr Cys Ser Asp Ser Ser Lys
        1075                1080                1085

CAG ACA GAG GCG GAA TGC AAG GGC AAC TAC ATC ACG TAC AAA GAC GGG   3312
Gln Thr Glu Ala Glu Cys Lys Gly Asn Tyr Ile Thr Tyr Lys Asp Gly
    1090                1095                1100

GAG GTT GAC CAC CCC ATC ATC CAA CCC CGC AGC TGG GAG AAC AGC AAG   3360
Glu Val Asp His Pro Ile Ile Gln Pro Arg Ser Trp Glu Asn Ser Lys
1105                1110                1115                1120

TTT GAC TTT GAC AAT GTT CTG GCA GCC ATG ATG GCC CTC TTC ACC GTC   3408
Phe Asp Phe Asp Asn Val Leu Ala Ala Met Met Ala Leu Phe Thr Val
                1125                1130                1135

TCC ACC TTC GAA GGG TGG CCA GAG CTG CTG TAC CGC TCC ATC GAC TCC   3456
Ser Thr Phe Glu Gly Trp Pro Glu Leu Leu Tyr Arg Ser Ile Asp Ser
            1140                1145                1150

CAC ACG GAA GAC AAG GGC CCC ATC TAC AAC TAC CGT GTG GAG ATC TCC   3504
His Thr Glu Asp Lys Gly Pro Ile Tyr Asn Tyr Arg Val Glu Ile Ser
        1155                1160                1165

ATC TTC TTC ATC ATC TAC ATC ATC ATC ATC GCC TTC TTC ATG ATG AAC   3552
Ile Phe Phe Ile Ile Tyr Ile Ile Ile Ile Ala Phe Phe Met Met Asn
    1170                1175                1180
```

-continued

ATC TTC GTG GGC TTC GTC ATC GTC ACC TTT CAG GAG CAG GGG GAG CAG 3600
Ile Phe Val Gly Phe Val Ile Val Thr Phe Gln Glu Gln Gly Glu Gln
1185 1190 1195 1200

GAG TAC AAG AAC TGT GAG CTG GAC AAG AAC CAG CGA CAG TGC GTG GAA 3648
Glu Tyr Lys Asn Cys Glu Leu Asp Lys Asn Gln Arg Gln Cys Val Glu
1205 1210 1215

TAC GCC CTC AAG GCC CGG CCC CTG CGG AGG TAC ATC CCC AAG AAC CAG 3696
Tyr Ala Leu Lys Ala Arg Pro Leu Arg Arg Tyr Ile Pro Lys Asn Gln
1220 1225 1230

CAC CAG TAC AAA GTG TGG TAC GTG GTC AAC TCC ACC TAC TTC GAG TAC 3744
His Gln Tyr Lys Val Trp Tyr Val Val Asn Ser Thr Tyr Phe Glu Tyr
1235 1240 1245

CTG ATG TTC GTC CTC ATC CTG CTC AAC ACC ATC TGC CTG GCC ATG CAG 3792
Leu Met Phe Val Leu Ile Leu Leu Asn Thr Ile Cys Leu Ala Met Gln
1250 1255 1260

CAC TAC GGC CAG AGC TGC CTG TTC AAA ATC GCC ATG AAC ATC CTC AAC 3840
His Tyr Gly Gln Ser Cys Leu Phe Lys Ile Ala Met Asn Ile Leu Asn
1265 1270 1275 1280

ATG CTC TTC ACT GGC CTC TTC ACC GTG GAG ATG ATC CTG AAG CTC ATT 3888
Met Leu Phe Thr Gly Leu Phe Thr Val Glu Met Ile Leu Lys Leu Ile
1285 1290 1295

GCC TTC AAA CCC AAG GGT TAC TTT AGT GAT CCC TGG AAT GTT TTT GAC 3936
Ala Phe Lys Pro Lys Gly Tyr Phe Ser Asp Pro Trp Asn Val Phe Asp
1300 1305 1310

TTC CTC ATC GTA ATT GGC AGC ATA ATT GAC GTC ATT CTC AGT GAG ACT 3984
Phe Leu Ile Val Ile Gly Ser Ile Ile Asp Val Ile Leu Ser Glu Thr
1315 1320 1325

AAT CCA GCT GAA CAT ACC CAA TGC TCT CCC TCT ATG AAC GCA GAG GAA 4032
Asn Pro Ala Glu His Thr Gln Cys Ser Pro Ser Met Asn Ala Glu Glu
1330 1335 1340

AAC TCC CGC ATC TCC ATC ACC TTC TTC CGC CTG TTC CGG GTC ATG CGT 4080
Asn Ser Arg Ile Ser Ile Thr Phe Phe Arg Leu Phe Arg Val Met Arg
1345 1350 1355 1360

CTG GTG AAG CTG CTG AGC CGT GGG GAG GGC ATC CGG ACG CTG CTG TGG 4128
Leu Val Lys Leu Leu Ser Arg Gly Glu Gly Ile Arg Thr Leu Leu Trp
1365 1370 1375

ACC TTC ATC AAG TCC TTC CAG GCC CTG CCC TAT GTG GCC CTC CTG ATC 4176
Thr Phe Ile Lys Ser Phe Gln Ala Leu Pro Tyr Val Ala Leu Leu Ile
1380 1385 1390

GTG ATG CTG TTC TTC ATC TAC GCG GTG ATC GGG ATG CAG GTG TTT GGG 4224
Val Met Leu Phe Phe Ile Tyr Ala Val Ile Gly Met Gln Val Phe Gly
1395 1400 1405

AAA ATT GCC CTG AAT GAT ACC ACA GAG ATC AAC CGG AAC AAC AAC TTT 4272
Lys Ile Ala Leu Asn Asp Thr Thr Glu Ile Asn Arg Asn Asn Asn Phe
1410 1415 1420

CAG ACC TTC CCC CAG GCC GTG CTG CTC CTC TTC AGG TGT GCC ACC GGG 4320
Gln Thr Phe Pro Gln Ala Val Leu Leu Leu Phe Arg Cys Ala Thr Gly
1425 1430 1435 1440

GAG GCC TGG CAG GAC ATC ATG CTG GCC TGC ATG CCA GGC AAG AAG TGT 4368
Glu Ala Trp Gln Asp Ile Met Leu Ala Cys Met Pro Gly Lys Lys Cys
1445 1450 1455

GCC CCA GAG TCC GAG CCC AGC AAC AGC ACG GAG GGT GAA ACA CCC TGT 4416
Ala Pro Glu Ser Glu Pro Ser Asn Ser Thr Glu Gly Glu Thr Pro Cys
1460 1465 1470

GGT AGC AGC TTT GCT GTC TTC TAC TTC ATC AGC TTC TAC ATG CGC TGT 4464
Gly Ser Ser Phe Ala Val Phe Tyr Phe Ile Ser Phe Tyr Met Arg Cys
1475 1480 1485

GCC TTC CTG ATC ATC AAC CTC TTT GTA GCT GTC ATC ATG GAC AAC TTT 4512
Ala Phe Leu Ile Ile Asn Leu Phe Val Ala Val Ile Met Asp Asn Phe
1490 1495 1500

-continued

GAC TAC CTG ACA AGG GAC TGG TCC ATC CTT GGT CCC CAC CAC CTG GAT 4560
Asp Tyr Leu Thr Arg Asp Trp Ser Ile Leu Gly Pro His His Leu Asp
1505 1510 1515 1520

GAG TTT AAA AGA ATC TGG GCA GAG TAT GAC CCT GAA GCC AAG GGT CGT 4608
Glu Phe Lys Arg Ile Trp Ala Glu Tyr Asp Pro Glu Ala Lys Gly Arg
1525 1530 1535

ATC AAA CAC CTG GAT GTG GTG ACC CTC CTC CGG CGG ATT CAG CCG CCA 4656
Ile Lys His Leu Asp Val Val Thr Leu Leu Arg Arg Ile Gln Pro Pro
1540 1545 1550

CTA GGT TTT GGG AAG CTG TGC CCT CAC CGC GTG GCT TGC AAA CGC CTG 4704
Leu Gly Phe Gly Lys Leu Cys Pro His Arg Val Ala Cys Lys Arg Leu
1555 1560 1565

GTC TCC ATG AAC ATG CCT CTG AAC AGC GAC GGG ACA GTC ATG TTC AAT 4752
Val Ser Met Asn Met Pro Leu Asn Ser Asp Gly Thr Val Met Phe Asn
1570 1575 1580

GCC ACC CTG TTT GCC CTG GTC AGG ACG GCC CTG AGG ATC AAA ACA GAA 4800
Ala Thr Leu Phe Ala Leu Val Arg Thr Ala Leu Arg Ile Lys Thr Glu
1585 1590 1595 1600

GGG AAC CTA GAA CAA GCC AAT GAG GAG CTG CGG GCG ATC ATC AAG AAG 4848
Gly Asn Leu Glu Gln Ala Asn Glu Glu Leu Arg Ala Ile Ile Lys Lys
1605 1610 1615

ATC TGG AAG CGG ACC AGC ATG AAG CTG CTG GAC CAG GTG GTG CCC CCT 4896
Ile Trp Lys Arg Thr Ser Met Lys Leu Leu Asp Gln Val Val Pro Pro
1620 1625 1630

GCA GGT GAT GAT GAG GTC ACC GTT GGC AAG TTC TAC GCC ACG TTC CTG 4944
Ala Gly Asp Asp Glu Val Thr Val Gly Lys Phe Tyr Ala Thr Phe Leu
1635 1640 1645

ATC CAG GAG TAC TTC CGG AAG TTC AAG AAG CGC AAA GAG CAG GGC CTT 4992
Ile Gln Glu Tyr Phe Arg Lys Phe Lys Lys Arg Lys Glu Gln Gly Leu
1650 1655 1660

GTG GGC AAG CCC TCC CAG AGG AAC GCG CTG TCT CTG CAG GCT GGC TTG 5040
Val Gly Lys Pro Ser Gln Arg Asn Ala Leu Ser Leu Gln Ala Gly Leu
1665 1670 1675 1680

CGC ACA CTG CAT GAC ATC GGG CCT GAG ATC CGA CGG GCC ATC TCT GGA 5088
Arg Thr Leu His Asp Ile Gly Pro Glu Ile Arg Arg Ala Ile Ser Gly
1685 1690 1695

GAT CTC ACC GCT GAG GAG GAG CTG GAC AAG GCC ATG AAG GAG GCT GTG 5136
Asp Leu Thr Ala Glu Glu Glu Leu Asp Lys Ala Met Lys Glu Ala Val
1700 1705 1710

TCC GCT GCT TCT GAA GAT GAC ATC TTC AGG AGG GCC GGT GGC CTG TTC 5184
Ser Ala Ala Ser Glu Asp Asp Ile Phe Arg Arg Ala Gly Gly Leu Phe
1715 1720 1725

GGC AAC CAC GTC AGC TAC TAC CAA AGC GAC GGC CGG AGC GCC TTC CCC 5232
Gly Asn His Val Ser Tyr Tyr Gln Ser Asp Gly Arg Ser Ala Phe Pro
1730 1735 1740

CAG ACC TTC ACC ACT CAG CGC CCG CTG CAC ATC AAC AAG GCG GGC AGC 5280
Gln Thr Phe Thr Thr Gln Arg Pro Leu His Ile Asn Lys Ala Gly Ser
1745 1750 1755 1760

AGC CAG GGC GAC ACT GAG TCG CCA TCC CAC GAG AAG CTG GTG GAC TCC 5328
Ser Gln Gly Asp Thr Glu Ser Pro Ser His Glu Lys Leu Val Asp Ser
1765 1770 1775

ACC TTC ACC CCG AGC AGC TAC TCG TCC ACC GGC TCC AAC GCC AAC ATC 5376
Thr Phe Thr Pro Ser Ser Tyr Ser Ser Thr Gly Ser Asn Ala Asn Ile
1780 1785 1790

AAC AAC GCC AAC AAC ACC GCC CTG GGT CGC CTC CCT CGC CCC GCC GGC 5424
Asn Asn Ala Asn Asn Thr Ala Leu Gly Arg Leu Pro Arg Pro Ala Gly
1795 1800 1805

TAC CCC AGC ACA GTC AGC ACT GTG GAG GGC CAC GGG CCC CCC TTG TCC 5472
Tyr Pro Ser Thr Val Ser Thr Val Glu Gly His Gly Pro Pro Leu Ser
1810 1815 1820

-continued

```
CCT GCC ATC CGG GTG CAG GAG GTG GCG TGG AAG CTC AGC TCC AAC AGG      5520
Pro Ala Ile Arg Val Gln Glu Val Ala Trp Lys Leu Ser Ser Asn Arg
1825                1830                1835                1840

TGC CAC TCC CGG GAG AGC CAG GCA GCC ATG GCG CGT CAG GAG GAG ACG      5568
Cys His Ser Arg Glu Ser Gln Ala Ala Met Ala Arg Gln Glu Glu Thr
                1845                1850                1855

TCT CAG GAT GAG ACC TAT GAA GTG AAG ATG AAC CAT GAC ACG GAG GCC      5616
Ser Gln Asp Glu Thr Tyr Glu Val Lys Met Asn His Asp Thr Glu Ala
            1860                1865                1870

TGC AGT GAG CCC AGC CTG CTC TCC ACA GAG ATG CTC TCC TAC CAG GAT      5664
Cys Ser Glu Pro Ser Leu Leu Ser Thr Glu Met Leu Ser Tyr Gln Asp
        1875                1880                1885

GAC GAA AAT CGG CAA CTG ACG CTC CCA GAG GAG GAC AAG AGG GAC ATC      5712
Asp Glu Asn Arg Gln Leu Thr Leu Pro Glu Glu Asp Lys Arg Asp Ile
    1890                1895                1900

CGG CAA TCT CCG AAG AGG GGT TTC CTC CGC TCT TCC TCA CTA GGT CGA      5760
Arg Gln Ser Pro Lys Arg Gly Phe Leu Arg Ser Ser Ser Leu Gly Arg
1905                1910                1915                1920

AGG GCC TCC TTC CAC CTG GAA TGT CTG AAG CGA CAG AAG GAC CGA GGG      5808
Arg Ala Ser Phe His Leu Glu Cys Leu Lys Arg Gln Lys Asp Arg Gly
                1925                1930                1935

GGA GAC ATC TCT CAG AAG ACA GTC CTG CCC TTG CAT CTG GTT CAT CAT      5856
Gly Asp Ile Ser Gln Lys Thr Val Leu Pro Leu His Leu Val His His
            1940                1945                1950

CAG GCA TTG GCA GTG GCA GGC CTG AGC CCC CTC CTC CAG AGA AGC CAT      5904
Gln Ala Leu Ala Val Ala Gly Leu Ser Pro Leu Leu Gln Arg Ser His
        1955                1960                1965
```

( 2 ) INFORMATION FOR SEQ ID NO:4:

( i ) SEQUENCE CHARACTERISTICS:
( A ) LENGTH: 132 base pairs
( B ) TYPE: nucleic acid
( C ) STRANDEDNESS: double
( D ) TOPOLOGY: linear ( i i ) MOLECULE TYPE: DNA (genomic)

( x i ) SEQUENCE DESCRIPTION: SEQ ID NO:4:

```
AGACCACGGC TTCCTCGAAT CTTGCGCGAA GCCGCCGGCC TCGGAGGAGG GATTAATCCA      60
GACCCGCCGG GGGGTGTTTT CACATTTCTT CCTCTTCGTG GCTGCTCCTC CTATTAAAAC     120
CATTTTTGGT CC                                                         132
```

( 2 ) INFORMATION FOR SEQ ID NO:5:

( i ) SEQUENCE CHARACTERISTICS:
( A ) LENGTH: 89 base pairs
( B ) TYPE: nucleic acid
( C ) STRANDEDNESS: double
( D ) TOPOLOGY: linear ( i i ) MOLECULE TYPE: DNA (genomic)

( x i ) SEQUENCE DESCRIPTION: SEQ ID NO:5:

```
CGCTGAGGGC CTTCCGCGTG CTGCGCCCCC TGCGGCTGGT GTCCGGAGTC CCAAGTCTCC      60
AGGTGGTCCT GAATTCCATC ATCAAGGCC                                        89
```

( 2 ) INFORMATION FOR SEQ ID NO:6:

( i ) SEQUENCE CHARACTERISTICS:
( A ) LENGTH: 84 base pairs
( B ) TYPE: nucleic acid
( C ) STRANDEDNESS: double -continued ( D ) TOPOLOGY: linear ( i i ) MOLECULE TYPE: DNA (genomic)

( i x ) FEATURE:
( A ) NAME/KEY: CDS
( B ) LOCATION: 1..84
( D ) OTHER INFORMATION: /note= "An alternative exon of alpha-1C."

( x i ) SEQUENCE DESCRIPTION: SEQ ID NO:6:

```
CAC TAT TTC TGT GAT GCA TGG AAT ACA TTT GAC GCC TTG ATT GTT GTG      48
His Tyr Phe Cys Asp Ala Trp Asn Thr Phe Asp Ala Leu Ile Val Val
  1               5                  10                  15

GGT AGC ATT GTT GAT ATA GCA ATC ACC GAG GTA AAC                      84
Gly Ser Ile Val Asp Ile Ala Ile Thr Glu Val Asn
            20                  25
```

( 2 ) INFORMATION FOR SEQ ID NO:7:

( i ) SEQUENCE CHARACTERISTICS:
( A ) LENGTH: 7362 base pairs
( B ) TYPE: nucleic acid
( C ) STRANDEDNESS: double
( D ) TOPOLOGY: linear ( i i ) MOLECULE TYPE: DNA (genomic)

( i x ) FEATURE:
( A ) NAME/KEY: CDS
( B ) LOCATION: 144..7163

( i x ) FEATURE:
( A ) NAME/KEY: 5'UTR
( B ) LOCATION: 1..143

( i x ) FEATURE:
( A ) NAME/KEY: 3'UTR
( B ) LOCATION: 7161..7362

( x i ) SEQUENCE DESCRIPTION: SEQ ID NO:7:

```
GCGGCGGCGG CTGCGGCGGT GGGGCCGGGC GAGGTCCGTG CGGTCCCGGC GGCTCCGTGG     60

CTGCTCCGCT CTGAGCGCCT GCGCGCCCCG CGCCCTCCCT GCCGGGGCCG CTGGGCCGGG    120

GATGCACGCG GGGCCCGGGA GCC ATG GTC CGC TTC GGG GAC GAG CTG GGC        170
                          Met Val Arg Phe Gly Asp Glu Leu Gly
                            1               5

GGC CGC TAT GGA GGC CCC GGC GGC GGA GAG CGG GCC CGG GGC GGC GGG      218
Gly Arg Tyr Gly Gly Pro Gly Gly Gly Glu Arg Ala Arg Gly Gly Gly
 10                  15                  20                  25

GCC GGC GGG GCG GGG GGC CCG GGT CCC GGG GGG CTG CAG CCC GGC CAG      266
Ala Gly Gly Ala Gly Gly Pro Gly Pro Gly Gly Leu Gln Pro Gly Gln
                 30                  35                  40

CGG GTC CTC TAC AAG CAA TCG ATC GCG CAG CGC GCG CGG ACC ATG GCG      314
Arg Val Leu Tyr Lys Gln Ser Ile Ala Gln Arg Ala Arg Thr Met Ala
             45                  50                  55

CTG TAC AAC CCC ATC CCG GTC AAG CAG AAC TGC TTC ACC GTC AAC CGC      362
Leu Tyr Asn Pro Ile Pro Val Lys Gln Asn Cys Phe Thr Val Asn Arg
         60                  65                  70

TCG CTC TTC GTC TTC AGC GAG GAC AAC GTC GTC CGC AAA TAC GCG AAG      410
Ser Leu Phe Val Phe Ser Glu Asp Asn Val Val Arg Lys Tyr Ala Lys
     75                  80                  85

CGC ATC ACC GAG TGG CCT CCA TTC GAG AAT ATG ATC CTG GCC ACC ATC      458
Arg Ile Thr Glu Trp Pro Pro Phe Glu Asn Met Ile Leu Ala Thr Ile
 90                  95                 100                 105

ATC GCC AAC TGC ATC GTG CTG GCC CTG GAG CAG CAC CTC CCT GAT GGG      506
Ile Ala Asn Cys Ile Val Leu Ala Leu Glu Gln His Leu Pro Asp Gly
                110                 115                 120
```

-continued

GAC AAA ACG CCC ATG TCC GAG CGG CTG GAC GAC ACG GAG CCC TAT TTC 554
Asp Lys Thr Pro Met Ser Glu Arg Leu Asp Asp Thr Glu Pro Tyr Phe
            125                 130                 135

ATC GGG ATC TTT TGC TTC GAG GCA GGG ATC AAA ATC ATC GCT CTG GGC 602
Ile Gly Ile Phe Cys Phe Glu Ala Gly Ile Lys Ile Ile Ala Leu Gly
        140                 145                 150

TTT GTC TTC CAC AAG GGC TCT TAC CTG CGG AAC GGC TGG AAC GTC ATG 650
Phe Val Phe His Lys Gly Ser Tyr Leu Arg Asn Gly Trp Asn Val Met
    155                 160                 165

GAC TTC GTG GTC GTC CTC ACA GGG ATC CTT GCC ACG GCT GGA ACT GAC 698
Asp Phe Val Val Val Leu Thr Gly Ile Leu Ala Thr Ala Gly Thr Asp
170                 175                 180                 185

TTC GAC CTG CGA ACA CTG AGG GCT GTG CGT GTG CTG AGG CCC CTG AAG 746
Phe Asp Leu Arg Thr Leu Arg Ala Val Arg Val Leu Arg Pro Leu Lys
                190                 195                 200

CTG GTG TCT GGG ATT CCA AGT TTG CAG GTG GTG CTC AAG TCC ATC ATG 794
Leu Val Ser Gly Ile Pro Ser Leu Gln Val Val Leu Lys Ser Ile Met
            205                 210                 215

AAG GCC ATG GTT CCA CTC CTG CAG ATT GGG CTG CTT CTC TTC TTT GCC 842
Lys Ala Met Val Pro Leu Leu Gln Ile Gly Leu Leu Leu Phe Phe Ala
        220                 225                 230

ATC CTC ATG TTT GCC ATC ATT GGC CTG GAG TTC TAC ATG GGC AAG TTC 890
Ile Leu Met Phe Ala Ile Ile Gly Leu Glu Phe Tyr Met Gly Lys Phe
    235                 240                 245

CAC AAG GCC TGT TTC CCC AAC AGC ACA GAT GCG GAG CCC GTG GGT GAC 938
His Lys Ala Cys Phe Pro Asn Ser Thr Asp Ala Glu Pro Val Gly Asp
250                 255                 260                 265

TTC CCC TGT GGC AAG GAG GCC CCA GCC CGG CTG TGC GAG GGC GAC ACT 986
Phe Pro Cys Gly Lys Glu Ala Pro Ala Arg Leu Cys Glu Gly Asp Thr
                270                 275                 280

GAG TGC CGG GAG TAC TGG CCA GGA CCC AAC TTT GGC ATC ACC AAC TTT 1034
Glu Cys Arg Glu Tyr Trp Pro Gly Pro Asn Phe Gly Ile Thr Asn Phe
            285                 290                 295

GAC AAT ATC CTG TTT GCC ATC TTG ACG GTG TTC CAG TGC ATC ACC ATG 1082
Asp Asn Ile Leu Phe Ala Ile Leu Thr Val Phe Gln Cys Ile Thr Met
        300                 305                 310

GAG GGC TGG ACT GAC ATC CTC TAT AAT ACA AAC GAT GCG GCC GGC AAC 1130
Glu Gly Trp Thr Asp Ile Leu Tyr Asn Thr Asn Asp Ala Ala Gly Asn
    315                 320                 325

ACC TGG AAC TGG CTC TAC TTC ATC CCT CTC ATC ATC ATC GGC TCC TTC 1178
Thr Trp Asn Trp Leu Tyr Phe Ile Pro Leu Ile Ile Ile Gly Ser Phe
330                 335                 340                 345

TTC ATG CTC AAC CTG GTG CTG GGC GTG CTC TCG GGG GAG TTT GCC AAG 1226
Phe Met Leu Asn Leu Val Leu Gly Val Leu Ser Gly Glu Phe Ala Lys
                350                 355                 360

GAG CGA GAG AGG GTG GAG AAC CGC CGC GCC TTC CTG AAG CTG CGC CGG 1274
Glu Arg Glu Arg Val Glu Asn Arg Arg Ala Phe Leu Lys Leu Arg Arg
            365                 370                 375

CAG CAG CAG ATC GAG CGA GAG CTC AAC GGG TAC CTG GAG TGG ATC TTC 1322
Gln Gln Gln Ile Glu Arg Glu Leu Asn Gly Tyr Leu Glu Trp Ile Phe
        380                 385                 390

AAG GCG GAG GAA GTC ATG CTG GCC GAG GAG GAC AGG AAT GCA GAG GAG 1370
Lys Ala Glu Glu Val Met Leu Ala Glu Glu Asp Arg Asn Ala Glu Glu
    395                 400                 405

AAG TCC CCT TTG GAC GTG CTG AAG AGA GCG GCC ACC AAG AAG AGC AGA 1418
Lys Ser Pro Leu Asp Val Leu Lys Arg Ala Ala Thr Lys Lys Ser Arg
410                 415                 420                 425

AAT GAC CTG ATC CAC GCA GAG GAG GGA GAG GAC CGG TTT GCA GAT CTC 1466
Asn Asp Leu Ile His Ala Glu Glu Gly Glu Asp Arg Phe Ala Asp Leu
                430                 435                 440

-continued

```
TGT GCT GTT GGA TCC CCC TTC GCC CGC GCC AGC CTC AAG AGC GGG AAG    1514
Cys Ala Val Gly Ser Pro Phe Ala Arg Ala Ser Leu Lys Ser Gly Lys
            445                 450                 455

ACA GAG AGC TCG TCA TAC TTC CGG AGG AAG GAG AAG ATG TTC CGG TTT    1562
Thr Glu Ser Ser Ser Tyr Phe Arg Arg Lys Glu Lys Met Phe Arg Phe
        460                 465                 470

TTT ATC CGG CGC ATG GTG AAG GCT CAG AGC TTC TAC TGG GTG GTG CTG    1610
Phe Ile Arg Arg Met Val Lys Ala Gln Ser Phe Tyr Trp Val Val Leu
    475                 480                 485

TGC GTG GTG GCC CTG AAC ACA CTG TGT GTG GCC ATG GTG CAT TAC AAC    1658
Cys Val Val Ala Leu Asn Thr Leu Cys Val Ala Met Val His Tyr Asn
490                 495                 500                 505

CAG CCG CGG CGG CTT ACC ACG ACC CTG TAT TTT GCA GAG TTT GTT TTC    1706
Gln Pro Arg Arg Leu Thr Thr Thr Leu Tyr Phe Ala Glu Phe Val Phe
                510                 515                 520

CTG GGT CTC TTC CTC ACA GAG ATG TCC CTG AAG ATG TAT GGC CTG GGG    1754
Leu Gly Leu Phe Leu Thr Glu Met Ser Leu Lys Met Tyr Gly Leu Gly
            525                 530                 535

CCC AGA AGC TAC TTC CGG TCC TCC TTC AAC TGC TTC GAC TTT GGG GTC    1802
Pro Arg Ser Tyr Phe Arg Ser Ser Phe Asn Cys Phe Asp Phe Gly Val
        540                 545                 550

ATC GTG GGG AGC GTC TTT GAA GTG GTC TGG GCG GCC ATC AAG CCG GGA    1850
Ile Val Gly Ser Val Phe Glu Val Val Trp Ala Ala Ile Lys Pro Gly
    555                 560                 565

AGC TCC TTT GGG ATC AGT GTG CTG CGG GCC CTC CGC CTG CTG AGG ATC    1898
Ser Ser Phe Gly Ile Ser Val Leu Arg Ala Leu Arg Leu Leu Arg Ile
570                 575                 580                 585

TTC AAA GTC ACG AAG TAC TGG AGC TCC CTG CGG AAC CTG GTG GTG TCC    1946
Phe Lys Val Thr Lys Tyr Trp Ser Ser Leu Arg Asn Leu Val Val Ser
                590                 595                 600

CTG CTG AAC TCC ATG AAG TCC ATC ATC AGC CTG CTC TTC TTG CTC TTC    1994
Leu Leu Asn Ser Met Lys Ser Ile Ile Ser Leu Leu Phe Leu Leu Phe
            605                 610                 615

CTG TTC ATT GTG GTC TTC GCC CTG CTG GGG ATG CAG CTG TTT GGG GGA    2042
Leu Phe Ile Val Val Phe Ala Leu Leu Gly Met Gln Leu Phe Gly Gly
        620                 625                 630

CAG TTC AAC TTC CAG GAT GAG ACT CCC ACA ACC AAC TTC GAC ACC TTC    2090
Gln Phe Asn Phe Gln Asp Glu Thr Pro Thr Thr Asn Phe Asp Thr Phe
    635                 640                 645

CCT GCC GCC ATC CTC ACT GTC TTC CAG ATC CTG ACG GGA GAG GAC TGG    2138
Pro Ala Ala Ile Leu Thr Val Phe Gln Ile Leu Thr Gly Glu Asp Trp
650                 655                 660                 665

AAT GCA GTG ATG TAT CAC GGG ATC GAA TCG CAA GGC GGC GTC AGC AAA    2186
Asn Ala Val Met Tyr His Gly Ile Glu Ser Gln Gly Gly Val Ser Lys
                670                 675                 680

GGC ATG TTC TCG TCC TTT TAC TTC ATT GTC CTG ACA CTG TTC GGA AAC    2234
Gly Met Phe Ser Ser Phe Tyr Phe Ile Val Leu Thr Leu Phe Gly Asn
            685                 690                 695

TAC ACT CTG CTG AAT GTC TTT CTG GCC ATC GCT GTG GAC AAC CTG GCC    2282
Tyr Thr Leu Leu Asn Val Phe Leu Ala Ile Ala Val Asp Asn Leu Ala
        700                 705                 710

AAC GCC CAA GAG CTG ACC AAG GAT GAA GAG GAG ATG GAA GAA GCA GCC    2330
Asn Ala Gln Glu Leu Thr Lys Asp Glu Glu Glu Met Glu Glu Ala Ala
    715                 720                 725

AAT CAG AAG CTT GCT CTG CAA AAG GCC AAA GAA GTG GCT GAA GTC AGC    2378
Asn Gln Lys Leu Ala Leu Gln Lys Ala Lys Glu Val Ala Glu Val Ser
730                 735                 740                 745

CCC ATG TCT GCC GCG AAC ATC TCC ATC GCC GCC AGG CAG CAG AAC TCG    2426
Pro Met Ser Ala Ala Asn Ile Ser Ile Ala Ala Arg Gln Gln Asn Ser
                750                 755                 760
```

-continued

```
GCC AAG GCG CGC TCG GTG TGG GAG CAG CGG GCC AGC CAG CTA CGG CTG     2474
Ala Lys Ala Arg Ser Val Trp Glu Gln Arg Ala Ser Gln Leu Arg Leu
            765                 770                 775

CAG AAC CTG CGG GCC AGC TGC GAG GCG CTG TAC AGC GAG ATG GAC CCC     2522
Gln Asn Leu Arg Ala Ser Cys Glu Ala Leu Tyr Ser Glu Met Asp Pro
        780                 785                 790

GAG GAG CGG CTG CGC TTC GCC ACT ACG CGC CAC CTG CGG CCC GAC ATG     2570
Glu Glu Arg Leu Arg Phe Ala Thr Thr Arg His Leu Arg Pro Asp Met
    795                 800                 805

AAG ACG CAC CTG GAC CGG CCG CTG GTG GTG GAG CTG GGC CGC GAC GGC     2618
Lys Thr His Leu Asp Arg Pro Leu Val Val Glu Leu Gly Arg Asp Gly
810                 815                 820                 825

GCG CGG GGG CCC GTG GGA GGC AAA GCC CGA CCT GAG GCT GCG GAG GCC     2666
Ala Arg Gly Pro Val Gly Gly Lys Ala Arg Pro Glu Ala Ala Glu Ala
                830                 835                 840

CCC GAG GGC GTC GAC CCT CCG CGC AGG CAC CAC CGG CAC CGC GAC AAG     2714
Pro Glu Gly Val Asp Pro Pro Arg Arg His His Arg His Arg Asp Lys
            845                 850                 855

GAC AAG ACC CCC GCG GCG GGG GAC CAG GAC CGA GCA GAG GCC CCG AAG     2762
Asp Lys Thr Pro Ala Ala Gly Asp Gln Asp Arg Ala Glu Ala Pro Lys
        860                 865                 870

GCG GAG AGC GGG GAG CCC GGT GCC CGG GAG GAG CGG CCG CGG CCG CAC     2810
Ala Glu Ser Gly Glu Pro Gly Ala Arg Glu Glu Arg Pro Arg Pro His
    875                 880                 885

CGC AGC CAC AGC AAG GAG GCC GCG GGG CCC CCG GAG GCG CGG AGC GAG     2858
Arg Ser His Ser Lys Glu Ala Ala Gly Pro Pro Glu Ala Arg Ser Glu
890                 895                 900                 905

CGC GGC CGA GGC CCA GGC CCC GAG GGC GGC CGG CGG CAC CAC CGG CGC     2906
Arg Gly Arg Gly Pro Gly Pro Glu Gly Gly Arg Arg His His Arg Arg
                910                 915                 920

GGC TCC CCG GAG GAG GCG GCC GAG CGG GAG CCC CGA CGC CAC CGC GCG     2954
Gly Ser Pro Glu Glu Ala Ala Glu Arg Glu Pro Arg Arg His Arg Ala
            925                 930                 935

CAC CGG CAC CAG GAT CCG AGC AAG GAG TGC GCC GGC GCC AAG GGC GAG     3002
His Arg His Gln Asp Pro Ser Lys Glu Cys Ala Gly Ala Lys Gly Glu
        940                 945                 950

CGG CGC GCG CGG CAC CGC GGC GGC CCC CGA GCG GGG CCC CGG GAG GCG     3050
Arg Arg Ala Arg His Arg Gly Gly Pro Arg Ala Gly Pro Arg Glu Ala
    955                 960                 965

GAG AGC GGG GAG GAG CCG GCG CGG CGG CAC CGG GCC CGG CAC AAG GCG     3098
Glu Ser Gly Glu Glu Pro Ala Arg Arg His Arg Ala Arg His Lys Ala
970                 975                 980                 985

CAG CCT GCT CAC GAG GCT GTG GAG AAG GAG ACC ACG GAG AAG GAG GCC     3146
Gln Pro Ala His Glu Ala Val Glu Lys Glu Thr Thr Glu Lys Glu Ala
                990                 995                 1000

ACG GAG AAG GAG GCT GAG ATA GTG GAA GCC GAC AAG GAA AAG GAG CTC     3194
Thr Glu Lys Glu Ala Glu Ile Val Glu Ala Asp Lys Glu Lys Glu Leu
            1005                1010                1015

CGG AAC CAC CAG CCC CGG GAG CCA CAC TGT GAC CTG GAG ACC AGT GGG     3242
Arg Asn His Gln Pro Arg Glu Pro His Cys Asp Leu Glu Thr Ser Gly
        1020                1025                1030

ACT GTG ACT GTG GGT CCC ATG CAC ACA CTG CCC AGC ACC TGT CTC CAG     3290
Thr Val Thr Val Gly Pro Met His Thr Leu Pro Ser Thr Cys Leu Gln
    1035                1040                1045

AAG GTG GAG GAA CAG CCA GAG GAT GCA GAC AAT CAG CGG AAC GTC ACT     3338
Lys Val Glu Glu Gln Pro Glu Asp Ala Asp Asn Gln Arg Asn Val Thr
1050                1055                1060                1065

CGC ATG GGC AGT CAG CCC CCA GAC CCG AAC ACT ATT GTA CAT ATC CCA     3386
Arg Met Gly Ser Gln Pro Pro Asp Pro Asn Thr Ile Val His Ile Pro
                1070                1075                1080
```

-continued

```
GTG ATG CTG ACG GGC CCT CTT GGG GAA GCC ACG GTC GTT CCC AGT GGT    3434
Val Met Leu Thr Gly Pro Leu Gly Glu Ala Thr Val Val Pro Ser Gly
            1085                1090                1095

AAC GTG GAC CTG GAA AGC CAA GCA GAG GGG AAG AAG GAG GTG GAA GCG    3482
Asn Val Asp Leu Glu Ser Gln Ala Glu Gly Lys Lys Glu Val Glu Ala
        1100                1105                1110

GAT GAC GTG ATG AGG AGC GGC CCC CGG CCT ATC GTC CCA TAC AGC TCC    3530
Asp Asp Val Met Arg Ser Gly Pro Arg Pro Ile Val Pro Tyr Ser Ser
    1115                1120                1125

ATG TTC TGT TTA AGC CCC ACC AAC CTG CTC CGC CGC TTC TGC CAC TAC    3578
Met Phe Cys Leu Ser Pro Thr Asn Leu Leu Arg Arg Phe Cys His Tyr
1130                1135                1140                1145

ATC GTG ACC ATG AGG TAC TTC GAG GTG GTC ATT CTC GTG GTC ATC GCC    3626
Ile Val Thr Met Arg Tyr Phe Glu Val Val Ile Leu Val Val Ile Ala
                1150                1155                1160

TTG AGC AGC ATC GCC CTG GCT GCT GAG GAC CCA GTG CGC ACA GAC TCG    3674
Leu Ser Ser Ile Ala Leu Ala Ala Glu Asp Pro Val Arg Thr Asp Ser
            1165                1170                1175

CCC AGG AAC AAC GCT CTG AAA TAC CTG GAT TAC ATT TTC ACT GGT GTC    3722
Pro Arg Asn Asn Ala Leu Lys Tyr Leu Asp Tyr Ile Phe Thr Gly Val
        1180                1185                1190

TTT ACC TTT GAG ATG GTG ATA AAG ATG ATC GAC TTG GGA CTG CTG CTT    3770
Phe Thr Phe Glu Met Val Ile Lys Met Ile Asp Leu Gly Leu Leu Leu
    1195                1200                1205

CAC CCT GGA GCC TAT TTC CGG GAC TTG TGG AAC ATT CTG GAC TTC ATT    3818
His Pro Gly Ala Tyr Phe Arg Asp Leu Trp Asn Ile Leu Asp Phe Ile
1210                1215                1220                1225

GTG GTC AGT GGC GCC CTG GTG GCG TTT GCT TTC TCA GGA TCC AAA GGG    3866
Val Val Ser Gly Ala Leu Val Ala Phe Ala Phe Ser Gly Ser Lys Gly
                1230                1235                1240

AAA GAC ATC AAT ACC ATC AAG TCT CTG AGA GTC CTT CGT GTC CTG CGG    3914
Lys Asp Ile Asn Thr Ile Lys Ser Leu Arg Val Leu Arg Val Leu Arg
            1245                1250                1255

CCC CTC AAG ACC ATC AAA CGG CTG CCC AAG CTC AAG GCT GTG TTT GAC    3962
Pro Leu Lys Thr Ile Lys Arg Leu Pro Lys Leu Lys Ala Val Phe Asp
        1260                1265                1270

TGT GTG GTG AAC TCC CTG AAG AAT GTC CTC AAC ATC TTG ATT GTC TAC    4010
Cys Val Val Asn Ser Leu Lys Asn Val Leu Asn Ile Leu Ile Val Tyr
    1275                1280                1285

ATG CTC TTC ATG TTC ATA TTT GCC GTC ATT GCG GTG CAG CTC TTC AAA    4058
Met Leu Phe Met Phe Ile Phe Ala Val Ile Ala Val Gln Leu Phe Lys
1290                1295                1300                1305

GGG AAG TTT TTC TAC TGC ACA GAT GAA TCC AAG GAG CTG GAG AGG GAC    4106
Gly Lys Phe Phe Tyr Cys Thr Asp Glu Ser Lys Glu Leu Glu Arg Asp
                1310                1315                1320

TGC AGG GGT CAG TAT TTG GAT TAT GAG AAG GAG GAA GTG GAA GCT CAG    4154
Cys Arg Gly Gln Tyr Leu Asp Tyr Glu Lys Glu Glu Val Glu Ala Gln
            1325                1330                1335

CCC AGG CAG TGG AAG AAA TAC GAC TTT CAC TAC GAC AAT GTG CTC TGG    4202
Pro Arg Gln Trp Lys Lys Tyr Asp Phe His Tyr Asp Asn Val Leu Trp
        1340                1345                1350

GCT CTG CTG ACG CTG TTC ACA GTG TCC ACG GGA GAA GGC TGG CCC ATG    4250
Ala Leu Leu Thr Leu Phe Thr Val Ser Thr Gly Glu Gly Trp Pro Met
    1355                1360                1365

GTG CTG AAA CAC TCC GTG GAT GCC ACC TAT GAG GAG CAG GGT CCA AGC    4298
Val Leu Lys His Ser Val Asp Ala Thr Tyr Glu Glu Gln Gly Pro Ser
1370                1375                1380                1385

CCT GGG TAC CGC ATG GAG CTG TCC ATC TTC TAC GTG GTC TAC TTT GTG    4346
Pro Gly Tyr Arg Met Glu Leu Ser Ile Phe Tyr Val Val Tyr Phe Val
                1390                1395                1400
```

-continued

GTC TTT CCC TTC TTC TTC GTC AAC ATC TTT GTG GCT TTG ATC ATC ATC 4394
Val Phe Pro Phe Phe Phe Val Asn Ile Phe Val Ala Leu Ile Ile Ile
1405 1410 1415

ACC TTC CAG GAG CAG GGG GAC AAG GTG ATG TCT GAA TGC AGC CTG GAG 4442
Thr Phe Gln Glu Gln Gly Asp Lys Val Met Ser Glu Cys Ser Leu Glu
1420 1425 1430

AAG AAC GAG AGG GCT TGC ATT GAC TTC GCC ATC AGC GCC AAA CCC CTG 4490
Lys Asn Glu Arg Ala Cys Ile Asp Phe Ala Ile Ser Ala Lys Pro Leu
1435 1440 1445

ACA CGG TAC ATG CCC CAA AAC CGG CAG TCG TTC CAG TAT AAG ACG TGG 4538
Thr Arg Tyr Met Pro Gln Asn Arg Gln Ser Phe Gln Tyr Lys Thr Trp
1450 1455 1460 1465

ACA TTT GTG GTC TCC CCG CCC TTT GAA TAC TTC ATC ATG GCC ATG ATA 4586
Thr Phe Val Val Ser Pro Pro Phe Glu Tyr Phe Ile Met Ala Met Ile
1470 1475 1480

GCC CTC AAC ACT GTG GTG CTG ATG ATG AAG TTC TAT GAT GCA CCC TAT 4634
Ala Leu Asn Thr Val Val Leu Met Met Lys Phe Tyr Asp Ala Pro Tyr
1485 1490 1495

GAG TAC GAG CTG ATG CTG AAA TGC CTG AAC ATC GTG TTC ACA TCC ATG 4682
Glu Tyr Glu Leu Met Leu Lys Cys Leu Asn Ile Val Phe Thr Ser Met
1500 1505 1510

TTC TCC ATG GAA TGC GTG CTG AAG ATC ATC GCC TTT GGG GTG CTG AAC 4730
Phe Ser Met Glu Cys Val Leu Lys Ile Ile Ala Phe Gly Val Leu Asn
1515 1520 1525

TAT TTC AGA GAT GCC TGG AAT GTC TTT GAC TTT GTC ACT GTG TTG GGA 4778
Tyr Phe Arg Asp Ala Trp Asn Val Phe Asp Phe Val Thr Val Leu Gly
1530 1535 1540 1545

AGT ATT ACT GAT ATT TTA GTA ACA GAG ATT GCG GAA ACG AAC AAT TTC 4826
Ser Ile Thr Asp Ile Leu Val Thr Glu Ile Ala Glu Thr Asn Asn Phe
1550 1555 1560

ATC AAC CTC AGC TTC CTC CGC CTC TTT CGA GCT GCG CGG CTG ATC AAG 4874
Ile Asn Leu Ser Phe Leu Arg Leu Phe Arg Ala Ala Arg Leu Ile Lys
1565 1570 1575

CTG CTC CGC CAG GGC TAC ACC ATC CGC ATC CTG CTG TGG ACC TTT GTC 4922
Leu Leu Arg Gln Gly Tyr Thr Ile Arg Ile Leu Leu Trp Thr Phe Val
1580 1585 1590

CAG TCC TTC AAG GCC CTG CCC TAC GTG TGT CTG CTC ATT GCC ATG CTG 4970
Gln Ser Phe Lys Ala Leu Pro Tyr Val Cys Leu Leu Ile Ala Met Leu
1595 1600 1605

TTC TTC ATC TAC GCC ATC ATC GGC ATG CAG GTG TTT GGG AAT ATT GCC 5018
Phe Phe Ile Tyr Ala Ile Ile Gly Met Gln Val Phe Gly Asn Ile Ala
1610 1615 1620 1625

CTG GAT GAT GAC ACC AGC ATC AAC CGC CAC AAC AAC TTC CGG ACG TTT 5066
Leu Asp Asp Asp Thr Ser Ile Asn Arg His Asn Asn Phe Arg Thr Phe
1630 1635 1640

TTG CAA GCC CTG ATG CTG CTG TTC AGG AGC GCC ACG GGG GAG GCC TGG 5114
Leu Gln Ala Leu Met Leu Leu Phe Arg Ser Ala Thr Gly Glu Ala Trp
1645 1650 1655

CAC GAG ATC ATG CTG TCC TGC CTG AGC AAC CAG GCC TGT GAT GAG CAG 5162
His Glu Ile Met Leu Ser Cys Leu Ser Asn Gln Ala Cys Asp Glu Gln
1660 1665 1670

GCC AAT GCC ACC GAG TGT GGA AGT GAC TTT GCC TAC TTC TAC TTC GTC 5210
Ala Asn Ala Thr Glu Cys Gly Ser Asp Phe Ala Tyr Phe Tyr Phe Val
1675 1680 1685

TCC TTC ATC TTC CTG TGC TCC TTT CTG ATG TTG AAC CTC TTT GTG GCT 5258
Ser Phe Ile Phe Leu Cys Ser Phe Leu Met Leu Asn Leu Phe Val Ala
1690 1695 1700 1705

GTG ATC ATG GAC AAT TTT GAG TAC CTC ACG CGG GAC TCT TCC ATC CTA 5306
Val Ile Met Asp Asn Phe Glu Tyr Leu Thr Arg Asp Ser Ser Ile Leu
1710 1715 1720

-continued

```
GGT CCT CAC CAC TTG GAT GAG TTC ATC CGG GTC TGG GCT GAA TAC GAC      5354
Gly Pro His His Leu Asp Glu Phe Ile Arg Val Trp Ala Glu Tyr Asp
            1725                1730                1735

CCG GCT GCG TGT GGG CGC ATC AGT TAC AAT GAC ATG TTT GAG ATG CTG      5402
Pro Ala Ala Cys Gly Arg Ile Ser Tyr Asn Asp Met Phe Glu Met Leu
        1740                1745                1750

AAA CAC ATG TCC CCG CCT CTG GGG CTG GGG AAG AAA TGC CCT GCT CGA      5450
Lys His Met Ser Pro Pro Leu Gly Leu Gly Lys Lys Cys Pro Ala Arg
    1755                1760                1765

GTT GCT TAC AAG CGC CTG GTT CGC ATG AAC ATG CCC ATC TCC AAC GAG      5498
Val Ala Tyr Lys Arg Leu Val Arg Met Asn Met Pro Ile Ser Asn Glu
1770                1775                1780                1785

GAC ATG ACT GTT CAC TTC ACG TCC ACG CTG ATG GCC CTC ATC CGG ACG      5546
Asp Met Thr Val His Phe Thr Ser Thr Leu Met Ala Leu Ile Arg Thr
                1790                1795                1800

GCA CTG GAG ATC AAG CTG GCC CCA GCT GGG ACA AAG CAG CAT CAG TGT      5594
Ala Leu Glu Ile Lys Leu Ala Pro Ala Gly Thr Lys Gln His Gln Cys
            1805                1810                1815

GAC GCG GAG TTG AGG AAG GAG ATT TCC GTT GTG TGG GCC AAT CTG CCC      5642
Asp Ala Glu Leu Arg Lys Glu Ile Ser Val Val Trp Ala Asn Leu Pro
        1820                1825                1830

CAG AAG ACT TTG GAC TTG CTG GTA CCA CCC CAT AAG CCT GAT GAG ATG      5690
Gln Lys Thr Leu Asp Leu Leu Val Pro Pro His Lys Pro Asp Glu Met
    1835                1840                1845

ACA GTG GGG AAG GTT TAT GCA GCT CTG ATG ATA TTT GAC TTC TAC AAG      5738
Thr Val Gly Lys Val Tyr Ala Ala Leu Met Ile Phe Asp Phe Tyr Lys
1850                1855                1860                1865

CAG AAC AAA ACC ACC AGA GAC CAG ATG CAG CAG GCT CCT GGA GGC CTC      5786
Gln Asn Lys Thr Thr Arg Asp Gln Met Gln Gln Ala Pro Gly Gly Leu
                1870                1875                1880

TCC CAG ATG GGT CCT GTG TCC CTG TTC CAC CCT CTG AAG GCC ACC CTG      5834
Ser Gln Met Gly Pro Val Ser Leu Phe His Pro Leu Lys Ala Thr Leu
            1885                1890                1895

GAG CAG ACA CAG CCG GCT GTG CTC CGA GGA GCC CGG GTT TTC CTT CGA      5882
Glu Gln Thr Gln Pro Ala Val Leu Arg Gly Ala Arg Val Phe Leu Arg
        1900                1905                1910

CAG AAG AGT TCC ACC TCC CTC AGC AAT GGC GGG GCC ATA CAA AAC CAA      5930
Gln Lys Ser Ser Thr Ser Leu Ser Asn Gly Gly Ala Ile Gln Asn Gln
    1915                1920                1925

GAG AGT GGC ATC AAA GAG TCT GTC TCC TGG GGC ACT CAA AGG ACC CAG      5978
Glu Ser Gly Ile Lys Glu Ser Val Ser Trp Gly Thr Gln Arg Thr Gln
1930                1935                1940                1945

GAT GCA CCC CAT GAG GCC AGG CCA CCC CTG GAG CGT GGC CAC TCC ACA      6026
Asp Ala Pro His Glu Ala Arg Pro Pro Leu Glu Arg Gly His Ser Thr
                1950                1955                1960

GAG ATC CCT GTG GGG CGG TCA GGA GCA CTG GCT GTG GAC GTT CAG ATG      6074
Glu Ile Pro Val Gly Arg Ser Gly Ala Leu Ala Val Asp Val Gln Met
            1965                1970                1975

CAG AGC ATA ACC CGG AGG GGC CCT GAT GGG GAG CCC CAG CCT GGG CTG      6122
Gln Ser Ile Thr Arg Arg Gly Pro Asp Gly Glu Pro Gln Pro Gly Leu
        1980                1985                1990

GAG AGC CAG GGT CGA GCG GCC TCC ATG CCC CGC CTT GCG GCC GAG ACT      6170
Glu Ser Gln Gly Arg Ala Ala Ser Met Pro Arg Leu Ala Ala Glu Thr
    1995                2000                2005

CAG CCC GTC ACA GAT GCC AGC CCC ATG AAG CGC TCC ATC TCC ACG CTG      6218
Gln Pro Val Thr Asp Ala Ser Pro Met Lys Arg Ser Ile Ser Thr Leu
2010                2015                2020                2025

GCC CAG CGG CCC CGT GGG ACT CAT CTT TGC AGC ACC ACC CCG GAC CGC      6266
Ala Gln Arg Pro Arg Gly Thr His Leu Cys Ser Thr Thr Pro Asp Arg
                2030                2035                2040
```

-continued

```
CCA CCC CCT AGC CAG GCG TCG TCG CAC CAC CAC CAC CAC CGC TGC CAC      6314
Pro Pro Pro Ser Gln Ala Ser Ser His His His His His Arg Cys His
            2045                2050                2055

CGC CGC AGG GAC AGG AAG CAG AGG TCC CTG GAG AAG GGG CCC AGC CTG      6362
Arg Arg Arg Asp Arg Lys Gln Arg Ser Leu Glu Lys Gly Pro Ser Leu
        2060                2065                2070

TCT GCC GAT ATG GAT GGC GCA CCA AGC AGT GCT GTG GGG CCG GGG CTG      6410
Ser Ala Asp Met Asp Gly Ala Pro Ser Ser Ala Val Gly Pro Gly Leu
    2075                2080                2085

CCC CCG GGA GAG GGG CCT ACA GGC TGC CGG CGG GAA CGA GAG CGC CGG      6458
Pro Pro Gly Glu Gly Pro Thr Gly Cys Arg Arg Glu Arg Glu Arg Arg
2090                2095                2100                2105

CAG GAG CGG GGC CGG TCC CAG GAG CGG AGG CAG CCC TCA TCC TCC TCC      6506
Gln Glu Arg Gly Arg Ser Gln Glu Arg Arg Gln Pro Ser Ser Ser Ser
                2110                2115                2120

TCG GAG AAG CAG CGC TTC TAC TCC TGC GAC CGC TTT GGG GGC CGT GAG      6554
Ser Glu Lys Gln Arg Phe Tyr Ser Cys Asp Arg Phe Gly Gly Arg Glu
            2125                2130                2135

CCC CCG AAG CCC AAG CCC TCC CTC AGC AGC CAC CCA ACG TCG CCA ACA      6602
Pro Pro Lys Pro Lys Pro Ser Leu Ser Ser His Pro Thr Ser Pro Thr
        2140                2145                2150

GCT GGC CAG GAG CCG GGA CCC CAC CCA CAG GGC AGT GGT TCC GTG AAT      6650
Ala Gly Gln Glu Pro Gly Pro His Pro Gln Gly Ser Gly Ser Val Asn
    2155                2160                2165

GGG AGC CCC TTG CTG TCA ACA TCT GGT GCT AGC ACC CCC GGC CGC GGT      6698
Gly Ser Pro Leu Leu Ser Thr Ser Gly Ala Ser Thr Pro Gly Arg Gly
2170                2175                2180                2185

GGG CGG AGG CAG CTC CCC CAG ACG CCC CTG ACT CCC CGC CCC AGC ATC      6746
Gly Arg Arg Gln Leu Pro Gln Thr Pro Leu Thr Pro Arg Pro Ser Ile
                2190                2195                2200

ACC TAC AAG ACG GCC AAC TCC TCA CCC ATC CAC TTC GCC GGG GCT CAG      6794
Thr Tyr Lys Thr Ala Asn Ser Ser Pro Ile His Phe Ala Gly Ala Gln
            2205                2210                2215

ACC AGC CTC CCT GCC TTC TCC CCA GGC CGG CTC AGC CGT GGG CTT TCC      6842
Thr Ser Leu Pro Ala Phe Ser Pro Gly Arg Leu Ser Arg Gly Leu Ser
        2220                2225                2230

GAA CAC AAC GCC CTG CTG CAG AGA GAC CCC CTC AGC CAG CCC CTG GCC      6890
Glu His Asn Ala Leu Leu Gln Arg Asp Pro Leu Ser Gln Pro Leu Ala
    2235                2240                2245

CCT GGC TCT CGA ATT GGC TCT GAC CCT TAC CTG GGG CAG CGT CTG GAC      6938
Pro Gly Ser Arg Ile Gly Ser Asp Pro Tyr Leu Gly Gln Arg Leu Asp
2250                2255                2260                2265

AGT GAG GCC TCT GTC CAC GCC CTG CCT GAG GAC ACG CTC ACT TTC GAG      6986
Ser Glu Ala Ser Val His Ala Leu Pro Glu Asp Thr Leu Thr Phe Glu
                2270                2275                2280

GAG GCT GTG GCC ACC AAC TCG GGC CGC TCC TCC AGG ACT TCC TAC GTG      7034
Glu Ala Val Ala Thr Asn Ser Gly Arg Ser Ser Arg Thr Ser Tyr Val
            2285                2290                2295

TCC TCC CTG ACC TCC CAG TCT CAC CCT CTC CGC CGC GTG CCC AAC GGT      7082
Ser Ser Leu Thr Ser Gln Ser His Pro Leu Arg Arg Val Pro Asn Gly
        2300                2305                2310

TAC CAC TGC ACC CTG GGA CTC AGC TCG GGT GGC CGA GCA CGG CAC AGC      7130
Tyr His Cys Thr Leu Gly Leu Ser Ser Gly Gly Arg Ala Arg His Ser
    2315                2320                2325

TAC CAC CAC CCT GAC CAA GAC CAC TGG TGC TAGCTGCACC GTGACCGCTC        7180
Tyr His His Pro Asp Gln Asp His Trp Cys
2330                2335

AGACGCCTGC ATGCAGCAGG CGTGTGTTCC AGTGGATGAG TTTTATCATC CACACGGGGC    7240

AGTCGGCCCT CGGGGGAGGC CTTGCCCACC TTGGTGAGGC TCCTGTGGCC CCTCCCTCCC    7300
```

-continued

CCTCCTCCCC TCTTTTACTC TAGACGACGA ATAAAGCCCT GTTGCTTGAG TGTACGTACC 7360

GC 7362

( 2 ) INFORMATION FOR SEQ ID NO:8:

( i ) SEQUENCE CHARACTERISTICS:
( A ) LENGTH: 7175 base pairs
( B ) TYPE: nucleic acid
( C ) STRANDEDNESS: double
( D ) TOPOLOGY: linear ( i i ) MOLECULE TYPE: DNA (genomic)

( i x ) FEATURE:
( A ) NAME/KEY: CDS
( B ) LOCATION: 144..6857

( i x ) FEATURE:
( A ) NAME/KEY: 5'UTR
( B ) LOCATION: 1..143

( i x ) FEATURE:
( A ) NAME/KEY: 3'UTR
( B ) LOCATION: 6855..7175

( x i ) SEQUENCE DESCRIPTION: SEQ ID NO:8:

GCGGCGGCGG CTGCGGCGGT GGGGCCGGGC GAGGTCCGTG CGGTCCCGGC GGCTCCGTGG 60

CTGCTCCGCT CTGAGCGCCT GCGCGCCCCG CGCCCTCCCT GCCGGGGCCG CTGGGCCGGG 120

GATGCACGCG GGGCCCGGGA GCC ATG GTC CGC TTC GGG GAC GAG CTG GGC 170
Met Val Arg Phe Gly Asp Glu Leu Gly
1 5

GGC CGC TAT GGA GGC CCC GGC GGC GGA GAG CGG GCC CGG GGC GGC GGG 218
Gly Arg Tyr Gly Gly Pro Gly Gly Gly Glu Arg Ala Arg Gly Gly Gly
10 15 20 25

GCC GGC GGG GCG GGG GGC CCG GGT CCC GGG GGG CTG CAG CCC GGC CAG 266
Ala Gly Gly Ala Gly Gly Pro Gly Pro Gly Gly Leu Gln Pro Gly Gln
30 35 40

CGG GTC CTC TAC AAG CAA TCG ATC GCG CAG CGC GCG CGG ACC ATG GCG 314
Arg Val Leu Tyr Lys Gln Ser Ile Ala Gln Arg Ala Arg Thr Met Ala
45 50 55

CTG TAC AAC CCC ATC CCG GTC AAG CAG AAC TGC TTC ACC GTC AAC CGC 362
Leu Tyr Asn Pro Ile Pro Val Lys Gln Asn Cys Phe Thr Val Asn Arg
60 65 70

TCG CTC TTC GTC TTC AGC GAG GAC AAC GTC GTC CGC AAA TAC GCG AAG 410
Ser Leu Phe Val Phe Ser Glu Asp Asn Val Val Arg Lys Tyr Ala Lys
75 80 85

CGC ATC ACC GAG TGG CCT CCA TTC GAG AAT ATG ATC CTG GCC ACC ATC 458
Arg Ile Thr Glu Trp Pro Pro Phe Glu Asn Met Ile Leu Ala Thr Ile
90 95 100 105

ATC GCC AAC TGC ATC GTG CTG GCC CTG GAG CAG CAC CTC CCT GAT GGG 506
Ile Ala Asn Cys Ile Val Leu Ala Leu Glu Gln His Leu Pro Asp Gly
110 115 120

GAC AAA ACG CCC ATG TCC GAG CGG CTG GAC GAC ACG GAG CCC TAT TTC 554
Asp Lys Thr Pro Met Ser Glu Arg Leu Asp Asp Thr Glu Pro Tyr Phe
125 130 135

ATC GGG ATC TTT TGC TTC GAG GCA GGG ATC AAA ATC ATC GCT CTG GGC 602
Ile Gly Ile Phe Cys Phe Glu Ala Gly Ile Lys Ile Ile Ala Leu Gly
140 145 150

TTT GTC TTC CAC AAG GGC TCT TAC CTG CGG AAC GGC TGG AAC GTC ATG 650
Phe Val Phe His Lys Gly Ser Tyr Leu Arg Asn Gly Trp Asn Val Met
155 160 165

GAC TTC GTG GTC GTC CTC ACA GGG ATC CTT GCC ACG GCT GGA ACT GAC 698
Asp Phe Val Val Val Leu Thr Gly Ile Leu Ala Thr Ala Gly Thr Asp

-continued

```
170                 175                 180                 185

TTC GAC CTG CGA ACA CTG AGG GCT GTG CGT GTG CTG AGG CCC CTG AAG      746
Phe Asp Leu Arg Thr Leu Arg Ala Val Arg Val Leu Arg Pro Leu Lys
                190                 195                 200

CTG GTG TCT GGG ATT CCA AGT TTG CAG GTG GTG CTC AAG TCC ATC ATG      794
Leu Val Ser Gly Ile Pro Ser Leu Gln Val Val Leu Lys Ser Ile Met
            205                 210                 215

AAG GCC ATG GTT CCA CTC CTG CAG ATT GGG CTG CTT CTC TTC TTT GCC      842
Lys Ala Met Val Pro Leu Leu Gln Ile Gly Leu Leu Leu Phe Phe Ala
        220                 225                 230

ATC CTC ATG TTT GCC ATC ATT GGC CTG GAG TTC TAC ATG GGC AAG TTC      890
Ile Leu Met Phe Ala Ile Ile Gly Leu Glu Phe Tyr Met Gly Lys Phe
    235                 240                 245

CAC AAG GCC TGT TTC CCC AAC AGC ACA GAT GCG GAG CCC GTG GGT GAC      938
His Lys Ala Cys Phe Pro Asn Ser Thr Asp Ala Glu Pro Val Gly Asp
250                 255                 260                 265

TTC CCC TGT GGC AAG GAG GCC CCA GCC CGG CTG TGC GAG GGC GAC ACT      986
Phe Pro Cys Gly Lys Glu Ala Pro Ala Arg Leu Cys Glu Gly Asp Thr
                270                 275                 280

GAG TGC CGG GAG TAC TGG CCA GGA CCC AAC TTT GGC ATC ACC AAC TTT     1034
Glu Cys Arg Glu Tyr Trp Pro Gly Pro Asn Phe Gly Ile Thr Asn Phe
            285                 290                 295

GAC AAT ATC CTG TTT GCC ATC TTG ACG GTG TTC CAG TGC ATC ACC ATG     1082
Asp Asn Ile Leu Phe Ala Ile Leu Thr Val Phe Gln Cys Ile Thr Met
        300                 305                 310

GAG GGC TGG ACT GAC ATC CTC TAT AAT ACA AAC GAT GCG GCC GGC AAC     1130
Glu Gly Trp Thr Asp Ile Leu Tyr Asn Thr Asn Asp Ala Ala Gly Asn
    315                 320                 325

ACC TGG AAC TGG CTC TAC TTC ATC CCT CTC ATC ATC ATC GGC TCC TTC     1178
Thr Trp Asn Trp Leu Tyr Phe Ile Pro Leu Ile Ile Ile Gly Ser Phe
330                 335                 340                 345

TTC ATG CTC AAC CTG GTG CTG GGC GTG CTC TCG GGG GAG TTT GCC AAG     1226
Phe Met Leu Asn Leu Val Leu Gly Val Leu Ser Gly Glu Phe Ala Lys
                350                 355                 360

GAG CGA GAG AGG GTG GAG AAC CGC CGC GCC TTC CTG AAG CTG CGC CGG     1274
Glu Arg Glu Arg Val Glu Asn Arg Arg Ala Phe Leu Lys Leu Arg Arg
            365                 370                 375

CAG CAG CAG ATC GAG CGA GAG CTC AAC GGG TAC CTG GAG TGG ATC TTC     1322
Gln Gln Gln Ile Glu Arg Glu Leu Asn Gly Tyr Leu Glu Trp Ile Phe
        380                 385                 390

AAG GCG GAG GAA GTC ATG CTG GCC GAG GAG GAC AGG AAT GCA GAG GAG     1370
Lys Ala Glu Glu Val Met Leu Ala Glu Glu Asp Arg Asn Ala Glu Glu
    395                 400                 405

AAG TCC CCT TTG GAC GTG CTG AAG AGA GCG GCC ACC AAG AAG AGC AGA     1418
Lys Ser Pro Leu Asp Val Leu Lys Arg Ala Ala Thr Lys Lys Ser Arg
410                 415                 420                 425

AAT GAC CTG ATC CAC GCA GAG GAG GGA GAG GAC CGG TTT GCA GAT CTC     1466
Asn Asp Leu Ile His Ala Glu Glu Gly Glu Asp Arg Phe Ala Asp Leu
                430                 435                 440

TGT GCT GTT GGA TCC CCC TTC GCC CGC GCC AGC CTC AAG AGC GGG AAG     1514
Cys Ala Val Gly Ser Pro Phe Ala Arg Ala Ser Leu Lys Ser Gly Lys
            445                 450                 455

ACA GAG AGC TCG TCA TAC TTC CGG AGG AAG GAG AAG ATG TTC CGG TTT     1562
Thr Glu Ser Ser Ser Tyr Phe Arg Arg Lys Glu Lys Met Phe Arg Phe
        460                 465                 470

TTT ATC CGG CGC ATG GTG AAG GCT CAG AGC TTC TAC TGG GTG GTG CTG     1610
Phe Ile Arg Arg Met Val Lys Ala Gln Ser Phe Tyr Trp Val Val Leu
    475                 480                 485

TGC GTG GTG GCC CTG AAC ACA CTG TGT GTG GCC ATG GTG CAT TAC AAC     1658
Cys Val Val Ala Leu Asn Thr Leu Cys Val Ala Met Val His Tyr Asn
```

-continued

```
490                 495                 500                 505

CAG CCG CGG CGG CTT ACC ACG ACC CTG TAT TTT GCA GAG TTT GTT TTC     1706
Gln Pro Arg Arg Leu Thr Thr Thr Leu Tyr Phe Ala Glu Phe Val Phe
                510                 515                 520

CTG GGT CTC TTC CTC ACA GAG ATG TCC CTG AAG ATG TAT GGC CTG GGG     1754
Leu Gly Leu Phe Leu Thr Glu Met Ser Leu Lys Met Tyr Gly Leu Gly
            525                 530                 535

CCC AGA AGC TAC TTC CGG TCC TCC TTC AAC TGC TTC GAC TTT GGG GTC     1802
Pro Arg Ser Tyr Phe Arg Ser Ser Phe Asn Cys Phe Asp Phe Gly Val
        540                 545                 550

ATC GTG GGG AGC GTC TTT GAA GTG GTC TGG GCG GCC ATC AAG CCG GGA     1850
Ile Val Gly Ser Val Phe Glu Val Val Trp Ala Ala Ile Lys Pro Gly
    555                 560                 565

AGC TCC TTT GGG ATC AGT GTG CTG CGG GCC CTC CGC CTG CTG AGG ATC     1898
Ser Ser Phe Gly Ile Ser Val Leu Arg Ala Leu Arg Leu Leu Arg Ile
570                 575                 580                 585

TTC AAA GTC ACG AAG TAC TGG AGC TCC CTG CGG AAC CTG GTG GTG TCC     1946
Phe Lys Val Thr Lys Tyr Trp Ser Ser Leu Arg Asn Leu Val Val Ser
                590                 595                 600

CTG CTG AAC TCC ATG AAG TCC ATC ATC AGC CTG CTC TTC TTG CTC TTC     1994
Leu Leu Asn Ser Met Lys Ser Ile Ile Ser Leu Leu Phe Leu Leu Phe
            605                 610                 615

CTG TTC ATT GTG GTC TTC GCC CTG CTG GGG ATG CAG CTG TTT GGG GGA     2042
Leu Phe Ile Val Val Phe Ala Leu Leu Gly Met Gln Leu Phe Gly Gly
        620                 625                 630

CAG TTC AAC TTC CAG GAT GAG ACT CCC ACA ACC AAC TTC GAC ACC TTC     2090
Gln Phe Asn Phe Gln Asp Glu Thr Pro Thr Thr Asn Phe Asp Thr Phe
    635                 640                 645

CCT GCC GCC ATC CTC ACT GTC TTC CAG ATC CTG ACG GGA GAG GAC TGG     2138
Pro Ala Ala Ile Leu Thr Val Phe Gln Ile Leu Thr Gly Glu Asp Trp
650                 655                 660                 665

AAT GCA GTG ATG TAT CAC GGG ATC GAA TCG CAA GGC GGC GTC AGC AAA     2186
Asn Ala Val Met Tyr His Gly Ile Glu Ser Gln Gly Gly Val Ser Lys
                670                 675                 680

GGC ATG TTC TCG TCC TTT TAC TTC ATT GTC CTG ACA CTG TTC GGA AAC     2234
Gly Met Phe Ser Ser Phe Tyr Phe Ile Val Leu Thr Leu Phe Gly Asn
            685                 690                 695

TAC ACT CTG CTG AAT GTC TTT CTG GCC ATC GCT GTG GAC AAC CTG GCC     2282
Tyr Thr Leu Leu Asn Val Phe Leu Ala Ile Ala Val Asp Asn Leu Ala
        700                 705                 710

AAC GCC CAA GAG CTG ACC AAG GAT GAA GAG GAG ATG GAA GAA GCA GCC     2330
Asn Ala Gln Glu Leu Thr Lys Asp Glu Glu Glu Met Glu Glu Ala Ala
    715                 720                 725

AAT CAG AAG CTT GCT CTG CAA AAG GCC AAA GAA GTG GCT GAA GTC AGC     2378
Asn Gln Lys Leu Ala Leu Gln Lys Ala Lys Glu Val Ala Glu Val Ser
730                 735                 740                 745

CCC ATG TCT GCC GCG AAC ATC TCC ATC GCC GCC AGG CAG CAG AAC TCG     2426
Pro Met Ser Ala Ala Asn Ile Ser Ile Ala Ala Arg Gln Gln Asn Ser
                750                 755                 760

GCC AAG GCG CGC TCG GTG TGG GAG CAG CGG GCC AGC CAG CTA CGG CTG     2474
Ala Lys Ala Arg Ser Val Trp Glu Gln Arg Ala Ser Gln Leu Arg Leu
            765                 770                 775

CAG AAC CTG CGG GCC AGC TGC GAG GCG CTG TAC AGC GAG ATG GAC CCC     2522
Gln Asn Leu Arg Ala Ser Cys Glu Ala Leu Tyr Ser Glu Met Asp Pro
        780                 785                 790

GAG GAG CGG CTG CGC TTC GCC ACT ACG CGC CAC CTG CGG CCC GAC ATG     2570
Glu Glu Arg Leu Arg Phe Ala Thr Thr Arg His Leu Arg Pro Asp Met
    795                 800                 805

AAG ACG CAC CTG GAC CGG CCG CTG GTG GTG GAG CTG GGC CGC GAC GGC     2618
Lys Thr His Leu Asp Arg Pro Leu Val Val Glu Leu Gly Arg Asp Gly
```

-continued

```
810                 815                 820                 825

GCG CGG GGG CCC GTG GGA GGC AAA GCC CGA CCT GAG GCT GCG GAG GCC    2666
Ala Arg Gly Pro Val Gly Gly Lys Ala Arg Pro Glu Ala Ala Glu Ala
                830                 835                 840

CCC GAG GGC GTC GAC CCT CCG CGC AGG CAC CAC CGG CAC CGC GAC AAG    2714
Pro Glu Gly Val Asp Pro Pro Arg Arg His His Arg His Arg Asp Lys
            845                 850                 855

GAC AAG ACC CCC GCG GCG GGG GAC CAG GAC CGA GCA GAG GCC CCG AAG    2762
Asp Lys Thr Pro Ala Ala Gly Asp Gln Asp Arg Ala Glu Ala Pro Lys
        860                 865                 870

GCG GAG AGC GGG GAG CCC GGT GCC CGG GAG GAG CGG CCG CGG CCG CAC    2810
Ala Glu Ser Gly Glu Pro Gly Ala Arg Glu Glu Arg Pro Arg Pro His
    875                 880                 885

CGC AGC CAC AGC AAG GAG GCC GCG GGG CCC CCG GAG GCG CGG AGC GAG    2858
Arg Ser His Ser Lys Glu Ala Ala Gly Pro Pro Glu Ala Arg Ser Glu
890                 895                 900                 905

CGC GGC CGA GGC CCA GGC CCC GAG GGC GGC CGG CGG CAC CAC CGG CGC    2906
Arg Gly Arg Gly Pro Gly Pro Glu Gly Gly Arg Arg His His Arg Arg
                910                 915                 920

GGC TCC CCG GAG GAG GCG GCC GAG CGG GAG CCC CGA CGC CAC CGC GCG    2954
Gly Ser Pro Glu Glu Ala Ala Glu Arg Glu Pro Arg Arg His Arg Ala
            925                 930                 935

CAC CGG CAC CAG GAT CCG AGC AAG GAG TGC GCC GGC GCC AAG GGC GAG    3002
His Arg His Gln Asp Pro Ser Lys Glu Cys Ala Gly Ala Lys Gly Glu
        940                 945                 950

CGG CGC GCG CGG CAC CGC GGC GGC CCC CGA GCG GGG CCC CGG GAG GCG    3050
Arg Arg Ala Arg His Arg Gly Gly Pro Arg Ala Gly Pro Arg Glu Ala
    955                 960                 965

GAG AGC GGG GAG GAG CCG GCG CGG CGG CAC CGG GCC CGG CAC AAG GCG    3098
Glu Ser Gly Glu Glu Pro Ala Arg Arg His Arg Ala Arg His Lys Ala
970                 975                 980                 985

CAG CCT GCT CAC GAG GCT GTG GAG AAG GAG ACC ACG GAG AAG GAG GCC    3146
Gln Pro Ala His Glu Ala Val Glu Lys Glu Thr Thr Glu Lys Glu Ala
                990                 995                 1000

ACG GAG AAG GAG GCT GAG ATA GTG GAA GCC GAC AAG GAA AAG GAG CTC    3194
Thr Glu Lys Glu Ala Glu Ile Val Glu Ala Asp Lys Glu Lys Glu Leu
            1005                1010                1015

CGG AAC CAC CAG CCC CGG GAG CCA CAC TGT GAC CTG GAG ACC AGT GGG    3242
Arg Asn His Gln Pro Arg Glu Pro His Cys Asp Leu Glu Thr Ser Gly
        1020                1025                1030

ACT GTG ACT GTG GGT CCC ATG CAC ACA CTG CCC AGC ACC TGT CTC CAG    3290
Thr Val Thr Val Gly Pro Met His Thr Leu Pro Ser Thr Cys Leu Gln
    1035                1040                1045

AAG GTG GAG GAA CAG CCA GAG GAT GCA GAC AAT CAG CGG AAC GTC ACT    3338
Lys Val Glu Glu Gln Pro Glu Asp Ala Asp Asn Gln Arg Asn Val Thr
1050                1055                1060                1065

CGC ATG GGC AGT CAG CCC CCA GAC CCG AAC ACT ATT GTA CAT ATC CCA    3386
Arg Met Gly Ser Gln Pro Pro Asp Pro Asn Thr Ile Val His Ile Pro
                1070                1075                1080

GTG ATG CTG ACG GGC CCT CTT GGG GAA GCC ACG GTC GTT CCC AGT GGT    3434
Val Met Leu Thr Gly Pro Leu Gly Glu Ala Thr Val Val Pro Ser Gly
            1085                1090                1095

AAC GTG GAC CTG GAA AGC CAA GCA GAG GGG AAG AAG GAG GTG GAA GCG    3482
Asn Val Asp Leu Glu Ser Gln Ala Glu Gly Lys Lys Glu Val Glu Ala
        1100                1105                1110

GAT GAC GTG ATG AGG AGC GGC CCC CGG CCT ATC GTC CCA TAC AGC TCC    3530
Asp Asp Val Met Arg Ser Gly Pro Arg Pro Ile Val Pro Tyr Ser Ser
    1115                1120                1125

ATG TTC TGT TTA AGC CCC ACC AAC CTG CTC CGC CGC TTC TGC CAC TAC    3578
Met Phe Cys Leu Ser Pro Thr Asn Leu Leu Arg Arg Phe Cys His Tyr
```

-continued

```
1130                1135                1140                1145

ATC GTG ACC ATG AGG TAC TTC GAG GTG GTC ATT CTC GTG GTC ATC GCC      3626
Ile Val Thr Met Arg Tyr Phe Glu Val Val Ile Leu Val Val Ile Ala
                1150                1155                1160

TTG AGC AGC ATC GCC CTG GCT GCT GAG GAC CCA GTG CGC ACA GAC TCG      3674
Leu Ser Ser Ile Ala Leu Ala Ala Glu Asp Pro Val Arg Thr Asp Ser
            1165                1170                1175

CCC AGG AAC AAC GCT CTG AAA TAC CTG GAT TAC ATT TTC ACT GGT GTC      3722
Pro Arg Asn Asn Ala Leu Lys Tyr Leu Asp Tyr Ile Phe Thr Gly Val
        1180                1185                1190

TTT ACC TTT GAG ATG GTG ATA AAG ATG ATC GAC TTG GGA CTG CTG CTT      3770
Phe Thr Phe Glu Met Val Ile Lys Met Ile Asp Leu Gly Leu Leu Leu
    1195                1200                1205

CAC CCT GGA GCC TAT TTC CGG GAC TTG TGG AAC ATT CTG GAC TTC ATT      3818
His Pro Gly Ala Tyr Phe Arg Asp Leu Trp Asn Ile Leu Asp Phe Ile
1210                1215                1220                1225

GTG GTC AGT GGC GCC CTG GTG GCG TTT GCT TTC TCA GGA TCC AAA GGG      3866
Val Val Ser Gly Ala Leu Val Ala Phe Ala Phe Ser Gly Ser Lys Gly
                1230                1235                1240

AAA GAC ATC AAT ACC ATC AAG TCT CTG AGA GTC CTT CGT GTC CTG CGG      3914
Lys Asp Ile Asn Thr Ile Lys Ser Leu Arg Val Leu Arg Val Leu Arg
            1245                1250                1255

CCC CTC AAG ACC ATC AAA CGG CTG CCC AAG CTC AAG GCT GTG TTT GAC      3962
Pro Leu Lys Thr Ile Lys Arg Leu Pro Lys Leu Lys Ala Val Phe Asp
        1260                1265                1270

TGT GTG GTG AAC TCC CTG AAG AAT GTC CTC AAC ATC TTG ATT GTC TAC      4010
Cys Val Val Asn Ser Leu Lys Asn Val Leu Asn Ile Leu Ile Val Tyr
    1275                1280                1285

ATG CTC TTC ATG TTC ATA TTT GCC GTC ATT GCG GTG CAG CTC TTC AAA      4058
Met Leu Phe Met Phe Ile Phe Ala Val Ile Ala Val Gln Leu Phe Lys
1290                1295                1300                1305

GGG AAG TTT TTC TAC TGC ACA GAT GAA TCC AAG GAG CTG GAG AGG GAC      4106
Gly Lys Phe Phe Tyr Cys Thr Asp Glu Ser Lys Glu Leu Glu Arg Asp
                1310                1315                1320

TGC AGG GGT CAG TAT TTG GAT TAT GAG AAG GAG GAA GTG GAA GCT CAG      4154
Cys Arg Gly Gln Tyr Leu Asp Tyr Glu Lys Glu Glu Val Glu Ala Gln
            1325                1330                1335

CCC AGG CAG TGG AAG AAA TAC GAC TTT CAC TAC GAC AAT GTG CTC TGG      4202
Pro Arg Gln Trp Lys Lys Tyr Asp Phe His Tyr Asp Asn Val Leu Trp
        1340                1345                1350

GCT CTG CTG ACG CTG TTC ACA GTG TCC ACG GGA GAA GGC TGG CCC ATG      4250
Ala Leu Leu Thr Leu Phe Thr Val Ser Thr Gly Glu Gly Trp Pro Met
    1355                1360                1365

GTG CTG AAA CAC TCC GTG GAT GCC ACC TAT GAG GAG CAG GGT CCA AGC      4298
Val Leu Lys His Ser Val Asp Ala Thr Tyr Glu Glu Gln Gly Pro Ser
1370                1375                1380                1385

CCT GGG TAC CGC ATG GAG CTG TCC ATC TTC TAC GTG GTC TAC TTT GTG      4346
Pro Gly Tyr Arg Met Glu Leu Ser Ile Phe Tyr Val Val Tyr Phe Val
                1390                1395                1400

GTC TTT CCC TTC TTC TTC GTC AAC ATC TTT GTG GCT TTG ATC ATC ATC      4394
Val Phe Pro Phe Phe Phe Val Asn Ile Phe Val Ala Leu Ile Ile Ile
            1405                1410                1415

ACC TTC CAG GAG CAG GGG GAC AAG GTG ATG TCT GAA TGC AGC CTG GAG      4442
Thr Phe Gln Glu Gln Gly Asp Lys Val Met Ser Glu Cys Ser Leu Glu
        1420                1425                1430

AAG AAC GAG AGG GCT TGC ATT GAC TTC GCC ATC AGC GCC AAA CCC CTG      4490
Lys Asn Glu Arg Ala Cys Ile Asp Phe Ala Ile Ser Ala Lys Pro Leu
    1435                1440                1445

ACA CGG TAC ATG CCC CAA AAC CGG CAG TCG TTC CAG TAT AAG ACG TGG      4538
Thr Arg Tyr Met Pro Gln Asn Arg Gln Ser Phe Gln Tyr Lys Thr Trp
```

-continued

```
1450                1455                1460                1465

ACA TTT GTG GTC TCC CCG CCC TTT GAA TAC TTC ATC ATG GCC ATG ATA    4586
Thr Phe Val Val Ser Pro Pro Phe Glu Tyr Phe Ile Met Ala Met Ile
                    1470                1475                1480

GCC CTC AAC ACT GTG GTG CTG ATG ATG AAG TTC TAT GAT GCA CCC TAT    4634
Ala Leu Asn Thr Val Val Leu Met Met Lys Phe Tyr Asp Ala Pro Tyr
            1485                1490                1495

GAG TAC GAG CTG ATG CTG AAA TGC CTG AAC ATC GTG TTC ACA TCC ATG    4682
Glu Tyr Glu Leu Met Leu Lys Cys Leu Asn Ile Val Phe Thr Ser Met
        1500                1505                1510

TTC TCC ATG GAA TGC GTG CTG AAG ATC ATC GCC TTT GGG GTG CTG AAC    4730
Phe Ser Met Glu Cys Val Leu Lys Ile Ile Ala Phe Gly Val Leu Asn
    1515                1520                1525

TAT TTC AGA GAT GCC TGG AAT GTC TTT GAC TTT GTC ACT GTG TTG GGA    4778
Tyr Phe Arg Asp Ala Trp Asn Val Phe Asp Phe Val Thr Val Leu Gly
1530                1535                1540                1545

AGT ATT ACT GAT ATT TTA GTA ACA GAG ATT GCG GAA ACG AAC AAT TTC    4826
Ser Ile Thr Asp Ile Leu Val Thr Glu Ile Ala Glu Thr Asn Asn Phe
                    1550                1555                1560

ATC AAC CTC AGC TTC CTC CGC CTC TTT CGA GCT GCG CGG CTG ATC AAG    4874
Ile Asn Leu Ser Phe Leu Arg Leu Phe Arg Ala Ala Arg Leu Ile Lys
            1565                1570                1575

CTG CTC CGC CAG GGC TAC ACC ATC CGC ATC CTG CTG TGG ACC TTT GTC    4922
Leu Leu Arg Gln Gly Tyr Thr Ile Arg Ile Leu Leu Trp Thr Phe Val
        1580                1585                1590

CAG TCC TTC AAG GCC CTG CCC TAC GTG TGT CTG CTC ATT GCC ATG CTG    4970
Gln Ser Phe Lys Ala Leu Pro Tyr Val Cys Leu Leu Ile Ala Met Leu
    1595                1600                1605

TTC TTC ATC TAC GCC ATC ATC GGC ATG CAG GTG TTT GGG AAT ATT GCC    5018
Phe Phe Ile Tyr Ala Ile Ile Gly Met Gln Val Phe Gly Asn Ile Ala
1610                1615                1620                1625

CTG GAT GAT GAC ACC AGC ATC AAC CGC CAC AAC AAC TTC CGG ACG TTT    5066
Leu Asp Asp Asp Thr Ser Ile Asn Arg His Asn Asn Phe Arg Thr Phe
                    1630                1635                1640

TTG CAA GCC CTG ATG CTG CTG TTC AGG AGC GCC ACG GGG GAG GCC TGG    5114
Leu Gln Ala Leu Met Leu Leu Phe Arg Ser Ala Thr Gly Glu Ala Trp
            1645                1650                1655

CAC GAG ATC ATG CTG TCC TGC CTG AGC AAC CAG GCC TGT GAT GAG CAG    5162
His Glu Ile Met Leu Ser Cys Leu Ser Asn Gln Ala Cys Asp Glu Gln
        1660                1665                1670

GCC AAT GCC ACC GAG TGT GGA AGT GAC TTT GCC TAC TTC TAC TTC GTC    5210
Ala Asn Ala Thr Glu Cys Gly Ser Asp Phe Ala Tyr Phe Tyr Phe Val
    1675                1680                1685

TCC TTC ATC TTC CTG TGC TCC TTT CTG ATG TTG AAC CTC TTT GTG GCT    5258
Ser Phe Ile Phe Leu Cys Ser Phe Leu Met Leu Asn Leu Phe Val Ala
1690                1695                1700                1705

GTG ATC ATG GAC AAT TTT GAG TAC CTC ACG CGG GAC TCT TCC ATC CTA    5306
Val Ile Met Asp Asn Phe Glu Tyr Leu Thr Arg Asp Ser Ser Ile Leu
                    1710                1715                1720

GGT CCT CAC CAC TTG GAT GAG TTC ATC CGG GTC TGG GCT GAA TAC GAC    5354
Gly Pro His His Leu Asp Glu Phe Ile Arg Val Trp Ala Glu Tyr Asp
            1725                1730                1735

CCG GCT GCG TGT GGG CGC ATC AGT TAC AAT GAC ATG TTT GAG ATG CTG    5402
Pro Ala Ala Cys Gly Arg Ile Ser Tyr Asn Asp Met Phe Glu Met Leu
        1740                1745                1750

AAA CAC ATG TCC CCG CCT CTG GGG CTG GGG AAG AAA TGC CCT GCT CGA    5450
Lys His Met Ser Pro Pro Leu Gly Leu Gly Lys Lys Cys Pro Ala Arg
    1755                1760                1765

GTT GCT TAC AAG CGC CTG GTT CGC ATG AAC ATG CCC ATC TCC AAC GAG    5498
Val Ala Tyr Lys Arg Leu Val Arg Met Asn Met Pro Ile Ser Asn Glu
```

-continued 1770 1775 1780 1785

GAC ATG ACT GTT CAC TTC ACG TCC ACG CTG ATG GCC CTC ATC CGG ACG 5546
Asp Met Thr Val His Phe Thr Ser Thr Leu Met Ala Leu Ile Arg Thr
1790 1795 1800

GCA CTG GAG ATC AAG CTG GCC CCA GCT GGG ACA AAG CAG CAT CAG TGT 5594
Ala Leu Glu Ile Lys Leu Ala Pro Ala Gly Thr Lys Gln His Gln Cys
1805 1810 1815

GAC GCG GAG TTG AGG AAG GAG ATT TCC GTT GTG TGG GCC AAT CTG CCC 5642
Asp Ala Glu Leu Arg Lys Glu Ile Ser Val Val Trp Ala Asn Leu Pro
1820 1825 1830

CAG AAG ACT TTG GAC TTG CTG GTA CCA CCC CAT AAG CCT GAT GAG ATG 5690
Gln Lys Thr Leu Asp Leu Leu Val Pro Pro His Lys Pro Asp Glu Met
1835 1840 1845

ACA GTG GGG AAG GTT TAT GCA GCT CTG ATG ATA TTT GAC TTC TAC AAG 5738
Thr Val Gly Lys Val Tyr Ala Ala Leu Met Ile Phe Asp Phe Tyr Lys
1850 1855 1860 1865

CAG AAC AAA ACC ACC AGA GAC CAG ATG CAG CAG GCT CCT GGA GGC CTC 5786
Gln Asn Lys Thr Thr Arg Asp Gln Met Gln Gln Ala Pro Gly Gly Leu
1870 1875 1880

TCC CAG ATG GGT CCT GTG TCC CTG TTC CAC CCT CTG AAG GCC ACC CTG 5834
Ser Gln Met Gly Pro Val Ser Leu Phe His Pro Leu Lys Ala Thr Leu
1885 1890 1895

GAG CAG ACA CAG CCG GCT GTG CTC CGA GGA GCC CGG GTT TTC CTT CGA 5882
Glu Gln Thr Gln Pro Ala Val Leu Arg Gly Ala Arg Val Phe Leu Arg
1900 1905 1910

CAG AAG AGT TCC ACC TCC CTC AGC AAT GGC GGG GCC ATA CAA AAC CAA 5930
Gln Lys Ser Ser Thr Ser Leu Ser Asn Gly Gly Ala Ile Gln Asn Gln
1915 1920 1925

GAG AGT GGC ATC AAA GAG TCT GTC TCC TGG GGC ACT CAA AGG ACC CAG 5978
Glu Ser Gly Ile Lys Glu Ser Val Ser Trp Gly Thr Gln Arg Thr Gln
1930 1935 1940 1945

GAT GCA CCC CAT GAG GCC AGG CCA CCC CTG GAG CGT GGC CAC TCC ACA 6026
Asp Ala Pro His Glu Ala Arg Pro Pro Leu Glu Arg Gly His Ser Thr
1950 1955 1960

GAG ATC CCT GTG GGG CGG TCA GGA GCA CTG GCT GTG GAC GTT CAG ATG 6074
Glu Ile Pro Val Gly Arg Ser Gly Ala Leu Ala Val Asp Val Gln Met
1965 1970 1975

CAG AGC ATA ACC CGG AGG GGC CCT GAT GGG GAG CCC CAG CCT GGG CTG 6122
Gln Ser Ile Thr Arg Arg Gly Pro Asp Gly Glu Pro Gln Pro Gly Leu
1980 1985 1990

GAG AGC CAG GGT CGA GCG GCC TCC ATG CCC CGC CTT GCG GCC GAG ACT 6170
Glu Ser Gln Gly Arg Ala Ala Ser Met Pro Arg Leu Ala Ala Glu Thr
1995 2000 2005

CAG CCC GTC ACA GAT GCC AGC CCC ATG AAG CGC TCC ATC TCC ACG CTG 6218
Gln Pro Val Thr Asp Ala Ser Pro Met Lys Arg Ser Ile Ser Thr Leu
2010 2015 2020 2025

GCC CAG CGG CCC CGT GGG ACT CAT CTT TGC AGC ACC ACC CCG GAC CGC 6266
Ala Gln Arg Pro Arg Gly Thr His Leu Cys Ser Thr Thr Pro Asp Arg
2030 2035 2040

CCA CCC CCT AGC CAG GCG TCG TCG CAC CAC CAC CAC CAC CGC TGC CAC 6314
Pro Pro Pro Ser Gln Ala Ser Ser His His His His His Arg Cys His
2045 2050 2055

CGC CGC AGG GAC AGG AAG CAG AGG TCC CTG GAG AAG GGG CCC AGC CTG 6362
Arg Arg Arg Asp Arg Lys Gln Arg Ser Leu Glu Lys Gly Pro Ser Leu
2060 2065 2070

TCT GCC GAT ATG GAT GGC GCA CCA AGC AGT GCT GTG GGG CCG GGG CTG 6410
Ser Ala Asp Met Asp Gly Ala Pro Ser Ser Ala Val Gly Pro Gly Leu
2075 2080 2085

CCC CCG GGA GAG GGG CCT ACA GGC TGC CGG CGG GAA CGA GAG CGC CGG 6458
Pro Pro Gly Glu Gly Pro Thr Gly Cys Arg Arg Glu Arg Glu Arg Arg

-continued

```
2090                2095                2100                2105

CAG GAG CGG GGC CGG TCC CAG GAG CGG AGG CAG CCC TCA TCC TCC TCC     6506
Gln Glu Arg Gly Arg Ser Gln Glu Arg Arg Gln Pro Ser Ser Ser Ser
                2110                2115                2120

TCG GAG AAG CAG CGC TTC TAC TCC TGC GAC CGC TTT GGG GGC CGT GAG     6554
Ser Glu Lys Gln Arg Phe Tyr Ser Cys Asp Arg Phe Gly Gly Arg Glu
            2125                2130                2135

CCC CCG AAG CCC AAG CCC TCC CTC AGC AGC CAC CCA ACG TCG CCA ACA     6602
Pro Pro Lys Pro Lys Pro Ser Leu Ser Ser His Pro Thr Ser Pro Thr
        2140                2145                2150

GCT GGC CAG GAG CCG GGA CCC CAC CCA CAG GCC GGC TCA GCC GTG GGC     6650
Ala Gly Gln Glu Pro Gly Pro His Pro Gln Ala Gly Ser Ala Val Gly
    2155                2160                2165

TTT CCG AAC ACA ACG CCC TGC TGC AGA GAG ACC CCC TCA GCC AGC CCC     6698
Phe Pro Asn Thr Thr Pro Cys Cys Arg Glu Thr Pro Ser Ala Ser Pro
2170                2175                2180                2185

TGG CCC CTG GCT CTC GAA TTG GCT CTG ACC CTT ACC TGG GGC AGC GTC     6746
Trp Pro Leu Ala Leu Glu Leu Ala Leu Thr Leu Thr Trp Gly Ser Val
                2190                2195                2200

TGG ACA GTG AGG CCT CTG TCC ACG CCC TGC CTG AGG ACA CGC TCA CTT     6794
Trp Thr Val Arg Pro Leu Ser Thr Pro Cys Leu Arg Thr Arg Ser Leu
            2205                2210                2215

TCG AGG AGG CTG TGG CCA CCA ACT CGG GCC GCT CCT CCA GGA CTT CCT     6842
Ser Arg Arg Leu Trp Pro Pro Thr Arg Ala Ala Pro Pro Gly Leu Pro
        2220                2225                2230

ACG TGT CCT CCC TGACCTCCCA GTCTCACCCT CTCCGCCGCG TGCCCAACGG         6894
Thr Cys Pro Pro
    2235

TTACCACTGC ACCCTGGGAC TCAGCTCGGG TGGCCGAGCA CGGCACAGCT ACCACCACCC   6954

TGACCAAGAC CACTGGTGCT AGCTGCACCG TGACCGCTCA GACGCCTGCA TGCAGCAGGC   7014

GTGTGTTCCA GTGGATGAGT TTTATCATCC ACACGGGGCA GTCGGCCCTC GGGGGAGGCC   7074

TTGCCCACCT TGGTGAGGCT CCTGTGGCCC CTCCCTCCCC CTCCTCCCCT CTTTTACTCT   7134

AGACGACGAA TAAAGCCCTG TTGCTTGAGT GTACGTACCG C                       7175
```

( 2 ) INFORMATION FOR SEQ ID NO:9:

( i ) SEQUENCE CHARACTERISTICS:
( A ) LENGTH: 1546 base pairs
( B ) TYPE: nucleic acid
( C ) STRANDEDNESS: double
( D ) TOPOLOGY: linear ( i i ) MOLECULE TYPE: DNA (genomic)

( i x ) FEATURE:
( A ) NAME/KEY: CDS
( B ) LOCATION: 1..1437

( i x ) FEATURE:
( A ) NAME/KEY: 3'UTR
( B ) LOCATION: 1435..1546

( x i ) SEQUENCE DESCRIPTION: SEQ ID NO:9:

```
ATG GTC CAG AAG ACC AGC ATG TCC CGG GGC CCT TAC CCA CCC TCC CAG      48
Met Val Gln Lys Thr Ser Met Ser Arg Gly Pro Tyr Pro Pro Ser Gln
  1               5                  10                  15

GAG ATC CCC ATG GAG GTC TTC GAC CCC AGC CCG CAG GGC AAA TAC AGC      96
Glu Ile Pro Met Glu Val Phe Asp Pro Ser Pro Gln Gly Lys Tyr Ser
            20                  25                  30

AAG AGG AAA GGG CGA TTC AAA CGG TCA GAT GGG AGC ACG TCC TCG GAT     144
Lys Arg Lys Gly Arg Phe Lys Arg Ser Asp Gly Ser Thr Ser Ser Asp
        35                  40                  45
```

-continued

```
ACC ACA TCC AAC AGC TTT GTC CGC CAG GGC TCA GCG GAG TCC TAC ACC     192
Thr Thr Ser Asn Ser Phe Val Arg Gln Gly Ser Ala Glu Ser Tyr Thr
    50                  55                  60

AGC CGT CCA TCA GAC TCT GAT GTA TCT CTG GAG GAG GAC CGG GAA GCC     240
Ser Arg Pro Ser Asp Ser Asp Val Ser Leu Glu Glu Asp Arg Glu Ala
65                  70                  75                  80

TTA AGG AAG GAA GCA GAG CGC CAG GCA TTA GCG CAG CTC GAG AAG GCC     288
Leu Arg Lys Glu Ala Glu Arg Gln Ala Leu Ala Gln Leu Glu Lys Ala
                85                  90                  95

AAG ACC AAG CCA GTG GCA TTT GCT GTG CGG ACA AAT GTT GGC TAC AAT     336
Lys Thr Lys Pro Val Ala Phe Ala Val Arg Thr Asn Val Gly Tyr Asn
            100                 105                 110

CCG TCT CCA GGG GAT GAG GTG CCT GTG CAG GGA GTG GCC ATC ACC TTC     384
Pro Ser Pro Gly Asp Glu Val Pro Val Gln Gly Val Ala Ile Thr Phe
        115                 120                 125

GAG CCC AAA GAC TTC CTG CAC ATC AAG GAG AAA TAC AAT AAT GAC TGG     432
Glu Pro Lys Asp Phe Leu His Ile Lys Glu Lys Tyr Asn Asn Asp Trp
    130                 135                 140

TGG ATC GGG CGG CTG GTG AAG GAG GGC TGT GAG GTT GGC TTC ATT CCC     480
Trp Ile Gly Arg Leu Val Lys Glu Gly Cys Glu Val Gly Phe Ile Pro
145                 150                 155                 160

AGC CCC GTC AAA CTG GAC AGC CTT CGC CTG CTG CAG GAA CAG AAG CTG     528
Ser Pro Val Lys Leu Asp Ser Leu Arg Leu Leu Gln Glu Gln Lys Leu
                165                 170                 175

CGC CAG AAC CGC CTC GGC TCC AGC AAA TCA GGC GAT AAC TCC AGT TCC     576
Arg Gln Asn Arg Leu Gly Ser Ser Lys Ser Gly Asp Asn Ser Ser Ser
            180                 185                 190

AGT CTG GGA GAT GTG GTG ACT GGC ACC CGC CGC CCC ACA CCC CCT GCC     624
Ser Leu Gly Asp Val Val Thr Gly Thr Arg Arg Pro Thr Pro Pro Ala
        195                 200                 205

AGT GCC AAA CAG AAG CAG AAG TCG ACA GAG CAT GTG CCC CCC TAT GAC     672
Ser Ala Lys Gln Lys Gln Lys Ser Thr Glu His Val Pro Pro Tyr Asp
    210                 215                 220

GTG GTG CCT TCC ATG AGG CCC ATC ATC CTG GTG GGA CCG TCG CTC AAG     720
Val Val Pro Ser Met Arg Pro Ile Ile Leu Val Gly Pro Ser Leu Lys
225                 230                 235                 240

GGC TAC GAG GTT ACA GAC ATG ATG CAG AAA GCT TTA TTT GAC TTC TTG     768
Gly Tyr Glu Val Thr Asp Met Met Gln Lys Ala Leu Phe Asp Phe Leu
                245                 250                 255

AAG CAT CGG TTT GAT GGC AGG ATC TCC ATC ACT CGT GTG ACG GCA GAT     816
Lys His Arg Phe Asp Gly Arg Ile Ser Ile Thr Arg Val Thr Ala Asp
            260                 265                 270

ATT TCC CTG GCT AAG CGC TCA GTT CTC AAC AAC CCC AGC AAA CAC ATC     864
Ile Ser Leu Ala Lys Arg Ser Val Leu Asn Asn Pro Ser Lys His Ile
        275                 280                 285

ATC ATT GAG CGC TCC AAC ACA CGC TCC AGC CTG GCT GAG GTG CAG AGT     912
Ile Ile Glu Arg Ser Asn Thr Arg Ser Ser Leu Ala Glu Val Gln Ser
    290                 295                 300

GAA ATC GAG CGA ATC TTC GAG CTG GCC CGG ACC CTT CAG TTG GTC GCT     960
Glu Ile Glu Arg Ile Phe Glu Leu Ala Arg Thr Leu Gln Leu Val Ala
305                 310                 315                 320

CTG GAT GCT GAC ACC ATC AAT CAC CCA GCC CAG CTG TCC AAG ACC TCG    1008
Leu Asp Ala Asp Thr Ile Asn His Pro Ala Gln Leu Ser Lys Thr Ser
                325                 330                 335

CTG GCC CCC ATC ATT GTT TAC ATC AAG ATC ACC TCT CCC AAG GTA CTT    1056
Leu Ala Pro Ile Ile Val Tyr Ile Lys Ile Thr Ser Pro Lys Val Leu
            340                 345                 350

CAA AGG CTC ATC AAG TCC CGA GGA AAG TCT CAG TCC AAA CAC CTC AAT    1104
Gln Arg Leu Ile Lys Ser Arg Gly Lys Ser Gln Ser Lys His Leu Asn
        355                 360                 365
```

-continued

```
GTC CAA ATA GCG GCC TCG GAA AAG CTG GCA CAG TGC CCC CCT GAA ATG     1152
Val Gln Ile Ala Ala Ser Glu Lys Leu Ala Gln Cys Pro Pro Glu Met
    370                 375                 380

TTT GAC ATC ATC CTG GAT GAG AAC CAA TTG GAG GAT GCC TGC GAG CAT     1200
Phe Asp Ile Ile Leu Asp Glu Asn Gln Leu Glu Asp Ala Cys Glu His
385                 390                 395                 400

CTG GCG GAG TAC TTG GAA GCC TAT TGG AAG GCC ACA CAC CCG CCC AGC     1248
Leu Ala Glu Tyr Leu Glu Ala Tyr Trp Lys Ala Thr His Pro Pro Ser
                405                 410                 415

AGC ACG CCA CCC AAT CCG CTG CTG AAC CGC ACC ATG GCT ACC GCA GCC     1296
Ser Thr Pro Pro Asn Pro Leu Leu Asn Arg Thr Met Ala Thr Ala Ala
            420                 425                 430

CTG GCT GCC AGC CCT GCC CCT GTC TCC AAC CTC CAG GTA CAG GTG CTC     1344
Leu Ala Ala Ser Pro Ala Pro Val Ser Asn Leu Gln Val Gln Val Leu
        435                 440                 445

ACC TCG CTC AGG AGA AAC CTC GGC TTC TGG GGC GGG CTG GAG TCC TCA     1392
Thr Ser Leu Arg Arg Asn Leu Gly Phe Trp Gly Gly Leu Glu Ser Ser
    450                 455                 460

CAG CGG GGC AGT GTG GTG CCC CAG GAG CAG GAA CAT GCC ATG TAGTGGGCGC  1444
Gln Arg Gly Ser Val Val Pro Gln Glu Gln Glu His Ala Met
465                 470                 475

CCTGCCCGTC TTCCCTCCTG CTCTGGGGTC GGAACTGGAG TGCAGGGAAC ATGGAGGAGG   1504

AAGGGAAGAG CTTTATTTTG TAAAAAAATA AGATGAGCGG CA                      1546
```

( 2 ) INFORMATION FOR SEQ ID NO:10:

( i ) SEQUENCE CHARACTERISTICS:
( A ) LENGTH: 1851 base pairs
( B ) TYPE: nucleic acid
( C ) STRANDEDNESS: double
( D ) TOPOLOGY: linear ( i i ) MOLECULE TYPE: DNA (genomic)

( i x ) FEATURE:
( A ) NAME/KEY: CDS
( B ) LOCATION: 1..1797
( D ) OTHER INFORMATION: /standard_name= "Beta-3"

( i x ) FEATURE:
( A ) NAME/KEY: 3'UTR
( B ) LOCATION: 1795..1851

( x i ) SEQUENCE DESCRIPTION: SEQ ID NO:10:

```
ATG GTC CAG AAG ACC AGC ATG TCC CGG GAG CCT TAC CCA CCC TCC CAG       48
Met Val Gln Lys Thr Ser Met Ser Arg Glu Pro Tyr Pro Pro Ser Gln
  1               5                  10                  15

GAG ATC CCC ATG GAG GTC TTC GAC CCC AGC CCG CAG GGC AAA TAC AGC       96
Glu Ile Pro Met Glu Val Phe Asp Pro Ser Pro Gln Gly Lys Tyr Ser
            20                  25                  30

AAG AGG AAA GGG CGA TTC AAA CGG TCA GAT GGG AGC ACG TCC TCG GAT      144
Lys Arg Lys Gly Arg Phe Lys Arg Ser Asp Gly Ser Thr Ser Ser Asp
        35                  40                  45

ACC ACA TCC AAC AGC TTT GTC CGC CAG GGC TCA GCG GAG TCC TAC ACC      192
Thr Thr Ser Asn Ser Phe Val Arg Gln Gly Ser Ala Glu Ser Tyr Thr
    50                  55                  60

AGC CGT CCA TCA GAC TCT GAT GTA TCT CTG GAG GAG GAC CGG GAA GCC      240
Ser Arg Pro Ser Asp Ser Asp Val Ser Leu Glu Glu Asp Arg Glu Ala
 65                  70                  75                  80

TTA AGG AAG GAA GCA GAG CGC CAG GCA TTA GCG CAG CTC GAG AAG GCC      288
Leu Arg Lys Glu Ala Glu Arg Gln Ala Leu Ala Gln Leu Glu Lys Ala
                85                  90                  95

AAG ACC AAG CCA GTG GCA TTT GCT GTG CGG ACA AAT GTT GGC TAC AAT      336
```

-continued

```
Lys Thr Lys Pro Val Ala Phe Ala Val Arg Thr Asn Val Gly Tyr Asn
            100                 105                 110

CCG TCT CCA GGG GAT GAG GTG CCT GTG CAG GGA GTG GCC ATC ACC TTC      384
Pro Ser Pro Gly Asp Glu Val Pro Val Gln Gly Val Ala Ile Thr Phe
        115                 120                 125

GAG CCC AAA GAC TTC CTG CAC ATC AAG GAG AAA TAC AAT AAT GAC TGG      432
Glu Pro Lys Asp Phe Leu His Ile Lys Glu Lys Tyr Asn Asn Asp Trp
    130                 135                 140

TGG ATC GGG CGG CTG GTG AAG GAG GGC TGT GAG GTT GGC TTC ATT CCC      480
Trp Ile Gly Arg Leu Val Lys Glu Gly Cys Glu Val Gly Phe Ile Pro
145                 150                 155                 160

AGC CCC GTC AAA CTG GAC AGC CTT CGC CTG CTG CAG GAA CAG AAG CTG      528
Ser Pro Val Lys Leu Asp Ser Leu Arg Leu Leu Gln Glu Gln Lys Leu
                165                 170                 175

CGC CAG AAC CGC CTC GGC TCC AGC AAA TCA GGC GAT AAC TCC AGT TCC      576
Arg Gln Asn Arg Leu Gly Ser Ser Lys Ser Gly Asp Asn Ser Ser Ser
            180                 185                 190

AGT CTG GGA GAT GTG GTG ACT GGC ACC CGC CGC CCC ACA CCC CCT GCC      624
Ser Leu Gly Asp Val Val Thr Gly Thr Arg Arg Pro Thr Pro Pro Ala
        195                 200                 205

AGT GCC AAA CAG AAG CAG AAG TCG ACA GAG CAT GTG CCC CCC TAT GAC      672
Ser Ala Lys Gln Lys Gln Lys Ser Thr Glu His Val Pro Pro Tyr Asp
    210                 215                 220

GTG GTG CCT TCC ATG AGG CCC ATC ATC CTG GTG GGA CCG TCG CTC AAG      720
Val Val Pro Ser Met Arg Pro Ile Ile Leu Val Gly Pro Ser Leu Lys
225                 230                 235                 240

GGC TAC GAG GTT ACA GAC ATG ATG CAG AAA GCT TTA TTT GAC TTC TTG      768
Gly Tyr Glu Val Thr Asp Met Met Gln Lys Ala Leu Phe Asp Phe Leu
                245                 250                 255

AAG CAT CGG TTT GAT GGC AGG ATC TCC ATC ACT CGT GTG ACG GCA GAT      816
Lys His Arg Phe Asp Gly Arg Ile Ser Ile Thr Arg Val Thr Ala Asp
            260                 265                 270

ATT TCC CTG GCT AAG CGC TCA GTT CTC AAC AAC CCC AGC AAA CAC ATC      864
Ile Ser Leu Ala Lys Arg Ser Val Leu Asn Asn Pro Ser Lys His Ile
        275                 280                 285

ATC ATT GAG CGC TCC AAC ACA CGC TCC AGC CTG GCT GAG GTG CAG AGT      912
Ile Ile Glu Arg Ser Asn Thr Arg Ser Ser Leu Ala Glu Val Gln Ser
    290                 295                 300

GAA ATC GAG CGA ATC TTC GAG CTG GCC CGG ACC CTT CAG TTG GTC GCT      960
Glu Ile Glu Arg Ile Phe Glu Leu Ala Arg Thr Leu Gln Leu Val Ala
305                 310                 315                 320

CTG GAT GCT GAC ACC ATC AAT CAC CCA GCC CAG CTG TCC AAG ACC TCG     1008
Leu Asp Ala Asp Thr Ile Asn His Pro Ala Gln Leu Ser Lys Thr Ser
                325                 330                 335

CTG GCC CCC ATC ATT GTT TAC ATC AAG ATC ACC TCT CCC AAG GTA CTT     1056
Leu Ala Pro Ile Ile Val Tyr Ile Lys Ile Thr Ser Pro Lys Val Leu
            340                 345                 350

CAA AGG CTC ATC AAG TCC CGA GGA AAG TCT CAG TCC AAA CAC CTC AAT     1104
Gln Arg Leu Ile Lys Ser Arg Gly Lys Ser Gln Ser Lys His Leu Asn
        355                 360                 365

GTC CAA ATA GCG GCC TCG GAA AAG CTG GCA CAG TGC CCC CCT GAA ATG     1152
Val Gln Ile Ala Ala Ser Glu Lys Leu Ala Gln Cys Pro Pro Glu Met
    370                 375                 380

TTT GAC ATC ATC CTG GAT GAG AAC CAA TTG GAG GAT GCC TGC GAG CAT     1200
Phe Asp Ile Ile Leu Asp Glu Asn Gln Leu Glu Asp Ala Cys Glu His
385                 390                 395                 400

CTG GCG GAG TAC TTG GAA GCC TAT TGG AAG GCC ACA CAC CCG CCC AGC     1248
Leu Ala Glu Tyr Leu Glu Ala Tyr Trp Lys Ala Thr His Pro Pro Ser
                405                 410                 415

AGC ACG CCA CCC AAT CCG CTG CTG AAC CGC ACC ATG GCT ACC GCA GCC     1296
```

-continued

```
Ser Thr Pro Pro Asn Pro Leu Leu Asn Arg Thr Met Ala Thr Ala Ala
            420                 425                 430

CTG GCT GCC AGC CCT GCC CCT GTC TCC AAC CTC CAG GGA CCC TAC CTT    1344
Leu Ala Ala Ser Pro Ala Pro Val Ser Asn Leu Gln Gly Pro Tyr Leu
        435                 440                 445

GCT TCC GGG GAC CAG CCA CTG GAA CGG GCC ACC GGG GAG CAC GCC AGC    1392
Ala Ser Gly Asp Gln Pro Leu Glu Arg Ala Thr Gly Glu His Ala Ser
    450                 455                 460

ATG CAC GAG TAC CCA GGG GAG CTG GGC CAG CCC CCA GGC CTT TAC CCC    1440
Met His Glu Tyr Pro Gly Glu Leu Gly Gln Pro Pro Gly Leu Tyr Pro
465                 470                 475                 480

AGC AGC CAC CCA CCA GGC CGG GCA GGC ACG CTA CGG GCA CTG TCC CGC    1488
Ser Ser His Pro Pro Gly Arg Ala Gly Thr Leu Arg Ala Leu Ser Arg
                485                 490                 495

CAA GAC ACT TTT GAT GCC GAC ACC CCC GGC AGC CGA AAC TCT GCC TAC    1536
Gln Asp Thr Phe Asp Ala Asp Thr Pro Gly Ser Arg Asn Ser Ala Tyr
            500                 505                 510

ACG GAG CTG GGA GAC TCA TGT GTG GAC ATG GAG ACT GAC CCC TCA GAG    1584
Thr Glu Leu Gly Asp Ser Cys Val Asp Met Glu Thr Asp Pro Ser Glu
        515                 520                 525

GGG CCA GGG CTT GGA GAC CCT GCA GGG GGC GGC ACG CCC CCA GCC CGA    1632
Gly Pro Gly Leu Gly Asp Pro Ala Gly Gly Gly Thr Pro Pro Ala Arg
    530                 535                 540

CAG GGA TCC TGG GAG GAC GAG GAA GAA GAC TAT GAG GAA GAG CTG ACC    1680
Gln Gly Ser Trp Glu Asp Glu Glu Glu Asp Tyr Glu Glu Glu Leu Thr
545                 550                 555                 560

GAC AAC CGG AAC CGG GGC CGG AAT AAG GCC CGC TAC TGC GCT GAG GGT    1728
Asp Asn Arg Asn Arg Gly Arg Asn Lys Ala Arg Tyr Cys Ala Glu Gly
                565                 570                 575

GGG GGT CCA GTT TTG GGG CGC AAC AAG AAT GAG CTG GAG GGC TGG GGA    1776
Gly Gly Pro Val Leu Gly Arg Asn Lys Asn Glu Leu Glu Gly Trp Gly
            580                 585                 590

CGA GGC GTC TAC ATT CGC TGAGAGGCAG GGGCCACACG GCGGGAGGAA           1824
Arg Gly Val Tyr Ile Arg
        595

GGGCTCTGAG CCCAGGGGAG GGGAGGG                                      1851
```

( 2 ) INFORMATION FOR SEQ ID NO:11:

( i ) SEQUENCE CHARACTERISTICS:
( A ) LENGTH: 3600 base pairs
( B ) TYPE: nucleic acid
( C ) STRANDEDNESS: double
( D ) TOPOLOGY: linear ( i i ) MOLECULE TYPE: DNA (genomic)

( i x ) FEATURE:
( A ) NAME/KEY: CDS
( B ) LOCATION: 35..3310
( D ) OTHER INFORMATION: /standard_name= "Alpha-2"

( i x ) FEATURE:
( A ) NAME/KEY: 5'UTR
( B ) LOCATION: 1..34

( i x ) FEATURE:
( A ) NAME/KEY: 3'UTR
( B ) LOCATION: 3308..3600

( x i ) SEQUENCE DESCRIPTION: SEQ ID NO:11:

```
GCGGGGGAGG GGGCATTGAT CTTCGATCGC GAAG ATG GCT GCT GGC TGC CTG       52
                                      Met Ala Ala Gly Cys Leu
                                       1                   5

CTG GCC TTG ACT CTG ACA CTT TTC CAA TCT TTG CTC ATC GGC CCC TCG    100
```

-continued

Leu Ala Leu Thr Leu Thr Leu Phe Gln Ser Leu Leu Ile Gly Pro Ser
10 15 20

TCG GAG GAG CCG TTC CCT TCG GCC GTC ACT ATC AAA TCA TGG GTG GAT 148
Ser Glu Glu Pro Phe Pro Ser Ala Val Thr Ile Lys Ser Trp Val Asp
25 30 35

AAG ATG CAA GAA GAC CTT GTC ACA CTG GCA AAA ACA GCA AGT GGA GTC 196
Lys Met Gln Glu Asp Leu Val Thr Leu Ala Lys Thr Ala Ser Gly Val
40 45 50

AAT CAG CTT GTT GAT ATT TAT GAG AAA TAT CAA GAT TTG TAT ACT GTG 244
Asn Gln Leu Val Asp Ile Tyr Glu Lys Tyr Gln Asp Leu Tyr Thr Val
55 60 65 70

GAA CCA AAT AAT GCA CGC CAG CTG GTA GAA ATT GCA GCC AGG GAT ATT 292
Glu Pro Asn Asn Ala Arg Gln Leu Val Glu Ile Ala Ala Arg Asp Ile
75 80 85

GAG AAA CTT CTG AGC AAC AGA TCT AAA GCC CTG GTG AGC CTG GCA TTG 340
Glu Lys Leu Leu Ser Asn Arg Ser Lys Ala Leu Val Ser Leu Ala Leu
90 95 100

GAA GCG GAG AAA GTT CAA GCA GCT CAC CAG TGG AGA GAA GAT TTT GCA 388
Glu Ala Glu Lys Val Gln Ala Ala His Gln Trp Arg Glu Asp Phe Ala
105 110 115

AGC AAT GAA GTT GTC TAC TAC AAT GCA AAG GAT GAT CTC GAT CCT GAG 436
Ser Asn Glu Val Val Tyr Tyr Asn Ala Lys Asp Asp Leu Asp Pro Glu
120 125 130

AAA AAT GAC AGT GAG CCA GGC AGC CAG AGG ATA AAA CCT GTT TTC ATT 484
Lys Asn Asp Ser Glu Pro Gly Ser Gln Arg Ile Lys Pro Val Phe Ile
135 140 145 150

GAA GAT GCT AAT TTT GGA CGA CAA ATA TCT TAT CAG CAC GCA GCA GTC 532
Glu Asp Ala Asn Phe Gly Arg Gln Ile Ser Tyr Gln His Ala Ala Val
155 160 165

CAT ATT CCT ACT GAC ATC TAT GAG GGC TCA ACA ATT GTG TTA AAT GAA 580
His Ile Pro Thr Asp Ile Tyr Glu Gly Ser Thr Ile Val Leu Asn Glu
170 175 180

CTC AAC TGG ACA AGT GCC TTA GAT GAA GTT TTC AAA AAG AAT CGC GAG 628
Leu Asn Trp Thr Ser Ala Leu Asp Glu Val Phe Lys Lys Asn Arg Glu
185 190 195

GAA GAC CCT TCA TTA TTG TGG CAG GTT TTT GGC AGT GCC ACT GGC CTA 676
Glu Asp Pro Ser Leu Leu Trp Gln Val Phe Gly Ser Ala Thr Gly Leu
200 205 210

GCT CGA TAT TAT CCA GCT TCA CCA TGG GTT GAT AAT AGT AGA ACT CCA 724
Ala Arg Tyr Tyr Pro Ala Ser Pro Trp Val Asp Asn Ser Arg Thr Pro
215 220 225 230

AAT AAG ATT GAC CTT TAT GAT GTA CGC AGA AGA CCA TGG TAC ATC CAA 772
Asn Lys Ile Asp Leu Tyr Asp Val Arg Arg Arg Pro Trp Tyr Ile Gln
235 240 245

GGA GCT GCA TCT CCT AAA GAC ATG CTT ATT CTG GTG GAT GTG AGT GGA 820
Gly Ala Ala Ser Pro Lys Asp Met Leu Ile Leu Val Asp Val Ser Gly
250 255 260

AGT GTT AGT GGA TTG ACA CTT AAA CTG ATC CGA ACA TCT GTC TCC GAA 868
Ser Val Ser Gly Leu Thr Leu Lys Leu Ile Arg Thr Ser Val Ser Glu
265 270 275

ATG TTA GAA ACC CTC TCA GAT GAT GAT TTC GTG AAT GTA GCT TCA TTT 916
Met Leu Glu Thr Leu Ser Asp Asp Asp Phe Val Asn Val Ala Ser Phe
280 285 290

AAC AGC AAT GCT CAG GAT GTA AGC TGT TTT CAG CAC CTT GTC CAA GCA 964
Asn Ser Asn Ala Gln Asp Val Ser Cys Phe Gln His Leu Val Gln Ala
295 300 305 310

AAT GTA AGA AAT AAA AAA GTG TTG AAA GAC GCG GTG AAT AAT ATC ACA 1012
Asn Val Arg Asn Lys Lys Val Leu Lys Asp Ala Val Asn Asn Ile Thr
315 320 325

GCC AAA GGA ATT ACA GAT TAT AAG AAG GGC TTT AGT TTT GCT TTT GAA 1060

-continued

| | | | | | | | | | | | | | | | | |
|---|---|---|---|---|---|---|---|---|---|---|---|---|---|---|---|---|
| Ala | Lys | Gly | Ile | Thr | Asp | Tyr | Lys | Lys | Gly | Phe | Ser | Phe | Ala | Phe | Glu | |
| | | | 330 | | | | | 335 | | | | | 340 | | | |
| CAG | CTG | CTT | AAT | TAT | AAT | GTT | TCC | AGA | GCA | AAC | TGC | AAT | AAG | ATT | ATT | 1108 |
| Gln | Leu | Leu | Asn | Tyr | Asn | Val | Ser | Arg | Ala | Asn | Cys | Asn | Lys | Ile | Ile | |
| | | 345 | | | | | 350 | | | | | 355 | | | | |
| ATG | CTA | TTC | ACG | GAT | GGA | GGA | GAA | GAG | AGA | GCC | CAG | GAG | ATA | TTT | AAC | 1156 |
| Met | Leu | Phe | Thr | Asp | Gly | Gly | Glu | Glu | Arg | Ala | Gln | Glu | Ile | Phe | Asn | |
| | 360 | | | | | 365 | | | | | 370 | | | | | |
| AAA | TAC | AAT | AAA | GAT | AAA | AAA | GTA | CGT | GTA | TTC | AGG | TTT | TCA | GTT | GGT | 1204 |
| Lys | Tyr | Asn | Lys | Asp | Lys | Lys | Val | Arg | Val | Phe | Arg | Phe | Ser | Val | Gly | |
| 375 | | | | | 380 | | | | | 385 | | | | | 390 | |
| CAA | CAC | AAT | TAT | GAG | AGA | GGA | CCT | ATT | CAG | TGG | ATG | GCC | TGT | GAA | AAC | 1252 |
| Gln | His | Asn | Tyr | Glu | Arg | Gly | Pro | Ile | Gln | Trp | Met | Ala | Cys | Glu | Asn | |
| | | | | 395 | | | | | 400 | | | | | 405 | | |
| AAA | GGT | TAT | TAT | TAT | GAA | ATT | CCT | TCC | ATT | GGT | GCA | ATA | AGA | ATC | AAT | 1300 |
| Lys | Gly | Tyr | Tyr | Tyr | Glu | Ile | Pro | Ser | Ile | Gly | Ala | Ile | Arg | Ile | Asn | |
| | | | 410 | | | | | 415 | | | | | 420 | | | |
| ACT | CAG | GAA | TAT | TTG | GAT | GTT | TTG | GGA | AGA | CCA | ATG | GTT | TTA | GCA | GGA | 1348 |
| Thr | Gln | Glu | Tyr | Leu | Asp | Val | Leu | Gly | Arg | Pro | Met | Val | Leu | Ala | Gly | |
| | | 425 | | | | | 430 | | | | | 435 | | | | |
| GAC | AAA | GCT | AAG | CAA | GTC | CAA | TGG | ACA | AAT | GTG | TAC | CTG | GAT | GCA | TTG | 1396 |
| Asp | Lys | Ala | Lys | Gln | Val | Gln | Trp | Thr | Asn | Val | Tyr | Leu | Asp | Ala | Leu | |
| | 440 | | | | | 445 | | | | | 450 | | | | | |
| GAA | CTG | GGA | CTT | GTC | ATT | ACT | GGA | ACT | CTT | CCG | GTC | TTC | AAC | ATA | ACC | 1444 |
| Glu | Leu | Gly | Leu | Val | Ile | Thr | Gly | Thr | Leu | Pro | Val | Phe | Asn | Ile | Thr | |
| 455 | | | | | 460 | | | | | 465 | | | | | 470 | |
| GGC | CAA | TTT | GAA | AAT | AAG | ACA | AAC | TTA | AAG | AAC | CAG | CTG | ATT | CTT | GGT | 1492 |
| Gly | Gln | Phe | Glu | Asn | Lys | Thr | Asn | Leu | Lys | Asn | Gln | Leu | Ile | Leu | Gly | |
| | | | | 475 | | | | | 480 | | | | | 485 | | |
| GTG | ATG | GGA | GTA | GAT | GTG | TCT | TTG | GAA | GAT | ATT | AAA | AGA | CTG | ACA | CCA | 1540 |
| Val | Met | Gly | Val | Asp | Val | Ser | Leu | Glu | Asp | Ile | Lys | Arg | Leu | Thr | Pro | |
| | | | 490 | | | | | 495 | | | | | 500 | | | |
| CGT | TTT | ACA | CTG | TGC | CCC | AAT | GGG | TAT | TAC | TTT | GCA | ATC | GAT | CCT | AAT | 1588 |
| Arg | Phe | Thr | Leu | Cys | Pro | Asn | Gly | Tyr | Tyr | Phe | Ala | Ile | Asp | Pro | Asn | |
| | | 505 | | | | | 510 | | | | | 515 | | | | |
| GGT | TAT | GTT | TTA | TTA | CAT | CCA | AAT | CTT | CAG | CCA | AAG | AAC | CCC | AAA | TCT | 1636 |
| Gly | Tyr | Val | Leu | Leu | His | Pro | Asn | Leu | Gln | Pro | Lys | Asn | Pro | Lys | Ser | |
| | 520 | | | | | 525 | | | | | 530 | | | | | |
| CAG | GAG | CCA | GTA | ACA | TTG | GAT | TTC | CTT | GAT | GCA | GAG | TTA | GAG | AAT | GAT | 1684 |
| Gln | Glu | Pro | Val | Thr | Leu | Asp | Phe | Leu | Asp | Ala | Glu | Leu | Glu | Asn | Asp | |
| 535 | | | | | 540 | | | | | 545 | | | | | 550 | |
| ATT | AAA | GTG | GAG | ATT | CGA | AAT | AAG | ATG | ATT | GAT | GGG | GAA | AGT | GGA | GAA | 1732 |
| Ile | Lys | Val | Glu | Ile | Arg | Asn | Lys | Met | Ile | Asp | Gly | Glu | Ser | Gly | Glu | |
| | | | | 555 | | | | | 560 | | | | | 565 | | |
| AAA | ACA | TTC | AGA | ACT | CTG | GTT | AAA | TCT | CAA | GAT | GAG | AGA | TAT | ATT | GAC | 1780 |
| Lys | Thr | Phe | Arg | Thr | Leu | Val | Lys | Ser | Gln | Asp | Glu | Arg | Tyr | Ile | Asp | |
| | | | 570 | | | | | 575 | | | | | 580 | | | |
| AAA | GGA | AAC | AGG | ACA | TAC | ACA | TGG | ACA | CCT | GTC | AAT | GGC | ACA | GAT | TAC | 1828 |
| Lys | Gly | Asn | Arg | Thr | Tyr | Thr | Trp | Thr | Pro | Val | Asn | Gly | Thr | Asp | Tyr | |
| | | 585 | | | | | 590 | | | | | 595 | | | | |
| AGT | TTG | GCC | TTG | GTA | TTA | CCA | ACC | TAC | AGT | TTT | TAC | TAT | ATA | AAA | GCC | 1876 |
| Ser | Leu | Ala | Leu | Val | Leu | Pro | Thr | Tyr | Ser | Phe | Tyr | Tyr | Ile | Lys | Ala | |
| | 600 | | | | | 605 | | | | | 610 | | | | | |
| AAA | CTA | GAA | GAG | ACA | ATA | ACT | CAG | GCC | AGA | TCA | AAA | AAG | GGC | AAA | ATG | 1924 |
| Lys | Leu | Glu | Glu | Thr | Ile | Thr | Gln | Ala | Arg | Ser | Lys | Lys | Gly | Lys | Met | |
| 615 | | | | | 620 | | | | | 625 | | | | | 630 | |
| AAG | GAT | TCG | GAA | ACC | CTG | AAG | CCA | GAT | AAT | TTT | GAA | GAA | TCT | GGC | TAT | 1972 |
| Lys | Asp | Ser | Glu | Thr | Leu | Lys | Pro | Asp | Asn | Phe | Glu | Glu | Ser | Gly | Tyr | |
| | | | | 635 | | | | | 640 | | | | | 645 | | |
| ACA | TTC | ATA | GCA | CCA | AGA | GAT | TAC | TGC | AAT | GAC | CTG | AAA | ATA | TCG | GAT | 2020 |

-continued

Thr Phe Ile Ala Pro Arg Asp Tyr Cys Asn Asp Leu Lys Ile Ser Asp
650 655 660

AAT AAC ACT GAA TTT CTT TTA AAT TTC AAC GAG TTT ATT GAT AGA AAA 2068
Asn Asn Thr Glu Phe Leu Leu Asn Phe Asn Glu Phe Ile Asp Arg Lys
665 670 675

ACT CCA AAC AAC CCA TCA TGT AAC GCG GAT TTG ATT AAT AGA GTC TTG 2116
Thr Pro Asn Asn Pro Ser Cys Asn Ala Asp Leu Ile Asn Arg Val Leu
680 685 690

CTT GAT GCA GGC TTT ACA AAT GAA CTT GTC CAA AAT TAC TGG AGT AAG 2164
Leu Asp Ala Gly Phe Thr Asn Glu Leu Val Gln Asn Tyr Trp Ser Lys
695 700 705 710

CAG AAA AAT ATC AAG GGA GTG AAA GCA CGA TTT GTT GTG ACT GAT GGT 2212
Gln Lys Asn Ile Lys Gly Val Lys Ala Arg Phe Val Val Thr Asp Gly
715 720 725

GGG ATT ACC AGA GTT TAT CCC AAA GAG GCT GGA GAA AAT TGG CAA GAA 2260
Gly Ile Thr Arg Val Tyr Pro Lys Glu Ala Gly Glu Asn Trp Gln Glu
730 735 740

AAC CCA GAG ACA TAT GAG GAC AGC TTC TAT AAA AGG AGC CTA GAT AAT 2308
Asn Pro Glu Thr Tyr Glu Asp Ser Phe Tyr Lys Arg Ser Leu Asp Asn
745 750 755

GAT AAC TAT GTT TTC ACT GCT CCC TAC TTT AAC AAA AGT GGA CCT GGT 2356
Asp Asn Tyr Val Phe Thr Ala Pro Tyr Phe Asn Lys Ser Gly Pro Gly
760 765 770

GCC TAT GAA TCG GGC ATT ATG GTA AGC AAA GCT GTA GAA ATA TAT ATT 2404
Ala Tyr Glu Ser Gly Ile Met Val Ser Lys Ala Val Glu Ile Tyr Ile
775 780 785 790

CAA GGG AAA CTT CTT AAA CCT GCA GTT GTT GGA ATT AAA ATT GAT GTA 2452
Gln Gly Lys Leu Leu Lys Pro Ala Val Val Gly Ile Lys Ile Asp Val
795 800 805

AAT TCC TGG ATA GAG AAT TTC ACC AAA ACC TCA ATC AGA GAT CCG TGT 2500
Asn Ser Trp Ile Glu Asn Phe Thr Lys Thr Ser Ile Arg Asp Pro Cys
810 815 820

GCT GGT CCA GTT TGT GAC TGC AAA AGA AAC AGT GAC GTA ATG GAT TGT 2548
Ala Gly Pro Val Cys Asp Cys Lys Arg Asn Ser Asp Val Met Asp Cys
825 830 835

GTG ATT CTG GAT GAT GGT GGG TTT CTT CTG ATG GCA AAT CAT GAT GAT 2596
Val Ile Leu Asp Asp Gly Gly Phe Leu Leu Met Ala Asn His Asp Asp
840 845 850

TAT ACT AAT CAG ATT GGA AGA TTT TTT GGA GAG ATT GAT CCC AGC TTG 2644
Tyr Thr Asn Gln Ile Gly Arg Phe Phe Gly Glu Ile Asp Pro Ser Leu
855 860 865 870

ATG AGA CAC CTG GTT AAT ATA TCA GTT TAT GCT TTT AAC AAA TCT TAT 2692
Met Arg His Leu Val Asn Ile Ser Val Tyr Ala Phe Asn Lys Ser Tyr
875 880 885

GAT TAT CAG TCA GTA TGT GAG CCC GGT GCT GCA CCA AAA CAA GGA GCA 2740
Asp Tyr Gln Ser Val Cys Glu Pro Gly Ala Ala Pro Lys Gln Gly Ala
890 895 900

GGA CAT CGC TCA GCA TAT GTG CCA TCA GTA GCA GAC ATA TTA CAA ATT 2788
Gly His Arg Ser Ala Tyr Val Pro Ser Val Ala Asp Ile Leu Gln Ile
905 910 915

GGC TGG TGG GCC ACT GCT GCT GCC TGG TCT ATT CTA CAG CAG TTT CTC 2836
Gly Trp Trp Ala Thr Ala Ala Ala Trp Ser Ile Leu Gln Gln Phe Leu
920 925 930

TTG AGT TTG ACC TTT CCA CGA CTC CTT GAG GCA GTT GAG ATG GAG GAT 2884
Leu Ser Leu Thr Phe Pro Arg Leu Leu Glu Ala Val Glu Met Glu Asp
935 940 945 950

GAT GAC TTC ACG GCC TCC CTG TCC AAG CAG AGC TGC ATT ACT GAA CAA 2932
Asp Asp Phe Thr Ala Ser Leu Ser Lys Gln Ser Cys Ile Thr Glu Gln
955 960 965

ACC CAG TAT TTC TTC GAT AAC GAC AGT AAA TCA TTC AGT GGT GTA TTA 2980

-continued

```
Thr Gln Tyr Phe Phe Asp Asn Asp Ser Lys Ser Phe Ser Gly Val Leu
            970                 975                 980

GAC TGT GGA AAC TGT TCC AGA ATC TTT CAT GGA GAA AAG CTT ATG AAC      3028
Asp Cys Gly Asn Cys Ser Arg Ile Phe His Gly Glu Lys Leu Met Asn
        985                 990                 995

ACC AAC TTA ATA TTC ATA ATG GTT GAG AGC AAA GGG ACA TGT CCA TGT      3076
Thr Asn Leu Ile Phe Ile Met Val Glu Ser Lys Gly Thr Cys Pro Cys
    1000                1005                1010

GAC ACA CGA CTG CTC ATA CAA GCG GAG CAG ACT TCT GAC GGT CCA AAT      3124
Asp Thr Arg Leu Leu Ile Gln Ala Glu Gln Thr Ser Asp Gly Pro Asn
1015                1020                1025                1030

CCT TGT GAC ATG GTT AAG CAA CCT AGA TAC CGA AAA GGG CCT GAT GTC      3172
Pro Cys Asp Met Val Lys Gln Pro Arg Tyr Arg Lys Gly Pro Asp Val
                1035                1040                1045

TGC TTT GAT AAC AAT GTC TTG GAG GAT TAT ACT GAC TGT GGT GGT GTT      3220
Cys Phe Asp Asn Asn Val Leu Glu Asp Tyr Thr Asp Cys Gly Gly Val
            1050                1055                1060

TCT GGA TTA AAT CCC TCC CTG TGG TAT ATC ATT GGA ATC CAG TTT CTA      3268
Ser Gly Leu Asn Pro Ser Leu Trp Tyr Ile Ile Gly Ile Gln Phe Leu
        1065                1070                1075

CTA CTT TGG CTG GTA TCT GGC AGC ACA CAC CGG CTG TTA TGACCTTCTA       3317
Leu Leu Trp Leu Val Ser Gly Ser Thr His Arg Leu Leu
    1080                1085                1090

AAAACCAAAT CTGCATAGTT AAACTCCAGA CCCTGCCAAA ACATGAGCCC TGCCCTCAAT    3377

TACAGTAACG TAGGGTCAGC TATAAAATCA GACAAACATT AGCTGGGCCT GTTCCATGGC    3437

ATAACACTAA GGCGCAGACT CCTAAGGCAC CCACTGGCTG CATGTCAGGG TGTCAGATCC    3497

TTAAACGTGT GTGAATGCTG CATCATCTAT GTGTAACATC AAAGCAAAAT CCTATACGTG    3557

TCCTCTATTG GAAAATTTGG GCGTTTGTTG TTGCATTGTT GGT                      3600
```

( 2 ) INFORMATION FOR SEQ ID NO:12:

( i ) SEQUENCE CHARACTERISTICS:
( A ) LENGTH: 323 base pairs
( B ) TYPE: nucleic acid
( C ) STRANDEDNESS: double
( D ) TOPOLOGY: linear ( i i ) MOLECULE TYPE: DNA (genomic)

( x i ) SEQUENCE DESCRIPTION: SEQ ID NO:12:

```
CCCCCTGCCA GTGGCCAAAC AGAAGCAGAA GTCGGGTAAT GAAATGACTA ACTTAGCCTT      60

TGAACTAGAC CCCCTAGAGT TAGAGGAGGA AGAGGCTGAG CTTGGTGAGC AGAGTGGCTC     120

TGCCAAGACT AGTGTTAGCA GTGTCACCAC CCCGCCACCC CATGGCAAAC GCATCCCCTT     180

CTTTAAGAAG ACAGAGCATG TGCCCCCCTA TGACGTGGTG CCTTCCATGA GGCCCATCAT     240

CCTGGTGGGA CCGTCGCTCA AGGGCTACGA GGTTACAGAC ATGATGCAGA AAGCTTTATT     300

TGACTTCTTG AAGCATCGGT TTG                                            323
```

( 2 ) INFORMATION FOR SEQ ID NO:13:

( i ) SEQUENCE CHARACTERISTICS:
( A ) LENGTH: 57 base pairs
( B ) TYPE: nucleic acid
( C ) STRANDEDNESS: double
( D ) TOPOLOGY: linear ( i i ) MOLECULE TYPE: DNA (genomic)

( x i ) SEQUENCE DESCRIPTION: SEQ ID NO:13:

```
CCTATTGGTG TAGGTATACC AACAATTAAT TTAAGAAAAA GGAGACCCAA TATCCAG        57
```

( 2 ) INFORMATION FOR SEQ ID NO:14:

( i ) SEQUENCE CHARACTERISTICS:
( A ) LENGTH: 180 base pairs
( B ) TYPE: nucleic acid
( C ) STRANDEDNESS: double
( D ) TOPOLOGY: linear ( i i ) MOLECULE TYPE: DNA (genomic)

( i x ) FEATURE:
( A ) NAME/KEY: CDS
( B ) LOCATION: 1..132

( x i ) SEQUENCE DESCRIPTION: SEQ ID NO:14:

```
TGG TCC TTT GCC TGC GCC TGT GCC GCC TTC ATC CTC CTC TTT CTC GGC      48
Trp Ser Phe Ala Cys Ala Cys Ala Ala Phe Ile Leu Leu Phe Leu Gly
 1               5                  10                  15

GGT CTC GCC CTC CTG CTG TTC TCC CTG CCT CGA ATG CCC CGG AAC CCA      96
Gly Leu Ala Leu Leu Leu Phe Ser Leu Pro Arg Met Pro Arg Asn Pro
            20                  25                  30

TGG GAG TCC TGC ATG GAT GCT GAG CCC GAG CAC TAACCCTCCT GCGGCCCTAG   149
Trp Glu Ser Cys Met Asp Ala Glu Pro Glu His
        35                  40

CGACCCTCAG GCTTCTTCCC AGGAAGCGGG G                                  180
```

( 2 ) INFORMATION FOR SEQ ID NO:15:

( i ) SEQUENCE CHARACTERISTICS:
( A ) LENGTH: 22 base pairs
( B ) TYPE: nucleic acid
( C ) STRANDEDNESS: single
( D ) TOPOLOGY: linear ( i i ) MOLECULE TYPE: Other nucleic acid;
( A ) DESCRIPTION: Oligonucleotide ( x i ) SEQUENCE DESCRIPTION: SEQ ID NO:15:

```
AATTCGGTAC GTACACTCGA GC                                            22
```

( 2 ) INFORMATION FOR SEQ ID NO:16:

( i ) SEQUENCE CHARACTERISTICS:
( A ) LENGTH: 18 base pairs
( B ) TYPE: nucleic acid
( C ) STRANDEDNESS: single
( D ) TOPOLOGY: linear ( i i ) MOLECULE TYPE: Other nucleic acid;
( A ) DESCRIPTION: Oligonucleotide ( x i ) SEQUENCE DESCRIPTION: SEQ ID NO:16:

```
GCTCGAGTGT ACGTACCG                                                 18
```

( 2 ) INFORMATION FOR SEQ ID NO:17:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear ( i i ) MOLECULE TYPE: Other nucleic acid;
( A ) DESCRIPTION: Oligonucleotide ( x i ) SEQUENCE DESCRIPTION: SEQ ID NO:17:

```
CCATGGTACC TTCGTTGACG                                               20
```

( 2 ) INFORMATION FOR SEQ ID NO:18:

( i ) SEQUENCE CHARACTERISTICS:
( A ) LENGTH: 24 base pairs
( B ) TYPE: nucleic acid
( C ) STRANDEDNESS: single
( D ) TOPOLOGY: linear ( i i ) MOLECULE TYPE: Other nucleic acid;
( A ) DESCRIPTION: Oligonucleotide ( x i ) SEQUENCE DESCRIPTION: SEQ ID NO:18:

AATTCGTCAA CGAAGGTACC ATGG 24

( 2 ) INFORMATION FOR SEQ ID NO:19:

( i ) SEQUENCE CHARACTERISTICS:
( A ) LENGTH: 1702 base pairs
( B ) TYPE: nucleic acid
( C ) STRANDEDNESS: double
( D ) TOPOLOGY: linear ( i i ) MOLECULE TYPE: Genomic DNA ( i i i ) HYPOTHETICAL: NO ( i v ) ANTI-SENSE: NO ( v ) FRAGMENT TYPE:

( v i ) ORIGINAL SOURCE:

( i x ) FEATURE:
( A ) NAME/KEY: Coding Sequence
( B ) LOCATION: 1...1590
( D ) OTHER INFORMATION:
( A ) NAME/KEY: 3'UTR
( B ) LOCATION: 1591...1702
( D ) OTHER INFORMATION:

( x i ) SEQUENCE DESCRIPTION: SEQ ID NO:19:

```
ATG GTC CAG AAG ACC AGC ATG TCC CGG GGC CCT TAC CCA CCC TCC CAG     48
Met Val Gln Lys Thr Ser Met Ser Arg Gly Pro Tyr Pro Pro Ser Gln
  1               5                  10                  15

GAG ATC CCC ATG GAG GTC TTC GAC CCC AGC CCG CAG GGC AAA TAC AGC     96
Glu Ile Pro Met Glu Val Phe Asp Pro Ser Pro Gln Gly Lys Tyr Ser
             20                  25                  30

AAG AGG AAA GGG CGA TTC AAA CGG TCA GAT GGG AGC ACG TCC TCG GAT    144
Lys Arg Lys Gly Arg Phe Lys Arg Ser Asp Gly Ser Thr Ser Ser Asp
         35                  40                  45

ACC ACA TCC AAC AGC TTT GTC CGC CAG GGC TCA GCG GAG TCC TAC ACC    192
Thr Thr Ser Asn Ser Phe Val Arg Gln Gly Ser Ala Glu Ser Tyr Thr
     50                  55                  60

AGC CGT CCA TCA GAC TCT GAT GTA TCT CTG GAG GAG GAC CGG GAA GCC    240
Ser Arg Pro Ser Asp Ser Asp Val Ser Leu Glu Glu Asp Arg Glu Ala
 65                  70                  75                  80

TTA AGG AAG GAA GCA GAG CGC CAG GCA TTA GCG CAG CTC GAG AAG GCC    288
Leu Arg Lys Glu Ala Glu Arg Gln Ala Leu Ala Gln Leu Glu Lys Ala
                 85                  90                  95

AAG ACC AAG CCA GTG GCA TTT GCT GTG CGG ACA AAT GTT GGC TAC AAT    336
Lys Thr Lys Pro Val Ala Phe Ala Val Arg Thr Asn Val Gly Tyr Asn
            100                 105                 110

CCG TCT CCA GGG GAT GAG GTG CCT GTG CAG GGA GTG GCC ATC ACC TTC    384
Pro Ser Pro Gly Asp Glu Val Pro Val Gln Gly Val Ala Ile Thr Phe
        115                 120                 125

GAG CCC AAA GAC TTC CTG CAC ATC AAG GAG AAA TAC AAT AAT GAC TGG    432
Glu Pro Lys Asp Phe Leu His Ile Lys Glu Lys Tyr Asn Asn Asp Trp
    130                 135                 140
```

-continued

TGG ATC GGG CGG CTG GTG AAG GAG GGC TGT GAG GTT GGC TTC ATT CCC 480
Trp Ile Gly Arg Leu Val Lys Glu Gly Cys Glu Val Gly Phe Ile Pro
145 150 155 160

AGC CCC GTC AAA CTG GAC AGC CTT CGC CTG CTG CAG GAA CAG AAG CTG 528
Ser Pro Val Lys Leu Asp Ser Leu Arg Leu Leu Gln Glu Gln Lys Leu
165 170 175

CGC CAG AAC CGC CTC GGC TCC AGC AAA TCA GGC GAT AAC TCC AGT TCC 576
Arg Gln Asn Arg Leu Gly Ser Ser Lys Ser Gly Asp Asn Ser Ser Ser
180 185 190

AGT CTG GGA GAT GTG GTG ACT GGC ACC CGC CGC CCC ACC CCC CTG CCA 624
Ser Leu Gly Asp Val Val Thr Gly Thr Arg Arg Pro Thr Pro Leu Pro
195 200 205

GTG GCC AAA CAG AAG CAG AAG TCG GGT AAT GAA ATG ACT AAC TTA GCC 672
Val Ala Lys Gln Lys Gln Lys Ser Gly Asn Glu Met Thr Asn Leu Ala
210 215 220

TTT GAA CTA GAC CCC CTA GAG TTA GAG GAG GAA GAG GCT GAG CTT GGT 720
Phe Glu Leu Asp Pro Leu Glu Leu Glu Glu Glu Glu Ala Glu Leu Gly
225 230 235 240

GAG CAG AGT GGC TCT GCC AAG ACT AGT GTT AGC AGT GTC ACC ACC CCG 768
Glu Gln Ser Gly Ser Ala Lys Thr Ser Val Ser Ser Val Thr Thr Pro
245 250 255

CCA CCC CAT GGC AAA CGC ATC CCC TTC TTT AAG AAG ACA GAG CAT GTG 816
Pro Pro His Gly Lys Arg Ile Pro Phe Phe Lys Lys Thr Glu His Val
260 265 270

CCC CCC TAT GAC GTG GTG CCT TCC ATG AGG CCC ATC ATC CTG GTG GGA 864
Pro Pro Tyr Asp Val Val Pro Ser Met Arg Pro Ile Ile Leu Val Gly
275 280 285

CCG TCG CTC AAG GGC TAC GAG GTT ACA GAC ATG ATG CAG AAA GCT TTA 912
Pro Ser Leu Lys Gly Tyr Glu Val Thr Asp Met Met Gln Lys Ala Leu
290 295 300

TTT GAC TTC TTG AAG CAT CGG TTT GAT GGC AGG ATC TCC ATC ACT CGT 960
Phe Asp Phe Leu Lys His Arg Phe Asp Gly Arg Ile Ser Ile Thr Arg
305 310 315 320

GTG ACG GCA GAT ATT TCC CTG GCT AAG CGC TCA GTT CTC AAC AAC CCC 1008
Val Thr Ala Asp Ile Ser Leu Ala Lys Arg Ser Val Leu Asn Asn Pro
325 330 335

AGC AAA CAC ATC ATC ATT GAG CGC TCC AAC ACA CGC TCC AGC CTG GCT 1056
Ser Lys His Ile Ile Ile Glu Arg Ser Asn Thr Arg Ser Ser Leu Ala
340 345 350

GAG GTG CAG AGT GAA ATC GAG CGA ATC TTC GAG CTG GCC CGG ACC CTT 1104
Glu Val Gln Ser Glu Ile Glu Arg Ile Phe Glu Leu Ala Arg Thr Leu
355 360 365

CAG TTG GTC GCT CTG GAT GCT GAC ACC ATC AAT CAC CCA GCC CAG CTG 1152
Gln Leu Val Ala Leu Asp Ala Asp Thr Ile Asn His Pro Ala Gln Leu
370 375 380

TCC AAG ACC TCG CTG GCC CCC ATC ATT GTT TAC ATC AAG ATC ACC TCT 1200
Ser Lys Thr Ser Leu Ala Pro Ile Ile Val Tyr Ile Lys Ile Thr Ser
385 390 395 400

CCC AAG GTA CTT CAA AGG CTC ATC AAG TCC CGA GGA AAG TCT CAG TCC 1248
Pro Lys Val Leu Gln Arg Leu Ile Lys Ser Arg Gly Lys Ser Gln Ser
405 410 415

AAA CAC CTC AAT GTC CAA ATA GCG GCC TCG GAA AAG CTG GCA CAG TGC 1296
Lys His Leu Asn Val Gln Ile Ala Ala Ser Glu Lys Leu Ala Gln Cys
420 425 430

CCC CCT GAA ATG TTT GAC ATC ATC CTG GAT GAG AAC CAA TTG GAG GAT 1344
Pro Pro Glu Met Phe Asp Ile Ile Leu Asp Glu Asn Gln Leu Glu Asp
435 440 445

GCC TGC GAG CAT CTG GCG GAG TAC TTG GAA GCC TAT TGG AAG GCC ACA 1392
Ala Cys Glu His Leu Ala Glu Tyr Leu Glu Ala Tyr Trp Lys Ala Thr
450 455 460

```
CAC CCG CCC AGC AGC ACG CCA CCC AAT CCG CTG CTG AAC CGC ACC ATG     1440
His Pro Pro Ser Ser Thr Pro Pro Asn Pro Leu Leu Asn Arg Thr Met
465                 470                 475                 480

GCT ACC GCA GCC CTG GCT GCC AGC CCT GCC CCT GTC TCC AAC CTC CAG     1488
Ala Thr Ala Ala Leu Ala Ala Ser Pro Ala Pro Val Ser Asn Leu Gln
                485                 490                 495

GTA CAG GTG CTC ACC TCG CTC AGG AGA AAC CTC GGC TTC TGG GGC GGG     1536
Val Gln Val Leu Thr Ser Leu Arg Arg Asn Leu Gly Phe Trp Gly Gly
            500                 505                 510

CTG GAG TCC TCA CAG CGG GGC AGT GTG GTG CCC CAG GAG CAG GAA CAT     1584
Leu Glu Ser Ser Gln Arg Gly Ser Val Val Pro Gln Glu Gln Glu His
        515                 520                 525

GCC ATG TAGTGGGCGC CCTGCCCGTC TTCCCTCCTG CTCTGGGGTC GGAACTGGAG TGC 1643
Ala Met
    530

AGGGAACATG GAGGAGGAAG GGAAGAGCTT TATTTTGTAA AAAAATAAGA TGAGCGGCA    1702
```

(2) INFORMATION FOR SEQ ID NO:20:

(i) SEQUENCE CHARACTERISTICS:
(A) LENGTH: 3657 base pairs
(B) TYPE: nucleic acid
(C) STRANDEDNESS: double
(D) TOPOLOGY: linear (ii) MOLECULE TYPE: Genomic DNA (iii) HYPOTHETICAL: NO (iv) ANTI-SENSE: NO (v) FRAGMENT TYPE:

(vi) ORIGINAL SOURCE:

(ix) FEATURE:
(A) NAME/KEY: Coding Sequence
(B) LOCATION: 35...3364
(D) OTHER INFORMATION: Standard name “alpha2”
(A) NAME/KEY: 5’UTR
(B) LOCATION: 1...34
(D) OTHER INFORMATION:
(A) NAME/KEY: 3’UTR
(B) LOCATION: 3365...3657
(D) OTHER INFORMATION:

(xi) SEQUENCE DESCRIPTION: SEQ ID NO:20:

```
GCGGGGGAGG GGGCATTGAT CTTCGATCGC GAAG ATG GCT GCT GGC TGC CTG CTG    55
                                      Met Ala Ala Gly Cys Leu Leu
                                      1                   5

GCC TTG ACT CTG ACA CTT TTC CAA TCT TTG CTC ATC GGC CCC TCG TCG     103
Ala Leu Thr Leu Thr Leu Phe Gln Ser Leu Leu Ile Gly Pro Ser Ser
        10                  15                  20

GAG GAG CCG TTC CCT TCG GCC GTC ACT ATC AAA TCA TGG GTG GAT AAG     151
Glu Glu Pro Phe Pro Ser Ala Val Thr Ile Lys Ser Trp Val Asp Lys
    25                  30                  35

ATG CAA GAA GAC CTT GTC ACA CTG GCA AAA ACA GCA AGT GGA GTC AAT     199
Met Gln Glu Asp Leu Val Thr Leu Ala Lys Thr Ala Ser Gly Val Asn
40                  45                  50                  55

CAG CTT GTT GAT ATT TAT GAG AAA TAT CAA GAT TTG TAT ACT GTG GAA     247
Gln Leu Val Asp Ile Tyr Glu Lys Tyr Gln Asp Leu Tyr Thr Val Glu
                60                  65                  70

CCA AAT AAT GCA CGC CAG CTG GTA GAA ATT GCA GCC AGG GAT ATT GAG     295
Pro Asn Asn Ala Arg Gln Leu Val Glu Ile Ala Ala Arg Asp Ile Glu
            75                  80                  85

AAA CTT CTG AGC AAC AGA TCT AAA GCC CTG GTG AGC CTG GCA TTG GAA     343
```

-continued

Lys Leu Leu Ser Asn Arg Ser Lys Ala Leu Val Ser Leu Ala Leu Glu
90 95 100

GCG GAG AAA GTT CAA GCA GCT CAC CAG TGG AGA GAA GAT TTT GCA AGC 391
Ala Glu Lys Val Gln Ala Ala His Gln Trp Arg Glu Asp Phe Ala Ser
105 110 115

AAT GAA GTT GTC TAC TAC AAT GCA AAG GAT GAT CTC GAT CCT GAG AAA 439
Asn Glu Val Val Tyr Tyr Asn Ala Lys Asp Asp Leu Asp Pro Glu Lys
120 125 130 135

AAT GAC AGT GAG CCA GGC AGC CAG AGG ATA AAA CCT GTT TTC ATT GAA 487
Asn Asp Ser Glu Pro Gly Ser Gln Arg Ile Lys Pro Val Phe Ile Glu
140 145 150

GAT GCT AAT TTT GGA CGA CAA ATA TCT TAT CAG CAC GCA GCA GTC CAT 535
Asp Ala Asn Phe Gly Arg Gln Ile Ser Tyr Gln His Ala Ala Val His
155 160 165

ATT CCT ACT GAC ATC TAT GAG GGC TCA ACA ATT GTG TTA AAT GAA CTC 583
Ile Pro Thr Asp Ile Tyr Glu Gly Ser Thr Ile Val Leu Asn Glu Leu
170 175 180

AAC TGG ACA AGT GCC TTA GAT GAA GTT TTC AAA AAG AAT CGC GAG GAA 631
Asn Trp Thr Ser Ala Leu Asp Glu Val Phe Lys Lys Asn Arg Glu Glu
185 190 195

GAC CCT TCA TTA TTG TGG CAG GTT TTT GGC AGT GCC ACT GGC CTA GCT 679
Asp Pro Ser Leu Leu Trp Gln Val Phe Gly Ser Ala Thr Gly Leu Ala
200 205 210 215

CGA TAT TAT CCA GCT TCA CCA TGG GTT GAT AAT AGT AGA ACT CCA AAT 727
Arg Tyr Tyr Pro Ala Ser Pro Trp Val Asp Asn Ser Arg Thr Pro Asn
220 225 230

AAG ATT GAC CTT TAT GAT GTA CGC AGA AGA CCA TGG TAC ATC CAA GGA 775
Lys Ile Asp Leu Tyr Asp Val Arg Arg Arg Pro Trp Tyr Ile Gln Gly
235 240 245

GCT GCA TCT CCT AAA GAC ATG CTT ATT CTG GTG GAT GTG AGT GGA AGT 823
Ala Ala Ser Pro Lys Asp Met Leu Ile Leu Val Asp Val Ser Gly Ser
250 255 260

GTT AGT GGA TTG ACA CTT AAA CTG ATC CGA ACA TCT GTC TCC GAA ATG 871
Val Ser Gly Leu Thr Leu Lys Leu Ile Arg Thr Ser Val Ser Glu Met
265 270 275

TTA GAA ACC CTC TCA GAT GAT GAT TTC GTG AAT GTA GCT TCA TTT AAC 919
Leu Glu Thr Leu Ser Asp Asp Asp Phe Val Asn Val Ala Ser Phe Asn
280 285 290 295

AGC AAT GCT CAG GAT GTA AGC TGT TTT CAG CAC CTT GTC CAA GCA AAT 967
Ser Asn Ala Gln Asp Val Ser Cys Phe Gln His Leu Val Gln Ala Asn
300 305 310

GTA AGA AAT AAA AAA GTG TTG AAA GAC GCG GTG AAT AAT ATC ACA GCC 1015
Val Arg Asn Lys Lys Val Leu Lys Asp Ala Val Asn Asn Ile Thr Ala
315 320 325

AAA GGA ATT ACA GAT TAT AAG AAG GGC TTT AGT TTT GCT TTT GAA CAG 1063
Lys Gly Ile Thr Asp Tyr Lys Lys Gly Phe Ser Phe Ala Phe Glu Gln
330 335 340

CTG CTT AAT TAT AAT GTT TCC AGA GCA AAC TGC AAT AAG ATT ATT ATG 1111
Leu Leu Asn Tyr Asn Val Ser Arg Ala Asn Cys Asn Lys Ile Ile Met
345 350 355

CTA TTC ACG GAT GGA GGA GAA GAG AGA GCC CAG GAG ATA TTT AAC AAA 1159
Leu Phe Thr Asp Gly Gly Glu Glu Arg Ala Gln Glu Ile Phe Asn Lys
360 365 370 375

TAC AAT AAA GAT AAA AAA GTA CGT GTA TTC AGG TTT TCA GTT GGT CAA 1207
Tyr Asn Lys Asp Lys Lys Val Arg Val Phe Arg Phe Ser Val Gly Gln
380 385 390

CAC AAT TAT GAG AGA GGA CCT ATT CAG TGG ATG GCC TGT GAA AAC AAA 1255
His Asn Tyr Glu Arg Gly Pro Ile Gln Trp Met Ala Cys Glu Asn Lys
395 400 405

GGT TAT TAT TAT GAA ATT CCT TCC ATT GGT GCA ATA AGA ATC AAT ACT 1303

-continued

Gly Tyr Tyr Tyr Glu Ile Pro Ser Ile Gly Ala Ile Arg Ile Asn Thr
410 415 420

CAG GAA TAT TTG GAT GTT TTG GGA AGA CCA ATG GTT TTA GCA GGA GAC 1351
Gln Glu Tyr Leu Asp Val Leu Gly Arg Pro Met Val Leu Ala Gly Asp
425 430 435

AAA GCT AAG CAA GTC CAA TGG ACA AAT GTG TAC CTG GAT GCA TTG GAA 1399
Lys Ala Lys Gln Val Gln Trp Thr Asn Val Tyr Leu Asp Ala Leu Glu
440 445 450 455

CTG GGA CTT GTC ATT ACT GGA ACT CTT CCG GTC TTC AAC ATA ACC GGC 1447
Leu Gly Leu Val Ile Thr Gly Thr Leu Pro Val Phe Asn Ile Thr Gly
460 465 470

CAA TTT GAA AAT AAG ACA AAC TTA AAG AAC CAG CTG ATT CTT GGT GTG 1495
Gln Phe Glu Asn Lys Thr Asn Leu Lys Asn Gln Leu Ile Leu Gly Val
475 480 485

ATG GGA GTA GAT GTG TCT TTG GAA GAT ATT AAA AGA CTG ACA CCA CGT 1543
Met Gly Val Asp Val Ser Leu Glu Asp Ile Lys Arg Leu Thr Pro Arg
490 495 500

TTT ACA CTG TGC CCC AAT GGG TAT TAC TTT GCA ATC GAT CCT AAT GGT 1591
Phe Thr Leu Cys Pro Asn Gly Tyr Tyr Phe Ala Ile Asp Pro Asn Gly
505 510 515

TAT GTT TTA TTA CAT CCA AAT CTT CAG CCA AAG CCT ATT GGT GTA GGT 1639
Tyr Val Leu Leu His Pro Asn Leu Gln Pro Lys Pro Ile Gly Val Gly
520 525 530 535

ATA CCA ACA ATT AAT TTA AGA AAA AGG AGA CCC AAT ATC CAG AAC CCC 1687
Ile Pro Thr Ile Asn Leu Arg Lys Arg Arg Pro Asn Ile Gln Asn Pro
540 545 550

AAA TCT CAG GAG CCA GTA ACA TTG GAT TTC CTT GAT GCA GAG TTA GAG 1735
Lys Ser Gln Glu Pro Val Thr Leu Asp Phe Leu Asp Ala Glu Leu Glu
555 560 565

AAT GAT ATT AAA GTG GAG ATT CGA AAT AAG ATG ATT GAT GGG GAA AGT 1783
Asn Asp Ile Lys Val Glu Ile Arg Asn Lys Met Ile Asp Gly Glu Ser
570 575 580

GGA GAA AAA ACA TTC AGA ACT CTG GTT AAA TCT CAA GAT GAG AGA TAT 1831
Gly Glu Lys Thr Phe Arg Thr Leu Val Lys Ser Gln Asp Glu Arg Tyr
585 590 595

ATT GAC AAA GGA AAC AGG ACA TAC ACA TGG ACA CCT GTC AAT GGC ACA 1879
Ile Asp Lys Gly Asn Arg Thr Tyr Thr Trp Thr Pro Val Asn Gly Thr
600 605 610 615

GAT TAC AGT TTG GCC TTG GTA TTA CCA ACC TAC AGT TTT TAC TAT ATA 1927
Asp Tyr Ser Leu Ala Leu Val Leu Pro Thr Tyr Ser Phe Tyr Tyr Ile
620 625 630

AAA GCC AAA CTA GAA GAG ACA ATA ACT CAG GCC AGA TCA AAA AAG GGC 1975
Lys Ala Lys Leu Glu Glu Thr Ile Thr Gln Ala Arg Ser Lys Lys Gly
635 640 645

AAA ATG AAG GAT TCG GAA ACC CTG AAG CCA GAT AAT TTT GAA GAA TCT 2023
Lys Met Lys Asp Ser Glu Thr Leu Lys Pro Asp Asn Phe Glu Glu Ser
650 655 660

GGC TAT ACA TTC ATA GCA CCA AGA GAT TAC TGC AAT GAC CTG AAA ATA 2071
Gly Tyr Thr Phe Ile Ala Pro Arg Asp Tyr Cys Asn Asp Leu Lys Ile
665 670 675

TCG GAT AAT AAC ACT GAA TTT CTT TTA AAT TTC AAC GAG TTT ATT GAT 2119
Ser Asp Asn Asn Thr Glu Phe Leu Leu Asn Phe Asn Glu Phe Ile Asp
680 685 690 695

AGA AAA ACT CCA AAC AAC CCA TCA TGT AAC GCG GAT TTG ATT AAT AGA 2167
Arg Lys Thr Pro Asn Asn Pro Ser Cys Asn Ala Asp Leu Ile Asn Arg
700 705 710

GTC TTG CTT GAT GCA GGC TTT ACA AAT GAA CTT GTC CAA AAT TAC TGG 2215
Val Leu Leu Asp Ala Gly Phe Thr Asn Glu Leu Val Gln Asn Tyr Trp
715 720 725

AGT AAG CAG AAA AAT ATC AAG GGA GTG AAA GCA CGA TTT GTT GTG ACT 2263

-continued

```
Ser Lys Gln Lys Asn Ile Lys Gly Val Lys Ala Arg Phe Val Val Thr
        730                 735                 740

GAT GGT GGG ATT ACC AGA GTT TAT CCC AAA GAG GCT GGA GAA AAT TGG     2311
Asp Gly Gly Ile Thr Arg Val Tyr Pro Lys Glu Ala Gly Glu Asn Trp
    745                 750                 755

CAA GAA AAC CCA GAG ACA TAT GAG GAC AGC TTC TAT AAA AGG AGC CTA     2359
Gln Glu Asn Pro Glu Thr Tyr Glu Asp Ser Phe Tyr Lys Arg Ser Leu
760                 765                 770                 775

GAT AAT GAT AAC TAT GTT TTC ACT GCT CCC TAC TTT AAC AAA AGT GGA     2407
Asp Asn Asp Asn Tyr Val Phe Thr Ala Pro Tyr Phe Asn Lys Ser Gly
                780                 785                 790

CCT GGT GCC TAT GAA TCG GGC ATT ATG GTA AGC AAA GCT GTA GAA ATA     2455
Pro Gly Ala Tyr Glu Ser Gly Ile Met Val Ser Lys Ala Val Glu Ile
            795                 800                 805

TAT ATT CAA GGG AAA CTT CTT AAA CCT GCA GTT GTT GGA ATT AAA ATT     2503
Tyr Ile Gln Gly Lys Leu Leu Lys Pro Ala Val Val Gly Ile Lys Ile
        810                 815                 820

GAT GTA AAT TCC TGG ATA GAG AAT TTC ACC AAA ACC TCA ATC AGA GAT     2551
Asp Val Asn Ser Trp Ile Glu Asn Phe Thr Lys Thr Ser Ile Arg Asp
    825                 830                 835

CCG TGT GCT GGT CCA GTT TGT GAC TGC AAA AGA AAC AGT GAC GTA ATG     2599
Pro Cys Ala Gly Pro Val Cys Asp Cys Lys Arg Asn Ser Asp Val Met
840                 845                 850                 855

GAT TGT GTG ATT CTG GAT GAT GGT GGG TTT CTT CTG ATG GCA AAT CAT     2647
Asp Cys Val Ile Leu Asp Asp Gly Gly Phe Leu Leu Met Ala Asn His
                860                 865                 870

GAT GAT TAT ACT AAT CAG ATT GGA AGA TTT TTT GGA GAG ATT GAT CCC     2695
Asp Asp Tyr Thr Asn Gln Ile Gly Arg Phe Phe Gly Glu Ile Asp Pro
            875                 880                 885

AGC TTG ATG AGA CAC CTG GTT AAT ATA TCA GTT TAT GCT TTT AAC AAA     2743
Ser Leu Met Arg His Leu Val Asn Ile Ser Val Tyr Ala Phe Asn Lys
        890                 895                 900

TCT TAT GAT TAT CAG TCA GTA TGT GAG CCC GGT GCT GCA CCA AAA CAA     2791
Ser Tyr Asp Tyr Gln Ser Val Cys Glu Pro Gly Ala Ala Pro Lys Gln
    905                 910                 915

GGA GCA GGA CAT CGC TCA GCA TAT GTG CCA TCA GTA GCA GAC ATA TTA     2839
Gly Ala Gly His Arg Ser Ala Tyr Val Pro Ser Val Ala Asp Ile Leu
920                 925                 930                 935

CAA ATT GGC TGG TGG GCC ACT GCT GCT GCC TGG TCT ATT CTA CAG CAG     2887
Gln Ile Gly Trp Trp Ala Thr Ala Ala Ala Trp Ser Ile Leu Gln Gln
                940                 945                 950

TTT CTC TTG AGT TTG ACC TTT CCA CGA CTC CTT GAG GCA GTT GAG ATG     2935
Phe Leu Leu Ser Leu Thr Phe Pro Arg Leu Leu Glu Ala Val Glu Met
            955                 960                 965

GAG GAT GAT GAC TTC ACG GCC TCC CTG TCC AAG CAG AGC TGC ATT ACT     2983
Glu Asp Asp Asp Phe Thr Ala Ser Leu Ser Lys Gln Ser Cys Ile Thr
        970                 975                 980

GAA CAA ACC CAG TAT TTC TTC GAT AAC GAC AGT AAA TCA TTC AGT GGT     3031
Glu Gln Thr Gln Tyr Phe Phe Asp Asn Asp Ser Lys Ser Phe Ser Gly
    985                 990                 995

GTA TTA GAC TGT GGA AAC TGT TCC AGA ATC TTT CAT GGA GAA AAG CTT     3079
Val Leu Asp Cys Gly Asn Cys Ser Arg Ile Phe His Gly Glu Lys Leu
1000                1005                1010                1015

ATG AAC ACC AAC TTA ATA TTC ATA ATG GTT GAG AGC AAA GGG ACA TGT     3127
Met Asn Thr Asn Leu Ile Phe Ile Met Val Glu Ser Lys Gly Thr Cys
                1020                1025                1030

CCA TGT GAC ACA CGA CTG CTC ATA CAA GCG GAG CAG ACT TCT GAC GGT     3175
Pro Cys Asp Thr Arg Leu Leu Ile Gln Ala Glu Gln Thr Ser Asp Gly
            1035                1040                1045

CCA AAT CCT TGT GAC ATG GTT AAG CAA CCT AGA TAC CGA AAA GGG CCT     3223
```

-continued

```
Pro Asn Pro Cys Asp Met Val Lys Gln Pro Arg Tyr Arg Lys Gly Pro
        1050                    1055                    1060

GAT GTC TGC TTT GAT AAC AAT GTC TTG GAG GAT TAT ACT GAC TGT GGT      3271
Asp Val Cys Phe Asp Asn Asn Val Leu Glu Asp Tyr Thr Asp Cys Gly
    1065                    1070                    1075

GGT GTT TCT GGA TTA AAT CCC TCC CTG TGG TAT ATC ATT GGA ATC CAG      3319
Gly Val Ser Gly Leu Asn Pro Ser Leu Trp Tyr Ile Ile Gly Ile Gln
1080                    1085                    1090                    1095

TTT CTA CTA CTT TGG CTG GTA TCT GGC AGC ACA CAC CGG CTG TTA TGACCT   3370
Phe Leu Leu Leu Trp Leu Val Ser Gly Ser Thr His Arg Leu Leu
                1100                    1105                    1110

TCTAAAAACC AAATCTGCAT AGTTAAACTC CAGACCCTGC CAAAACATGA GCCCTGCCCT    3430

CAATTACAGT AACGTAGGGT CAGCTATAAA ATCAGACAAA CATTAGCTGG GCCTGTTCCA    3490

TGGCATAACA CTAAGGCGCA GACTCCTAAG GCACCCACTG GCTGCATGTC AGGGTGTCAG    3550

ATCCTTAAAC GTGTGTGAAT GCTGCATCAT CTATGTGTAA CATCAAAGCA AAATCCTATA    3610

CGTGTCCTCT ATTGGAAAAT TTGGGCGTTT GTTGTTGCAT TGTTGGT                  3657
```

( 2 ) INFORMATION FOR SEQ ID NO:21:

( i ) SEQUENCE CHARACTERISTICS:
( A ) LENGTH: 15 base pairs
( B ) TYPE: nucleic acid
( C ) STRANDEDNESS: double
( D ) TOPOLOGY: linear ( i i ) MOLECULE TYPE: DNA (genomic)

( x i ) SEQUENCE DESCRIPTION: SEQ ID NO:21:

```
AACCCCAAAT CTCAG                                                     15
```

( 2 ) INFORMATION FOR SEQ ID NO:22:

( i ) SEQUENCE CHARACTERISTICS:
( A ) LENGTH: 21 base pairs
( B ) TYPE: nucleic acid
( C ) STRANDEDNESS: double
( D ) TOPOLOGY: linear ( i i ) MOLECULE TYPE: DNA (genomic)

( x i ) SEQUENCE DESCRIPTION: SEQ ID NO:22:

```
CAAAAAAGGG CAAAATGAAG G                                              21
```

( 2 ) INFORMATION FOR SEQ ID NO:23:

( i ) SEQUENCE CHARACTERISTICS:
( A ) LENGTH: 7635 base pairs
( B ) TYPE: nucleic acid
( C ) STRANDEDNESS: double
( D ) TOPOLOGY: linear ( i i ) MOLECULE TYPE: Genomic DNA ( i i i ) HYPOTHETICAL: NO ( i v ) ANTI-SENSE: NO ( v ) FRAGMENT TYPE:

( v i ) ORIGINAL SOURCE:

( i x ) FEATURE:
( A ) NAME/KEY: Coding Sequence
( B ) LOCATION: 511...6996
( D ) OTHER INFORMATION:
( A ) NAME/KEY: 5'UTR
( B ) LOCATION: 1...510

( D ) OTHER INFORMATION:
( A ) NAME/KEY: 3'UTR
( B ) LOCATION: 6994...7635
( D ) OTHER INFORMATION:

( x i ) SEQUENCE DESCRIPTION: SEQ ID NO:23:

GGGCGAGCGC CTCCGTCCCC GGATGTGAGC TCCGGCTGCC CGCGGTCCCG AGCCAGCGGC 60

GCGCGGGCGG CGGCGGCGGG CACCGGGCAC CGCGGCGGGC GGGCAGACGG GCGGGCATGG 120

GGGGAGCGCC GAGCGGCCCC GGCGGCCGGG CCGGCATCAC CGCGGCGTCT CTCCGCTAGA 180

GGAGGGGACA AGCCAGTTCT CCTTTGCAGC AAAAAATTAC ATGTATATAT TATTAAGATA 240

ATATATACAT TGGATTTTAT TTTTTTAAAA AGTTTATTTT GCTCCATTTT TGAAAAAGAG 300

AGAGCTTGGG TGGCGAGCGG TTTTTTTTTA AAATCAATTA TCCTTATTTT CTGTTATTTG 360

TCCCCGTCCC TCCCCACCCC CCTGCTGAAG CGAGAATAAG GGCAGGGACC GCGGCTCCTA 420

CCTCTTGGTG ATCCCCTTCC CCATTCCGCC CCCGCCCCAA CGCCCAGCAC AGTGCCCTGC 480

ACACAGTAGT CGCTCAATAA ATGTTCGTGG ATG ATG ATG ATG ATG ATG ATG AAA 534
Met Met Met Met Met Met Met Lys
1 5

AAA ATG CAG CAT CAA CGG CAG CAG CAA GCG GAC CAC GCG AAC GAG GCA 582
Lys Met Gln His Gln Arg Gln Gln Gln Ala Asp His Ala Asn Glu Ala
10 15 20

AAC TAT GCA AGA GGC ACC AGA CTT CCT CTT TCT GGT GAA GGA CCA ACT 630
Asn Tyr Ala Arg Gly Thr Arg Leu Pro Leu Ser Gly Glu Gly Pro Thr
25 30 35 40

TCT CAG CCG AAT AGC TCC AAG CAA ACT GTC CTG TCT TGG CAA GCT GCA 678
Ser Gln Pro Asn Ser Ser Lys Gln Thr Val Leu Ser Trp Gln Ala Ala
45 50 55

ATC GAT GCT GCT AGA CAG GCC AAG GCT GCC CAA ACT ATG AGC ACC TCT 726
Ile Asp Ala Ala Arg Gln Ala Lys Ala Ala Gln Thr Met Ser Thr Ser
60 65 70

GCA CCC CCA CCT GTA GGA TCT CTC TCC CAA AGA AAA CGT CAG CAA TAC 774
Ala Pro Pro Pro Val Gly Ser Leu Ser Gln Arg Lys Arg Gln Gln Tyr
75 80 85

GCC AAG AGC AAA AAA CAG GGT AAC TCG TCC AAC AGC CGA CCT GCC CGC 822
Ala Lys Ser Lys Lys Gln Gly Asn Ser Ser Asn Ser Arg Pro Ala Arg
90 95 100

GCC CTT TTC TGT TTA TCA CTC AAT AAC CCC ATC CGA AGA GCC TGC ATT 870
Ala Leu Phe Cys Leu Ser Leu Asn Asn Pro Ile Arg Arg Ala Cys Ile
105 110 115 120

AGT ATA GTG GAA TGG AAA CCA TTT GAC ATA TTT ATA TTA TTG GCT ATT 918
Ser Ile Val Glu Trp Lys Pro Phe Asp Ile Phe Ile Leu Leu Ala Ile
125 130 135

TTT GCC AAT TGT GTG GCC TTA GCT ATT TAC ATC CCA TTC CCT GAA GAT 966
Phe Ala Asn Cys Val Ala Leu Ala Ile Tyr Ile Pro Phe Pro Glu Asp
140 145 150

GAT TCT AAT TCA ACA AAT CAT AAC TTG GAA AAA GTA GAA TAT GCC TTC 1014
Asp Ser Asn Ser Thr Asn His Asn Leu Glu Lys Val Glu Tyr Ala Phe
155 160 165

CTG ATT ATT TTT ACA GTC GAG ACA TTT TTG AAG ATT ATA GCG TAT GGA 1062
Leu Ile Ile Phe Thr Val Glu Thr Phe Leu Lys Ile Ile Ala Tyr Gly
170 175 180

TTA TTG CTA CAT CCT AAT GCT TAT GTT AGG AAT GGA TGG AAT TTA CTG 1110
Leu Leu Leu His Pro Asn Ala Tyr Val Arg Asn Gly Trp Asn Leu Leu
185 190 195 200

GAT TTT GTT ATA GTA ATA GTA GGA TTG TTT AGT GTA ATT TTG GAA CAA 1158
Asp Phe Val Ile Val Ile Val Gly Leu Phe Ser Val Ile Leu Glu Gln
205 210 215

TTA ACC AAA GAA ACA GAA GGC GGG AAC CAC TCA AGC GGC AAA TCT GGA 1206

-continued

```
Leu Thr Lys Glu Thr Glu Gly Gly Asn His Ser Ser Gly Lys Ser Gly
            220                 225                 230

GGC TTT GAT GTC AAA GCC CTC CGT GCC TTT CGA GTG TTG CGA CCA CTT     1254
Gly Phe Asp Val Lys Ala Leu Arg Ala Phe Arg Val Leu Arg Pro Leu
        235                 240                 245

CGA CTA GTG TCA GGA GTG CCC AGT TTA CAA GTT GTC CTG AAC TCC ATT     1302
Arg Leu Val Ser Gly Val Pro Ser Leu Gln Val Val Leu Asn Ser Ile
    250                 255                 260

ATA AAA GCC ATG GTT CCC CTC CTT CAC ATA GCC CTT TTG GTA TTA TTT     1350
Ile Lys Ala Met Val Pro Leu Leu His Ile Ala Leu Leu Val Leu Phe
265                 270                 275                 280

GTA ATC ATA ATC TAT GCT ATT ATA GGA TTG GAA CTT TTT ATT GGA AAA     1398
Val Ile Ile Ile Tyr Ala Ile Ile Gly Leu Glu Leu Phe Ile Gly Lys
                285                 290                 295

ATG CAC AAA ACA TGT TTT TTT GCT GAC TCA GAT ATC GTA GCT GAA GAG     1446
Met His Lys Thr Cys Phe Phe Ala Asp Ser Asp Ile Val Ala Glu Glu
            300                 305                 310

GAC CCA GCT CCA TGT GCG TTC TCA GGG AAT GGA CGC CAG TGT ACT GCC     1494
Asp Pro Ala Pro Cys Ala Phe Ser Gly Asn Gly Arg Gln Cys Thr Ala
        315                 320                 325

AAT GGC ACG GAA TGT AGG AGT GGC TGG GTT GGC CCG AAC GGA GGC ATC     1542
Asn Gly Thr Glu Cys Arg Ser Gly Trp Val Gly Pro Asn Gly Gly Ile
    330                 335                 340

ACC AAC TTT GAT AAC TTT GCC TTT GCC ATG CTT ACT GTG TTT CAG TGC     1590
Thr Asn Phe Asp Asn Phe Ala Phe Ala Met Leu Thr Val Phe Gln Cys
345                 350                 355                 360

ATC ACC ATG GAG GGC TGG ACA GAC GTG CTC TAC TGG GTA AAT GAT GCG     1638
Ile Thr Met Glu Gly Trp Thr Asp Val Leu Tyr Trp Val Asn Asp Ala
                365                 370                 375

ATA GGA TGG GAA TGG CCA TGG GTG TAT TTT GTT AGT CTG ATC ATC CTT     1686
Ile Gly Trp Glu Trp Pro Trp Val Tyr Phe Val Ser Leu Ile Ile Leu
            380                 385                 390

GGC TCA TTT TTC GTC CTT AAC CTG GTT CTT GGT GTC CTT AGT GGA GAA     1734
Gly Ser Phe Phe Val Leu Asn Leu Val Leu Gly Val Leu Ser Gly Glu
        395                 400                 405

TTC TCA AAG GAA AGA GAG AAG GCA AAA GCA CGG GGA GAT TTC CAG AAG     1782
Phe Ser Lys Glu Arg Glu Lys Ala Lys Ala Arg Gly Asp Phe Gln Lys
    410                 415                 420

CTC CGG GAG AAG CAG CAG CTG GAG GAG GAT CTA AAG GGC TAC TTG GAT     1830
Leu Arg Glu Lys Gln Gln Leu Glu Glu Asp Leu Lys Gly Tyr Leu Asp
425                 430                 435                 440

TGG ATC ACC CAA GCT GAG GAC ATC GAT CCG GAG AAT GAG GAA GAA GGA     1878
Trp Ile Thr Gln Ala Glu Asp Ile Asp Pro Glu Asn Glu Glu Glu Gly
                445                 450                 455

GGA GAG GAA GGC AAA CGA AAT ACT AGC ATG CCC ACC AGC GAG ACT GAG     1926
Gly Glu Glu Gly Lys Arg Asn Thr Ser Met Pro Thr Ser Glu Thr Glu
            460                 465                 470

TCT GTG AAC ACA GAG AAC GTC AGC GGT GAA GGC GAG AAC CGA GGC TGC     1974
Ser Val Asn Thr Glu Asn Val Ser Gly Glu Gly Glu Asn Arg Gly Cys
        475                 480                 485

TGT GGA AGT CTC TGT CAA GCC ATC TCA AAA TCC AAA CTC AGC CGA CGC     2022
Cys Gly Ser Leu Cys Gln Ala Ile Ser Lys Ser Lys Leu Ser Arg Arg
    490                 495                 500

TGG CGT CGC TGG AAC CGA TTC AAT CGC AGA AGA TGT AGG GCC GCC GTG     2070
Trp Arg Arg Trp Asn Arg Phe Asn Arg Arg Arg Cys Arg Ala Ala Val
505                 510                 515                 520

AAG TCT GTC ACG TTT TAC TGG CTG GTT ATC GTC CTG GTG TTT CTG AAC     2118
Lys Ser Val Thr Phe Tyr Trp Leu Val Ile Val Leu Val Phe Leu Asn
                525                 530                 535

ACC TTA ACC ATT TCC TCT GAG CAC TAC AAT CAG CCA GAT TGG TTG ACA     2166
```

-continued

Thr Leu Thr Ile Ser Ser Glu His Tyr Asn Gln Pro Asp Trp Leu Thr
540 545 550

CAG ATT CAA GAT ATT GCC AAC AAA GTC CTC TTG GCT CTG TTC ACC TGC 2214
Gln Ile Gln Asp Ile Ala Asn Lys Val Leu Leu Ala Leu Phe Thr Cys
555 560 565

GAG ATG CTG GTA AAA ATG TAC AGC TTG GGC CTC CAA GCA TAT TTC GTC 2262
Glu Met Leu Val Lys Met Tyr Ser Leu Gly Leu Gln Ala Tyr Phe Val
570 575 580

TCT CTT TTC AAC CGG TTT GAT TGC TTC GTG GTG TGT GGT GGA ATC ACT 2310
Ser Leu Phe Asn Arg Phe Asp Cys Phe Val Val Cys Gly Gly Ile Thr
585 590 595 600

GAG ACG ATC TTG GTG GAA CTG GAA ATC ATG TCT CCC CTG GGG ATC TCT 2358
Glu Thr Ile Leu Val Glu Leu Glu Ile Met Ser Pro Leu Gly Ile Ser
605 610 615

GTG TTT CGG TGT GTG CGC CTC TTA AGA ATC TTC AAA GTG ACC AGG CAC 2406
Val Phe Arg Cys Val Arg Leu Leu Arg Ile Phe Lys Val Thr Arg His
620 625 630

TGG ACT TCC CTG AGC AAC TTA GTG GCA TCC TTA TTA AAC TCC ATG AAG 2454
Trp Thr Ser Leu Ser Asn Leu Val Ala Ser Leu Leu Asn Ser Met Lys
635 640 645

TCC ATC GCT TCG CTG TTG CTT CTG CTT TTT CTC TTC ATT ATC ATC TTT 2502
Ser Ile Ala Ser Leu Leu Leu Leu Leu Phe Leu Phe Ile Ile Ile Phe
650 655 660

TCC TTG CTT GGG ATG CAG CTG TTT GGC GGC AAG TTT AAT TTT GAT GAA 2550
Ser Leu Leu Gly Met Gln Leu Phe Gly Gly Lys Phe Asn Phe Asp Glu
665 670 675 680

ACG CAA ACC AAG CGG AGC ACC TTT GAC AAT TTC CCT CAA GCA CTT CTC 2598
Thr Gln Thr Lys Arg Ser Thr Phe Asp Asn Phe Pro Gln Ala Leu Leu
685 690 695

ACA GTG TTC CAG ATC CTG ACA GGC GAA GAC TGG AAT GCT GTG ATG TAC 2646
Thr Val Phe Gln Ile Leu Thr Gly Glu Asp Trp Asn Ala Val Met Tyr
700 705 710

GAT GGC ATC ATG GCT TAC GGG GGC CCA TCC TCT TCA GGA ATG ATC GTC 2694
Asp Gly Ile Met Ala Tyr Gly Gly Pro Ser Ser Ser Gly Met Ile Val
715 720 725

TGC ATC TAC TTC ATC ATC CTC TTC ATT TGT GGT AAC TAT ATT CTA CTG 2742
Cys Ile Tyr Phe Ile Ile Leu Phe Ile Cys Gly Asn Tyr Ile Leu Leu
730 735 740

AAT GTC TTC TTG GCC ATC GCT GTA GAC AAT TTG GCT GAT GCT GAA AGT 2790
Asn Val Phe Leu Ala Ile Ala Val Asp Asn Leu Ala Asp Ala Glu Ser
745 750 755 760

CTG AAC ACT GCT CAG AAA GAA GAA GCG GAA GAA AAG GAG AGG AAA AAG 2838
Leu Asn Thr Ala Gln Lys Glu Glu Ala Glu Glu Lys Glu Arg Lys Lys
765 770 775

ATT GCC AGA AAA GAG AGC CTA GAA AAT AAA AAG AAC AAC AAA CCA GAA 2886
Ile Ala Arg Lys Glu Ser Leu Glu Asn Lys Lys Asn Asn Lys Pro Glu
780 785 790

GTC AAC CAG ATA GCC AAC AGT GAC AAC AAG GTT ACA ATT GAT GAC TAT 2934
Val Asn Gln Ile Ala Asn Ser Asp Asn Lys Val Thr Ile Asp Asp Tyr
795 800 805

AGA GAA GAG GAT GAA GAC AAG GAC CCC TAT CCG CCT TGC GAT GTG CCA 2982
Arg Glu Glu Asp Glu Asp Lys Asp Pro Tyr Pro Pro Cys Asp Val Pro
810 815 820

GTA GGG GAA GAG GAA GAG GAA GAG GAG GAG GAT GAA CCT GAG GTT CCT 3030
Val Gly Glu Glu Glu Glu Glu Glu Glu Glu Asp Glu Pro Glu Val Pro
825 830 835 840

GCC GGA CCC CGT CCT CGA AGG ATC TCG GAG TTG AAC ATG AAG GAA AAA 3078
Ala Gly Pro Arg Pro Arg Arg Ile Ser Glu Leu Asn Met Lys Glu Lys
845 850 855

ATT GCC CCC ATC CCT GAA GGG AGC GCT TTC TTC ATT CTT AGC AAG ACC 3126

-continued

Ile Ala Pro Ile Pro Glu Gly Ser Ala Phe Phe Ile Leu Ser Lys Thr
860 865 870

AAC CCG ATC CGC GTA GGC TGC CAC AAG CTC ATC AAC CAC CAC ATC TTC 3174
Asn Pro Ile Arg Val Gly Cys His Lys Leu Ile Asn His His Ile Phe
875 880 885

ACC AAC CTC ATC CTT GTC TTC ATC ATG CTG AGC AGT GCT GCC CTG GCC 3222
Thr Asn Leu Ile Leu Val Phe Ile Met Leu Ser Ser Ala Ala Leu Ala
890 895 900

GCA GAG GAC CCC ATC CGC AGC CAC TCC TTC CGG AAC ACG ATA CTG GGT 3270
Ala Glu Asp Pro Ile Arg Ser His Ser Phe Arg Asn Thr Ile Leu Gly
905 910 915 920

TAC TTT GAC TAT GCC TTC ACA GCC ATC TTT ACT GTT GAG ATC CTG TTG 3318
Tyr Phe Asp Tyr Ala Phe Thr Ala Ile Phe Thr Val Glu Ile Leu Leu
925 930 935

AAG ATG ACA ACT TTT GGA GCT TTC CTC CAC AAA GGG GCC TTC TGC AGG 3366
Lys Met Thr Thr Phe Gly Ala Phe Leu His Lys Gly Ala Phe Cys Arg
940 945 950

AAC TAC TTC AAT TTG CTG GAT ATG CTG GTG GTT GGG GTG TCT CTG GTG 3414
Asn Tyr Phe Asn Leu Leu Asp Met Leu Val Val Gly Val Ser Leu Val
955 960 965

TCA TTT GGG ATT CAA TCC AGT GCC ATC TCC GTT GTG AAG ATT CTG AGG 3462
Ser Phe Gly Ile Gln Ser Ser Ala Ile Ser Val Val Lys Ile Leu Arg
970 975 980

GTC TTA AGG GTC CTG CGT CCC CTC AGG GCC ATC AAC AGA GCA AAA GGA 3510
Val Leu Arg Val Leu Arg Pro Leu Arg Ala Ile Asn Arg Ala Lys Gly
985 990 995 1000

CTT AAG CAC GTG GTC CAG TGC GTC TTC GTG GCC ATC CGG ACC ATC GGC 3558
Leu Lys His Val Val Gln Cys Val Phe Val Ala Ile Arg Thr Ile Gly
1005 1010 1015

AAC ATC ATG ATC GTC ACC ACC CTC CTG CAG TTC ATG TTT GCC TGT ATC 3606
Asn Ile Met Ile Val Thr Thr Leu Leu Gln Phe Met Phe Ala Cys Ile
1020 1025 1030

GGG GTC CAG TTG TTC AAG GGG AAG TTC TAT CGC TGT ACG GAT GAA GCC 3654
Gly Val Gln Leu Phe Lys Gly Lys Phe Tyr Arg Cys Thr Asp Glu Ala
1035 1040 1045

AAA AGT AAC CCT GAA GAA TGC AGG GGA CTT TTC ATC CTC TAC AAG GAT 3702
Lys Ser Asn Pro Glu Glu Cys Arg Gly Leu Phe Ile Leu Tyr Lys Asp
1050 1055 1060

GGG GAT GTT GAC AGT CCT GTG GTC CGT GAA CGG ATC TGG CAA AAC AGT 3750
Gly Asp Val Asp Ser Pro Val Val Arg Glu Arg Ile Trp Gln Asn Ser
1065 1070 1075 1080

GAT TTC AAC TTC GAC AAC GTC CTC TCT GCT ATG ATG GCG CTC TTC ACA 3798
Asp Phe Asn Phe Asp Asn Val Leu Ser Ala Met Met Ala Leu Phe Thr
1085 1090 1095

GTC TCC ACG TTT GAG GGC TGG CCT GCG TTG CTG TAT AAA GCC ATC GAC 3846
Val Ser Thr Phe Glu Gly Trp Pro Ala Leu Leu Tyr Lys Ala Ile Asp
1100 1105 1110

TCG AAT GGA GAG AAC ATC GGC CCA ATC TAC AAC CAC CGC GTG GAG ATC 3894
Ser Asn Gly Glu Asn Ile Gly Pro Ile Tyr Asn His Arg Val Glu Ile
1115 1120 1125

TCC ATC TTC TTC ATC ATC TAC ATC ATC ATT GTA GCT TTC TTC ATG ATG 3942
Ser Ile Phe Phe Ile Ile Tyr Ile Ile Ile Val Ala Phe Phe Met Met
1130 1135 1140

AAC ATC TTT GTG GGC TTT GTC ATC GTT ACA TTT CAG GAA CAA GGA GAA 3990
Asn Ile Phe Val Gly Phe Val Ile Val Thr Phe Gln Glu Gln Gly Glu
1145 1150 1155 1160

AAA GAG TAT AAG AAC TGT GAG CTG GAC AAA AAT CAG CGT CAG TGT GTT 4038
Lys Glu Tyr Lys Asn Cys Glu Leu Asp Lys Asn Gln Arg Gln Cys Val
1165 1170 1175

GAA TAC GCC TTG AAA GCA CGT CCC TTG CGG AGA TAC ATC CCC AAA AAC 4086

-continued

Glu Tyr Ala Leu Lys Ala Arg Pro Leu Arg Arg Tyr Ile Pro Lys Asn
1180 1185 1190

CCC TAC CAG TAC AAG TTC TGG TAC GTG GTG AAC TCT TCG CCT TTC GAA 4134
Pro Tyr Gln Tyr Lys Phe Trp Tyr Val Val Asn Ser Ser Pro Phe Glu
1195 1200 1205

TAC ATG ATG TTT GTC CTC ATC ATG CTC AAC ACA CTC TGC TTG GCC ATG 4182
Tyr Met Met Phe Val Leu Ile Met Leu Asn Thr Leu Cys Leu Ala Met
1210 1215 1220

CAG CAC TAC GAG CAG TCC AAG ATG TTC AAT GAT GCC ATG GAC ATT CTG 4230
Gln His Tyr Glu Gln Ser Lys Met Phe Asn Asp Ala Met Asp Ile Leu
1225 1230 1235 1240

AAC ATG GTC TTC ACC GGG GTG TTC ACC GTC GAG ATG GTT TTG AAA GTC 4278
Asn Met Val Phe Thr Gly Val Phe Thr Val Glu Met Val Leu Lys Val
1245 1250 1255

ATC GCA TTT AAG CCT AAG GGG TAT TTT AGT GAC GCC TGG AAC ACG TTT 4326
Ile Ala Phe Lys Pro Lys Gly Tyr Phe Ser Asp Ala Trp Asn Thr Phe
1260 1265 1270

GAC TCC CTC ATC GTA ATC GGC AGC ATT ATA GAC GTG GCC CTC AGC GAA 4374
Asp Ser Leu Ile Val Ile Gly Ser Ile Ile Asp Val Ala Leu Ser Glu
1275 1280 1285

GCA GAC CCA ACT GAA AGT GAA AAT GTC CCT GTC CCA ACT GCT ACA CCT 4422
Ala Asp Pro Thr Glu Ser Glu Asn Val Pro Val Pro Thr Ala Thr Pro
1290 1295 1300

GGG AAC TCT GAA GAG AGC AAT AGA ATC TCC ATC ACC TTT TTC CGT CTT 4470
Gly Asn Ser Glu Glu Ser Asn Arg Ile Ser Ile Thr Phe Phe Arg Leu
1305 1310 1315 1320

TTC CGA GTG ATG CGA TTG GTG AAG CTT CTC AGC AGG GGG GAA GGC ATC 4518
Phe Arg Val Met Arg Leu Val Lys Leu Leu Ser Arg Gly Glu Gly Ile
1325 1330 1335

CGG ACA TTG CTG TGG ACT TTT ATT AAG TTC TTT CAG GCG CTC CCG TAT 4566
Arg Thr Leu Leu Trp Thr Phe Ile Lys Phe Phe Gln Ala Leu Pro Tyr
1340 1345 1350

GTG GCC CTC CTC ATA GCC ATG CTG TTC TTC ATC TAT GCG GTC ATT GGC 4614
Val Ala Leu Leu Ile Ala Met Leu Phe Phe Ile Tyr Ala Val Ile Gly
1355 1360 1365

ATG CAG ATG TTT GGG AAA GTT GCC ATG AGA GAT AAC AAC CAG ATC AAT 4662
Met Gln Met Phe Gly Lys Val Ala Met Arg Asp Asn Asn Gln Ile Asn
1370 1375 1380

AGG AAC AAT AAC TTC CAG ACG TTT CCC CAG GCG GTG CTG CTG CTC TTC 4710
Arg Asn Asn Asn Phe Gln Thr Phe Pro Gln Ala Val Leu Leu Leu Phe
1385 1390 1395 1400

AGG TGT GCA ACA GGT GAG GCC TGG CAG GAG ATC ATG CTG GCC TGT CTC 4758
Arg Cys Ala Thr Gly Glu Ala Trp Gln Glu Ile Met Leu Ala Cys Leu
1405 1410 1415

CCA GGG AAG CTC TGT GAC CCT GAG TCA GAT TAC AAC CCC GGG GAG GAG 4806
Pro Gly Lys Leu Cys Asp Pro Glu Ser Asp Tyr Asn Pro Gly Glu Glu
1420 1425 1430

CAT ACA TGT GGG AGC AAC TTT GCC ATT GTC TAT TTC ATC AGT TTT TAC 4854
His Thr Cys Gly Ser Asn Phe Ala Ile Val Tyr Phe Ile Ser Phe Tyr
1435 1440 1445

ATG CTC TGT GCA TTT CTG ATC ATC AAT CTG TTT GTG GCT GTC ATC ATG 4902
Met Leu Cys Ala Phe Leu Ile Ile Asn Leu Phe Val Ala Val Ile Met
1450 1455 1460

GAT AAT TTC GAC TAT CTG ACC CGG GAC TGG TCT ATT TTG GGG CCT CAC 4950
Asp Asn Phe Asp Tyr Leu Thr Arg Asp Trp Ser Ile Leu Gly Pro His
1465 1470 1475 1480

CAT TTA GAT GAA TTC AAA AGA ATA TGG TCA GAA TAT GAC CCT GAG GCA 4998
His Leu Asp Glu Phe Lys Arg Ile Trp Ser Glu Tyr Asp Pro Glu Ala
1485 1490 1495

AAG GGA AGG ATA AAA CAC CTT GAT GTG GTC ACT CTG CTT CGA CGC ATC 5046

-continued

Lys Gly Arg Ile Lys His Leu Asp Val Val Thr Leu Leu Arg Arg Ile
1500 1505 1510

CAG CCT CCC CTG GGG TTT GGG AAG TTA TGT CCA CAC AGG GTA GCG TGC 5094
Gln Pro Pro Leu Gly Phe Gly Lys Leu Cys Pro His Arg Val Ala Cys
1515 1520 1525

AAG AGA TTA GTT GCC ATG AAC ATG CCT CTC AAC AGT GAC GGG ACA GTC 5142
Lys Arg Leu Val Ala Met Asn Met Pro Leu Asn Ser Asp Gly Thr Val
1530 1535 1540

ATG TTT AAT GCA ACC CTG TTT GCT TTG GTT CGA ACG GCT CTT AAG ATC 5190
Met Phe Asn Ala Thr Leu Phe Ala Leu Val Arg Thr Ala Leu Lys Ile
1545 1550 1555 1560

AAG ACC GAA GGG AAC CTG GAG CAA GCT AAT GAA GAA CTT CGG GCT GTG 5238
Lys Thr Glu Gly Asn Leu Glu Gln Ala Asn Glu Glu Leu Arg Ala Val
1565 1570 1575

ATA AAG AAA ATT TGG AAG AAA ACC AGC ATG AAA TTA CTT GAC CAA GTT 5286
Ile Lys Lys Ile Trp Lys Lys Thr Ser Met Lys Leu Leu Asp Gln Val
1580 1585 1590

GTC CCT CCA GCT GGT GAT GAT GAG GTA ACC GTG GGG AAG TTC TAT GCC 5334
Val Pro Pro Ala Gly Asp Asp Glu Val Thr Val Gly Lys Phe Tyr Ala
1595 1600 1605

ACT TTC CTG ATA CAG GAC TAC TTT AGG AAA TTC AAG AAA CGG AAA GAA 5382
Thr Phe Leu Ile Gln Asp Tyr Phe Arg Lys Phe Lys Lys Arg Lys Glu
1610 1615 1620

CAA GGA CTG GTG GGA AAG TAC CCT GCG AAG AAC ACC ACA ATT GCC CTA 5430
Gln Gly Leu Val Gly Lys Tyr Pro Ala Lys Asn Thr Thr Ile Ala Leu
1625 1630 1635 1640

CAG GCG GGA TTA AGG ACA CTG CAT GAC ATT GGG CCA GAA ATC CGG CGT 5478
Gln Ala Gly Leu Arg Thr Leu His Asp Ile Gly Pro Glu Ile Arg Arg
1645 1650 1655

GCT ATA TCG TGT GAT TTG CAA GAT GAC GAG CCT GAG GAA ACA AAA CGA 5526
Ala Ile Ser Cys Asp Leu Gln Asp Asp Glu Pro Glu Glu Thr Lys Arg
1660 1665 1670

GAA GAA GAA GAT GAT GTG TTC AAA AGA AAT GGT GCC CTG CTT GGA AAC 5574
Glu Glu Glu Asp Asp Val Phe Lys Arg Asn Gly Ala Leu Leu Gly Asn
1675 1680 1685

CAT GTC AAT CAT GTT AAT AGT GAT AGG AGA GAT TCC CTT CAG CAG ACC 5622
His Val Asn His Val Asn Ser Asp Arg Arg Asp Ser Leu Gln Gln Thr
1690 1695 1700

AAT ACC ACC CAC CGT CCC CTG CAT GTC CAA AGG CCT TCA ATT CCA CCT 5670
Asn Thr Thr His Arg Pro Leu His Val Gln Arg Pro Ser Ile Pro Pro
1705 1710 1715 1720

GCA AGT GAT ACT GAG AAA CCG CTG TTT CCT CCA GCA GGA AAT TCG GTG 5718
Ala Ser Asp Thr Glu Lys Pro Leu Phe Pro Pro Ala Gly Asn Ser Val
1725 1730 1735

TGT CAT AAC CAT CAT AAC CAT AAT TCC ATA GGA AAG CAA GTT CCC ACC 5766
Cys His Asn His His Asn His Asn Ser Ile Gly Lys Gln Val Pro Thr
1740 1745 1750

TCA ACA AAT GCC AAT CTC AAT AAT GCC AAT ATG TCC AAA GCT GCC CAT 5814
Ser Thr Asn Ala Asn Leu Asn Asn Ala Asn Met Ser Lys Ala Ala His
1755 1760 1765

GGA AAG CGG CCC AGC ATT GGG AAC CTT GAG CAT GTG TCT GAA AAT GGG 5862
Gly Lys Arg Pro Ser Ile Gly Asn Leu Glu His Val Ser Glu Asn Gly
1770 1775 1780

CAT CAT TCT TCC CAC AAG CAT GAC CGG GAG CCT CAG AGA AGG TCC AGT 5910
His His Ser Ser His Lys His Asp Arg Glu Pro Gln Arg Arg Ser Ser
1785 1790 1795 1800

GTG AAA AGA ACC CGC TAT TAT GAA ACT TAC ATT AGG TCC GAC TCA GGA 5958
Val Lys Arg Thr Arg Tyr Tyr Glu Thr Tyr Ile Arg Ser Asp Ser Gly
1805 1810 1815

GAT GAA CAG CTC CCA ACT ATT TGC CGG GAA GAC CCA GAG ATA CAT GGC 6006

-continued

```
Asp Glu Gln Leu Pro Thr Ile Cys Arg Glu Asp Pro Glu Ile His Gly
            1820                1825                1830

TAT TTC AGG GAC CCC CAC TGC TTG GGG GAG CAG GAG TAT TTC AGT AGT      6054
Tyr Phe Arg Asp Pro His Cys Leu Gly Glu Gln Glu Tyr Phe Ser Ser
        1835                1840                1845

GAG GAA TGC TAC GAG GAT GAC AGC TCG CCC ACC TGG AGC AGG CAA AAC      6102
Glu Glu Cys Tyr Glu Asp Asp Ser Ser Pro Thr Trp Ser Arg Gln Asn
    1850                1855                1860

TAT GGC TAC TAC AGC AGA TAC CCA GGC AGA AAC ATC GAC TCT GAG AGG      6150
Tyr Gly Tyr Tyr Ser Arg Tyr Pro Gly Arg Asn Ile Asp Ser Glu Arg
1865                1870                1875                1880

CCC CGA GGC TAC CAT CAT CCC CAA GGA TTC TTG GAG GAC GAT GAC TCG      6198
Pro Arg Gly Tyr His His Pro Gln Gly Phe Leu Glu Asp Asp Asp Ser
                1885                1890                1895

CCC GTT TGC TAT GAT TCA CGG AGA TCT CCA AGG AGA CGC CTA CTA CCT      6246
Pro Val Cys Tyr Asp Ser Arg Arg Ser Pro Arg Arg Arg Leu Leu Pro
            1900                1905                1910

CCC ACC CCA GCA TCC CAC CGG AGA TCC TCC TTC AAC TTT GAG TGC CTG      6294
Pro Thr Pro Ala Ser His Arg Arg Ser Ser Phe Asn Phe Glu Cys Leu
        1915                1920                1925

CGC CGG CAG AGC AGC CAG GAA GAG GTC CCG TCG TCT CCC ATC TTC CCC      6342
Arg Arg Gln Ser Ser Gln Glu Glu Val Pro Ser Ser Pro Ile Phe Pro
    1930                1935                1940

CAT CGC ACG GCC CTG CCT CTG CAT CTA ATG CAG CAA CAG ATC ATG GCA      6390
His Arg Thr Ala Leu Pro Leu His Leu Met Gln Gln Gln Ile Met Ala
1945                1950                1955                1960

GTT GCC GGC CTA GAT TCA AGT AAA GCC CAG AAG TAC TCA CCG AGT CAC      6438
Val Ala Gly Leu Asp Ser Ser Lys Ala Gln Lys Tyr Ser Pro Ser His
                1965                1970                1975

TCG ACC CGG TCG TGG GCC ACC CCT CCA GCA ACC CCT CCC TAC CGG GAC      6486
Ser Thr Arg Ser Trp Ala Thr Pro Pro Ala Thr Pro Pro Tyr Arg Asp
            1980                1985                1990

TGG ACA CCG TGC TAC ACC CCC CTG ATC CAA GTG GAG CAG TCA GAG GCC      6534
Trp Thr Pro Cys Tyr Thr Pro Leu Ile Gln Val Glu Gln Ser Glu Ala
        1995                2000                2005

CTG GAC CAG GTG AAC GGC AGC CTG CCG TCC CTG CAC CGC AGC TCC TGG      6582
Leu Asp Gln Val Asn Gly Ser Leu Pro Ser Leu His Arg Ser Ser Trp
    2010                2015                2020

TAC ACA GAC GAG CCC GAC ATC TCC TAC CGG ACT TTC ACA CCA GCC AGC      6630
Tyr Thr Asp Glu Pro Asp Ile Ser Tyr Arg Thr Phe Thr Pro Ala Ser
2025                2030                2035                2040

CTG ACT GTC CCC AGC AGC TTC CGG AAC AAA AAC AGC GAC AAG CAG AGG      6678
Leu Thr Val Pro Ser Ser Phe Arg Asn Lys Asn Ser Asp Lys Gln Arg
                2045                2050                2055

AGT GCG GAC AGC TTG GTG GAG GCA GTC CTG ATA TCC GAA GGC TTG GGA      6726
Ser Ala Asp Ser Leu Val Glu Ala Val Leu Ile Ser Glu Gly Leu Gly
            2060                2065                2070

CGC TAT GCA AGG GAC CCA AAA TTT GTG TCA GCA ACA AAA CAC GAA ATC      6774
Arg Tyr Ala Arg Asp Pro Lys Phe Val Ser Ala Thr Lys His Glu Ile
        2075                2080                2085

GCT GAT GCC TGT GAC CTC ACC ATC GAC GAG ATG GAG AGT GCA GCC AGC      6822
Ala Asp Ala Cys Asp Leu Thr Ile Asp Glu Met Glu Ser Ala Ala Ser
    2090                2095                2100

ACC CTG CTT AAT GGG AAC GTG CGT CCC CGA GCC AAC GGG GAT GTG GGC      6870
Thr Leu Leu Asn Gly Asn Val Arg Pro Arg Ala Asn Gly Asp Val Gly
2105                2110                2115                2120

CCC CTC TCA CAC CGG CAG GAC TAT GAG CTA CAG GAC TTT GGT CCT GGC      6918
Pro Leu Ser His Arg Gln Asp Tyr Glu Leu Gln Asp Phe Gly Pro Gly
                2125                2130                2135

TAC AGC GAC GAA GAG CCA GAC CCT GGG AGG GAT GAG GAG GAC CTG GCG      6966
```

-continued

```
Tyr Ser Asp Glu Glu Pro Asp Pro Gly Arg Asp Glu Glu Asp Leu Ala
          2140                     2145                     2150

GAT GAA ATG ATA TGC ATC ACC ACC TTG TAG CCCCCAGCGA GGGGCAGACT GGCT 7020
Asp Glu Met Ile Cys Ile Thr Thr Leu  *
        2155                2160

CTGGCCTCAG GTGGGGCGCA GGAGAGCCAG GGGAAAAGTG CCTCATAGTT AGGAAAGTTT 7080

AGGCACTAGT TGGGAGTAAT ATTCAATTAA TTAGACTTTT GTATAAGAGA TGTCATGCCT 7140

CAAGAAAGCC ATAAACCTGG TAGGAACAGG TCCCAAGCGG TTGAGCCTGG CAGAGTACCA 7200

TGCGCTCGGC CCCAGCTGCA GGAAACAGCA GGCCCCGCCC TCTCACAGAG GATGGGTGAG 7260

GAGGCCAGAC CTGCCCTGCC CCATTGTCCA GATGGGCACT GCTGTGGAGT CTGCTTCTCC 7320

CATGTACCAG GGCACCAGGC CCACCCAACT GAAGGCATGG CGGCGGGGTG CAGGGGAAAG 7380

TTAAAGGTGA TGACGATCAT CACACCTGTG TCGTTACCTC AGCCATCGGT CTAGCATATC 7440

AGTCACTGGG CCCAACATAT CCATTTTTAA ACCCTTTCCC CCAAATACAC TGCGTCCTGG 7500

TTCCTGTTTA GCTGTTCTGA AATACGGTGT GTAAGTAAGT CAGAACCCAG CTACCAGTGA 7560

TTATTGCGAG GGCAATGGGA CCTCATAAAT AAGGTTTTCT GTGATGTGAC GCCAGTTTAC 7620

ATAAGAGAAT ATCAC                                                  7635
```

(2) INFORMATION FOR SEQ ID NO:24:

(i) SEQUENCE CHARACTERISTICS:
(A) LENGTH: 962 base pairs
(B) TYPE: nucleic acid
(C) STRANDEDNESS: double
(D) TOPOLOGY: linear (ii) MOLECULE TYPE: DNA (genomic)

(ix) FEATURE:
(A) NAME/KEY: CDS
(B) LOCATION: 1..962

(ix) FEATURE:
(D) OTHER INFORMATION: /note= "IMR32 1.157"

(xi) SEQUENCE DESCRIPTION: SEQ ID NO:24:

```
CGCTGAGGGC CTTCCGCGTG CTGCGCCCCC TGCGGCTGGT GTCCGGAGTC CCAAGTCTCC  60

AGGTGGTCCT GAATTCCATC ATCAAGGCCA TGGTCAATGA GAATACGAGG ATGTACATTC 120

CAGAGGAAAA CCACCAAGGT TCCAACTATG GGAGCCCACG CCCCGCCCAT GCCAACATGA 180

ATGCCAATGC GGCAGCGGGG CTGGCCCCTG AGCACATCCC CACCCCGGGG GCTGCCCTGT 240

CGTGGCAGGC GGCCATCGAC GCAGCCCGGC AGGCTAAGCT GATGGGCAGC GCTGGCAATG 300

CGACCATCTC CACAGTCAGC TCCACGCAGC GGAAGCGCCA GCAATATGGG AAACCCAAGA 360

AGCAGGGCAG CACCACGGCC ACACGCCCGC CCCGAGCCCT GCTCTGCCTG ACCCTGAAGA 420

ACCCCATCCG GAGGGCCTGC ATCAGCATTG TCGAATGGAA ACCATTTGAA ATAATTATTT 480

TACTGACTAT TTTTGCCAAT TGTGTGGCCT TAGCGATCTA TATTCCCTTT CCAGAAGATG 540

ATTCCAACGC CACCAATTCC AACCTGGAAC GAGTGGAATA TCTCTTTCTC ATAATTTTTA 600

CGGTGGAAGC GTTTTTAAAA GTAATCGCCT ATGGACTCCT CTTTCACCCC AATGCCTACC 660

TCCGCAACGG CTGGAACCTA CTAGATTTTA TAATTGTGGT TGTGGGGCTT TTTAGTGCAA 720

TTTTAGAACA AGCAACCAAA GCAGATGGGG CAAACGCTCT CGGAGGGAAA GGGGCCGGAT 780

TTGATGTGAA GGCGCTGAGG GCCTTCCGCG TGCTGCGCCC CCTGCGGCTG GTGTCCGGAG 840

TCCCAAGTCT CCAGGTGGTC CTGAATTCCA TCATCAAGGC CATGGTCCCC CTGCTGCACA 900

TCGCCCTGCT TGTGCTGTTT GTCATCATCA TCTACGCCAT CATCGGCTTG GAGCTCTTCA 960
```

T G 9 6 2

( 2 ) INFORMATION FOR SEQ ID NO:25:

( i ) SEQUENCE CHARACTERISTICS:
( A ) LENGTH: 100 base pairs
( B ) TYPE: nucleic acid
( C ) STRANDEDNESS: double
( D ) TOPOLOGY: linear ( i i ) MOLECULE TYPE: DNA (genomic)

( i x ) FEATURE:
( A ) NAME/KEY: CDS
( B ) LOCATION: 1..100

( i x ) FEATURE:
( D ) OTHER INFORMATION: /note= "fragment of IMR32 1.66 "

( x i ) SEQUENCE DESCRIPTION: SEQ ID NO:25:

G G C T G C T C C T C C T A T T A A A A C C A T T T T T G G T C C A T G G T C A A T G A G A A T A C G A G G A T G T A C 6 0

A T T C C A G A G G A A A A C C A C C A A G G T T C C A A C T A T G G G A G C C 1 0 0

( 2 ) INFORMATION FOR SEQ ID NO:26:

( i ) SEQUENCE CHARACTERISTICS:
( A ) LENGTH: 100 base pairs
( B ) TYPE: nucleic acid
( C ) STRANDEDNESS: double
( D ) TOPOLOGY: linear ( i i ) MOLECULE TYPE: DNA (genomic)

( i x ) FEATURE:
( A ) NAME/KEY: CDS
( B ) LOCATION: 1..100

( i x ) FEATURE:
( D ) OTHER INFORMATION: /note= "CACB-receptor"

( x i ) SEQUENCE DESCRIPTION: SEQ ID NO:26:

G C T G C T T C T C C T T T T G A C A C A A T T T T T T G G T C C A T G G T C A A T G A G A A T A C G A G G A T G T A C 6 0

A T T C C T G A G G A A A A C C A C C A A G G T T C C A A C T A T G G G A G C C 1 0 0

( 2 ) INFORMATION FOR SEQ ID NO:27:

( i ) SEQUENCE CHARACTERISTICS:
( A ) LENGTH: 44 base pairs
( B ) TYPE: nucleic acid
( C ) STRANDEDNESS: double
( D ) TOPOLOGY: linear ( i i ) MOLECULE TYPE: DNA (genomic)

( i x ) FEATURE:
( D ) OTHER INFORMATION: /note= "polylinker sense"

( x i ) SEQUENCE DESCRIPTION: SEQ ID NO:27:

G G C C G C G A A T T C G T C G A C C T G C A G G A T A T C A A G C T T A G A T C T G T 4 4

( 2 ) INFORMATION FOR SEQ ID NO:28:

( i ) SEQUENCE CHARACTERISTICS:
( A ) LENGTH: 44 base pairs
( B ) TYPE: nucleic acid
( C ) STRANDEDNESS: double
( D ) TOPOLOGY: linear ( i i ) MOLECULE TYPE: DNA (genomic)

( ix ) FEATURE:
( D ) OTHER INFORMATION: /note= "polylinker antisense"

( xi ) SEQUENCE DESCRIPTION: SEQ ID NO:28:

CGCTTAAGCA GCTGGACGTC CTATAGTTCG AATCTAGACA CCGG 44

( 2 ) INFORMATION FOR SEQ ID NO:29:

( i ) SEQUENCE CHARACTERISTICS:
( A ) LENGTH: 1789 base pairs
( B ) TYPE: nucleic acid
( C ) STRANDEDNESS: double
( D ) TOPOLOGY: linear ( ii ) MOLECULE TYPE: Genomic DNA ( iii ) HYPOTHETICAL: NO ( iv ) ANTI-SENSE: NO ( v ) FRAGMENT TYPE:

( vi ) ORIGINAL SOURCE:

( ix ) FEATURE:
( A ) NAME/KEY: Coding Sequence
( B ) LOCATION: 2...1789
( D ) OTHER INFORMATION: Note "CNS 1.30"

( xi ) SEQUENCE DESCRIPTION: SEQ ID NO:29:

```
G AAT TCG GTG ATG TAT GAT GGG ATC ATG GCT TAT GGG GGC CCC TCT TTT     49
  Asn Ser Val Met Tyr Asp Gly Ile Met Ala Tyr Gly Gly Pro Ser Phe
    1               5                  10                  15

CCA GGG ATG TTA GTC TGT ATT TAC TTC ATC ATC CTC TTC ATC TCT GGA       97
Pro Gly Met Leu Val Cys Ile Tyr Phe Ile Ile Leu Phe Ile Ser Gly
             20                  25                  30

AAC TAT ATC CTA CTG AAT GTG TTC TTG GCC ATT GCT GTG GAC AAC CTG      145
Asn Tyr Ile Leu Leu Asn Val Phe Leu Ala Ile Ala Val Asp Asn Leu
         35                  40                  45

GCT GAT GCT GAG AGC CTC ACA TCT GCC CTA AAG GAG GAG GAA GAG GAG      193
Ala Asp Ala Glu Ser Leu Thr Ser Ala Leu Lys Glu Glu Glu Glu Glu
     50                  55                  60

AAG GAG AGA AAG AAG CTG GCC AGG ACT GCC AGC CCA GAG AAG AAA CAA      241
Lys Glu Arg Lys Lys Leu Ala Arg Thr Ala Ser Pro Glu Lys Lys Gln
 65                  70                  75                  80

GAG TTG GTG GAG AAG CCG GCA GTG GGG GAA TCC AAG GAG GAG AAG ATT      289
Glu Leu Val Glu Lys Pro Ala Val Gly Glu Ser Lys Glu Glu Lys Ile
                 85                  90                  95

GAG CTG AAA TCC ATC ACG GCT GAC GGA GAG TCT CCA CCC GCC ACC AAG      337
Glu Leu Lys Ser Ile Thr Ala Asp Gly Glu Ser Pro Pro Ala Thr Lys
            100                 105                 110

ATC AAC ATG GAT GAC CTC CAG CCC AAT GAA AAT GAG GAT AAG AGC CCC      385
Ile Asn Met Asp Asp Leu Gln Pro Asn Glu Asn Glu Asp Lys Ser Pro
        115                 120                 125

TAC CCC AAC CCA GAA ACT ACA GGA GAA GAG GAT GAG GAG GAG CCA GAG      433
Tyr Pro Asn Pro Glu Thr Thr Gly Glu Glu Asp Glu Glu Glu Pro Glu
    130                 135                 140

ATG CCT GTC GGC CCT CGC CCA CGA CCA CTC TCT GAG CTT CAC CTT AAG      481
Met Pro Val Gly Pro Arg Pro Arg Pro Leu Ser Glu Leu His Leu Lys
145                 150                 155                 160

GAA AAG GCA GTG CCC ATG CCA GAA GCC AGC GCG TTT TTC ATC TTC AGC      529
Glu Lys Ala Val Pro Met Pro Glu Ala Ser Ala Phe Phe Ile Phe Ser
                165                 170                 175

TCT AAC AAC AGG TTT CGC CTC CAG TGC CAC CGC ATT GTC AAT GAC ACG      577
Ser Asn Asn Arg Phe Arg Leu Gln Cys His Arg Ile Val Asn Asp Thr
            180                 185                 190
```

-continued

```
ATC TTC ACC AAC CTG ATC CTC TTC TTC ATT CTG CTC AGC AGC ATT TCC     625
Ile Phe Thr Asn Leu Ile Leu Phe Phe Ile Leu Leu Ser Ser Ile Ser
        195                 200                 205

CTG GCT GCT GAG GAC CCG GTC CAG CAC ACC TCC TTC AGG AAC CAT ATT     673
Leu Ala Ala Glu Asp Pro Val Gln His Thr Ser Phe Arg Asn His Ile
    210                 215                 220

CTG TTT TAT TTT GAT ATT GTT TTT ACC ACC ATT TTC ACC ATT GAA ATT     721
Leu Phe Tyr Phe Asp Ile Val Phe Thr Thr Ile Phe Thr Ile Glu Ile
225                 230                 235                 240

GCT CTG AAG ATG ACT GCT TAT GGG GCT TTC TTG CAC AAG GGT TCT TTC     769
Ala Leu Lys Met Thr Ala Tyr Gly Ala Phe Leu His Lys Gly Ser Phe
                245                 250                 255

TGC CGG AAC TAC TTC AAC ATC CTG GAC CTG CTG GTG GTC AGC GTG TCC     817
Cys Arg Asn Tyr Phe Asn Ile Leu Asp Leu Leu Val Val Ser Val Ser
            260                 265                 270

CTC ATC TCC TTT GGC ATC CAG TCC AGT GCA ATC AAT GTC GTG AAG ATC     865
Leu Ile Ser Phe Gly Ile Gln Ser Ser Ala Ile Asn Val Val Lys Ile
        275                 280                 285

TTG CGA GTC CTG CGA GTA CTC AGG CCC CTG AGG GCC ATC AAC AGG GCC     913
Leu Arg Val Leu Arg Val Leu Arg Pro Leu Arg Ala Ile Asn Arg Ala
    290                 295                 300

AAG GGG CTA AAG CAT GTG GTT CAG TGT GTG TTT GTC GCC ATC CGG ACC     961
Lys Gly Leu Lys His Val Val Gln Cys Val Phe Val Ala Ile Arg Thr
305                 310                 315                 320

ATC GGG AAC ATC GTG ATT GTC ACC ACC CTG CTG CAG TTC ATG TTT GCC    1009
Ile Gly Asn Ile Val Ile Val Thr Thr Leu Leu Gln Phe Met Phe Ala
                325                 330                 335

TGC ATC GGG GTC CAG CTC TTC AAG GGA AAG CTG TAC ACC TGT TCA GAC    1057
Cys Ile Gly Val Gln Leu Phe Lys Gly Lys Leu Tyr Thr Cys Ser Asp
            340                 345                 350

AGT TCC AAG CAG ACA GAG GCG GAA TGC AAG GGC AAC TAC ATC ACG TAC    1105
Ser Ser Lys Gln Thr Glu Ala Glu Cys Lys Gly Asn Tyr Ile Thr Tyr
        355                 360                 365

AAA GAC GGG GAG GTT GAC CAC CCC ATC ATC CAA CCC CGC AGC TGG GAG    1153
Lys Asp Gly Glu Val Asp His Pro Ile Ile Gln Pro Arg Ser Trp Glu
    370                 375                 380

AAC AGC AAG TTT GAC TTT GAC AAT GTT CTG GCA GCC ATG ATG GCC CTC    1201
Asn Ser Lys Phe Asp Phe Asp Asn Val Leu Ala Ala Met Met Ala Leu
385                 390                 395                 400

TTC ACC GTC TCC ACC TTC GAA GGG TGG CCA GAG CTG CTG TAC CGC TCC    1249
Phe Thr Val Ser Thr Phe Glu Gly Trp Pro Glu Leu Leu Tyr Arg Ser
                405                 410                 415

ATC GAC TCC CAC ACG GAA GAC AAG GGC CCC ATC TAC AAC TAC CGT GTG    1297
Ile Asp Ser His Thr Glu Asp Lys Gly Pro Ile Tyr Asn Tyr Arg Val
            420                 425                 430

GAG ATC TCC ATC TTC TTC ATC ATC TAC ATC ATC ATC ATC GCC TTC TTC    1345
Glu Ile Ser Ile Phe Phe Ile Ile Tyr Ile Ile Ile Ile Ala Phe Phe
        435                 440                 445

ATG ATG AAC ATC TTC GTG GGC TTC GTC ATC GTC ACC TTT CAG GAG CAG    1393
Met Met Asn Ile Phe Val Gly Phe Val Ile Val Thr Phe Gln Glu Gln
    450                 455                 460

GGG GAG CAG GAG TAC AAG AAC TGT GAG CTG GAC AAG AAC CAG CGA CAG    1441
Gly Glu Gln Glu Tyr Lys Asn Cys Glu Leu Asp Lys Asn Gln Arg Gln
465                 470                 475                 480

TGC GTG GAA TAC GCC CTC AAG GCC CGG CCC CTG CGG AGG TAC ATC CCC    1489
Cys Val Glu Tyr Ala Leu Lys Ala Arg Pro Leu Arg Arg Tyr Ile Pro
                485                 490                 495

AAG AAC CAG CAC CAG TAC AAA GTG TGG TAC GTG GTC AAC TCC ACC TAC    1537
Lys Asn Gln His Gln Tyr Lys Val Trp Tyr Val Val Asn Ser Thr Tyr
            500                 505                 510
```

-continued

```
TTC GAG TAC CTG ATG TTC GTC CTC ATC CTG CTC AAC ACC ATC TGC CTG    1585
Phe Glu Tyr Leu Met Phe Val Leu Ile Leu Leu Asn Thr Ile Cys Leu
        515                 520                 525

GCC ATG CAG CAC TAC GGC CAG AGC TGC CTG TTC AAA ATC GCC ATG AAC    1633
Ala Met Gln His Tyr Gly Gln Ser Cys Leu Phe Lys Ile Ala Met Asn
    530                 535                 540

ATC CTC AAC ATG CTC TTC ACT GGC CTC TTC ACC GTG GAG ATG ATC CTG    1681
Ile Leu Asn Met Leu Phe Thr Gly Leu Phe Thr Val Glu Met Ile Leu
545                 550                 555                 560

AAG CTC ATT GCC TTC AAA CCC AAG CAC TAT TTC TGT GAT GCA TGG AAT    1729
Lys Leu Ile Ala Phe Lys Pro Lys His Tyr Phe Cys Asp Ala Trp Asn
                565                 570                 575

ACA TTT GAC GCC TTG ATT GTT GTG GGT AGC ATT GTT GAT ATA GCA ATC    1777
Thr Phe Asp Ala Leu Ile Val Val Gly Ser Ile Val Asp Ile Ala Ile
            580                 585                 590

ACC GAG GTA AAC                                                    1789
Thr Glu Val Asn
        595
```

(2) INFORMATION FOR SEQ ID NO:30:

(i) SEQUENCE CHARACTERISTICS:
(A) LENGTH: 1048 base pairs
(B) TYPE: nucleic acid
(C) STRANDEDNESS: double
(D) TOPOLOGY: linear (ii) MOLECULE TYPE: Genomic DNA (iii) HYPOTHETICAL: NO (iv) ANTI-SENSE: NO (v) FRAGMENT TYPE:

(vi) ORIGINAL SOURCE:

(ix) FEATURE:

(xi) SEQUENCE DESCRIPTION: SEQ ID NO:30:

```
AGACCACGGC TTCCTCGAAT CTTGCGCGAA GCCGCCGGCC TCGGAGGAGG GATTAATCCA     60
GACCCGCCGG GGGGTGTTTT CACATTTCTT CCTCTTCGTG GCTGCTCCTC CTATTAAAAC    120
CATTTTTGGT CCATGGTCAA TGAGAATACG AGGATGTACA TTCCAGAGGA AAACCACCAA    180
GGTTCCAACT ATGGGAGCCC ACGCCCCGCC CATGCCAACA TGAATGCCAA TGCGGCAGCG    240
GGGCTGGCCC CTGAGCACAT CCCCACCCCG GGGGCTGCCC TGTCGTGGCA GGCGGCCATC    300
GACGCAGCCC GGCAGGCTAA GCTGATGGGC AGCGCTGGCA ATGCGACCAT CTCCACAGTC    360
AGCTCCACGC AGCGGAAGCG CCAGCAATAT GGGAAACCCA AGAAGCAGGG CAGCACCACG    420
GCCACACGCC CGCCCCGAGC CCTGCTCTGC CTGACCCTGA AGAACCCCAT CCGGAGGGCC    480
TGCATCAGCA TTGTCGAATG GAAACCATTT GAAATAATTA TTTTACTGAC TATTTTTGCC    540
AATTGTGTGG CCTTAGCGAT CTATATTCCC TTTCCAGAAG ATGATTCCAA CGCCACCAAT    600
TCCAACCTGG AACGAGTGGA ATATCTCTTT CTCATAATTT TTACGGTGGA AGCGTTTTTA    660
AAAGTAATCG CCTATGGACT CCTCTTTCAC CCCAATGCCT ACCTCCGCAA CGGCTGGAAC    720
CTACTAGATT TTATAATTGT GGTTGTGGGG CTTTTTAGTG CAATTTTAGA ACAAGCAACC    780
AAAGCAGATG GGGCAAACGC TCTCGGAGGG AAAGGGGCCG GATTTGATGT GAAGGCGCTG    840
AGGGCCTTCC GCGTGCTGCG CCCCCTGCGG CTGGTGTCCG GAGTCCCAAG TCTCCAGGTG    900
GTCCTGAATT CCATCATCAA GGCCATGGTC CCCCTGCTGC ACATCGCCCT GCTTGTGCTG    960
```

```
TTTGTCATCA TCATCTACGC CATCATCGGC TTGGAGCTCT TCATGGGGAA GATGCACAAG   1020

ACCTGCTACA ACCAGGAGGG CATAGCAG                                      1048
```

(2) INFORMATION FOR SEQ ID NO:31:

(i) SEQUENCE CHARACTERISTICS:
(A) LENGTH: 2338 base pairs
(B) TYPE: nucleic acid
(C) STRANDEDNESS: single
(D) TOPOLOGY: linear (ii) MOLECULE TYPE: DNA (genomic)

(ix) FEATURE:
(D) OTHER INFORMATION: /note= "IMR32 1.38"

(xi) SEQUENCE DESCRIPTION: SEQ ID NO:31:

```
G GAG AAG CCG GCA GTG GGG GAA TCC AAG GAG GAG AAG ATT GAG CTG AAA    49
  Glu Lys Pro Ala Val Gly Glu Ser Lys Glu Glu Lys Ile Glu Leu Lys
    1               5                  10                  15

TCC ATC ACG GCT GAC GGA GAG TCT CCA CCC GCC ACC AAG ATC AAC ATG      97
Ser Ile Thr Ala Asp Gly Glu Ser Pro Pro Ala Thr Lys Ile Asn Met
                20                  25                  30

GAT GAC CTC CAG CCC AAT GAA AAT GAG GAT AAG AGC CCC TAC CCC AAC     145
Asp Asp Leu Gln Pro Asn Glu Asn Glu Asp Lys Ser Pro Tyr Pro Asn
            35                  40                  45

CCA GAA ACT ACA GGA GAA GAG GAT GAG GAG GAG CCA GAG ATG CCT GTC     193
Pro Glu Thr Thr Gly Glu Glu Asp Glu Glu Glu Pro Glu Met Pro Val
        50                  55                  60

GGC CCT CGC CCA CGA CCA CTC TCT GAG CTT CAC CTT AAG GAA AAG GCA     241
Gly Pro Arg Pro Arg Pro Leu Ser Glu Leu His Leu Lys Glu Lys Ala
 65                  70                  75                  80

GTG CCC ATG CCA GAA GCC AGC GCG TTT TTC ATC TTC AGC TCT AAC AAC     289
Val Pro Met Pro Glu Ala Ser Ala Phe Phe Ile Phe Ser Ser Asn Asn
                 85                  90                  95

AGG TTT CGC CTC CAG TGC CAC CGC ATT GTC AAT GAC ACG ATC TTC ACC     337
Arg Phe Arg Leu Gln Cys His Arg Ile Val Asn Asp Thr Ile Phe Thr
            100                 105                 110

AAC CTG ATC CTC TTC TTC ATT CTG CTC AGC AGC ATT TCC CTG GCT GCT     385
Asn Leu Ile Leu Phe Phe Ile Leu Leu Ser Ser Ile Ser Leu Ala Ala
        115                 120                 125

GAG GAC CCG GTC CAG CAC ACC TCC TTC AGG AAC CAT ATT CTG TTT TAT     433
Glu Asp Pro Val Gln His Thr Ser Phe Arg Asn His Ile Leu Phe Tyr
    130                 135                 140

TTT GAT ATT GTT TTT ACC ACC ATT TTC ACC ATT GAA ATT GCT CTG AAG     481
Phe Asp Ile Val Phe Thr Thr Ile Phe Thr Ile Glu Ile Ala Leu Lys
145                 150                 155                 160

ATG ACT GCT TAT GGG GCT TTC TTG CAC AAG GGT TCT TTC TGC CGG AAC     529
Met Thr Ala Tyr Gly Ala Phe Leu His Lys Gly Ser Phe Cys Arg Asn
                165                 170                 175

TAC TTC AAC ATC CTG GAC CTG CTG GTG GTC AGC GTG TCC CTC ATC TCC     577
Tyr Phe Asn Ile Leu Asp Leu Leu Val Val Ser Val Ser Leu Ile Ser
            180                 185                 190

TTT GGC ATC CAG TCC AGT GCA ATC AAT GTC GTG AAG ATC TTG CGA GTC     625
Phe Gly Ile Gln Ser Ser Ala Ile Asn Val Val Lys Ile Leu Arg Val
        195                 200                 205

CTG CGA GTA CTC AGG CCC CTG AGG GCC ATC AAC AGG GCC AAG GGG CTA     673
Leu Arg Val Leu Arg Pro Leu Arg Ala Ile Asn Arg Ala Lys Gly Leu
    210                 215                 220

AAG CAT GTG GTT CAG TGT GTG TTT GTC GCC ATC CGG ACC ATC GGG AAC     721
Lys His Val Val Gln Cys Val Phe Val Ala Ile Arg Thr Ile Gly Asn
225                 230                 235                 240
```

-continued

ATC GTG ATT GTC ACC ACC CTG CTG CAG TTC ATG TTT GCC TGC ATC GGG 769
Ile Val Ile Val Thr Thr Leu Leu Gln Phe Met Phe Ala Cys Ile Gly
245 250 255

GTC CAG CTC TTC AAG GGA AAG CTG TAC ACC TGT TCA GAC AGT TCC AAG 817
Val Gln Leu Phe Lys Gly Lys Leu Tyr Thr Cys Ser Asp Ser Ser Lys
260 265 270

CAG ACA GAG GCG GAA TGC AAG GGC AAC TAC ATC ACG TAC AAA GAC GGG 865
Gln Thr Glu Ala Glu Cys Lys Gly Asn Tyr Ile Thr Tyr Lys Asp Gly
275 280 285

GAG GTT GAC CAC CCC ATC ATC CAA CCC CGC AGC TGG GAG AAC AGC AAG 913
Glu Val Asp His Pro Ile Ile Gln Pro Arg Ser Trp Glu Asn Ser Lys
290 295 300

TTT GAC TTT GAC AAT GTT CTG GCA GCC ATG ATG GCC CTC TTC ACC GTC 961
Phe Asp Phe Asp Asn Val Leu Ala Ala Met Met Ala Leu Phe Thr Val
305 310 315 320

TCC ACC TTC GAA GGG TGG CCA GAG CTG CTG TAC CGC TCC ATC GAC TCC 1009
Ser Thr Phe Glu Gly Trp Pro Glu Leu Leu Tyr Arg Ser Ile Asp Ser
325 330 335

CAC ACG GAA GAC AAG GGC CCC ATC TAC AAC TAC CGT GTG GAG ATC TCC 1057
His Thr Glu Asp Lys Gly Pro Ile Tyr Asn Tyr Arg Val Glu Ile Ser
340 345 350

ATC TTC TTC ATC ATC TAC ATC ATC ATC ATC GCC TTC TTC ATG ATG AAC 1105
Ile Phe Phe Ile Ile Tyr Ile Ile Ile Ile Ala Phe Phe Met Met Asn
355 360 365

ATC TTC GTG GGC TTC GTC ATC GTC ACC TTT CAG GAG CAG GGG GAG CAG 1153
Ile Phe Val Gly Phe Val Ile Val Thr Phe Gln Glu Gln Gly Glu Gln
370 375 380

GAG TAC AAG AAC TGT GAG CTG GAC AAG AAC CAG CGA CAG TGC GTG GAA 1201
Glu Tyr Lys Asn Cys Glu Leu Asp Lys Asn Gln Arg Gln Cys Val Glu
385 390 395 400

TAC GCC CTC AAG GCC CGG CCC CTG CGG AGG TAC ATC CCC AAG AAC CAG 1249
Tyr Ala Leu Lys Ala Arg Pro Leu Arg Arg Tyr Ile Pro Lys Asn Gln
405 410 415

CAC CAG TAC AAA GTG TGG TAC GTG GTC AAC TCC ACC TAC TTC GAG TAC 1297
His Gln Tyr Lys Val Trp Tyr Val Val Asn Ser Thr Tyr Phe Glu Tyr
420 425 430

CTG ATG TTC GTC CTC ATC CTG CTC AAC ACC ATC TGC CTG GCC ATG CAG 1345
Leu Met Phe Val Leu Ile Leu Leu Asn Thr Ile Cys Leu Ala Met Gln
435 440 445

CAC TAC GGC CAG AGC TGC CTG TTC AAA ATC GCC ATG AAC ATC CTC AAC 1393
His Tyr Gly Gln Ser Cys Leu Phe Lys Ile Ala Met Asn Ile Leu Asn
450 455 460

ATG CTC TTC ACT GGC CTC TTC ACC GTG GAG ATG ATC CTG AAG CTC ATT 1441
Met Leu Phe Thr Gly Leu Phe Thr Val Glu Met Ile Leu Lys Leu Ile
465 470 475 480

GCC TTC AAA CCC AAG GGT TAC TTT AGT GAT CCC TGG AAT GTT TTT GAC 1489
Ala Phe Lys Pro Lys Gly Tyr Phe Ser Asp Pro Trp Asn Val Phe Asp
485 490 495

TTC CTC ATC GTA ATT GGC AGC ATA ATT GAC GTC ATT CTC AGT GAG ACT 1537
Phe Leu Ile Val Ile Gly Ser Ile Ile Asp Val Ile Leu Ser Glu Thr
500 505 510

AAT CCA GCT GAA CAT ACC CAA TGC TCT CCC TCT ATG AAC GCA GAG GAA 1585
Asn Pro Ala Glu His Thr Gln Cys Ser Pro Ser Met Asn Ala Glu Glu
515 520 525

AAC TCC CGC ATC TCC ATC ACC TTC TTC CGC CTG TTC CGG GTC ATG CGT 1633
Asn Ser Arg Ile Ser Ile Thr Phe Phe Arg Leu Phe Arg Val Met Arg
530 535 540

CTG GTG AAG CTG CTG AGC CGT GGG GAG GGC ATC CGG ACG CTG CTG TGG 1681
Leu Val Lys Leu Leu Ser Arg Gly Glu Gly Ile Arg Thr Leu Leu Trp
545 550 555 560

-continued

```
ACC TTC ATC AAG TCC TTC CAG GCC CTG CCC TAT GTG GCC CTC CTG ATC    1729
Thr Phe Ile Lys Ser Phe Gln Ala Leu Pro Tyr Val Ala Leu Leu Ile
                565                 570                 575

GTG ATG CTG TTC TTC ATC TAC GCG GTG ATC GGG ATG CAG GTG TTT GGG    1777
Val Met Leu Phe Phe Ile Tyr Ala Val Ile Gly Met Gln Val Phe Gly
            580                 585                 590

AAA ATT GCC CTG AAT GAT ACC ACA GAG ATC AAC CGG AAC AAC AAC TTT    1825
Lys Ile Ala Leu Asn Asp Thr Thr Glu Ile Asn Arg Asn Asn Asn Phe
        595                 600                 605

CAG ACC TTC CCC CAG GCC GTG CTG CTC CTC TTC AGG TGT GCC ACC GGG    1873
Gln Thr Phe Pro Gln Ala Val Leu Leu Leu Phe Arg Cys Ala Thr Gly
    610                 615                 620

GAG GCC TGG CAG GAC ATC ATG CTG GCC TGC ATG CCA GGC AAG AAG TGT    1921
Glu Ala Trp Gln Asp Ile Met Leu Ala Cys Met Pro Gly Lys Lys Cys
625                 630                 635                 640

GCC CCA GAG TCC GAG CCC AGC AAC AGC ACG GAG GGT GAA ACA CCC TGT    1969
Ala Pro Glu Ser Glu Pro Ser Asn Ser Thr Glu Gly Glu Thr Pro Cys
                645                 650                 655

GGT AGC AGC TTT GCT GTC TTC TAC TTC ATC AGC TTC TAC ATG CGC TGT    2017
Gly Ser Ser Phe Ala Val Phe Tyr Phe Ile Ser Phe Tyr Met Arg Cys
            660                 665                 670

GCC TTC CTG ATC ATC AAC CTC TTT GTA GCT GTC ATC ATG GAC AAC TTT    2065
Ala Phe Leu Ile Ile Asn Leu Phe Val Ala Val Ile Met Asp Asn Phe
        675                 680                 685

GAC TAC CTG ACA AGG GAC TGG TCC ATC CTT GGT CCC CAC CAC CTG GAT    2113
Asp Tyr Leu Thr Arg Asp Trp Ser Ile Leu Gly Pro His His Leu Asp
    690                 695                 700

GAG TTT AAA AGA ATC TGG GCA GAG TAT GAC CCT GAA GCC AAG GGT CGT    2161
Glu Phe Lys Arg Ile Trp Ala Glu Tyr Asp Pro Glu Ala Lys Gly Arg
705                 710                 715                 720

ATC AAA CAC CTG GAT GTG GTG ACC CTC CTC CGG CGG ATT CAG CCG CCA    2209
Ile Lys His Leu Asp Val Val Thr Leu Leu Arg Arg Ile Gln Pro Pro
                725                 730                 735

CTA GGT TTT GGG AAG CTG TGC CCT CAC CGC GTG GCT TGC AAA CGC CAC    2257
Leu Gly Phe Gly Lys Leu Cys Pro His Arg Val Ala Cys Lys Arg His
            740                 745                 750

TAT TTC TGT GAT GCA TGG AAT ACA TTT GAC GCC TTG ATT GTT GTG GGT    2305
Tyr Phe Cys Asp Ala Trp Asn Thr Phe Asp Ala Leu Ile Val Val Gly
        755                 760                 765

AGC ATT GTT GAT ATA GCA ATC ACC GAG GTA AAC                        2338
Ser Ile Val Asp Ile Ala Ile Thr Glu Val Asn
    770                 775
```

( 2 ) INFORMATION FOR SEQ ID NO:32:

( i ) SEQUENCE CHARACTERISTICS:
( A ) LENGTH: 3636 base pairs
( B ) TYPE: nucleic acid
( C ) STRANDEDNESS: double
( D ) TOPOLOGY: linear ( i i ) MOLECULE TYPE: DNA (genomic)

( i x ) FEATURE:
( A ) NAME/KEY: CDS
( B ) LOCATION: 35..3346
( D ) OTHER INFORMATION: /standard_name= "Alpha-2a"

( i x ) FEATURE:
( A ) NAME/KEY: 5'UTR
( B ) LOCATION: 1..34

( i x ) FEATURE:
( A ) NAME/KEY: 3'UTR
( B ) LOCATION: 3347..3636

-continued ( x i ) SEQUENCE DESCRIPTION: SEQ ID NO:32:

```
GCGGGGGAGG GGGCATTGAT CTTCGATCGC GAAG ATG GCT GCT GGC TGC CTG     52
                                      Met Ala Ala Gly Cys Leu
                                       1                   5

CTG GCC TTG ACT CTG ACA CTT TTC CAA TCT TTG CTC ATC GGC CCC TCG     100
Leu Ala Leu Thr Leu Thr Leu Phe Gln Ser Leu Leu Ile Gly Pro Ser
             10                  15                  20

TCG GAG GAG CCG TTC CCT TCG GCC GTC ACT ATC AAA TCA TGG GTG GAT     148
Ser Glu Glu Pro Phe Pro Ser Ala Val Thr Ile Lys Ser Trp Val Asp
         25                  30                  35

AAG ATG CAA GAA GAC CTT GTC ACA CTG GCA AAA ACA GCA AGT GGA GTC     196
Lys Met Gln Glu Asp Leu Val Thr Leu Ala Lys Thr Ala Ser Gly Val
     40                  45                  50

AAT CAG CTT GTT GAT ATT TAT GAG AAA TAT CAA GAT TTG TAT ACT GTG     244
Asn Gln Leu Val Asp Ile Tyr Glu Lys Tyr Gln Asp Leu Tyr Thr Val
 55                  60                  65                  70

GAA CCA AAT AAT GCA CGC CAG CTG GTA GAA ATT GCA GCC AGG GAT ATT     292
Glu Pro Asn Asn Ala Arg Gln Leu Val Glu Ile Ala Ala Arg Asp Ile
                 75                  80                  85

GAG AAA CTT CTG AGC AAC AGA TCT AAA GCC CTG GTG AGC CTG GCA TTG     340
Glu Lys Leu Leu Ser Asn Arg Ser Lys Ala Leu Val Ser Leu Ala Leu
             90                  95                 100

GAA GCG GAG AAA GTT CAA GCA GCT CAC CAG TGG AGA GAA GAT TTT GCA     388
Glu Ala Glu Lys Val Gln Ala Ala His Gln Trp Arg Glu Asp Phe Ala
        105                 110                 115

AGC AAT GAA GTT GTC TAC TAC AAT GCA AAG GAT GAT CTC GAT CCT GAG     436
Ser Asn Glu Val Val Tyr Tyr Asn Ala Lys Asp Asp Leu Asp Pro Glu
    120                 125                 130

AAA AAT GAC AGT GAG CCA GGC AGC CAG AGG ATA AAA CCT GTT TTC ATT     484
Lys Asn Asp Ser Glu Pro Gly Ser Gln Arg Ile Lys Pro Val Phe Ile
135                 140                 145                 150

GAA GAT GCT AAT TTT GGA CGA CAA ATA TCT TAT CAG CAC GCA GCA GTC     532
Glu Asp Ala Asn Phe Gly Arg Gln Ile Ser Tyr Gln His Ala Ala Val
                155                 160                 165

CAT ATT CCT ACT GAC ATC TAT GAG GGC TCA ACA ATT GTG TTA AAT GAA     580
His Ile Pro Thr Asp Ile Tyr Glu Gly Ser Thr Ile Val Leu Asn Glu
            170                 175                 180

CTC AAC TGG ACA AGT GCC TTA GAT GAA GTT TTC AAA AAG AAT CGC GAG     628
Leu Asn Trp Thr Ser Ala Leu Asp Glu Val Phe Lys Lys Asn Arg Glu
        185                 190                 195

GAA GAC CCT TCA TTA TTG TGG CAG GTT TTT GGC AGT GCC ACT GGC CTA     676
Glu Asp Pro Ser Leu Leu Trp Gln Val Phe Gly Ser Ala Thr Gly Leu
    200                 205                 210

GCT CGA TAT TAT CCA GCT TCA CCA TGG GTT GAT AAT AGT AGA ACT CCA     724
Ala Arg Tyr Tyr Pro Ala Ser Pro Trp Val Asp Asn Ser Arg Thr Pro
215                 220                 225                 230

AAT AAG ATT GAC CTT TAT GAT GTA CGC AGA AGA CCA TGG TAC ATC CAA     772
Asn Lys Ile Asp Leu Tyr Asp Val Arg Arg Arg Pro Trp Tyr Ile Gln
                235                 240                 245

GGA GCT GCA TCT CCT AAA GAC ATG CTT ATT CTG GTG GAT GTG AGT GGA     820
Gly Ala Ala Ser Pro Lys Asp Met Leu Ile Leu Val Asp Val Ser Gly
            250                 255                 260

AGT GTT AGT GGA TTG ACA CTT AAA CTG ATC CGA ACA TCT GTC TCC GAA     868
Ser Val Ser Gly Leu Thr Leu Lys Leu Ile Arg Thr Ser Val Ser Glu
        265                 270                 275

ATG TTA GAA ACC CTC TCA GAT GAT GAT TTC GTG AAT GTA GCT TCA TTT     916
Met Leu Glu Thr Leu Ser Asp Asp Asp Phe Val Asn Val Ala Ser Phe
    280                 285                 290

AAC AGC AAT GCT CAG GAT GTA AGC TGT TTT CAG CAC CTT GTC CAA GCA     964
Asn Ser Asn Ala Gln Asp Val Ser Cys Phe Gln His Leu Val Gln Ala
```

-continued

```
295                 300                 305                 310

AAT GTA AGA AAT AAA AAA GTG TTG AAA GAC GCG GTG AAT AAT ATC ACA     1012
Asn Val Arg Asn Lys Lys Val Leu Lys Asp Ala Val Asn Asn Ile Thr
                315                 320                 325

GCC AAA GGA ATT ACA GAT TAT AAG AAG GGC TTT AGT TTT GCT TTT GAA     1060
Ala Lys Gly Ile Thr Asp Tyr Lys Lys Gly Phe Ser Phe Ala Phe Glu
            330                 335                 340

CAG CTG CTT AAT TAT AAT GTT TCC AGA GCA AAC TGC AAT AAG ATT ATT     1108
Gln Leu Leu Asn Tyr Asn Val Ser Arg Ala Asn Cys Asn Lys Ile Ile
        345                 350                 355

ATG CTA TTC ACG GAT GGA GGA GAA GAG AGA GCC CAG GAG ATA TTT AAC     1156
Met Leu Phe Thr Asp Gly Gly Glu Glu Arg Ala Gln Glu Ile Phe Asn
    360                 365                 370

AAA TAC AAT AAA GAT AAA AAA GTA CGT GTA TTC AGG TTT TCA GTT GGT     1204
Lys Tyr Asn Lys Asp Lys Lys Val Arg Val Phe Arg Phe Ser Val Gly
375                 380                 385                 390

CAA CAC AAT TAT GAG AGA GGA CCT ATT CAG TGG ATG GCC TGT GAA AAC     1252
Gln His Asn Tyr Glu Arg Gly Pro Ile Gln Trp Met Ala Cys Glu Asn
                395                 400                 405

AAA GGT TAT TAT TAT GAA ATT CCT TCC ATT GGT GCA ATA AGA ATC AAT     1300
Lys Gly Tyr Tyr Tyr Glu Ile Pro Ser Ile Gly Ala Ile Arg Ile Asn
            410                 415                 420

ACT CAG GAA TAT TTG GAT GTT TTG GGA AGA CCA ATG GTT TTA GCA GGA     1348
Thr Gln Glu Tyr Leu Asp Val Leu Gly Arg Pro Met Val Leu Ala Gly
        425                 430                 435

GAC AAA GCT AAG CAA GTC CAA TGG ACA AAT GTG TAC CTG GAT GCA TTG     1396
Asp Lys Ala Lys Gln Val Gln Trp Thr Asn Val Tyr Leu Asp Ala Leu
    440                 445                 450

GAA CTG GGA CTT GTC ATT ACT GGA ACT CTT CCG GTC TTC AAC ATA ACC     1444
Glu Leu Gly Leu Val Ile Thr Gly Thr Leu Pro Val Phe Asn Ile Thr
455                 460                 465                 470

GGC CAA TTT GAA AAT AAG ACA AAC TTA AAG AAC CAG CTG ATT CTT GGT     1492
Gly Gln Phe Glu Asn Lys Thr Asn Leu Lys Asn Gln Leu Ile Leu Gly
                475                 480                 485

GTG ATG GGA GTA GAT GTG TCT TTG GAA GAT ATT AAA AGA CTG ACA CCA     1540
Val Met Gly Val Asp Val Ser Leu Glu Asp Ile Lys Arg Leu Thr Pro
            490                 495                 500

CGT TTT ACA CTG TGC CCC AAT GGG TAT TAC TTT GCA ATC GAT CCT AAT     1588
Arg Phe Thr Leu Cys Pro Asn Gly Tyr Tyr Phe Ala Ile Asp Pro Asn
        505                 510                 515

GGT TAT GTT TTA TTA CAT CCA AAT CTT CAG CCA AAG CCT ATT GGT GTA     1636
Gly Tyr Val Leu Leu His Pro Asn Leu Gln Pro Lys Pro Ile Gly Val
    520                 525                 530

GGT ATA CCA ACA ATT AAT TTA AGA AAA AGG AGA CCC AAT ATC CAG AAC     1684
Gly Ile Pro Thr Ile Asn Leu Arg Lys Arg Arg Pro Asn Ile Gln Asn
535                 540                 545                 550

CCC AAA TCT CAG GAG CCA GTA ACA TTG GAT TTC CTT GAT GCA GAG TTA     1732
Pro Lys Ser Gln Glu Pro Val Thr Leu Asp Phe Leu Asp Ala Glu Leu
                555                 560                 565

GAG AAT GAT ATT AAA GTG GAG ATT CGA AAT AAG ATG ATT GAT GGG GAA     1780
Glu Asn Asp Ile Lys Val Glu Ile Arg Asn Lys Met Ile Asp Gly Glu
            570                 575                 580

AGT GGA GAA AAA ACA TTC AGA ACT CTG GTT AAA TCT CAA GAT GAG AGA     1828
Ser Gly Glu Lys Thr Phe Arg Thr Leu Val Lys Ser Gln Asp Glu Arg
        585                 590                 595

TAT ATT GAC AAA GGA AAC AGG ACA TAC ACA TGG ACA CCT GTC AAT GGC     1876
Tyr Ile Asp Lys Gly Asn Arg Thr Tyr Thr Trp Thr Pro Val Asn Gly
    600                 605                 610

ACA GAT TAC AGT TTG GCC TTG GTA TTA CCA ACC TAC AGT TTT TAC TAT     1924
Thr Asp Tyr Ser Leu Ala Leu Val Leu Pro Thr Tyr Ser Phe Tyr Tyr
```

-continued 615 620 625 630

ATA AAA GCC AAA CTA GAA GAG ACA ATA ACT CAG GCC AGA TAT TCG GAA 1972
Ile Lys Ala Lys Leu Glu Glu Thr Ile Thr Gln Ala Arg Tyr Ser Glu
635 640 645

ACC CTG AAG CCA GAT AAT TTT GAA GAA TCT GGC TAT ACA TTC ATA GCA 2020
Thr Leu Lys Pro Asp Asn Phe Glu Glu Ser Gly Tyr Thr Phe Ile Ala
650 655 660

CCA AGA GAT TAC TGC AAT GAC CTG AAA ATA TCG GAT AAT AAC ACT GAA 2068
Pro Arg Asp Tyr Cys Asn Asp Leu Lys Ile Ser Asp Asn Asn Thr Glu
665 670 675

TTT CTT TTA AAT TTC AAC GAG TTT ATT GAT AGA AAA ACT CCA AAC AAC 2116
Phe Leu Leu Asn Phe Asn Glu Phe Ile Asp Arg Lys Thr Pro Asn Asn
680 685 690

CCA TCA TGT AAC GCG GAT TTG ATT AAT AGA GTC TTG CTT GAT GCA GGC 2164
Pro Ser Cys Asn Ala Asp Leu Ile Asn Arg Val Leu Leu Asp Ala Gly
695 700 705 710

TTT ACA AAT GAA CTT GTC CAA AAT TAC TGG AGT AAG CAG AAA AAT ATC 2212
Phe Thr Asn Glu Leu Val Gln Asn Tyr Trp Ser Lys Gln Lys Asn Ile
715 720 725

AAG GGA GTG AAA GCA CGA TTT GTT GTG ACT GAT GGT GGG ATT ACC AGA 2260
Lys Gly Val Lys Ala Arg Phe Val Val Thr Asp Gly Gly Ile Thr Arg
730 735 740

GTT TAT CCC AAA GAG GCT GGA GAA AAT TGG CAA GAA AAC CCA GAG ACA 2308
Val Tyr Pro Lys Glu Ala Gly Glu Asn Trp Gln Glu Asn Pro Glu Thr
745 750 755

TAT GAG GAC AGC TTC TAT AAA AGG AGC CTA GAT AAT GAT AAC TAT GTT 2356
Tyr Glu Asp Ser Phe Tyr Lys Arg Ser Leu Asp Asn Asp Asn Tyr Val
760 765 770

TTC ACT GCT CCC TAC TTT AAC AAA AGT GGA CCT GGT GCC TAT GAA TCG 2404
Phe Thr Ala Pro Tyr Phe Asn Lys Ser Gly Pro Gly Ala Tyr Glu Ser
775 780 785 790

GGC ATT ATG GTA AGC AAA GCT GTA GAA ATA TAT ATT CAA GGG AAA CTT 2452
Gly Ile Met Val Ser Lys Ala Val Glu Ile Tyr Ile Gln Gly Lys Leu
795 800 805

CTT AAA CCT GCA GTT GTT GGA ATT AAA ATT GAT GTA AAT TCC TGG ATA 2500
Leu Lys Pro Ala Val Val Gly Ile Lys Ile Asp Val Asn Ser Trp Ile
810 815 820

GAG AAT TTC ACC AAA ACC TCA ATC AGA GAT CCG TGT GCT GGT CCA GTT 2548
Glu Asn Phe Thr Lys Thr Ser Ile Arg Asp Pro Cys Ala Gly Pro Val
825 830 835

TGT GAC TGC AAA AGA AAC AGT GAC GTA ATG GAT TGT GTG ATT CTG GAT 2596
Cys Asp Cys Lys Arg Asn Ser Asp Val Met Asp Cys Val Ile Leu Asp
840 845 850

GAT GGT GGG TTT CTT CTG ATG GCA AAT CAT GAT GAT TAT ACT AAT CAG 2644
Asp Gly Gly Phe Leu Leu Met Ala Asn His Asp Asp Tyr Thr Asn Gln
855 860 865 870

ATT GGA AGA TTT TTT GGA GAG ATT GAT CCC AGC TTG ATG AGA CAC CTG 2692
Ile Gly Arg Phe Phe Gly Glu Ile Asp Pro Ser Leu Met Arg His Leu
875 880 885

GTT AAT ATA TCA GTT TAT GCT TTT AAC AAA TCT TAT GAT TAT CAG TCA 2740
Val Asn Ile Ser Val Tyr Ala Phe Asn Lys Ser Tyr Asp Tyr Gln Ser
890 895 900

GTA TGT GAG CCC GGT GCT GCA CCA AAA CAA GGA GCA GGA CAT CGC TCA 2788
Val Cys Glu Pro Gly Ala Ala Pro Lys Gln Gly Ala Gly His Arg Ser
905 910 915

GCA TAT GTG CCA TCA GTA GCA GAC ATA TTA CAA ATT GGC TGG TGG GCC 2836
Ala Tyr Val Pro Ser Val Ala Asp Ile Leu Gln Ile Gly Trp Trp Ala
920 925 930

ACT GCT GCT GCC TGG TCT ATT CTA CAG CAG TTT CTC TTG AGT TTG ACC 2884
Thr Ala Ala Ala Trp Ser Ile Leu Gln Gln Phe Leu Leu Ser Leu Thr

-continued

```
935                      940                      945                      950

TTT CCA CGA CTC CTT GAG GCA GTT GAG ATG GAG GAT GAT GAC TTC ACG     2932
Phe Pro Arg Leu Leu Glu Ala Val Glu Met Glu Asp Asp Asp Phe Thr
                955                      960                      965

GCC TCC CTG TCC AAG CAG AGC TGC ATT ACT GAA CAA ACC CAG TAT TTC     2980
Ala Ser Leu Ser Lys Gln Ser Cys Ile Thr Glu Gln Thr Gln Tyr Phe
            970                      975                      980

TTC GAT AAC GAC AGT AAA TCA TTC AGT GGT GTA TTA GAC TGT GGA AAC     3028
Phe Asp Asn Asp Ser Lys Ser Phe Ser Gly Val Leu Asp Cys Gly Asn
        985                      990                      995

TGT TCC AGA ATC TTT CAT GGA GAA AAG CTT ATG AAC ACC AAC TTA ATA     3076
Cys Ser Arg Ile Phe His Gly Glu Lys Leu Met Asn Thr Asn Leu Ile
    1000                     1005                     1010

TTC ATA ATG GTT GAG AGC AAA GGG ACA TGT CCA TGT GAC ACA CGA CTG     3124
Phe Ile Met Val Glu Ser Lys Gly Thr Cys Pro Cys Asp Thr Arg Leu
1015                     1020                     1025                     1030

CTC ATA CAA GCG GAG CAG ACT TCT GAC GGT CCA AAT CCT TGT GAC ATG     3172
Leu Ile Gln Ala Glu Gln Thr Ser Asp Gly Pro Asn Pro Cys Asp Met
                1035                     1040                     1045

GTT AAG CAA CCT AGA TAC CGA AAA GGG CCT GAT GTC TGC TTT GAT AAC     3220
Val Lys Gln Pro Arg Tyr Arg Lys Gly Pro Asp Val Cys Phe Asp Asn
            1050                     1055                     1060

AAT GTC TTG GAG GAT TAT ACT GAC TGT GGT GGT GTT TCT GGA TTA AAT     3268
Asn Val Leu Glu Asp Tyr Thr Asp Cys Gly Gly Val Ser Gly Leu Asn
        1065                     1070                     1075

CCC TCC CTG TGG TAT ATC ATT GGA ATC CAG TTT CTA CTA CTT TGG CTG     3316
Pro Ser Leu Trp Tyr Ile Ile Gly Ile Gln Phe Leu Leu Leu Trp Leu
    1080                     1085                     1090

GTA TCT GGC AGC ACA CAC CGG CTG TTA TGACCTTCTA AAAACCAAAT           3363
Val Ser Gly Ser Thr His Arg Leu Leu
1095                     1100

CTGCATAGTT AAACTCCAGA CCCTGCCAAA ACATGAGCCC TGCCCTCAAT TACAGTAACG    3423

TAGGGTCAGC TATAAAATCA GACAAACATT AGCTGGGCCT GTTCCATGGC ATAACACTAA    3483

GGCGCAGACT CCTAAGGCAC CCACTGGCTG CATGTCAGGG TGTCAGATCC TTAAACGTGT    3543

GTGAATGCTG CATCATCTAT GTGTAACATC AAAGCAAAAT CCTATACGTG TCCTCTATTG    3603

GAAAATTTGG GCGTTTGTTG TTGCATTGTT GGT                                 3636
```

( 2 ) INFORMATION FOR SEQ ID NO:33:

( i ) SEQUENCE CHARACTERISTICS:
( A ) LENGTH: 3600 base pairs
( B ) TYPE: nucleic acid
( C ) STRANDEDNESS: double
( D ) TOPOLOGY: linear ( i i ) MOLECULE TYPE: DNA (genomic)

( i x ) FEATURE:
( A ) NAME/KEY: CDS
( B ) LOCATION: 35..3310
( D ) OTHER INFORMATION: /standard_name= "Alpha-2b"

( i x ) FEATURE:
( A ) NAME/KEY: 5'UTR
( B ) LOCATION: 1..34

( i x ) FEATURE:
( A ) NAME/KEY: 3'UTR
( B ) LOCATION: 3308..3600

( x i ) SEQUENCE DESCRIPTION: SEQ ID NO:33:

```
GCGGGGGAGG GGGCATTGAT CTTCGATCGC GAAG ATG GCT GCT GGC TGC CTG        52
                                      Met Ala Ala Gly Cys Leu
```

-continued 1 5

CTG GCC TTG ACT CTG ACA CTT TTC CAA TCT TTG CTC ATC GGC CCC TCG 100
Leu Ala Leu Thr Leu Thr Leu Phe Gln Ser Leu Leu Ile Gly Pro Ser
10 15 20

TCG GAG GAG CCG TTC CCT TCG GCC GTC ACT ATC AAA TCA TGG GTG GAT 148
Ser Glu Glu Pro Phe Pro Ser Ala Val Thr Ile Lys Ser Trp Val Asp
25 30 35

AAG ATG CAA GAA GAC CTT GTC ACA CTG GCA AAA ACA GCA AGT GGA GTC 196
Lys Met Gln Glu Asp Leu Val Thr Leu Ala Lys Thr Ala Ser Gly Val
40 45 50

AAT CAG CTT GTT GAT ATT TAT GAG AAA TAT CAA GAT TTG TAT ACT GTG 244
Asn Gln Leu Val Asp Ile Tyr Glu Lys Tyr Gln Asp Leu Tyr Thr Val
55 60 65 70

GAA CCA AAT AAT GCA CGC CAG CTG GTA GAA ATT GCA GCC AGG GAT ATT 292
Glu Pro Asn Asn Ala Arg Gln Leu Val Glu Ile Ala Ala Arg Asp Ile
75 80 85

GAG AAA CTT CTG AGC AAC AGA TCT AAA GCC CTG GTG AGC CTG GCA TTG 340
Glu Lys Leu Leu Ser Asn Arg Ser Lys Ala Leu Val Ser Leu Ala Leu
90 95 100

GAA GCG GAG AAA GTT CAA GCA GCT CAC CAG TGG AGA GAA GAT TTT GCA 388
Glu Ala Glu Lys Val Gln Ala Ala His Gln Trp Arg Glu Asp Phe Ala
105 110 115

AGC AAT GAA GTT GTC TAC TAC AAT GCA AAG GAT GAT CTC GAT CCT GAG 436
Ser Asn Glu Val Val Tyr Tyr Asn Ala Lys Asp Asp Leu Asp Pro Glu
120 125 130

AAA AAT GAC AGT GAG CCA GGC AGC CAG AGG ATA AAA CCT GTT TTC ATT 484
Lys Asn Asp Ser Glu Pro Gly Ser Gln Arg Ile Lys Pro Val Phe Ile
135 140 145 150

GAA GAT GCT AAT TTT GGA CGA CAA ATA TCT TAT CAG CAC GCA GCA GTC 532
Glu Asp Ala Asn Phe Gly Arg Gln Ile Ser Tyr Gln His Ala Ala Val
155 160 165

CAT ATT CCT ACT GAC ATC TAT GAG GGC TCA ACA ATT GTG TTA AAT GAA 580
His Ile Pro Thr Asp Ile Tyr Glu Gly Ser Thr Ile Val Leu Asn Glu
170 175 180

CTC AAC TGG ACA AGT GCC TTA GAT GAA GTT TTC AAA AAG AAT CGC GAG 628
Leu Asn Trp Thr Ser Ala Leu Asp Glu Val Phe Lys Lys Asn Arg Glu
185 190 195

GAA GAC CCT TCA TTA TTG TGG CAG GTT TTT GGC AGT GCC ACT GGC CTA 676
Glu Asp Pro Ser Leu Leu Trp Gln Val Phe Gly Ser Ala Thr Gly Leu
200 205 210

GCT CGA TAT TAT CCA GCT TCA CCA TGG GTT GAT AAT AGT AGA ACT CCA 724
Ala Arg Tyr Tyr Pro Ala Ser Pro Trp Val Asp Asn Ser Arg Thr Pro
215 220 225 230

AAT AAG ATT GAC CTT TAT GAT GTA CGC AGA AGA CCA TGG TAC ATC CAA 772
Asn Lys Ile Asp Leu Tyr Asp Val Arg Arg Arg Pro Trp Tyr Ile Gln
235 240 245

GGA GCT GCA TCT CCT AAA GAC ATG CTT ATT CTG GTG GAT GTG AGT GGA 820
Gly Ala Ala Ser Pro Lys Asp Met Leu Ile Leu Val Asp Val Ser Gly
250 255 260

AGT GTT AGT GGA TTG ACA CTT AAA CTG ATC CGA ACA TCT GTC TCC GAA 868
Ser Val Ser Gly Leu Thr Leu Lys Leu Ile Arg Thr Ser Val Ser Glu
265 270 275

ATG TTA GAA ACC CTC TCA GAT GAT GAT TTC GTG AAT GTA GCT TCA TTT 916
Met Leu Glu Thr Leu Ser Asp Asp Asp Phe Val Asn Val Ala Ser Phe
280 285 290

AAC AGC AAT GCT CAG GAT GTA AGC TGT TTT CAG CAC CTT GTC CAA GCA 964
Asn Ser Asn Ala Gln Asp Val Ser Cys Phe Gln His Leu Val Gln Ala
295 300 305 310

AAT GTA AGA AAT AAA AAA GTG TTG AAA GAC GCG GTG AAT AAT ATC ACA 1012
Asn Val Arg Asn Lys Lys Val Leu Lys Asp Ala Val Asn Asn Ile Thr

-continued 315 320 325

GCC AAA GGA ATT ACA GAT TAT AAG AAG GGC TTT AGT TTT GCT TTT GAA 1060
Ala Lys Gly Ile Thr Asp Tyr Lys Lys Gly Phe Ser Phe Ala Phe Glu
330 335 340

CAG CTG CTT AAT TAT AAT GTT TCC AGA GCA AAC TGC AAT AAG ATT ATT 1108
Gln Leu Leu Asn Tyr Asn Val Ser Arg Ala Asn Cys Asn Lys Ile Ile
345 350 355

ATG CTA TTC ACG GAT GGA GGA GAA GAG AGA GCC CAG GAG ATA TTT AAC 1156
Met Leu Phe Thr Asp Gly Gly Glu Glu Arg Ala Gln Glu Ile Phe Asn
360 365 370

AAA TAC AAT AAA GAT AAA AAA GTA CGT GTA TTC AGG TTT TCA GTT GGT 1204
Lys Tyr Asn Lys Asp Lys Lys Val Arg Val Phe Arg Phe Ser Val Gly
375 380 385 390

CAA CAC AAT TAT GAG AGA GGA CCT ATT CAG TGG ATG GCC TGT GAA AAC 1252
Gln His Asn Tyr Glu Arg Gly Pro Ile Gln Trp Met Ala Cys Glu Asn
395 400 405

AAA GGT TAT TAT TAT GAA ATT CCT TCC ATT GGT GCA ATA AGA ATC AAT 1300
Lys Gly Tyr Tyr Tyr Glu Ile Pro Ser Ile Gly Ala Ile Arg Ile Asn
410 415 420

ACT CAG GAA TAT TTG GAT GTT TTG GGA AGA CCA ATG GTT TTA GCA GGA 1348
Thr Gln Glu Tyr Leu Asp Val Leu Gly Arg Pro Met Val Leu Ala Gly
425 430 435

GAC AAA GCT AAG CAA GTC CAA TGG ACA AAT GTG TAC CTG GAT GCA TTG 1396
Asp Lys Ala Lys Gln Val Gln Trp Thr Asn Val Tyr Leu Asp Ala Leu
440 445 450

GAA CTG GGA CTT GTC ATT ACT GGA ACT CTT CCG GTC TTC AAC ATA ACC 1444
Glu Leu Gly Leu Val Ile Thr Gly Thr Leu Pro Val Phe Asn Ile Thr
455 460 465 470

GGC CAA TTT GAA AAT AAG ACA AAC TTA AAG AAC CAG CTG ATT CTT GGT 1492
Gly Gln Phe Glu Asn Lys Thr Asn Leu Lys Asn Gln Leu Ile Leu Gly
475 480 485

GTG ATG GGA GTA GAT GTG TCT TTG GAA GAT ATT AAA AGA CTG ACA CCA 1540
Val Met Gly Val Asp Val Ser Leu Glu Asp Ile Lys Arg Leu Thr Pro
490 495 500

CGT TTT ACA CTG TGC CCC AAT GGG TAT TAC TTT GCA ATC GAT CCT AAT 1588
Arg Phe Thr Leu Cys Pro Asn Gly Tyr Tyr Phe Ala Ile Asp Pro Asn
505 510 515

GGT TAT GTT TTA TTA CAT CCA AAT CTT CAG CCA AAG AAC CCC AAA TCT 1636
Gly Tyr Val Leu Leu His Pro Asn Leu Gln Pro Lys Asn Pro Lys Ser
520 525 530

CAG GAG CCA GTA ACA TTG GAT TTC CTT GAT GCA GAG TTA GAG AAT GAT 1684
Gln Glu Pro Val Thr Leu Asp Phe Leu Asp Ala Glu Leu Glu Asn Asp
535 540 545 550

ATT AAA GTG GAG ATT CGA AAT AAG ATG ATT GAT GGG GAA AGT GGA GAA 1732
Ile Lys Val Glu Ile Arg Asn Lys Met Ile Asp Gly Glu Ser Gly Glu
555 560 565

AAA ACA TTC AGA ACT CTG GTT AAA TCT CAA GAT GAG AGA TAT ATT GAC 1780
Lys Thr Phe Arg Thr Leu Val Lys Ser Gln Asp Glu Arg Tyr Ile Asp
570 575 580

AAA GGA AAC AGG ACA TAC ACA TGG ACA CCT GTC AAT GGC ACA GAT TAC 1828
Lys Gly Asn Arg Thr Tyr Thr Trp Thr Pro Val Asn Gly Thr Asp Tyr
585 590 595

AGT TTG GCC TTG GTA TTA CCA ACC TAC AGT TTT TAC TAT ATA AAA GCC 1876
Ser Leu Ala Leu Val Leu Pro Thr Tyr Ser Phe Tyr Tyr Ile Lys Ala
600 605 610

AAA CTA GAA GAG ACA ATA ACT CAG GCC AGA TCA AAA AAG GGC AAA ATG 1924
Lys Leu Glu Glu Thr Ile Thr Gln Ala Arg Ser Lys Lys Gly Lys Met
615 620 625 630

AAG GAT TCG GAA ACC CTG AAG CCA GAT AAT TTT GAA GAA TCT GGC TAT 1972
Lys Asp Ser Glu Thr Leu Lys Pro Asp Asn Phe Glu Glu Ser Gly Tyr

-continued

```
                635                     640                     645

ACA TTC ATA GCA CCA AGA GAT TAC TGC AAT GAC CTG AAA ATA TCG GAT        2020
Thr Phe Ile Ala Pro Arg Asp Tyr Cys Asn Asp Leu Lys Ile Ser Asp
            650                     655                     660

AAT AAC ACT GAA TTT CTT TTA AAT TTC AAC GAG TTT ATT GAT AGA AAA        2068
Asn Asn Thr Glu Phe Leu Leu Asn Phe Asn Glu Phe Ile Asp Arg Lys
        665                     670                     675

ACT CCA AAC AAC CCA TCA TGT AAC GCG GAT TTG ATT AAT AGA GTC TTG        2116
Thr Pro Asn Asn Pro Ser Cys Asn Ala Asp Leu Ile Asn Arg Val Leu
    680                     685                     690

CTT GAT GCA GGC TTT ACA AAT GAA CTT GTC CAA AAT TAC TGG AGT AAG        2164
Leu Asp Ala Gly Phe Thr Asn Glu Leu Val Gln Asn Tyr Trp Ser Lys
695                     700                     705                     710

CAG AAA AAT ATC AAG GGA GTG AAA GCA CGA TTT GTT GTG ACT GAT GGT        2212
Gln Lys Asn Ile Lys Gly Val Lys Ala Arg Phe Val Val Thr Asp Gly
                715                     720                     725

GGG ATT ACC AGA GTT TAT CCC AAA GAG GCT GGA GAA AAT TGG CAA GAA        2260
Gly Ile Thr Arg Val Tyr Pro Lys Glu Ala Gly Glu Asn Trp Gln Glu
            730                     735                     740

AAC CCA GAG ACA TAT GAG GAC AGC TTC TAT AAA AGG AGC CTA GAT AAT        2308
Asn Pro Glu Thr Tyr Glu Asp Ser Phe Tyr Lys Arg Ser Leu Asp Asn
        745                     750                     755

GAT AAC TAT GTT TTC ACT GCT CCC TAC TTT AAC AAA AGT GGA CCT GGT        2356
Asp Asn Tyr Val Phe Thr Ala Pro Tyr Phe Asn Lys Ser Gly Pro Gly
    760                     765                     770

GCC TAT GAA TCG GGC ATT ATG GTA AGC AAA GCT GTA GAA ATA TAT ATT        2404
Ala Tyr Glu Ser Gly Ile Met Val Ser Lys Ala Val Glu Ile Tyr Ile
775                     780                     785                     790

CAA GGG AAA CTT CTT AAA CCT GCA GTT GTT GGA ATT AAA ATT GAT GTA        2452
Gln Gly Lys Leu Leu Lys Pro Ala Val Val Gly Ile Lys Ile Asp Val
                795                     800                     805

AAT TCC TGG ATA GAG AAT TTC ACC AAA ACC TCA ATC AGA GAT CCG TGT        2500
Asn Ser Trp Ile Glu Asn Phe Thr Lys Thr Ser Ile Arg Asp Pro Cys
            810                     815                     820

GCT GGT CCA GTT TGT GAC TGC AAA AGA AAC AGT GAC GTA ATG GAT TGT        2548
Ala Gly Pro Val Cys Asp Cys Lys Arg Asn Ser Asp Val Met Asp Cys
        825                     830                     835

GTG ATT CTG GAT GAT GGT GGG TTT CTT CTG ATG GCA AAT CAT GAT GAT        2596
Val Ile Leu Asp Asp Gly Gly Phe Leu Leu Met Ala Asn His Asp Asp
    840                     845                     850

TAT ACT AAT CAG ATT GGA AGA TTT TTT GGA GAG ATT GAT CCC AGC TTG        2644
Tyr Thr Asn Gln Ile Gly Arg Phe Phe Gly Glu Ile Asp Pro Ser Leu
855                     860                     865                     870

ATG AGA CAC CTG GTT AAT ATA TCA GTT TAT GCT TTT AAC AAA TCT TAT        2692
Met Arg His Leu Val Asn Ile Ser Val Tyr Ala Phe Asn Lys Ser Tyr
                875                     880                     885

GAT TAT CAG TCA GTA TGT GAG CCC GGT GCT GCA CCA AAA CAA GGA GCA        2740
Asp Tyr Gln Ser Val Cys Glu Pro Gly Ala Ala Pro Lys Gln Gly Ala
            890                     895                     900

GGA CAT CGC TCA GCA TAT GTG CCA TCA GTA GCA GAC ATA TTA CAA ATT        2788
Gly His Arg Ser Ala Tyr Val Pro Ser Val Ala Asp Ile Leu Gln Ile
        905                     910                     915

GGC TGG TGG GCC ACT GCT GCT GCC TGG TCT ATT CTA CAG CAG TTT CTC        2836
Gly Trp Trp Ala Thr Ala Ala Ala Trp Ser Ile Leu Gln Gln Phe Leu
    920                     925                     930

TTG AGT TTG ACC TTT CCA CGA CTC CTT GAG GCA GTT GAG ATG GAG GAT        2884
Leu Ser Leu Thr Phe Pro Arg Leu Leu Glu Ala Val Glu Met Glu Asp
935                     940                     945                     950

GAT GAC TTC ACG GCC TCC CTG TCC AAG CAG AGC TGC ATT ACT GAA CAA        2932
Asp Asp Phe Thr Ala Ser Leu Ser Lys Gln Ser Cys Ile Thr Glu Gln
```

-continued

```
                    955                       960                       965

ACC CAG TAT TTC TTC GAT AAC GAC AGT AAA TCA TTC AGT GGT GTA TTA      2980
Thr Gln Tyr Phe Phe Asp Asn Asp Ser Lys Ser Phe Ser Gly Val Leu
            970                       975                       980

GAC TGT GGA AAC TGT TCC AGA ATC TTT CAT GGA GAA AAG CTT ATG AAC      3028
Asp Cys Gly Asn Cys Ser Arg Ile Phe His Gly Glu Lys Leu Met Asn
        985                       990                       995

ACC AAC TTA ATA TTC ATA ATG GTT GAG AGC AAA GGG ACA TGT CCA TGT      3076
Thr Asn Leu Ile Phe Ile Met Val Glu Ser Lys Gly Thr Cys Pro Cys
    1000                      1005                      1010

GAC ACA CGA CTG CTC ATA CAA GCG GAG CAG ACT TCT GAC GGT CCA AAT      3124
Asp Thr Arg Leu Leu Ile Gln Ala Glu Gln Thr Ser Asp Gly Pro Asn
1015                      1020                      1025                      1030

CCT TGT GAC ATG GTT AAG CAA CCT AGA TAC CGA AAA GGG CCT GAT GTC      3172
Pro Cys Asp Met Val Lys Gln Pro Arg Tyr Arg Lys Gly Pro Asp Val
                1035                      1040                      1045

TGC TTT GAT AAC AAT GTC TTG GAG GAT TAT ACT GAC TGT GGT GGT GTT      3220
Cys Phe Asp Asn Asn Val Leu Glu Asp Tyr Thr Asp Cys Gly Gly Val
            1050                      1055                      1060

TCT GGA TTA AAT CCC TCC CTG TGG TAT ATC ATT GGA ATC CAG TTT CTA      3268
Ser Gly Leu Asn Pro Ser Leu Trp Tyr Ile Ile Gly Ile Gln Phe Leu
        1065                      1070                      1075

CTA CTT TGG CTG GTA TCT GGC AGC ACA CAC CGG CTG TTA TGACCTTCTA       3317
Leu Leu Trp Leu Val Ser Gly Ser Thr His Arg Leu Leu
    1080                      1085                      1090

AAAACCAAAT CTGCATAGTT AAACTCCAGA CCCTGCCAAA ACATGAGCCC TGCCCTCAAT    3377

TACAGTAACG TAGGGTCAGC TATAAAATCA GACAAACATT AGCTGGGCCT GTTCCATGGC    3437

ATAACACTAA GGCGCAGACT CCTAAGGCAC CCACTGGCTG CATGTCAGGG TGTCAGATCC    3497

TTAAACGTGT GTGAATGCTG CATCATCTAT GTGTAACATC AAAGCAAAAT CCTATACGTG    3557

TCCTCTATTG GAAAATTTGG GCGTTTGTTG TTGCATTGTT GGT                      3600
```

( 2 ) INFORMATION FOR SEQ ID NO:34:

( i ) SEQUENCE CHARACTERISTICS:
( A ) LENGTH: 3585 base pairs
( B ) TYPE: nucleic acid
( C ) STRANDEDNESS: double
( D ) TOPOLOGY: linear ( i i ) MOLECULE TYPE: DNA (genomic)

( i x ) FEATURE:
( A ) NAME/KEY: CDS
( B ) LOCATION: 35..3295
( D ) OTHER INFORMATION: /standard_name= “Alpha-2c”

( i x ) FEATURE:
( A ) NAME/KEY: 5’UTR
( B ) LOCATION: 1..34

( i x ) FEATURE:
( A ) NAME/KEY: 3’UTR
( B ) LOCATION: 3296..3585

( x i ) SEQUENCE DESCRIPTION: SEQ ID NO:34:

```
GCGGGGGAGG GGGCATTGAT CTTCGATCGC GAAG ATG GCT GCT GGC TGC CTG          52
                                      Met Ala Ala Gly Cys Leu
                                        1                   5

CTG GCC TTG ACT CTG ACA CTT TTC CAA TCT TTG CTC ATC GGC CCC TCG       100
Leu Ala Leu Thr Leu Thr Leu Phe Gln Ser Leu Leu Ile Gly Pro Ser
             10                       15                       20

TCG GAG GAG CCG TTC CCT TCG GCC GTC ACT ATC AAA TCA TGG GTG GAT       148
Ser Glu Glu Pro Phe Pro Ser Ala Val Thr Ile Lys Ser Trp Val Asp
```

-continued

```
            25                                      30                                      35

AAG ATG CAA GAA GAC CTT GTC ACA CTG GCA AAA ACA GCA AGT GGA GTC     196
Lys Met Gln Glu Asp Leu Val Thr Leu Ala Lys Thr Ala Ser Gly Val
     40                      45                      50

AAT CAG CTT GTT GAT ATT TAT GAG AAA TAT CAA GAT TTG TAT ACT GTG     244
Asn Gln Leu Val Asp Ile Tyr Glu Lys Tyr Gln Asp Leu Tyr Thr Val
 55                      60                      65                      70

GAA CCA AAT AAT GCA CGC CAG CTG GTA GAA ATT GCA GCC AGG GAT ATT     292
Glu Pro Asn Asn Ala Arg Gln Leu Val Glu Ile Ala Ala Arg Asp Ile
                 75                      80                      85

GAG AAA CTT CTG AGC AAC AGA TCT AAA GCC CTG GTG AGC CTG GCA TTG     340
Glu Lys Leu Leu Ser Asn Arg Ser Lys Ala Leu Val Ser Leu Ala Leu
             90                      95                     100

GAA GCG GAG AAA GTT CAA GCA GCT CAC CAG TGG AGA GAA GAT TTT GCA     388
Glu Ala Glu Lys Val Gln Ala Ala His Gln Trp Arg Glu Asp Phe Ala
        105                     110                     115

AGC AAT GAA GTT GTC TAC TAC AAT GCA AAG GAT GAT CTC GAT CCT GAG     436
Ser Asn Glu Val Val Tyr Tyr Asn Ala Lys Asp Asp Leu Asp Pro Glu
    120                     125                     130

AAA AAT GAC AGT GAG CCA GGC AGC CAG AGG ATA AAA CCT GTT TTC ATT     484
Lys Asn Asp Ser Glu Pro Gly Ser Gln Arg Ile Lys Pro Val Phe Ile
135                     140                     145                     150

GAA GAT GCT AAT TTT GGA CGA CAA ATA TCT TAT CAG CAC GCA GCA GTC     532
Glu Asp Ala Asn Phe Gly Arg Gln Ile Ser Tyr Gln His Ala Ala Val
                155                     160                     165

CAT ATT CCT ACT GAC ATC TAT GAG GGC TCA ACA ATT GTG TTA AAT GAA     580
His Ile Pro Thr Asp Ile Tyr Glu Gly Ser Thr Ile Val Leu Asn Glu
            170                     175                     180

CTC AAC TGG ACA AGT GCC TTA GAT GAA GTT TTC AAA AAG AAT CGC GAG     628
Leu Asn Trp Thr Ser Ala Leu Asp Glu Val Phe Lys Lys Asn Arg Glu
        185                     190                     195

GAA GAC CCT TCA TTA TTG TGG CAG GTT TTT GGC AGT GCC ACT GGC CTA     676
Glu Asp Pro Ser Leu Leu Trp Gln Val Phe Gly Ser Ala Thr Gly Leu
    200                     205                     210

GCT CGA TAT TAT CCA GCT TCA CCA TGG GTT GAT AAT AGT AGA ACT CCA     724
Ala Arg Tyr Tyr Pro Ala Ser Pro Trp Val Asp Asn Ser Arg Thr Pro
215                     220                     225                     230

AAT AAG ATT GAC CTT TAT GAT GTA CGC AGA AGA CCA TGG TAC ATC CAA     772
Asn Lys Ile Asp Leu Tyr Asp Val Arg Arg Arg Pro Trp Tyr Ile Gln
                235                     240                     245

GGA GCT GCA TCT CCT AAA GAC ATG CTT ATT CTG GTG GAT GTG AGT GGA     820
Gly Ala Ala Ser Pro Lys Asp Met Leu Ile Leu Val Asp Val Ser Gly
            250                     255                     260

AGT GTT AGT GGA TTG ACA CTT AAA CTG ATC CGA ACA TCT GTC TCC GAA     868
Ser Val Ser Gly Leu Thr Leu Lys Leu Ile Arg Thr Ser Val Ser Glu
        265                     270                     275

ATG TTA GAA ACC CTC TCA GAT GAT GAT TTC GTG AAT GTA GCT TCA TTT     916
Met Leu Glu Thr Leu Ser Asp Asp Asp Phe Val Asn Val Ala Ser Phe
    280                     285                     290

AAC AGC AAT GCT CAG GAT GTA AGC TGT TTT CAG CAC CTT GTC CAA GCA     964
Asn Ser Asn Ala Gln Asp Val Ser Cys Phe Gln His Leu Val Gln Ala
295                     300                     305                     310

AAT GTA AGA AAT AAA AAA GTG TTG AAA GAC GCG GTG AAT AAT ATC ACA    1012
Asn Val Arg Asn Lys Lys Val Leu Lys Asp Ala Val Asn Asn Ile Thr
                315                     320                     325

GCC AAA GGA ATT ACA GAT TAT AAG AAG GGC TTT AGT TTT GCT TTT GAA    1060
Ala Lys Gly Ile Thr Asp Tyr Lys Lys Gly Phe Ser Phe Ala Phe Glu
            330                     335                     340

CAG CTG CTT AAT TAT AAT GTT TCC AGA GCA AAC TGC AAT AAG ATT ATT    1108
Gln Leu Leu Asn Tyr Asn Val Ser Arg Ala Asn Cys Asn Lys Ile Ile
```

-continued 345                                     350                                     355

ATG CTA TTC ACG GAT GGA GGA GAA GAG AGA GCC CAG GAG ATA TTT AAC 1156
Met Leu Phe Thr Asp Gly Gly Glu Glu Arg Ala Gln Glu Ile Phe Asn
    360                 365                 370

AAA TAC AAT AAA GAT AAA AAA GTA CGT GTA TTC AGG TTT TCA GTT GGT 1204
Lys Tyr Asn Lys Asp Lys Lys Val Arg Val Phe Arg Phe Ser Val Gly
375                 380                 385                 390

CAA CAC AAT TAT GAG AGA GGA CCT ATT CAG TGG ATG GCC TGT GAA AAC 1252
Gln His Asn Tyr Glu Arg Gly Pro Ile Gln Trp Met Ala Cys Glu Asn
                395                 400                 405

AAA GGT TAT TAT TAT GAA ATT CCT TCC ATT GGT GCA ATA AGA ATC AAT 1300
Lys Gly Tyr Tyr Tyr Glu Ile Pro Ser Ile Gly Ala Ile Arg Ile Asn
            410                 415                 420

ACT CAG GAA TAT TTG GAT GTT TTG GGA AGA CCA ATG GTT TTA GCA GGA 1348
Thr Gln Glu Tyr Leu Asp Val Leu Gly Arg Pro Met Val Leu Ala Gly
        425                 430                 435

GAC AAA GCT AAG CAA GTC CAA TGG ACA AAT GTG TAC CTG GAT GCA TTG 1396
Asp Lys Ala Lys Gln Val Gln Trp Thr Asn Val Tyr Leu Asp Ala Leu
    440                 445                 450

GAA CTG GGA CTT GTC ATT ACT GGA ACT CTT CCG GTC TTC AAC ATA ACC 1444
Glu Leu Gly Leu Val Ile Thr Gly Thr Leu Pro Val Phe Asn Ile Thr
455                 460                 465                 470

GGC CAA TTT GAA AAT AAG ACA AAC TTA AAG AAC CAG CTG ATT CTT GGT 1492
Gly Gln Phe Glu Asn Lys Thr Asn Leu Lys Asn Gln Leu Ile Leu Gly
                475                 480                 485

GTG ATG GGA GTA GAT GTG TCT TTG GAA GAT ATT AAA AGA CTG ACA CCA 1540
Val Met Gly Val Asp Val Ser Leu Glu Asp Ile Lys Arg Leu Thr Pro
            490                 495                 500

CGT TTT ACA CTG TGC CCC AAT GGG TAT TAC TTT GCA ATC GAT CCT AAT 1588
Arg Phe Thr Leu Cys Pro Asn Gly Tyr Tyr Phe Ala Ile Asp Pro Asn
        505                 510                 515

GGT TAT GTT TTA TTA CAT CCA AAT CTT CAG CCA AAG GAG CCA GTA ACA 1636
Gly Tyr Val Leu Leu His Pro Asn Leu Gln Pro Lys Glu Pro Val Thr
    520                 525                 530

TTG GAT TTC CTT GAT GCA GAG TTA GAG AAT GAT ATT AAA GTG GAG ATT 1684
Leu Asp Phe Leu Asp Ala Glu Leu Glu Asn Asp Ile Lys Val Glu Ile
535                 540                 545                 550

CGA AAT AAG ATG ATT GAT GGG GAA AGT GGA GAA AAA ACA TTC AGA ACT 1732
Arg Asn Lys Met Ile Asp Gly Glu Ser Gly Glu Lys Thr Phe Arg Thr
                555                 560                 565

CTG GTT AAA TCT CAA GAT GAG AGA TAT ATT GAC AAA GGA AAC AGG ACA 1780
Leu Val Lys Ser Gln Asp Glu Arg Tyr Ile Asp Lys Gly Asn Arg Thr
            570                 575                 580

TAC ACA TGG ACA CCT GTC AAT GGC ACA GAT TAC AGT TTG GCC TTG GTA 1828
Tyr Thr Trp Thr Pro Val Asn Gly Thr Asp Tyr Ser Leu Ala Leu Val
        585                 590                 595

TTA CCA ACC TAC AGT TTT TAC TAT ATA AAA GCC AAA CTA GAA GAG ACA 1876
Leu Pro Thr Tyr Ser Phe Tyr Tyr Ile Lys Ala Lys Leu Glu Glu Thr
    600                 605                 610

ATA ACT CAG GCC AGA TCA AAA AAG GGC AAA ATG AAG GAT TCG GAA ACC 1924
Ile Thr Gln Ala Arg Ser Lys Lys Gly Lys Met Lys Asp Ser Glu Thr
615                 620                 625                 630

CTG AAG CCA GAT AAT TTT GAA GAA TCT GGC TAT ACA TTC ATA GCA CCA 1972
Leu Lys Pro Asp Asn Phe Glu Glu Ser Gly Tyr Thr Phe Ile Ala Pro
                635                 640                 645

AGA GAT TAC TGC AAT GAC CTG AAA ATA TCG GAT AAT AAC ACT GAA TTT 2020
Arg Asp Tyr Cys Asn Asp Leu Lys Ile Ser Asp Asn Asn Thr Glu Phe
            650                 655                 660

CTT TTA AAT TTC AAC GAG TTT ATT GAT AGA AAA ACT CCA AAC AAC CCA 2068
Leu Leu Asn Phe Asn Glu Phe Ile Asp Arg Lys Thr Pro Asn Asn Pro

-continued

```
          665                      670                      675

TCA TGT AAC GCG GAT TTG ATT AAT AGA GTC TTG CTT GAT GCA GGC TTT      2116
Ser Cys Asn Ala Asp Leu Ile Asn Arg Val Leu Leu Asp Ala Gly Phe
    680                 685                 690

ACA AAT GAA CTT GTC CAA AAT TAC TGG AGT AAG CAG AAA AAT ATC AAG      2164
Thr Asn Glu Leu Val Gln Asn Tyr Trp Ser Lys Gln Lys Asn Ile Lys
695                 700                 705                 710

GGA GTG AAA GCA CGA TTT GTT GTG ACT GAT GGT GGG ATT ACC AGA GTT      2212
Gly Val Lys Ala Arg Phe Val Val Thr Asp Gly Gly Ile Thr Arg Val
                715                 720                 725

TAT CCC AAA GAG GCT GGA GAA AAT TGG CAA GAA AAC CCA GAG ACA TAT      2260
Tyr Pro Lys Glu Ala Gly Glu Asn Trp Gln Glu Asn Pro Glu Thr Tyr
            730                 735                 740

GAG GAC AGC TTC TAT AAA AGG AGC CTA GAT AAT GAT AAC TAT GTT TTC      2308
Glu Asp Ser Phe Tyr Lys Arg Ser Leu Asp Asn Asp Asn Tyr Val Phe
        745                 750                 755

ACT GCT CCC TAC TTT AAC AAA AGT GGA CCT GGT GCC TAT GAA TCG GGC      2356
Thr Ala Pro Tyr Phe Asn Lys Ser Gly Pro Gly Ala Tyr Glu Ser Gly
    760                 765                 770

ATT ATG GTA AGC AAA GCT GTA GAA ATA TAT ATT CAA GGG AAA CTT CTT      2404
Ile Met Val Ser Lys Ala Val Glu Ile Tyr Ile Gln Gly Lys Leu Leu
775                 780                 785                 790

AAA CCT GCA GTT GTT GGA ATT AAA ATT GAT GTA AAT TCC TGG ATA GAG      2452
Lys Pro Ala Val Val Gly Ile Lys Ile Asp Val Asn Ser Trp Ile Glu
                795                 800                 805

AAT TTC ACC AAA ACC TCA ATC AGA GAT CCG TGT GCT GGT CCA GTT TGT      2500
Asn Phe Thr Lys Thr Ser Ile Arg Asp Pro Cys Ala Gly Pro Val Cys
            810                 815                 820

GAC TGC AAA AGA AAC AGT GAC GTA ATG GAT TGT GTG ATT CTG GAT GAT      2548
Asp Cys Lys Arg Asn Ser Asp Val Met Asp Cys Val Ile Leu Asp Asp
        825                 830                 835

GGT GGG TTT CTT CTG ATG GCA AAT CAT GAT GAT TAT ACT AAT CAG ATT      2596
Gly Gly Phe Leu Leu Met Ala Asn His Asp Asp Tyr Thr Asn Gln Ile
    840                 845                 850

GGA AGA TTT TTT GGA GAG ATT GAT CCC AGC TTG ATG AGA CAC CTG GTT      2644
Gly Arg Phe Phe Gly Glu Ile Asp Pro Ser Leu Met Arg His Leu Val
855                 860                 865                 870

AAT ATA TCA GTT TAT GCT TTT AAC AAA TCT TAT GAT TAT CAG TCA GTA      2692
Asn Ile Ser Val Tyr Ala Phe Asn Lys Ser Tyr Asp Tyr Gln Ser Val
                875                 880                 885

TGT GAG CCC GGT GCT GCA CCA AAA CAA GGA GCA GGA CAT CGC TCA GCA      2740
Cys Glu Pro Gly Ala Ala Pro Lys Gln Gly Ala Gly His Arg Ser Ala
            890                 895                 900

TAT GTG CCA TCA GTA GCA GAC ATA TTA CAA ATT GGC TGG TGG GCC ACT      2788
Tyr Val Pro Ser Val Ala Asp Ile Leu Gln Ile Gly Trp Trp Ala Thr
        905                 910                 915

GCT GCT GCC TGG TCT ATT CTA CAG CAG TTT CTC TTG AGT TTG ACC TTT      2836
Ala Ala Ala Trp Ser Ile Leu Gln Gln Phe Leu Leu Ser Leu Thr Phe
    920                 925                 930

CCA CGA CTC CTT GAG GCA GTT GAG ATG GAG GAT GAT GAC TTC ACG GCC      2884
Pro Arg Leu Leu Glu Ala Val Glu Met Glu Asp Asp Asp Phe Thr Ala
935                 940                 945                 950

TCC CTG TCC AAG CAG AGC TGC ATT ACT GAA CAA ACC CAG TAT TTC TTC      2932
Ser Leu Ser Lys Gln Ser Cys Ile Thr Glu Gln Thr Gln Tyr Phe Phe
                955                 960                 965

GAT AAC GAC AGT AAA TCA TTC AGT GGT GTA TTA GAC TGT GGA AAC TGT      2980
Asp Asn Asp Ser Lys Ser Phe Ser Gly Val Leu Asp Cys Gly Asn Cys
            970                 975                 980

TCC AGA ATC TTT CAT GGA GAA AAG CTT ATG AAC ACC AAC TTA ATA TTC      3028
Ser Arg Ile Phe His Gly Glu Lys Leu Met Asn Thr Asn Leu Ile Phe
```

-continued

```
          985                     990                     995

ATA ATG GTT GAG AGC AAA GGG ACA TGT CCA TGT GAC ACA CGA CTG CTC     3076
Ile Met Val Glu Ser Lys Gly Thr Cys Pro Cys Asp Thr Arg Leu Leu
    1000                    1005                    1010

ATA CAA GCG GAG CAG ACT TCT GAC GGT CCA AAT CCT TGT GAC ATG GTT     3124
Ile Gln Ala Glu Gln Thr Ser Asp Gly Pro Asn Pro Cys Asp Met Val
1015                    1020                    1025                    1030

AAG CAA CCT AGA TAC CGA AAA GGG CCT GAT GTC TGC TTT GAT AAC AAT     3172
Lys Gln Pro Arg Tyr Arg Lys Gly Pro Asp Val Cys Phe Asp Asn Asn
                1035                    1040                    1045

GTC TTG GAG GAT TAT ACT GAC TGT GGT GGT GTT TCT GGA TTA AAT CCC     3220
Val Leu Glu Asp Tyr Thr Asp Cys Gly Gly Val Ser Gly Leu Asn Pro
            1050                    1055                    1060

TCC CTG TGG TAT ATC ATT GGA ATC CAG TTT CTA CTA CTT TGG CTG GTA     3268
Ser Leu Trp Tyr Ile Ile Gly Ile Gln Phe Leu Leu Leu Trp Leu Val
        1065                    1070                    1075

TCT GGC AGC ACA CAC CGG CTG TTA TGACCTTCTA AAAACCAAAT CTGCATAGTT     3322
Ser Gly Ser Thr His Arg Leu Leu
    1080                    1085

AAACTCCAGA CCCTGCCAAA ACATGAGCCC TGCCCTCAAT TACAGTAACG TAGGGTCAGC     3382

TATAAAATCA GACAAACATT AGCTGGGCCT GTTCCATGGC ATAACACTAA GGCGCAGACT     3442

CCTAAGGCAC CCACTGGCTG CATGTCAGGG TGTCAGATCC TTAAACGTGT GTGAATGCTG     3505

CATCATCTAT GTGTAACATC AAAGCAAAAT CCTATACGTG TCCTCTATTG GAAAATTTGG     3562

GCGTTTGTTG TTGCATTGTT GGT                                            3585
```

( 2 ) INFORMATION FOR SEQ ID NO:35:

( i ) SEQUENCE CHARACTERISTICS:
( A ) LENGTH: 3564 base pairs
( B ) TYPE: nucleic acid
( C ) STRANDEDNESS: double
( D ) TOPOLOGY: linear ( i i ) MOLECULE TYPE: Genomic DNA ( i i i ) HYPOTHETICAL: NO ( i v ) ANTI-SENSE: NO ( v ) FRAGMENT TYPE:

( v i ) ORIGINAL SOURCE:

( i x ) FEATURE:
( A ) NAME/KEY: Coding Sequence
( B ) LOCATION: 35...3274
( D ) OTHER INFORMATION: Standard name "alpha-2d"
( A ) NAME/KEY: 5'UTR
( B ) LOCATION: 1...34
( D ) OTHER INFORMATION:
( A ) NAME/KEY: 3'UTR
( B ) LOCATION: 3275...3564
( D ) OTHER INFORMATION:

( x i ) SEQUENCE DESCRIPTION: SEQ ID NO:35:

```
GCGGGGGAGG GGGCATTGAT CTTCGATCGC GAAG ATG GCT GCT GGC TGC CTG CTG     55
                                      Met Ala Ala Gly Cys Leu Leu
                                       1                      5

GCC TTG ACT CTG ACA CTT TTC CAA TCT TTG CTC ATC GGC CCC TCG TCG     103
Ala Leu Thr Leu Thr Leu Phe Gln Ser Leu Leu Ile Gly Pro Ser Ser
        10                  15                      20

GAG GAG CCG TTC CCT TCG GCC GTC ACT ATC AAA TCA TGG GTG GAT AAG     151
Glu Glu Pro Phe Pro Ser Ala Val Thr Ile Lys Ser Trp Val Asp Lys
    25                      30                      35
```

-continued

ATG CAA GAA GAC CTT GTC ACA CTG GCA AAA ACA GCA AGT GGA GTC AAT 199
Met Gln Glu Asp Leu Val Thr Leu Ala Lys Thr Ala Ser Gly Val Asn
40 45 50 55

CAG CTT GTT GAT ATT TAT GAG AAA TAT CAA GAT TTG TAT ACT GTG GAA 247
Gln Leu Val Asp Ile Tyr Glu Lys Tyr Gln Asp Leu Tyr Thr Val Glu
60 65 70

CCA AAT AAT GCA CGC CAG CTG GTA GAA ATT GCA GCC AGG GAT ATT GAG 295
Pro Asn Asn Ala Arg Gln Leu Val Glu Ile Ala Ala Arg Asp Ile Glu
75 80 85

AAA CTT CTG AGC AAC AGA TCT AAA GCC CTG GTG AGC CTG GCA TTG GAA 343
Lys Leu Leu Ser Asn Arg Ser Lys Ala Leu Val Ser Leu Ala Leu Glu
90 95 100

GCG GAG AAA GTT CAA GCA GCT CAC CAG TGG AGA GAA GAT TTT GCA AGC 391
Ala Glu Lys Val Gln Ala Ala His Gln Trp Arg Glu Asp Phe Ala Ser
105 110 115

AAT GAA GTT GTC TAC TAC AAT GCA AAG GAT GAT CTC GAT CCT GAG AAA 439
Asn Glu Val Val Tyr Tyr Asn Ala Lys Asp Asp Leu Asp Pro Glu Lys
120 125 130 135

AAT GAC AGT GAG CCA GGC AGC CAG AGG ATA AAA CCT GTT TTC ATT GAA 487
Asn Asp Ser Glu Pro Gly Ser Gln Arg Ile Lys Pro Val Phe Ile Glu
140 145 150

GAT GCT AAT TTT GGA CGA CAA ATA TCT TAT CAG CAC GCA GCA GTC CAT 535
Asp Ala Asn Phe Gly Arg Gln Ile Ser Tyr Gln His Ala Ala Val His
155 160 165

ATT CCT ACT GAC ATC TAT GAG GGC TCA ACA ATT GTG TTA AAT GAA CTC 583
Ile Pro Thr Asp Ile Tyr Glu Gly Ser Thr Ile Val Leu Asn Glu Leu
170 175 180

AAC TGG ACA AGT GCC TTA GAT GAA GTT TTC AAA AAG AAT CGC GAG GAA 631
Asn Trp Thr Ser Ala Leu Asp Glu Val Phe Lys Lys Asn Arg Glu Glu
185 190 195

GAC CCT TCA TTA TTG TGG CAG GTT TTT GGC AGT GCC ACT GGC CTA GCT 679
Asp Pro Ser Leu Leu Trp Gln Val Phe Gly Ser Ala Thr Gly Leu Ala
200 205 210 215

CGA TAT TAT CCA GCT TCA CCA TGG GTT GAT AAT AGT AGA ACT CCA AAT 727
Arg Tyr Tyr Pro Ala Ser Pro Trp Val Asp Asn Ser Arg Thr Pro Asn
220 225 230

AAG ATT GAC CTT TAT GAT GTA CGC AGA AGA CCA TGG TAC ATC CAA GGA 775
Lys Ile Asp Leu Tyr Asp Val Arg Arg Arg Pro Trp Tyr Ile Gln Gly
235 240 245

GCT GCA TCT CCT AAA GAC ATG CTT ATT CTG GTG GAT GTG AGT GGA AGT 823
Ala Ala Ser Pro Lys Asp Met Leu Ile Leu Val Asp Val Ser Gly Ser
250 255 260

GTT AGT GGA TTG ACA CTT AAA CTG ATC CGA ACA TCT GTC TCC GAA ATG 871
Val Ser Gly Leu Thr Leu Lys Leu Ile Arg Thr Ser Val Ser Glu Met
265 270 275

TTA GAA ACC CTC TCA GAT GAT GAT TTC GTG AAT GTA GCT TCA TTT AAC 919
Leu Glu Thr Leu Ser Asp Asp Asp Phe Val Asn Val Ala Ser Phe Asn
280 285 290 295

AGC AAT GCT CAG GAT GTA AGC TGT TTT CAG CAC CTT GTC CAA GCA AAT 967
Ser Asn Ala Gln Asp Val Ser Cys Phe Gln His Leu Val Gln Ala Asn
300 305 310

GTA AGA AAT AAA AAA GTG TTG AAA GAC GCG GTG AAT AAT ATC ACA GCC 1015
Val Arg Asn Lys Lys Val Leu Lys Asp Ala Val Asn Asn Ile Thr Ala
315 320 325

AAA GGA ATT ACA GAT TAT AAG AAG GGC TTT AGT TTT GCT TTT GAA CAG 1063
Lys Gly Ile Thr Asp Tyr Lys Lys Gly Phe Ser Phe Ala Phe Glu Gln
330 335 340

CTG CTT AAT TAT AAT GTT TCC AGA GCA AAC TGC AAT AAG ATT ATT ATG 1111
Leu Leu Asn Tyr Asn Val Ser Arg Ala Asn Cys Asn Lys Ile Ile Met
345 350 355

-continued

CTA TTC ACG GAT GGA GGA GAA GAG AGA GCC CAG GAG ATA TTT AAC AAA 1159
Leu Phe Thr Asp Gly Gly Glu Glu Arg Ala Gln Glu Ile Phe Asn Lys
360 365 370 375

TAC AAT AAA GAT AAA AAA GTA CGT GTA TTC AGG TTT TCA GTT GGT CAA 1207
Tyr Asn Lys Asp Lys Lys Val Arg Val Phe Arg Phe Ser Val Gly Gln
380 385 390

CAC AAT TAT GAG AGA GGA CCT ATT CAG TGG ATG GCC TGT GAA AAC AAA 1255
His Asn Tyr Glu Arg Gly Pro Ile Gln Trp Met Ala Cys Glu Asn Lys
395 400 405

GGT TAT TAT TAT GAA ATT CCT TCC ATT GGT GCA ATA AGA ATC AAT ACT 1303
Gly Tyr Tyr Tyr Glu Ile Pro Ser Ile Gly Ala Ile Arg Ile Asn Thr
410 415 420

CAG GAA TAT TTG GAT GTT TTG GGA AGA CCA ATG GTT TTA GCA GGA GAC 1351
Gln Glu Tyr Leu Asp Val Leu Gly Arg Pro Met Val Leu Ala Gly Asp
425 430 435

AAA GCT AAG CAA GTC CAA TGG ACA AAT GTG TAC CTG GAT GCA TTG GAA 1399
Lys Ala Lys Gln Val Gln Trp Thr Asn Val Tyr Leu Asp Ala Leu Glu
440 445 450 455

CTG GGA CTT GTC ATT ACT GGA ACT CTT CCG GTC TTC AAC ATA ACC GGC 1447
Leu Gly Leu Val Ile Thr Gly Thr Leu Pro Val Phe Asn Ile Thr Gly
460 465 470

CAA TTT GAA AAT AAG ACA AAC TTA AAG AAC CAG CTG ATT CTT GGT GTG 1495
Gln Phe Glu Asn Lys Thr Asn Leu Lys Asn Gln Leu Ile Leu Gly Val
475 480 485

ATG GGA GTA GAT GTG TCT TTG GAA GAT ATT AAA AGA CTG ACA CCA CGT 1543
Met Gly Val Asp Val Ser Leu Glu Asp Ile Lys Arg Leu Thr Pro Arg
490 495 500

TTT ACA CTG TGC CCC AAT GGG TAT TAC TTT GCA ATC GAT CCT AAT GGT 1591
Phe Thr Leu Cys Pro Asn Gly Tyr Tyr Phe Ala Ile Asp Pro Asn Gly
505 510 515

TAT GTT TTA TTA CAT CCA AAT CTT CAG CCA AAG GAG CCA GTA ACA TTG 1639
Tyr Val Leu Leu His Pro Asn Leu Gln Pro Lys Glu Pro Val Thr Leu
520 525 530 535

GAT TTC CTT GAT GCA GAG TTA GAG AAT GAT ATT AAA GTG GAG ATT CGA 1687
Asp Phe Leu Asp Ala Glu Leu Glu Asn Asp Ile Lys Val Glu Ile Arg
540 545 550

AAT AAG ATG ATT GAT GGG GAA AGT GGA GAA AAA ACA TTC AGA ACT CTG 1735
Asn Lys Met Ile Asp Gly Glu Ser Gly Glu Lys Thr Phe Arg Thr Leu
555 560 565

GTT AAA TCT CAA GAT GAG AGA TAT ATT GAC AAA GGA AAC AGG ACA TAC 1783
Val Lys Ser Gln Asp Glu Arg Tyr Ile Asp Lys Gly Asn Arg Thr Tyr
570 575 580

ACA TGG ACA CCT GTC AAT GGC ACA GAT TAC AGT TTG GCC TTG GTA TTA 1831
Thr Trp Thr Pro Val Asn Gly Thr Asp Tyr Ser Leu Ala Leu Val Leu
585 590 595

CCA ACC TAC AGT TTT TAC TAT ATA AAA GCC AAA CTA GAA GAG ACA ATA 1879
Pro Thr Tyr Ser Phe Tyr Tyr Ile Lys Ala Lys Leu Glu Glu Thr Ile
600 605 610 615

ACT CAG GCC AGA TAT TCG GAA ACC CTG AAG CCA GAT AAT TTT GAA GAA 1927
Thr Gln Ala Arg Tyr Ser Glu Thr Leu Lys Pro Asp Asn Phe Glu Glu
620 625 630

TCT GGC TAT ACA TTC ATA GCA CCA AGA GAT TAC TGC AAT GAC CTG AAA 1975
Ser Gly Tyr Thr Phe Ile Ala Pro Arg Asp Tyr Cys Asn Asp Leu Lys
635 640 645

ATA TCG GAT AAT AAC ACT GAA TTT CTT TTA AAT TTC AAC GAG TTT ATT 2023
Ile Ser Asp Asn Asn Thr Glu Phe Leu Leu Asn Phe Asn Glu Phe Ile
650 655 660

GAT AGA AAA ACT CCA AAC AAC CCA TCA TGT AAC GCG GAT TTG ATT AAT 2071
Asp Arg Lys Thr Pro Asn Asn Pro Ser Cys Asn Ala Asp Leu Ile Asn
665 670 675

-continued

```
AGA GTC TTG CTT GAT GCA GGC TTT ACA AAT GAA CTT GTC CAA AAT TAC      2119
Arg Val Leu Leu Asp Ala Gly Phe Thr Asn Glu Leu Val Gln Asn Tyr
680                 685                 690                 695

TGG AGT AAG CAG AAA AAT ATC AAG GGA GTG AAA GCA CGA TTT GTT GTG      2167
Trp Ser Lys Gln Lys Asn Ile Lys Gly Val Lys Ala Arg Phe Val Val
                700                 705                 710

ACT GAT GGT GGG ATT ACC AGA GTT TAT CCC AAA GAG GCT GGA GAA AAT      2215
Thr Asp Gly Gly Ile Thr Arg Val Tyr Pro Lys Glu Ala Gly Glu Asn
            715                 720                 725

TGG CAA GAA AAC CCA GAG ACA TAT GAG GAC AGC TTC TAT AAA AGG AGC      2263
Trp Gln Glu Asn Pro Glu Thr Tyr Glu Asp Ser Phe Tyr Lys Arg Ser
        730                 735                 740

CTA GAT AAT GAT AAC TAT GTT TTC ACT GCT CCC TAC TTT AAC AAA AGT      2311
Leu Asp Asn Asp Asn Tyr Val Phe Thr Ala Pro Tyr Phe Asn Lys Ser
    745                 750                 755

GGA CCT GGT GCC TAT GAA TCG GGC ATT ATG GTA AGC AAA GCT GTA GAA      2359
Gly Pro Gly Ala Tyr Glu Ser Gly Ile Met Val Ser Lys Ala Val Glu
760                 765                 770                 775

ATA TAT ATT CAA GGG AAA CTT CTT AAA CCT GCA GTT GTT GGA ATT AAA      2407
Ile Tyr Ile Gln Gly Lys Leu Leu Lys Pro Ala Val Val Gly Ile Lys
                780                 785                 790

ATT GAT GTA AAT TCC TGG ATA GAG AAT TTC ACC AAA ACC TCA ATC AGA      2455
Ile Asp Val Asn Ser Trp Ile Glu Asn Phe Thr Lys Thr Ser Ile Arg
            795                 800                 805

GAT CCG TGT GCT GGT CCA GTT TGT GAC TGC AAA AGA AAC AGT GAC GTA      2503
Asp Pro Cys Ala Gly Pro Val Cys Asp Cys Lys Arg Asn Ser Asp Val
        810                 815                 820

ATG GAT TGT GTG ATT CTG GAT GAT GGT GGG TTT CTT CTG ATG GCA AAT      2551
Met Asp Cys Val Ile Leu Asp Asp Gly Gly Phe Leu Leu Met Ala Asn
    825                 830                 835

CAT GAT GAT TAT ACT AAT CAG ATT GGA AGA TTT TTT GGA GAG ATT GAT      2599
His Asp Asp Tyr Thr Asn Gln Ile Gly Arg Phe Phe Gly Glu Ile Asp
840                 845                 850                 855

CCC AGC TTG ATG AGA CAC CTG GTT AAT ATA TCA GTT TAT GCT TTT AAC      2647
Pro Ser Leu Met Arg His Leu Val Asn Ile Ser Val Tyr Ala Phe Asn
                860                 865                 870

AAA TCT TAT GAT TAT CAG TCA GTA TGT GAG CCC GGT GCT GCA CCA AAA      2695
Lys Ser Tyr Asp Tyr Gln Ser Val Cys Glu Pro Gly Ala Ala Pro Lys
            875                 880                 885

CAA GGA GCA GGA CAT CGC TCA GCA TAT GTG CCA TCA GTA GCA GAC ATA      2743
Gln Gly Ala Gly His Arg Ser Ala Tyr Val Pro Ser Val Ala Asp Ile
        890                 895                 900

TTA CAA ATT GGC TGG TGG GCC ACT GCT GCT GCC TGG TCT ATT CTA CAG      2791
Leu Gln Ile Gly Trp Trp Ala Thr Ala Ala Ala Trp Ser Ile Leu Gln
    905                 910                 915

CAG TTT CTC TTG AGT TTG ACC TTT CCA CGA CTC CTT GAG GCA GTT GAG      2839
Gln Phe Leu Leu Ser Leu Thr Phe Pro Arg Leu Leu Glu Ala Val Glu
920                 925                 930                 935

ATG GAG GAT GAT GAC TTC ACG GCC TCC CTG TCC AAG CAG AGC TGC ATT      2887
Met Glu Asp Asp Asp Phe Thr Ala Ser Leu Ser Lys Gln Ser Cys Ile
                940                 945                 950

ACT GAA CAA ACC CAG TAT TTC TTC GAT AAC GAC AGT AAA TCA TTC AGT      2935
Thr Glu Gln Thr Gln Tyr Phe Phe Asp Asn Asp Ser Lys Ser Phe Ser
            955                 960                 965

GGT GTA TTA GAC TGT GGA AAC TGT TCC AGA ATC TTT CAT GGA GAA AAG      2983
Gly Val Leu Asp Cys Gly Asn Cys Ser Arg Ile Phe His Gly Glu Lys
        970                 975                 980

CTT ATG AAC ACC AAC TTA ATA TTC ATA ATG GTT GAG AGC AAA GGG ACA      3031
Leu Met Asn Thr Asn Leu Ile Phe Ile Met Val Glu Ser Lys Gly Thr
    985                 990                 995
```

-continued

```
TGT CCA TGT GAC ACA CGA CTG CTC ATA CAA GCG GAG CAG ACT TCT GAC      3079
Cys Pro Cys Asp Thr Arg Leu Leu Ile Gln Ala Glu Gln Thr Ser Asp
1000                1005                1010                1015

GGT CCA AAT CCT TGT GAC ATG GTT AAG CAA CCT AGA TAC CGA AAA GGG      3127
Gly Pro Asn Pro Cys Asp Met Val Lys Gln Pro Arg Tyr Arg Lys Gly
                1020                1025                1030

CCT GAT GTC TGC TTT GAT AAC AAT GTC TTG GAG GAT TAT ACT GAC TGT      3175
Pro Asp Val Cys Phe Asp Asn Asn Val Leu Glu Asp Tyr Thr Asp Cys
            1035                1040                1045

GGT GGT GTT TCT GGA TTA AAT CCC TCC CTG TGG TAT ATC ATT GGA ATC      3223
Gly Gly Val Ser Gly Leu Asn Pro Ser Leu Trp Tyr Ile Ile Gly Ile
        1050                1055                1060

CAG TTT CTA CTA CTT TGG CTG GTA TCT GGC AGC ACA CAC CGG CTG TTA      3271
Gln Phe Leu Leu Leu Trp Leu Val Ser Gly Ser Thr His Arg Leu Leu
    1065                1070                1075

TGA CCTTCTAAAA ACCAAATCTG CATAGTTAAA CTCCAGACCC TGCCAAAACA TGAGCCC 3331
 *

TGCCCTCAAT TACAGTAACG TAGGGTCAGC TATAAAATCA GACAAACATT AGCTGGGCCT    3391

GTTCCATGGC ATAACACTAA GGCGCAGACT CCTAAGGCAC CCACTGGCTG CATGTCAGGG    3451

TGTCAGATCC TTAAACGTGT GTGAATGCTG CATCATCTAT GTGTAACATC AAAGCAAAAT    3511

CCTATACGTG TCCTCTATTG GAAAATTTGG GCGTTTGTTG TTGCATTGTT GGT           3564
```

( 2 ) INFORMATION FOR SEQ ID NO:36:

( i ) SEQUENCE CHARACTERISTICS:
( A ) LENGTH: 3579 base pairs
( B ) TYPE: nucleic acid
( C ) STRANDEDNESS: double
( D ) TOPOLOGY: linear ( i i ) MOLECULE TYPE: Genomic DNA ( i i i ) HYPOTHETICAL: NO ( i v ) ANTI-SENSE: NO ( v ) FRAGMENT TYPE:

( v i ) ORIGINAL SOURCE:

( i x ) FEATURE:
( A ) NAME/KEY: Coding Sequence
( B ) LOCATION: 35...3289
( D ) OTHER INFORMATION: Standard name "alpha2e"
( A ) NAME/KEY: 5'UTR
( B ) LOCATION: 1...34
( D ) OTHER INFORMATION:
( A ) NAME/KEY: 3'UTR
( B ) LOCATION: 3290...3579
( D ) OTHER INFORMATION:

( x i ) SEQUENCE DESCRIPTION: SEQ ID NO:36:

```
GCGGGGGAGG GGGCATTGAT CTTCGATCGC GAAG ATG GCT GCT GGC TGC CTG CTG      55
                                      Met Ala Ala Gly Cys Leu Leu
                                       1                   5

GCC TTG ACT CTG ACA CTT TTC CAA TCT TTG CTC ATC GGC CCC TCG TCG      103
Ala Leu Thr Leu Thr Leu Phe Gln Ser Leu Leu Ile Gly Pro Ser Ser
        10                  15                  20

GAG GAG CCG TTC CCT TCG GCC GTC ACT ATC AAA TCA TGG GTG GAT AAG      151
Glu Glu Pro Phe Pro Ser Ala Val Thr Ile Lys Ser Trp Val Asp Lys
    25                  30                  35

ATG CAA GAA GAC CTT GTC ACA CTG GCA AAA ACA GCA AGT GGA GTC AAT      199
Met Gln Glu Asp Leu Val Thr Leu Ala Lys Thr Ala Ser Gly Val Asn
 40                 45                  50                  55

CAG CTT GTT GAT ATT TAT GAG AAA TAT CAA GAT TTG TAT ACT GTG GAA      247
```

-continued

```
Gln Leu Val Asp Ile Tyr Glu Lys Tyr Gln Asp Leu Tyr Thr Val Glu
                60                  65                  70

CCA AAT AAT GCA CGC CAG CTG GTA GAA ATT GCA GCC AGG GAT ATT GAG       295
Pro Asn Asn Ala Arg Gln Leu Val Glu Ile Ala Ala Arg Asp Ile Glu
            75                  80                  85

AAA CTT CTG AGC AAC AGA TCT AAA GCC CTG GTG AGC CTG GCA TTG GAA       343
Lys Leu Leu Ser Asn Arg Ser Lys Ala Leu Val Ser Leu Ala Leu Glu
        90                  95                  100

GCG GAG AAA GTT CAA GCA GCT CAC CAG TGG AGA GAA GAT TTT GCA AGC       391
Ala Glu Lys Val Gln Ala Ala His Gln Trp Arg Glu Asp Phe Ala Ser
    105                 110                 115

AAT GAA GTT GTC TAC TAC AAT GCA AAG GAT GAT CTC GAT CCT GAG AAA       439
Asn Glu Val Val Tyr Tyr Asn Ala Lys Asp Asp Leu Asp Pro Glu Lys
120                 125                 130                 135

AAT GAC AGT GAG CCA GGC AGC CAG AGG ATA AAA CCT GTT TTC ATT GAA       487
Asn Asp Ser Glu Pro Gly Ser Gln Arg Ile Lys Pro Val Phe Ile Glu
                140                 145                 150

GAT GCT AAT TTT GGA CGA CAA ATA TCT TAT CAG CAC GCA GCA GTC CAT       535
Asp Ala Asn Phe Gly Arg Gln Ile Ser Tyr Gln His Ala Ala Val His
            155                 160                 165

ATT CCT ACT GAC ATC TAT GAG GGC TCA ACA ATT GTG TTA AAT GAA CTC       583
Ile Pro Thr Asp Ile Tyr Glu Gly Ser Thr Ile Val Leu Asn Glu Leu
        170                 175                 180

AAC TGG ACA AGT GCC TTA GAT GAA GTT TTC AAA AAG AAT CGC GAG GAA       631
Asn Trp Thr Ser Ala Leu Asp Glu Val Phe Lys Lys Asn Arg Glu Glu
    185                 190                 195

GAC CCT TCA TTA TTG TGG CAG GTT TTT GGC AGT GCC ACT GGC CTA GCT       679
Asp Pro Ser Leu Leu Trp Gln Val Phe Gly Ser Ala Thr Gly Leu Ala
200                 205                 210                 215

CGA TAT TAT CCA GCT TCA CCA TGG GTT GAT AAT AGT AGA ACT CCA AAT       727
Arg Tyr Tyr Pro Ala Ser Pro Trp Val Asp Asn Ser Arg Thr Pro Asn
                220                 225                 230

AAG ATT GAC CTT TAT GAT GTA CGC AGA AGA CCA TGG TAC ATC CAA GGA       775
Lys Ile Asp Leu Tyr Asp Val Arg Arg Arg Pro Trp Tyr Ile Gln Gly
            235                 240                 245

GCT GCA TCT CCT AAA GAC ATG CTT ATT CTG GTG GAT GTG AGT GGA AGT       823
Ala Ala Ser Pro Lys Asp Met Leu Ile Leu Val Asp Val Ser Gly Ser
        250                 255                 260

GTT AGT GGA TTG ACA CTT AAA CTG ATC CGA ACA TCT GTC TCC GAA ATG       871
Val Ser Gly Leu Thr Leu Lys Leu Ile Arg Thr Ser Val Ser Glu Met
    265                 270                 275

TTA GAA ACC CTC TCA GAT GAT GAT TTC GTG AAT GTA GCT TCA TTT AAC       919
Leu Glu Thr Leu Ser Asp Asp Asp Phe Val Asn Val Ala Ser Phe Asn
280                 285                 290                 295

AGC AAT GCT CAG GAT GTA AGC TGT TTT CAG CAC CTT GTC CAA GCA AAT       967
Ser Asn Ala Gln Asp Val Ser Cys Phe Gln His Leu Val Gln Ala Asn
                300                 305                 310

GTA AGA AAT AAA AAA GTG TTG AAA GAC GCG GTG AAT AAT ATC ACA GCC      1015
Val Arg Asn Lys Lys Val Leu Lys Asp Ala Val Asn Asn Ile Thr Ala
            315                 320                 325

AAA GGA ATT ACA GAT TAT AAG AAG GGC TTT AGT TTT GCT TTT GAA CAG      1063
Lys Gly Ile Thr Asp Tyr Lys Lys Gly Phe Ser Phe Ala Phe Glu Gln
        330                 335                 340

CTG CTT AAT TAT AAT GTT TCC AGA GCA AAC TGC AAT AAG ATT ATT ATG      1111
Leu Leu Asn Tyr Asn Val Ser Arg Ala Asn Cys Asn Lys Ile Ile Met
    345                 350                 355

CTA TTC ACG GAT GGA GGA GAA GAG AGA GCC CAG GAG ATA TTT AAC AAA      1159
Leu Phe Thr Asp Gly Gly Glu Glu Arg Ala Gln Glu Ile Phe Asn Lys
360                 365                 370                 375

TAC AAT AAA GAT AAA AAA GTA CGT GTA TTC AGG TTT TCA GTT GGT CAA      1207
```

-continued

```
Tyr  Asn  Lys  Asp  Lys  Lys  Val  Arg  Val  Phe  Arg  Phe  Ser  Val  Gly  Gln
                    380                      385                      390

CAC  AAT  TAT  GAG  AGA  GGA  CCT  ATT  CAG  TGG  ATG  GCC  TGT  GAA  AAC  AAA      1255
His  Asn  Tyr  Glu  Arg  Gly  Pro  Ile  Gln  Trp  Met  Ala  Cys  Glu  Asn  Lys
               395                      400                      405

GGT  TAT  TAT  TAT  GAA  ATT  CCT  TCC  ATT  GGT  GCA  ATA  AGA  ATC  AAT  ACT      1303
Gly  Tyr  Tyr  Tyr  Glu  Ile  Pro  Ser  Ile  Gly  Ala  Ile  Arg  Ile  Asn  Thr
          410                      415                      420

CAG  GAA  TAT  TTG  GAT  GTT  TTG  GGA  AGA  CCA  ATG  GTT  TTA  GCA  GGA  GAC      1351
Gln  Glu  Tyr  Leu  Asp  Val  Leu  Gly  Arg  Pro  Met  Val  Leu  Ala  Gly  Asp
     425                      430                      435

AAA  GCT  AAG  CAA  GTC  CAA  TGG  ACA  AAT  GTG  TAC  CTG  GAT  GCA  TTG  GAA      1399
Lys  Ala  Lys  Gln  Val  Gln  Trp  Thr  Asn  Val  Tyr  Leu  Asp  Ala  Leu  Glu
440                      445                      450                      455

CTG  GGA  CTT  GTC  ATT  ACT  GGA  ACT  CTT  CCG  GTC  TTC  AAC  ATA  ACC  GGC      1447
Leu  Gly  Leu  Val  Ile  Thr  Gly  Thr  Leu  Pro  Val  Phe  Asn  Ile  Thr  Gly
                    460                      465                      470

CAA  TTT  GAA  AAT  AAG  ACA  AAC  TTA  AAG  AAC  CAG  CTG  ATT  CTT  GGT  GTG      1495
Gln  Phe  Glu  Asn  Lys  Thr  Asn  Leu  Lys  Asn  Gln  Leu  Ile  Leu  Gly  Val
               475                      480                      485

ATG  GGA  GTA  GAT  GTG  TCT  TTG  GAA  GAT  ATT  AAA  AGA  CTG  ACA  CCA  CGT      1543
Met  Gly  Val  Asp  Val  Ser  Leu  Glu  Asp  Ile  Lys  Arg  Leu  Thr  Pro  Arg
          490                      495                      500

TTT  ACA  CTG  TGC  CCC  AAT  GGG  TAT  TAC  TTT  GCA  ATC  GAT  CCT  AAT  GGT      1591
Phe  Thr  Leu  Cys  Pro  Asn  Gly  Tyr  Tyr  Phe  Ala  Ile  Asp  Pro  Asn  Gly
     505                      510                      515

TAT  GTT  TTA  TTA  CAT  CCA  AAT  CTT  CAG  CCA  AAG  AAC  CCC  AAA  TCT  CAG      1639
Tyr  Val  Leu  Leu  His  Pro  Asn  Leu  Gln  Pro  Lys  Asn  Pro  Lys  Ser  Gln
520                      525                      530                      535

GAG  CCA  GTA  ACA  TTG  GAT  TTC  CTT  GAT  GCA  GAG  TTA  GAG  AAT  GAT  ATT      1687
Glu  Pro  Val  Thr  Leu  Asp  Phe  Leu  Asp  Ala  Glu  Leu  Glu  Asn  Asp  Ile
                    540                      545                      550

AAA  GTG  GAG  ATT  CGA  AAT  AAG  ATG  ATT  GAT  GGG  GAA  AGT  GGA  GAA  AAA      1735
Lys  Val  Glu  Ile  Arg  Asn  Lys  Met  Ile  Asp  Gly  Glu  Ser  Gly  Glu  Lys
               555                      560                      565

ACA  TTC  AGA  ACT  CTG  GTT  AAA  TCT  CAA  GAT  GAG  AGA  TAT  ATT  GAC  AAA      1783
Thr  Phe  Arg  Thr  Leu  Val  Lys  Ser  Gln  Asp  Glu  Arg  Tyr  Ile  Asp  Lys
          570                      575                      580

GGA  AAC  AGG  ACA  TAC  ACA  TGG  ACA  CCT  GTC  AAT  GGC  ACA  GAT  TAC  AGT      1831
Gly  Asn  Arg  Thr  Tyr  Thr  Trp  Thr  Pro  Val  Asn  Gly  Thr  Asp  Tyr  Ser
     585                      590                      595

TTG  GCC  TTG  GTA  TTA  CCA  ACC  TAC  AGT  TTT  TAC  TAT  ATA  AAA  GCC  AAA      1879
Leu  Ala  Leu  Val  Leu  Pro  Thr  Tyr  Ser  Phe  Tyr  Tyr  Ile  Lys  Ala  Lys
600                      605                      610                      615

CTA  GAA  GAG  ACA  ATA  ACT  CAG  GCC  AGA  TAT  TCG  GAA  ACC  CTG  AAG  CCA      1927
Leu  Glu  Glu  Thr  Ile  Thr  Gln  Ala  Arg  Tyr  Ser  Glu  Thr  Leu  Lys  Pro
                    620                      625                      630

GAT  AAT  TTT  GAA  GAA  TCT  GGC  TAT  ACA  TTC  ATA  GCA  CCA  AGA  GAT  TAC      1975
Asp  Asn  Phe  Glu  Glu  Ser  Gly  Tyr  Thr  Phe  Ile  Ala  Pro  Arg  Asp  Tyr
               635                      640                      645

TGC  AAT  GAC  CTG  AAA  ATA  TCG  GAT  AAT  AAC  ACT  GAA  TTT  CTT  TTA  AAT      2023
Cys  Asn  Asp  Leu  Lys  Ile  Ser  Asp  Asn  Asn  Thr  Glu  Phe  Leu  Leu  Asn
          650                      655                      660

TTC  AAC  GAG  TTT  ATT  GAT  AGA  AAA  ACT  CCA  AAC  AAC  CCA  TCA  TGT  AAC      2071
Phe  Asn  Glu  Phe  Ile  Asp  Arg  Lys  Thr  Pro  Asn  Asn  Pro  Ser  Cys  Asn
     665                      670                      675

GCG  GAT  TTG  ATT  AAT  AGA  GTC  TTG  CTT  GAT  GCA  GGC  TTT  ACA  AAT  GAA      2119
Ala  Asp  Leu  Ile  Asn  Arg  Val  Leu  Leu  Asp  Ala  Gly  Phe  Thr  Asn  Glu
680                      685                      690                      695

CTT  GTC  CAA  AAT  TAC  TGG  AGT  AAG  CAG  AAA  AAT  ATC  AAG  GGA  GTG  AAA      2167
```

-continued

```
Leu Val Gln Asn Tyr Trp Ser Lys Gln Lys Asn Ile Lys Gly Val Lys
                700                 705                 710

GCA CGA TTT GTT GTG ACT GAT GGT GGG ATT ACC AGA GTT TAT CCC AAA     2215
Ala Arg Phe Val Val Thr Asp Gly Gly Ile Thr Arg Val Tyr Pro Lys
            715                 720                 725

GAG GCT GGA GAA AAT TGG CAA GAA AAC CCA GAG ACA TAT GAG GAC AGC     2263
Glu Ala Gly Glu Asn Trp Gln Glu Asn Pro Glu Thr Tyr Glu Asp Ser
            730                 735                 740

TTC TAT AAA AGG AGC CTA GAT AAT GAT AAC TAT GTT TTC ACT GCT CCC     2311
Phe Tyr Lys Arg Ser Leu Asp Asn Asp Asn Tyr Val Phe Thr Ala Pro
    745                 750                 755

TAC TTT AAC AAA AGT GGA CCT GGT GCC TAT GAA TCG GGC ATT ATG GTA     2359
Tyr Phe Asn Lys Ser Gly Pro Gly Ala Tyr Glu Ser Gly Ile Met Val
760                 765                 770                 775

AGC AAA GCT GTA GAA ATA TAT ATT CAA GGG AAA CTT CTT AAA CCT GCA     2407
Ser Lys Ala Val Glu Ile Tyr Ile Gln Gly Lys Leu Leu Lys Pro Ala
                780                 785                 790

GTT GTT GGA ATT AAA ATT GAT GTA AAT TCC TGG ATA GAG AAT TTC ACC     2455
Val Val Gly Ile Lys Ile Asp Val Asn Ser Trp Ile Glu Asn Phe Thr
            795                 800                 805

AAA ACC TCA ATC AGA GAT CCG TGT GCT GGT CCA GTT TGT GAC TGC AAA     2503
Lys Thr Ser Ile Arg Asp Pro Cys Ala Gly Pro Val Cys Asp Cys Lys
        810                 815                 820

AGA AAC AGT GAC GTA ATG GAT TGT GTG ATT CTG GAT GAT GGT GGG TTT     2551
Arg Asn Ser Asp Val Met Asp Cys Val Ile Leu Asp Asp Gly Gly Phe
    825                 830                 835

CTT CTG ATG GCA AAT CAT GAT GAT TAT ACT AAT CAG ATT GGA AGA TTT     2599
Leu Leu Met Ala Asn His Asp Asp Tyr Thr Asn Gln Ile Gly Arg Phe
840                 845                 850                 855

TTT GGA GAG ATT GAT CCC AGC TTG ATG AGA CAC CTG GTT AAT ATA TCA     2647
Phe Gly Glu Ile Asp Pro Ser Leu Met Arg His Leu Val Asn Ile Ser
                860                 865                 870

GTT TAT GCT TTT AAC AAA TCT TAT GAT TAT CAG TCA GTA TGT GAG CCC     2695
Val Tyr Ala Phe Asn Lys Ser Tyr Asp Tyr Gln Ser Val Cys Glu Pro
            875                 880                 885

GGT GCT GCA CCA AAA CAA GGA GCA GGA CAT CGC TCA GCA TAT GTG CCA     2743
Gly Ala Ala Pro Lys Gln Gly Ala Gly His Arg Ser Ala Tyr Val Pro
        890                 895                 900

TCA GTA GCA GAC ATA TTA CAA ATT GGC TGG TGG GCC ACT GCT GCT GCC     2791
Ser Val Ala Asp Ile Leu Gln Ile Gly Trp Trp Ala Thr Ala Ala Ala
    905                 910                 915

TGG TCT ATT CTA CAG CAG TTT CTC TTG AGT TTG ACC TTT CCA CGA CTC     2839
Trp Ser Ile Leu Gln Gln Phe Leu Leu Ser Leu Thr Phe Pro Arg Leu
920                 925                 930                 935

CTT GAG GCA GTT GAG ATG GAG GAT GAT GAC TTC ACG GCC TCC CTG TCC     2887
Leu Glu Ala Val Glu Met Glu Asp Asp Asp Phe Thr Ala Ser Leu Ser
                940                 945                 950

AAG CAG AGC TGC ATT ACT GAA CAA ACC CAG TAT TTC TTC GAT AAC GAC     2935
Lys Gln Ser Cys Ile Thr Glu Gln Thr Gln Tyr Phe Phe Asp Asn Asp
            955                 960                 965

AGT AAA TCA TTC AGT GGT GTA TTA GAC TGT GGA AAC TGT TCC AGA ATC     2983
Ser Lys Ser Phe Ser Gly Val Leu Asp Cys Gly Asn Cys Ser Arg Ile
            970                 975                 980

TTT CAT GGA GAA AAG CTT ATG AAC ACC AAC TTA ATA TTC ATA ATG GTT     3031
Phe His Gly Glu Lys Leu Met Asn Thr Asn Leu Ile Phe Ile Met Val
    985                 990                 995

GAG AGC AAA GGG ACA TGT CCA TGT GAC ACA CGA CTG CTC ATA CAA GCG     3079
Glu Ser Lys Gly Thr Cys Pro Cys Asp Thr Arg Leu Leu Ile Gln Ala
1000                1005                1010                1015

GAG CAG ACT TCT GAC GGT CCA AAT CCT TGT GAC ATG GTT AAG CAA CCT     3127
```

```
Glu Gln Thr Ser Asp Gly Pro Asn Pro Cys Asp Met Val Lys Gln Pro
                1020                1025                1030

AGA TAC CGA AAA GGG CCT GAT GTC TGC TTT GAT AAC AAT GTC TTG GAG    3175
Arg Tyr Arg Lys Gly Pro Asp Val Cys Phe Asp Asn Asn Val Leu Glu
            1035                1040                1045

GAT TAT ACT GAC TGT GGT GGT GTT TCT GGA TTA AAT CCC TCC CTG TGG    3223
Asp Tyr Thr Asp Cys Gly Gly Val Ser Gly Leu Asn Pro Ser Leu Trp
        1050                1055                1060

TAT ATC ATT GGA ATC CAG TTT CTA CTA CTT TGG CTG GTA TCT GGC AGC    3271
Tyr Ile Ile Gly Ile Gln Phe Leu Leu Leu Trp Leu Val Ser Gly Ser
    1065                1070                1075

ACA CAC CGG CTG TTA TGA CCTTCTAAAA ACCAAATCTG CATAGTTAAA CTCCAGACC 3328
Thr His Arg Leu Leu
1080

CTGCCAAAAC ATGAGCCCTG CCCTCAATTA CAGTAACGTA GGGTCAGCTA TAAAATCAGA  3388

CAAACATTAG CTGGGCCTGT TCCATGGCAT AACACTAAGG CGCAGACTCC TAAGGCACCC  3448

ACTGGCTGCA TGTCAGGGTG TCAGATCCTT AAACGTGTGT GAATGCTGCA TCATCTATGT  3508

GTAACATCAA AGCAAAATCC TATACGTGTC CTCTATTGGA AAATTTGGGC GTTTGTTGTT  3568

GCATTGTTGG T                                                       3579
```

(2) INFORMATION FOR SEQ ID NO:37:

(i) SEQUENCE CHARACTERISTICS:
- (A) LENGTH: 1681 base pairs
- (B) TYPE: nucleic acid
- (C) STRANDEDNESS: double
- (D) TOPOLOGY: linear (ii) MOLECULE TYPE: Genomic DNA (iii) HYPOTHETICAL: NO (iv) ANTI-SENSE: NO (v) FRAGMENT TYPE:

(vi) ORIGINAL SOURCE:

(ix) FEATURE:
- (A) NAME/KEY: Coding Sequence
- (B) LOCATION: 1...1572
- (D) OTHER INFORMATION: Standard name "beta1"
- (A) NAME/KEY: 3'UTR
- (B) LOCATION: 1573...1681
- (D) OTHER INFORMATION:

(xi) SEQUENCE DESCRIPTION: SEQ ID NO:37:

```
ATG GTC CAG AAG ACC AGC ATG TCC CGG GGC CCT TAC CCA CCC TCC CAG     48
Met Val Gln Lys Thr Ser Met Ser Arg Gly Pro Tyr Pro Pro Ser Gln
  1               5                  10                  15

GAG ATC CCC ATG GAG GTC TTC GAC CCC AGC CCG CAG GGC AAA TAC AGC     96
Glu Ile Pro Met Glu Val Phe Asp Pro Ser Pro Gln Gly Lys Tyr Ser
            20                  25                  30

AAG AGG AAA GGG CGA TTC AAA CGG TCA GAT GGG AGC ACG TCC TCG GAT    144
Lys Arg Lys Gly Arg Phe Lys Arg Ser Asp Gly Ser Thr Ser Ser Asp
        35                  40                  45

ACC ACA TCC AAC AGC TTT GTC CGC CAG GGC TCA GCG GAG TCC TAC ACC    192
Thr Thr Ser Asn Ser Phe Val Arg Gln Gly Ser Ala Glu Ser Tyr Thr
    50                  55                  60

AGC CGT CCA TCA GAC TCT GAT GTA TCT CTG GAG GAG GAC CGG GAA GCC    240
Ser Arg Pro Ser Asp Ser Asp Val Ser Leu Glu Glu Asp Arg Glu Ala
 65                  70                  75                  80

TTA AGG AAG GAA GCA GAG CGC CAG GCA TTA GCG CAG CTC GAG AAG GCC    288
Leu Arg Lys Glu Ala Glu Arg Gln Ala Leu Ala Gln Leu Glu Lys Ala
```

-continued

```
                                    85                                  90                                  95

AAG ACC AAG CCA GTG GCA TTT GCT GTG CGG ACA AAT GTT GGC TAC AAT    336
Lys Thr Lys Pro Val Ala Phe Ala Val Arg Thr Asn Val Gly Tyr Asn
            100                 105                 110

CCG TCT CCA GGG GAT GAG GTG CCT GTG CAG GGA GTG GCC ATC ACC TTC    384
Pro Ser Pro Gly Asp Glu Val Pro Val Gln Gly Val Ala Ile Thr Phe
        115                 120                 125

GAG CCC AAA GAC TTC CTG CAC ATC AAG GAG AAA TAC AAT AAT GAC TGG    432
Glu Pro Lys Asp Phe Leu His Ile Lys Glu Lys Tyr Asn Asn Asp Trp
    130                 135                 140

TGG ATC GGG CGG CTG GTG AAG GAG GGC TGT GAG GTT GGC TTC ATT CCC    480
Trp Ile Gly Arg Leu Val Lys Glu Gly Cys Glu Val Gly Phe Ile Pro
145                 150                 155                 160

AGC CCC GTC AAA CTG GAC AGC CTT CGC CTG CTG CAG GAA CAG AAG CTG    528
Ser Pro Val Lys Leu Asp Ser Leu Arg Leu Leu Gln Glu Gln Lys Leu
                165                 170                 175

CGC CAG AAC CGC CTC GGC TCC AGC AAA TCA GGC GAT AAC TCC AGT TCC    576
Arg Gln Asn Arg Leu Gly Ser Ser Lys Ser Gly Asp Asn Ser Ser Ser
            180                 185                 190

AGT CTG GGA GAT GTG GTG ACT GGC ACC CGC CGC CCC ACA CCC CCT GCC    624
Ser Leu Gly Asp Val Val Thr Gly Thr Arg Arg Pro Thr Pro Pro Ala
        195                 200                 205

AGT GGT AAT GAA ATG ACT AAC TTA GCC TTT GAA CTA GAC CCC CTA GAG    672
Ser Gly Asn Glu Met Thr Asn Leu Ala Phe Glu Leu Asp Pro Leu Glu
    210                 215                 220

TTA GAG GAG GAA GAG GCT GAG CTT GGT GAG CAG AGT GGC TCT GCC AAG    720
Leu Glu Glu Glu Glu Ala Glu Leu Gly Glu Gln Ser Gly Ser Ala Lys
225                 230                 235                 240

ACT AGT GTT AGC AGT GTC ACC ACC CCG CCA CCC CAT GGC AAA CGC ATC    768
Thr Ser Val Ser Ser Val Thr Thr Pro Pro Pro His Gly Lys Arg Ile
                245                 250                 255

CCC TTC TTT AAG AAG ACA GAG CAT GTG CCC CCC TAT GAC GTG GTG CCT    816
Pro Phe Phe Lys Lys Thr Glu His Val Pro Pro Tyr Asp Val Val Pro
            260                 265                 270

TCC ATG AGG CCC ATC ATC CTG GTG GGA CCG TCG CTC AAG GGC TAC GAG    864
Ser Met Arg Pro Ile Ile Leu Val Gly Pro Ser Leu Lys Gly Tyr Glu
        275                 280                 285

GTT ACA GAC ATG ATG CAG AAA GCT TTA TTT GAC TTC TTG AAG CAT CGG    912
Val Thr Asp Met Met Gln Lys Ala Leu Phe Asp Phe Leu Lys His Arg
    290                 295                 300

TTT GAT GGC AGG ATC TCC ATC ACT CGT GTG ACG GCA GAT ATT TCC CTG    960
Phe Asp Gly Arg Ile Ser Ile Thr Arg Val Thr Ala Asp Ile Ser Leu
305                 310                 315                 320

GCT AAG CGC TCA GTT CTC AAC AAC CCC AGC AAA CAC ATC ATC ATT GAG   1008
Ala Lys Arg Ser Val Leu Asn Asn Pro Ser Lys His Ile Ile Ile Glu
                325                 330                 335

CGC TCC AAC ACA CGC TCC AGC CTG GCT GAG GTG CAG AGT GAA ATC GAG   1056
Arg Ser Asn Thr Arg Ser Ser Leu Ala Glu Val Gln Ser Glu Ile Glu
            340                 345                 350

CGA ATC TTC GAG CTG GCC CGG ACC CTT CAG TTG GTC GCT CTG GAT GCT   1104
Arg Ile Phe Glu Leu Ala Arg Thr Leu Gln Leu Val Ala Leu Asp Ala
        355                 360                 365

GAC ACC ATC AAT CAC CCA GCC CAG CTG TCC AAG ACC TCG CTG GCC CCC   1152
Asp Thr Ile Asn His Pro Ala Gln Leu Ser Lys Thr Ser Leu Ala Pro
    370                 375                 380

ATC ATT GTT TAC ATC AAG ATC ACC TCT CCC AAG GTA CTT CAA AGG CTC   1200
Ile Ile Val Tyr Ile Lys Ile Thr Ser Pro Lys Val Leu Gln Arg Leu
385                 390                 395                 400

ATC AAG TCC CGA GGA AAG TCT CAG TCC AAA CAC CTC AAT GTC CAA ATA   1248
Ile Lys Ser Arg Gly Lys Ser Gln Ser Lys His Leu Asn Val Gln Ile
```

-continued

```
                    405                      410                      415

GCG GCC TCG GAA AAG CTG GCA CAG TGC CCC CCT GAA ATG TTT GAC ATC    1296
Ala Ala Ser Glu Lys Leu Ala Gln Cys Pro Pro Glu Met Phe Asp Ile
            420                     425                     430

ATC CTG GAT GAG AAC CAA TTG GAG GAT GCC TGC GAG CAT CTG GCG GAG    1344
Ile Leu Asp Glu Asn Gln Leu Glu Asp Ala Cys Glu His Leu Ala Glu
        435                     440                     445

TAC TTG GAA GCC TAT TGG AAG GCC ACA CAC CCG CCC AGC AGC ACG CCA    1392
Tyr Leu Glu Ala Tyr Trp Lys Ala Thr His Pro Pro Ser Ser Thr Pro
    450                     455                     460

CCC AAT CCG CTG CTG AAC CGC ACC ATG GCT ACC GCA GCC CTG GCT GCC    1440
Pro Asn Pro Leu Leu Asn Arg Thr Met Ala Thr Ala Ala Leu Ala Ala
465                     470                     475                 480

AGC CCT GCC CCT GTC TCC AAC CTC CAG GTA CAG GTG CTC ACC TCG CTC    1488
Ser Pro Ala Pro Val Ser Asn Leu Gln Val Gln Val Leu Thr Ser Leu
                485                     490                     495

AGG AGA AAC CTC GGC TTC TGG GGC GGG CTG GAG TCC TCA CAG CGG GGC    1536
Arg Arg Asn Leu Gly Phe Trp Gly Gly Leu Glu Ser Ser Gln Arg Gly
            500                     505                     510

AGT GTG GTG CCC CAG GAG CAG GAA CAT GCC ATG TAG TGGGCGCCCT GCCCGTC 1589
Ser Val Val Pro Gln Glu Gln Glu His Ala Met  *
        515                     520

TTCCCTCCTG CTCTGGGGTC GGAACTGGAG TGCAGGGAAC ATGGAGGAGG AAGGGAAGAG   1649

CTTTATTTTG TAAAAAAATA AGATGAGCGG CA                                 1681
```

( 2 ) INFORMATION FOR SEQ ID NO:38:

( i ) SEQUENCE CHARACTERISTICS:
( A ) LENGTH: 1526 base pairs
( B ) TYPE: nucleic acid
( C ) STRANDEDNESS: double
( D ) TOPOLOGY: linear ( i i ) MOLECULE TYPE: DNA (genomic)

( i x ) FEATURE:
( A ) NAME/KEY: CDS
( B ) LOCATION: 1..651
( D ) OTHER INFORMATION: /standard_name= “Beta4”

( x i ) SEQUENCE DESCRIPTION: SEQ ID NO:38:

```
ATG GTC CAG AAG ACC AGC ATG TCC CGG GGC CCT TAC CCA CCC TCC CAG      48
Met Val Gln Lys Thr Ser Met Ser Arg Gly Pro Tyr Pro Pro Ser Gln
  1               5                  10                  15

GAG ATC CCC ATG GAG GTC TTC GAC CCC AGC CCG CAG GGC AAA TAC AGC      96
Glu Ile Pro Met Glu Val Phe Asp Pro Ser Pro Gln Gly Lys Tyr Ser
            20                  25                  30

AAG AGG AAA GGG CGA TTC AAA CGG TCA GAT GGG AGC ACG TCC TCG GAT     144
Lys Arg Lys Gly Arg Phe Lys Arg Ser Asp Gly Ser Thr Ser Ser Asp
        35                  40                  45

ACC ACA TCC AAC AGC TTT GTC CGC CAG GGC TCA GCG GAG TCC TAC ACC     192
Thr Thr Ser Asn Ser Phe Val Arg Gln Gly Ser Ala Glu Ser Tyr Thr
    50                  55                  60

AGC CGT CCA TCA GAC TCT GAT GTA TCT CTG GAG GAG GAC CGG GAA GCC     240
Ser Arg Pro Ser Asp Ser Asp Val Ser Leu Glu Glu Asp Arg Glu Ala
 65                  70                  75                  80

TTA AGG AAG GAA GCA GAG CGC CAG GCA TTA GCG CAG CTC GAG AAG GCC     288
Leu Arg Lys Glu Ala Glu Arg Gln Ala Leu Ala Gln Leu Glu Lys Ala
                85                  90                  95

AAG ACC AAG CCA GTG GCA TTT GCT GTG CGG ACA AAT GTT GGC TAC AAT     336
Lys Thr Lys Pro Val Ala Phe Ala Val Arg Thr Asn Val Gly Tyr Asn
            100                 105                 110
```

-continued

CCG TCT CCA GGG GAT GAG GTG CCT GTG CAG GGA GTG GCC ATC ACC TTC 384
Pro Ser Pro Gly Asp Glu Val Pro Val Gln Gly Val Ala Ile Thr Phe
115 120 125

GAG CCC AAA GAC TTC CTG CAC ATC AAG GAG AAA TAC AAT AAT GAC TGG 432
Glu Pro Lys Asp Phe Leu His Ile Lys Glu Lys Tyr Asn Asn Asp Trp
130 135 140

TGG ATC GGG CGG CTG GTG AAG GAG GGC TGT GAG GTT GGC TTC ATT CCC 480
Trp Ile Gly Arg Leu Val Lys Glu Gly Cys Glu Val Gly Phe Ile Pro
145 150 155 160

AGC CCC GTC AAA CTG GAC AGC CTT CGC CTG CTG CAG GAA CAG AAG CTG 528
Ser Pro Val Lys Leu Asp Ser Leu Arg Leu Leu Gln Glu Gln Lys Leu
165 170 175

CGC CAG AAC CGC CTC GGC TCC AGC AAA TCA GGC GAT AAC TCC AGT TCC 576
Arg Gln Asn Arg Leu Gly Ser Ser Lys Ser Gly Asp Asn Ser Ser Ser
180 185 190

AGT CTG GGA GAT GTG GTG ACT GGC ACC CGC CGC CCC ACA CCC CCT GCC 624
Ser Leu Gly Asp Val Val Thr Gly Thr Arg Arg Pro Thr Pro Pro Ala
195 200 205

AGT GAC AGA GCA TGT GCC CCC CTA TGACGTGGTG CCTTCCATGA GGCCCATCAT 678
Ser Asp Arg Ala Cys Ala Pro Leu
210 215

CCTGGTGGGA CCGTCGCTCA AGGGCTACGA GGTTACAGAC ATGATGCAGA AAGCTTTATT 738

TGACTTCTTG AAGCATCGGT TTGATGGCAG GATCTCCATC ACTCGTGTGA CGGCAGATAT 798

TTCCCTGGCT AAGCGCTCAG TTCTCAACAA CCCCAGCAAA CACATCATCA TTGAGCGCTC 858

CAACACACGC TCCAGCCTGG CTGAGGTGCA GAGTGAAATC GAGCGAATCT TCGAGCTGGC 918

CCGGACCCTT CAGTTGGTCG CTCTGGATGC TGACACCATC AATCACCCAG CCCAGCTGTC 978

CAAGACCTCG CTGGCCCCCA TCATTGTTTA CATCAAGATC ACCTCTCCCA AGGTACTTCA 1038

AAGGCTCATC AAGTCCCGAG GAAAGTCTCA GTCCAAACAC CTCAATGTCC AAATAGCGGC 1098

CTCGGAAAAG CTGGCACAGT GCCCCCCTGA AATGTTTGAC ATCATCCTGG ATGAGAACCA 1158

ATTGGAGGAT GCCTGCGAGC ATCTGGCGGA GTACTTGGAA GCCTATTGGA AGGCCACACA 1218

CCCGCCCAGC AGCACGCCAC CCAATCCGCT GCTGAACCGC ACCATGGCTA CCGCAGCCCT 1278

GGCTGCCAGC CCTGCCCCTG TCTCCAACCT CCAGGTACAG GTGCTCACCT CGCTCAGGAG 1338

AAACCTCGGC TTCTGGGGCG GGCTGGAGTC CTCACAGCGG GGCAGTGTGG TGCCCCAGGA 1398

GCAGGAACAT GCCATGTAGT GGGCGCCCTG CCCGTCTTCC CTCCTGCTCT GGGGTCGGAA 1458

CTGGAGTGCA GGGAACATGG AGGAGGAAGG GAAGAGCTTT ATTTTGTAAA AAAATAAGAT 1518

GAGCGGCA 1526

( 2 ) INFORMATION FOR SEQ ID NO:39:

( i ) SEQUENCE CHARACTERISTICS:
( A ) LENGTH: 1393 base pairs
( B ) TYPE: nucleic acid
( C ) STRANDEDNESS: double
( D ) TOPOLOGY: linear ( i i ) MOLECULE TYPE: DNA (genomic)

( i x ) FEATURE:
( A ) NAME/KEY: CDS
( B ) LOCATION: 1..660
( D ) OTHER INFORMATION: /standard_name= "Beta5"

( x i ) SEQUENCE DESCRIPTION: SEQ ID NO:39:

ATG GTC CAG AAG ACC AGC ATG TCC CGG GGC CCT TAC CCA CCC TCC CAG 48
Met Val Gln Lys Thr Ser Met Ser Arg Gly Pro Tyr Pro Pro Ser Gln
1 5 10 15

-continued

```
GAG ATC CCC ATG GAG GTC TTC GAC CCC AGC CCG CAG GGC AAA TAC AGC      96
Glu Ile Pro Met Glu Val Phe Asp Pro Ser Pro Gln Gly Lys Tyr Ser
            20                  25                  30

AAG AGG AAA GGG CGA TTC AAA CGG TCA GAT GGG AGC ACG TCC TCG GAT     144
Lys Arg Lys Gly Arg Phe Lys Arg Ser Asp Gly Ser Thr Ser Ser Asp
        35                  40                  45

ACC ACA TCC AAC AGC TTT GTC CGC CAG GGC TCA GCG GAG TCC TAC ACC     192
Thr Thr Ser Asn Ser Phe Val Arg Gln Gly Ser Ala Glu Ser Tyr Thr
    50                  55                  60

AGC CGT CCA TCA GAC TCT GAT GTA TCT CTG GAG GAG GAC CGG GAA GCC     240
Ser Arg Pro Ser Asp Ser Asp Val Ser Leu Glu Glu Asp Arg Glu Ala
65                  70                  75                  80

TTA AGG AAG GAA GCA GAG CGC CAG GCA TTA GCG CAG CTC GAG AAG GCC     288
Leu Arg Lys Glu Ala Glu Arg Gln Ala Leu Ala Gln Leu Glu Lys Ala
                85                  90                  95

AAG ACC AAG CCA GTG GCA TTT GCT GTG CGG ACA AAT GTT GGC TAC AAT     336
Lys Thr Lys Pro Val Ala Phe Ala Val Arg Thr Asn Val Gly Tyr Asn
            100                 105                 110

CCG TCT CCA GGG GAT GAG GTG CCT GTG CAG GGA GTG GCC ATC ACC TTC     384
Pro Ser Pro Gly Asp Glu Val Pro Val Gln Gly Val Ala Ile Thr Phe
        115                 120                 125

GAG CCC AAA GAC TTC CTG CAC ATC AAG GAG AAA TAC AAT AAT GAC TGG     432
Glu Pro Lys Asp Phe Leu His Ile Lys Glu Lys Tyr Asn Asn Asp Trp
    130                 135                 140

TGG ATC GGG CGG CTG GTG AAG GAG GGC TGT GAG GTT GGC TTC ATT CCC     480
Trp Ile Gly Arg Leu Val Lys Glu Gly Cys Glu Val Gly Phe Ile Pro
145                 150                 155                 160

AGC CCC GTC AAA CTG GAC AGC CTT CGC CTG CTG CAG GAA CAG AAG CTG     528
Ser Pro Val Lys Leu Asp Ser Leu Arg Leu Leu Gln Glu Gln Lys Leu
                165                 170                 175

CGC CAG AAC CGC CTC GGC TCC AGC AAA TCA GGC GAT AAC TCC AGT TCC     576
Arg Gln Asn Arg Leu Gly Ser Ser Lys Ser Gly Asp Asn Ser Ser Ser
            180                 185                 190

AGT CTG GGA GAT GTG GTG ACT GGC ACC CGC CGC CCC ACA CCC CCT GCC     624
Ser Leu Gly Asp Val Val Thr Gly Thr Arg Arg Pro Thr Pro Pro Ala
        195                 200                 205

AGT GGT TAC AGA CAT GAT GCA GAA AGC TTT ATT TGACTTCTTG AAGCATCGGT   677
Ser Gly Tyr Arg His Asp Ala Glu Ser Phe Ile
    210                 215                 220

TTGATGGCAG GATCTCCATC ACTCGTGTGA CGGCAGATAT TTCCCTGGCT AAGCGCTCAG   737

TTCTCAACAA CCCCAGCAAA CACATCATCA TTGAGCGCTC CAACACACGC TCCAGCCTGG   797

CTGAGGTGCA GAGTGAAATC GAGCGAATCT TCGAGCTGGC CCGGACCCTT CAGTTGGTCG   857

CTCTGGATGC TGACACCATC AATCACCCAG CCCAGCTGTC CAAGACCTCG CTGGCCCCCA   917

TCATTGTTTA CATCAAGATC ACCTCTCCCA AGGTACTTCA AAGGCTCATC AAGTCCCGAG   977

GAAAGTCTCA GTCCAAACAC CTCAATGTCC AAATAGCGGC CTCGGAAAAG CTGGCACAGT  1037

GCCCCCCTGA AATGTTTGAC ATCATCCTGG ATGAGAACCA ATTGGAGGAT GCCTGCGAGC  1097

ATCTGGCGGA GTACTTGGAA GCCTATTGGA AGGCCACACA CCCGCCCAGC AGCACGCCAC  1157

CCAATCCGCT GCTGAACCGC ACCATGGCTA CCGCAGCCCT GGCTGCCAGC CCTGCCCCTG  1217

TCTCCAACCT CCAGGTACAG GTGCTCACCT CGCTCAGGAG AAACCTCGGC TTCTGGGGCG  1277

GGCTGGAGTC CTCACAGCGG GGCAGTGTGG TGCCCCAGGA GCAGGAACAT GCCATGTAGT  1337

GGGCGCCCTG CCCGTCTTCC CTCCTGCTCT GGGGTCGGAA CTGGAGTGCA GGGAAC      1393
```

( 2 ) INFORMATION FOR SEQ ID NO:40:

( i ) SEQUENCE CHARACTERISTICS:

( A ) LENGTH: 478 amino acids
( B ) TYPE: amino acid
( C ) STRANDEDNESS: single
( D ) TOPOLOGY: linear ( i i ) MOLECULE TYPE: protein ( v ) FRAGMENT TYPE: internal ( x i ) SEQUENCE DESCRIPTION: SEQ ID NO:40:

Met Val Gln Lys Thr Ser Met Ser Arg Gly Pro Tyr Pro Pro Ser Gln
1 5 10 15

Glu Ile Pro Met Glu Val Phe Asp Pro Ser Pro Gln Gly Lys Tyr Ser
20 25 30

Lys Arg Lys Gly Arg Phe Lys Arg Ser Asp Gly Ser Thr Ser Ser Asp
35 40 45

Thr Thr Ser Asn Ser Phe Val Arg Gln Gly Ser Ala Glu Ser Tyr Thr
50 55 60

Ser Arg Pro Ser Asp Ser Asp Val Ser Leu Glu Glu Asp Arg Glu Ala
65 70 75 80

Leu Arg Lys Glu Ala Glu Arg Gln Ala Leu Ala Gln Leu Glu Lys Ala
85 90 95

Lys Thr Lys Pro Val Ala Phe Ala Val Arg Thr Asn Val Gly Tyr Asn
100 105 110

Pro Ser Pro Gly Asp Glu Val Pro Val Gln Gly Val Ala Ile Thr Phe
115 120 125

Glu Pro Lys Asp Phe Leu His Ile Lys Glu Lys Tyr Asn Asn Asp Trp
130 135 140

Trp Ile Gly Arg Leu Val Lys Glu Gly Cys Glu Val Gly Phe Ile Pro
145 150 155 160

Ser Pro Val Lys Leu Asp Ser Leu Arg Leu Leu Gln Glu Gln Lys Leu
165 170 175

Arg Gln Asn Arg Leu Gly Ser Ser Lys Ser Gly Asp Asn Ser Ser Ser
180 185 190

Ser Leu Gly Asp Val Val Thr Gly Thr Arg Arg Pro Thr Pro Pro Ala
195 200 205

Ser Ala Lys Gln Lys Gln Lys Ser Thr Glu His Val Pro Pro Tyr Asp
210 215 220

Val Val Pro Ser Met Arg Pro Ile Ile Leu Val Gly Pro Ser Leu Lys
225 230 235 240

Gly Tyr Glu Val Thr Asp Met Met Gln Lys Ala Leu Phe Asp Phe Leu
245 250 255

Lys His Arg Phe Asp Gly Arg Ile Ser Ile Thr Arg Val Thr Ala Asp
260 265 270

Ile Ser Leu Ala Lys Arg Ser Val Leu Asn Asn Pro Ser Lys His Ile
275 280 285

Ile Ile Glu Arg Ser Asn Thr Arg Ser Ser Leu Ala Glu Val Gln Ser
290 295 300

Glu Ile Glu Arg Ile Phe Glu Leu Ala Arg Thr Leu Gln Leu Val Ala
305 310 315 320

Leu Asp Ala Asp Thr Ile Asn His Pro Ala Gln Leu Ser Lys Thr Ser
325 330 335

Leu Ala Pro Ile Ile Val Tyr Ile Lys Ile Thr Ser Pro Lys Val Leu
340 345 350

Gln Arg Leu Ile Lys Ser Arg Gly Lys Ser Gln Ser Lys His Leu Asn
355 360 365

-continued

Val Gln Ile Ala Ala Ser Glu Lys Leu Ala Gln Cys Pro Pro Glu Met
370 375 380

Phe Asp Ile Ile Leu Asp Glu Asn Gln Leu Glu Asp Ala Cys Glu His
385 390 395 400

Leu Ala Glu Tyr Leu Glu Ala Tyr Trp Lys Ala Thr His Pro Pro Ser
405 410 415

Ser Thr Pro Pro Asn Pro Leu Leu Asn Arg Thr Met Ala Thr Ala Ala
420 425 430

Leu Ala Ala Ser Pro Ala Pro Val Ser Asn Leu Gln Val Gln Val Leu
435 440 445

Thr Ser Leu Arg Arg Asn Leu Gly Phe Trp Gly Gly Leu Glu Ser Ser
450 455 460

Gln Arg Gly Ser Val Val Pro Gln Glu Gln Glu His Ala Met
465 470 475

( 2 ) INFORMATION FOR SEQ ID NO:41:

( i ) SEQUENCE CHARACTERISTICS:
( A ) LENGTH: 598 amino acids
( B ) TYPE: amino acid
( C ) STRANDEDNESS: single
( D ) TOPOLOGY: linear ( i i ) MOLECULE TYPE: protein ( v ) FRAGMENT TYPE: internal ( x i ) SEQUENCE DESCRIPTION: SEQ ID NO:41:

Met Val Gln Lys Thr Ser Met Ser Arg Glu Pro Tyr Pro Pro Ser Gln
1 5 10 15

Glu Ile Pro Met Glu Val Phe Asp Pro Ser Pro Gln Gly Lys Tyr Ser
20 25 30

Lys Arg Lys Gly Arg Phe Lys Arg Ser Asp Gly Ser Thr Ser Ser Asp
35 40 45

Thr Thr Ser Asn Ser Phe Val Arg Gln Gly Ser Ala Glu Ser Tyr Thr
50 55 60

Ser Arg Pro Ser Asp Ser Asp Val Ser Leu Glu Glu Asp Arg Glu Ala
65 70 75 80

Leu Arg Lys Glu Ala Glu Arg Gln Ala Leu Ala Gln Leu Glu Lys Ala
85 90 95

Lys Thr Lys Pro Val Ala Phe Ala Val Arg Thr Asn Val Gly Tyr Asn
100 105 110

Pro Ser Pro Gly Asp Glu Val Pro Val Gln Gly Val Ala Ile Thr Phe
115 120 125

Glu Pro Lys Asp Phe Leu His Ile Lys Glu Lys Tyr Asn Asn Asp Trp
130 135 140

Trp Ile Gly Arg Leu Val Lys Glu Gly Cys Glu Val Gly Phe Ile Pro
145 150 155 160

Ser Pro Val Lys Leu Asp Ser Leu Arg Leu Leu Gln Glu Gln Lys Leu
165 170 175

Arg Gln Asn Arg Leu Gly Ser Ser Lys Ser Gly Asp Asn Ser Ser Ser
180 185 190

Ser Leu Gly Asp Val Val Thr Gly Thr Arg Arg Pro Thr Pro Pro Ala
195 200 205

Ser Ala Lys Gln Lys Gln Lys Ser Thr Glu His Val Pro Pro Tyr Asp
210 215 220

Val Val Pro Ser Met Arg Pro Ile Ile Leu Val Gly Pro Ser Leu Lys
225 230 235 240

-continued

| | | | | | | | | | | | | | | | |
|---|---|---|---|---|---|---|---|---|---|---|---|---|---|---|---|
| Gly | Tyr | Glu | Val | Thr | Asp | Met | Met | Gln | Lys | Ala | Leu | Phe | Asp | Phe | Leu |
| | | | | 245 | | | | | 250 | | | | | 255 | |
| Lys | His | Arg | Phe | Asp | Gly | Arg | Ile | Ser | Ile | Thr | Arg | Val | Thr | Ala | Asp |
| | | | 260 | | | | | 265 | | | | | 270 | | |
| Ile | Ser | Leu | Ala | Lys | Arg | Ser | Val | Leu | Asn | Asn | Pro | Ser | Lys | His | Ile |
| | | 275 | | | | | 280 | | | | | 285 | | | |
| Ile | Ile | Glu | Arg | Ser | Asn | Thr | Arg | Ser | Ser | Leu | Ala | Glu | Val | Gln | Ser |
| | 290 | | | | | 295 | | | | | 300 | | | | |
| Glu | Ile | Glu | Arg | Ile | Phe | Glu | Leu | Ala | Arg | Thr | Leu | Gln | Leu | Val | Ala |
| 305 | | | | | 310 | | | | | 315 | | | | | 320 |
| Leu | Asp | Ala | Asp | Thr | Ile | Asn | His | Pro | Ala | Gln | Leu | Ser | Lys | Thr | Ser |
| | | | | 325 | | | | | 330 | | | | | 335 | |
| Leu | Ala | Pro | Ile | Ile | Val | Tyr | Ile | Lys | Ile | Thr | Ser | Pro | Lys | Val | Leu |
| | | | 340 | | | | | 345 | | | | | 350 | | |
| Gln | Arg | Leu | Ile | Lys | Ser | Arg | Gly | Lys | Ser | Gln | Ser | Lys | His | Leu | Asn |
| | | 355 | | | | | 360 | | | | | 365 | | | |
| Val | Gln | Ile | Ala | Ala | Ser | Glu | Lys | Leu | Ala | Gln | Cys | Pro | Pro | Glu | Met |
| | 370 | | | | | 375 | | | | | 380 | | | | |
| Phe | Asp | Ile | Ile | Leu | Asp | Glu | Asn | Gln | Leu | Glu | Asp | Ala | Cys | Glu | His |
| 385 | | | | | 390 | | | | | 395 | | | | | 400 |
| Leu | Ala | Glu | Tyr | Leu | Glu | Ala | Tyr | Trp | Lys | Ala | Thr | His | Pro | Pro | Ser |
| | | | | 405 | | | | | 410 | | | | | 415 | |
| Ser | Thr | Pro | Pro | Asn | Pro | Leu | Leu | Asn | Arg | Thr | Met | Ala | Thr | Ala | Ala |
| | | | 420 | | | | | 425 | | | | | 430 | | |
| Leu | Ala | Ala | Ser | Pro | Ala | Pro | Val | Ser | Asn | Leu | Gln | Gly | Pro | Tyr | Leu |
| | | 435 | | | | | 440 | | | | | 445 | | | |
| Ala | Ser | Gly | Asp | Gln | Pro | Leu | Glu | Arg | Ala | Thr | Gly | Glu | His | Ala | Ser |
| | 450 | | | | | 455 | | | | | 460 | | | | |
| Met | His | Glu | Tyr | Pro | Gly | Glu | Leu | Gly | Gln | Pro | Pro | Gly | Leu | Tyr | Pro |
| 465 | | | | | 470 | | | | | 475 | | | | | 480 |
| Ser | Ser | His | Pro | Pro | Gly | Arg | Ala | Gly | Thr | Leu | Arg | Ala | Leu | Ser | Arg |
| | | | | 485 | | | | | 490 | | | | | 495 | |
| Gln | Asp | Thr | Phe | Asp | Ala | Asp | Thr | Pro | Gly | Ser | Arg | Asn | Ser | Ala | Tyr |
| | | | 500 | | | | | 505 | | | | | 510 | | |
| Thr | Glu | Leu | Gly | Asp | Ser | Cys | Val | Asp | Met | Glu | Thr | Asp | Pro | Ser | Glu |
| | | 515 | | | | | 520 | | | | | 525 | | | |
| Gly | Pro | Gly | Leu | Gly | Asp | Pro | Ala | Gly | Gly | Gly | Thr | Pro | Pro | Ala | Arg |
| | 530 | | | | | 535 | | | | | 540 | | | | |
| Gln | Gly | Ser | Trp | Glu | Asp | Glu | Glu | Glu | Asp | Tyr | Glu | Glu | Glu | Leu | Thr |
| 545 | | | | | 550 | | | | | 555 | | | | | 560 |
| Asp | Asn | Arg | Asn | Arg | Gly | Arg | Asn | Lys | Ala | Arg | Tyr | Cys | Ala | Glu | Gly |
| | | | | 565 | | | | | 570 | | | | | 575 | |
| Gly | Gly | Pro | Val | Leu | Gly | Arg | Asn | Lys | Asn | Glu | Leu | Glu | Gly | Trp | Gly |
| | | | 580 | | | | | 585 | | | | | 590 | | |
| Arg | Gly | Val | Tyr | Ile | Arg | | | | | | | | | | |
| | | 595 | | | | | | | | | | | | | |

( 2 ) INFORMATION FOR SEQ ID NO:42:

( i ) SEQUENCE CHARACTERISTICS:
( A ) LENGTH: 523 amino acids
( B ) TYPE: amino acid
( C ) STRANDEDNESS: single
( D ) TOPOLOGY: linear ( i i ) MOLECULE TYPE: protein -continued ( v ) FRAGMENT TYPE: internal ( x i ) SEQUENCE DESCRIPTION: SEQ ID NO:42:

```
Met Val Gln Lys Thr Ser Met Ser Arg Gly Pro Tyr Pro Pro Ser Gln
  1               5                  10                  15

Glu Ile Pro Met Glu Val Phe Asp Pro Ser Pro Gln Gly Lys Tyr Ser
             20                  25                  30

Lys Arg Lys Gly Arg Phe Lys Arg Ser Asp Gly Ser Thr Ser Ser Asp
         35                  40                  45

Thr Thr Ser Asn Ser Phe Val Arg Gln Gly Ser Ala Glu Ser Tyr Thr
     50                  55                  60

Ser Arg Pro Ser Asp Ser Asp Val Ser Leu Glu Glu Asp Arg Glu Ala
 65                  70                  75                  80

Leu Arg Lys Glu Ala Glu Arg Gln Ala Leu Ala Gln Leu Glu Lys Ala
                 85                  90                  95

Lys Thr Lys Pro Val Ala Phe Ala Val Arg Thr Asn Val Gly Tyr Asn
            100                 105                 110

Pro Ser Pro Gly Asp Glu Val Pro Val Gln Gly Val Ala Ile Thr Phe
        115                 120                 125

Glu Pro Lys Asp Phe Leu His Ile Lys Glu Lys Tyr Asn Asn Asp Trp
    130                 135                 140

Trp Ile Gly Arg Leu Val Lys Glu Gly Cys Glu Val Gly Phe Ile Pro
145                 150                 155                 160

Ser Pro Val Lys Leu Asp Ser Leu Arg Leu Leu Gln Glu Gln Lys Leu
                165                 170                 175

Arg Gln Asn Arg Leu Gly Ser Ser Lys Ser Gly Asp Asn Ser Ser Ser
            180                 185                 190

Ser Leu Gly Asp Val Val Thr Gly Thr Arg Arg Pro Thr Pro Pro Ala
        195                 200                 205

Ser Gly Asn Glu Met Thr Asn Leu Ala Phe Glu Leu Asp Pro Leu Glu
    210                 215                 220

Leu Glu Glu Glu Glu Ala Glu Leu Gly Glu Gln Ser Gly Ser Ala Lys
225                 230                 235                 240

Thr Ser Val Ser Ser Val Thr Thr Pro Pro Pro His Gly Lys Arg Ile
                245                 250                 255

Pro Phe Phe Lys Lys Thr Glu His Val Pro Pro Tyr Asp Val Val Pro
            260                 265                 270

Ser Met Arg Pro Ile Ile Leu Val Gly Pro Ser Leu Lys Gly Tyr Glu
        275                 280                 285

Val Thr Asp Met Met Gln Lys Ala Leu Phe Asp Phe Leu Lys His Arg
    290                 295                 300

Phe Asp Gly Arg Ile Ser Ile Thr Arg Val Thr Ala Asp Ile Ser Leu
305                 310                 315                 320

Ala Lys Arg Ser Val Leu Asn Asn Pro Ser Lys His Ile Ile Ile Glu
                325                 330                 335

Arg Ser Asn Thr Arg Ser Ser Leu Ala Glu Val Gln Ser Glu Ile Glu
            340                 345                 350

Arg Ile Phe Glu Leu Ala Arg Thr Leu Gln Leu Val Ala Leu Asp Ala
        355                 360                 365

Asp Thr Ile Asn His Pro Ala Gln Leu Ser Lys Thr Ser Leu Ala Pro
    370                 375                 380

Ile Ile Val Tyr Ile Lys Ile Thr Ser Pro Lys Val Leu Gln Arg Leu
385                 390                 395                 400
```

Ile Lys Ser Arg Gly Lys Ser Gln Ser Lys His Leu Asn Val Gln Ile
405 410 415

Ala Ala Ser Glu Lys Leu Ala Gln Cys Pro Pro Glu Met Phe Asp Ile
420 425 430

Ile Leu Asp Glu Asn Gln Leu Glu Asp Ala Cys Glu His Leu Ala Glu
435 440 445

Tyr Leu Glu Ala Tyr Trp Lys Ala Thr His Pro Pro Ser Ser Thr Pro
450 455 460

Pro Asn Pro Leu Leu Asn Arg Thr Met Ala Thr Ala Ala Leu Ala Ala
465 470 475 480

Ser Pro Ala Pro Val Ser Asn Leu Gln Val Gln Val Leu Thr Ser Leu
485 490 495

Arg Arg Asn Leu Gly Phe Trp Gly Gly Leu Glu Ser Ser Gln Arg Gly
500 505 510

Ser Val Val Pro Gln Glu Gln Glu His Ala Met
515 520

( 2 ) INFORMATION FOR SEQ ID NO:43:

( i ) SEQUENCE CHARACTERISTICS:
( A ) LENGTH: 216 amino acids
( B ) TYPE: amino acid
( C ) STRANDEDNESS: single
( D ) TOPOLOGY: linear ( i i ) MOLECULE TYPE: protein ( v ) FRAGMENT TYPE: internal ( x i ) SEQUENCE DESCRIPTION: SEQ ID NO:43:

Met Val Gln Lys Thr Ser Met Ser Arg Gly Pro Tyr Pro Pro Ser Gln
1 5 10 15

Glu Ile Pro Met Glu Val Phe Asp Pro Ser Pro Gln Gly Lys Tyr Ser
20 25 30

Lys Arg Lys Gly Arg Phe Lys Arg Ser Asp Gly Ser Thr Ser Ser Asp
35 40 45

Thr Thr Ser Asn Ser Phe Val Arg Gln Gly Ser Ala Glu Ser Tyr Thr
50 55 60

Ser Arg Pro Ser Asp Ser Asp Val Ser Leu Glu Glu Asp Arg Glu Ala
65 70 75 80

Leu Arg Lys Glu Ala Glu Arg Gln Ala Leu Ala Gln Leu Glu Lys Ala
85 90 95

Lys Thr Lys Pro Val Ala Phe Ala Val Arg Thr Asn Val Gly Tyr Asn
100 105 110

Pro Ser Pro Gly Asp Glu Val Pro Val Gln Gly Val Ala Ile Thr Phe
115 120 125

Glu Pro Lys Asp Phe Leu His Ile Lys Glu Lys Tyr Asn Asn Asp Trp
130 135 140

Trp Ile Gly Arg Leu Val Lys Glu Gly Cys Glu Val Gly Phe Ile Pro
145 150 155 160

Ser Pro Val Lys Leu Asp Ser Leu Arg Leu Leu Gln Glu Gln Lys Leu
165 170 175

Arg Gln Asn Arg Leu Gly Ser Ser Lys Ser Gly Asp Asn Ser Ser Ser
180 185 190

Ser Leu Gly Asp Val Val Thr Gly Thr Arg Arg Pro Thr Pro Pro Ala
195 200 205

Ser Asp Arg Ala Cys Ala Pro Leu
210 215

( 2 ) INFORMATION FOR SEQ ID NO:44:

( i ) SEQUENCE CHARACTERISTICS:
( A ) LENGTH: 219 amino acids
( B ) TYPE: amino acid
( C ) STRANDEDNESS: single
( D ) TOPOLOGY: linear ( i i ) MOLECULE TYPE: protein ( v ) FRAGMENT TYPE: internal ( x i ) SEQUENCE DESCRIPTION: SEQ ID NO:44:

Met Val Gln Lys Thr Ser Met Ser Arg Gly Pro Tyr Pro Pro Ser Gln
1 5 10 15

Glu Ile Pro Met Glu Val Phe Asp Pro Ser Pro Gln Gly Lys Tyr Ser
20 25 30

Lys Arg Lys Gly Arg Phe Lys Arg Ser Asp Gly Ser Thr Ser Ser Asp
35 40 45

Thr Thr Ser Asn Ser Phe Val Arg Gln Gly Ser Ala Glu Ser Tyr Thr
50 55 60

Ser Arg Pro Ser Asp Ser Asp Val Ser Leu Glu Glu Asp Arg Glu Ala
65 70 75 80

Leu Arg Lys Glu Ala Glu Arg Gln Ala Leu Ala Gln Leu Glu Lys Ala
85 90 95

Lys Thr Lys Pro Val Ala Phe Ala Val Arg Thr Asn Val Gly Tyr Asn
100 105 110

Pro Ser Pro Gly Asp Glu Val Pro Val Gln Gly Val Ala Ile Thr Phe
115 120 125

Glu Pro Lys Asp Phe Leu His Ile Lys Glu Lys Tyr Asn Asn Asp Trp
130 135 140

Trp Ile Gly Arg Leu Val Lys Glu Gly Cys Glu Val Gly Phe Ile Pro
145 150 155 160

Ser Pro Val Lys Leu Asp Ser Leu Arg Leu Leu Gln Glu Gln Lys Leu
165 170 175

Arg Gln Asn Arg Leu Gly Ser Ser Lys Ser Gly Asp Asn Ser Ser Ser
180 185 190

Ser Leu Gly Asp Val Val Thr Gly Thr Arg Arg Pro Thr Pro Pro Ala
195 200 205

Ser Gly Tyr Arg His Asp Ala Glu Ser Phe Ile
210 215

( 2 ) INFORMATION FOR SEQ ID NO:45:

( i ) SEQUENCE CHARACTERISTICS:
( A ) LENGTH: 1968 amino acids
( B ) TYPE: amino acid
( C ) STRANDEDNESS: single
( D ) TOPOLOGY: linear ( i i ) MOLECULE TYPE: protein ( v ) FRAGMENT TYPE: internal ( x i ) SEQUENCE DESCRIPTION: SEQ ID NO:45:

Met Val Asn Glu Asn Thr Arg Met Tyr Ile Pro Glu Glu Asn His Gln
1 5 10 15

Gly Ser Asn Tyr Gly Ser Pro Arg Pro Ala His Ala Asn Met Asn Ala
20 25 30

Asn Ala Ala Ala Gly Leu Ala Pro Glu His Ile Pro Thr Pro Gly Ala

-continued 35 40 45

Ala Leu Ser Trp Gln Ala Ala Ile Asp Ala Ala Arg Gln Ala Lys Leu
50 55 60

Met Gly Ser Ala Gly Asn Ala Thr Ile Ser Thr Val Ser Ser Thr Gln
65 70 75 80

Arg Lys Arg Gln Gln Tyr Gly Lys Pro Lys Lys Gln Gly Ser Thr Thr
85 90 95

Ala Thr Arg Pro Pro Arg Ala Leu Leu Cys Leu Thr Leu Lys Asn Pro
100 105 110

Ile Arg Arg Ala Cys Ile Ser Ile Val Glu Trp Lys Pro Phe Glu Ile
115 120 125

Ile Ile Leu Leu Thr Ile Phe Ala Asn Cys Val Ala Leu Ala Ile Tyr
130 135 140

Ile Pro Phe Pro Glu Asp Asp Ser Asn Ala Thr Asn Ser Asn Leu Glu
145 150 155 160

Arg Val Glu Tyr Leu Phe Leu Ile Ile Phe Thr Val Glu Ala Phe Leu
165 170 175

Lys Val Ile Ala Tyr Gly Leu Leu Phe His Pro Asn Ala Tyr Leu Arg
180 185 190

Asn Gly Trp Asn Leu Leu Asp Phe Ile Ile Val Val Val Gly Leu Phe
195 200 205

Ser Ala Ile Leu Glu Gln Ala Thr Lys Ala Asp Gly Ala Asn Ala Leu
210 215 220

Gly Gly Lys Gly Ala Gly Phe Asp Val Lys Ala Leu Arg Ala Phe Arg
225 230 235 240

Val Leu Arg Pro Leu Arg Leu Val Ser Gly Val Pro Ser Leu Gln Val
245 250 255

Val Leu Asn Ser Ile Ile Lys Ala Met Val Pro Leu Leu His Ile Ala
260 265 270

Leu Leu Val Leu Phe Val Ile Ile Ile Tyr Ala Ile Ile Gly Leu Glu
275 280 285

Leu Phe Met Gly Lys Met His Lys Thr Cys Tyr Asn Gln Glu Gly Ile
290 295 300

Ala Asp Val Pro Ala Glu Asp Asp Pro Ser Pro Cys Ala Leu Glu Thr
305 310 315 320

Gly His Gly Arg Gln Cys Gln Asn Gly Thr Val Cys Lys Pro Gly Trp
325 330 335

Asp Gly Pro Lys His Gly Ile Thr Asn Phe Asp Asn Phe Ala Phe Ala
340 345 350

Met Leu Thr Val Phe Gln Cys Ile Thr Met Glu Gly Trp Thr Asp Val
355 360 365

Leu Tyr Trp Val Asn Asp Ala Val Gly Arg Asp Trp Pro Trp Ile Tyr
370 375 380

Phe Val Thr Leu Ile Ile Ile Gly Ser Phe Phe Val Leu Asn Leu Val
385 390 395 400

Leu Gly Val Leu Ser Gly Glu Phe Ser Lys Glu Arg Glu Lys Ala Lys
405 410 415

Ala Arg Gly Asp Phe Gln Lys Leu Arg Glu Lys Gln Gln Leu Glu Glu
420 425 430

Asp Leu Lys Gly Tyr Leu Asp Trp Ile Thr Gln Ala Glu Asp Ile Xaa
435 440 445

Pro Glu Asn Glu Asp Glu Gly Met Asp Glu Glu Lys Pro Arg Asn Arg
450 455 460

-continued

Gly Thr Pro Ala Gly Met Leu Asp Gln Lys Lys Gly Lys Phe Ala Trp
465                 470                 475                 480

Phe Ser His Ser Thr Glu Thr His Val Ser Met Pro Thr Ser Glu Thr
                485                 490                 495

Glu Ser Val Asn Thr Glu Asn Val Ala Gly Gly Asp Ile Glu Gly Glu
            500                 505                 510

Asn Cys Gly Ala Arg Leu Ala His Arg Ile Ser Lys Ser Lys Phe Ser
        515                 520                 525

Arg Tyr Trp Arg Arg Trp Asn Arg Phe Cys Arg Arg Lys Cys Arg Ala
    530                 535                 540

Ala Val Lys Ser Asn Val Phe Tyr Trp Leu Val Ile Phe Leu Val Phe
545                 550                 555                 560

Leu Asn Thr Leu Thr Ile Ala Ser Glu His Tyr Asn Gln Pro Asn Trp
                565                 570                 575

Leu Thr Glu Val Gln Asp Thr Ala Asn Lys Ala Leu Leu Ala Leu Phe
            580                 585                 590

Thr Ala Glu Met Leu Leu Lys Met Tyr Ser Leu Gly Leu Gln Ala Tyr
        595                 600                 605

Phe Val Ser Leu Phe Asn Arg Phe Asp Cys Phe Val Val Cys Gly Gly
    610                 615                 620

Ile Leu Glu Thr Ile Leu Val Glu Thr Lys Ile Met Ser Pro Leu Gly
625                 630                 635                 640

Ile Ser Val Leu Arg Cys Val Arg Leu Leu Arg Ile Phe Lys Ile Thr
                645                 650                 655

Arg Tyr Trp Asn Ser Leu Ser Asn Leu Val Ala Ser Leu Leu Asn Ser
            660                 665                 670

Val Arg Ser Ile Ala Ser Leu Leu Leu Leu Leu Phe Leu Phe Ile Ile
        675                 680                 685

Ile Phe Ser Leu Leu Gly Met Gln Leu Phe Gly Gly Lys Phe Asn Phe
    690                 695                 700

Asp Glu Met Gln Thr Arg Arg Ser Thr Phe Asp Asn Phe Pro Gln Ser
705                 710                 715                 720

Leu Leu Thr Val Phe Gln Ile Leu Thr Gly Glu Asp Trp Asn Ser Val
                725                 730                 735

Met Tyr Asp Gly Ile Met Ala Tyr Gly Gly Pro Ser Phe Pro Gly Met
            740                 745                 750

Leu Val Cys Ile Tyr Phe Ile Ile Leu Phe Ile Ser Gly Asn Tyr Ile
        755                 760                 765

Leu Leu Asn Val Phe Leu Ala Ile Ala Val Asp Asn Leu Ala Asp Ala
    770                 775                 780

Glu Ser Leu Thr Ser Ala Leu Lys Glu Glu Glu Glu Glu Lys Glu Arg
785                 790                 795                 800

Lys Lys Leu Ala Arg Thr Ala Ser Pro Glu Lys Lys Gln Glu Leu Val
                805                 810                 815

Glu Lys Pro Ala Val Gly Glu Ser Lys Glu Glu Lys Ile Glu Leu Lys
            820                 825                 830

Ser Ile Thr Ala Asp Gly Glu Ser Pro Pro Ala Thr Lys Ile Asn Met
        835                 840                 845

Asp Asp Leu Gln Pro Asn Glu Asn Glu Asp Lys Ser Pro Tyr Pro Asn
    850                 855                 860

Pro Glu Thr Thr Gly Glu Glu Asp Glu Glu Glu Pro Glu Met Pro Val
865                 870                 875                 880

Gly Pro Arg Pro Arg Pro Leu Ser Glu Leu His Leu Lys Glu Lys Ala
                885                 890                 895

-continued

Val Pro Met Pro Glu Ala Ser Ala Phe Phe Ile Phe Ser Ser Asn Asn
900 905 910

Arg Phe Arg Leu Gln Cys His Arg Ile Val Asn Asp Thr Ile Phe Thr
915 920 925

Asn Leu Ile Leu Phe Phe Ile Leu Leu Ser Ser Ile Ser Leu Ala Ala
930 935 940

Glu Asp Pro Val Gln His Thr Ser Phe Arg Asn His Ile Leu Phe Tyr
945 950 955 960

Phe Asp Ile Val Phe Thr Thr Ile Phe Thr Ile Glu Ile Ala Leu Lys
965 970 975

Met Thr Ala Tyr Gly Ala Phe Leu His Lys Gly Ser Phe Cys Arg Asn
980 985 990

Tyr Phe Asn Ile Leu Asp Leu Leu Val Val Ser Val Ser Leu Ile Ser
995 1000 1005

Phe Gly Ile Gln Ser Ser Ala Ile Asn Val Val Lys Ile Leu Arg Val
1010 1015 1020

Leu Arg Val Leu Arg Pro Leu Arg Ala Ile Asn Arg Ala Lys Gly Leu
1025 1030 1035 1040

Lys His Val Val Gln Cys Val Phe Val Ala Ile Arg Thr Ile Gly Asn
1045 1050 1055

Ile Val Ile Val Thr Thr Leu Leu Gln Phe Met Phe Ala Cys Ile Gly
1060 1065 1070

Val Gln Leu Phe Lys Gly Lys Leu Tyr Thr Cys Ser Asp Ser Ser Lys
1075 1080 1085

Gln Thr Glu Ala Glu Cys Lys Gly Asn Tyr Ile Thr Tyr Lys Asp Gly
1090 1095 1100

Glu Val Asp His Pro Ile Ile Gln Pro Arg Ser Trp Glu Asn Ser Lys
1105 1110 1115 1120

Phe Asp Phe Asp Asn Val Leu Ala Ala Met Met Ala Leu Phe Thr Val
1125 1130 1135

Ser Thr Phe Glu Gly Trp Pro Glu Leu Leu Tyr Arg Ser Ile Asp Ser
1140 1145 1150

His Thr Glu Asp Lys Gly Pro Ile Tyr Asn Tyr Arg Val Glu Ile Ser
1155 1160 1165

Ile Phe Phe Ile Ile Tyr Ile Ile Ile Ile Ala Phe Phe Met Met Asn
1170 1175 1180

Ile Phe Val Gly Phe Val Ile Val Thr Phe Gln Glu Gln Gly Glu Gln
1185 1190 1195 1200

Glu Tyr Lys Asn Cys Glu Leu Asp Lys Asn Gln Arg Gln Cys Val Glu
1205 1210 1215

Tyr Ala Leu Lys Ala Arg Pro Leu Arg Arg Tyr Ile Pro Lys Asn Gln
1220 1225 1230

His Gln Tyr Lys Val Trp Tyr Val Val Asn Ser Thr Tyr Phe Glu Tyr
1235 1240 1245

Leu Met Phe Val Leu Ile Leu Leu Asn Thr Ile Cys Leu Ala Met Gln
1250 1255 1260

His Tyr Gly Gln Ser Cys Leu Phe Lys Ile Ala Met Asn Ile Leu Asn
1265 1270 1275 1280

Met Leu Phe Thr Gly Leu Phe Thr Val Glu Met Ile Leu Lys Leu Ile
1285 1290 1295

Ala Phe Lys Pro Lys Gly Tyr Phe Ser Asp Pro Trp Asn Val Phe Asp
1300 1305 1310

Phe Leu Ile Val Ile Gly Ser Ile Ile Asp Val Ile Leu Ser Glu Thr

-continued 1315 1320 1325

Asn Pro Ala Glu His Thr Gln Cys Ser Pro Ser Met Asn Ala Glu Glu
1330 1335 1340

Asn Ser Arg Ile Ser Ile Thr Phe Phe Arg Leu Phe Arg Val Met Arg
1345 1350 1355 1360

Leu Val Lys Leu Leu Ser Arg Gly Glu Gly Ile Arg Thr Leu Leu Trp
1365 1370 1375

Thr Phe Ile Lys Ser Phe Gln Ala Leu Pro Tyr Val Ala Leu Leu Ile
1380 1385 1390

Val Met Leu Phe Phe Ile Tyr Ala Val Ile Gly Met Gln Val Phe Gly
1395 1400 1405

Lys Ile Ala Leu Asn Asp Thr Thr Glu Ile Asn Arg Asn Asn Asn Phe
1410 1415 1420

Gln Thr Phe Pro Gln Ala Val Leu Leu Leu Phe Arg Cys Ala Thr Gly
1425 1430 1435 1440

Glu Ala Trp Gln Asp Ile Met Leu Ala Cys Met Pro Gly Lys Lys Cys
1445 1450 1455

Ala Pro Glu Ser Glu Pro Ser Asn Ser Thr Glu Gly Glu Thr Pro Cys
1460 1465 1470

Gly Ser Ser Phe Ala Val Phe Tyr Phe Ile Ser Phe Tyr Met Arg Cys
1475 1480 1485

Ala Phe Leu Ile Ile Asn Leu Phe Val Ala Val Ile Met Asp Asn Phe
1490 1495 1500

Asp Tyr Leu Thr Arg Asp Trp Ser Ile Leu Gly Pro His His Leu Asp
1505 1510 1515 1520

Glu Phe Lys Arg Ile Trp Ala Glu Tyr Asp Pro Glu Ala Lys Gly Arg
1525 1530 1535

Ile Lys His Leu Asp Val Val Thr Leu Leu Arg Arg Ile Gln Pro Pro
1540 1545 1550

Leu Gly Phe Gly Lys Leu Cys Pro His Arg Val Ala Cys Lys Arg Leu
1555 1560 1565

Val Ser Met Asn Met Pro Leu Asn Ser Asp Gly Thr Val Met Phe Asn
1570 1575 1580

Ala Thr Leu Phe Ala Leu Val Arg Thr Ala Leu Arg Ile Lys Thr Glu
1585 1590 1595 1600

Gly Asn Leu Glu Gln Ala Asn Glu Glu Leu Arg Ala Ile Ile Lys Lys
1605 1610 1615

Ile Trp Lys Arg Thr Ser Met Lys Leu Leu Asp Gln Val Val Pro Pro
1620 1625 1630

Ala Gly Asp Asp Glu Val Thr Val Gly Lys Phe Tyr Ala Thr Phe Leu
1635 1640 1645

Ile Gln Glu Tyr Phe Arg Lys Phe Lys Lys Arg Lys Glu Gln Gly Leu
1650 1655 1660

Val Gly Lys Pro Ser Gln Arg Asn Ala Leu Ser Leu Gln Ala Gly Leu
1665 1670 1675 1680

Arg Thr Leu His Asp Ile Gly Pro Glu Ile Arg Arg Ala Ile Ser Gly
1685 1690 1695

Asp Leu Thr Ala Glu Glu Glu Leu Asp Lys Ala Met Lys Glu Ala Val
1700 1705 1710

Ser Ala Ala Ser Glu Asp Asp Ile Phe Arg Arg Ala Gly Gly Leu Phe
1715 1720 1725

Gly Asn His Val Ser Tyr Tyr Gln Ser Asp Gly Arg Ser Ala Phe Pro
1730 1735 1740

Gln Thr Phe Thr Thr Gln Arg Pro Leu His Ile Asn Lys Ala Gly Ser
1745 1750 1755 1760

Ser Gln Gly Asp Thr Glu Ser Pro Ser His Glu Lys Leu Val Asp Ser
1765 1770 1775

Thr Phe Thr Pro Ser Ser Tyr Ser Ser Thr Gly Ser Asn Ala Asn Ile
1780 1785 1790

Asn Asn Ala Asn Asn Thr Ala Leu Gly Arg Leu Pro Arg Pro Ala Gly
1795 1800 1805

Tyr Pro Ser Thr Val Ser Thr Val Glu Gly His Gly Pro Pro Leu Ser
1810 1815 1820

Pro Ala Ile Arg Val Gln Glu Val Ala Trp Lys Leu Ser Ser Asn Arg
1825 1830 1835 1840

Cys His Ser Arg Glu Ser Gln Ala Ala Met Ala Arg Gln Glu Glu Thr
1845 1850 1855

Ser Gln Asp Glu Thr Tyr Glu Val Lys Met Asn His Asp Thr Glu Ala
1860 1865 1870

Cys Ser Glu Pro Ser Leu Leu Ser Thr Glu Met Leu Ser Tyr Gln Asp
1875 1880 1885

Asp Glu Asn Arg Gln Leu Thr Leu Pro Glu Glu Asp Lys Arg Asp Ile
1890 1895 1900

Arg Gln Ser Pro Lys Arg Gly Phe Leu Arg Ser Ser Ser Leu Gly Arg
1905 1910 1915 1920

Arg Ala Ser Phe His Leu Glu Cys Leu Lys Arg Gln Lys Asp Arg Gly
1925 1930 1935

Gly Asp Ile Ser Gln Lys Thr Val Leu Pro Leu His Leu Val His His
1940 1945 1950

Gln Ala Leu Ala Val Ala Gly Leu Ser Pro Leu Leu Gln Arg Ser His
1955 1960 1965

( 2 ) INFORMATION FOR SEQ ID NO:46:

( i ) SEQUENCE CHARACTERISTICS:
( A ) LENGTH: 28 amino acids
( B ) TYPE: amino acid
( C ) STRANDEDNESS: single
( D ) TOPOLOGY: linear ( i i ) MOLECULE TYPE: protein ( v ) FRAGMENT TYPE: internal ( x i ) SEQUENCE DESCRIPTION: SEQ ID NO:46:

His Tyr Phe Cys Asp Ala Trp Asn Thr Phe Asp Ala Leu Ile Val Val
1 5 10 15

Gly Ser Ile Val Asp Ile Ala Ile Thr Glu Val Asn
20 25

( 2 ) INFORMATION FOR SEQ ID NO:47:

( i ) SEQUENCE CHARACTERISTICS:
( A ) LENGTH: 2339 amino acids
( B ) TYPE: amino acid
( C ) STRANDEDNESS: single
( D ) TOPOLOGY: linear ( i i ) MOLECULE TYPE: protein ( v ) FRAGMENT TYPE: internal ( x i ) SEQUENCE DESCRIPTION: SEQ ID NO:47:

Met Val Arg Phe Gly Asp Glu Leu Gly Gly Arg Tyr Gly Gly Pro Gly
1 5 10 15

-continued

| | | | | | | | | | | | | | | | |
|---|---|---|---|---|---|---|---|---|---|---|---|---|---|---|---|
| Gly | Gly | Glu | Arg | Ala | Arg | Gly | Gly | Gly | Ala | Gly | Gly | Ala | Gly | Gly | Pro |
| | | | 20 | | | | | 25 | | | | | 30 | | |
| Gly | Pro | Gly | Gly | Leu | Gln | Pro | Gly | Gln | Arg | Val | Leu | Tyr | Lys | Gln | Ser |
| | | 35 | | | | | 40 | | | | | 45 | | | |
| Ile | Ala | Gln | Arg | Ala | Arg | Thr | Met | Ala | Leu | Tyr | Asn | Pro | Ile | Pro | Val |
| | 50 | | | | | 55 | | | | | 60 | | | | |
| Lys | Gln | Asn | Cys | Phe | Thr | Val | Asn | Arg | Ser | Leu | Phe | Val | Phe | Ser | Glu |
| 65 | | | | | 70 | | | | | 75 | | | | | 80 |
| Asp | Asn | Val | Val | Arg | Lys | Tyr | Ala | Lys | Arg | Ile | Thr | Glu | Trp | Pro | Pro |
| | | | | 85 | | | | | 90 | | | | | 95 | |
| Phe | Glu | Asn | Met | Ile | Leu | Ala | Thr | Ile | Ile | Ala | Asn | Cys | Ile | Val | Leu |
| | | | 100 | | | | | 105 | | | | | 110 | | |
| Ala | Leu | Glu | Gln | His | Leu | Pro | Asp | Gly | Asp | Lys | Thr | Pro | Met | Ser | Glu |
| | | 115 | | | | | 120 | | | | | 125 | | | |
| Arg | Leu | Asp | Asp | Thr | Glu | Pro | Tyr | Phe | Ile | Gly | Ile | Phe | Cys | Phe | Glu |
| | 130 | | | | | 135 | | | | | 140 | | | | |
| Ala | Gly | Ile | Lys | Ile | Ile | Ala | Leu | Gly | Phe | Val | Phe | His | Lys | Gly | Ser |
| 145 | | | | | 150 | | | | | 155 | | | | | 160 |
| Tyr | Leu | Arg | Asn | Gly | Trp | Asn | Val | Met | Asp | Phe | Val | Val | Val | Leu | Thr |
| | | | | 165 | | | | | 170 | | | | | 175 | |
| Gly | Ile | Leu | Ala | Thr | Ala | Gly | Thr | Asp | Phe | Asp | Leu | Arg | Thr | Leu | Arg |
| | | | 180 | | | | | 185 | | | | | 190 | | |
| Ala | Val | Arg | Val | Leu | Arg | Pro | Leu | Lys | Leu | Val | Ser | Gly | Ile | Pro | Ser |
| | | 195 | | | | | 200 | | | | | 205 | | | |
| Leu | Gln | Val | Val | Leu | Lys | Ser | Ile | Met | Lys | Ala | Met | Val | Pro | Leu | Leu |
| | 210 | | | | | 215 | | | | | 220 | | | | |
| Gln | Ile | Gly | Leu | Leu | Leu | Phe | Phe | Ala | Ile | Leu | Met | Phe | Ala | Ile | Ile |
| 225 | | | | | 230 | | | | | 235 | | | | | 240 |
| Gly | Leu | Glu | Phe | Tyr | Met | Gly | Lys | Phe | His | Lys | Ala | Cys | Phe | Pro | Asn |
| | | | | 245 | | | | | 250 | | | | | 255 | |
| Ser | Thr | Asp | Ala | Glu | Pro | Val | Gly | Asp | Phe | Pro | Cys | Gly | Lys | Glu | Ala |
| | | | 260 | | | | | 265 | | | | | 270 | | |
| Pro | Ala | Arg | Leu | Cys | Glu | Gly | Asp | Thr | Glu | Cys | Arg | Glu | Tyr | Trp | Pro |
| | | 275 | | | | | 280 | | | | | 285 | | | |
| Gly | Pro | Asn | Phe | Gly | Ile | Thr | Asn | Phe | Asp | Asn | Ile | Leu | Phe | Ala | Ile |
| | 290 | | | | | 295 | | | | | 300 | | | | |
| Leu | Thr | Val | Phe | Gln | Cys | Ile | Thr | Met | Glu | Gly | Trp | Thr | Asp | Ile | Leu |
| 305 | | | | | 310 | | | | | 315 | | | | | 320 |
| Tyr | Asn | Thr | Asn | Asp | Ala | Ala | Gly | Asn | Thr | Trp | Asn | Trp | Leu | Tyr | Phe |
| | | | | 325 | | | | | 330 | | | | | 335 | |
| Ile | Pro | Leu | Ile | Ile | Ile | Gly | Ser | Phe | Phe | Met | Leu | Asn | Leu | Val | Leu |
| | | | 340 | | | | | 345 | | | | | 350 | | |
| Gly | Val | Leu | Ser | Gly | Glu | Phe | Ala | Lys | Glu | Arg | Glu | Arg | Val | Glu | Asn |
| | | 355 | | | | | 360 | | | | | 365 | | | |
| Arg | Arg | Ala | Phe | Leu | Lys | Leu | Arg | Arg | Gln | Gln | Gln | Ile | Glu | Arg | Glu |
| | 370 | | | | | 375 | | | | | 380 | | | | |
| Leu | Asn | Gly | Tyr | Leu | Glu | Trp | Ile | Phe | Lys | Ala | Glu | Glu | Val | Met | Leu |
| 385 | | | | | 390 | | | | | 395 | | | | | 400 |
| Ala | Glu | Glu | Asp | Arg | Asn | Ala | Glu | Glu | Lys | Ser | Pro | Leu | Asp | Val | Leu |
| | | | | 405 | | | | | 410 | | | | | 415 | |
| Lys | Arg | Ala | Ala | Thr | Lys | Lys | Ser | Arg | Asn | Asp | Leu | Ile | His | Ala | Glu |
| | | | 420 | | | | | 425 | | | | | 430 | | |
| Glu | Gly | Glu | Asp | Arg | Phe | Ala | Asp | Leu | Cys | Ala | Val | Gly | Ser | Pro | Phe |

-continued 435 440 445

Ala Arg Ala Ser Leu Lys Ser Gly Lys Thr Glu Ser Ser Ser Tyr Phe
450 455 460

Arg Arg Lys Glu Lys Met Phe Arg Phe Phe Ile Arg Arg Met Val Lys
465 470 475 480

Ala Gln Ser Phe Tyr Trp Val Val Leu Cys Val Val Ala Leu Asn Thr
485 490 495

Leu Cys Val Ala Met Val His Tyr Asn Gln Pro Arg Arg Leu Thr Thr
500 505 510

Thr Leu Tyr Phe Ala Glu Phe Val Phe Leu Gly Leu Phe Leu Thr Glu
515 520 525

Met Ser Leu Lys Met Tyr Gly Leu Gly Pro Arg Ser Tyr Phe Arg Ser
530 535 540

Ser Phe Asn Cys Phe Asp Phe Gly Val Ile Val Gly Ser Val Phe Glu
545 550 555 560

Val Val Trp Ala Ala Ile Lys Pro Gly Ser Ser Phe Gly Ile Ser Val
565 570 575

Leu Arg Ala Leu Arg Leu Leu Arg Ile Phe Lys Val Thr Lys Tyr Trp
580 585 590

Ser Ser Leu Arg Asn Leu Val Val Ser Leu Leu Asn Ser Met Lys Ser
595 600 605

Ile Ile Ser Leu Leu Phe Leu Leu Phe Leu Phe Ile Val Val Phe Ala
610 615 620

Leu Leu Gly Met Gln Leu Phe Gly Gly Gln Phe Asn Phe Gln Asp Glu
625 630 635 640

Thr Pro Thr Thr Asn Phe Asp Thr Phe Pro Ala Ala Ile Leu Thr Val
645 650 655

Phe Gln Ile Leu Thr Gly Glu Asp Trp Asn Ala Val Met Tyr His Gly
660 665 670

Ile Glu Ser Gln Gly Gly Val Ser Lys Gly Met Phe Ser Ser Phe Tyr
675 680 685

Phe Ile Val Leu Thr Leu Phe Gly Asn Tyr Thr Leu Leu Asn Val Phe
690 695 700

Leu Ala Ile Ala Val Asp Asn Leu Ala Asn Ala Gln Glu Leu Thr Lys
705 710 715 720

Asp Glu Glu Glu Met Glu Glu Ala Ala Asn Gln Lys Leu Ala Leu Gln
725 730 735

Lys Ala Lys Glu Val Ala Glu Val Ser Pro Met Ser Ala Ala Asn Ile
740 745 750

Ser Ile Ala Ala Arg Gln Gln Asn Ser Ala Lys Ala Arg Ser Val Trp
755 760 765

Glu Gln Arg Ala Ser Gln Leu Arg Leu Gln Asn Leu Arg Ala Ser Cys
770 775 780

Glu Ala Leu Tyr Ser Glu Met Asp Pro Glu Glu Arg Leu Arg Phe Ala
785 790 795 800

Thr Thr Arg His Leu Arg Pro Asp Met Lys Thr His Leu Asp Arg Pro
805 810 815

Leu Val Val Glu Leu Gly Arg Asp Gly Ala Arg Gly Pro Val Gly Gly
820 825 830

Lys Ala Arg Pro Glu Ala Ala Glu Ala Pro Glu Gly Val Asp Pro Pro
835 840 845

Arg Arg His His Arg His Arg Asp Lys Asp Lys Thr Pro Ala Ala Gly
850 855 860

-continued

Asp Gln Asp Arg Ala Glu Ala Pro Lys Ala Glu Ser Gly Glu Pro Gly
865 870 875 880

Ala Arg Glu Glu Arg Pro Arg Pro His Arg Ser His Ser Lys Glu Ala
885 890 895

Ala Gly Pro Pro Glu Ala Arg Ser Glu Arg Gly Arg Gly Pro Gly Pro
900 905 910

Glu Gly Gly Arg Arg His His Arg Arg Gly Ser Pro Glu Glu Ala Ala
915 920 925

Glu Arg Glu Pro Arg Arg His Arg Ala His Arg His Gln Asp Pro Ser
930 935 940

Lys Glu Cys Ala Gly Ala Lys Gly Glu Arg Arg Ala Arg His Arg Gly
945 950 955 960

Gly Pro Arg Ala Gly Pro Arg Glu Ala Glu Ser Gly Glu Glu Pro Ala
965 970 975

Arg Arg His Arg Ala Arg His Lys Ala Gln Pro Ala His Glu Ala Val
980 985 990

Glu Lys Glu Thr Thr Glu Lys Glu Ala Thr Glu Lys Glu Ala Glu Ile
995 1000 1005

Val Glu Ala Asp Lys Glu Lys Glu Leu Arg Asn His Gln Pro Arg Glu
1010 1015 1020

Pro His Cys Asp Leu Glu Thr Ser Gly Thr Val Thr Val Gly Pro Met
1025 1030 1035 1040

His Thr Leu Pro Ser Thr Cys Leu Gln Lys Val Glu Glu Gln Pro Glu
1045 1050 1055

Asp Ala Asp Asn Gln Arg Asn Val Thr Arg Met Gly Ser Gln Pro Pro
1060 1065 1070

Asp Pro Asn Thr Ile Val His Ile Pro Val Met Leu Thr Gly Pro Leu
1075 1080 1085

Gly Glu Ala Thr Val Val Pro Ser Gly Asn Val Asp Leu Glu Ser Gln
1090 1095 1100

Ala Glu Gly Lys Lys Glu Val Glu Ala Asp Asp Val Met Arg Ser Gly
1105 1110 1115 1120

Pro Arg Pro Ile Val Pro Tyr Ser Ser Met Phe Cys Leu Ser Pro Thr
1125 1130 1135

Asn Leu Leu Arg Arg Phe Cys His Tyr Ile Val Thr Met Arg Tyr Phe
1140 1145 1150

Glu Val Val Ile Leu Val Val Ile Ala Leu Ser Ser Ile Ala Leu Ala
1155 1160 1165

Ala Glu Asp Pro Val Arg Thr Asp Ser Pro Arg Asn Asn Ala Leu Lys
1170 1175 1180

Tyr Leu Asp Tyr Ile Phe Thr Gly Val Phe Thr Phe Glu Met Val Ile
1185 1190 1195 1200

Lys Met Ile Asp Leu Gly Leu Leu Leu His Pro Gly Ala Tyr Phe Arg
1205 1210 1215

Asp Leu Trp Asn Ile Leu Asp Phe Ile Val Val Ser Gly Ala Leu Val
1220 1225 1230

Ala Phe Ala Phe Ser Gly Ser Lys Gly Lys Asp Ile Asn Thr Ile Lys
1235 1240 1245

Ser Leu Arg Val Leu Arg Val Leu Arg Pro Leu Lys Thr Ile Lys Arg
1250 1255 1260

Leu Pro Lys Leu Lys Ala Val Phe Asp Cys Val Val Asn Ser Leu Lys
1265 1270 1275 1280

Asn Val Leu Asn Ile Leu Ile Val Tyr Met Leu Phe Met Phe Ile Phe
1285 1290 1295

Ala Val Ile Ala Val Gln Leu Phe Lys Gly Lys Phe Phe Tyr Cys Thr
1300 1305 1310

Asp Glu Ser Lys Glu Leu Glu Arg Asp Cys Arg Gly Gln Tyr Leu Asp
1315 1320 1325

Tyr Glu Lys Glu Glu Val Glu Ala Gln Pro Arg Gln Trp Lys Lys Tyr
1330 1335 1340

Asp Phe His Tyr Asp Asn Val Leu Trp Ala Leu Leu Thr Leu Phe Thr
1345 1350 1355 1360

Val Ser Thr Gly Glu Gly Trp Pro Met Val Leu Lys His Ser Val Asp
1365 1370 1375

Ala Thr Tyr Glu Glu Gln Gly Pro Ser Pro Gly Tyr Arg Met Glu Leu
1380 1385 1390

Ser Ile Phe Tyr Val Val Tyr Phe Val Val Phe Pro Phe Phe Phe Val
1395 1400 1405

Asn Ile Phe Val Ala Leu Ile Ile Ile Thr Phe Gln Glu Gln Gly Asp
1410 1415 1420

Lys Val Met Ser Glu Cys Ser Leu Glu Lys Asn Glu Arg Ala Cys Ile
1425 1430 1435 1440

Asp Phe Ala Ile Ser Ala Lys Pro Leu Thr Arg Tyr Met Pro Gln Asn
1445 1450 1455

Arg Gln Ser Phe Gln Tyr Lys Thr Trp Thr Phe Val Val Ser Pro Pro
1460 1465 1470

Phe Glu Tyr Phe Ile Met Ala Met Ile Ala Leu Asn Thr Val Val Leu
1475 1480 1485

Met Met Lys Phe Tyr Asp Ala Pro Tyr Glu Tyr Glu Leu Met Leu Lys
1490 1495 1500

Cys Leu Asn Ile Val Phe Thr Ser Met Phe Ser Met Glu Cys Val Leu
1505 1510 1515 1520

Lys Ile Ile Ala Phe Gly Val Leu Asn Tyr Phe Arg Asp Ala Trp Asn
1525 1530 1535

Val Phe Asp Phe Val Thr Val Leu Gly Ser Ile Thr Asp Ile Leu Val
1540 1545 1550

Thr Glu Ile Ala Glu Thr Asn Asn Phe Ile Asn Leu Ser Phe Leu Arg
1555 1560 1565

Leu Phe Arg Ala Ala Arg Leu Ile Lys Leu Leu Arg Gln Gly Tyr Thr
1570 1575 1580

Ile Arg Ile Leu Leu Trp Thr Phe Val Gln Ser Phe Lys Ala Leu Pro
1585 1590 1595 1600

Tyr Val Cys Leu Leu Ile Ala Met Leu Phe Phe Ile Tyr Ala Ile Ile
1605 1610 1615

Gly Met Gln Val Phe Gly Asn Ile Ala Leu Asp Asp Asp Thr Ser Ile
1620 1625 1630

Asn Arg His Asn Asn Phe Arg Thr Phe Leu Gln Ala Leu Met Leu Leu
1635 1640 1645

Phe Arg Ser Ala Thr Gly Glu Ala Trp His Glu Ile Met Leu Ser Cys
1650 1655 1660

Leu Ser Asn Gln Ala Cys Asp Glu Gln Ala Asn Ala Thr Glu Cys Gly
1665 1670 1675 1680

Ser Asp Phe Ala Tyr Phe Tyr Phe Val Ser Phe Ile Phe Leu Cys Ser
1685 1690 1695

Phe Leu Met Leu Asn Leu Phe Val Ala Val Ile Met Asp Asn Phe Glu
1700 1705 1710

Tyr Leu Thr Arg Asp Ser Ser Ile Leu Gly Pro His His Leu Asp Glu 1715 1720 1725

Phe Ile Arg Val Trp Ala Glu Tyr Asp Pro Ala Ala Cys Gly Arg Ile
1730 1735 1740

Ser Tyr Asn Asp Met Phe Glu Met Leu Lys His Met Ser Pro Pro Leu
1745 1750 1755 1760

Gly Leu Gly Lys Lys Cys Pro Ala Arg Val Ala Tyr Lys Arg Leu Val
1765 1770 1775

Arg Met Asn Met Pro Ile Ser Asn Glu Asp Met Thr Val His Phe Thr
1780 1785 1790

Ser Thr Leu Met Ala Leu Ile Arg Thr Ala Leu Glu Ile Lys Leu Ala
1795 1800 1805

Pro Ala Gly Thr Lys Gln His Gln Cys Asp Ala Glu Leu Arg Lys Glu
1810 1815 1820

Ile Ser Val Val Trp Ala Asn Leu Pro Gln Lys Thr Leu Asp Leu Leu
1825 1830 1835 1840

Val Pro Pro His Lys Pro Asp Glu Met Thr Val Gly Lys Val Tyr Ala
1845 1850 1855

Ala Leu Met Ile Phe Asp Phe Tyr Lys Gln Asn Lys Thr Thr Arg Asp
1860 1865 1870

Gln Met Gln Gln Ala Pro Gly Gly Leu Ser Gln Met Gly Pro Val Ser
1875 1880 1885

Leu Phe His Pro Leu Lys Ala Thr Leu Glu Gln Thr Gln Pro Ala Val
1890 1895 1900

Leu Arg Gly Ala Arg Val Phe Leu Arg Gln Lys Ser Ser Thr Ser Leu
1905 1910 1915 1920

Ser Asn Gly Gly Ala Ile Gln Asn Gln Glu Ser Gly Ile Lys Glu Ser
1925 1930 1935

Val Ser Trp Gly Thr Gln Arg Thr Gln Asp Ala Pro His Glu Ala Arg
1940 1945 1950

Pro Pro Leu Glu Arg Gly His Ser Thr Glu Ile Pro Val Gly Arg Ser
1955 1960 1965

Gly Ala Leu Ala Val Asp Val Gln Met Gln Ser Ile Thr Arg Arg Gly
1970 1975 1980

Pro Asp Gly Glu Pro Gln Pro Gly Leu Glu Ser Gln Gly Arg Ala Ala
1985 1990 1995 2000

Ser Met Pro Arg Leu Ala Ala Glu Thr Gln Pro Val Thr Asp Ala Ser
2005 2010 2015

Pro Met Lys Arg Ser Ile Ser Thr Leu Ala Gln Arg Pro Arg Gly Thr
2020 2025 2030

His Leu Cys Ser Thr Thr Pro Asp Arg Pro Pro Pro Ser Gln Ala Ser
2035 2040 2045

Ser His His His His His Arg Cys His Arg Arg Arg Asp Arg Lys Gln
2050 2055 2060

Arg Ser Leu Glu Lys Gly Pro Ser Leu Ser Ala Asp Met Asp Gly Ala
2065 2070 2075 2080

Pro Ser Ser Ala Val Gly Pro Gly Leu Pro Pro Gly Glu Gly Pro Thr
2085 2090 2095

Gly Cys Arg Arg Glu Arg Glu Arg Arg Gln Glu Arg Gly Arg Ser Gln
2100 2105 2110

Glu Arg Arg Gln Pro Ser Ser Ser Ser Ser Glu Lys Gln Arg Phe Tyr
2115 2120 2125

Ser Cys Asp Arg Phe Gly Gly Arg Glu Pro Pro Lys Pro Lys Pro Ser
2130 2135 2140

Leu Ser Ser His Pro Thr Ser Pro Thr Ala Gly Gln Glu Pro Gly Pro
2145 2150 2155 2160

His Pro Gln Gly Ser Gly Ser Val Asn Gly Ser Pro Leu Leu Ser Thr
2165 2170 2175

Ser Gly Ala Ser Thr Pro Gly Arg Gly Gly Arg Arg Gln Leu Pro Gln
2180 2185 2190

Thr Pro Leu Thr Pro Arg Pro Ser Ile Thr Tyr Lys Thr Ala Asn Ser
2195 2200 2205

Ser Pro Ile His Phe Ala Gly Ala Gln Thr Ser Leu Pro Ala Phe Ser
2210 2215 2220

Pro Gly Arg Leu Ser Arg Gly Leu Ser Glu His Asn Ala Leu Leu Gln
2225 2230 2235 2240

Arg Asp Pro Leu Ser Gln Pro Leu Ala Pro Gly Ser Arg Ile Gly Ser
2245 2250 2255

Asp Pro Tyr Leu Gly Gln Arg Leu Asp Ser Glu Ala Ser Val His Ala
2260 2265 2270

Leu Pro Glu Asp Thr Leu Thr Phe Glu Glu Ala Val Ala Thr Asn Ser
2275 2280 2285

Gly Arg Ser Ser Arg Thr Ser Tyr Val Ser Ser Leu Thr Ser Gln Ser
2290 2295 2300

His Pro Leu Arg Arg Val Pro Asn Gly Tyr His Cys Thr Leu Gly Leu
2305 2310 2315 2320

Ser Ser Gly Gly Arg Ala Arg His Ser Tyr His His Pro Asp Gln Asp
2325 2330 2335

His Trp Cys ( 2 ) INFORMATION FOR SEQ ID NO:48:

( i ) SEQUENCE CHARACTERISTICS:
( A ) LENGTH: 2237 amino acids
( B ) TYPE: amino acid
( C ) STRANDEDNESS: single
( D ) TOPOLOGY: linear ( i i ) MOLECULE TYPE: protein ( v ) FRAGMENT TYPE: internal ( x i ) SEQUENCE DESCRIPTION: SEQ ID NO:48:

Met Val Arg Phe Gly Asp Glu Leu Gly Gly Arg Tyr Gly Gly Pro Gly
1 5 10 15

Gly Gly Glu Arg Ala Arg Gly Gly Gly Ala Gly Gly Ala Gly Gly Pro
20 25 30

Gly Pro Gly Gly Leu Gln Pro Gly Gln Arg Val Leu Tyr Lys Gln Ser
35 40 45

Ile Ala Gln Arg Ala Arg Thr Met Ala Leu Tyr Asn Pro Ile Pro Val
50 55 60

Lys Gln Asn Cys Phe Thr Val Asn Arg Ser Leu Phe Val Phe Ser Glu
65 70 75 80

Asp Asn Val Val Arg Lys Tyr Ala Lys Arg Ile Thr Glu Trp Pro Pro
85 90 95

Phe Glu Asn Met Ile Leu Ala Thr Ile Ile Ala Asn Cys Ile Val Leu
100 105 110

Ala Leu Glu Gln His Leu Pro Asp Gly Asp Lys Thr Pro Met Ser Glu
115 120 125

Arg Leu Asp Asp Thr Glu Pro Tyr Phe Ile Gly Ile Phe Cys Phe Glu
130 135 140

-continued

| | | | | | | | | | | | | | | | |
|---|---|---|---|---|---|---|---|---|---|---|---|---|---|---|---|
| Ala | Gly | Ile | Lys | Ile | Ile | Ala | Leu | Gly | Phe | Val | Phe | His | Lys | Gly | Ser |
| 145 | | | | | 150 | | | | | 155 | | | | | 160 |
| Tyr | Leu | Arg | Asn | Gly | Trp | Asn | Val | Met | Asp | Phe | Val | Val | Val | Leu | Thr |
| | | | | 165 | | | | | 170 | | | | | 175 | |
| Gly | Ile | Leu | Ala | Thr | Ala | Gly | Thr | Asp | Phe | Asp | Leu | Arg | Thr | Leu | Arg |
| | | | 180 | | | | | 185 | | | | | 190 | | |
| Ala | Val | Arg | Val | Leu | Arg | Pro | Leu | Lys | Leu | Val | Ser | Gly | Ile | Pro | Ser |
| | | 195 | | | | | 200 | | | | | 205 | | | |
| Leu | Gln | Val | Val | Leu | Lys | Ser | Ile | Met | Lys | Ala | Met | Val | Pro | Leu | Leu |
| | 210 | | | | | 215 | | | | | 220 | | | | |
| Gln | Ile | Gly | Leu | Leu | Leu | Phe | Phe | Ala | Ile | Leu | Met | Phe | Ala | Ile | Ile |
| 225 | | | | | 230 | | | | | 235 | | | | | 240 |
| Gly | Leu | Glu | Phe | Tyr | Met | Gly | Lys | Phe | His | Lys | Ala | Cys | Phe | Pro | Asn |
| | | | | 245 | | | | | 250 | | | | | 255 | |
| Ser | Thr | Asp | Ala | Glu | Pro | Val | Gly | Asp | Phe | Pro | Cys | Gly | Lys | Glu | Ala |
| | | | 260 | | | | | 265 | | | | | 270 | | |
| Pro | Ala | Arg | Leu | Cys | Glu | Gly | Asp | Thr | Glu | Cys | Arg | Glu | Tyr | Trp | Pro |
| | | 275 | | | | | 280 | | | | | 285 | | | |
| Gly | Pro | Asn | Phe | Gly | Ile | Thr | Asn | Phe | Asp | Asn | Ile | Leu | Phe | Ala | Ile |
| | 290 | | | | | 295 | | | | | 300 | | | | |
| Leu | Thr | Val | Phe | Gln | Cys | Ile | Thr | Met | Glu | Gly | Trp | Thr | Asp | Ile | Leu |
| 305 | | | | | 310 | | | | | 315 | | | | | 320 |
| Tyr | Asn | Thr | Asn | Asp | Ala | Ala | Gly | Asn | Thr | Trp | Asn | Trp | Leu | Tyr | Phe |
| | | | | 325 | | | | | 330 | | | | | 335 | |
| Ile | Pro | Leu | Ile | Ile | Ile | Gly | Ser | Phe | Phe | Met | Leu | Asn | Leu | Val | Leu |
| | | | 340 | | | | | 345 | | | | | 350 | | |
| Gly | Val | Leu | Ser | Gly | Glu | Phe | Ala | Lys | Glu | Arg | Glu | Arg | Val | Glu | Asn |
| | | 355 | | | | | 360 | | | | | 365 | | | |
| Arg | Arg | Ala | Phe | Leu | Lys | Leu | Arg | Arg | Gln | Gln | Gln | Ile | Glu | Arg | Glu |
| | 370 | | | | | 375 | | | | | 380 | | | | |
| Leu | Asn | Gly | Tyr | Leu | Glu | Trp | Ile | Phe | Lys | Ala | Glu | Glu | Val | Met | Leu |
| 385 | | | | | 390 | | | | | 395 | | | | | 400 |
| Ala | Glu | Glu | Asp | Arg | Asn | Ala | Glu | Glu | Lys | Ser | Pro | Leu | Asp | Val | Leu |
| | | | | 405 | | | | | 410 | | | | | 415 | |
| Lys | Arg | Ala | Ala | Thr | Lys | Lys | Ser | Arg | Asn | Asp | Leu | Ile | His | Ala | Glu |
| | | | 420 | | | | | 425 | | | | | 430 | | |
| Glu | Gly | Glu | Asp | Arg | Phe | Ala | Asp | Leu | Cys | Ala | Val | Gly | Ser | Pro | Phe |
| | | 435 | | | | | 440 | | | | | 445 | | | |
| Ala | Arg | Ala | Ser | Leu | Lys | Ser | Gly | Lys | Thr | Glu | Ser | Ser | Ser | Tyr | Phe |
| | 450 | | | | | 455 | | | | | 460 | | | | |
| Arg | Arg | Lys | Glu | Lys | Met | Phe | Arg | Phe | Phe | Ile | Arg | Arg | Met | Val | Lys |
| 465 | | | | | 470 | | | | | 475 | | | | | 480 |
| Ala | Gln | Ser | Phe | Tyr | Trp | Val | Val | Leu | Cys | Val | Val | Ala | Leu | Asn | Thr |
| | | | | 485 | | | | | 490 | | | | | 495 | |
| Leu | Cys | Val | Ala | Met | Val | His | Tyr | Asn | Gln | Pro | Arg | Arg | Leu | Thr | Thr |
| | | | 500 | | | | | 505 | | | | | 510 | | |
| Thr | Leu | Tyr | Phe | Ala | Glu | Phe | Val | Phe | Leu | Gly | Leu | Phe | Leu | Thr | Glu |
| | | 515 | | | | | 520 | | | | | 525 | | | |
| Met | Ser | Leu | Lys | Met | Tyr | Gly | Leu | Gly | Pro | Arg | Ser | Tyr | Phe | Arg | Ser |
| | 530 | | | | | 535 | | | | | 540 | | | | |
| Ser | Phe | Asn | Cys | Phe | Asp | Phe | Gly | Val | Ile | Val | Gly | Ser | Val | Phe | Glu |
| 545 | | | | | 550 | | | | | 555 | | | | | 560 |
| Val | Val | Trp | Ala | Ala | Ile | Lys | Pro | Gly | Ser | Ser | Phe | Gly | Ile | Ser | Val |
| | | | | 565 | | | | | 570 | | | | | 575 | |

-continued

Leu Arg Ala Leu Arg Leu Leu Arg Ile Phe Lys Val Thr Lys Tyr Trp
580 585 590

Ser Ser Leu Arg Asn Leu Val Val Ser Leu Leu Asn Ser Met Lys Ser
595 600 605

Ile Ile Ser Leu Leu Phe Leu Leu Phe Leu Phe Ile Val Val Phe Ala
610 615 620

Leu Leu Gly Met Gln Leu Phe Gly Gly Gln Phe Asn Phe Gln Asp Glu
625 630 635 640

Thr Pro Thr Thr Asn Phe Asp Thr Phe Pro Ala Ala Ile Leu Thr Val
645 650 655

Phe Gln Ile Leu Thr Gly Glu Asp Trp Asn Ala Val Met Tyr His Gly
660 665 670

Ile Glu Ser Gln Gly Gly Val Ser Lys Gly Met Phe Ser Ser Phe Tyr
675 680 685

Phe Ile Val Leu Thr Leu Phe Gly Asn Tyr Thr Leu Leu Asn Val Phe
690 695 700

Leu Ala Ile Ala Val Asp Asn Leu Ala Asn Ala Gln Glu Leu Thr Lys
705 710 715 720

Asp Glu Glu Glu Met Glu Glu Ala Ala Asn Gln Lys Leu Ala Leu Gln
725 730 735

Lys Ala Lys Glu Val Ala Glu Val Ser Pro Met Ser Ala Ala Asn Ile
740 745 750

Ser Ile Ala Ala Arg Gln Gln Asn Ser Ala Lys Ala Arg Ser Val Trp
755 760 765

Glu Gln Arg Ala Ser Gln Leu Arg Leu Gln Asn Leu Arg Ala Ser Cys
770 775 780

Glu Ala Leu Tyr Ser Glu Met Asp Pro Glu Glu Arg Leu Arg Phe Ala
785 790 795 800

Thr Thr Arg His Leu Arg Pro Asp Met Lys Thr His Leu Asp Arg Pro
805 810 815

Leu Val Val Glu Leu Gly Arg Asp Gly Ala Arg Gly Pro Val Gly Gly
820 825 830

Lys Ala Arg Pro Glu Ala Ala Glu Ala Pro Glu Gly Val Asp Pro Pro
835 840 845

Arg Arg His His Arg His Arg Asp Lys Asp Lys Thr Pro Ala Ala Gly
850 855 860

Asp Gln Asp Arg Ala Glu Ala Pro Lys Ala Glu Ser Gly Glu Pro Gly
865 870 875 880

Ala Arg Glu Glu Arg Pro Arg Pro His Arg Ser His Ser Lys Glu Ala
885 890 895

Ala Gly Pro Pro Glu Ala Arg Ser Glu Arg Gly Arg Gly Pro Gly Pro
900 905 910

Glu Gly Gly Arg Arg His His Arg Arg Gly Ser Pro Glu Glu Ala Ala
915 920 925

Glu Arg Glu Pro Arg Arg His Arg Ala His Arg His Gln Asp Pro Ser
930 935 940

Lys Glu Cys Ala Gly Ala Lys Gly Glu Arg Arg Ala Arg His Arg Gly
945 950 955 960

Gly Pro Arg Ala Gly Pro Arg Glu Ala Glu Ser Gly Glu Glu Pro Ala
965 970 975

Arg Arg His Arg Ala Arg His Lys Ala Gln Pro Ala His Glu Ala Val
980 985 990

Glu Lys Glu Thr Thr Glu Lys Glu Ala Thr Glu Lys Glu Ala Glu Ile

-continued 995 1000 1005

Val Glu Ala Asp Lys Glu Lys Glu Leu Arg Asn His Gln Pro Arg Glu
1010 1015 1020

Pro His Cys Asp Leu Glu Thr Ser Gly Thr Val Thr Val Gly Pro Met
1025 1030 1035 1040

His Thr Leu Pro Ser Thr Cys Leu Gln Lys Val Glu Glu Gln Pro Glu
1045 1050 1055

Asp Ala Asp Asn Gln Arg Asn Val Thr Arg Met Gly Ser Gln Pro Pro
1060 1065 1070

Asp Pro Asn Thr Ile Val His Ile Pro Val Met Leu Thr Gly Pro Leu
1075 1080 1085

Gly Glu Ala Thr Val Val Pro Ser Gly Asn Val Asp Leu Glu Ser Gln
1090 1095 1100

Ala Glu Gly Lys Lys Glu Val Glu Ala Asp Asp Val Met Arg Ser Gly
1105 1110 1115 1120

Pro Arg Pro Ile Val Pro Tyr Ser Ser Met Phe Cys Leu Ser Pro Thr
1125 1130 1135

Asn Leu Leu Arg Arg Phe Cys His Tyr Ile Val Thr Met Arg Tyr Phe
1140 1145 1150

Glu Val Val Ile Leu Val Val Ile Ala Leu Ser Ser Ile Ala Leu Ala
1155 1160 1165

Ala Glu Asp Pro Val Arg Thr Asp Ser Pro Arg Asn Asn Ala Leu Lys
1170 1175 1180

Tyr Leu Asp Tyr Ile Phe Thr Gly Val Phe Thr Phe Glu Met Val Ile
1185 1190 1195 1200

Lys Met Ile Asp Leu Gly Leu Leu Leu His Pro Gly Ala Tyr Phe Arg
1205 1210 1215

Asp Leu Trp Asn Ile Leu Asp Phe Ile Val Val Ser Gly Ala Leu Val
1220 1225 1230

Ala Phe Ala Phe Ser Gly Ser Lys Gly Lys Asp Ile Asn Thr Ile Lys
1235 1240 1245

Ser Leu Arg Val Leu Arg Val Leu Arg Pro Leu Lys Thr Ile Lys Arg
1250 1255 1260

Leu Pro Lys Leu Lys Ala Val Phe Asp Cys Val Val Asn Ser Leu Lys
1265 1270 1275 1280

Asn Val Leu Asn Ile Leu Ile Val Tyr Met Leu Phe Met Phe Ile Phe
1285 1290 1295

Ala Val Ile Ala Val Gln Leu Phe Lys Gly Lys Phe Phe Tyr Cys Thr
1300 1305 1310

Asp Glu Ser Lys Glu Leu Glu Arg Asp Cys Arg Gly Gln Tyr Leu Asp
1315 1320 1325

Tyr Glu Lys Glu Glu Val Glu Ala Gln Pro Arg Gln Trp Lys Lys Tyr
1330 1335 1340

Asp Phe His Tyr Asp Asn Val Leu Trp Ala Leu Leu Thr Leu Phe Thr
1345 1350 1355 1360

Val Ser Thr Gly Glu Gly Trp Pro Met Val Leu Lys His Ser Val Asp
1365 1370 1375

Ala Thr Tyr Glu Glu Gln Gly Pro Ser Pro Gly Tyr Arg Met Glu Leu
1380 1385 1390

Ser Ile Phe Tyr Val Val Tyr Phe Val Val Phe Pro Phe Phe Phe Val
1395 1400 1405

Asn Ile Phe Val Ala Leu Ile Ile Ile Thr Phe Gln Glu Gln Gly Asp
1410 1415 1420

-continued

Lys Val Met Ser Glu Cys Ser Leu Glu Lys Asn Glu Arg Ala Cys Ile
1425 1430 1435 1440

Asp Phe Ala Ile Ser Ala Lys Pro Leu Thr Arg Tyr Met Pro Gln Asn
1445 1450 1455

Arg Gln Ser Phe Gln Tyr Lys Thr Trp Thr Phe Val Val Ser Pro Pro
1460 1465 1470

Phe Glu Tyr Phe Ile Met Ala Met Ile Ala Leu Asn Thr Val Val Leu
1475 1480 1485

Met Met Lys Phe Tyr Asp Ala Pro Tyr Glu Tyr Glu Leu Met Leu Lys
1490 1495 1500

Cys Leu Asn Ile Val Phe Thr Ser Met Phe Ser Met Glu Cys Val Leu
1505 1510 1515 1520

Lys Ile Ile Ala Phe Gly Val Leu Asn Tyr Phe Arg Asp Ala Trp Asn
1525 1530 1535

Val Phe Asp Phe Val Thr Val Leu Gly Ser Ile Thr Asp Ile Leu Val
1540 1545 1550

Thr Glu Ile Ala Glu Thr Asn Asn Phe Ile Asn Leu Ser Phe Leu Arg
1555 1560 1565

Leu Phe Arg Ala Ala Arg Leu Ile Lys Leu Leu Arg Gln Gly Tyr Thr
1570 1575 1580

Ile Arg Ile Leu Leu Trp Thr Phe Val Gln Ser Phe Lys Ala Leu Pro
1585 1590 1595 1600

Tyr Val Cys Leu Leu Ile Ala Met Leu Phe Phe Ile Tyr Ala Ile Ile
1605 1610 1615

Gly Met Gln Val Phe Gly Asn Ile Ala Leu Asp Asp Asp Thr Ser Ile
1620 1625 1630

Asn Arg His Asn Asn Phe Arg Thr Phe Leu Gln Ala Leu Met Leu Leu
1635 1640 1645

Phe Arg Ser Ala Thr Gly Glu Ala Trp His Glu Ile Met Leu Ser Cys
1650 1655 1660

Leu Ser Asn Gln Ala Cys Asp Glu Gln Ala Asn Ala Thr Glu Cys Gly
1665 1670 1675 1680

Ser Asp Phe Ala Tyr Phe Tyr Phe Val Ser Phe Ile Phe Leu Cys Ser
1685 1690 1695

Phe Leu Met Leu Asn Leu Phe Val Ala Val Ile Met Asp Asn Phe Glu
1700 1705 1710

Tyr Leu Thr Arg Asp Ser Ser Ile Leu Gly Pro His His Leu Asp Glu
1715 1720 1725

Phe Ile Arg Val Trp Ala Glu Tyr Asp Pro Ala Ala Cys Gly Arg Ile
1730 1735 1740

Ser Tyr Asn Asp Met Phe Glu Met Leu Lys His Met Ser Pro Pro Leu
1745 1750 1755 1760

Gly Leu Gly Lys Lys Cys Pro Ala Arg Val Ala Tyr Lys Arg Leu Val
1765 1770 1775

Arg Met Asn Met Pro Ile Ser Asn Glu Asp Met Thr Val His Phe Thr
1780 1785 1790

Ser Thr Leu Met Ala Leu Ile Arg Thr Ala Leu Glu Ile Lys Leu Ala
1795 1800 1805

Pro Ala Gly Thr Lys Gln His Gln Cys Asp Ala Glu Leu Arg Lys Glu
1810 1815 1820

Ile Ser Val Val Trp Ala Asn Leu Pro Gln Lys Thr Leu Asp Leu Leu
1825 1830 1835 1840

Val Pro Pro His Lys Pro Asp Glu Met Thr Val Gly Lys Val Tyr Ala
1845 1850 1855

-continued

Ala Leu Met Ile Phe Asp Phe Tyr Lys Gln Asn Lys Thr Thr Arg Asp
1860 1865 1870

Gln Met Gln Gln Ala Pro Gly Gly Leu Ser Gln Met Gly Pro Val Ser
1875 1880 1885

Leu Phe His Pro Leu Lys Ala Thr Leu Glu Gln Thr Gln Pro Ala Val
1890 1895 1900

Leu Arg Gly Ala Arg Val Phe Leu Arg Gln Lys Ser Ser Thr Ser Leu
1905 1910 1915 1920

Ser Asn Gly Gly Ala Ile Gln Asn Gln Glu Ser Gly Ile Lys Glu Ser
1925 1930 1935

Val Ser Trp Gly Thr Gln Arg Thr Gln Asp Ala Pro His Glu Ala Arg
1940 1945 1950

Pro Pro Leu Glu Arg Gly His Ser Thr Glu Ile Pro Val Gly Arg Ser
1955 1960 1965

Gly Ala Leu Ala Val Asp Val Gln Met Gln Ser Ile Thr Arg Arg Gly
1970 1975 1980

Pro Asp Gly Glu Pro Gln Pro Gly Leu Glu Ser Gln Gly Arg Ala Ala
1985 1990 1995 2000

Ser Met Pro Arg Leu Ala Ala Glu Thr Gln Pro Val Thr Asp Ala Ser
2005 2010 2015

Pro Met Lys Arg Ser Ile Ser Thr Leu Ala Gln Arg Pro Arg Gly Thr
2020 2025 2030

His Leu Cys Ser Thr Thr Pro Asp Arg Pro Pro Ser Gln Ala Ser
2035 2040 2045

Ser His His His His His Arg Cys His Arg Arg Arg Asp Arg Lys Gln
2050 2055 2060

Arg Ser Leu Glu Lys Gly Pro Ser Leu Ser Ala Asp Met Asp Gly Ala
2065 2070 2075 2080

Pro Ser Ser Ala Val Gly Pro Gly Leu Pro Pro Gly Glu Gly Pro Thr
2085 2090 2095

Gly Cys Arg Arg Glu Arg Glu Arg Arg Gln Glu Arg Gly Arg Ser Gln
2100 2105 2110

Glu Arg Arg Gln Pro Ser Ser Ser Ser Ser Glu Lys Gln Arg Phe Tyr
2115 2120 2125

Ser Cys Asp Arg Phe Gly Gly Arg Glu Pro Pro Lys Pro Lys Pro Ser
2130 2135 2140

Leu Ser Ser His Pro Thr Ser Pro Thr Ala Gly Gln Glu Pro Gly Pro
2145 2150 2155 2160

His Pro Gln Ala Gly Ser Ala Val Gly Phe Pro Asn Thr Thr Pro Cys
2165 2170 2175

Cys Arg Glu Thr Pro Ser Ala Ser Pro Trp Pro Leu Ala Leu Glu Leu
2180 2185 2190

Ala Leu Thr Leu Thr Trp Gly Ser Val Trp Thr Val Arg Pro Leu Ser
2195 2200 2205

Thr Pro Cys Leu Arg Thr Arg Ser Leu Ser Arg Arg Leu Trp Pro Pro
2210 2215 2220

Thr Arg Ala Ala Pro Pro Gly Leu Pro Thr Cys Pro Pro
2225 2230 2235

( 2 ) INFORMATION FOR SEQ ID NO:49:

( i ) SEQUENCE CHARACTERISTICS:
( A ) LENGTH: 2161 amino acids
( B ) TYPE: amino acid
( C ) STRANDEDNESS: single ( D ) TOPOLOGY: linear ( i i ) MOLECULE TYPE: protein ( v ) FRAGMENT TYPE: internal ( x i ) SEQUENCE DESCRIPTION: SEQ ID NO:49:

Met Met Met Met Met Met Met Lys Lys Met Gln His Gln Arg Gln Gln
1 5 10 15

Gln Ala Asp His Ala Asn Glu Ala Asn Tyr Ala Arg Gly Thr Arg Leu
20 25 30

Pro Leu Ser Gly Glu Gly Pro Thr Ser Gln Pro Asn Ser Ser Lys Gln
35 40 45

Thr Val Leu Ser Trp Gln Ala Ala Ile Asp Ala Ala Arg Gln Ala Lys
50 55 60

Ala Ala Gln Thr Met Ser Thr Ser Ala Pro Pro Pro Val Gly Ser Leu
65 70 75 80

Ser Gln Arg Lys Arg Gln Gln Tyr Ala Lys Ser Lys Lys Gln Gly Asn
85 90 95

Ser Ser Asn Ser Arg Pro Ala Arg Ala Leu Phe Cys Leu Ser Leu Asn
100 105 110

Asn Pro Ile Arg Arg Ala Cys Ile Ser Ile Val Glu Trp Lys Pro Phe
115 120 125

Asp Ile Phe Ile Leu Leu Ala Ile Phe Ala Asn Cys Val Ala Leu Ala
130 135 140

Ile Tyr Ile Pro Phe Pro Glu Asp Asp Ser Asn Ser Thr Asn His Asn
145 150 155 160

Leu Glu Lys Val Glu Tyr Ala Phe Leu Ile Ile Phe Thr Val Glu Thr
165 170 175

Phe Leu Lys Ile Ile Ala Tyr Gly Leu Leu Leu His Pro Asn Ala Tyr
180 185 190

Val Arg Asn Gly Trp Asn Leu Leu Asp Phe Val Ile Val Ile Val Gly
195 200 205

Leu Phe Ser Val Ile Leu Glu Gln Leu Thr Lys Glu Thr Glu Gly Gly
210 215 220

Asn His Ser Ser Gly Lys Ser Gly Gly Phe Asp Val Lys Ala Leu Arg
225 230 235 240

Ala Phe Arg Val Leu Arg Pro Leu Arg Leu Val Ser Gly Val Pro Ser
245 250 255

Leu Gln Val Val Leu Asn Ser Ile Ile Lys Ala Met Val Pro Leu Leu
260 265 270

His Ile Ala Leu Leu Val Leu Phe Val Ile Ile Ile Tyr Ala Ile Ile
275 280 285

Gly Leu Glu Leu Phe Ile Gly Lys Met His Lys Thr Cys Phe Phe Ala
290 295 300

Asp Ser Asp Ile Val Ala Glu Glu Asp Pro Ala Pro Cys Ala Phe Ser
305 310 315 320

Gly Asn Gly Arg Gln Cys Thr Ala Asn Gly Thr Glu Cys Arg Ser Gly
325 330 335

Trp Val Gly Pro Asn Gly Gly Ile Thr Asn Phe Asp Asn Phe Ala Phe
340 345 350

Ala Met Leu Thr Val Phe Gln Cys Ile Thr Met Glu Gly Trp Thr Asp
355 360 365

Val Leu Tyr Trp Met Asn Asp Ala Met Gly Phe Glu Leu Pro Trp Val
370 375 380

-continued

Tyr Phe Val Ser Leu Val Ile Phe Gly Ser Phe Phe Val Leu Asn Leu
385                 390                 395                 400

Val Leu Gly Val Leu Ser Gly Glu Phe Ser Lys Glu Arg Glu Lys Ala
                405                 410                 415

Lys Ala Arg Gly Asp Phe Gln Lys Leu Arg Glu Lys Gln Gln Leu Glu
            420                 425                 430

Glu Asp Leu Lys Gly Tyr Leu Asp Trp Ile Thr Gln Ala Glu Asp Ile
        435                 440                 445

Asp Pro Glu Asn Glu Glu Glu Gly Gly Glu Glu Gly Lys Arg Asn Thr
    450                 455                 460

Ser Met Pro Thr Ser Glu Thr Glu Ser Val Asn Thr Glu Asn Val Ser
465                 470                 475                 480

Gly Glu Gly Glu Asn Arg Gly Cys Cys Gly Ser Leu Cys Gln Ala Ile
                485                 490                 495

Ser Lys Ser Lys Leu Ser Arg Arg Trp Arg Arg Trp Asn Arg Phe Asn
            500                 505                 510

Arg Arg Arg Cys Arg Ala Ala Val Lys Ser Val Thr Phe Tyr Trp Leu
        515                 520                 525

Val Ile Val Leu Val Phe Leu Asn Thr Leu Thr Ile Ser Ser Glu His
    530                 535                 540

Tyr Asn Gln Pro Asp Trp Leu Thr Gln Ile Gln Asp Ile Ala Asn Lys
545                 550                 555                 560

Val Leu Leu Ala Leu Phe Thr Cys Glu Met Leu Val Lys Met Tyr Ser
                565                 570                 575

Leu Gly Leu Gln Ala Tyr Phe Val Ser Leu Phe Asn Arg Phe Asp Cys
            580                 585                 590

Phe Val Val Cys Gly Gly Ile Thr Glu Thr Ile Leu Val Glu Leu Glu
        595                 600                 605

Ile Met Ser Pro Leu Gly Ile Ser Val Phe Arg Cys Val Arg Leu Leu
    610                 615                 620

Arg Ile Phe Lys Val Thr Arg His Trp Thr Ser Leu Ser Asn Leu Val
625                 630                 635                 640

Ala Ser Leu Leu Asn Ser Met Lys Ser Ile Ala Ser Leu Leu Leu Leu
                645                 650                 655

Leu Phe Leu Phe Ile Ile Ile Phe Ser Leu Leu Gly Met Gln Leu Phe
            660                 665                 670

Gly Gly Lys Phe Asn Phe Asp Glu Thr Gln Thr Lys Arg Ser Thr Phe
        675                 680                 685

Asp Asn Phe Pro Gln Ala Leu Leu Thr Val Phe Gln Ile Leu Thr Gly
    690                 695                 700

Glu Asp Trp Asn Ala Val Met Tyr Asp Gly Ile Met Ala Tyr Gly Gly
705                 710                 715                 720

Pro Ser Ser Ser Gly Met Ile Val Cys Ile Tyr Phe Ile Ile Leu Phe
                725                 730                 735

Ile Cys Gly Asn Tyr Ile Leu Leu Asn Val Phe Leu Ala Ile Ala Val
            740                 745                 750

Asp Asn Leu Ala Asp Ala Glu Ser Leu Asn Thr Ala Gln Lys Glu Glu
        755                 760                 765

Ala Glu Glu Lys Glu Arg Lys Lys Ile Ala Arg Lys Glu Ser Leu Glu
    770                 775                 780

Asn Lys Lys Asn Asn Lys Pro Glu Val Asn Gln Ile Ala Asn Ser Asp
785                 790                 795                 800

Asn Lys Val Thr Ile Asp Asp Tyr Arg Glu Glu Asp Glu Asp Lys Asp
                805                 810                 815

Pro Tyr Pro Pro Cys Asp Val Pro Val Gly Glu Glu Glu Glu Glu Glu
820 825 830

Glu Glu Asp Glu Pro Glu Val Pro Ala Gly Pro Arg Pro Arg Arg Ile
835 840 845

Ser Glu Leu Asn Met Lys Glu Lys Ile Ala Pro Ile Pro Glu Gly Ser
850 855 860

Ala Phe Phe Ile Leu Ser Lys Thr Asn Pro Ile Arg Val Gly Cys His
865 870 875 880

Lys Leu Ile Asn His His Ile Phe Thr Asn Leu Ile Leu Val Phe Ile
885 890 895

Met Leu Ser Ser Ala Ala Leu Ala Ala Glu Asp Pro Ile Arg Ser His
900 905 910

Ser Phe Arg Asn Thr Ile Leu Gly Tyr Phe Asp Tyr Ala Phe Thr Ala
915 920 925

Ile Phe Thr Val Glu Ile Leu Leu Lys Met Thr Thr Phe Gly Ala Phe
930 935 940

Leu His Lys Gly Ala Phe Cys Arg Asn Tyr Phe Asn Leu Leu Asp Met
945 950 955 960

Leu Val Val Gly Val Ser Leu Val Ser Phe Gly Ile Gln Ser Ser Ala
965 970 975

Ile Ser Val Val Lys Ile Leu Arg Val Leu Arg Val Leu Arg Pro Leu
980 985 990

Arg Ala Ile Asn Arg Ala Lys Gly Leu Lys His Val Val Gln Cys Val
995 1000 1005

Phe Val Ala Ile Arg Thr Ile Gly Asn Ile Met Ile Val Thr Thr Leu
1010 1015 1020

Leu Gln Phe Met Phe Ala Cys Ile Gly Val Gln Leu Phe Lys Gly Lys
1025 1030 1035 1040

Phe Tyr Arg Cys Thr Asp Glu Ala Lys Ser Asn Pro Glu Glu Cys Arg
1045 1050 1055

Gly Leu Phe Ile Leu Tyr Lys Asp Gly Asp Val Asp Ser Pro Val Val
1060 1065 1070

Arg Glu Arg Ile Trp Gln Asn Ser Asp Phe Asn Phe Asp Asn Val Leu
1075 1080 1085

Ser Ala Met Met Ala Leu Phe Thr Val Ser Thr Phe Glu Gly Trp Pro
1090 1095 1100

Ala Leu Leu Tyr Lys Ala Ile Asp Ser Asn Gly Glu Asn Ile Gly Pro
1105 1110 1115 1120

Ile Tyr Asn His Arg Val Glu Ile Ser Ile Phe Phe Ile Ile Tyr Ile
1125 1130 1135

Ile Ile Val Ala Phe Phe Met Met Asn Ile Phe Val Gly Phe Val Ile
1140 1145 1150

Val Thr Phe Gln Glu Gln Gly Glu Lys Glu Tyr Lys Asn Cys Glu Leu
1155 1160 1165

Asp Lys Asn Gln Arg Gln Cys Val Glu Tyr Ala Leu Lys Ala Arg Pro
1170 1175 1180

Leu Arg Arg Tyr Ile Pro Lys Asn Pro Tyr Gln Tyr Lys Phe Trp Tyr
1185 1190 1195 1200

Val Val Asn Ser Ser Pro Phe Glu Tyr Met Met Phe Val Leu Ile Met
1205 1210 1215

Leu Asn Thr Leu Cys Leu Ala Met Gln His Tyr Glu Gln Ser Lys Met
1220 1225 1230

Phe Asn Asp Ala Met Asp Ile Leu Asn Met Val Phe Thr Gly Val Phe 1235 1240 1245

Thr Val Glu Met Val Leu Lys Val Ile Ala Phe Lys Pro Lys Gly Tyr
1250 1255 1260

Phe Ser Asp Ala Trp Asn Thr Phe Asp Ser Leu Ile Val Ile Gly Ser
1265 1270 1275 1280

Ile Ile Asp Val Ala Leu Ser Glu Ala Asp Pro Thr Glu Ser Glu Asn
1285 1290 1295

Val Pro Val Pro Thr Ala Thr Pro Gly Asn Ser Glu Glu Ser Asn Arg
1300 1305 1310

Ile Ser Ile Thr Phe Phe Arg Leu Phe Arg Val Met Arg Leu Val Lys
1315 1320 1325

Leu Leu Ser Arg Gly Glu Gly Ile Arg Thr Leu Leu Trp Thr Phe Ile
1330 1335 1340

Lys Phe Phe Gln Ala Leu Pro Tyr Val Ala Leu Leu Ile Ala Met Leu
1345 1350 1355 1360

Phe Phe Ile Tyr Ala Val Ile Gly Met Gln Met Phe Gly Lys Val Ala
1365 1370 1375

Met Arg Asp Asn Asn Gln Ile Asn Arg Asn Asn Asn Phe Gln Thr Phe
1380 1385 1390

Pro Gln Ala Val Leu Leu Leu Phe Arg Cys Ala Thr Gly Glu Ala Trp
1395 1400 1405

Gln Glu Ile Met Leu Ala Cys Leu Pro Gly Lys Leu Cys Asp Pro Glu
1410 1415 1420

Ser Asp Tyr Asn Pro Gly Glu Glu His Thr Cys Gly Ser Asn Phe Ala
1425 1430 1435 1440

Ile Val Tyr Phe Ile Ser Phe Tyr Met Leu Cys Ala Phe Leu Ile Ile
1445 1450 1455

Asn Leu Phe Val Ala Val Ile Met Asp Asn Phe Asp Tyr Leu Thr Arg
1460 1465 1470

Asp Trp Ser Ile Leu Gly Pro His His Leu Asp Glu Phe Lys Arg Ile
1475 1480 1485

Trp Ser Glu Tyr Asp Pro Glu Ala Lys Gly Arg Ile Lys His Leu Asp
1490 1495 1500

Val Val Thr Leu Leu Arg Arg Ile Gln Pro Pro Leu Gly Phe Gly Lys
1505 1510 1515 1520

Leu Cys Pro His Arg Val Ala Cys Lys Arg Leu Val Ala Met Asn Met
1525 1530 1535

Pro Leu Asn Ser Asp Gly Thr Val Met Phe Asn Ala Thr Leu Phe Ala
1540 1545 1550

Leu Val Arg Thr Ala Leu Lys Ile Lys Thr Glu Gly Asn Leu Glu Gln
1555 1560 1565

Ala Asn Glu Glu Leu Arg Ala Val Ile Lys Lys Ile Trp Lys Lys Thr
1570 1575 1580

Ser Met Lys Leu Leu Asp Gln Val Val Pro Pro Ala Gly Asp Asp Glu
1585 1590 1595 1600

Val Thr Val Gly Lys Phe Tyr Ala Thr Phe Leu Ile Gln Asp Tyr Phe
1605 1610 1615

Arg Lys Phe Lys Lys Arg Lys Glu Gln Gly Leu Val Gly Lys Tyr Pro
1620 1625 1630

Ala Lys Asn Thr Thr Ile Ala Leu Gln Ala Gly Leu Arg Thr Leu His
1635 1640 1645

Asp Ile Gly Pro Glu Ile Arg Arg Ala Ile Ser Cys Asp Leu Gln Asp
1650 1655 1660

-continued

Asp Glu Pro Glu Glu Thr Lys Arg Glu Glu Glu Asp Asp Val Phe Lys
1665 1670 1675 1680

Arg Asn Gly Ala Leu Leu Gly Asn His Val Asn His Val Asn Ser Asp
1685 1690 1695

Arg Arg Asp Ser Leu Gln Gln Thr Asn Thr Thr His Arg Pro Leu His
1700 1705 1710

Val Gln Arg Pro Ser Ile Pro Pro Ala Ser Asp Thr Glu Lys Pro Leu
1715 1720 1725

Phe Pro Pro Ala Gly Asn Ser Val Cys His Asn His His Asn His Asn
1730 1735 1740

Ser Ile Gly Lys Gln Val Pro Thr Ser Thr Asn Ala Asn Leu Asn Asn
1745 1750 1755 1760

Ala Asn Met Ser Lys Ala Ala His Gly Lys Arg Pro Ser Ile Gly Asn
1765 1770 1775

Leu Glu His Val Ser Glu Asn Gly His His Ser Ser His Lys His Asp
1780 1785 1790

Arg Glu Pro Gln Arg Arg Ser Ser Val Lys Arg Thr Arg Tyr Tyr Glu
1795 1800 1805

Thr Tyr Ile Arg Ser Asp Ser Gly Asp Glu Gln Leu Pro Thr Ile Cys
1810 1815 1820

Arg Glu Asp Pro Glu Ile His Gly Tyr Phe Arg Asp Pro His Cys Leu
1825 1830 1835 1840

Gly Glu Gln Glu Tyr Phe Ser Ser Glu Glu Cys Tyr Glu Asp Asp Ser
1845 1850 1855

Ser Pro Thr Trp Ser Arg Gln Asn Tyr Gly Tyr Tyr Ser Arg Tyr Pro
1860 1865 1870

Gly Arg Asn Ile Asp Ser Glu Arg Pro Arg Gly Tyr His His Pro Gln
1875 1880 1885

Gly Phe Leu Glu Asp Asp Asp Ser Pro Val Cys Tyr Asp Ser Arg Arg
1890 1895 1900

Ser Pro Arg Arg Arg Leu Leu Pro Pro Thr Pro Ala Ser His Arg Arg
1905 1910 1915 1920

Ser Ser Phe Asn Phe Glu Cys Leu Arg Arg Gln Ser Ser Gln Glu Glu
1925 1930 1935

Val Pro Ser Ser Pro Ile Phe Pro His Arg Thr Ala Leu Pro Leu His
1940 1945 1950

Leu Met Gln Gln Gln Ile Met Ala Val Ala Gly Leu Asp Ser Ser Lys
1955 1960 1965

Ala Gln Lys Tyr Ser Pro Ser His Ser Thr Arg Ser Trp Ala Thr Pro
1970 1975 1980

Pro Ala Thr Pro Pro Tyr Arg Asp Trp Thr Pro Cys Tyr Thr Pro Leu
1985 1990 1995 2000

Ile Gln Val Glu Gln Ser Glu Ala Leu Asp Gln Val Asn Gly Ser Leu
2005 2010 2015

Pro Ser Leu His Arg Ser Ser Trp Tyr Thr Asp Glu Pro Asp Ile Ser
2020 2025 2030

Tyr Arg Thr Phe Thr Pro Ala Ser Leu Thr Val Pro Ser Ser Phe Arg
2035 2040 2045

Asn Lys Asn Ser Asp Lys Gln Arg Ser Ala Asp Ser Leu Val Glu Ala
2050 2055 2060

Val Leu Ile Ser Glu Gly Leu Gly Arg Tyr Ala Arg Asp Pro Lys Phe
2065 2070 2075 2080

Val Ser Ala Thr Lys His Glu Ile Ala Asp Ala Cys Asp Leu Thr Ile
2085 2090 2095

Asp Glu Met Glu Ser Ala Ala Ser Thr Leu Leu Asn Gly Asn Val Arg
2100 2105 2110

Pro Arg Ala Asn Gly Asp Val Gly Pro Leu Ser His Arg Gln Asp Tyr
2115 2120 2125

Glu Leu Gln Asp Phe Gly Pro Gly Tyr Ser Asp Glu Glu Pro Asp Pro
2130 2135 2140

Gly Arg Asp Glu Glu Asp Leu Ala Asp Glu Met Ile Cys Ile Thr Thr
2145 2150 2155 2160

Leu (2) INFORMATION FOR SEQ ID NO:50:

(i) SEQUENCE CHARACTERISTICS:
(A) LENGTH: 34 amino acids
(B) TYPE: amino acid
(C) STRANDEDNESS: single
(D) TOPOLOGY: linear (ii) MOLECULE TYPE: protein (v) FRAGMENT TYPE: internal (xi) SEQUENCE DESCRIPTION: SEQ ID NO:50:

Val Asn Asp Ala Ile Gly Trp Glu Trp Pro Trp Val Tyr Phe Val Ser
1 5 10 15

Leu Ile Ile Leu Gly Ser Phe Phe Val Leu Asn Leu Val Leu Gly Val
20 25 30

Leu Ser (2) INFORMATION FOR SEQ ID NO:51:

(i) SEQUENCE CHARACTERISTICS:
(A) LENGTH: 2161 amino acids
(B) TYPE: amino acid
(C) STRANDEDNESS: single
(D) TOPOLOGY: linear (ii) MOLECULE TYPE: protein (v) FRAGMENT TYPE: internal (xi) SEQUENCE DESCRIPTION: SEQ ID NO:51:

Met Met Met Met Met Met Met Lys Lys Met Gln His Gln Arg Gln Gln
1 5 10 15

Gln Ala Asp His Ala Asn Glu Ala Asn Tyr Ala Arg Gly Thr Arg Leu
20 25 30

Pro Leu Ser Gly Glu Gly Pro Thr Ser Gln Pro Asn Ser Ser Lys Gln
35 40 45

Thr Val Leu Ser Trp Gln Ala Ala Ile Asp Ala Ala Arg Gln Ala Lys
50 55 60

Ala Ala Gln Thr Met Ser Thr Ser Ala Pro Pro Pro Val Gly Ser Leu
65 70 75 80

Ser Gln Arg Lys Arg Gln Gln Tyr Ala Lys Ser Lys Lys Gln Gly Asn
85 90 95

Ser Ser Asn Ser Arg Pro Ala Arg Ala Leu Phe Cys Leu Ser Leu Asn
100 105 110

Asn Pro Ile Arg Arg Ala Cys Ile Ser Ile Val Glu Trp Lys Pro Phe
115 120 125

Asp Ile Phe Ile Leu Leu Ala Ile Phe Ala Asn Cys Val Ala Leu Ala
130 135 140

-continued

| | | | | | | | | | | | | | | | |
|---|---|---|---|---|---|---|---|---|---|---|---|---|---|---|---|
| Ile | Tyr | Ile | Pro | Phe | Pro | Glu | Asp | Asp | Ser | Asn | Ser | Thr | Asn | His | Asn |
| 145 | | | | | 150 | | | | | 155 | | | | | 160 |
| Leu | Glu | Lys | Val | Glu | Tyr | Ala | Phe | Leu | Ile | Ile | Phe | Thr | Val | Glu | Thr |
| | | | | 165 | | | | | 170 | | | | | 175 | |
| Phe | Leu | Lys | Ile | Ile | Ala | Tyr | Gly | Leu | Leu | Leu | His | Pro | Asn | Ala | Tyr |
| | | | 180 | | | | | 185 | | | | | 190 | | |
| Val | Arg | Asn | Gly | Trp | Asn | Leu | Leu | Asp | Phe | Val | Ile | Val | Ile | Val | Gly |
| | | 195 | | | | | 200 | | | | | 205 | | | |
| Leu | Phe | Ser | Val | Ile | Leu | Glu | Gln | Leu | Thr | Lys | Glu | Thr | Glu | Gly | Gly |
| | 210 | | | | | 215 | | | | | 220 | | | | |
| Asn | His | Ser | Ser | Gly | Lys | Ser | Gly | Gly | Phe | Asp | Val | Lys | Ala | Leu | Arg |
| 225 | | | | | 230 | | | | | 235 | | | | | 240 |
| Ala | Phe | Arg | Val | Leu | Arg | Pro | Leu | Arg | Leu | Val | Ser | Gly | Val | Pro | Ser |
| | | | | 245 | | | | | 250 | | | | | 255 | |
| Leu | Gln | Val | Val | Leu | Asn | Ser | Ile | Ile | Lys | Ala | Met | Val | Pro | Leu | Leu |
| | | | 260 | | | | | 265 | | | | | 270 | | |
| His | Ile | Ala | Leu | Leu | Val | Leu | Phe | Val | Ile | Ile | Ile | Tyr | Ala | Ile | Ile |
| | | 275 | | | | | 280 | | | | | 285 | | | |
| Gly | Leu | Glu | Leu | Phe | Ile | Gly | Lys | Met | His | Lys | Thr | Cys | Phe | Phe | Ala |
| | 290 | | | | | 295 | | | | | 300 | | | | |
| Asp | Ser | Asp | Ile | Val | Ala | Glu | Glu | Asp | Pro | Ala | Pro | Cys | Ala | Phe | Ser |
| 305 | | | | | 310 | | | | | 315 | | | | | 320 |
| Gly | Asn | Gly | Arg | Gln | Cys | Thr | Ala | Asn | Gly | Thr | Glu | Cys | Arg | Ser | Gly |
| | | | | 325 | | | | | 330 | | | | | 335 | |
| Trp | Val | Gly | Pro | Asn | Gly | Gly | Ile | Thr | Asn | Phe | Asp | Asn | Phe | Ala | Phe |
| | | | 340 | | | | | 345 | | | | | 350 | | |
| Ala | Met | Leu | Thr | Val | Phe | Gln | Cys | Ile | Thr | Met | Glu | Gly | Trp | Thr | Asp |
| | | 355 | | | | | 360 | | | | | 365 | | | |
| Val | Leu | Tyr | Trp | Val | Asn | Asp | Ala | Ile | Gly | Trp | Glu | Trp | Pro | Trp | Val |
| | 370 | | | | | 375 | | | | | 380 | | | | |
| Tyr | Phe | Val | Ser | Leu | Ile | Ile | Leu | Gly | Ser | Phe | Phe | Val | Leu | Asn | Leu |
| 385 | | | | | 390 | | | | | 395 | | | | | 400 |
| Val | Leu | Gly | Val | Leu | Ser | Gly | Glu | Phe | Ser | Lys | Glu | Arg | Glu | Lys | Ala |
| | | | | 405 | | | | | 410 | | | | | 415 | |
| Lys | Ala | Arg | Gly | Asp | Phe | Gln | Lys | Leu | Arg | Glu | Lys | Gln | Gln | Leu | Glu |
| | | | 420 | | | | | 425 | | | | | 430 | | |
| Glu | Asp | Leu | Lys | Gly | Tyr | Leu | Asp | Trp | Ile | Thr | Gln | Ala | Glu | Asp | Ile |
| | | 435 | | | | | 440 | | | | | 445 | | | |
| Asp | Pro | Glu | Asn | Glu | Glu | Glu | Gly | Gly | Glu | Glu | Gly | Lys | Arg | Asn | Thr |
| | 450 | | | | | 455 | | | | | 460 | | | | |
| Ser | Met | Pro | Thr | Ser | Glu | Thr | Glu | Ser | Val | Asn | Thr | Glu | Asn | Val | Ser |
| 465 | | | | | 470 | | | | | 475 | | | | | 480 |
| Gly | Glu | Gly | Glu | Asn | Arg | Gly | Cys | Cys | Gly | Ser | Leu | Cys | Gln | Ala | Ile |
| | | | | 485 | | | | | 490 | | | | | 495 | |
| Ser | Lys | Ser | Lys | Leu | Ser | Arg | Arg | Trp | Arg | Arg | Trp | Asn | Arg | Phe | Asn |
| | | | 500 | | | | | 505 | | | | | 510 | | |
| Arg | Arg | Arg | Cys | Arg | Ala | Ala | Val | Lys | Ser | Val | Thr | Phe | Tyr | Trp | Leu |
| | | 515 | | | | | 520 | | | | | 525 | | | |
| Val | Ile | Val | Leu | Val | Phe | Leu | Asn | Thr | Leu | Thr | Ile | Ser | Ser | Glu | His |
| | 530 | | | | | 535 | | | | | 540 | | | | |
| Tyr | Asn | Gln | Pro | Asp | Trp | Leu | Thr | Gln | Ile | Gln | Asp | Ile | Ala | Asn | Lys |
| 545 | | | | | 550 | | | | | 555 | | | | | 560 |
| Val | Leu | Leu | Ala | Leu | Phe | Thr | Cys | Glu | Met | Leu | Val | Lys | Met | Tyr | Ser |
| | | | | 565 | | | | | 570 | | | | | 575 | |

-continued

| | | | | | | | | | | | | | | | |
|---|---|---|---|---|---|---|---|---|---|---|---|---|---|---|---|
| Leu | Gly | Leu | Gln | Ala | Tyr | Phe | Val | Ser | Leu | Phe | Asn | Arg | Phe | Asp | Cys |
| | | | 580 | | | | | 585 | | | | | 590 | | |
| Phe | Val | Val | Cys | Gly | Gly | Ile | Thr | Glu | Thr | Ile | Leu | Val | Glu | Leu | Glu |
| | | 595 | | | | | 600 | | | | | 605 | | | |
| Ile | Met | Ser | Pro | Leu | Gly | Ile | Ser | Val | Phe | Arg | Cys | Val | Arg | Leu | Leu |
| | 610 | | | | | 615 | | | | | 620 | | | | |
| Arg | Ile | Phe | Lys | Val | Thr | Arg | His | Trp | Thr | Ser | Leu | Ser | Asn | Leu | Val |
| 625 | | | | | 630 | | | | | 635 | | | | | 640 |
| Ala | Ser | Leu | Leu | Asn | Ser | Met | Lys | Ser | Ile | Ala | Ser | Leu | Leu | Leu | Leu |
| | | | | 645 | | | | | 650 | | | | | 655 | |
| Leu | Phe | Leu | Phe | Ile | Ile | Ile | Phe | Ser | Leu | Leu | Gly | Met | Gln | Leu | Phe |
| | | | 660 | | | | | 665 | | | | | 670 | | |
| Gly | Gly | Lys | Phe | Asn | Phe | Asp | Glu | Thr | Gln | Thr | Lys | Arg | Ser | Thr | Phe |
| | | 675 | | | | | 680 | | | | | 685 | | | |
| Asp | Asn | Phe | Pro | Gln | Ala | Leu | Leu | Thr | Val | Phe | Gln | Ile | Leu | Thr | Gly |
| | 690 | | | | | 695 | | | | | 700 | | | | |
| Glu | Asp | Trp | Asn | Ala | Val | Met | Tyr | Asp | Gly | Ile | Met | Ala | Tyr | Gly | Gly |
| 705 | | | | | 710 | | | | | 715 | | | | | 720 |
| Pro | Ser | Ser | Ser | Gly | Met | Ile | Val | Cys | Ile | Tyr | Phe | Ile | Ile | Leu | Phe |
| | | | | 725 | | | | | 730 | | | | | 735 | |
| Ile | Cys | Gly | Asn | Tyr | Ile | Leu | Leu | Asn | Val | Phe | Leu | Ala | Ile | Ala | Val |
| | | | 740 | | | | | 745 | | | | | 750 | | |
| Asp | Asn | Leu | Ala | Asp | Ala | Glu | Ser | Leu | Asn | Thr | Ala | Gln | Lys | Glu | Glu |
| | | 755 | | | | | 760 | | | | | 765 | | | |
| Ala | Glu | Glu | Lys | Glu | Arg | Lys | Lys | Ile | Ala | Arg | Lys | Glu | Ser | Leu | Glu |
| | 770 | | | | | 775 | | | | | 780 | | | | |
| Asn | Lys | Lys | Asn | Asn | Lys | Pro | Glu | Val | Asn | Gln | Ile | Ala | Asn | Ser | Asp |
| 785 | | | | | 790 | | | | | 795 | | | | | 800 |
| Asn | Lys | Val | Thr | Ile | Asp | Asp | Tyr | Arg | Glu | Glu | Asp | Glu | Asp | Lys | Asp |
| | | | | 805 | | | | | 810 | | | | | 815 | |
| Pro | Tyr | Pro | Pro | Cys | Asp | Val | Pro | Val | Gly | Glu | Glu | Glu | Glu | Glu | Glu |
| | | | 820 | | | | | 825 | | | | | 830 | | |
| Glu | Glu | Asp | Glu | Pro | Glu | Val | Pro | Ala | Gly | Pro | Arg | Pro | Arg | Arg | Ile |
| | | 835 | | | | | 840 | | | | | 845 | | | |
| Ser | Glu | Leu | Asn | Met | Lys | Glu | Lys | Ile | Ala | Pro | Ile | Pro | Glu | Gly | Ser |
| | 850 | | | | | 855 | | | | | 860 | | | | |
| Ala | Phe | Phe | Ile | Leu | Ser | Lys | Thr | Asn | Pro | Ile | Arg | Val | Gly | Cys | His |
| 865 | | | | | 870 | | | | | 875 | | | | | 880 |
| Lys | Leu | Ile | Asn | His | His | Ile | Phe | Thr | Asn | Leu | Ile | Leu | Val | Phe | Ile |
| | | | | 885 | | | | | 890 | | | | | 895 | |
| Met | Leu | Ser | Ser | Ala | Ala | Leu | Ala | Ala | Glu | Asp | Pro | Ile | Arg | Ser | His |
| | | | 900 | | | | | 905 | | | | | 910 | | |
| Ser | Phe | Arg | Asn | Thr | Ile | Leu | Gly | Tyr | Phe | Asp | Tyr | Ala | Phe | Thr | Ala |
| | | 915 | | | | | 920 | | | | | 925 | | | |
| Ile | Phe | Thr | Val | Glu | Ile | Leu | Leu | Lys | Met | Thr | Thr | Phe | Gly | Ala | Phe |
| | 930 | | | | | 935 | | | | | 940 | | | | |
| Leu | His | Lys | Gly | Ala | Phe | Cys | Arg | Asn | Tyr | Phe | Asn | Leu | Leu | Asp | Met |
| 945 | | | | | 950 | | | | | 955 | | | | | 960 |
| Leu | Val | Val | Gly | Val | Ser | Leu | Val | Ser | Phe | Gly | Ile | Gln | Ser | Ser | Ala |
| | | | | 965 | | | | | 970 | | | | | 975 | |
| Ile | Ser | Val | Val | Lys | Ile | Leu | Arg | Val | Leu | Arg | Val | Leu | Arg | Pro | Leu |
| | | | 980 | | | | | 985 | | | | | 990 | | |
| Arg | Ala | Ile | Asn | Arg | Ala | Lys | Gly | Leu | Lys | His | Val | Val | Gln | Cys | Val |

```
        995                 1000                1005

Phe Val Ala Ile Arg Thr Ile Gly Asn Ile Met Ile Val Thr Thr Leu
    1010                1015                1020

Leu Gln Phe Met Phe Ala Cys Ile Gly Val Gln Leu Phe Lys Gly Lys
1025                1030                1035                1040

Phe Tyr Arg Cys Thr Asp Glu Ala Lys Ser Asn Pro Glu Glu Cys Arg
                1045                1050                1055

Gly Leu Phe Ile Leu Tyr Lys Asp Gly Asp Val Asp Ser Pro Val Val
            1060                1065                1070

Arg Glu Arg Ile Trp Gln Asn Ser Asp Phe Asn Phe Asp Asn Val Leu
        1075                1080                1085

Ser Ala Met Met Ala Leu Phe Thr Val Ser Thr Phe Glu Gly Trp Pro
    1090                1095                1100

Ala Leu Leu Tyr Lys Ala Ile Asp Ser Asn Gly Glu Asn Ile Gly Pro
1105                1110                1115                1120

Ile Tyr Asn His Arg Val Glu Ile Ser Ile Phe Phe Ile Ile Tyr Ile
                1125                1130                1135

Ile Ile Val Ala Phe Phe Met Met Asn Ile Phe Val Gly Phe Val Ile
            1140                1145                1150

Val Thr Phe Gln Glu Gln Gly Glu Lys Glu Tyr Lys Asn Cys Glu Leu
        1155                1160                1165

Asp Lys Asn Gln Arg Gln Cys Val Glu Tyr Ala Leu Lys Ala Arg Pro
    1170                1175                1180

Leu Arg Arg Tyr Ile Pro Lys Asn Pro Tyr Gln Tyr Lys Phe Trp Tyr
1185                1190                1195                1200

Val Val Asn Ser Ser Pro Phe Glu Tyr Met Met Phe Val Leu Ile Met
                1205                1210                1215

Leu Asn Thr Leu Cys Leu Ala Met Gln His Tyr Glu Gln Ser Lys Met
            1220                1225                1230

Phe Asn Asp Ala Met Asp Ile Leu Asn Met Val Phe Thr Gly Val Phe
        1235                1240                1245

Thr Val Glu Met Val Leu Lys Val Ile Ala Phe Lys Pro Lys Gly Tyr
    1250                1255                1260

Phe Ser Asp Ala Trp Asn Thr Phe Asp Ser Leu Ile Val Ile Gly Ser
1265                1270                1275                1280

Ile Ile Asp Val Ala Leu Ser Glu Ala Asp Pro Thr Glu Ser Glu Asn
                1285                1290                1295

Val Pro Val Pro Thr Ala Thr Pro Gly Asn Ser Glu Glu Ser Asn Arg
            1300                1305                1310

Ile Ser Ile Thr Phe Phe Arg Leu Phe Arg Val Met Arg Leu Val Lys
        1315                1320                1325

Leu Leu Ser Arg Gly Glu Gly Ile Arg Thr Leu Leu Trp Thr Phe Ile
    1330                1335                1340

Lys Phe Phe Gln Ala Leu Pro Tyr Val Ala Leu Leu Ile Ala Met Leu
1345                1350                1355                1360

Phe Phe Ile Tyr Ala Val Ile Gly Met Gln Met Phe Gly Lys Val Ala
                1365                1370                1375

Met Arg Asp Asn Asn Gln Ile Asn Arg Asn Asn Asn Phe Gln Thr Phe
            1380                1385                1390

Pro Gln Ala Val Leu Leu Leu Phe Arg Cys Ala Thr Gly Glu Ala Trp
        1395                1400                1405

Gln Glu Ile Met Leu Ala Cys Leu Pro Gly Lys Leu Cys Asp Pro Glu
    1410                1415                1420
```

Ser Asp Tyr Asn Pro Gly Glu Glu His Thr Cys Gly Ser Asn Phe Ala
1425 1430 1435 1440

Ile Val Tyr Phe Ile Ser Phe Tyr Met Leu Cys Ala Phe Leu Ile Ile
1445 1450 1455

Asn Leu Phe Val Ala Val Ile Met Asp Asn Phe Asp Tyr Leu Thr Arg
1460 1465 1470

Asp Trp Ser Ile Leu Gly Pro His His Leu Asp Glu Phe Lys Arg Ile
1475 1480 1485

Trp Ser Glu Tyr Asp Pro Glu Ala Lys Gly Arg Ile Lys His Leu Asp
1490 1495 1500

Val Val Thr Leu Leu Arg Arg Ile Gln Pro Pro Leu Gly Phe Gly Lys
1505 1510 1515 1520

Leu Cys Pro His Arg Val Ala Cys Lys Arg Leu Val Ala Met Asn Met
1525 1530 1535

Pro Leu Asn Ser Asp Gly Thr Val Met Phe Asn Ala Thr Leu Phe Ala
1540 1545 1550

Leu Val Arg Thr Ala Leu Lys Ile Lys Thr Glu Gly Asn Leu Glu Gln
1555 1560 1565

Ala Asn Glu Glu Leu Arg Ala Val Ile Lys Lys Ile Trp Lys Lys Thr
1570 1575 1580

Ser Met Lys Leu Leu Asp Gln Val Val Pro Pro Ala Gly Asp Asp Glu
1585 1590 1595 1600

Val Thr Val Gly Lys Phe Tyr Ala Thr Phe Leu Ile Gln Asp Tyr Phe
1605 1610 1615

Arg Lys Phe Lys Lys Arg Lys Glu Gln Gly Leu Val Gly Lys Tyr Pro
1620 1625 1630

Ala Lys Asn Thr Thr Ile Ala Leu Gln Ala Gly Leu Arg Thr Leu His
1635 1640 1645

Asp Ile Gly Pro Glu Ile Arg Arg Ala Ile Ser Cys Asp Leu Gln Asp
1650 1655 1660

Asp Glu Pro Glu Glu Thr Lys Arg Glu Glu Glu Asp Asp Val Phe Lys
1665 1670 1675 1680

Arg Asn Gly Ala Leu Leu Gly Asn His Val Asn His Val Asn Ser Asp
1685 1690 1695

Arg Arg Asp Ser Leu Gln Gln Thr Asn Thr Thr His Arg Pro Leu His
1700 1705 1710

Val Gln Arg Pro Ser Ile Pro Pro Ala Ser Asp Thr Glu Lys Pro Leu
1715 1720 1725

Phe Pro Pro Ala Gly Asn Ser Val Cys His Asn His His Asn His Asn
1730 1735 1740

Ser Ile Gly Lys Gln Val Pro Thr Ser Thr Asn Ala Asn Leu Asn Asn
1745 1750 1755 1760

Ala Asn Met Ser Lys Ala Ala His Gly Lys Arg Pro Ser Ile Gly Asn
1765 1770 1775

Leu Glu His Val Ser Glu Asn Gly His His Ser Ser His Lys His Asp
1780 1785 1790

Arg Glu Pro Gln Arg Arg Ser Ser Val Lys Arg Thr Arg Tyr Tyr Glu
1795 1800 1805

Thr Tyr Ile Arg Ser Asp Ser Gly Asp Glu Gln Leu Pro Thr Ile Cys
1810 1815 1820

Arg Glu Asp Pro Glu Ile His Gly Tyr Phe Arg Asp Pro His Cys Leu
1825 1830 1835 1840

Gly Glu Gln Glu Tyr Phe Ser Ser Glu Glu Cys Tyr Glu Asp Asp Ser
1845 1850 1855

Ser Pro Thr Trp Ser Arg Gln Asn Tyr Gly Tyr Tyr Ser Arg Tyr Pro
1860 1865 1870

Gly Arg Asn Ile Asp Ser Glu Arg Pro Arg Gly Tyr His His Pro Gln
1875 1880 1885

Gly Phe Leu Glu Asp Asp Asp Ser Pro Val Cys Tyr Asp Ser Arg Arg
1890 1895 1900

Ser Pro Arg Arg Arg Leu Leu Pro Pro Thr Pro Ala Ser His Arg Arg
1905 1910 1915 1920

Ser Ser Phe Asn Phe Glu Cys Leu Arg Arg Gln Ser Ser Gln Glu Glu
1925 1930 1935

Val Pro Ser Ser Pro Ile Phe Pro His Arg Thr Ala Leu Pro Leu His
1940 1945 1950

Leu Met Gln Gln Gln Ile Met Ala Val Ala Gly Leu Asp Ser Ser Lys
1955 1960 1965

Ala Gln Lys Tyr Ser Pro Ser His Ser Thr Arg Ser Trp Ala Thr Pro
1970 1975 1980

Pro Ala Thr Pro Pro Tyr Arg Asp Trp Thr Pro Cys Tyr Thr Pro Leu
1985 1990 1995 2000

Ile Gln Val Glu Gln Ser Glu Ala Leu Asp Gln Val Asn Gly Ser Leu
2005 2010 2015

Pro Ser Leu His Arg Ser Ser Trp Tyr Thr Asp Glu Pro Asp Ile Ser
2020 2025 2030

Tyr Arg Thr Phe Thr Pro Ala Ser Leu Thr Val Pro Ser Ser Phe Arg
2035 2040 2045

Asn Lys Asn Ser Asp Lys Gln Arg Ser Ala Asp Ser Leu Val Glu Ala
2050 2055 2060

Val Leu Ile Ser Glu Gly Leu Gly Arg Tyr Ala Arg Asp Pro Lys Phe
2065 2070 2075 2080

Val Ser Ala Thr Lys His Glu Ile Ala Asp Ala Cys Asp Leu Thr Ile
2085 2090 2095

Asp Glu Met Glu Ser Ala Ala Ser Thr Leu Leu Asn Gly Asn Val Arg
2100 2105 2110

Pro Arg Ala Asn Gly Asp Val Gly Pro Leu Ser His Arg Gln Asp Tyr
2115 2120 2125

Glu Leu Gln Asp Phe Gly Pro Gly Tyr Ser Asp Glu Glu Pro Asp Pro
2130 2135 2140

Gly Arg Asp Glu Glu Asp Leu Ala Asp Glu Met Ile Cys Ile Thr Thr
2145 2150 2155 2160

Leu ( 2 ) INFORMATION FOR SEQ ID NO:52:

( i ) SEQUENCE CHARACTERISTICS:
( A ) LENGTH: 1091 amino acids
( B ) TYPE: amino acid
( C ) STRANDEDNESS: single
( D ) TOPOLOGY: linear ( i i ) MOLECULE TYPE: protein ( v ) FRAGMENT TYPE: internal ( x i ) SEQUENCE DESCRIPTION: SEQ ID NO:52:

Met Ala Ala Gly Cys Leu Leu Ala Leu Thr Leu Thr Leu Phe Gln Ser
1 5 10 15

Leu Leu Ile Gly Pro Ser Ser Glu Glu Pro Phe Pro Ser Ala Val Thr
20 25 30

-continued

Ile Lys Ser Trp Val Asp Lys Met Gln Glu Asp Leu Val Thr Leu Ala
35 40 45

Lys Thr Ala Ser Gly Val Asn Gln Leu Val Asp Ile Tyr Glu Lys Tyr
50 55 60

Gln Asp Leu Tyr Thr Val Glu Pro Asn Asn Ala Arg Gln Leu Val Glu
65 70 75 80

Ile Ala Ala Arg Asp Ile Glu Lys Leu Leu Ser Asn Arg Ser Lys Ala
85 90 95

Leu Val Ser Leu Ala Leu Glu Ala Glu Lys Val Gln Ala Ala His Gln
100 105 110

Trp Arg Glu Asp Phe Ala Ser Asn Glu Val Val Tyr Tyr Asn Ala Lys
115 120 125

Asp Asp Leu Asp Pro Glu Lys Asn Asp Ser Glu Pro Gly Ser Gln Arg
130 135 140

Ile Lys Pro Val Phe Ile Glu Asp Ala Asn Phe Gly Arg Gln Ile Ser
145 150 155 160

Tyr Gln His Ala Ala Val His Ile Pro Thr Asp Ile Tyr Glu Gly Ser
165 170 175

Thr Ile Val Leu Asn Glu Leu Asn Trp Thr Ser Ala Leu Asp Glu Val
180 185 190

Phe Lys Lys Asn Arg Glu Glu Asp Pro Ser Leu Leu Trp Gln Val Phe
195 200 205

Gly Ser Ala Thr Gly Leu Ala Arg Tyr Tyr Pro Ala Ser Pro Trp Val
210 215 220

Asp Asn Ser Arg Thr Pro Asn Lys Ile Asp Leu Tyr Asp Val Arg Arg
225 230 235 240

Arg Pro Trp Tyr Ile Gln Gly Ala Ala Ser Pro Lys Asp Met Leu Ile
245 250 255

Leu Val Asp Val Ser Gly Ser Val Ser Gly Leu Thr Leu Lys Leu Ile
260 265 270

Arg Thr Ser Val Ser Glu Met Leu Glu Thr Leu Ser Asp Asp Phe
275 280 285

Val Asn Val Ala Ser Phe Asn Ser Asn Ala Gln Asp Val Ser Cys Phe
290 295 300

Gln His Leu Val Gln Ala Asn Val Arg Asn Lys Lys Val Leu Lys Asp
305 310 315 320

Ala Val Asn Asn Ile Thr Ala Lys Gly Ile Thr Asp Tyr Lys Lys Gly
325 330 335

Phe Ser Phe Ala Phe Glu Gln Leu Leu Asn Tyr Asn Val Ser Arg Ala
340 345 350

Asn Cys Asn Lys Ile Ile Met Leu Phe Thr Asp Gly Gly Glu Glu Arg
355 360 365

Ala Gln Glu Ile Phe Asn Lys Tyr Asn Lys Asp Lys Lys Val Arg Val
370 375 380

Phe Arg Phe Ser Val Gly Gln His Asn Tyr Glu Arg Gly Pro Ile Gln
385 390 395 400

Trp Met Ala Cys Glu Asn Lys Gly Tyr Tyr Tyr Glu Ile Pro Ser Ile
405 410 415

Gly Ala Ile Arg Ile Asn Thr Gln Glu Tyr Leu Asp Val Leu Gly Arg
420 425 430

Pro Met Val Leu Ala Gly Asp Lys Ala Lys Gln Val Gln Trp Thr Asn
435 440 445

Val Tyr Leu Asp Ala Leu Glu Leu Gly Leu Val Ile Thr Gly Thr Leu

-continued 450 455 460

Pro Val Phe Asn Ile Thr Gly Gln Phe Glu Asn Lys Thr Asn Leu Lys
465 470 475 480

Asn Gln Leu Ile Leu Gly Val Met Gly Val Asp Val Ser Leu Glu Asp
485 490 495

Ile Lys Arg Leu Thr Pro Arg Phe Thr Leu Cys Pro Asn Gly Tyr Tyr
500 505 510

Phe Ala Ile Asp Pro Asn Gly Tyr Val Leu Leu His Pro Asn Leu Gln
515 520 525

Pro Lys Asn Pro Lys Ser Gln Glu Pro Val Thr Leu Asp Phe Leu Asp
530 535 540

Ala Glu Leu Glu Asn Asp Ile Lys Val Glu Ile Arg Asn Lys Met Ile
545 550 555 560

Asp Gly Glu Ser Gly Glu Lys Thr Phe Arg Thr Leu Val Lys Ser Gln
565 570 575

Asp Glu Arg Tyr Ile Asp Lys Gly Asn Arg Thr Tyr Thr Trp Thr Pro
580 585 590

Val Asn Gly Thr Asp Tyr Ser Leu Ala Leu Val Leu Pro Thr Tyr Ser
595 600 605

Phe Tyr Tyr Ile Lys Ala Lys Leu Glu Glu Thr Ile Thr Gln Ala Arg
610 615 620

Ser Lys Lys Gly Lys Met Lys Asp Ser Glu Thr Leu Lys Pro Asp Asn
625 630 635 640

Phe Glu Glu Ser Gly Tyr Thr Phe Ile Ala Pro Arg Asp Tyr Cys Asn
645 650 655

Asp Leu Lys Ile Ser Asp Asn Asn Thr Glu Phe Leu Leu Asn Phe Asn
660 665 670

Glu Phe Ile Asp Arg Lys Thr Pro Asn Asn Pro Ser Cys Asn Ala Asp
675 680 685

Leu Ile Asn Arg Val Leu Leu Asp Ala Gly Phe Thr Asn Glu Leu Val
690 695 700

Gln Asn Tyr Trp Ser Lys Gln Lys Asn Ile Lys Gly Val Lys Ala Arg
705 710 715 720

Phe Val Val Thr Asp Gly Gly Ile Thr Arg Val Tyr Pro Lys Glu Ala
725 730 735

Gly Glu Asn Trp Gln Glu Asn Pro Glu Thr Tyr Glu Asp Ser Phe Tyr
740 745 750

Lys Arg Ser Leu Asp Asn Asp Asn Tyr Val Phe Thr Ala Pro Tyr Phe
755 760 765

Asn Lys Ser Gly Pro Gly Ala Tyr Glu Ser Gly Ile Met Val Ser Lys
770 775 780

Ala Val Glu Ile Tyr Ile Gln Gly Lys Leu Leu Lys Pro Ala Val Val
785 790 795 800

Gly Ile Lys Ile Asp Val Asn Ser Trp Ile Glu Asn Phe Thr Lys Thr
805 810 815

Ser Ile Arg Asp Pro Cys Ala Gly Pro Val Cys Asp Cys Lys Arg Asn
820 825 830

Ser Asp Val Met Asp Cys Val Ile Leu Asp Asp Gly Gly Phe Leu Leu
835 840 845

Met Ala Asn His Asp Asp Tyr Thr Asn Gln Ile Gly Arg Phe Phe Gly
850 855 860

Glu Ile Asp Pro Ser Leu Met Arg His Leu Val Asn Ile Ser Val Tyr
865 870 875 880

-continued

Ala Phe Asn Lys Ser Tyr Asp Tyr Gln Ser Val Cys Glu Pro Gly Ala
885 890 895

Ala Pro Lys Gln Gly Ala Gly His Arg Ser Ala Tyr Val Pro Ser Val
900 905 910

Ala Asp Ile Leu Gln Ile Gly Trp Trp Ala Thr Ala Ala Ala Trp Ser
915 920 925

Ile Leu Gln Gln Phe Leu Leu Ser Leu Thr Phe Pro Arg Leu Leu Glu
930 935 940

Ala Val Glu Met Glu Asp Asp Asp Phe Thr Ala Ser Leu Ser Lys Gln
945 950 955 960

Ser Cys Ile Thr Glu Gln Thr Gln Tyr Phe Phe Asp Asn Asp Ser Lys
965 970 975

Ser Phe Ser Gly Val Leu Asp Cys Gly Asn Cys Ser Arg Ile Phe His
980 985 990

Gly Glu Lys Leu Met Asn Thr Asn Leu Ile Phe Ile Met Val Glu Ser
995 1000 1005

Lys Gly Thr Cys Pro Cys Asp Thr Arg Leu Leu Ile Gln Ala Glu Gln
1010 1015 1020

Thr Ser Asp Gly Pro Asn Pro Cys Asp Met Val Lys Gln Pro Arg Tyr
1025 1030 1035 1040

Arg Lys Gly Pro Asp Val Cys Phe Asp Asn Asn Val Leu Glu Asp Tyr
1045 1050 1055

Thr Asp Cys Gly Gly Val Ser Gly Leu Asn Pro Ser Leu Trp Tyr Ile
1060 1065 1070

Ile Gly Ile Gln Phe Leu Leu Leu Trp Leu Val Ser Gly Ser Thr His
1075 1080 1085

Arg Leu Leu
1090

( 2 ) INFORMATION FOR SEQ ID NO:53:

( i ) SEQUENCE CHARACTERISTICS:
( A ) LENGTH: 1103 amino acids
( B ) TYPE: amino acid
( C ) STRANDEDNESS: single
( D ) TOPOLOGY: linear ( i i ) MOLECULE TYPE: protein ( v ) FRAGMENT TYPE: internal ( x i ) SEQUENCE DESCRIPTION: SEQ ID NO:53:

Met Ala Ala Gly Cys Leu Leu Ala Leu Thr Leu Thr Leu Phe Gln Ser
1 5 10 15

Leu Leu Ile Gly Pro Ser Ser Glu Glu Pro Phe Pro Ser Ala Val Thr
20 25 30

Ile Lys Ser Trp Val Asp Lys Met Gln Glu Asp Leu Val Thr Leu Ala
35 40 45

Lys Thr Ala Ser Gly Val Asn Gln Leu Val Asp Ile Tyr Glu Lys Tyr
50 55 60

Gln Asp Leu Tyr Thr Val Glu Pro Asn Asn Ala Arg Gln Leu Val Glu
65 70 75 80

Ile Ala Ala Arg Asp Ile Glu Lys Leu Leu Ser Asn Arg Ser Lys Ala
85 90 95

Leu Val Ser Leu Ala Leu Glu Ala Glu Lys Val Gln Ala Ala His Gln
100 105 110

Trp Arg Glu Asp Phe Ala Ser Asn Glu Val Val Tyr Tyr Asn Ala Lys
115 120 125

```
Asp Asp Leu Asp Pro Glu Lys Asn Asp Ser Glu Pro Gly Ser Gln Arg
    130                 135                 140

Ile Lys Pro Val Phe Ile Glu Asp Ala Asn Phe Gly Arg Gln Ile Ser
145                 150                 155                 160

Tyr Gln His Ala Ala Val His Ile Pro Thr Asp Ile Tyr Glu Gly Ser
                165                 170                 175

Thr Ile Val Leu Asn Glu Leu Asn Trp Thr Ser Ala Leu Asp Glu Val
            180                 185                 190

Phe Lys Lys Asn Arg Glu Glu Asp Pro Ser Leu Leu Trp Gln Val Phe
        195                 200                 205

Gly Ser Ala Thr Gly Leu Ala Arg Tyr Tyr Pro Ala Ser Pro Trp Val
    210                 215                 220

Asp Asn Ser Arg Thr Pro Asn Lys Ile Asp Leu Tyr Asp Val Arg Arg
225                 230                 235                 240

Arg Pro Trp Tyr Ile Gln Gly Ala Ala Ser Pro Lys Asp Met Leu Ile
                245                 250                 255

Leu Val Asp Val Ser Gly Ser Val Ser Gly Leu Thr Leu Lys Leu Ile
            260                 265                 270

Arg Thr Ser Val Ser Glu Met Leu Glu Thr Leu Ser Asp Asp Asp Phe
        275                 280                 285

Val Asn Val Ala Ser Phe Asn Ser Asn Ala Gln Asp Val Ser Cys Phe
    290                 295                 300

Gln His Leu Val Gln Ala Asn Val Arg Asn Lys Lys Val Leu Lys Asp
305                 310                 315                 320

Ala Val Asn Asn Ile Thr Ala Lys Gly Ile Thr Asp Tyr Lys Lys Gly
                325                 330                 335

Phe Ser Phe Ala Phe Glu Gln Leu Leu Asn Tyr Asn Val Ser Arg Ala
            340                 345                 350

Asn Cys Asn Lys Ile Ile Met Leu Phe Thr Asp Gly Gly Glu Glu Arg
        355                 360                 365

Ala Gln Glu Ile Phe Asn Lys Tyr Asn Lys Asp Lys Lys Val Arg Val
    370                 375                 380

Phe Arg Phe Ser Val Gly Gln His Asn Tyr Glu Arg Gly Pro Ile Gln
385                 390                 395                 400

Trp Met Ala Cys Glu Asn Lys Gly Tyr Tyr Tyr Glu Ile Pro Ser Ile
                405                 410                 415

Gly Ala Ile Arg Ile Asn Thr Gln Glu Tyr Leu Asp Val Leu Gly Arg
            420                 425                 430

Pro Met Val Leu Ala Gly Asp Lys Ala Lys Gln Val Gln Trp Thr Asn
        435                 440                 445

Val Tyr Leu Asp Ala Leu Glu Leu Gly Leu Val Ile Thr Gly Thr Leu
    450                 455                 460

Pro Val Phe Asn Ile Thr Gly Gln Phe Glu Asn Lys Thr Asn Leu Lys
465                 470                 475                 480

Asn Gln Leu Ile Leu Gly Val Met Gly Val Asp Val Ser Leu Glu Asp
                485                 490                 495

Ile Lys Arg Leu Thr Pro Arg Phe Thr Leu Cys Pro Asn Gly Tyr Tyr
            500                 505                 510

Phe Ala Ile Asp Pro Asn Gly Tyr Val Leu Leu His Pro Asn Leu Gln
        515                 520                 525

Pro Lys Pro Ile Gly Val Gly Ile Pro Thr Ile Asn Leu Arg Lys Arg
    530                 535                 540

Arg Pro Asn Ile Gln Asn Pro Lys Ser Gln Glu Pro Val Thr Leu Asp
```

545 550 555 560

Phe Leu Asp Ala Glu Leu Glu Asn Asp Ile Lys Val Glu Ile Arg Asn
565 570 575

Lys Met Ile Asp Gly Glu Ser Gly Glu Lys Thr Phe Arg Thr Leu Val
580 585 590

Lys Ser Gln Asp Glu Arg Tyr Ile Asp Lys Gly Asn Arg Thr Tyr Thr
595 600 605

Trp Thr Pro Val Asn Gly Thr Asp Tyr Ser Leu Ala Leu Val Leu Pro
610 615 620

Thr Tyr Ser Phe Tyr Tyr Ile Lys Ala Lys Leu Glu Glu Thr Ile Thr
625 630 635 640

Gln Ala Arg Tyr Ser Glu Thr Leu Lys Pro Asp Asn Phe Glu Glu Ser
645 650 655

Gly Tyr Thr Phe Ile Ala Pro Arg Asp Tyr Cys Asn Asp Leu Lys Ile
660 665 670

Ser Asp Asn Asn Thr Glu Phe Leu Leu Asn Phe Asn Glu Phe Ile Asp
675 680 685

Arg Lys Thr Pro Asn Asn Pro Ser Cys Asn Ala Asp Leu Ile Asn Arg
690 695 700

Val Leu Leu Asp Ala Gly Phe Thr Asn Glu Leu Val Gln Asn Tyr Trp
705 710 715 720

Ser Lys Gln Lys Asn Ile Lys Gly Val Lys Ala Arg Phe Val Val Thr
725 730 735

Asp Gly Gly Ile Thr Arg Val Tyr Pro Lys Glu Ala Gly Glu Asn Trp
740 745 750

Gln Glu Asn Pro Glu Thr Tyr Glu Asp Ser Phe Tyr Lys Arg Ser Leu
755 760 765

Asp Asn Asp Asn Tyr Val Phe Thr Ala Pro Tyr Phe Asn Lys Ser Gly
770 775 780

Pro Gly Ala Tyr Glu Ser Gly Ile Met Val Ser Lys Ala Val Glu Ile
785 790 795 800

Tyr Ile Gln Gly Lys Leu Leu Lys Pro Ala Val Val Gly Ile Lys Ile
805 810 815

Asp Val Asn Ser Trp Ile Glu Asn Phe Thr Lys Thr Ser Ile Arg Asp
820 825 830

Pro Cys Ala Gly Pro Val Cys Asp Cys Lys Arg Asn Ser Asp Val Met
835 840 845

Asp Cys Val Ile Leu Asp Asp Gly Gly Phe Leu Leu Met Ala Asn His
850 855 860

Asp Asp Tyr Thr Asn Gln Ile Gly Arg Phe Phe Gly Glu Ile Asp Pro
865 870 875 880

Ser Leu Met Arg His Leu Val Asn Ile Ser Val Tyr Ala Phe Asn Lys
885 890 895

Ser Tyr Asp Tyr Gln Ser Val Cys Glu Pro Gly Ala Ala Pro Lys Gln
900 905 910

Gly Ala Gly His Arg Ser Ala Tyr Val Pro Ser Val Ala Asp Ile Leu
915 920 925

Gln Ile Gly Trp Trp Ala Thr Ala Ala Ala Trp Ser Ile Leu Gln Gln
930 935 940

Phe Leu Leu Ser Leu Thr Phe Pro Arg Leu Leu Glu Ala Val Glu Met
945 950 955 960

Glu Asp Asp Asp Phe Thr Ala Ser Leu Ser Lys Gln Ser Cys Ile Thr
965 970 975

-continued

Glu Gln Thr Gln Tyr Phe Phe Asp Asn Asp Ser Lys Ser Phe Ser Gly
980 985 990

Val Leu Asp Cys Gly Asn Cys Ser Arg Ile Phe His Gly Glu Lys Leu
995 1000 1005

Met Asn Thr Asn Leu Ile Phe Ile Met Val Glu Ser Lys Gly Thr Cys
1010 1015 1020

Pro Cys Asp Thr Arg Leu Leu Ile Gln Ala Glu Gln Thr Ser Asp Gly
1025 1030 1035 1040

Pro Asn Pro Cys Asp Met Val Lys Gln Pro Arg Tyr Arg Lys Gly Pro
1045 1050 1055

Asp Val Cys Phe Asp Asn Asn Val Leu Glu Asp Tyr Thr Asp Cys Gly
1060 1065 1070

Gly Val Ser Gly Leu Asn Pro Ser Leu Trp Tyr Ile Ile Gly Ile Gln
1075 1080 1085

Phe Leu Leu Leu Trp Leu Val Ser Gly Ser Thr His Arg Leu Leu
1090 1095 1100

( 2 ) INFORMATION FOR SEQ ID NO:54:

( i ) SEQUENCE CHARACTERISTICS:
( A ) LENGTH: 1086 amino acids
( B ) TYPE: amino acid
( C ) STRANDEDNESS: single
( D ) TOPOLOGY: linear ( i i ) MOLECULE TYPE: protein ( v ) FRAGMENT TYPE: internal ( x i ) SEQUENCE DESCRIPTION: SEQ ID NO:54:

Met Ala Ala Gly Cys Leu Leu Ala Leu Thr Leu Thr Leu Phe Gln Ser
1 5 10 15

Leu Leu Ile Gly Pro Ser Ser Glu Glu Pro Phe Pro Ser Ala Val Thr
20 25 30

Ile Lys Ser Trp Val Asp Lys Met Gln Glu Asp Leu Val Thr Leu Ala
35 40 45

Lys Thr Ala Ser Gly Val Asn Gln Leu Val Asp Ile Tyr Glu Lys Tyr
50 55 60

Gln Asp Leu Tyr Thr Val Glu Pro Asn Asn Ala Arg Gln Leu Val Glu
65 70 75 80

Ile Ala Ala Arg Asp Ile Glu Lys Leu Leu Ser Asn Arg Ser Lys Ala
85 90 95

Leu Val Ser Leu Ala Leu Glu Ala Glu Lys Val Gln Ala Ala His Gln
100 105 110

Trp Arg Glu Asp Phe Ala Ser Asn Glu Val Val Tyr Tyr Asn Ala Lys
115 120 125

Asp Asp Leu Asp Pro Glu Lys Asn Asp Ser Glu Pro Gly Ser Gln Arg
130 135 140

Ile Lys Pro Val Phe Ile Glu Asp Ala Asn Phe Gly Arg Gln Ile Ser
145 150 155 160

Tyr Gln His Ala Ala Val His Ile Pro Thr Asp Ile Tyr Glu Gly Ser
165 170 175

Thr Ile Val Leu Asn Glu Leu Asn Trp Thr Ser Ala Leu Asp Glu Val
180 185 190

Phe Lys Lys Asn Arg Glu Glu Asp Pro Ser Leu Leu Trp Gln Val Phe
195 200 205

Gly Ser Ala Thr Gly Leu Ala Arg Tyr Tyr Pro Ala Ser Pro Trp Val
210 215 220

-continued

Asp Asn Ser Arg Thr Pro Asn Lys Ile Asp Leu Tyr Asp Val Arg Arg
225 230 235 240

Arg Pro Trp Tyr Ile Gln Gly Ala Ala Ser Pro Lys Asp Met Leu Ile
245 250 255

Leu Val Asp Val Ser Gly Ser Val Ser Gly Leu Thr Leu Lys Leu Ile
260 265 270

Arg Thr Ser Val Ser Glu Met Leu Glu Thr Leu Ser Asp Asp Asp Phe
275 280 285

Val Asn Val Ala Ser Phe Asn Ser Asn Ala Gln Asp Val Ser Cys Phe
290 295 300

Gln His Leu Val Gln Ala Asn Val Arg Asn Lys Lys Val Leu Lys Asp
305 310 315 320

Ala Val Asn Asn Ile Thr Ala Lys Gly Ile Thr Asp Tyr Lys Lys Gly
325 330 335

Phe Ser Phe Ala Phe Glu Gln Leu Leu Asn Tyr Asn Val Ser Arg Ala
340 345 350

Asn Cys Asn Lys Ile Ile Met Leu Phe Thr Asp Gly Gly Glu Glu Arg
355 360 365

Ala Gln Glu Ile Phe Asn Lys Tyr Asn Lys Asp Lys Lys Val Arg Val
370 375 380

Phe Arg Phe Ser Val Gly Gln His Asn Tyr Glu Arg Gly Pro Ile Gln
385 390 395 400

Trp Met Ala Cys Glu Asn Lys Gly Tyr Tyr Tyr Glu Ile Pro Ser Ile
405 410 415

Gly Ala Ile Arg Ile Asn Thr Gln Glu Tyr Leu Asp Val Leu Gly Arg
420 425 430

Pro Met Val Leu Ala Gly Asp Lys Ala Lys Gln Val Gln Trp Thr Asn
435 440 445

Val Tyr Leu Asp Ala Leu Glu Leu Gly Leu Val Ile Thr Gly Thr Leu
450 455 460

Pro Val Phe Asn Ile Thr Gly Gln Phe Glu Asn Lys Thr Asn Leu Lys
465 470 475 480

Asn Gln Leu Ile Leu Gly Val Met Gly Val Asp Val Ser Leu Glu Asp
485 490 495

Ile Lys Arg Leu Thr Pro Arg Phe Thr Leu Cys Pro Asn Gly Tyr Tyr
500 505 510

Phe Ala Ile Asp Pro Asn Gly Tyr Val Leu Leu His Pro Asn Leu Gln
515 520 525

Pro Lys Glu Pro Val Thr Leu Asp Phe Leu Asp Ala Glu Leu Glu Asn
530 535 540

Asp Ile Lys Val Glu Ile Arg Asn Lys Met Ile Asp Gly Glu Ser Gly
545 550 555 560

Glu Lys Thr Phe Arg Thr Leu Val Lys Ser Gln Asp Glu Arg Tyr Ile
565 570 575

Asp Lys Gly Asn Arg Thr Tyr Thr Trp Thr Pro Val Asn Gly Thr Asp
580 585 590

Tyr Ser Leu Ala Leu Val Leu Pro Thr Tyr Ser Phe Tyr Tyr Ile Lys
595 600 605

Ala Lys Leu Glu Glu Thr Ile Thr Gln Ala Arg Ser Lys Lys Gly Lys
610 615 620

Met Lys Asp Ser Glu Thr Leu Lys Pro Asp Asn Phe Glu Glu Ser Gly
625 630 635 640

Tyr Thr Phe Ile Ala Pro Arg Asp Tyr Cys Asn Asp Leu Lys Ile Ser

-continued 645 650 655

Asp Asn Asn Thr Glu Phe Leu Leu Asn Phe Asn Glu Phe Ile Asp Arg
660 665 670

Lys Thr Pro Asn Asn Pro Ser Cys Asn Ala Asp Leu Ile Asn Arg Val
675 680 685

Leu Leu Asp Ala Gly Phe Thr Asn Glu Leu Val Gln Asn Tyr Trp Ser
690 695 700

Lys Gln Lys Asn Ile Lys Gly Val Lys Ala Arg Phe Val Val Thr Asp
705 710 715 720

Gly Gly Ile Thr Arg Val Tyr Pro Lys Glu Ala Gly Glu Asn Trp Gln
725 730 735

Glu Asn Pro Glu Thr Tyr Glu Asp Ser Phe Tyr Lys Arg Ser Leu Asp
740 745 750

Asn Asp Asn Tyr Val Phe Thr Ala Pro Tyr Phe Asn Lys Ser Gly Pro
755 760 765

Gly Ala Tyr Glu Ser Gly Ile Met Val Ser Lys Ala Val Glu Ile Tyr
770 775 780

Ile Gln Gly Lys Leu Leu Lys Pro Ala Val Val Gly Ile Lys Ile Asp
785 790 795 800

Val Asn Ser Trp Ile Glu Asn Phe Thr Lys Thr Ser Ile Arg Asp Pro
805 810 815

Cys Ala Gly Pro Val Cys Asp Cys Lys Arg Asn Ser Asp Val Met Asp
820 825 830

Cys Val Ile Leu Asp Asp Gly Gly Phe Leu Leu Met Ala Asn His Asp
835 840 845

Asp Tyr Thr Asn Gln Ile Gly Arg Phe Phe Gly Glu Ile Asp Pro Ser
850 855 860

Leu Met Arg His Leu Val Asn Ile Ser Val Tyr Ala Phe Asn Lys Ser
865 870 875 880

Tyr Asp Tyr Gln Ser Val Cys Glu Pro Gly Ala Ala Pro Lys Gln Gly
885 890 895

Ala Gly His Arg Ser Ala Tyr Val Pro Ser Val Ala Asp Ile Leu Gln
900 905 910

Ile Gly Trp Trp Ala Thr Ala Ala Ala Trp Ser Ile Leu Gln Gln Phe
915 920 925

Leu Leu Ser Leu Thr Phe Pro Arg Leu Leu Glu Ala Val Glu Met Glu
930 935 940

Asp Asp Asp Phe Thr Ala Ser Leu Ser Lys Gln Ser Cys Ile Thr Glu
945 950 955 960

Gln Thr Gln Tyr Phe Phe Asp Asn Asp Ser Lys Ser Phe Ser Gly Val
965 970 975

Leu Asp Cys Gly Asn Cys Ser Arg Ile Phe His Gly Glu Lys Leu Met
980 985 990

Asn Thr Asn Leu Ile Phe Ile Met Val Glu Ser Lys Gly Thr Cys Pro
995 1000 1005

Cys Asp Thr Arg Leu Leu Ile Gln Ala Glu Gln Thr Ser Asp Gly Pro
1010 1015 1020

Asn Pro Cys Asp Met Val Lys Gln Pro Arg Tyr Arg Lys Gly Pro Asp
1025 1030 1035 1040

Val Cys Phe Asp Asn Asn Val Leu Glu Asp Tyr Thr Asp Cys Gly Gly
1045 1050 1055

Val Ser Gly Leu Asn Pro Ser Leu Trp Tyr Ile Ile Gly Ile Gln Phe
1060 1065 1070

Leu Leu Leu Trp Leu Val Ser Gly Ser Thr His Arg Leu Leu
1075 1080 1085

(2) INFORMATION FOR SEQ ID NO:55:

(i) SEQUENCE CHARACTERISTICS:
(A) LENGTH: 1079 amino acids
(B) TYPE: amino acid
(C) STRANDEDNESS: single
(D) TOPOLOGY: linear (ii) MOLECULE TYPE: protein (v) FRAGMENT TYPE: internal (xi) SEQUENCE DESCRIPTION: SEQ ID NO:55:

Met Ala Ala Gly Cys Leu Leu Ala Leu Thr Leu Thr Leu Phe Gln Ser
1 5 10 15

Leu Leu Ile Gly Pro Ser Ser Glu Glu Pro Phe Pro Ser Ala Val Thr
20 25 30

Ile Lys Ser Trp Val Asp Lys Met Gln Glu Asp Leu Val Thr Leu Ala
35 40 45

Lys Thr Ala Ser Gly Val Asn Gln Leu Val Asp Ile Tyr Glu Lys Tyr
50 55 60

Gln Asp Leu Tyr Thr Val Glu Pro Asn Asn Ala Arg Gln Leu Val Glu
65 70 75 80

Ile Ala Ala Arg Asp Ile Glu Lys Leu Leu Ser Asn Arg Ser Lys Ala
85 90 95

Leu Val Ser Leu Ala Leu Glu Ala Glu Lys Val Gln Ala Ala His Gln
100 105 110

Trp Arg Glu Asp Phe Ala Ser Asn Glu Val Val Tyr Tyr Asn Ala Lys
115 120 125

Asp Asp Leu Asp Pro Glu Lys Asn Asp Ser Glu Pro Gly Ser Gln Arg
130 135 140

Ile Lys Pro Val Phe Ile Glu Asp Ala Asn Phe Gly Arg Gln Ile Ser
145 150 155 160

Tyr Gln His Ala Ala Val His Ile Pro Thr Asp Ile Tyr Glu Gly Ser
165 170 175

Thr Ile Val Leu Asn Glu Leu Asn Trp Thr Ser Ala Leu Asp Glu Val
180 185 190

Phe Lys Lys Asn Arg Glu Glu Asp Pro Ser Leu Leu Trp Gln Val Phe
195 200 205

Gly Ser Ala Thr Gly Leu Ala Arg Tyr Tyr Pro Ala Ser Pro Trp Val
210 215 220

Asp Asn Ser Arg Thr Pro Asn Lys Ile Asp Leu Tyr Asp Val Arg Arg
225 230 235 240

Arg Pro Trp Tyr Ile Gln Gly Ala Ala Ser Pro Lys Asp Met Leu Ile
245 250 255

Leu Val Asp Val Ser Gly Ser Val Ser Gly Leu Thr Leu Lys Leu Ile
260 265 270

Arg Thr Ser Val Ser Glu Met Leu Glu Thr Leu Ser Asp Asp Asp Phe
275 280 285

Val Asn Val Ala Ser Phe Asn Ser Asn Ala Gln Asp Val Ser Cys Phe
290 295 300

Gln His Leu Val Gln Ala Asn Val Arg Asn Lys Lys Val Leu Lys Asp
305 310 315 320

Ala Val Asn Asn Ile Thr Ala Lys Gly Ile Thr Asp Tyr Lys Lys Gly
325 330 335

-continued

```
Phe Ser Phe Ala Phe Glu Gln Leu Leu Asn Tyr Asn Val Ser Arg Ala
            340                 345                 350

Asn Cys Asn Lys Ile Ile Met Leu Phe Thr Asp Gly Gly Glu Glu Arg
        355                 360                 365

Ala Gln Glu Ile Phe Asn Lys Tyr Asn Lys Asp Lys Lys Val Arg Val
    370                 375                 380

Phe Arg Phe Ser Val Gly Gln His Asn Tyr Glu Arg Gly Pro Ile Gln
385                 390                 395                 400

Trp Met Ala Cys Glu Asn Lys Gly Tyr Tyr Tyr Glu Ile Pro Ser Ile
                405                 410                 415

Gly Ala Ile Arg Ile Asn Thr Gln Glu Tyr Leu Asp Val Leu Gly Arg
            420                 425                 430

Pro Met Val Leu Ala Gly Asp Lys Ala Lys Gln Val Gln Trp Thr Asn
        435                 440                 445

Val Tyr Leu Asp Ala Leu Glu Leu Gly Leu Val Ile Thr Gly Thr Leu
    450                 455                 460

Pro Val Phe Asn Ile Thr Gly Gln Phe Glu Asn Lys Thr Asn Leu Lys
465                 470                 475                 480

Asn Gln Leu Ile Leu Gly Val Met Gly Val Asp Val Ser Leu Glu Asp
                485                 490                 495

Ile Lys Arg Leu Thr Pro Arg Phe Thr Leu Cys Pro Asn Gly Tyr Tyr
            500                 505                 510

Phe Ala Ile Asp Pro Asn Gly Tyr Val Leu Leu His Pro Asn Leu Gln
        515                 520                 525

Pro Lys Glu Pro Val Thr Leu Asp Phe Leu Asp Ala Glu Leu Glu Asn
    530                 535                 540

Asp Ile Lys Val Glu Ile Arg Asn Lys Met Ile Asp Gly Glu Ser Gly
545                 550                 555                 560

Glu Lys Thr Phe Arg Thr Leu Val Lys Ser Gln Asp Glu Arg Tyr Ile
                565                 570                 575

Asp Lys Gly Asn Arg Thr Tyr Thr Trp Thr Pro Val Asn Gly Thr Asp
            580                 585                 590

Tyr Ser Leu Ala Leu Val Leu Pro Thr Tyr Ser Phe Tyr Tyr Ile Lys
        595                 600                 605

Ala Lys Leu Glu Glu Thr Ile Thr Gln Ala Arg Tyr Ser Glu Thr Leu
    610                 615                 620

Lys Pro Asp Asn Phe Glu Glu Ser Gly Tyr Thr Phe Ile Ala Pro Arg
625                 630                 635                 640

Asp Tyr Cys Asn Asp Leu Lys Ile Ser Asp Asn Asn Thr Glu Phe Leu
                645                 650                 655

Leu Asn Phe Asn Glu Phe Ile Asp Arg Lys Thr Pro Asn Asn Pro Ser
            660                 665                 670

Cys Asn Ala Asp Leu Ile Asn Arg Val Leu Leu Asp Ala Gly Phe Thr
        675                 680                 685

Asn Glu Leu Val Gln Asn Tyr Trp Ser Lys Gln Lys Asn Ile Lys Gly
    690                 695                 700

Val Lys Ala Arg Phe Val Val Thr Asp Gly Gly Ile Thr Arg Val Tyr
705                 710                 715                 720

Pro Lys Glu Ala Gly Glu Asn Trp Gln Glu Asn Pro Glu Thr Tyr Glu
                725                 730                 735

Asp Ser Phe Tyr Lys Arg Ser Leu Asp Asn Asp Asn Tyr Val Phe Thr
            740                 745                 750

Ala Pro Tyr Phe Asn Lys Ser Gly Pro Gly Ala Tyr Glu Ser Gly Ile
```

-continued 755 760 765

Met Val Ser Lys Ala Val Glu Ile Tyr Ile Gln Gly Lys Leu Leu Lys
770 775 780

Pro Ala Val Val Gly Ile Lys Ile Asp Val Asn Ser Trp Ile Glu Asn
785 790 795 800

Phe Thr Lys Thr Ser Ile Arg Asp Pro Cys Ala Gly Pro Val Cys Asp
805 810 815

Cys Lys Arg Asn Ser Asp Val Met Asp Cys Val Ile Leu Asp Asp Gly
820 825 830

Gly Phe Leu Leu Met Ala Asn His Asp Asp Tyr Thr Asn Gln Ile Gly
835 840 845

Arg Phe Phe Gly Glu Ile Asp Pro Ser Leu Met Arg His Leu Val Asn
850 855 860

Ile Ser Val Tyr Ala Phe Asn Lys Ser Tyr Asp Tyr Gln Ser Val Cys
865 870 875 880

Glu Pro Gly Ala Ala Pro Lys Gln Gly Ala Gly His Arg Ser Ala Tyr
885 890 895

Val Pro Ser Val Ala Asp Ile Leu Gln Ile Gly Trp Trp Ala Thr Ala
900 905 910

Ala Ala Trp Ser Ile Leu Gln Gln Phe Leu Leu Ser Leu Thr Phe Pro
915 920 925

Arg Leu Leu Glu Ala Val Glu Met Glu Asp Asp Asp Phe Thr Ala Ser
930 935 940

Leu Ser Lys Gln Ser Cys Ile Thr Glu Gln Thr Gln Tyr Phe Phe Asp
945 950 955 960

Asn Asp Ser Lys Ser Phe Ser Gly Val Leu Asp Cys Gly Asn Cys Ser
965 970 975

Arg Ile Phe His Gly Glu Lys Leu Met Asn Thr Asn Leu Ile Phe Ile
980 985 990

Met Val Glu Ser Lys Gly Thr Cys Pro Cys Asp Thr Arg Leu Leu Ile
995 1000 1005

Gln Ala Glu Gln Thr Ser Asp Gly Pro Asn Pro Cys Asp Met Val Lys
1010 1015 1020

Gln Pro Arg Tyr Arg Lys Gly Pro Asp Val Cys Phe Asp Asn Asn Val
1025 1030 1035 1040

Leu Glu Asp Tyr Thr Asp Cys Gly Gly Val Ser Gly Leu Asn Pro Ser
1045 1050 1055

Leu Trp Tyr Ile Ile Gly Ile Gln Phe Leu Leu Leu Trp Leu Val Ser
1060 1065 1070

Gly Ser Thr His Arg Leu Leu
1075

( 2 ) INFORMATION FOR SEQ ID NO:56:

( i ) SEQUENCE CHARACTERISTICS:
( A ) LENGTH: 1084 amino acids
( B ) TYPE: amino acid
( C ) STRANDEDNESS: single
( D ) TOPOLOGY: linear ( i i ) MOLECULE TYPE: protein ( v ) FRAGMENT TYPE: internal ( x i ) SEQUENCE DESCRIPTION: SEQ ID NO:56:

Met Ala Ala Gly Cys Leu Leu Ala Leu Thr Leu Thr Leu Phe Gln Ser
1 5 10 15

-continued

Leu Leu Ile Gly Pro Ser Ser Glu Glu Pro Phe Pro Ser Ala Val Thr
20 25 30

Ile Lys Ser Trp Val Asp Lys Met Gln Glu Asp Leu Val Thr Leu Ala
35 40 45

Lys Thr Ala Ser Gly Val Asn Gln Leu Val Asp Ile Tyr Glu Lys Tyr
50 55 60

Gln Asp Leu Tyr Thr Val Glu Pro Asn Asn Ala Arg Gln Leu Val Glu
65 70 75 80

Ile Ala Ala Arg Asp Ile Glu Lys Leu Leu Ser Asn Arg Ser Lys Ala
85 90 95

Leu Val Ser Leu Ala Leu Glu Ala Glu Lys Val Gln Ala Ala His Gln
100 105 110

Trp Arg Glu Asp Phe Ala Ser Asn Glu Val Val Tyr Tyr Asn Ala Lys
115 120 125

Asp Asp Leu Asp Pro Glu Lys Asn Asp Ser Glu Pro Gly Ser Gln Arg
130 135 140

Ile Lys Pro Val Phe Ile Glu Asp Ala Asn Phe Gly Arg Gln Ile Ser
145 150 155 160

Tyr Gln His Ala Ala Val His Ile Pro Thr Asp Ile Tyr Glu Gly Ser
165 170 175

Thr Ile Val Leu Asn Glu Leu Asn Trp Thr Ser Ala Leu Asp Glu Val
180 185 190

Phe Lys Lys Asn Arg Glu Glu Asp Pro Ser Leu Leu Trp Gln Val Phe
195 200 205

Gly Ser Ala Thr Gly Leu Ala Arg Tyr Tyr Pro Ala Ser Pro Trp Val
210 215 220

Asp Asn Ser Arg Thr Pro Asn Lys Ile Asp Leu Tyr Asp Val Arg Arg
225 230 235 240

Arg Pro Trp Tyr Ile Gln Gly Ala Ala Ser Pro Lys Asp Met Leu Ile
245 250 255

Leu Val Asp Val Ser Gly Ser Val Ser Gly Leu Thr Leu Lys Leu Ile
260 265 270

Arg Thr Ser Val Ser Glu Met Leu Glu Thr Leu Ser Asp Asp Asp Phe
275 280 285

Val Asn Val Ala Ser Phe Asn Ser Asn Ala Gln Asp Val Ser Cys Phe
290 295 300

Gln His Leu Val Gln Ala Asn Val Arg Asn Lys Lys Val Leu Lys Asp
305 310 315 320

Ala Val Asn Asn Ile Thr Ala Lys Gly Ile Thr Asp Tyr Lys Lys Gly
325 330 335

Phe Ser Phe Ala Phe Glu Gln Leu Leu Asn Tyr Asn Val Ser Arg Ala
340 345 350

Asn Cys Asn Lys Ile Ile Met Leu Phe Thr Asp Gly Gly Glu Glu Arg
355 360 365

Ala Gln Glu Ile Phe Asn Lys Tyr Asn Lys Asp Lys Lys Val Arg Val
370 375 380

Phe Arg Phe Ser Val Gly Gln His Asn Tyr Glu Arg Gly Pro Ile Gln
385 390 395 400

Trp Met Ala Cys Glu Asn Lys Gly Tyr Tyr Tyr Glu Ile Pro Ser Ile
405 410 415

Gly Ala Ile Arg Ile Asn Thr Gln Glu Tyr Leu Asp Val Leu Gly Arg
420 425 430

Pro Met Val Leu Ala Gly Asp Lys Ala Lys Gln Val Gln Trp Thr Asn
435 440 445

-continued

| | | | | | | | | | | | | | | | |
|---|---|---|---|---|---|---|---|---|---|---|---|---|---|---|---|
| Val | Tyr | Leu | Asp | Ala | Leu | Glu | Leu | Gly | Leu | Val | Ile | Thr | Gly | Thr | Leu |
| | 450 | | | | | 455 | | | | | 460 | | | | |
| Pro | Val | Phe | Asn | Ile | Thr | Gly | Gln | Phe | Glu | Asn | Lys | Thr | Asn | Leu | Lys |
| 465 | | | | | 470 | | | | | 475 | | | | | 480 |
| Asn | Gln | Leu | Ile | Leu | Gly | Val | Met | Gly | Val | Asp | Val | Ser | Leu | Glu | Asp |
| | | | | 485 | | | | | 490 | | | | | 495 | |
| Ile | Lys | Arg | Leu | Thr | Pro | Arg | Phe | Thr | Leu | Cys | Pro | Asn | Gly | Tyr | Tyr |
| | | | 500 | | | | | 505 | | | | | 510 | | |
| Phe | Ala | Ile | Asp | Pro | Asn | Gly | Tyr | Val | Leu | Leu | His | Pro | Asn | Leu | Gln |
| | | 515 | | | | | 520 | | | | | 525 | | | |
| Pro | Lys | Asn | Pro | Lys | Ser | Gln | Glu | Pro | Val | Thr | Leu | Asp | Phe | Leu | Asp |
| | 530 | | | | | 535 | | | | | 540 | | | | |
| Ala | Glu | Leu | Glu | Asn | Asp | Ile | Lys | Val | Glu | Ile | Arg | Asn | Lys | Met | Ile |
| 545 | | | | | 550 | | | | | 555 | | | | | 560 |
| Asp | Gly | Glu | Ser | Gly | Glu | Lys | Thr | Phe | Arg | Thr | Leu | Val | Lys | Ser | Gln |
| | | | | 565 | | | | | 570 | | | | | 575 | |
| Asp | Glu | Arg | Tyr | Ile | Asp | Lys | Gly | Asn | Arg | Thr | Tyr | Thr | Trp | Thr | Pro |
| | | | 580 | | | | | 585 | | | | | 590 | | |
| Val | Asn | Gly | Thr | Asp | Tyr | Ser | Leu | Ala | Leu | Val | Leu | Pro | Thr | Tyr | Ser |
| | | 595 | | | | | 600 | | | | | 605 | | | |
| Phe | Tyr | Tyr | Ile | Lys | Ala | Lys | Leu | Glu | Glu | Thr | Ile | Thr | Gln | Ala | Arg |
| | 610 | | | | | 615 | | | | | 620 | | | | |
| Tyr | Ser | Glu | Thr | Leu | Lys | Pro | Asp | Asn | Phe | Glu | Glu | Ser | Gly | Tyr | Thr |
| 625 | | | | | 630 | | | | | 635 | | | | | 640 |
| Phe | Ile | Ala | Pro | Arg | Asp | Tyr | Cys | Asn | Asp | Leu | Lys | Ile | Ser | Asp | Asn |
| | | | | 645 | | | | | 650 | | | | | 655 | |
| Asn | Thr | Glu | Phe | Leu | Leu | Asn | Phe | Asn | Glu | Phe | Ile | Asp | Arg | Lys | Thr |
| | | | 660 | | | | | 665 | | | | | 670 | | |
| Pro | Asn | Asn | Pro | Ser | Cys | Asn | Ala | Asp | Leu | Ile | Asn | Arg | Val | Leu | Leu |
| | | 675 | | | | | 680 | | | | | 685 | | | |
| Asp | Ala | Gly | Phe | Thr | Asn | Glu | Leu | Val | Gln | Asn | Tyr | Trp | Ser | Lys | Gln |
| | 690 | | | | | 695 | | | | | 700 | | | | |
| Lys | Asn | Ile | Lys | Gly | Val | Lys | Ala | Arg | Phe | Val | Val | Thr | Asp | Gly | Gly |
| 705 | | | | | 710 | | | | | 715 | | | | | 720 |
| Ile | Thr | Arg | Val | Tyr | Pro | Lys | Glu | Ala | Gly | Glu | Asn | Trp | Gln | Glu | Asn |
| | | | | 725 | | | | | 730 | | | | | 735 | |
| Pro | Glu | Thr | Tyr | Glu | Asp | Ser | Phe | Tyr | Lys | Arg | Ser | Leu | Asp | Asn | Asp |
| | | | 740 | | | | | 745 | | | | | 750 | | |
| Asn | Tyr | Val | Phe | Thr | Ala | Pro | Tyr | Phe | Asn | Lys | Ser | Gly | Pro | Gly | Ala |
| | | 755 | | | | | 760 | | | | | 765 | | | |
| Tyr | Glu | Ser | Gly | Ile | Met | Val | Ser | Lys | Ala | Val | Glu | Ile | Tyr | Ile | Gln |
| | 770 | | | | | 775 | | | | | 780 | | | | |
| Gly | Lys | Leu | Leu | Lys | Pro | Ala | Val | Val | Gly | Ile | Lys | Ile | Asp | Val | Asn |
| 785 | | | | | 790 | | | | | 795 | | | | | 800 |
| Ser | Trp | Ile | Glu | Asn | Phe | Thr | Lys | Thr | Ser | Ile | Arg | Asp | Pro | Cys | Ala |
| | | | | 805 | | | | | 810 | | | | | 815 | |
| Gly | Pro | Val | Cys | Asp | Cys | Lys | Arg | Asn | Ser | Asp | Val | Met | Asp | Cys | Val |
| | | | 820 | | | | | 825 | | | | | 830 | | |
| Ile | Leu | Asp | Asp | Gly | Gly | Phe | Leu | Leu | Met | Ala | Asn | His | Asp | Asp | Tyr |
| | | 835 | | | | | 840 | | | | | 845 | | | |
| Thr | Asn | Gln | Ile | Gly | Arg | Phe | Phe | Gly | Glu | Ile | Asp | Pro | Ser | Leu | Met |
| | 850 | | | | | 855 | | | | | 860 | | | | |
| Arg | His | Leu | Val | Asn | Ile | Ser | Val | Tyr | Ala | Phe | Asn | Lys | Ser | Tyr | Asp |

-continued

```
865                     870                     875                     880

Tyr Gln Ser Val Cys Glu Pro Gly Ala Ala Pro Lys Gln Gly Ala Gly
                885                 890                 895

His Arg Ser Ala Tyr Val Pro Ser Val Ala Asp Ile Leu Gln Ile Gly
            900                 905                 910

Trp Trp Ala Thr Ala Ala Ala Trp Ser Ile Leu Gln Gln Phe Leu Leu
        915                 920                 925

Ser Leu Thr Phe Pro Arg Leu Leu Glu Ala Val Glu Met Glu Asp Asp
    930                 935                 940

Asp Phe Thr Ala Ser Leu Ser Lys Gln Ser Cys Ile Thr Glu Gln Thr
945                 950                 955                 960

Gln Tyr Phe Phe Asp Asn Asp Ser Lys Ser Phe Ser Gly Val Leu Asp
                965                 970                 975

Cys Gly Asn Cys Ser Arg Ile Phe His Gly Glu Lys Leu Met Asn Thr
            980                 985                 990

Asn Leu Ile Phe Ile Met Val Glu Ser Lys Gly Thr Cys Pro Cys Asp
        995                 1000                1005

Thr Arg Leu Leu Ile Gln Ala Glu Gln Thr Ser Asp Gly Pro Asn Pro
    1010                1015                1020

Cys Asp Met Val Lys Gln Pro Arg Tyr Arg Lys Gly Pro Asp Val Cys
1025                1030                1035                1040

Phe Asp Asn Asn Val Leu Glu Asp Tyr Thr Asp Cys Gly Gly Val Ser
                1045                1050                1055

Gly Leu Asn Pro Ser Leu Trp Tyr Ile Ile Gly Ile Gln Phe Leu Leu
            1060                1065                1070

Leu Trp Leu Val Ser Gly Ser Thr His Arg Leu Leu
        1075                1080
```

( 2 ) INFORMATION FOR SEQ ID NO:57:

( i ) SEQUENCE CHARACTERISTICS:
( A ) LENGTH: 43 amino acids
( B ) TYPE: amino acid
( C ) STRANDEDNESS: single
( D ) TOPOLOGY: linear ( i i ) MOLECULE TYPE: protein ( v ) FRAGMENT TYPE: internal ( x i ) SEQUENCE DESCRIPTION: SEQ ID NO:57:

```
Trp Ser Phe Ala Cys Ala Cys Ala Ala Phe Ile Leu Leu Phe Leu Gly
 1               5                  10                  15

Gly Leu Ala Leu Leu Leu Phe Ser Leu Pro Arg Met Pro Arg Asn Pro
            20                  25                  30

Trp Glu Ser Cys Met Asp Ala Glu Pro Glu His
        35                  40
```